US010858367B2

(12) United States Patent
Ding et al.

(10) Patent No.: US 10,858,367 B2
(45) Date of Patent: Dec. 8, 2020

(54) COMPOUNDS

(71) Applicant: GLAXOSMITHKLINE INTELLECTUAL PROPERTY DEVELOPMENT LIMITED, Brentford (GB)

(72) Inventors: Xiao Ding, Shanghai (CN); Feng Ren, Shanghai (CN); Yingxia Sang, Shanghai (CN); Weiqiang Xing, Shanghai (CN); Yang Zhan, Shanghai (CN); Baowei Zhao, Shanghai (CN)

(73) Assignee: GLAXOSMITHKLINE INTELLECTUAL PROPERTY DEVELOPMENT LIMITED, Middlesex (GB)

( * ) Notice: Subject to any disclaimer, the term of this patent is extended or adjusted under 35 U.S.C. 154(b) by 0 days.

(21) Appl. No.: 16/480,797

(22) PCT Filed: Jan. 23, 2018

(86) PCT No.: PCT/CN2018/073729
§ 371 (c)(1),
(2) Date: Jul. 25, 2019

(87) PCT Pub. No.: WO2018/137593
PCT Pub. Date: Aug. 2, 2018

(65) Prior Publication Data
US 2019/0359623 A1  Nov. 28, 2019

(30) Foreign Application Priority Data
Jan. 25, 2017 (CN) ................. PCT/CN2017/072601

(51) Int. Cl.
*C07D 491/08* (2006.01)
*C07D 401/14* (2006.01)

(52) U.S. Cl.
CPC ......... *C07D 491/08* (2013.01); *C07D 401/14* (2013.01)

(58) Field of Classification Search
CPC ..... A61P 25/16; C07D 487/08; C07D 491/08; C07D 498/08; C07D 401/14; C07D 405/14
See application file for complete search history.

(56) References Cited

U.S. PATENT DOCUMENTS

2020/0002323 A1* 1/2020 Cui ...................... C07D 401/14

FOREIGN PATENT DOCUMENTS

| WO | WO 2011/038572 A1 | 4/2011 |
| WO | WO 2014/134772 A1 | 9/2014 |
| WO | WO 2015/113452 A1 | 8/2015 |
| WO | WO 2016/036586 A1 | 3/2016 |
| WO | WO 2017/012576 A1 | 1/2017 |

* cited by examiner

*Primary Examiner* — Mark L Shibuya
*Assistant Examiner* — Ebenezer O Sackey
(74) *Attorney, Agent, or Firm* — Robert H. Brink; Duke M. Fitch; Edward R. Gimmi

(57) ABSTRACT

Provided are novel compounds that inhibit LRRK2 kinase activity, processes for their preparation, compositions containing them and their use in the treatment of or prevention of diseases associated with or characterized by LRRK2 kinase activity, for example Parkinson's disease, Alzheimer's disease and amyotrophic lateral sclerosis (ALS).

18 Claims, No Drawings
Specification includes a Sequence Listing.

COMPOUNDS

This application is a 371 of International Application No. PCT/CN2018/073729, filed Jan. 23, 2018, which claims the benefit of International Application No. PCT/CN2017/072601, filed Jan. 25, 2017, which are incorporated herein in their entireties.

FIELD OF THE INVENTION

The present invention relates to novel compounds that inhibit LRRK2 kinase activity, processes for their preparation, compositions containing them and their use in the treatment of diseases associated with or characterized by LRRK2 kinase activity, for example, Parkinson's disease, Alzheimer's disease and amyotrophic lateral sclerosis (ALS).

BACKGROUND OF THE INVENTION

Parkinson's disease (PD) is a neurodegenerative disorder characterized by selective degeneration and cell death of dopaminergic neurons in the substantia nigra region of the brain. Parkinson's disease was generally considered to be sporadic and of unknown etiology, but, in the last 15 years, there has been an important development of the understanding of the genetic basis of this disease and associated pathogenic mechanisms. One area of the development is the understanding of leucine rich repeat kinase 2 (LRRK2) protein. A number of mis-sense mutations in the LRRK2 gene have been strongly linked with autosomal dominant Parkinson's disease in familial studies (See WO2006068492 and WO2006045392; Trinh and Farrer 2013, Nature Reviews in Neurology 9: 445-454; Paisan-Ruiz et al., 2013, J. Parkinson's Disease 3: 85-103). The G2019S mutation in LRRK2 is the most frequent mis-sense mutation and is associated with a clinical phenotype that closely resembles sporadic Parkinson's disease. The LRRK2 G2019S mutation is also present in approximately 1.5% of sporadic Parkinson's disease cases (See Gilks et al., 2005, Lancet, 365: 415-416). In addition to the known pathogenic coding mutations in LRRK2, additional amino acid coding variants of LRRK2 have been identified that are also associated with risk of developing Parkinson's disease (See Ross et al., 2011 Lancet Neurology 10: 898-908). Furthermore, genome-wide association studies (GWAS) have identified LRRK2 as a Parkinson's disease susceptibility locus, which indicates that LRRK2 may be also relevant to sporadic Parkinson's disease cases without mutations that cause amino acid substitutions in the LRRK2 protein. (See Satake et al., 2009 Nature Genetics 41:1303-1307; Simon-Sanchez et al 2009 Nature Genetics 41: 1308-1312)

LRRK2 is a member of the ROCO protein family and all members of this family share five conserved domains. The most common pathogenic mutation G2019S occurs in the highly conserved kinase domain of LRRK2. This mutation confers an increase in the LRRK2 kinase activity in in vitro enzyme assays of recombinant LRRK2 proteins (See Jaleel et al., 2007, Biochem J, 405: 307-317) and in LRRK2 proteins purified from G2019S PD patient-derived cells (See Dzamko et al., 2010 Biochem. J. 430: 405-413). A less frequent LRRK2 pathogenic mutation that confers amino acid substitution at a different residue, R1441, has also been shown to elevate LRRK2 kinase activity by decreasing the rate of GTP hydrolysis by the GTPase domain of LRRK2 (See Guo et al., 2007 Exp Cell Res. 313: 3658-3670; West et al., 2007 Hum. Mol Gen. 16: 223-232). Moreover, phosphorylation of Rab protein physiologic substrates of LRRK2 has been shown to be increased by a range of Parkinson's disease pathogenic mutations of LRRK2 (See Steger et al., 2016 eLife 5 e12813). Therefore, the evidence indicates that the kinase and GTPase activities of LRRK2 are important for pathogenesis, and that the LRRK2 kinase domain may regulate overall LRRK2 function (See Cookson, 2010 Nat. Rev. Neurosci. 11: 791-797).

There is evidence to show that the increased LRRK2 kinase activity is associated with neuronal toxicity in cell culture models (See Smith et al., 2006 Nature Neuroscience 9: 1231-1233) and kinase inhibitor compounds protect against LRRK2-mediated cell death (See Lee et al., 2010 Nat. Med. 16: 998-1000). LRRK2 has also been reported to act as a negative regulator of microglial-mediated clearance of alpha-synuclein (See Maekawa et al., 2016 BMC Neuroscience 17:77), suggesting a possible utility of LRRK2 inhibitors in promoting clearance of neurotoxic forms of alpha-synuclein in the treatment of Parkinson's disease.

Induced pluripotent stem cells (iPSCs) derived from LRRK2 G2019S Parkinson's disease patients have been found to exhibit defects in neurite outgrowth and increased susceptibility to rotenone, that may be ameliorated by either genetic correction of the G2019S mutation or treatment of cells with small molecule inhibitors of LRRK2 kinase activity (See Reinhardt et al., 2013 Cell Stem Cell 12: 354-367). Mitochondrial DNA damage has been reported as a molecular marker of vulnerable dopamine neurons in substantia nigra of postmortem Parkinson's disease specimens (See Sanders et al 2014 Neurobiol. Dis. 70: 214-223). Increased levels of such mitochondrial DNA damage associated with LRRK2 G2019S mutation in iSPCs is blocked by genetic correction of the G2019S mutation (See Sanders et al., 2014 Neurobiol. Dis. 62: 381-386).

Additional evidence links LRRK2 function and dysfunction with autophagy-lysosomal pathways (See Manzoni and Lewis, 2013 Faseb J. 27:3234-3429). LRRK2 proteins confer defects in chaperone-mediated autophagy that negatively impact the ability of cells to degrade alpha-synuclein (Orenstein et al., 2013 Nature Neurosci. 16 394-406). In other cell models, selective LRRK2 inhibitors have been shown to stimulate macroautophagy (See Manzoni et al., 2013 BBA Mol. Cell Res. 1833: 2900-2910). These data suggest that small molecule inhibitors of LRRK2 kinase activity may have utility in the treatment of diseases characterized by defects in cellular proteostasis that result from aberrant autophagy/lysosomal degradation pathways including forms of Parkinson's disease associated with GBA mutations (See Swan and Saunders-Pullman 2013 Curr. Neurol. Neurosci Rep. 13: 368), other alpha-synucleinopathies, tauopathies, Alzheimer's disease (See Li et al., 2010 Neurodegen. Dis. 7: 265-271) and other neurodegenerative diseases (See Nixon 2013 Nat. Med. 19: 983-997) and Gaucher disease (See Westbroek et al., 2011 Trends. Mol. Med. 17: 485-493). As promoters of autophagy, small molecule inhibitors of LRRK2 kinase may also have utility in treatment of other diseases including diabetes, obesity, motor neuron disease, epilepsy and some cancers (See Rubinsztein et al., 2012 Nat. Rev. Drug Discovery 11: 709-730), pulmonary diseases such as chronic obstructive pulmonary disease and idiopathic pulmonary fibrosis (See Araya et al., 2013 Intern. Med. 52: 2295-2303) and autoimmune diseases such as systemic lupus erythematosus (See Martinez et al., 2016 Nature 533: 115-119). As promoters of autophagy and phagocytic processes, small molecule inhibitors of LRRK2 kinase may also have utility in augmenting host responses in treatment of a range of intracellular bacterial infections, parasitic infections and viral infections, including diseases such as tuberculosis (See Rubinsztein et al., 2012 Nat. Rev. Drug Discovery 11: 709-730; Araya et al., 2013 Intern. Med. 52: 2295-2303; Gutierrez, Biochemical Society Conference; Leucine rich repeat kinase 2: ten years along the road to therapeutic intervention, Henley Business School, UK 12 Jul. 2016), HIV, West Nile Virus and chikungunya virus (see Shoji-Kawata et al., 2013 Nature 494: 201-206). LRRK2 inhibitors may have utility in treatment of such diseases alone, or in combination with drugs that directly target the infectious agent. Further, significantly elevated levels of LRRK2 mRNA have also been observed in fibroblasts of Niemann-Pick Type C (NPC) disease patients compared with fibroblasts of normal subjects, which indicates that aberrant LRRK2 function may play a role in lysosomal disorders (See Reddy et al., 2006 PLOS One 1 (1):e19 doi: 10.1371/journal.pone.0000019—supporting information Dataset S1). This observation suggests that LRRK2 inhibitors may have utility for treatment of NPC.

The PD-associated G2019S mutant form of LRRK2 has also been reported to enhance phosphorylation of tubulin-associated Tau (See Kawakami et al., 2012 PLoS ONE 7: e30834, doi 10.1371), and disease models have been proposed in which LRRK2 acts upstream of the pathogenic effects of Tau and alpha-synuclein (See Taymans & Cookson, 2010, BioEssays 32: 227-235). In support of this, LRRK2 expression has been associated with increased aggregation of insoluble Tau, and increased Tau phosphorylation, in a transgenic mouse model (See Bailey et al., 2013 Acta Neuropath. 126:809-827). Over-expression of the PD pathogenic mutant protein LRRK2 R1441G is reported to cause symptoms of Parkinson's disease and hyperphosphorylation of Tau in transgenic mouse models (See Li, Y. et al. 2009, Nature Neuroscience 12: 826-828). Therefore, these data suggest that LRRK2 inhibitors of kinase catalytic activity may be useful for the treatment of tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) (See Goedert, M and Jakes, R (2005) Biochemica et Biophysica Acta 1739, 240-250). In addition, LRRK2 inhibitors may have utility in treatment of other diseases characterized by diminished dopamine levels such as withdrawal symptoms/relapse associated with drug addiction (See Rothman et al., 2008, Prog. Brain Res, 172: 385).

Other studies have also shown that overexpression of the G2019S mutant form of LRRK2 confers defects in subventricular zone (SVZ) neuroprogenitor cell proliferation and migration in transgenic mouse models (See Winner et al., 2011 Neurobiol. Dis. 41: 706-716) and reduces neurite length and branching cell culture models (See Dachsel et al., 2010 Parkinsonism & Related Disorders 16: 650-655). Moreover, it was reported that agents that promote SVZ neuroprogenitor cell proliferation and migration also improve neurological outcomes following ischemic injury in rodent models of stroke (See Zhang et al., 2010 J. Neurosci. Res. 88: 3275-3281). These findings suggest that compounds that inhibit aberrant activity of LRRK2 may have utility for the treatments designed to stimulate restoration of CNS functions following neuronal injury, such as ischemic stroke, traumatic brain injury, spinal cord injury.

Mutations in LRRK2 have also been identified that are clinically associated with the transition from mild cognitive impairment (MCI) to Alzheimer's disease (See WO2007149798). These data suggest that inhibitors of LRRK2 kinase activity may be useful for the treatment diseases such as Alzheimer's disease, other dementias and related neurodegenerative disorders.

Aberrant regulation of normal LRRK2 proteins is also observed in some disease tissues and models of disease. Normal mechanisms of translational control of LRRK2 by miR-205 are perturbed in some sporadic PD cases, where significant decreases in miR-205 levels in PD brain samples concur with elevated LRRK2 protein levels in those samples (See Cho et al., (2013) Hum. Mol. Gen. 22: 608-620). Therefore, LRRK2 inhibitors may be used in treatment of sporadic PD patients who have elevated levels of normal LRRK2 proteins.

In an experimental model of Parkinson's disease in marmosets, an elevation of LRRK2 mRNA is observed in a manner that correlates with the level of L-Dopa induced dyskinesia (See Hurley, M. J et al., 2007 Eur. J. Neurosci. 26: 171-177). This suggests that LRRK2 inhibitors may have a utility in amelioration of such dyskinesias.

Significantly elevated levels of LRRK2 mRNA have been reported in ALS patient muscle biopsy samples (See Shtilbans et al., 2011 Amyotrophic Lateral Sclerosis 12: 250-256) It is suggested that elevated levels of LRRK2 kinase activity may be a characteristic feature of ALS. Therefore, this observation indicated that LRRK2 inhibitor may have utility for treatment of ALS.

There is also evidence indicating that LRRK2 kinase activity may play a role in mediating microglial proinflammatory responses (See Moehle et al., 2012, J. Neuroscience 32: 1602-1611). This observation suggests a possible utility of LRRK2 inhibitors for treatment of aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury. Some evidence also indicates that LRRK2 plays a role in regulating neuronal progenitor differentiation in vitro (See Milosevic, J. et al., 2009 Mol. Neurodegen. 4: 25). This evidence suggests that inhibitors of LRRK2 may have a utility in production of neuronal progenitor cells in vitro for consequent therapeutic application in cell based-treatment of CNS disorders.

It has been reported that Parkinson's disease patients bearing LRRK2 G2019S mutation display increased frequency of non-skin cancers, including renal, breast, lung, prostate cancers as well as acute myelogenous leukemia (AML). Since there is evidence to show that G2019S mutation in LRRK2 increases catalytic activity of the LRRK2 kinase domain, small molecule inhibitors of LRRK2 may have a utility in treatment of cancers, for example kidney cancer, breast cancer, lung cancer, prostate cancer (e.g. solid tumors) and blood cancer (See. AML; Saunders-Pullman et al., 2010, Movement Disorders, 25:2536-2541; Inzelberg et al., 2012 Neurology 78: 781-786). Amplification and over-expression of LRRK2 has also been reported in papillary renal and thyroid carcinomas, where co-operativity between LRRK2 and the MET oncogene may promote tumor cell growth and survival (See Looyenga et al., 2011 PNAS 108: 1439-1444.)

Some studies suggested that genetic association of common LRRK2 variants with susceptibility to ankylosing spondylitis (See Danoy P, et al., 2010. PLoS Genet.; 6(12): e1001195; and leprosy infection. (See Zhang F R, et al. 2009, N Engl J Med. 361:2609-18.) These findings suggest that inhibitors of LRRK2 may have a utility in the treatment of ankylosing spondylitis and leprosy infection.

Meta-analysis of three genome wide associated scans for Crohn's disease identified a number of loci associated with the disease, including the locus containing the LRRK2 gene (See Barrett et al., 2008, Nature Genetics, 40: 955-962). Evidence has also emerged that LRRK2 is an IFN-γ target gene that may be involved in signaling pathways relevant to Crohn's disease pathogenesis (See Gardet et al., 2010, J. Immunology, 185: 5577-5585). These findings suggest that inhibitors of LRRK2 may have utility in the treatment of Crohn's disease.

As an IFN-γ target gene, LRRK2 may also play a role in T cell mechanisms that underlie other diseases of the immune system such as multiple sclerosis and rheumatoid arthritis. Further potential utility of LRRK2 inhibitors comes from the reported finding that B lymphocytes constitute a major population of LRRK2 expressing cells (See Maekawa et al. 2010, BBRC 392: 431-435). This suggests that LRRK2 inhibitors may be effective in treatment of diseases of the immune system for which B cell depletion is, or may be, effective in diseases such as lymphomas, leukemias, multiple sclerosis (See Ray et al., 2011 J. Immunol. 230: 109), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies (See Engel et al., 2011 Pharmacol. Rev. 63: 127-156; Homam et al., 2010 J. Clin. Neuromuscular Disease 12: 91-102).

WO2016036586 and WO2017012576 disclose a series of compounds described as inhibitors of LRRK2 kinase and their use in the treatment of diseases, including, inter alia, Parkinson's disease. Unmet needs exist for new treatments that will halt or slow disease progression both in terms of motor (e.g. control of gait dysfunction, freezing, and postural imbalance) and non-motor symptoms (e.g. PD-associated dementia), reducing the need for escalating use of symptomatic medications and associated long-term adverse effects of currently available treatment (e.g. dyskinesia and on/off fluctuations) maintaining independence for longer.

SUMMARY OF THE INVENTION

The present invention provides, in a first aspect, compounds of Formula (I) and salts thereof:

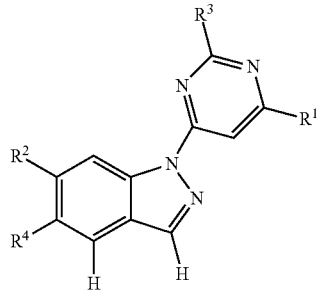

Formula (I)

wherein
$R^1$ is an N-linked 6-9 membered bridged heterocyclyl ring optionally substituted with one, two or three substituents independently selected from the group consisting of
$C_{3-6}$cycloalkyl,
$C_{4-6}$heterocyclyl,
halo,
hydroxyl,
$C_{1-3}$alkyl,
$C_{1-3}$ alkoxyl and
$CO_2R^5$;
wherein $R^5$ is selected from the group consisting of H, methyl, $NH_2$, and $NHCH_3$; wherein each of said $C_{3-6}$cycloalkyl, $C_{4-6}$heterocyclyl, $C_{1-3}$alkyl and $C_{1-3}$ alkoxyl is optionally substituted with one, two or three substituents independently selected from the group consisting of halo, hydroxyl, unsubstituted $C_{1-3}$alkyl and unsubstituted $C_{1-3}$ alkoxyl, and with the proviso that an $C_{3-6}$cycloalkyl or $C_{4-6}$heterocyclyl substituent is only permitted on a substitutable nitrogen atom;
$R^2$ is selected from the group consisting of:
a) 4-7 membered heterocyclyl ring, optionally substituted with one, two or three substituents independently selected from the group consisting of:
$C_{1-3}$alkyl, which alkyl group is optionally substituted with one, two or three substituents independently selected from the group consisting of:
halo,
hydroxyl,
$CO_2H$,
—$CH_2CH_2$— and
$C_{1-3}$alkoxy;
cyano,
halo,
hydroxyl,
—$SO_2CH_3$,
—$COCH_3$, and
—$COCH_2OH$,
wherein when the 4-7 membered heterocyclyl ring contains a substitutable nitrogen atom, the group of substituents also includes a 4-6 membered heterocyclyl ring attached to said substitutable nitrogen atom, which 4-6 membered heterocyclyl ring is optionally substituted with one or two substituents independently selected from the group consisting of
cyano,
halo,
hydroxyl,
$CH_2OH$ and
$C_{3-6}$cycloalkyl, optionally substituted with one or two substituents independently selected from the group consisting of halo, hydroxyl, cyano, $CH_2OH$, unsubstituted $C_{1-3}$alkyl and unsubstituted $C_{1-3}$ alkoxyl;
b) O-linked 4-6 membered heterocyclyl ring, optionally substituted with one or two substituents independently selected from the group consisting of: cyano, hydroxyl, $C_{1-3}$alkyl, $CH_2OH$ and —$CO_2H$;
c) $C_{3-6}$ cycloalkyl optionally substituted with one or two substituents independently selected from the group consisting of cyano, halo, hydroxyl, $C_{1-3}$alkyl, $C_{1-3}$alkoxyl, $CO_2H$ and a 4-6 membered heterocyclyl ring;
d) O-linked $C_{3-6}$ cycloalkyl wherein the cycloalkyl group is optionally substituted with one or two substituents independently selected from the group consisting of cyano, hydroxyl, $C_{1-3}$alkyl, $CH_2OH$ and $CO_2H$;
e) $C_{1-6}$alkoxy optionally substituted by one or two substituents independently selected from the group consisting of halo, hydroxyl, $C_{1-3}$alkyl, $C_{1-3}$ alkoxyl, $CO_2H$ and a 4-6 membered heterocyclyl ring; and
f) C-linked 6-9 membered fused cyclyl ring, optionally having one or two heteroatom ring members independently selected from 0 and N, optionally substituted with one, two or three substituents independently selected from the group consisting of:

C$_{1-3}$alkyl, which alkyl group is optionally substituted with one, two or three substituents independently selected from the group consisting of:
halo,
hydroxyl,
CO$_2$H,
—CH$_2$CH$_2$— and
C$_{1-3}$alkoxy;
cyano,
halo,
hydroxyl,
—SO$_2$CH$_3$,
—COCH$_3$, and
—COCH$_2$OH,
wherein when the C-linked 6-9 membered fused cyclyl ring contains a substitutable nitrogen atom, the group of substituents also includes a 4-6 membered heterocyclyl ring attached to said substitutable nitrogen atom, which 4-6 membered heterocyclyl ring is optionally substituted with one or two substituents independently selected from the group consisting of
cyano,
halo,
hydroxyl,
CH$_2$OH and
C$_{3-6}$cycloalkyl, optionally substituted with one or two substituents independently selected from the group consisting of halo, hydroxyl, cyano, CH$_2$OH, unsubstituted C$_{1-3}$alkyl and unsubstituted C$_{1-3}$alkoxyl;

R$^3$ is selected from the group consisting of halo CN, C$_{1-3}$alkyl, C$_{1-3}$alkoxy, C$_{1-3}$haloalkyl, C$_{1-3}$haloalkoxy and C$_{3-6}$ cycloalkyl; and R$^4$ is selected from the group consisting of H, halo, CN, C$_{1-3}$alkyl, C$_{1-3}$alkoxy, C$_{1-3}$haloalkyl, C$_{1-3}$haloalkoxy and C$_{3-6}$ cycloalkyl.

In a further aspect of the invention, the invention provides a pharmaceutical composition comprising a compound of Formula (I) or a pharmaceutically acceptable salt thereof and a pharmaceutically acceptable carrier.

A further aspect of the invention provides a compound of Formula (I) or a pharmaceutically acceptable salt thereof for use in the treatment or prevention of Parkinson's disease, Alzheimer's disease, or amyotrophic lateral sclerosis (ALS).

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will Fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

A. Definitions

As used herein, "alkyl" refers to a monovalent, saturated hydrocarbon chain having a specified number of carbon atoms. For example, C$_{1-3}$ alkyl refers to an alkyl group having from 1 to 3 carbon atoms. Alkyl groups may be straight or branched. In some embodiments, branched alkyl groups may have one, two, or three branches. Exemplary alkyl groups include, but are not limited to, methyl, ethyl, and propyl (n-propyl and isopropyl).

As used herein, "alkoxy" refers to the group —O-alkyl. For example, C$_{1-6}$ alkoxy groups contain from 1 to 6 carbon atoms. C$_{1-3}$ alkoxy groups contain from 1 to 3 carbon atoms. Exemplary alkoxy groups include, but are not limited to, methoxy, ethoxy, propoxy, butoxyl, pentyloxy, and hexyloxy.

As used herein, "cycloalkyl" refers to a saturated monocyclic hydrocarbon ring having a specified number of carbon atoms. For example, C$_{3-6}$ cycloalkyl contains 3 to 6 carbon atoms as member atoms in the ring. Examples of C$_{3-6}$ cycloalkyl include cyclopropyl, cyclobutyl, cyclopentyl and cyclohexyl.

As used herein, "halogen" refers to fluorine (F), chlorine (Cl), bromine (Br), or iodine (I). "Halo" refers to the halogen radicals: fluoro (—F), chloro (—Cl), bromo (—Br), or iodo (—I).

As used herein, "haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms and which may be the same or different. For example, C$_{1-3}$haloalkyl refers to a C$_{1-3}$alkyl group substituted with one or more halogen atoms. In some embodiments, "haloalkyl" refers to an alkyl group substituted with one or more halogen atoms independently selected from F or Cl. Exemplary haloalkyl groups include, but are not limited to, chloromethyl, bromoethyl, trifluoromethyl, and dichloromethyl.

As used herein, "heterocyclyl" or "herterocyclyl ring" is a monovalent radical derived by removal of a hydrogen atom from a saturated monocyclic ring, which ring consists of ring carbon atoms and 1 or more ring heteroatoms independently selected from nitrogen, oxygen or sulphur. In one embodiment, the ring consists of ring carbon atoms and 1 to 3 ring heteroatoms independently selected from nitrogen, oxygen or sulphur. In one embodiment, the ring-heteroatoms are independently selected from nitrogen or oxygen. The number of ring atoms may be specified. For example, a "4-7 membered heterocyclyl" a heterocyclyl as defined above consisting of 4-7 ring atoms. The term O-linked 4-6 membered heterocyclyl refers to a 4-6 membered heterocyclyl ring as defined above that contains at least one oxygen ring atom through which it is linked to the core. Other ring heteroatoms (nitrogen, oxygen or sulphur) may additionally be present. The term nitrogen containing heterocyclyl refers to heterocyclyl ring as defined above that contains at least one nitrogen ring atom. Other ring heteroatoms (nitrogen, oxygen or sulphur) may additionally be present. The term oxygen containing heterocyclyl should be construed in an analogous manner. Examples of herterocyclyl rings include, but are not limited to, azetidinyl, tetrahydrofuranyl (including, for example, tetrahydrofuran-2-yl and tetrahydrofuran-3-yl), pyrrolidinyl (including, for example, pyrrolidin-1-yl and pyrrolidin-3-yl), piperidinyl (including, for example, piperidin-3-yl and piperidin-4-y), morpholinyl (including, for example, morpholin-2-yl and morpholin-4-yl).

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Examples of substituted heterocyclyl rings rings include, but are not limited to,

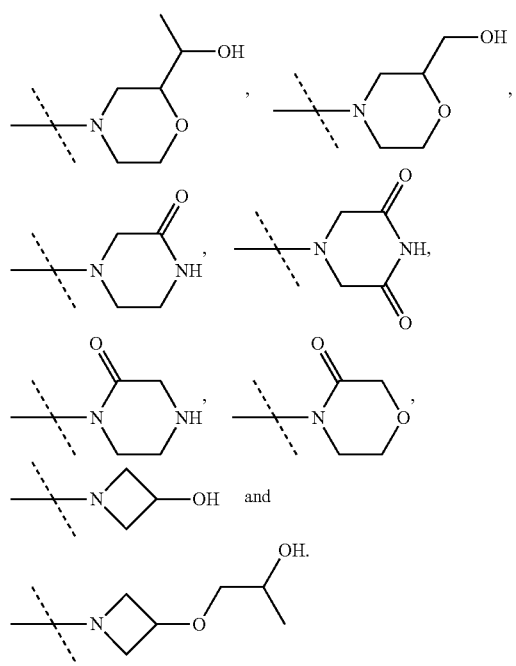

As used herein, "optionally substituted" indicates that a particular group, such as alkyl, heterocyclyl, cycloalkyl,

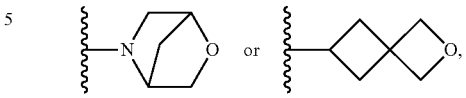

may be unsubstituted, or may be substituted as further defined.

As used herein, the term "bridged heterocyclyl ring" refers to a monovalent radical derived by removal of a hydrogen atom from a bridged ring (a ring in which two non adjacent ring atoms are linked by a bridge containing at least one atom), which consists of carbon atoms and 1 to 2 heteroatoms independently selected from nitrogen and oxygen. The number of atoms in the ring and bridge may be specified. For example, the term 6-9 membered bridged heterocyclyl ring refers to a bridged heterocyclyl ring that has a total of 6 to 9 atoms in the ring plus bridge. The term "N-linked 6-9 membered bridged heterocyclyl ring" refers to a 6-9 membered bridged cyclyl ring as defined above that contains one nitrogen ring atom through which it is linked to the core. Examples of bridged heterocyclyl rings include, but are not limited to,

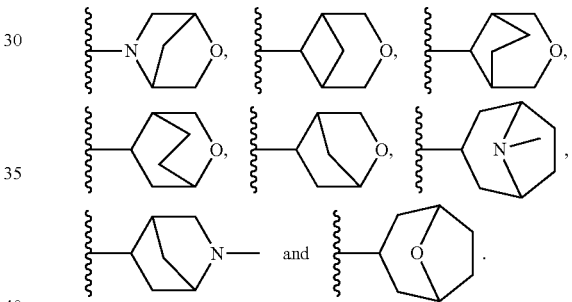

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease. Symptomatic treatment refers to treatment as referred to in point (1), (3) and (5). Disease modifying treatment refers to treatment as defined in point (2) and (4).

As used herein, "prevent", "preventing" or "prevention" means the prophylactic administration of a drug to diminish the likelihood of the onset of or to delay the onset of a disease or biological manifestation thereof.

As used herein, "subject" means a mammalian subject (e.g., dog, cat, horse, cow, sheep, goat, monkey, etc.), and human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically acceptable salt(s)" refers to salt(s) that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, "therapeutically effective amount" in reference to a compound of the invention or other pharmaceutically-active agent means an amount of the compound sufficient to treat or prevent the patient's disease but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical disease of the patient being treated; the medical history of the patient to be treated; the duration of the treatment; the nature of concurrent therapy; the desired therapeutic effect; and like factors, but can nevertheless be routinely determined by the skilled artisan.

B. Compounds

This invention provides, in a first aspect, a compound of Formula (I) and salts thereof:

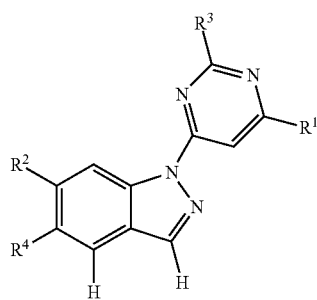

Formula (I)

wherein
$R^1$ is an N-linked 6-9 membered bridged heterocyclyl ring optionally substituted with one, two or three substituents independently selected from the group consisting of
$C_{3-6}$cycloalkyl,
$C_{4-6}$heterocyclyl,
halo,
hydroxyl,
$C_{1-3}$ alkoxyl and
—$CO_2R^5$;
wherein $R^5$ is selected from the group consisting of H, methyl, $NH_2$, and $NHCH_3$; wherein each of said $C_{3-6}$cycloalkyl, $C_{4-6}$heterocyclyl, $C_{1-3}$alkyl and $C_{1-3}$ alkoxyl is optionally substituted with one, two or three substituents independently selected from the group consisting of halo, hydroxyl, unsubstituted $C_{1-3}$alkyl and unsubstituted $C_{1-3}$ alkoxyl, and with the proviso that an $C_{3-6}$cycloalkyl or $C_{4-6}$heterocyclyl substituent is only permitted on a substitutable nitrogen atom;

$R^2$ is selected from the group consisting of:
a) 4-7 membered heterocyclyl ring, optionally substituted with one, two or three substituents independently selected from the group consisting of:
$C_{1-3}$alkyl, which alkyl group is optionally substituted with one, two or three substituents independently selected from the group consisting of:
halo,
hydroxyl,
$CO_2H$,
—$CH_2CH_2$— and
$C_{1-3}$alkoxy;
cyano,
halo,
hydroxyl,
—$SO_2CH_3$,
—$COCH_3$, and
—$COCH_2OH$,
wherein when the 4-7 membered heterocyclyl ring contains a substitutable nitrogen atom, the group of substituents also includes a 4-6 membered heterocyclyl ring attached to said substitutable nitrogen atom, which 4-6 membered heterocyclyl ring is optionally substituted with one or two substituents independently selected from the group consisting of
cyano,
halo,
hydroxyl,
$C_{1-3}$alkyl,
$C_{1-3}$alkoxyl,
$CH_2OH$ and
$C_{3-6}$cycloalkyl, optionally substituted with one or two substituents independently selected from the group consisting of halo, hydroxyl, cyano, $CH_2OH$, unsubstituted $C_{1-3}$alkyl and unsubstituted $C_{1-3}$alkoxyl;
b) O-linked 4-6 membered heterocyclyl ring, optionally substituted with one or two substituents independently selected from the group consisting of: cyano, hydroxyl, $C_{1-3}$alkyl, $C_{1-3}$alkoxyl, $CH_2OH$ and —$CO_2H$;
c) $C_{3-6}$ cycloalkyl optionally substituted with one or two substituents independently selected from the group consisting of cyano, halo, hydroxyl, $C_{1-3}$alkyl, $C_{1-3}$alkoxyl, $CO_2H$ and a 4-6 membered heterocyclyl ring;
d) O-linked $C_{3-6}$ cycloalkyl wherein the cycloalkyl group is optionally substituted with one or two substituents independently selected from the group consisting of cyano, hydroxyl, $C_{1-3}$alkyl, $C_{1-3}$alkoxyl, $CH_2OH$ and $CO_2H$;
e) $C_{1-6}$alkoxy optionally substituted by one or two substituents independently selected from the group consisting of halo, hydroxyl, $C_{1-3}$alkyl, $C_{1-3}$alkoxyl, $CO_2H$ and a 4-6 membered heterocyclyl ring; and
f) C-linked 6-9 membered fused cyclyl ring, optionally having one or two heteroatom ring members independently selected from 0 and N, optionally substituted with one, two or three substituents independently selected from the group consisting of:
$C_{1-3}$alkyl, which alkyl group is optionally substituted with one, two or three substituents independently selected from the group consisting of:

halo,
hydroxyl,
CO$_2$H,
—CH$_2$CH$_2$— and
C$_{1-3}$alkoxy;
cyano,
halo,
hydroxyl,
—SO$_2$CH$_3$,
—COCH$_3$, and
—COCH$_2$OH,
wherein when the C-linked 6-9 membered fused cyclyl ring contains a substitutable nitrogen atom, the group of substituents also includes a 4-6 membered heterocyclyl ring attached to said substitutable nitrogen atom, which 4-6 membered heterocyclyl ring is optionally substituted with one or two substituents independently selected from the group consisting of
cyano,
halo,
hydroxyl,
CH$_2$OH and
C$_{3-6}$cycloalkyl, optionally substituted with one or two substituents independently selected from the group consisting of halo, hydroxyl, cyano, CH$_2$OH, unsubstituted C$_{1-3}$alkyl and unsubstituted C$_{1-3}$alkoxyl;

R$^3$ is selected from the group consisting of halo CN, C$_{1-3}$ alkyl, C$_{1-3}$ alkoxy, C$_{1-3}$haloalkyl, C$_{1-3}$haloalkoxy and C$_{3-6}$ cycloalkyl; and R$^4$ is selected from the group consisting of H, halo, CN, C$_{1-3}$alkyl, C$_{1-3}$ alkoxy, C$_{1-3}$haloalkyl, C$_{1-3}$haloalkoxy and C$_{3-6}$ cycloalkyl.

In one embodiment, R$^1$ is an N-linked 7-9 membered bridged heterocyclyl ring optionally substituted with one, two or three substituents independently selected from the group consisting of: C$_{4-6}$heterocyclyl, halo, hydroxyl, C$_{1-3}$alkyl, C$_{1-3}$alkoxyl and —CO$_2$R$^5$, wherein R$^5$ is selected from the group consisting of H, methyl, NH$_2$, and NHCH$_3$, with the proviso that a C$_{4-6}$heterocyclyl substituent is only permitted on a substitutable nitrogen atom.

In one embodiment, R$^1$ is an N-linked 7-9 membered bridged heterocyclyl ring optionally substituted with one, two or three substituents independently selected from the group consisting of: oxetanyl, halo, hydroxyl, C$_{1-3}$alkyl, C$_{1-3}$alkoxyl and —CO$_2$R$^5$, wherein R$^5$ is selected from the group consisting of H, methyl, NH$_2$, and NHCH$_3$, with the proviso that an oxetanyl substituent is only permitted on a substitutable nitrogen atom.

In one embodiment, R$^1$ is a ring selected from: an N-linked azabicycloheptanyl ring, an N-linked azabicyclooctanyl ring, an N-linked azabicyclononanyl ring, an N-linked diazabicycloheptanyl ring, an N-linked diazabicyclooctanyl ring, an N-linked diazabicyclononanyl ring, an N-linked oxazabicycloheptanyl ring, an N-linked oxazabicyclooctanyl ring, an N-linked oxazabicyclononanyl ring, an N-linked dioxazaheptanyl ring, an N-linked dioxazaoctanyl ring, an N-linked dioxazanonanyl ring, an N-linked oxadiazaheptanyl ring, an N-linked oxadiazaoctanyl ring and an N-linked oxadiazanonanyl ring, which ring is optionally substituted with one, two or three substituents independently selected from the group consisting of: C$_{4-6}$heterocyclyl, halo, hydroxyl, C$_{1-3}$alkyl, C$_{1-3}$ alkoxyl and —CO$_2$R$^5$, wherein R$^5$ is selected from the group consisting of H, methyl, NH$_2$, and NHCH$_3$, with the proviso that a C$_{4-6}$heterocyclyl substituent is only permitted on a substitutable nitrogen atom.

In one embodiment, R$^1$ is a ring selected from: an N-linked azabicycloheptanyl ring, an N-linked azabicyclooctanyl ring, an N-linked azabicyclononanyl ring, an N-linked diazabicycloheptanyl ring, an N-linked diazabicyclooctanyl ring, an N-linked diazabicyclononanyl ring, an N-linked oxazabicycloheptanyl ring, an N-linked oxazabicyclooctanyl ring, an N-linked oxazabicyclononanyl ring, an N-linked dioxazaheptanyl ring, an N-linked dioxazaoctanyl ring, an N-linked dioxazanonanyl ring, an N-linked oxadiazaheptanyl ring, an N-linked oxadiazaoctanyl ring and an N-linked oxadiazanonanyl ring, which ring is optionally substituted with one, two or three substituents independently selected from the group consisting of: oxetanyl, halo, hydroxyl, C$_{1-3}$alkyl, C$_{1-3}$ alkoxyl and —CO$_2$R$^5$, wherein R$^5$ is selected from the group consisting of H, methyl, NH$_2$, and NHCH$_3$, with the proviso that an oxetanyl substituent is only permitted on a substitutable nitrogen atom.

In another embodiment, R$^1$ is a ring selected from the group consisting of 2-oxa-5-azabicyclo[2.2.1]heptan-5-yl. 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl, 3,7-dioxa-9-azabicyclo[3.3.1]nonan-9-yl, 2-azabicyclo[2.2.1]heptan-2-yl and 3-azabicyclo[3.1.1]heptan-3-yl, which ring is optionally substituted with with one, two or three substituents independently selected from the group consisting of: C$_{4-6}$heterocyclyl, halo, hydroxyl, C$_{1-3}$alkyl, C$_{1-3}$ alkoxyl and —CO$_2$R$^5$, wherein R$^5$ is selected from the group consisting of H, methyl, NH$_2$, and NHCH$_3$, with the proviso that a C$_{4-6}$heterocyclyl substituent is only permitted on a substitutable nitrogen atom.

In another embodiment, R$^1$ is a ring selected from the group consisting of 2-oxa-5-azabicyclo[2.2.1]heptan-5-yl. 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl, 3,7-dioxa-9-azabicyclo[3.3.1]nonan-9-yl, 2-azabicyclo[2.2.1]heptan-2-yl and 3-azabicyclo[3.1.1]heptan-3-yl, which ring is optionally substituted with with one, two or three substituents independently selected from the group consisting of: oxetanyl, halo, hydroxyl, C$_{1-3}$alkyl, C$_{1-3}$ alkoxyl and —CO$_2$R$^5$, wherein R$^5$ is selected from the group consisting of H, methyl, NH$_2$, and NHCH$_3$, with the proviso that an oxetanyl substituent is only permitted on a substitutable nitrogen atom.

In one embodiment, R$^1$ is an N-linked 7-9 membered bridged heterocyclyl ring optionally substituted with one substituent selected from the group consisting of: C$_{4-6}$heterocyclyl, halo, hydroxyl, C$_{1-3}$alkyl, alkoxyl and —CO$_2$R$^5$, wherein R$^5$ is selected from the group consisting of H, methyl, NH$_2$, and NHCH$_3$, with the proviso that a C$_{4-6}$heterocyclyl substituent is only permitted on a substitutable nitrogen atom.

In one embodiment, R$^1$ is an N-linked 7-9 membered bridged heterocyclyl ring optionally substituted with one substituent selected from the group consisting of: oxetanyl, halo, hydroxyl, C$_{1-3}$alkyl, C$_{1-3}$ alkoxyl and —CO$_2$R$^5$, wherein R$^5$ is selected from the group consisting of H, methyl, NH$_2$, and NHCH$_3$, with the proviso that an oxetanyl substituent is only permitted on a substitutable nitrogen atom.

In one embodiment, R$^1$ is a ring selected from: an N-linked azabicycloheptanyl ring, an N-linked azabicyclooctanyl ring, an N-linked azabicyclononanyl ring, an N-linked diazabicycloheptanyl ring, an N-linked diazabicyclooctanyl ring, an N-linked diazabicyclononanyl ring, an N-linked oxazabicycloheptanyl ring, an N-linked oxazabicyclooctanyl ring, an N-linked oxazabicyclononanyl ring, an N-linked dioxazaheptanyl ring, an N-linked dioxazaoctanyl ring, an N-linked dioxazanonanyl ring, an N-linked oxadiazaheptanyl ring, an N-linked oxadiazaoctanyl ring and an N-linked oxadiazanonanyl ring, which ring is optionally substituted with one substituent selected from the group consisting of: $C_{4-6}$heterocyclyl, halo, hydroxyl, $C_{1-3}$alkyl, $C_{1-3}$ alkoxyl and —$CO_2R^5$, wherein $R^5$ is selected from the group consisting of H, methyl, $NH_2$, and $NHCH_3$, with the proviso that a $C_{4-6}$heterocyclyl substituent is only permitted on a substitutable nitrogen atom.

In one embodiment, $R^1$ is a ring selected from: an N-linked azabicycloheptanyl ring, an N-linked azabicyclooctanyl ring, an N-linked azabicyclononanyl ring, an N-linked diazabicycloheptanyl ring, an N-linked diazabicyclooctanyl ring, an N-linked diazabicyclononanyl ring, an N-linked oxazabicycloheptanyl ring, an N-linked oxazabicyclooctanyl ring, an N-linked oxazabicyclononanyl ring, an N-linked dioxazaheptanyl ring, an N-linked dioxazaoctanyl ring, an N-linked dioxazanonanyl ring, an N-linked oxadiazaheptanyl ring, an N-linked oxadiazaoctanyl ring and an N-linked oxadiazanonanyl ring, which ring is optionally substituted with one substituent selected from the group consisting of: oxetanyl, halo, hydroxyl, $C_{1-3}$alkyl, $C_{1-3}$ alkoxyl and —$CO_2R^5$, wherein $R^5$ is selected from the group consisting of H, methyl, $NH_2$, and $NHCH_3$, with the proviso that an oxetanyl substituent is only permitted on a substitutable nitrogen atom.

In another embodiment, $R^1$ is a ring selected from the group consisting of 2-oxa-5-azabicyclo[2.2.1]heptan-5-yl. 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl, 3,7-dioxa-9-azabicyclo[3.3.1]nonan-9-yl, 2-azabicyclo[2.2.1]heptan-2-yl and 3-azabicyclo[3.1.1]heptan-3-yl, which ring is optionally substituted with one substituent selected from the group consisting of: $C_{4-6}$heterocyclyl, halo, hydroxyl, $C_{1-3}$alkyl, $C_{1-3}$alkoxyl and —$CO_2R^5$, wherein $R^5$ is selected from the group consisting of H, methyl, $NH_2$, and $NHCH_3$, with the proviso that a $C_{4-6}$heterocyclyl substituent is only permitted on a substitutable nitrogen atom.

In another embodiment, $R^1$ is a ring selected from the group consisting of 2-oxa-5-azabicyclo[2.2.1]heptan-5-yl. 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl, 3,7-dioxa-9-azabicyclo[3.3.1]nonan-9-yl, 2-azabicyclo[2.2.1]heptan-2-yl and 3-azabicyclo[3.1.1]heptan-3-yl, which ring is optionally substituted with one substituent selected from the group consisting of: oxetanyl, halo, hydroxyl, $C_{1-3}$alkyl, $C_{1-3}$alkoxyl and —$CO_2R^5$, wherein $R^5$ is selected from the group consisting of H, methyl, $NH_2$, and $NHCH_3$, with the proviso that an oxetanyl substituent is only permitted on a substitutable nitrogen atom.

In one embodiment, $R^1$ is an N-linked 7-9 membered bridged heterocyclyl ring optionally substituted with one substituent selected from the group consisting of oxetanyl and —$CO_2H$ and with the proviso that an oxetanyl substituent is only permitted on a substitutable nitrogen atom.

In one embodiment, $R^1$ is a ring selected from: an N-linked azabicycloheptanyl ring, an N-linked azabicyclooctanyl ring, an N-linked azabicyclononanyl ring, an N-linked diazabicycloheptanyl ring, an N-linked diazabicyclooctanyl ring, an N-linked diazabicyclononanyl ring, an N-linked oxazabicycloheptanyl ring, an N-linked oxazabicyclooctanyl ring, an N-linked oxazabicyclononanyl ring, an N-linked dioxazaheptanyl ring, an N-linked dioxazaoctanyl ring, an N-linked dioxazanonanyl ring, an N-linked oxadiazaheptanyl ring, an N-linked oxadiazaoctanyl ring and an N-linked oxadiazanonanyl ring, which ring is optionally substituted with one substituent selected from the group consisting of oxetanyl and —$CO_2H$ and with the proviso that an oxetanyl substituent is only permitted on a substitutable nitrogen atom.

In another embodiment, R' is a ring selected from the group consisting of 2-oxa-5-azabicyclo[2.2.1]heptan-5-yl. 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl, 3,7-dioxa-9-azabicyclo[3.3.1]nonan-9-yl, 2-azabicyclo[2.2.1]heptan-2-yl and 3-azabicyclo[3.1.1]heptan-3-yl, which ring is optionally substituted with one substituent selected from the group consisting of oxetanyl and —$CO_2H$ and with the proviso that an oxetanyl substituent is only permitted on a substitutable nitrogen atom.

In one embodiment, R1 is selected from the group consisting of: 2-oxa-5-azabicyclo[2.2.1]heptan-5-yl, 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl, 3,7-dioxa-9-azabicyclo[3.3.1]nonan-9-yl, 5-(oxetan-3-yl)-2,5-diazabicyclo[2.2.1]heptan-2-yl, 6-carboxylic acid-3-azabicyclo[3.1.1]heptan-3-yl and 5-carboxylic acid-2-azabicyclo[2.2.1]heptan-2-yl.

In another embodiment, $R^1$ is an unsubstituted N-linked 7-9 membered bridged heterocyclyl ring.

In another embodiment, $R^1$ is an unsubstituted ring selected from: an N-linked azabicycloheptanyl ring, an N-linked azabicyclooctanyl ring, an N-linked azabicyclononanyl ring, an N-linked diazabicycloheptanyl ring, an N-linked diazabicyclooctanyl ring, an N-linked diazabicyclononanyl ring, an N-linked oxazabicycloheptanyl ring, an N-linked oxazabicyclooctanyl ring, an N-linked oxazabicyclononanyl ring, an N-linked dioxazaheptanyl ring, an N-linked dioxazaoctanyl ring, an N-linked dioxazanonanyl ring, an N-linked oxadiazaheptanyl ring, an N-linked oxadiazaoctanyl ring and an N-linked oxadiazanonanyl ring.

In another embodiment, $R^1$ is 2-oxa-5-azabicyclo[2.2.1]heptan-5-yl. 2,5-diazabicyclo[2.2.1]heptan-2-yl, 8-oxa-3-azabicyclo[3.2.1]octan-3-yl, 6-oxa-3-azabicyclo[3.1.1]heptan-3-yl, 3-oxa-8-azabicyclo[3.2.1]octan-8-yl and 3,7-dioxa-9-azabicyclo[3.3.1]nonan-9-yl.

In one embodiment, $R^2$ is selected from the group consisting of:
5-6 membered heterocyclyl ring optionally substituted with one, two or three substituents independently selected from the group consisting of:
$C_{1-3}$alkyl, which alkyl group is optionally substituted with one halo, hydroxyl or $C_{1-3}$alkoxy group,
halo,
hydroxyl,
—SO2CH3,
—COCH3, and
—COCH2OH,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom;
—O-4-6 membered heterocyclyl ring wherein the heterocyclyl ring is optionally substituted with one or two $C_{1-3}$alkyl groups which may be the same or different;

$C_{3-6}$ cycloalkyl optionally substituted with one or two substituents independently selected from the group consisting of hydroxyl and $C_{1-3}$alkyl;

—O—$C_{3-6}$ cycloalkyl wherein the cycloalkyl group is optionally substituted with one or two substituents independently selected from the group consisting of hydroxyl and $C_{1-3}$alkyl; and $C_{1-6}$alkoxy.

In one embodiment, $R^2$ is selected from the group consisting of:

5-6 membered heterocyclyl ring optionally substituted with one, two or three substituents independently selected from the group consisting of:

$C_{1-3}$alkyl, which alkyl group is optionally substituted with one halo, hydroxyl or $C_{1-3}$alkoxy group, halo, hydroxyl,

—SO2CH3,

—COCH3, and

—COCH2OH, wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom;

—O— 4-6 membered heterocyclyl ring wherein the heterocyclyl ring is optionally substituted with one or two $C_{1-3}$alkyl groups which may be the same or different;

$C_{3-6}$ cycloalkyl optionally substituted with one or two substituents independently selected from the group consisting of hydroxyl and $C_{1-3}$alkyl;

—O— $C_{3-6}$ cycloalkyl wherein the cycloalkyl group is optionally substituted with one or two substituents independently selected from the group consisting of hydroxyl and $C_{1-3}$alkyl.

In one embodiment, $R^2$ is selected from the group consisting of:

5-6 membered heterocyclyl ring optionally substituted with one, two or three substituents independently selected from the group consisting of:

$C_{1-3}$alkyl, which alkyl group is optionally substituted with one halo, hydroxyl or $C_{1-3}$alkoxy group, halo, hydroxyl, and

—COCH$_2$OH, wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom;

—O— 4-6 membered heterocyclyl ring;

$C_{3-6}$ cycloalkyl optionally substituted with one or two substituents independently selected from the group consisting of hydroxyl and $C_{1-3}$alkyl; and —O—$C_{3-6}$ cycloalkyl wherein the cycloalkyl group is optionally substituted with one or two substituents independently selected from the group consisting of hydroxyl and $C_{1-3}$alkyl.

In one embodiment, $R^2$ is a 4-7 membered heterocyclyl ring optionally substituted with one, two or three substituents independently selected from the group consisting of:

$C_{1-3}$alkyl, which alkyl group is optionally substituted with one, two or three substituents independently selected from the group consisting of: halo, hydroxyl, $CO_2H$, —$CH_2CH_2$— and $C_{1-3}$alkoxy, cyano, halo, hydroxyl,

—SO2CH3,

—COCH3, and

—COCH2OH, wherein when the 4-7 membered heterocyclyl ring contains a substitutable nitrogen atom, the group of substituents also includes a 4-6 membered heterocyclyl ring which 4-6 membered heterocyclyl ring is optionally substituted with one or two substituents independently selected from the group consisting of: cyano, halo, hydroxyl, $C_{1-3}$alkyl, $C_{1-3}$alkoxyl and $CH_2OH$, with the proviso that the 4-6 membered heterocyclyl ring is attached to said substitutable nitrogen atom.

In one embodiment, $R^2$ is a 5-6 membered heterocyclyl ring optionally substituted with one, two or three substituents independently selected from the group consisting of:

$C_{1-3}$alkyl, which alkyl group is optionally substituted with one halo, hydroxyl or $C_{1-3}$alkoxy group, halo, hydroxyl,

—$SO_2CH_3$,

—$COCH_3$, and

—$COCH_2OH$, wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is a 5-6 membered heterocyclyl ring optionally substituted with one, two or three substituents independently selected from the group consisting of:

$C_{1-3}$alkyl, which alkyl group is optionally substituted with one halo, hydroxyl or $C_{1-3}$alkoxy group, halo, hydroxyl, and

—COCH$_2$OH, wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is a 5-6 membered heterocyclyl ring selected from the group consisting of: piperazinyl, piperidinyl, pyrrolidinyl, tetrahydropyridinyl, tetrahydropyranyl, tetrahydrofuranyl and morpholinyl, which heterocyclyl ring is optionally substituted with one, two or three substituents independently selected from the group consisting of:

$C_{1-3}$alkyl, which alkyl group is optionally substituted with one halo, hydroxyl or $C_{1-3}$alkoxy group, halo, hydroxyl, and

—COCH$_2$OH, wherein where the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is piperidinyl or pyrrolidinyl ring, which ring is optionally substituted with one, two or three substituents independently selected from the group consisting of: $C_{1-3}$alkyl, which alkyl group is optionally substituted with one halo, hydroxyl or $C_{1-3}$alkoxy group,
halo,
hydroxyl,
—COCH$_2$OH, and
an oxygen containing 4-6 membered heterocyclyl ring with the proviso that the oxygen containing heterocyclyl ring is attached to the nitrogen atom of the piperidinyl or pyrrolidinyl ring.

In one embodiment, R$^2$ is a piperidinyl ring optionally substituted with with one, two or three substituents independently selected from the group consisting of:
an oxygen containing 4-6 membered heterocyclyl ring with the proviso that the oxygen containing heterocyclyl ring is attached to the nitrogen atom of the piperidinyl ring;
C$_{1-3}$alkyl, which alkyl group is optionally substituted with one halo, hydroxyl or C$_{1-3}$alkoxy group;
halo;
hydroxyl, and
COCH$_2$OH.

In one embodiment, R$^2$ is a piperidinyl ring optionally substituted with one oxygen containing 4-6 membered heterocyclyl ring with the proviso that the oxygen containing heterocyclyl ring is attached to the nitrogen atom of the piperidinyl ring.

In one embodiment, R$^2$ is a piperidinyl ring optionally substituted with with an oxetanyl ring, or a tetrahydrofuran ring with the proviso that the oxetanyl or tetrahydrofuran ring is attached to the nitrogen atom of the piperidinyl ring.

In one embodiment, R$^2$ is a piperidinyl ring optionally substituted with with an oxetanyl ring, or a tetrahydrofuran ring with the proviso that the oxetanyl or tetrahydrofuran ring is attached to the nitrogen atom of the piperidinyl ring.

In one embodiment, R$^2$ is 1-(oxetan-3-yl)piperidin-4-yl or 1-(tetrahydrofuran-3-yl)piperidin-4-yl.

In one embodiment, R$^2$ is 1-(oxetan-3-yl)piperidin-4-yl.

In one embodiment, R$^2$ is a pyrrolidinyl ring optionally substituted with with one, two or three substituents independently selected from the group consisting of C$_{1-3}$alkyl and hydroxyl.

In one embodiment, R$^2$ is —O—C$_{3-6}$ cycloalkyl wherein the cycloalkyl group is optionally substituted with one or two substituents independently selected from the group consisting of cyano, hydroxyl, C$_{1-3}$alkyl, C$_{1-3}$alkoxyl, CH$_2$OH and CO$_2$H.

In one embodiment, R$^2$ is —O—C$_{3-6}$ cycloalkyl wherein the cycloalkyl group is optionally substituted with one or two substituents independently selected from the group consisting of hydroxyl and C$_{1-3}$alkyl.

In one embodiment, R$^2$ is cyclopropyloxy wherein the cyclopropyl group is optionally substituted with one or two substituents independently selected from the group consisting of hydroxyl and C$_{1-3}$alkyl.

In one embodiment, R$^2$ is C$_{3-6}$ cycloalkyl optionally substituted with one or two substituents independently selected from the group consisting of cyano, halo, hydroxyl, C$_{1-3}$alkyl, C$_{1-3}$alkoxyl, CO$_2$H and a 4-6 membered heterocyclyl ring.

In one embodiment, R$^2$ is C$_{3-6}$ cycloalkyl optionally substituted with one or two substituents independently selected from the group consisting of cyano, halo, hydroxyl, C$_{1-3}$alkyl, C$_{1-3}$alkoxyl and CO$_2$H.

In one embodiment, R$^2$ is C$_{3-6}$ cycloalkyl optionally substituted with one or two substituents independently selected from the group consisting of hydroxyl and C$_{1-3}$alkyl.

In one embodiment, R$^2$ is cyclohexyl optionally substituted with one or two substituents independently selected from the group consisting of hydroxyl and C$_{1-3}$alkyl.

In one embodiment, R$^3$ is selected from the group consisting of CN, C$_{1-3}$ alkyl, C$_{1-3}$ alkoxy, C$_{1-3}$haloalkyl, and C$_3$ cycloalkyl. In one embodiment, R$^3$ is selected from the group consisting of C$_{1-3}$ alkyl and C$_{1-3}$ alkoxyl. In one embodiment, R$^3$ is selected from the group consisting of methyl and methoxy.

In one embodiment, R$^4$ is selected from the group consisting of H, halo, CN, C$_{1-3}$alkyl and C$_{1-3}$haloalkyl. In one embodiment, R$^4$ is selected from the group consisting of H, halo and C$_{1-3}$alkyl. In one embodiment, R$^4$ is selected from the group consisting of H, halo and methyl. In one embodiment, R$^4$ is selected from the group consisting of H, fluoro, chloro and methyl. In one embodiment, R$^4$ is selected from the group consisting of H, chloro and methyl. In one embodiment, R$^4$ is selected from the group consisting of chloro and methyl. In one particular embodiment, R$^4$ is methyl.

In one embodiment, the invention provides a compound of Formula (I) or a salt thereof wherein R$^1$, R$^2$ and R$^4$ are as defined above and R$^3$ is selected from the group consisting of C$_{1-3}$ alkyl and C$_{1-3}$ alkoxyl. In this embodiment, R$^1$, R$^2$ and R$^4$ may be further defined as in any of the preceding embodiments.

In one embodiment, the invention provides a compound of Formula (I) or a salt thereof wherein R$^1$ and R$^4$ are as defined above and wherein:

R$^2$ is a 5-6 membered heterocyclyl ring selected from the group consisting of: piperazinyl, piperidinyl, pyrrolidinyl, tetrahydropyridinyl, tetrahydropyranyl, tetrahydrofuranyl, morpholinyl, which heterocyclyl ring is optionally substituted with one, two or three substituents independently selected from the group consisting of:

C$_{1-3}$alkyl, which alkyl group is optionally substituted with one halo, hydroxyl or C$_{1-3}$alkoxy group, halo, hydroxyl, and

—COCH$_2$OH, wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom; and R$^3$ is selected from the group consisting of C$_{1-3}$ alkyl and C$_{1-3}$ alkoxyl.

In this embodiment, R$^1$ and R$^4$ may be further defined as in any of the preceding embodiments.

In one embodiment, the compound of formula (I) or pharmaceutically acceptable salt thereof is the compound of any one of Examples 1-180, or a pharmaceutically acceptable salt thereof.

In one embodiment, the compound or formula (I) or salt thereof is (1R,4R)-5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.1]heptane, or a salt thereof. In one embodiment, the compound of formula (I) is (1R,4R)-5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.1]heptane.

In one embodiment, this invention relates to a compound selected from

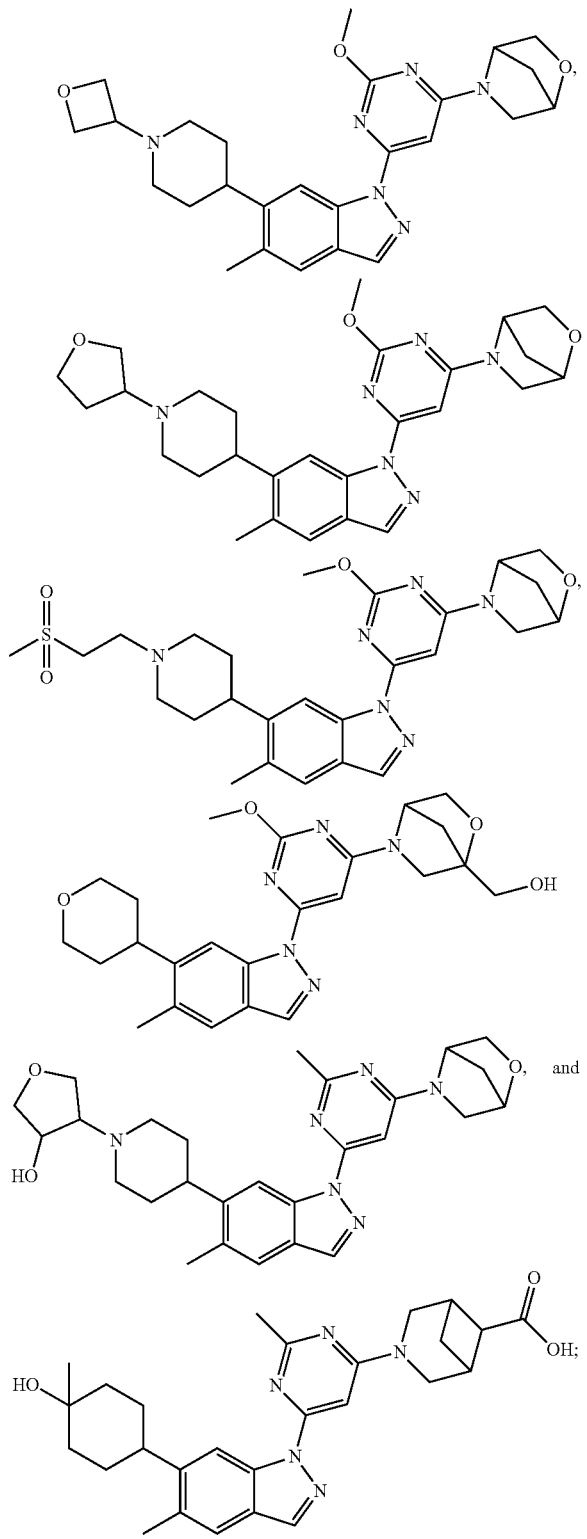

or a pharmaceutically acceptable salt thereof.

In one embodiment the invention provides a compound selected from 5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.1]heptane, 5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.1]heptane, 3-{6-[6-(4-Hydroxy-4-methyl-cyclohexyl)-5-methyl-indazol-1-yl]-2-methyl-pyrimidin-4-yl}-3-aza-bicyclo[3.1.1]heptane-6-carboxylic acid, 4-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)tetrahydrofuran-3-ol, 5-(2-methoxy-6-(5-methyl-6-(1-(2-(methylsulfonyl)ethyl)piperidin-4-yl)-1H-indazol-1-yl)pyrimidin-4-yl)-2-oxa-5-azabicyclo[2.2.1]heptane, and 5-(2-methoxy-6-(5-methyl-6-(tetrahydro-2H-pyran-4-yl)-1H-indazol-1-yl)pyrimidin-4-yl)-2-oxa-5-azabicyclo[2.2.1]heptan-1-yl)methanol;

or a pharmaceutically acceptable salt thereof.

In one embodiment the invention provides (5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.1]heptane, or a pharmaceutically acceptable salt thereof.

In one embodiment the invention provides 5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.1]heptane, or a pharmaceutically acceptable salt thereof.

In one embodiment, the invention provides 3-{6-[6-(4-Hydroxy-4-methyl-cyclohexyl)-5-methyl-indazol-1-yl]-2-methyl-pyrimidin-4-yl}-3-aza-bicyclo[3.1.1]heptane-6-carboxylic acid, or a pharmaceutically acceptable salt thereof In one embodiment, the invention provides 5-(2-methoxy-6-(5-methyl-6-(1-(2-(methylsulfonyl)ethyl)piperidin-4-yl)-1H-indazol-1-yl)pyrimidin-4-yl)-2-oxa-5-azabicyclo[2.2.1]heptane, or a pharmaceutically acceptable salt thereof.

5-(2-methoxy-6-(5-methyl-6-(tetrahydro-2H-pyran-4-yl)-1H-indazol-1-yl)pyrimidin-4-yl)-2-oxa-5-azabicyclo[2.2.1]heptan-1-yl)methanol, or a pharmaceutically acceptable salt thereof.

In one embodiment, the compound of formula (I) or a pharmaceutically acceptable salt thereof is a compound of any one of Examples 1 to 180 or a pharmaceutically acceptable salt thereof. In one embodiment, the compound of formula (I) is a compound of any one of Examples 1 to 180.

In addition to the free base form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

Certain compounds of formula (I) contain a basic group and are therefore capable of forming pharmaceutically-acceptable acid addition salts by treatment with a suitable acid. Suitable acids include pharmaceutically-acceptable inorganic acids and pharmaceutically-acceptable organic acids. Exemplary pharmaceutically-acceptable acid addition salts include hydrochloride, hydrobromide, nitrate, methyl-nitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. In certain embodiments, some of these salts form solvates. In certain embodiments, some of these salts are crystalline.

Certain compounds of Formula (I) or salts thereof may exist in stereoisomeric forms (e.g., they may contain one or more asymmetric carbon atoms). The individual stereoisomers (enantiomers and diastereomers) and mixtures of these are included within the scope of the present invention. The different isomeric forms may be separated or resolved one from the other by conventional methods, or any given isomer may be obtained by conventional synthetic methods or by stereospecific or asymmetric syntheses.

Certain compounds of Formula (I) are capable of existing in tautomeric forms. For example, certain compounds exhibit keto-enol tautomerism. In some cases, only one of a pair of tautomeric forms fall within Formula (I). Such alternative tautomers also form part of the invention.

The invention also includes isotopically-labelled compounds and salts, which are identical to compounds of Formula (I) or salts thereof, but for the fact that one or more atoms are replaced by an atom having an atomic mass or mass number different from the atomic mass or mass number most commonly found in nature. Examples of isotopes that can be incorporated into compounds of Formula (I) or salts thereof isotopes of hydrogen, carbon, nitrogen, fluorine, such as $^3H$, $^{11}C$, $^{14}C$ and $^{18}F$. Such isotopically-labelled compound of Formula (I) or salts thereof are useful in drug and/or substrate tissue distribution assays. For example, $^{11}C$ and $^{18}F$ isotopes are useful in PET (positron emission tomography). PET is useful in brain imaging. Isotopically-labelled compounds of Formula (I) and salts thereof can generally be prepared by carrying out the procedures disclosed below, by substituting a readily available isotopically-labelled reagent for a non-isotopically labelled reagent. In one embodiment, compounds of Formula (I) or salts thereof are not isotopically labelled.

Certain compounds of Formula (I) or salts thereof may exist in solid or liquid form. In the solid state, compounds of Formula (I) or salts may exist in crystalline or noncrystalline form, or as a mixture thereof. For compounds of Formula (I) or salts that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water.

The skilled artisan will further appreciate that certain compounds of Formula (I), pharmaceutically acceptable salts or solvates thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The skilled artisan also appreciates that this invention may contain various deuterated forms of compounds of Formula (I), or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), or pharmaceutically acceptable salts thereof. Commercially available deuterated starting materials may be employed in the preparation of deuterated forms of compounds of Formula (I) or pharmaceutically acceptable salts thereof, or they may be synthesized using conventional techniques employing deuterated reagents (e.g. lithium aluminum deuteride).

C. Methods of Use

Compounds of Formula (I) or pharmaceutically acceptable salts thereof are inhibitors of LRRK2 kinase activity and are thus believed to be of potential use in the treatment of or prevention of the following neurological diseases: Parkinson's disease, Alzheimer's disease, dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, spinal cord injury and multiple sclerosis. Other diseases potentially treatable by inhibition of LRRK2 include, but are not limited to, lysosomal disorders (for example, Niemann-Pick Type C disease, Gaucher disease), Crohn's disease, cancers (including thyroid, renal (including papillary renal), breast, lung and prostate cancers, leukemias (including acute myelogenous leukemia (AML)) and lymphomas), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, obesity, epilepsy, pulmonary diseases such as chronic obstructive pulmonary disease, idiopathic pulmonary fibrosis, Sjogren's syndrome, Devic's disease, inflammatory myopathies, ankylosing spondylitis, bacterial infections (including leprosy), viral infections (including tuberculosis, HIV, West Nile virus and chikungunya virus) and parasitic infections.

One aspect of the invention provides a compound of Formula (I) or a pharmaceutically acceptable salt thereof for use in therapy. In one embodiment, the invention provides a compound of Formula (I) or a pharmaceutically acceptable salt thereof for use in the treatment of or prevention of the above disorders (i.e. the neurological diseases and other diseases listed above). In one embodiment, the invention provides a compound of Formula (I) or a pharmaceutically acceptable salt thereof for use in the treatment of or prevention of Parkinson's disease. In one embodiment, the invention provides a compound of Formula (I) or a pharmaceutically acceptable salt thereof for use in the treatment of Parkinson's disease. In another embodiment, the invention provides a compound of Formula (I) or a pharmaceutically acceptable salt thereof for use in the treatment of or prevention of Alzheimer's disease. In one embodiment, the invention provides a compound of Formula (I) or a pharmaceutically acceptable salt thereof for use in the treatment of Alzheimer's disease. In another embodiment, the invention provides a compound of Formula (I) or a pharmaceutically acceptable salt thereof for use in the treatment of amyotrophic lateral sclerosis (ALS).

In one embodiment, the invention provides a compound of Formula (I) or a pharmaceutically acceptable salt thereof for use in the treatment or prevention of Parkinson's disease, Alzheimer's disease or amyotrophic lateral sclerosis (ALS).

In another embodiment, the invention provides a compound of Formula (I) or a pharmaceutically acceptable salt thereof for use in the treatment of Parkinson's disease.

A further aspect of the invention provides the use of a compound of Formula (I) or a pharmaceutically acceptable salt thereof in the manufacture of a medicament for the treatment or prevention of the above disorders (i.e. the neurological diseases and other diseases listed above). A further aspect of the invention provides the use of a compound of Formula (I) or a pharmaceutically acceptable salt thereof in the manufacture of a medicament for the treatment of or prevention of Parkinson's disease. A further aspect of the invention provides the use of a compound of Formula (I) or a pharmaceutically acceptable salt thereof in the manufacture of a medicament for the treatment of Parkinson's disease. In another embodiment, the invention provides the use of a compound of Formula (I) or a pharmaceutically acceptable salt thereof in the manufacture of a medicament for the treatment or prevention of Alzheimer's disease. In one embodiment, the invention provides the use of a compound of Formula (I) or a pharmaceutically acceptable salt thereof in the manufacture of a medicament for the treatment of Alzheimer's disease. In another embodiment, the invention provides use of a compound of Formula (I) or a pharmaceutically acceptable salt thereof in the manufacture of a medicament for the treatment of amyotrophic lateral sclerosis (ALS).

In one embodiment, the invention provides the use of a compound of Formula (I) or a pharmaceutically acceptable salt thereof in the manufacture of a medicament for the treatment or prevention of Parkinson's disease, Alzheimer's disease or amyotrophic lateral sclerosis (ALS).

In another embodiment, the invention provides the use of a compound of Formula (I) or a pharmaceutically acceptable salt thereof in the manufacture of a medicament for the treatment or prevention of Parkinson's disease.

In yet another embodiment, the invention provides the use of a compound of Formula (I) or a pharmaceutically acceptable salt thereof in the manufacture of a medicament for the treatment of Parkinson's disease.

A further aspect of the invention provides a method of treatment or prevention of a disorder listed above (i.e. selected from the neurological diseases and other diseases listed above), which comprises administering to a subject in need thereof a therapeutically effective amount of a compound of Formula (I) or a pharmaceutically acceptable salt thereof. A further aspect of the invention provides a method of treatment or prevention of Parkinson's disease, which comprises administering to a subject in need thereof a therapeutically effective amount of a compound of Formula (I) or a pharmaceutically acceptable salt thereof. A further aspect of the invention provides a method of treatment of Parkinson's disease, which comprises administering to a subject in need thereof a therapeutically effective amount of a compound of Formula (I) or a pharmaceutically acceptable salt thereof. A further aspect of the invention provides a method of treatment or prevention of Alzheimer's disease, which comprises administering to a subject in need thereof a therapeutically effective amount of a compound of Formula (I) or a pharmaceutically acceptable salt thereof. A further aspect of the invention provides a method of treatment of Alzheimer's disease, which comprises administering to a subject in need thereof a therapeutically effective amount of a compound of Formula (I) or a pharmaceutically acceptable salt thereof. A further aspect of the invention provides a method of treatment of tuberculosis, which comprises administering to a subject in need thereof a therapeutically effective amount of a compound of Formula (I) or a pharmaceutically acceptable salt thereof. In an embodiment, the subject is human.

In one embodiment, the invention provides a method of treatment of Parkinson's disease, Alzheimer's disease or amyotrophic lateral sclerosis (ALS), which comprises administering to a subject in need thereof a therapeutically effective amount of a compound of Formula (I) or a pharmaceutically acceptable salt thereof.

In one embodiment, the invention provides a method of treatment of Parkinson's disease, Alzheimer's disease or amyotrophic lateral sclerosis (ALS), which comprises administering to a human in need thereof a therapeutically effective amount of a compound of Formula (I) or a pharmaceutically acceptable salt thereof.

In one embodiment, the invention provides a method of treatment of Parkinson's disease, which comprises administering to a subject in need thereof a therapeutically effective amount of a compound of Formula (I) or a pharmaceutically acceptable salt thereof.

In one embodiment, the invention provides a method of treatment of Parkinson's disease, which comprises administering to a human in need thereof a therapeutically effective amount of a compound of Formula (I) or a pharmaceutically acceptable salt thereof.

In one embodiment, the invention provides a method of treatment of Parkinson's disease, which comprises administering to a human in need thereof a therapeutically effective amount of a compound selected from

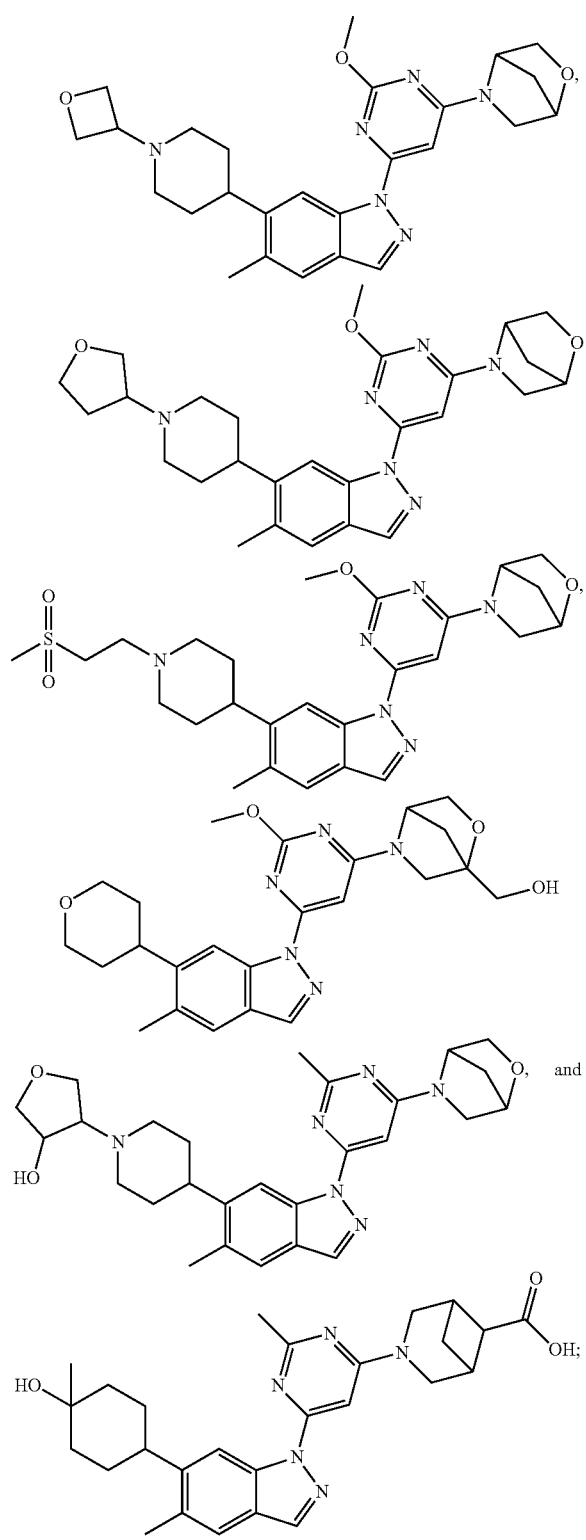

or a pharmaceutically acceptable salt thereof.

In one embodiment, the invention provides a method of treatment of Parkinson's disease, which comprises administering to a human in need thereof a therapeutically effective amount of a compound of Formula (I).

In one embodiment, the invention provides a method of treatment of Parkinson's disease, which comprises administering to a human in need thereof a therapeutically effective amount of a compound of Formula (I) or a pharmaceutically acceptable salt thereof.

In the context of the present invention, treatment of Parkinson's disease refers to the treatment of sporadic Parkinson's disease, and/or familial Parkinson's disease. In one embodiment, treatment of Parkinson's disease refers to treatment of familial Parkinson's disease. Familial Parkinson's disease patients are those expressing one or more of the following LRRK2 kinase mutations: G2019S mutation, N1437H mutation, R1441G mutation, R1441C mutation, R1441H mutation, Y1699C mutation, S1761R mutation, or I2020T mutation. In another embodiment, familial Parkinson's disease patients express other coding mutations (such as G2385R) or non-coding single nucleotide polymorphisms at the LRRK2 locus that are associated with Parkinson's disease In a more particular embodiment, familial Parkinson's disease includes patients expressing the G2019S mutation or the R1441G mutation in LRRK2 kinase. In one embodiment, treatment of Parkinson's disease refers to the treatment of familial Parkinson's disease includes patients expressing LRRK2 kinase bearing G2019S mutation. In another embodiment, familial Parkinson's disease patients express aberrantly high levels of normal LRRK2 kinase.

In one embodiment, the invention provides a method of treatment of Parkinson's disease, which comprises administering to a human expressing the G2019S mutation in LRRK2 kinase in need thereof a therapeutically effective amount of a compound of Formula (I) or a pharmaceutically acceptable salt thereof.

In one embodiment, the invention provides a method of treatment of Parkinson's disease, which comprises testing in a human for the G2019S mutation in LRRK2 kinase and administering to the human expressing the G2019S mutation in LRRK2 kinase in need thereof a therapeutically effective amount of a compound of Formula (I) or a pharmaceutically acceptable salt thereof.

Treatment of Parkinson's disease may be symptomatic or may be disease modifying. In one embodiment, treatment of Parkinson's disease refers to symptomatic treatment. In one embodiment, treatment of Parkinson's disease refers to disease modifying treatment.

Compounds of the present invention may also be useful in treating patients identified as susceptible to progression to severe Parkinsonism by means of one or more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of sporadic Alzheimer's disease and/or familial Alzheimer's disease. Treatment of Alzheimer's disease may be symptomatic or may be disease modifying. In one embodiment, treatment of Alzheimer's disease refers to symptomatic treatment.

In the context of the present invention, treatment of dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), multiple sclerosis, lysosomal disorders (for example, Niemann-Pick Type C disease, Gaucher disease), Crohn's disease, cancers (including thyroid, renal (including papillary renal), breast, lung and prostate cancers, leukemias (including acute myelogenous leukemia (AML)) and lymphomas), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, obesity, epilepsy, pulmonary diseases such as chronic obstructive pulmonary disease, idiopathic pulmonary fibrosis, Sjogren's syndrome, Devic's disease, inflammatory myopathies, ankylosing spondylitis, may be symptomatic or disease modifying. In certain embodiments, treatment of these disorders refers to symptomatic treatment.

The invention also provides the use of inhibitors of LRRK2 in the production of neuronal progenitor cells in vitro for consequent therapeutic application in cell based-treatment of CNS disorders.

When a compound of Formula (I) or a pharmaceutically acceptable salt thereof is intended for use in the treatment of Parkinson's disease, it may be used in combination with medicaments alleged to be useful as symptomatic treatments of Parkinson's disease. Suitable examples of such other therapeutic agents include L-dopa, and dopamine agonists (e.g. pramipexole, ropinirole).

When a compound of Formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride rivastigmine, and galantamine), nicotinic receptor agonists or allosteric modulators (such as $\alpha 7$ agonists or allosteric modulators or $\alpha 4\beta 2$ agonists or allosteric modulators), PPAR agonists (such as PPAR$\gamma$ agonists), 5-HT$_4$ receptor partial agonists, 5-HT$_6$ receptor antagonists e.g. SB-742457 or 5HT1A receptor antagonists and NMDA receptor antagonists or modulators, or disease modifying agents such as $\beta$ or $\gamma$-secretase inhibitors e.g semagacestat, mitochondrial stabilizers, microtubule stabilizers or modulators of Tau pathology such as Tau aggregation inhibitors (e.g. methylene blue and REMBER™), NSAIDS, e.g. tarenflurbil, tramiprosil; or antibodies for example bapineuzumab or solanezumab; proteoglycans for example tramiprosate.

When a compound of Formula (I) or a pharmaceutically acceptable salt thereof is intended for use in the treatment of bacterial infections, parasitic infections or viral infections, it may be used in combination with medicaments alleged to be useful as symptomatic treatments that directly target the infectious agent.

When a compound of Formula (I) or a pharmaceutically acceptable salt thereof is used in combination with other therapeutic agents, the compound may be administered either sequentially or simultaneously by any convenient route.

The invention also provides, in a further aspect, a combination comprising a compound of Formula (I) or a pharmaceutically acceptable salt thereof together with one or more further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of Formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

D. Composition

Compounds of Formula (I) or pharmaceutically acceptable salts thereof may be formulated into pharmaceutical compositions prior to administration to a subject. According to one aspect, the invention provides a pharmaceutical composition comprising a compound of Formula (I) or a pharmaceutically acceptable salt thereof and a pharmaceutically acceptable excipient. According to another aspect, the invention provides a process for the preparation of a pharmaceutical composition comprising admixing a compound of Formula (I) or a pharmaceutically acceptable salt thereof, with a pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the disease being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of Formula (I) will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of formula (I) for the treatment of diseases described in the present invention will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A therapeutically effective amount of a pharmaceutically acceptable salt or solvate, etc., may be determined as a proportion of the therapeutically effective amount of the compound of Formula (I) per se. It is envisaged that similar dosages would be appropriate for treatment of the other diseases referred to above.

The pharmaceutical compositions of the invention may contain one or more compounds of Formula (I) or a pharmaceutically acceptable salt thereof. In some embodiments, the pharmaceutical compositions may contain more than one compound of the invention. For example, in some embodiments, the pharmaceutical compositions may contain two or more compounds of Formula (I) or a pharmaceutically acceptable salt thereof. In addition, the pharmaceutical compositions may optionally further comprise one or more additional active pharmaceutical ingredients (APIs).

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate.

The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiments, the present invention is directed to a pharmaceutical composition comprising 0.01 to 1000 mg of one or more of a compound of Formula (I) or a pharmaceutically acceptable salt thereof and 0.01 to 5 g of one or more pharmaceutically acceptable excipients.

In another embodiment, the present invention is directed to a pharmaceutical composition for the treatment of a neurodegeneration disease comprising a compound of formula (I) or a pharmaceutically acceptable salt thereof and a pharmaceutically acceptable excipient. In another embodiment, the present invention is directed to a pharmaceutical composition for the treatment of Parkinson's disease comprising a compound of formula (I) or a pharmaceutically acceptable salt thereof and a pharmaceutically acceptable excipient.

E. Process of Preparing Compounds

The process to be utilized in the preparation of compounds of formula (I) or salts thereof described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of formula (I) are set forth below. All starting material and reagents described in the below general experimental schemes are commercially available or can be prepared by methods known to one skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Scheme 1 provides exemplary processes of synthesis for preparing compounds of the present invention.

General Scheme 1

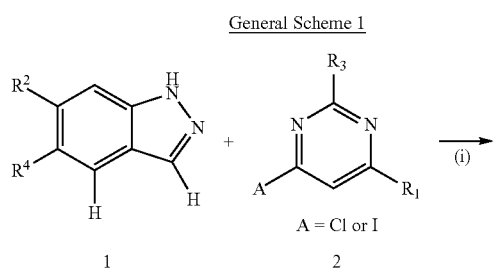

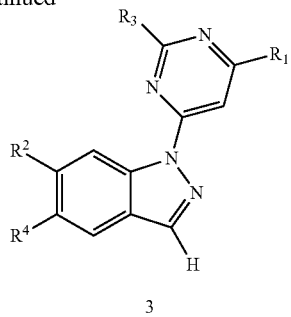

General Scheme 1 provides an exemplary synthesis for preparing compound 3 which represents compounds of Formula (I). In Scheme 1, $R_1$, $R_2$, $R_3$ and R4 are as defined in Formula I.

Step (i) may be a substitution reaction by reacting compound 1 with compound 2 using appropriate base such as $Cs_2CO_3$ in an appropriate solvent such as N, N-dimethylformamide (DMF) under suitable temperature such as about 100° C. to provide compound 3.

Step (i) may alternatively be a coupling reaction using appropriate reagents such as CuI and N,N'-dimethyl-cyclohexane-1,2-diamine in the presence of suitable base such as $K_3PO_4$ in a suitable solvent such as toluene at suitable temperature such as reflux condition to provide compound 3.

Step (i) may alternatively be a coupling reaction using appropriate reagents such as $Pd_2dba_3$ and di-tert-butyl(2',4',6'-triisopropyl-[1,1-biphenyl]-2-yl)phosphine in the presence of suitable base such as sodium tert-butoxide in a suitable solvent such as toluene at suitable temperature such as 100° C. to provide compound 3.

General Scheme 2

35

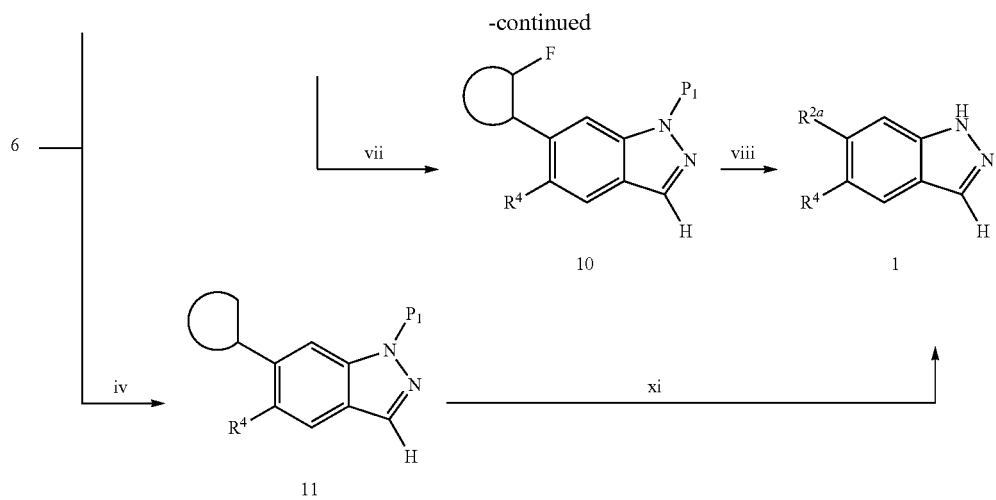

General Scheme 2 provides an exemplary synthesis for preparing intermediate 1 where $R^2$ is connected to the indazole ring though a carbon atom of $R^2$. $R^{2a}$ represents $R^2$ where this is connected to the indazole ring though a carbon atom of $R^2$. The protecting group, $P_1$, can be any suitable protecting groups for example, tetrahydro-2H-pyran-2-yl (THP), (trimethylsilyl)ethoxy)methyl (SEM) or or Acetyl (Ac).

Intermediate 5 can be obtained in step (i) by reacting starting material 4 with suitable reagents such as DHP in the presence of suitable acids such as TsOH in appropriate solvents such as DCM under suitable temperatures such as 20° C. to 40° C.

Step (ii) is a cross-coupling reaction between intermediate 5 and boronic acid or esters using appropriate palladium catalysts such as $Pd(dppf)Cl_2$ in the presence of suitable bases such as $Na_2CO_3$ in appropriate solvents such as 1,4-dioxane at suitable temperatures such as 60° C. to 100° C.

36

Step (iii) involves reaction with suitable oxidation reagents such as $H_2O_2$ in a suitable solvent such as THF under suitable temperatures such as −60° C. to −10° C. to provide intermediate 7.

Step (iv) is a reaction with a suitable reducing reagent such as hydrogen in the presence of suitable catalysts such Pd/C in polar solvents such as MeOH at appropriate temperatures such as 25° C. to 80° C.

Step (v) may be an oxidation reaction with oxidants such as DMP in suitable solvents such as DCM under suitable temperatures such as 0° C. to 25° C. to give intermediate 8.

Steps (vi) and (viii) involve reaction with a fluridizer such as DAST in suitable solvents such as DCM under suitable temperatures such as −78° C. to 0° C.

Steps (viii) (x) and (xi) are de-protection reactions. Typically, the intermediate is reacted with suitable acids such HCl in suitable solvents such as 1,4-dioxane under suitable temperatures such as 25° C. to 40° C. to give intermediate 1.

General scheme 3

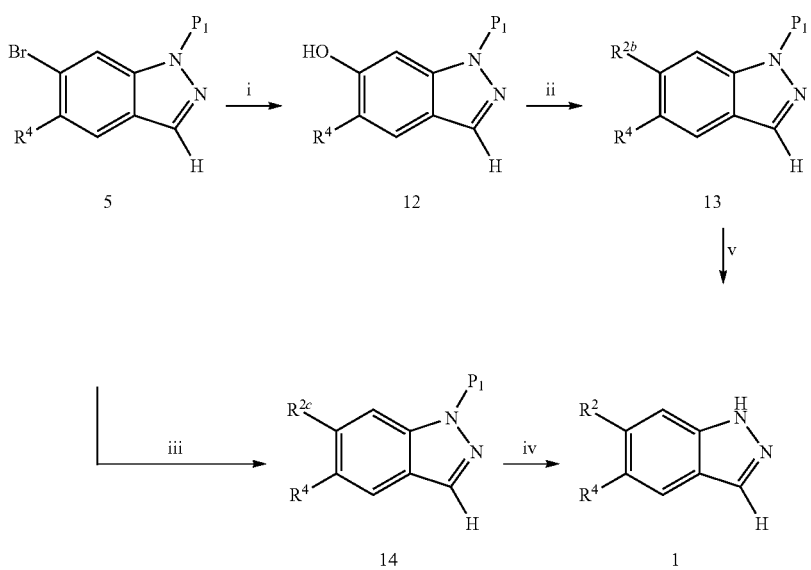

General Scheme 3 provides an exemplary synthesis for preparing intermediate 1. when $R^2$ connects to the indazole ring through an oxygen or nitrogen atom of $R^2$. $R^{2b}$ represents $R^2$ when $R^2$ connects to the indazole ring through an oxygen atom of $R^2$. $R^{2c}$ represents $R^2$ when $R^2$ connects to the indazole ring through the nitrogen atom of $R^2$. The protecting group, $P_1$, can be any suitable protecting group for example, tetrahydro-2H-pyran-2-yl (THP), (trimethylsilyl)ethoxy)methyl (SEM) or Acetyl (Ac).

Step (i) is a reaction with suitable reagents such as 4,4,4',4',5,5,5',5'-octamethyl-2,2'-bi(1,3,2-dioxaborolane) using appropriate catalysts such as $Pd(PPh_3)_4$ in the presence of appropriate bases such as KOAc in appropriate solvents such as DMF at a suitable temperatures such as 80° C. to 120° C., followed by reaction with suitable reagents such $H_2O_2$ in the presence of appropriate bases such as NaOH in suitable solvents such as THF at appropriate temperatures such as 25° C. to 80° C.

Step (ii) is a reaction with a suitable alkylating reagent such as 2-iodopropane in the presence of suitable bases such as $Cs_2CO_3$ in appropriate solvents such as ACN at a suitable temperatures such as 25° C. to 100° C.

Step (iii) can be a Buchwald coupling reaction with different amines such as 1-methylpiperazine using appropriate palladium catalysts such as $Pd_2(dba)_3$ in the presence of appropriate bases such as $Cs_2CO_3$ and appropriate ligands such as BINAP in appropriate solvents such as PhMe under suitable temperatures such as 80° C. to 130° C., or an Ullman coupling reaction with different amides such as 4-hydroxy-4-methylpiperidin-2-one using appropriate copper catalysts such as Cu(OAc)2 in the presence of appropriate bases such as LiHMDS and appropriate ligands such as DMEDA (or in absence of ligand) in appropriate solvents such as DCM under suitable temperatures such as 80° C. to 130° C.

Steps (iv) and (v) are deprotection reactions with suitable acids such HCl in suitable solvents such as 1,4-dioxane under suitable temperatures such as 25° C. to 40.

General scheme 4

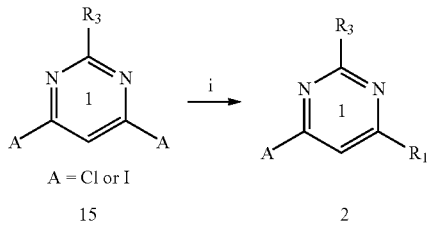

A = Cl or I

General Scheme 4 provides an exemplary synthesis for preparing intermediates 2. Step (i) can be a reaction with different amines using appropriate bases such as TEA in appropriate solvents such as EtOH under suitable temperatures such as 25° C. to 100° C. to provide intermediate 2.

EXAMPLES

General Experimental Procedures

The following descriptions and examples illustrate the invention. These examples are not intended to limit the scope of the present invention, but rather to provide guidance to the skilled chemist to prepare and use the compounds, compositions and methods of the present invention. While particular embodiments of the present invention are described, the skilled chemist will appreciate that various changes and modifications can be made without departing from the spirit and scope of the invention.

The chemical names of compounds described in the present application were generally created from ChemDraw Ultra (ChambridgeSoft) and/or generally follow the principle of IUPAC nomenclature.

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or re-crystallization using suitable solvents. Chromatographic methods are known to the skilled person and include e.g. column chromatography, flash chromatography, HPLC (high performance liquid chromatography), and MDAP (mass directed auto-preparation, also referred to as mass directed LCMS purification). MDAP is described in e.g. W. Goetzinger et al, *Int. J. Mass Spectrom.*, 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5 u C18(2) 100A reverse phase column eluting with a 10-80 gradient (0.1% FA in acetonitrile/0.1% aqueous FA) or a 10-80 gradient (acetonitrile/water). The CombiFlash system used for purification in this application was purchased from Isco, Inc. CombiFlash purification was carried out using a pre-packed $SiO_2$ column, a detector with UV wavelength at 254 nm and mixed solvents.

The terms "CombiFlash", "Biotage®", "Biotage 75" and "Biotage SP4®" when used herein refer to commercially available automated purification systems using pre-packed silica gel cartridges.

Final compounds were characterized with LCMS (conditions listed below) or NMR. $^1$H NMR or $^{19}$FNMR spectra were recorded using a Bruker Avance 400 MHz spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (ppm) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

All temperatures are reported in degrees Celsius. All other abbreviations are as described in the ACS Style Guide (American Chemical Society, Washington, D.C., 1986).

Absolute stereochemistry can be determined by methods known to one skilled in the art, for example X-ray or Vibrational Circular Dichroism (VCD).

When an enantiomer or a diasteroisomer is described and the absolute stereochemistry of a chiral center is not known, the use of "*" at the chiral centre denotes that the absolute stereochemistry of the chiral center is not known, i.e. the compound as drawn may be either a single R enantiomer or a single S enantiomer. Where the absolute stereochemistry at a chiral center of an enantiomer or a diasteroisomer is known, a bold wedge symbol ( ▬◀ ) or a hashed wedge symbol ( ⦀⦀⦀ ) is used as appropriate, without the use of "*" at the chiral centre.

When a geometric or cis-trans isomer is described and the absolute configuration of the isomer is not known, the use of "*" at one of the atoms relevant to the geometric or cis-trans isomerism denotes that the absolute configuration at or around that atom is not known, i.e. the compound as drawn may be either a single cis isomer or a single trans enantiomer.

In the procedures that follow, after each starting material, reference to an intermediate is typically provided. This is provided merely for assistance to the skilled chemist. The starting material may not necessarily have been prepared from the batch referred to.

LCMS Conditions:
1) Acidic Method:
a. Instruments: HPLC: Waters UPC2 and MS: Qda
Mobile phase: water containing 0.1% FA/0.1% MeCN
Column: ACQUITY UPLC BEH $C_{18}$ 1.7 μm 2.1×50 mm and 1.7 μm 2.1×100 mm
Detection: MS and photodiode array detector (PDA)
b. Instruments: HPLC: Shimadzu and MS: 2020
Mobile phase: water containing 0.1% FA/0.1% MeCN
Column: Sunfire $C_{18}$ 5 μm 50×4.6 mm and Sunfire $C_{18}$ 5 μm 150×4.6 mm
Detection: MS and photodiode array detector (PDA)
2) Basic Conditions:
Instruments: HPLC: Agilent 1260 and MS: 6120
Mobile phase: 0.1% $NH_4OH$ in $H_2O$/0.1% $NH_4OH$ in ACN
Column: Xbridge $C_{18}$ 5 μm 50×4.6 mm and Xbridge $C_{18}$ 5 μm 150×4.6 mm
Detection: MS and photodiode array detector (DAD)

Prep-HPLC Conditions
Instrument: Waters instrument
Column: Xbridge Prep $C_{18}$ column OBD (10 μm, 19×250 mm), Xbridge prep $C_{18}$ 10 ↑m OBD TM 19×150 mm, Sunfire Prep $C_{18}$ 10×25 0 mm 5 μm, XBRIDGE Prep $C_{18}$ 10×150 mm 5 μm, etc
Acidic Method:
Mobile phase: water containing 0.1% TFA/acetonitrile.
Basic Method:
Mobile phase: water containing 0.1% $NH_4OH$/acetonitrile.
Chiral Prep-HPLC:
Thar SFC Prep 80 (TharSFC ABPR1, TharSFC SFC Prep 80 $CO_2$ Pump, TharSFC Co-Solvent Pump, TharSFC Cooling Heat Exchanger and Circulating Bath, TharSFC Mass Flow Meter, TharSFC Static Mixer, TharSFC Injection Module, Gilson UV Detector, TharSFC Fraction Collection Module
Chiral-HPLC Analysis:
Instrument: Thar SFC Prep 80 (TharSFC ABPR1, TharSFC SFC Prep 80 $CO_2$Pump, TharSFC Co-Solvent Pump, TharSFC Cooling Heat Exchanger and Circulating Bath, TharSFC Mass Flow Meter, TharSFC Static Mixer, TharSFC Injection Module, Gilson UV Detector, TharSFC Fraction Collection Module
Column and mobile phase: are described in below examples.

Abbreviations and Resource Sources

The following abbreviations and resources are used herein below:

Ac—acetyl
MeCN—acetonitrile
Atm—atmosphere
Aq.—aqueous
BINAP—2,2'-bis(diphenylphosphino)-1,1-binaphthyl
Boc—tert-butyloxycarbonyl
$Boc_2O$—di-tert-butyl dicarbonate
Bn—benzyl
t-Bu—tert-butyl
conc.—concentrated
DAST—N,N-diethylaminosulfur trifluoride
DCE—1,2-dichloroethane
DCM—dichloromethane
DEA—diethanolamine
DMEDA—N,N'-Dimethylethylenediamine
Dess-Martin—1,1,1-Tris(acetyloxy)-1,1-dihydro-1,2-benziodoxol-3-(1H)-one
DHP—3,4-dihydro-2H-pyran
DIBAL-H—diisobutylaluminum hydride
DIEA—N,N-diisopropylethylamine
DIPEA—N, N-diisopropylethylamine
DMA—N, N-dimethylacetamide
DMAP—4-dimethylaminopyridine
DMEDA—N,N'-dimethylethylenediamine
DMF—N, N-dimethylformamide
DMP—Dess-Martin periodinane
DMSO—dimethyl sulfoxide
DPPF—1,1'-bis(diphenylphosphino)ferrocene
EA—ethyl acetate
EDC—1-ethyl-3-(3-dimethylaminopropyl)carbodiimide hydrochloride
EDCI—3-(ethyliminomethyleneamino)-N,N-dimethylpropan-1-amine
EtOH/EtOH—ethanol
$Et_2O$—diethyl ether
EtOAc—ethyl acetate
$Et_3N$—triethylamine
FA—formic acid
HEP—heptane
Hex—hexane
HOAc—acetic acid
HATU—2-(1H-7-azabenzotriazol-1-yl)-1,1,3,3-tetramethyl uranium hexafluorophosphate
HOBT—hydroxybenzotriazole
IPA—isopropyl alcohol
$^iPrOH$/iPrOH—isopropyl alcohol
m-CPBA—meta-chloroperoxybenzoic acid
MOMCl—monochlorodimethyl ether
Me—methyl
MeOH—methanol
MsCl—methanesulfonyl chloride
NaHMDS—sodium bis(trimethylsilyl)amide
NIS—N-iodosuccinimide
NMP—1-methyl-2-pyrrolidone
NMO—4-methylmorpholine 4-oxide
PE—petroleum ether
PMB—p-methoxybenzyl
$Pd_2(dba)_3$—Tris(dibenzylideneacetone)dipalladium
$Pd(dppf)Cl_2$—1,1'-Bis(diphenylphosphino)ferrocenepalladium(II)dichloride dichloromethane complex
$Ph_3P$—triphenylphosphine
$PhNTf_2$—N,N-bis-(Trifluoromethanesulfonyl)aniline
PPTS—pyridinium p-toluenesulfonate
PTSA—p-toluenesulfonic acid
rt/RT—room temperature
Rt—retention time
sat.—saturated SEM-Cl—2-(trimethylsilyl)ethoxymethyl chloride
SFC—Supercritical Fluid Chromatography
TBAI—Tetrabutylammonium iodide
TBDPSCl—tert-Butyl(chloro)diphenylsilane
TEA—triethylamine
TFA—trifluoroacetic acid
TFAA—trifluoroacetic anhydride
THF—tetrahydrofuran
TLC—thin layer chromatography
TsCl—4-toluenesulfonyl chloride
TsOH—p-toluenesulfonic acid Description 1

4,6-Diiodo-2-methylpyrimidine (D1)

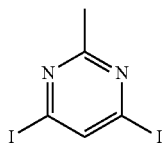

To a solution of NaI (11.9 g, 79.7 mmol) in HI (55%, 50 mL) was added 4,6-dichloro-2-methylpyrimidine (10.0 g, 61.3 mmol) in portions. The resulting suspension was heated to 40° C. and stirred for 1 hour. The reaction mixture was cooled and filtered. The solid was washed with water and then triturated with methanol (50 mL). The mixture was filtered to give the title compound (9.0 g, yield 42%) as white solid.

$^1$H NMR (400 MHz, CDCl$_3$): δ 8.07 (s, 1H), 2.67 (s, 3H).

LCMS: [mobile phase: 5-95% acetonitrile in 2.5 min), Rt=1.59 min, MS Calcd: 346; MS Found: 347 [M+H]$^+$.

Description 2

4,6-diiodo-2-methoxypyrimidine (D2)

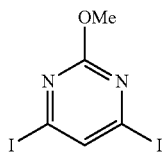

To a solution of NaI (5.5 g, 36.3 mmol) in HI (55% in water, 30 mL) was added 4,6-dichloro-2-methoxypyrimidine (5 g, 27.9 mmol). The mixture was heated to 40° C. and stirred for 14 h. The reaction mixture was cooled to room temperature and poured into ice water (50 mL). The filtered was washed with ice water three times to give product as a white solid (3.2 g, yield 32%).

LC-MS [mobile phase: from 80% water (0.1% TFA) and 20% ACN (0.1% TFA) to 20% water (0.1% TFA) and 80% ACN (0.1% TFA) in 10 min]: purity 100%, Rt=4.72 min; MS Calcd.: 362, MS Found: 363 [M+H]$^+$.

Description 3

(1R,4R)-5-(6-iodo-2-methoxypyrimidin-4-yl)-2-oxa-5-azabicyclo[2.2.1]heptane (D3)

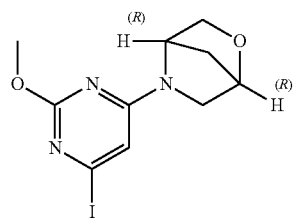

4,6-diiodo-2-methoxypyrimidine (822 mg, 2.27 mmol) and DIEA (1.2 mL) was dissolved in a mixture of THF (5 mL) and EtOH (5 mL), then (1R,4R)-2-oxa-5-azabicyclo[2.2.1]heptane hydrochloride (280 mg, 2.07 mmol) was added at rt and the reaction mixture was stirred at rt for 2 days, concentrated purified by silica gel chromatography (eluted with PE/EtOAc=3/1) to give the desired product as a white solid (680 mg, yield 90%).

LC-MS [mobile phase: from 80% water (0.1% TFA) and 20% ACN (0.1% TFA) to 20% water (0.1% TFA) and 80% ACN (0.1% TFA) in 2 min]: Rt=0.41 min; MS Calcd.: 333, MS Found: 334 [M+H]$^+$.

Description 4

(1S,4S)-5-(6-iodo-2-methoxypyrimidin-4-yl)-2-oxa-5-azabicyclo[2.2.1]heptane (D4)

4,6-diiodo-2-methoxypyrimidine (822 mg, 2.27 mmol) and DIEA (1.2 mL) was dissolved in a mixture of THF (5 mL) and EtOH (5 mL), then (1S,4S)-2-oxa-5-azabicyclo[2.2.1]heptane hydrochloride (280 mg, 2.07 mmol) was added and the reaction was stirred at rt for 2 days. The reaction solution was concentrated and the residue was purified by silica gel chromatography (eluted with PE/EtOAc=3/1) to give product as white solid (610 mg, yield 81%).

LC-MS [mobile phase: from 80% water (0.1% TFA) and 20% ACN (0.1% TFA) to 20% water (0.1% TFA) and 80% ACN (0.1% TFA) in 2 min]: Rt=0.41 min; MS Calcd.: 333, MS Found: 334 [M+H]$^+$.

Description 5

(1R,4R)-5-(6-iodo-2-methylpyrimidin-4-yl)-2-oxa-5-azabicyclo[2.2.1]heptane (D5)

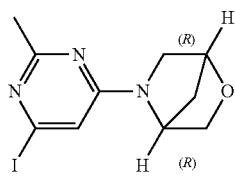

To a solution of 4,6-diiodo-2-methylpyrimidine (1.0 g, 2.9 mmol) and (1R,4R)-2-oxa-5-azabicyclo[2.2.1]heptane hydrochloride (392 mg, 2.9 mmol) in THF (30 ml) and EtOH (30 ml) at room temperature was added DIPEA (1.45 ml, 8.7 mmol). The reaction was stirred at room temperature for 48 hours. Removal of solvents and purification by silica gel chromatography (EtOAc/PE=1/5) gave desired product as yellow oil (557 mg, yield: 60).

LC-MS [mobile phase: from 90% water (0.1% FA) and 10% ACN (0.1% FA) to 5% water (0.1% FA) and 95% ACN (0.1% FA) in 2.0 min]: Rt=0.35 min; MS Calcd: 317, MS Found: 318 [M+H]$^+$.

Description 6

(1S,4S)-5-(6-iodo-2-methylpyrimidin-4-yl)-2-oxa-5-azabicyclo[2.2.1]heptane (D6)

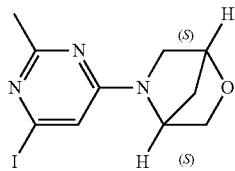

To a solution of 4,6-diiodo-2-methylpyrimidine (1.0 g, 2.9 mmol) and (1S,4S)-2-oxa-5-azabicyclo[2.2.1]heptane hydrochloride (392 mg, 2.9 mmol) in THF (30 ml) and EtOH (30 ml) at room temperature was added DIPEA (1.45 ml, 8.7 mmol). The reaction was stirred at room temperature for 48 hours. Removal solvents and purification (EtOAc/PE=1/5) via silica gel chromatography gave the title compound as white oil (540 mg, Yield: 58.7%).

LC-MS [mobile phase: from 90% water (0.1% FA) and 10% ACN (0.1% FA) to 5% water (0.1% FA) and 95% ACN (0.1% FA) in 2.0 min]: Rt=0.31 min; MS Calcd: 317.0, MS Found: 318.0 [M+H]$^+$.

Description 7

5-(6-iodo-2-methoxypyrimidin-4-yl)-2-oxa-5-azabicyclo[2.2.2]octane (D7)

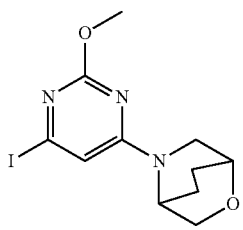 [SMILES: COc1nc(I)cc(N2CC3CCC2CO3)n1]

A solution of 4,6-diiodo-2-methoxypyrimidine (72 mg, 0.2 mmol), 2-oxa-5-azabicyclo[2.2.2]octane oxalate (70 mg, 0.34 mmol) and TEA (101 mg, 1.0 mmol) in i-PrOH (6 mL) was stirred at room temperature for 6 hours. The mixture was diluted with water (30 mL) extracted with EtOAc (30 mL×2). The combined organic phase was dried over Na$_2$SO$_4$, filtered, the filtrate was by silica gel chromatography column (petroleum ether/EtOAc=2:1) to give the title compound (65 mg, 94%) as colorless oil.

LC-MS [C$_{18}$; column size: 4.6×30 mm 5 μm; Dikwa Diamonsil plus; mobile phase: B (ACN): A1 (0.02% NH$_4$OAc+ 5% ACN); gradient (B %) in 4 mins. 10-95-POS; flow rate: 1.5 ml/min]: Rt=2.053 min; MS Calcd.: 347, MS Found: 348 [M+H]$^+$.

Description 8

3-(6-Iodo-2-methoxypyrimidin-4-yl)-8-oxa-3-azabicyclo[3.2.1]octane (D8)

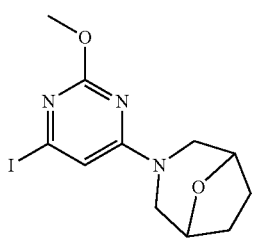 [SMILES: COc1nc(I)cc(N2CC3CCC(C2)O3)n1]

To a suspension of 4,6-diiodo-2-methoxypyrimidine (200 mg, 0.550 mmol) and 8-oxa-3-azabicyclo[3.2.1]octane hydrochloride (99 mg, 0.66 mmol) in i-PrOH (5 mL) was added TEA (171 mg, 1.69 mmol). The resulting mixture was stirred at 70° C. for 2 hrs. The mixture was concentrated and the residue was purified by column (PE:EtOAc=5:1) to give the title compound (160 mg, yield 84%) as a colorless oil.

$^1$H NMR (300 MHz, CDCl$_3$): δ 6.55 (s, 1H), 4.43 (br 2H), 4.12-3.61 (m, 5H), 3.18-3.14 (m, 2H), 1.96-1.93 (m, 2H), 1.75-1.73 (m, 2H).

Description 9

3-(6-Iodo-2-methylpyrimidin-4-yl)-8-oxa-3-azabicyclo[3.2.1]octane (D9)

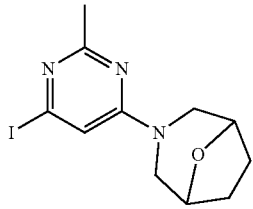 [SMILES: Cc1nc(I)cc(N2CC3CCC(C2)O3)n1]

To a suspension of 4,6-diiodo-2-methylpyrimidine (200 mg, 0.580 mmol) and 8-oxa-3-azabicyclo[3.2.1]octane hydrochloride (105 mg, 0.702 mmol) in i-PrOH (5 mL) was added TEA (171 mg, 1.69 mmol). The resulting mixture was stirred at 70° C. for 2 hrs. TLC showed the reaction was completed. The mixture was concentrated and the residue was purified by column (PE:EtOAc=6:1) to give the title compound (180 mg, yield 94%) as a white solid.

$^1$H NMR (300 MHz, CDCl$_3$): δ 6.70 (s, 1H), 4.44 (br 2H), 3.87 (br 2H), 3.15-3.11 (m, 2H), 2.43 (s, 3H), 1.97-1.93 (m, 2H), 1.77-1.70 (m, 2H).

Description 10

3-(6-Iodo-2-methoxypyrimidin-4-yl)-6-oxa-3-azabicyclo[3.1.1]heptane (D10)

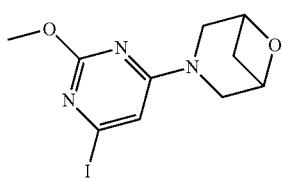 [SMILES: COc1nc(I)cc(N2CC3CC(C2)O3)n1]

To a solution of 4,6-diiodo-2-methoxy-pyrimidine (200 mg, 0.554 mmol) in EtOH (5 mL) was added 6-oxa-3-azabicyclo[3.1.1]heptane 4-methylbenzenesulfonate (150 mg, 0.554 mmol) and Et$_3$N (1 mL). The resulting mixture was refluxed for 2 hrs. The mixture was cooled to rt and concentrated. The residue was purified by column chromatography (PE: ethyl acetate=3:1) to give the title compound (145 mg, yield 78%) as a white solid.

$^1$H NMR (300 MHz, CDCl$_3$): δ 6.62 (s, 1H), 4.75-4.73 (m, 2H), 4.00-3.94 (m, 4H), 3.82-3.68 (m, 2H), 3.49-3.45 (m, 1H), 3.34-3.26 (m, 1H), 1.91-1.88 (m, 1H).

Description 11

3-(6-Iodo-2-methylpyrimidin-4-yl)-6-oxa-3-azabicyclo[3.1.1]heptane (D11)

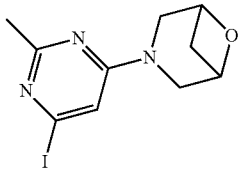

To a solution of 6-oxa-3-azabicyclo[3.1.1]heptane 4-methylbenzenesulfonate (250 mg, 0.922 mmol) in EtOH (5 mL) was added 4,6-diiodo-2-methylpyrimidine (383 mg, 1.11 mmol) and Et$_3$N (0.5 mL). The resulting mixture was refluxed for 3 hrs. The mixture was cooled to rt and concentrated. The residue was purified by column chromatography (PE:ethyl acetate=5:1) to give the title compound (230 mg, yield 79%) as colorless oil.

$^1$H NMR (300 MHz, CDCl$_3$): δ 6.76 (s, 1H), 4.75-4.73 (m, 2H), 4.03-3.91 (m, 1H), 3.80-3.62 (m, 2H), 3.50-3.40 (m, 1H), 3.33-3.26 (m, 1H), 2.50 (s, 3H), 1.91-1.88 (m, 1H).

Description 12

8-(6-iodo-2-methylpyrimidin-4-yl)-3-oxa-8-azabicyclo[3.2.1]octane (D12)

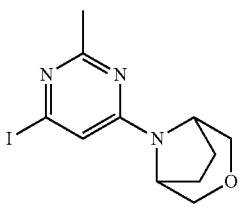 [SMILES: Cc1nc(I)cc(N2C3CCC2COC3)n1]

To a suspension of 4,6-diiodo-2-methylpyrimidine (0.5 g, 1.45 mmol) and 1,8-diazaspiro[4.5]decan-2-one hydrochloride (216 mg, 1.45 mmol) in EtOH/THF (8 mL/8 mL) was added DIPEA (561 mg, 4.35 mmol). The mixture was stirred at rt. for 2 days. The reaction mixture was concentrated. The residue was purified by column chromatography on silica gel (DCM:MeOH=20:1) to give title compound as a yellow solid (280 mg, yield: 58%).

LC-MS [mobile phase: from 80% water (0.1% FA) and 20% ACN (0.1% FA) to 5% water (0.1% FA) and 95% ACN (0.1% FA) in 2 min]: Rt=1.01 min; MS Calcd: 331 MS Found: 332 [M+H]$^+$.

Description 13

9-(6-iodo-2-methylpyrimidin-4-yl)-3,7-dioxa-9-azabicyclo[3.3.1]nonane (D13)

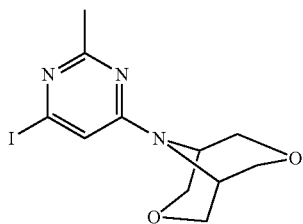 [SMILES: Cc1nc(I)cc(N2C3COCC2COC3)n1]

A mixture of 4,6-diiodo-2-methylpyrimidine (260 mg, 0.75 mmol), 3,7-dioxa-9-azabicyclo[3.3.1]nonane (88 mg, 0.68 mmol) and TEA (206 mg, 2.04 mmol) in DMSO (5 mL) was stirred at 60° C. for 6 hours. The mixture was diluted with $H_2O$ (20 mL) and extracted with EtOAc (20 mL×3). The extracts were combined and dried over $Na_2SO_4$. The organic phase was filtered and concentrated. The residue was purified by silica gel chromatography column (petroleum ether/EtOAc=10/1 to 2/1) to give the title compound (110 mg, 47%) as a white solid.

$^1$HNMR (400 MHz, $CDCl_3$): δ 6.72 (s, 1H), 4.79 (br 1H), 4.13-3.88 (m, 8H), 3.64 (br 1H), 2.46 (s, 3H).

Description 14

6-Bromo-5-methyl-1H-indazole (D14)

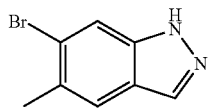

To a solution of 5-bromo-2,4-dimethylaniline (15.0 g, 75.0 mmol) in chloroform (150 mL) was added $Ac_2O$ (15.0, 150 mmol) under ice bath. KOAc (8.00 g, 82.5 mmol), 18-crown-6 (10.0 g, 37.5 mmol) and isoamyl nitrite (26.3 g, 225 mmol) were added. The mixture was refluxed for 36 hrs. The reaction mixture was concentrated and the residue was dissolved in EtOAc (500 mL). The organic solution was washed with water (100 mL), dried over $Na_2SO_4$ and concentrated. The residue was dissolved in THF (100 mL) and NaOH (4 M, 40.0 mL, 160 mmol) was added. The mixture was stirred at rt for 1 h. The solvent was removed under vacuum and the residue was partitioned between EtOAc (400 mL) and water (200 mL). The organic layer was washed with brine, dried over $Na_2SO_4$ and concentrated. The crude was purified by column chromatography (PE:EtOAc from 10:1 to 5:1) to give the title compound (5.1 g, yield 32%) as an orange solid.

$^1$H NMR (300 MHz, $CDCl_3$): δ 10.20 (br, 1H), 7.99 (s, 1H), 7.75 (s, 1H), 7.61 (s, 1H), 2.50 (s, 3H).

Description 15

6-Bromo-5-methyl-1-(tetrahydro-2H-pyran-2-yl)-1H-indazole (D15)

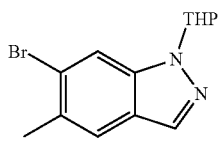

To a solution of 6-bromo-5-methyl-1H-indazole (5.10 g, 24.2 mmol) in dry DCM (120 mL) was added DHP (4.10 g, 48.4 mmol), TsOH (0.800 g, 4.80 mmol) and $Mg_2SO_4$ (5.0 g) at rt.

The reaction mixture was heated to 35° C. and stirred for an hour. The reaction mixture was filtered and the filtrate was washed with $Na_2CO_3$ (10%, 100 mL), dried over $Na_2SO_4$ and concentrated. The crude was purified by column chromatography (PE:EtOAc from 50:1 to 20:1) to give the title compound (6.0 g, yield 84%) as an orange solid.

$^1$H NMR (300 MHz, $CDCl_3$): δ 7.90 (s, 1H), 7.84 (s, 1H), 7.55 (s, 1H), 5.63 (dd, J=9.6, 3.0 Hz, 1H), 4.05-4.00 (m, 1H), 3.78-3.70 (m, 1H), 2.58-2.44 (m, 4H), 2.20-2.02 (m, 2H), 1.78-1.65 (m, 3H).

LCMS: [mobile phase: 5-95% ACN), Rt=2.19 min in 3 min; MS Calcd: 294; MS Found: 295 [M+H]$^+$.

Description 16

Tert-butyl 4-(5-methyl-1-(tetrahydro-2H-pyran-2-yl)-1H-indazol-6-yl)-5,6-dihydropyridine-1(2H)-carboxylate (D16)

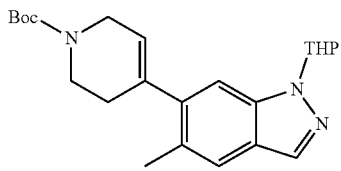

To a suspension of 6-bromo-5-methyl-1-(tetrahydro-2H-pyran-2-yl)-1H-indazole (5.50 g, 18.6 mmol), tert-butyl 4-(4,4,5,5-tetramethyl-1,3,2-dioxaborolan-2-yl)-5,6-dihydropyridine-1(2H)— carboxylate (6.90 g, 22.3 mmol) and $Na_2CO_3$ (4.90 g, 46.5 mmol) in dioxane (150 mL) and water (130 mL) was added Pd(dppf)$Cl_2$ (658 mg, 0.900 mmol). The mixture was degassed with $N_2$ for 3 times and then stirred at 80° C. overnight. The solvent was removed under vacuum and the residue was partitioned between EtOAc (300 mL) and water (200 mL). The combined organic layers were washed with brine, dried over $Na_2SO_4$ and concentrated. The crude was purified by column chromatography (PE:EtOAc=10:1) to give the title compound (7.3 g, yield 99%) as a slight brown solid.

$^1$H NMR (400 MHz, $CDCl_3$): δ 7.92 (s, 1H), 7.48 (s, 1H), 7.28 (s, 1H), 5.67 (dd, J=9.6, 2.8 Hz, 1H), 5.63 (br 1H), 4.07-4.01 (m, 3H), 3.78-3.70 (m, 1H), 3.67-3.64 (m, 2H), 2.62-2.53 (m, 1H), 2.45-2.39 (m, 2H), 2.34 (s, 3H), 2.18-2.12 (m, 1H), 2.07-2.02 (m, 1H), 1.81-1.73 (m, 2H), 1.69-1.61 (m, 1H), 1.52 (s, 9H).

Descriptions 17 and 18

Trans-tert-butyl 3-hydroxy-4-(5-methyl-1-(tetrahydro-2H-pyran-2-yl)-1H-indazol-6-yl)piperidine-1-carboxylate (D17 and D18)

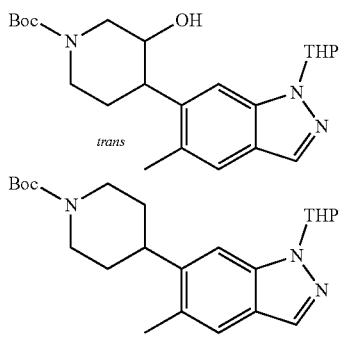

To a solution of tert-butyl 4-(5-methyl-1-(tetrahydro-2H-pyran-2-yl)-1H-indazol-6-yl)-5,6-dihydropyridine-1(2H)-carboxylate (6.00 g, 15.1 mmol) in dry THF (120 mL) was added BH$_3$-THF solution (1 M, 151 mL, 151 mmol) under N$_2$ and kept the internal temperature below 10° C. The mixture was warmed to rt and stirred overnight. After the reaction mixture was cooled to to 0° C., NaOH (aq, 2 M, 22.7 mL, 45.3 mmol) was added carefully and the internal temperature was kept below 10° C. Then, H$_2$O$_2$ (30%, 20.0 mL, 151 mmol) was added dropwise and the internal temperature was kept below 10° C. The mixture was stirred at 40° C. for an hour. The solvent was evaporated and EtOAc (50 mL×2) was added. The combined organic layers were washed with brine, dried over Na$_2$SO$_4$ and evaporated. The residue was purified by column chromatography (PE:EtOAc from 5:1 to 2:1) to give the title compound tert-butyl 3-hydroxy-4-(5-methyl-1-(tetrahydro-2H-pyran-2-yl)-1H-indazol-6-yl)piperidine-1-carboxylate (2.0 g of pure and 3.45 g with 80% purity) as a white solid.

$^1$H NMR (300 MHz, CDCl$_3$): δ 7.89 (s, 1H), 7.51 (s, 1H), 7.41 (s, 1H), 5.68-5.65 (m, 1H), 4.48-4.45 (m, 1H), 4.22 (br 1H), 4.02-4.00 (m, 1H), 3.96-3.89 (m, 1H), 3.80-3.71 (m, 1H), 3.03-2.95 (m, 1H), 2.83-2.68 (m, 2H), 2.60-2.50 (m, 1H), 2.47 (s, 3H), 2.20-2.10 (m, 1H), 2.06-2.02 (m, 1H), 1.94-1.62 (m, 6H), 1.51 (s, 9H).

To a solution of tert-butyl 4-(5-methyl-1-(tetrahydro-2H-pyran-2-yl)-1H-indazol-6-yl)-5,6-dihydropyridine-1(2H)-carboxylate (33.0 g, 83.0 mmol) in dry THF (300 mL) was added BH$_3$-THF (1 M, 332 mL, 332 mmol) at 10° C. The mixture was gradually warmed to rt and stirred overnight. The reaction mixture was cooled to 0° C. and NaOH (aq, 2 M, 125 mL, 249 mmol) was added carefully. H$_2$O$_2$ (30%, 87 mL, 830 mmol) was followed. The temperature was kept below 10° C. during the addition of NaOH and H$_2$O$_2$. The mixture was stirred for an hour at rt. Na$_2$SO$_3$ (10%, 100 mL) was added to the reaction mixture and stirred for 20 min. The organic layer was separated and the aqueous was extracted with EtOAc (100 mL×2). The combined organic layers were washed with brine, dried over Na$_2$SO$_4$ and evaporated. The crude was purified by column chromatography (PE:EtOAc from 3:1 to 1:1) to give tert-butyl 3-hydroxy-4-(5-methyl-1-(tetrahydro-2H-pyran-2-yl)-1H-indazol-6-yl)piperidine-1-carboxylate as major product (D17) (23 g, yield 67%) as a white solid and tert-butyl 4-(5-methyl-1-(tetrahydro-2H-pyran-2-yl)-1H-indazol-6-yl)piperidine-1-carboxylate as minor product (D18) (6.7 g, yield 20%) as a slight brown solid.

D17: $^1$H NMR (300 MHz, CDCl$_3$): δ 7.90 (s, 1H), 7.48 (s, 1H), 7.34 (s, 1H), 5.68 (dd, J=9.6 Hz, 2.7 Hz, 1H), 4.33-4.28 (m, 2H), 4.06-4.02 (m, 1H), 3.80-3.72 (m, 1H), 3.00-2.82 (m, 3H), 2.65-2.51 (m, 1H), 2.44 (s, 3H), 2.22-2.11 (m, 1H), 2.08-2.00 (m, 1H), 1.88-1.80 (m, 2H), 1.77-1.63 (m, 5H), 1.51 (s, 9H).

Description 19

5-Methyl-6-(piperidin-4-yl)-1H-indazole hydrochloride (D19)

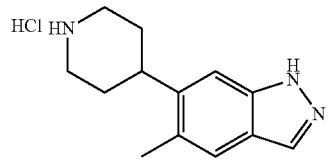 [SMILES: Cl ; Cc1cc2cn[nH]c2cc1C1CCNCC1]

tert-Butyl 4-(5-methyl-1-(tetrahydro-2H-pyran-2-yl)-1H-indazol-6-yl)piperidine-1-carboxylate (1.0 g, 2.5 mmol) was dissolved in HCl/MeOH (5 mol/L, 10 mL). Then, the mixture was stirred for 6 hrs. The mixture was concentrated under reduced pressure to afford the title compound (820 mg, yield >100%) as a light yellow solid used for next step without purification.

LC-MS: 5-95% ACN, Rt=1.13 min, MS Calcd.: 215, MS Found: 216 [M+H]$^+$.

Description 20

5-methyl-6-(piperidin-4-yl)-1H-indazole (D20)

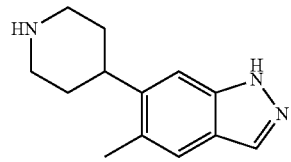 [SMILES: Cc1cc2cn[nH]c2cc1C1CCNCC1]

HCl/MeOH (5M, 200 mL) was added to a solution of tert-butyl 4-(5-methyl-1-(tetrahydro-2H-pyran-2-yl)-1H-indazol-6-yl)piperidine-1-carboxylate (55.4 g, 138.8 mmol) in MeOH (150 mL). The reaction was stirred at r.t overnight. The solution was concentrated and then Na$_2$CO$_3$ aq. and NaOH aq. were added until pH>12. The mixture was filtered and the solid was dried to give product as a white solid. (29.3 g, yield=98%)

LC-MS [mobile phase: from 90% water (0.1% FA) and 10% ACN (0.1% FA) to 5% water (0.1% FA) and 95% ACN (0.1% FA) in 2.0 min]: Rt=0.85 min; MS Calcd.: 215, MS Found: 216 [M+H]$^+$.

Description 21

Tert-Butyl 4-(5-methyl-1H-indazol-6-yl)piperidine-1-carboxylate (D21)

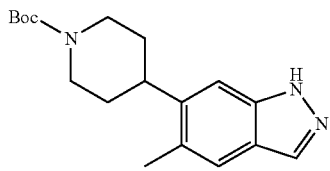 [SMILES: Cc1cc2cn[nH]c2cc1C1CCN(C(=O)OC(C)(C)C)CC1]

To a solution of 5-methyl-6-(piperidin-4-yl)-1H-indazole hydrochloride (600 mg, 2.39 mmol) in CH$_3$OH (10 mL) and H$_2$O (2 mL) was added KOH (268 mg, 4.78 mmol) and (Boc)$_2$O (781 mg, 3.58 mmol) under ice bath. The reaction mixture was stirred at rt for 2 hrs. The reaction mixture was diluted with water (50 mL) and extracted with EtOAc (50 mL×3). The combined organic layers were dried over Na$_2$SO$_4$ and concentrated. The residue was purified by column chromatograph (PE:EtOAc from 10:1 to 4:1) to give the title compound (353 mg, yield 47%) as a yellow oil.

$^1$H NMR (300 MHz, CDCl$_3$): δ 10.15 (br 1H), 7.95 (s, 1H), 7.53 (s, 1H), 7.29 (s, 1H), 4.34 (br 2H), 2.95-2.81 (m, 3H), 2.45 (s, 3H), 1.86-1.81 (m, 2H), 1.69-1.61 (m, 2H), 1.51 (s, 9H).

Description 22

6-(1-(3-deuterooxetan-3-yl)piperidin-4-yl)-5-methyl-1H-indazole (D22)

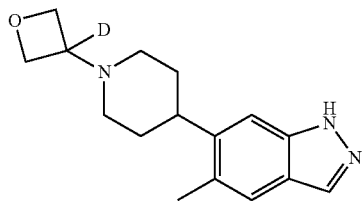 [SMILES: [2H]C1(N2CCC(c3cc4[nH]ncc4cc3C)CC2)COC1]

NaBD$_3$CN (472 mg, 7.17 mmol) was added to a mixture of 5-methyl-6-(piperidin-4-yl)-1H-indazole (800 mg, 3.72 mmol), oxetan-3-one (672 mg, 9.33 mmol), AcOH (80 mg) and 4Å molecular sieves (672 mg) in CH$_2$Cl$_2$/MeOH (16 mL/4 mL) under Ar at 0° C. The reaction was stirred at room temperature overnight. The reaction mixture was filtered and the filtrate was washed with aq. NaHCO$_3$ (2×50 ml) and brine, dried over anhydrous Na$_2$SO$_4$, filtered. The filtrate was concentrated and the residue was purified by column chromatography (eluent: CH$_2$Cl$_2$:MeOH=50:1 to 15:1, 20 g of silica gel) to afford desired product as a white solid (710 mg, yield: 70%).

LC-MS [mobile phase: from 90% water (0.1% FA) and 10% ACN (0.1% FA) to 5% water (0.1% FA) and 95% ACN (0.1% FA) in 2.0 min]: Rt=0.87 min; MS Calcd: 272, MS Found: 273 [M+H]$^+$.

Description 23

5-Methyl-6-(1-(oxetan-3-yl)piperidin-4-yl)-1H-indazole (D23)

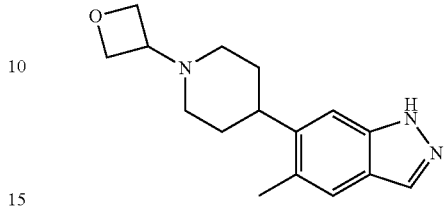

To a solution of 5-methyl-6-(piperidin-4-yl)-1H-indazole hydrochloride (820 mg of crude, 2.50 mmol) in DCE (15 mL) was added oxetan-3-one (1.80 g, 25.0 mmol). The mixture was stirred at room temperature for 40 min. Then the mixture was cooled under ice bath and NaBH$_3$CN (473 mg, 7.50 mmol) was added to the mixture. The mixture was warmed to room temperature and stirred for 2 hrs. Then the reaction mixture was poured into Na$_2$CO$_3$ aqueous solution (10%, 100 mL) and stirred for 15 min. Then the mixture was extracted with EtOAc (30 mL×3). The combined organic layers were washed with brine, dried over Na$_2$SO$_4$ and concentrated. The residue was purified by column chromatography (DCM:MeOH=40:1) to afford the title compound (473 mg, yield 70%) as a white solid $^1$H NMR (300 MHz, CDCl$_3$): δ 10.11 (br 1H), 7.96 (s, 1H), 7.53 (s, 1H), 7.38 (s, 1H), 4.72-4.69 (m, 4H), 3.61-3.52 (m, 1H), 2.96-2.93 (m, 2H), 2.88-2.78 (m, 1H), 2.44 (s, 3H), 2.06-1.98 (m, 2H), 1.90-1.82 (m, 4H).

LC-MS [mobile phase: 5-95% Acetonitrile in 2.5 min], Rt=1.37 min; MS Calcd: 271; MS Found: 272 [M+H]$^+$.

Description 24

5-methyl-6-(1-(tetrahydrofuran-3-yl)piperidin-4-yl)-1H-indazole (D24)

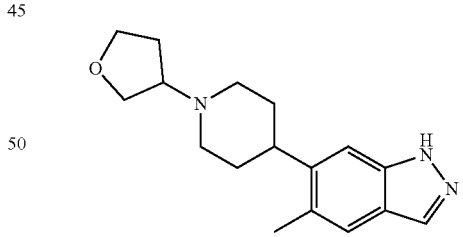

To a stirred mixture of 5-methyl-6-(piperidin-4-yl)-1H-indazole (900 mg, 4.18 mmol), dihydrofuran-3(2H)-one (900 mg, 10.45 mmol), 4 Å molecular sieves (747 mg) in MeOH/CH$_2$Cl$_2$ (9 mL/36 mL) at 0° C. were added AcOH (88 mg, 1.463 mmol) and NaBH$_3$CN (525 mg, 8.36 mmol). The reaction was warmed to room temperature and stirred overnight. The reaction mixture was filtered and the filtrate was washed with aqueous NaHCO$_3$ (10 mL), dried, filtered. The filtrate was concentrated and the residue was purified by column chromatography (eluent: PE:EtOAc=1:1, followed by CH$_2$Cl$_2$:MeOH=20:1) afforded desired product as a white solid (1.125 g, yield: 94%).

LC-MS [mobile phase: from 90% water (0.1% FA) and 10% ACN (0.1% FA) to 5% water (0.1% FA) and 95% ACN (0.1% FA) in 2.0 min]: Rt=0.29 min; MS Calcd: 285; MS Found: 286 [M+H]⁺.
¹H NMR (400 MHz, DMSO-d₆) δ 12.80 (br 1H), 7.90 (s, 1H), 7.50 (s, 1H), 7.30 (s, 1H), 3.85-3.78 (m, 2H), 3.70-3.61 (m, 2H), 3.13-3.11 (m, 2H), 2.93 (brs, 1H), 2.83-2.81 (m, 1H), 2.39 (s, 3H), 2.36-2.31 (m, 2H), 2.06-2.04 (m, 1H), 1.80-1.68 (m, 5H).

Description 25

(cis)-tert-Butyl 3-fluoro-4-(5-methyl-1-(tetrahydro-2H-pyran-2-yl)-1H-indazol-6-yl) piperidine-1-carboxylate (D25)

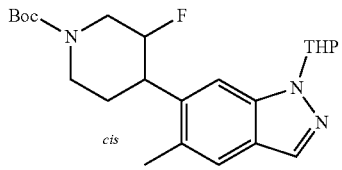

To a solution of (trans)-tert-Butyl 3-hydroxy-4-(5-methyl-1-(tetrahydro-2H-pyran-2-yl)-1H-indazol-6-yl)piperidine-1-carboxylate (24.5 g, 59.0 mmol) in dry DCM (200 mL) was added DAST (38.0 g, 236 mmol) under N₂ at −65° C. The mixture was gradually warmed to rt and stirred for 2 hrs. The reaction mixture was carefully poured into Na₂CO₃ aqueous solution (10%, 300 mL) and stirred for 20 min. The organic layer was separated and the aqueous was extracted with DCM (250 mL×2). The combined organic layers were washed with brine, dried over Na₂SO₄ and evaporated. The crude was purified by column chromatography (PE:EtOAc=10:1) to give the title compound (11.8 g, yield 48%) as a white solid.
¹H NMR (400 MHz, CDCl₃): δ 7.92 (s, 1H), 7.52 (s, 1H), 7.41 (s, 1H), 5.74-5.67 (m, 1H), 4.80-4.59 (m, 2H), 4.21 (br 1H), 4.07-3.99 (m, 1H), 3.80-3.71 (m, 1H), 3.25-3.19 (m, 1H), 2.89-2.79 (m, 2H), 2.65-2.51 (m, 1H), 2.45 (s, 3H), 2.19-2.15 (m, 1H), 2.15-2.04 (m, 1H), 1.93-1.88 (m, 1H), 1.80-1.74 (m, 5H), 1.52 (s, 9H).
LCMS: 5-95% ACN, Rt=2.25 min in 3 min; MS Calcd: 417; MS Found: 418 [M+H]⁺.

Description 26

((cis)-6-(3-Fluoropiperidin-4-yl)-5-methyl-1-(tetrahydro-2H-pyran-2-yl)-1H-indazole (D26)

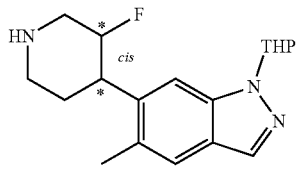

To a solution of (cis)-tert-butyl 3-fluoro-4-(5-methyl-1-(tetrahydro-2H-pyran-2-yl)-1H-indazol-6-yl) piperidine-1-carboxylate (1.60 g, 3.84 mmol) in CH₃OH (10 mL) was added HCl/CH₃OH (5 M, 20 mL). The mixture was stirred at 0° C. for 1 h. The reaction mixture was poured into sat.NaHCO₃ solution (200 mL). The mixture was extracted with EtOAc (50 mL×3). The combined organic layers were washed with brine (50 mL), dried over Na₂SO₄ and concentrated. The residue was purified by column C18 (5%-60% ACN in water) to give the title compound (600 mg, yield 49%) as a yellow oil.
LCMS [mobile phase: 5-95% Acetonitrile in 2.5 min]: Rt=1.46 min; MS Calcd: 317; MS Found: 318 [M+H]⁺.

Description 27

(cis)-6-(3-Fluoropiperidin-4-yl)-5-methyl-1H-indazole Hydrochloride (D27)

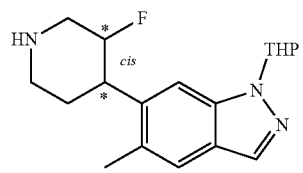

A mixture of (cis)-tert-butyl 3-fluoro-4-(5-methyl-1-(tetrahydro-2H-pyran-2-yl)-1H-indazol-6-yl) piperidine-1-carboxylate (2.50 g, 6.00 mmol) in HCl/dioxane (6 mol/L, 40 mL) was stirred at rt for 6 hrs. The reaction mixture was cooled to 0° C. and filtered. The solid was washed with cold 1,4-dioxane (5 mL) to get the title compound (1.4 g, yield 100%) as a white solid which was used for next step directly.
LC-MS: 5-95% ACN, Rt=1.73 min; MS Calcd.: 233, MS Found: 234 [M+H]⁺.

Description 28

(cis)-6-(3-Fluoro-1-(oxetan-3-yl)piperidin-4-yl)-5-methyl-1H-indazole (D28)

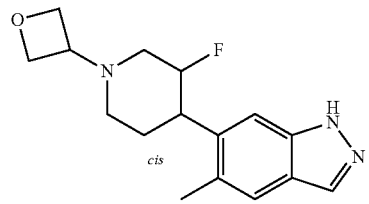 [SMILES: Cc1cc2cn[nH]c2cc1C1CCN(C2COC2)CC1F]

To a solution of (cis)-6-(3-fluoropiperidin-4-yl)-5-methyl-1H-indazole hydrochloride (1.40 g, 6.00 mmol) and oxetan-3-one (2.16 g, 30.0 mmol) in methanol (5 mL) and 1,2-dichloroethane (50 mL) was added NaBH₃CN (1.13 g, 18.0 mmol). Then the mixture was stirred at rt for 3 hrs. The reaction mixture was diluted with water (100 mL) and extracted with dichloromethane (100 mL×3). The combined organic layers were dried over MgSO₄, filtered and concentrated. The crude was purified by column chromatography (DCM:MeOH=30:1) to give the title compound (1.0 g, yield 57.6%) as a white solid.
LC-MS: 5%-95% ACN, Rt=1.85 min; MS Calcd.: 289, MS Found: 290 [M+H]⁺.

Description 29

(cis)-tert-Butyl 3-fluoro-4-(5-methyl-1H-indazol-6-yl)piperidine-1-carboxylate (D29)

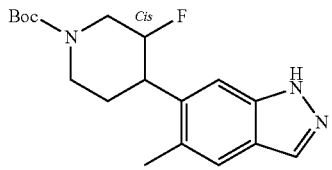 [SMILES: Cc1cc2cn[nH]c2cc1C1CCN(C(=O)OC(C)(C)C)CC1F]

A mixture of (cis)-tert-Butyl 3-fluoro-4-(5-methyl-1-(tetrahydro-2H-pyran-2-yl)-1H-indazol-6-yl)piperidine-1-carboxylate (6.50 g, 15.6 mmol) in MeOH (80 mL) was added HCl/MeOH (8 mol/L, 40 mL). The mixture was stirred at rt for 3 hrs. The reaction mixture was concentrated to give the crude title compound (6.0 g) as yellow oil which was used for next step directly. To a solution of (cis)-6-(3-fluoropiperidin-4-yl)-5-methyl-1H-indazole hydrochloride (6.0 g, crude) in $CH_3OH$ (80 mL) was added KOH solution (2.60 g, 46.4 mmol, in 40 mL of $H_2O$ and $(Boc)_2O$ (4.08 g, 18.7 mmol) under ice bath. The reaction mixture was stirred at rt overnight. The reaction mixture was diluted with water (40 mL) and extracted with EtOAc (200 mL×3). The combined organic layers were concentrated. The residue was purified by column chromatograph (PE:EtOAc from 10:1 to 5:1) to give the title compound (4.7 g) as a yellow oil.

$^1$H NMR (300 MHz, $CDCl_3$): δ 10.32 (s, 1H), 7.97 (s, 1H), 7.56 (s, 1H), 7.39 (s, 1H), 4.79-4.56 (m, 2H), 4.29-4.16 (m, 1H), 3.26-3.15 (m, 1H), 2.91-2.78 (m, 2H), 2.47 (s, 3H), 1.93-1.62 (m, 2H), 1.51 (s, 9H).

Descriptions 30 and 31

(cis)-tert-Butyl 3-fluoro-4-(5-methyl-1H-indazol-6-yl)piperidine-1-carboxylate (Peak 1 and Peak 2)

(cis)-tert-Butyl 3-fluoro-4-(5-methyl-1H-indazol-6-yl)piperidine-1-carboxylate (4.70 g, 14.1 mmol, 85% purity by H NMR) was separated by chiral prep. HPLC (Chiralpak IB 5 μm 20×250 nm, $CO_2$:i-PrOH=80:20, Flow rate: 20 mL/min, 205 nm, Temperature=30° C.) to give the peak 1 (D30, 1.5 g, yield 38%) as a white solid and peak 2 (D31, 1.3 g, yield 33%) as a white solid.

Peak 1 (D30)

$^1$H NMR (300 MHz, $CDCl_3$): δ 9.95 (s, 1H), 7.97 (s, 1H), 7.56 (s, 1H), 7.39 (s, 1H), 4.79-4.51 (m, 2H), 4.23-4.15 (m, 1H), 3.27-3.15 (m, 1H), 2.95-2.78 (m, 2H), 2.47 (s, 3H), 1.98-1.88 (m, 1H), 1.72-1.64 (m, 1H), 1.51 (s, 9H).

Chiral HPLC: Chiralpak IB 5 μm 4.6×250 mm, Phase: Hex/IPA=80/20, flowrate: 1 mL/min, temperature: 30° C., Rt: 5.897 min, 100% ee.

Peak 2 (D31)

$^1$H NMR (300 MHz, $CDCl_3$): δ 9.99 (br 1H), 7.97 (s, 1H), 7.56 (s, 1H), 7.39 (s, 1H), 4.80-4.52 (m, 2H), 4.26-4.15 (m, 1H), 3.26-3.14 (m, 1H), 2.91-2.76 (m, 2H), 2.47 (s, 3H), 1.94-1.89 (m, 1H), 1.74-1.66 (m, 1H), 1.51 (s, 9H).

Chiral HPLC: Chiralpak IB 5 μm 4.6×250 mm, Phase: Hex/IPA=80/20, flowrate: 1 mL/min, temperature: 30° C., Rt: 7.217 min, 99.7% ee.

Description 32

Cis-tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (Peak 1) (D32)

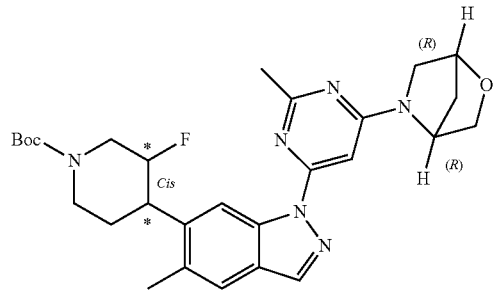

A mixture of cis-tert-butyl 3-fluoro-4-(5-methyl-1H-indazol-6-yl)piperidine-1-carboxylate (Peak 1, 50 mg, 0.15 mmol), (1R,4R)-5-(6-iodo-2-methylpyrimidin-4-yl)-2-oxa-5-azabicyclo[2.2.1]heptane (70 mg, 0.22 mmol), CuI (10 mg), $K_3PO_4$ (212 mg, 1.0 mmol) in toluene/THF (10 mL) was degassed before DMEDA (10 mg) was added. The reaction mixture was then stirred at 90° C. for 1 hour. The reaction was then concentrated and the residue was purified by silica gel chromatography eluted with (EtOAc:Petroleum Ether=1:3) to give the product as a white solid (85 mg).

LC-MS [mobile phase: from 80% water (0.1% FA) and 20% ACN (0.1% FA) to 5% water (0.1% FA) and 95% ACN (0.1% FA) in 9.0 min]: Rt=7.09 min; MS Calcd.: 522, MS Found: 523 $[M+H]^+$.

Description 33

Cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hydrochloride (D33)

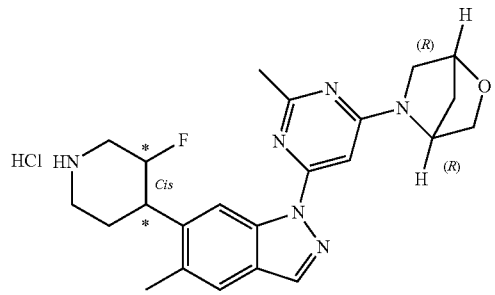

A solution of Cis-(tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 1, 85 mg, 0.15 mmol) in HCl/EtOAc (5 mL, 1

N) was stirred at rt for 4 hours, then concentrated to give the product as an off-white solid (65 mg).

Description 34

Cis-ethyl 2-(4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidin-1-yl)acetate (D34)

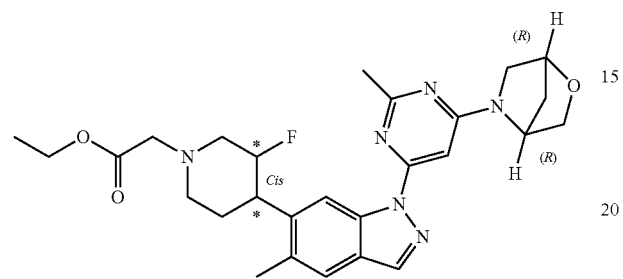

Ethyl 2-bromoacetate (51 mg, 0.3 mmol) was slowly added to the solution of Cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride (from Peak 1, 65 mg, 0.15 mmol) and Et$_3$N (0.5 mL) in DMF (5 mL) and the reaction was stirred at rt overnight. More Ethyl 2-bromoacetate (51 mg, 0.3 mmol) in DMF (0.5 mL) was added and stirred for 1 hour. The reaction was then diluted with EtOAc (50 mL) and washed with brine (50 mL×3). The solution was dried and concentrated. The residue was purified by prep-TLC (EtOAc/PE=1/2) to give the product as a colorless oil (60 mg, 79% yield).

LC-MS [mobile phase: from 90% water (0.1% FA) and 10% ACN (0.1% FA) to 5% water (0.1% FA) and 95% ACN (0.1% FA) in 2.0 min]: Rt=1.61 min; MS Calcd.: 508, MS Found: 509 [M+H]$^+$.

Description 35

Cis-tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (Peak 2) (D35)

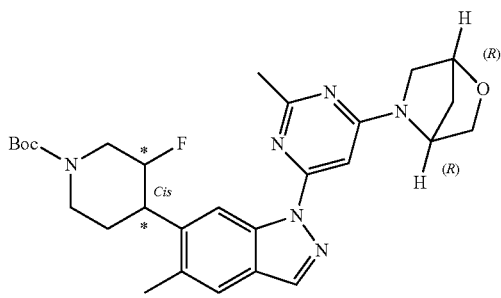

A mixture of Cis-tert-butyl 3-fluoro-4-(5-methyl-1H-indazol-6-yl)piperidine-1-carboxylate (Peak 2, 50 mg, 0.15 mmol), (1R,4R)-5-(6-iodo-2-methylpyrimidin-4-yl)-2-oxa-5-azabicyclo[2.2.1]heptane (70 mg, 0.22 mmol), CuI (10 mg), K$_3$PO$_4$ (212 mg, 1.0 mmol) in toluene/THF (10 mL) was degassed before DMEDA (10 mg) was added. The reaction was then stirred at 90° C. for 1 hour. The reaction was then concentrated and the residue was purified by silica gel chromatography eluted with (EtOAc:Petroleum Ether=1:3) to give the product as a white solid (85 mg).

Description 36

Cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hydrochloride (D36)

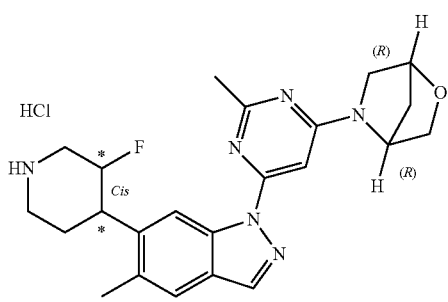

A solution of Cis-(tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 2, 85 mg, 0.15 mmol) in HCl/EtOAc (5 mL, 1 N) was stirred at rt for 4 hours. The reaction was then concentrated to give the product as an off-white solid (65 mg).

Description 37

Cis-ethyl 2-(4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidin-1-yl)acetate (D37)

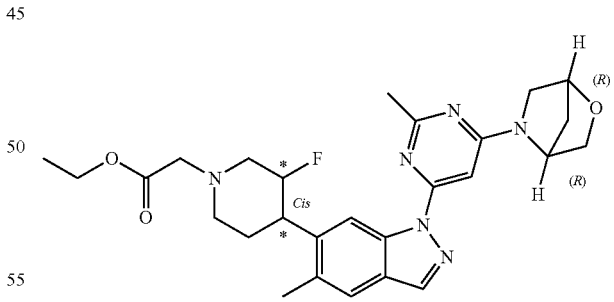

Ethyl 2-bromoacetate (51 mg, 0.3 mmol) was slowly added to the solution of cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride (from Peak 2, 65 mg, 0.15 mmol) and Et$_3$N (0.5 mL) in DMF (5 mL) and the reaction was stirred at rt overnight. More Ethyl 2-bromoacetate (51 mg, 0.3 mmol) in DMF (0.5 mL) was added and stirred for 1 hour. The reaction was then diluted with EtOAc (50 mL) and washed with brine (50 mL×3). The solution was dried and concentrated. The residue was purified by prep-TLC (EtOAc/PE=1/2) to give the product as a colorless oil (51 mg, 67% yield)

Description 38

Tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidine-1-carboxylate (D38)

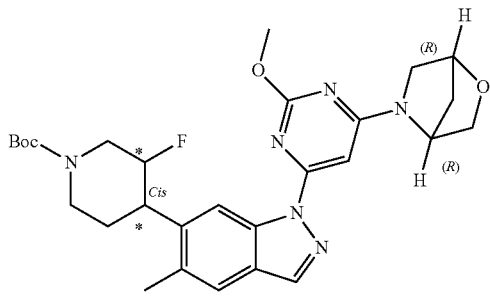

Tert-butyl 3-fluoro-4-(5-methyl-1H-indazol-6-yl)piperidine-1-carboxylate (Peak 1, 50 mg, 0.15 mmol) and (1R,4R)-5-(6-iodo-2-methoxypyrimidin-4-yl)-2-oxa-5-azabicyclo[2.2.1]heptane (56 mg, 0.17 mmol) were dissolved in toluene/THF (5 mL/1 mL), $N^1,N^2$-dimethylethane-1,2-diamine (17 mg, 0.20 mmol), CuI (29 mg, 0.15 mmol) and $K_3PO_4$ (70 mg, 0.3 mmol) were added to the solution. The mixture was stirred at 90° C. for 2 hours under $N_2$. The mixture was diluted with aq.$NH_3.H_2O$ (50 mL) and extracted with EtOAc (60 mL×2). The organic layer was concentrated and the residue was purified by column chromatography (PE:EtOAc=2:1) to give target product as a white solid (66 mg, yield: 84%).

LC-MS [mobile phase: 40% water (0.1% FA) and 60% ACN (0.1% FA) to 5% water (0.1% FA) and 95% ACN (0.1% FA) in 2.0 min]: Rt=1.71 min; MS Calcd.: 538, MS Found: 539 [M+H]+.

Description 39

(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane HCl Salt (D39)

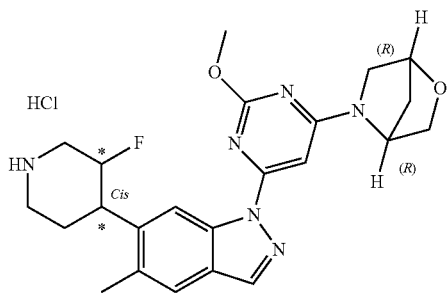

tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidine-1-carboxylate (from Peak 1, 66 mg, 0.12 mmol) was dissolved in EtOAc (4 mL), HCl-EtOAc (2 mL, 3.5 mol/L) was slowly dropped to the solution under ice bath. The mixture was stirred at rt for 30 min. The solution was concentrated and the target product was obtained as a white solid (crude, 80 mg).

LC-MS [mobile phase: 70% water (0.1% FA) and 30% ACN (0.1% FA) to 5% water (0.1% FA) and 95% ACN (0.1% FA) in 2.0 min]: Rt=0.67 min; MS Calcd.: 438, MS Found: 439 [M+H]+.

Description 40

Ethyl 2-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)acetate (D40)

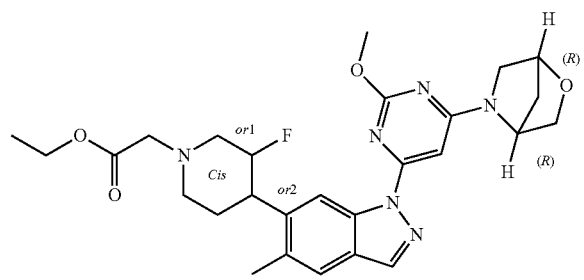

(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane HCl salt (from Peak 1, 80 mg, crude product obtained in Description 62-2) was dissolved in DMF (2 mL), $Et_3N$ (52 mg, 0.51 mmol) and ethyl 2-bromoacetate (57 mg, 0.34 mmol) were added to the solution under ice bath and the reaction was stirred at Rt for 2 hours. Water (20 mL) was added into the solution and the mixture was extracted with EtOAc (50 mL×2). The organic layer was dried over anhydrous $Na_2SO_4$ and concentrated to give target product as a colorless oil (60 mg, yield: 95%).

LC-MS [mobile phase: 80% water (0.1% FA) and 20% ACN (0.1% FA) to 5% water (0.1% FA) and 95% ACN (0.1% FA) in 2.0 min]: Rt=1.59 min; MS Calcd.: 524, MS Found: 525 [M+H]+.

Description 41

Tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidine-1-carboxylate (D41)

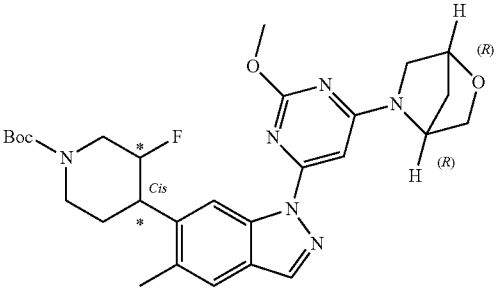

Tert-butyl 3-fluoro-4-(5-methyl-1H-indazol-6-yl)piperidine-1-carboxylate (Peak 2, 50 mg, 0.15 mmol) and (1R,4R)-5-(6-iodo-2-methoxypyrimidin-4-yl)-2-oxa-5-azabicyclo[2.2.1]heptane (56 mg, 0.17 mmol) were dissolved in toluene/THF (5 mL/1 mL), N',N²-dimethylethane-1,2-diamine (17 mg, 0.20 mmol), CuI (29 mg, 0.15 mmol) and K₃PO₄ (70 mg, 0.3 mmol) were added to the solution. The mixture was stirred at 90° C. for 2 hours under N₂. The mixture was diluted with aq. NH₃.H₂O (50 mL) and the mixture was extracted with EtOAc (60 mL×2). The organic layer was concentrated and the residue was purified by column chromatography (PE:EtOAc=2:1) to give target product as a white solid (75 mg, yield: 93%).

LC-MS [mobile phase: 40% water (0.1% FA) and 60% ACN (0.1% FA) to 5% water (0.1% FA) and 95% ACN (0.1% FA) in 2.0 min]: Rt=1.71 min; MS Calcd.: 538, MS Found: 539 [M+H]⁺.

Description 42

(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane HCl Salt (D42)

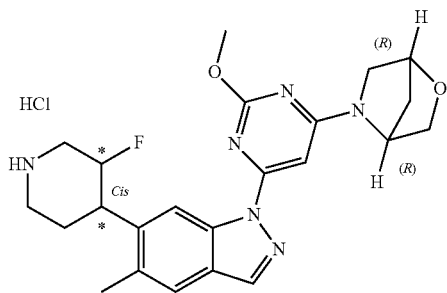

Tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidine-1-carboxylate (from Peak 2, 70 mg, 0.13 mmol) was dissolved in EtOAc (4 mL), HCl.EtOAc (2 mL, 3.5 mol/L) was slowly dropped to the solution under ice bath. The mixture was stirred at Rt for 30 min. The solution was concentrated and the target product was obtained as a white solid (crude, 90 mg).

LC-MS [mobile phase: 70% water (0.1% FA) and 30% ACN (0.1% FA) to 5% water (0.1% FA) and 95% ACN (0.1% FA) in 2.0 min]: Rt=0.76 min; MS Calcd.: 438, MS Found: 439 [M+H]⁺.

Description 43

Ethyl 2-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)acetate (D43)

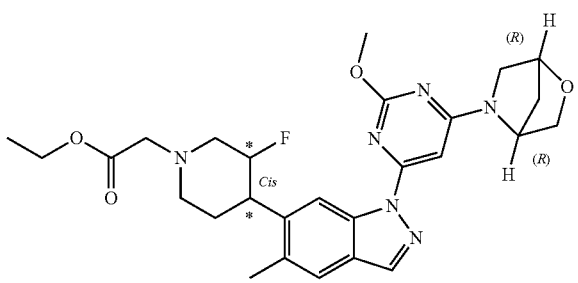

(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (from Peak 2, 90 mg, crude product from Description 62-5) was dissolved in DMF (2 mL), Et₃N (58 mg, 0.57 mmol) and ethyl 2-bromoacetate (57 mg, 0.34 mmol) were was added to the solution under ice bath. The mixture was stirred at Rt for 2 hours. Water (20 mL) was added into the solution and the mixture was extracted with EtOAc (50 mL×2). The organic layer was dried with anhydrous Na₂SO₄ and concentrated to give target product as a colorless oil (80 mg, yield: 81%).

LC-MS [mobile phase: 80% water (0.1% FA) and 20% ACN (0.1% FA) to 5% water (0.1% FA) and 95% ACN (0.1% FA) in 2.0 min]: Rt=1.55 min; MS Calcd.: 524, MS Found: 525 [M+H]⁺.

Description 44

Cis-tert-butyl 4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (from Peak 1) (D44)

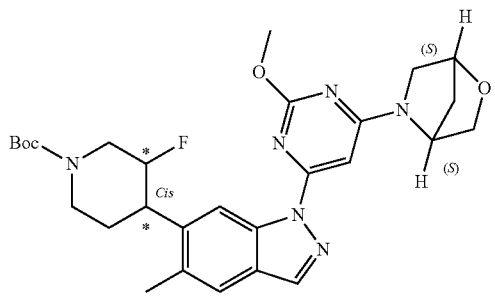

A mixture of cis-tert-butyl 3-fluoro-4-(5-methyl-1H-indazol-6-yl)piperidine-1-carboxylate (Peak 1, 50 mg, 0.15 mmol), (1S,4S)-5-(6-iodo-2-methoxypyrimidin-4-yl)-2-oxa-5-azabicyclo[2.2.1]heptane (60 mg, 0.18 mmol), CuI (29 mg, 0.15 mmol), K₃PO₄ (67 mg, 0.31 mmol) in toluene/THF (5 mL/1 mL) was degassed before DMEDA (26 mg, 0.30 mmol) was added. The reaction was then stirred at 80° C. for 3 hour. EtOAc (15 mL) was added and the resulting mixture was washed with sat. NH₄Cl (15 mL) and brine (15 mL). The organic solution was dried over anhydrous Na₂SO₄ and concentrated. The residue was purified by silica gel chromatography eluted with (silica del: 2 g, PE:EtOAc=2:1) to give the product as a white solid (68 mg, yield: 84%).

LC-MS [mobile phase: from 90% water (0.1% FA) and 10% ACN (0.1% FA) to 5% water (0.1% FA) and 95% ACN (0.1% FA) in 9.0 min]: Rt=6.90 min; MS Calcd.: 538, MS Found: 539 [M+H]⁺.

Description 45

Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane Hydrochloride (from Peak 1) (D45)

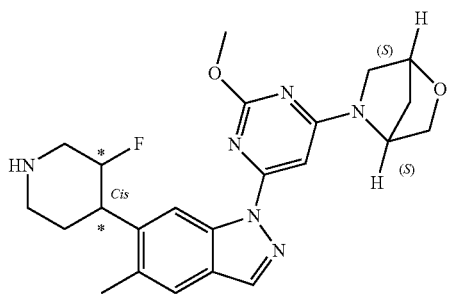

To a solution of Cis-(tert-butyl-4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (from Peak 1, 67 mg, 0.12 mmol) in EtOAc (4 mL) was dropwise added HCl/EtOAc (3 N, 2 mL), The reaction was stirred at rt for 60 min. The reaction suspension was concentrated to give the product as a white solid (58 mg), which was used in next step without further purification.

LC-MS [mobile phase: from 90% water (0.1% FA) and 10% ACN (0.1% FA) to 5% water (0.1% FA) and 95% ACN (0.1% FA) in 2.0 min]: Rt=1.16 min; MS Calcd.: 438, MS Found: 439 [M+H]⁺.

Description 46

Cis-ethyl 2-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl) acetate (from Peak 1) (D46)

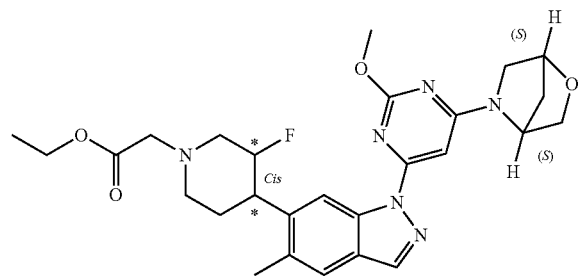

Ethyl 2-bromoacetate (65 mg, 0.39 mmol) was slowly added to the solution of Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane hydrochloride (from Peak 1, 57 mg, 0.13 mmol) and Et₃N (66 mg, 0.65 mmol) in DMF (2 mL) and the reaction was stirred at rt for 60 min. EtOAc (20 mL) was added and the resulting mixture was washed with brine (50 mL). The solution was dried and concentrated. The residue was purified by prep-TLC (EtOAc/PE=1/1) to give the product as a white solid (54 mg).

LC-MS [mobile phase: from 90% water (0.1% FA) and 10% ACN (0.1% FA) to 5% water (0.1% FA) and 95% ACN (0.1% FA) in 2.0 min]: Rt=1.39 min; MS Calcd.: 524, MS Found: 525 [M+H]⁺.

Description 47

Cis-tert-butyl 4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (from Peak 2) (D47)

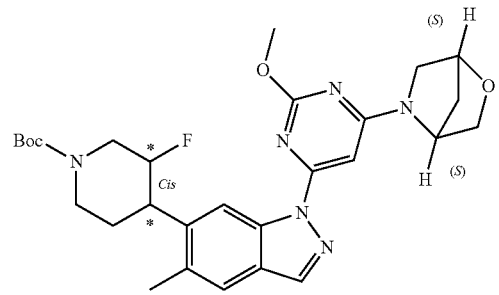

A mixture of Cis-tert-butyl 3-fluoro-4-(5-methyl-1H-indazol-6-yl)piperidine-1-carboxylate (Peak 2, 50 mg, 0.15 mmol), (1S,4S)-5-(6-iodo-2-methoxypyrimidin-4-yl)-2-oxa-5-azabicyclo[2.2.1]heptane (60 mg, 0.18 mmol), CuI (29 mg, 0.15 mmol), K₃PO₄ (67 mg, 0.31 mmol) in toluene/THF (5 mL/1 mL) was degassed before DMEDA (26 mg, 0.30 mmol) was added. The reaction was then stirred at 80° C. for 3 hour. EtOAc (15 mL) was added and the resulting mixture was washed with sat. NH₄Cl (15 mL) and brine (15 mL). The organic solution was dried over anhydrous Na₂SO₄ and concentrated. The residue was purified by silica gel chromatography eluted with (silica del: 2 g, PE:EtOAc=2:1) to give the product as a white solid (75 mg, yield: 92%).

LC-MS [mobile phase: from 90% water (0.1% FA) and 10% ACN (0.1% FA) to 5% water (0.1% FA) and 95% ACN (0.1% FA) in 2.0 min]: Rt=1.64 min; MS Calcd.: 538, MS Found: 539 [M+H]⁺.

Description 48

Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane Hydrochloride (from Peak 2) (D48)

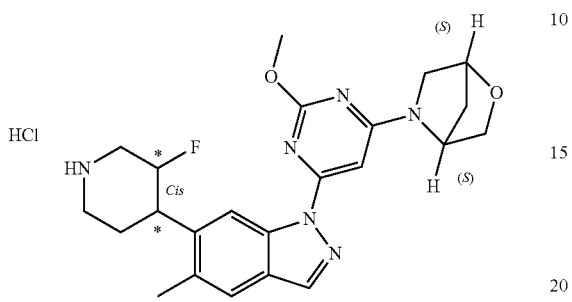

To a solution of Cis-(tert-butyl-4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (from Peak 2, 74 mg, 0.14 mmol) in EtOAc (4 mL) was drop-wise added HCl/EtOAc (3 N, 2 mL), The reaction was stirred at Rt for 60 min. The reaction suspension was concentrated to give the product as a white solid (65 mg), which was used in next step without further purification.

LC-MS [mobile phase: from 90% water (0.1% FA) and 10% ACN (0.1% FA) to 5% water (0.1% FA) and 95% ACN (0.1% FA) in 2.0 min]: Rt=0.99 min; MS Calcd.: 438, MS Found: 439. [M+H]+.

Description 49

Cis-ethyl 2-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)acetate (from Peak 2) (D49)

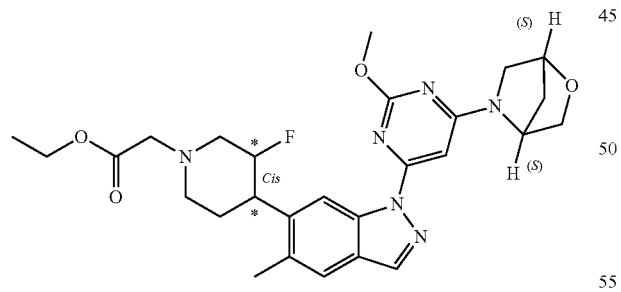

Ethyl 2-bromoacetate (73 mg, 0.44 mmol) was slowly added to the solution of cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane hydrochloride (from Peak 2, 64 mg, 0.15 mmol) and Et3N (74 mg, 0.73 mmol) in DMF (2 mL) and the reaction was stirred at Rt for 60 min. EtOAc (20 mL) was added and the resulting mixture was washed with brine (50 mL). The solution was dried and concentrated. The residue was purified by prep-TLC (EtOAc/PE=1/1) to give the product as a white solid (55 mg).

LC-MS [mobile phase: from 90% water (0.1% FA) and 10% ACN (0.1% FA) to 5% water (0.1% FA) and 95% ACN (0.1% FA) in 9.0 min]: Rt=5.76 min; MS Calcd.: 524, MS Found: 525 [M+H]+.

Description 50

Cis-tert-butyl 4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 1) (D50)

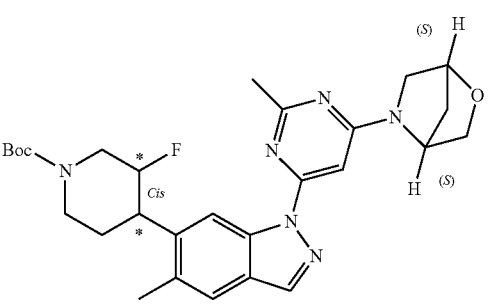

A mixture of Cis-tert-butyl 3-fluoro-4-(5-methyl-1H-indazol-6-yl)piperidine-1-carboxylate (Peak 1, 50 mg, 0.15 mmol), (1S,4S)-5-(6-iodo-2-methylpyrimidin-4-yl)-2-oxa-5-azabicyclo[2.2.1]heptane (57 mg, 0.18 mmol), CuI (29 mg, 0.15 mmol), K3PO4 (67 mg, 0.31 mmol) in toluene/THF (5 mL/1 mL) was degassed before DMEDA (26 mg, 0.30 mmol) was added. The reaction was then stirred at 80° C. for 3 hour. EtOAc (15 mL) was added and the resulting mixture was washed with sat. NH4Cl (15 mL) and brine (15 mL). The organic solution was dried over anhydrous Na2SO4 and concentrated. The residue was purified by silica gel chromatography eluted with (silica del: 2 g, PE:EtOAc=2:1) to give the product as a white solid (72 mg, yield: 92%).

LC-MS [mobile phase: from 90% water (0.1% FA) and 10% ACN (0.1% FA) to 5% water (0.1% FA) and 95% ACN (0.1% FA) in 9.0 min]: Rt=6.67 min; MS Calcd.: 522, MS Found: 523 [M+H]+.

Description 51

Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hidrochloride (from Peak 1) (D51)

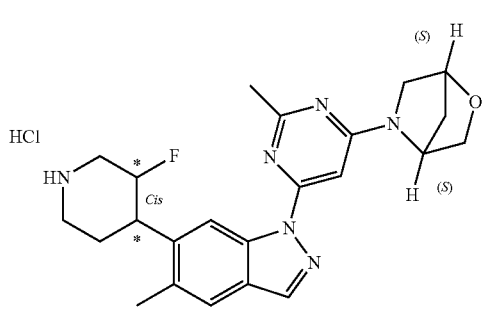

To a solution of Cis-(tert-butyl-4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 1, 70 mg, 0.13 mmol) in EtOAc (4 mL) was drop-wise added HCl/EtOAc (3 N, 2 mL). The reaction was stirred at Rt for 60 min. The reaction suspension was concentrated to give the product as a white solid (60 mg), which was used in next step without further purification.

LC-MS [mobile phase: from 90% water (0.1% FA) and 10% ACN (0.1% FA) to 5% water (0.1% FA) and 95% ACN (0.1% FA) in 2.0 min]: Rt=1.11 min; MS Calcd.: 422, MS Found: 423. [M+H]$^+$.

Description 52

Cis-ethyl 2-(4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)acetate (from Peak 1) (D52)

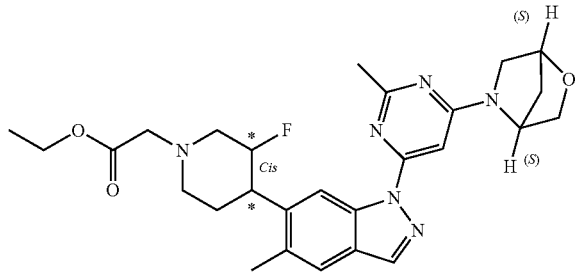

Ethyl 2-bromoacetate (59 mg, 0.36 mmol) was slowly added to the solution of Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride (from Peak 1, 50 mg, 0.12 mmol) and Et$_3$N (60 mg, 0.59 mmol) in DMF (2 mL) and the reaction was stirred at rt for 60 min. EtOAc (20 mL) was added and the resulting mixture was washed with brine (50 mL). The solution was dried and concentrated. The residue was purified by prep-TLC (EtOAc/PE=1/1) to give the product as a white solid (59 mg).

LC-MS [mobile phase: from 90% water (0.1% FA) and 10% ACN (0.1% FA) to 5% water (0.1% FA) and 95% ACN (0.1% FA) in 2.0 min]: Rt=1.29 min; MS Calcd.: 508, MS Found: 509 [M+H]$^+$.

Description 53

Cis-tert-butyl 4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 2) (D53)

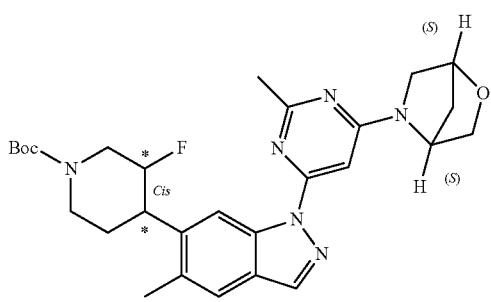

A mixture of Cis-tert-butyl 3-fluoro-4-(5-methyl-1H-indazol-6-yl)piperidine-1-carboxylate (Peak 2, 50 mg, 0.15 mmol), (1S,4S)-5-(6-iodo-2-methylpyrimidin-4-yl)-2-oxa-5-azabicyclo[2.2.1]heptane (57 mg, 0.18 mmol), CuI (29 mg, 0.15 mmol), K$_3$PO$_4$ (67 mg, 0.31 mmol) in toluene/THF (5 mL/1 mL) was degassed before DMEDA (26 mg, 0.30 mmol) was added. The reaction was then stirred at 80° C. for 3 hour. EtOAc (15 mL) was added and the resulting mixture was washed with sat. NH$_4$Cl (15 mL) and brine (15 mL). The organic solution was dried over anhydrous Na$_2$SO$_4$ and concentrated. The residue was purified by silica gel chromatography eluted with (silica del: 2 g, PE:EtOAc=2:1) to give the product as a white solid (75 mg, yield: 96%).

LC-MS [mobile phase: from 90% water (0.1% FA) and 10% ACN (0.1% FA) to 5% water (0.1% FA) and 95% ACN (0.1% FA) in 2.0 min]: Rt=1.62 min; MS Calcd.: 522, MS Found: 523 [M+H]$^+$.

Description 54

Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hidrochloride (from Peak 2) (D54)

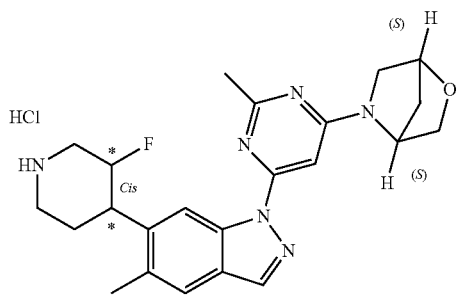

To a solution of Cis-(tert-butyl-4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 2, 74 mg, 0.14 mmol) in EtOAc (4 mL) was drop-wise added HCl/EtOAc (3 N, 2 mL), The reaction was stirred at Rt for 60 min. The reaction suspension was concentrated to give the product as a white solid (65 mg), which was used in next step without further purifications.

LC-MS [mobile phase: from 90% water (0.1% FA) and 10% ACN (0.1% FA) to 5% water (0.1% FA) and 95% ACN (0.1% FA) in 2.0 min]: Rt=0.91 min; MS Calcd.: 422, MS Found: 423 [M+H]$^+$.

Description 55

Cis-ethyl 2-(4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)acetate (from Peak 2) (D55)

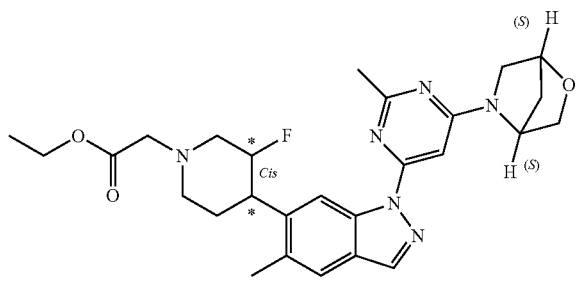

Ethyl 2-bromoacetate (76 mg, 0.45 mmol) was slowly added to the solution of Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride (from Peak 2, 64 mg, 0.15 mmol) and Et₃N (77 mg, 0.76 mmol) in DMF (2 mL) and the reaction was stirred at rt for 60 min. EtOAc (20 mL) was added and the resulting mixture was washed with brine (50 mL). The solution was dried and concentrated. The residue was purified by prep-TLC (EtOAc/PE=1/1) to give the product as a white solid (52 mg).

LC-MS [mobile phase: from 90% water (0.1% FA) and 10% ACN (0.1% FA) to 5% water (0.1% FA) and 95% ACN (0.1% FA) in 9.0 min]: Rt=5.16 min; MS Calcd.: 508, MS Found: 509 [M+H]⁺.

Descriptions 56 and 57

(cis)-6-(3-Fluoro-1-(oxetan-3-yl)piperidin-4-yl)-5-methyl-1H-indazole (enantiomer 1) (D56 and D57)

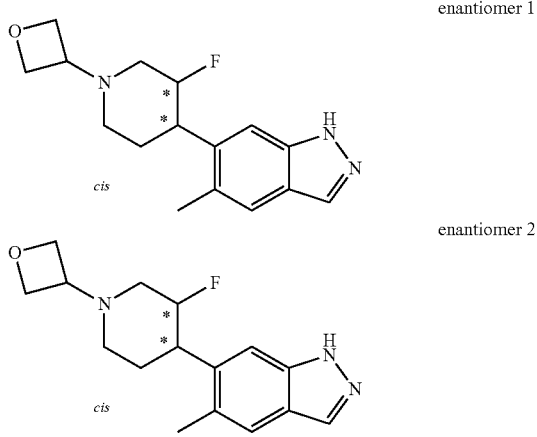

The racemate (cis)-6-(3-Fluoro-1-(oxetan-3-yl)piperidin-4-yl)-5-methyl-1H-indazole (1.20 g, 4.15 mmol) was separated by chiral HPLC (Chiralpak OJ-H 5 μm 4.6×250 mm; mobile phase: Hex/EtOH=50/50; flow rate: 1.0 mL/min) to give (cis)-6-(3-Fluoro-1-(oxetan-3-yl)piperidin-4-yl)-5-methyl-1H-indazole (enantiomer 1) (D56) (350 mg, Rt=8.07 min, yield 29%) and (cis)-6-(3-Fluoro-1-(oxetan-3-yl)piperidin-4-yl)-5-methyl-1H-indazole (enantiomer 2) (D57) (350 mg, Rt=14.21 min, yield 29%) both as a white solid.

D56: ¹H NMR (400 MHz, CDCl₃): δ 10.02 (br 1H), 7.97 (s, 1H), 7.56 (s, 1H), 7.45 (s, 1H), 4.95-4.76 (m, 1H), 4.73-4.69 (m, 2H), 4.69-4.64 (m, 2H), 3.66-3.63 (m, 1H), 3.26-3.23 (m, 1H), 3.15-3.07 (m, 1H), 2.84-2.81 (m, 1H), 2.46 (s, 3H), 2.13-2.08 (m, 1H), 2.07-1.93 (m, 2H), 1.86-1.83 (m, 1H).

D57: ¹H NMR (400 MHz, CDCl₃): δ 10.02 (br 1H), 7.97 (s, 1H), 7.56 (s, 1H), 7.46 (s, 1H), 4.95-4.76 (m, 1H), 4.73-4.69 (m, 2H), 4.69-4.64 (m, 2H), 3.67-3.61 (m, 1H), 3.28-3.22 (m, 1H), 3.14-3.04 (m, 1H), 2.84-2.81 (m, 1H), 2.46 (s, 3H), 2.13-2.08 (m, 1H), 2.07-1.93 (m, 2H), 1.86-1.83 (m, 1H).

Description 58

5-methyl-1-(tetrahydro-2H-pyran-2-yl)-6-(4,4,5,5-tetramethyl-1,3,2-dioxaborolan-2-yl)-1H-indazole (D58)

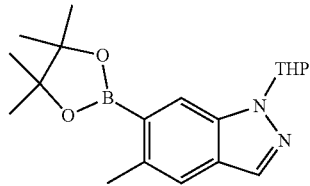

To a mixture of 6-bromo-5-methyl-1-(tetrahydro-2H-pyran-2-yl)-1H-indazole (5.78 g, 19.6 mmol), bis(pinacolato)diboron (9.95 g, 39.2 mmol) and CH₃COO⁻K⁺ (7.68 g, 78.3 mmol) in dioxane (50 mL) was added Pd(PPh₃)₄ (6.60 g, 5.09 mmol). The mixture was heated to 90° C. and stirred under N₂ overnight. The mixture was filtered and the filtrate was concentrated under vacuum. The residue was purified by silica column (PE:EtOAc from 100:1 to 60:1) to give the desired product (2.7 g, yield 41%) as a yellow solid.

¹H NMR (400 MHz, CDCl₃): δ 7.98 (s, 1H), 7.94 (s, 1H), 7.47 (s, 1H), 5.77 (dd, J=9.6, 2.8 Hz, 1H), 4.05-4.02 (m, 1H), 3.81-3.75 (m, 1H), 2.61 (s, 3H), 2.19-2.13 (m, 1H), 2.04-2.00 (m, 1H), 1.84-1.72 (m, 2H), 1.65-1.59 (m, 2H), 1.38 (s, 12H).

LC-MS: [mobile phase: from 90% water (0.02% NH₄OAc) and 10% ACN to 5% water (0.02% NH₄OAc) and 95% ACN in 4 min]: Rt=2.914 min MS Calcd.: 342, MS Found: 343 [M+H]⁺.

Description 59

5-Methyl-1-(tetrahydro-2H-pyran-2-yl)-1H-indazol-6-ol (D59)

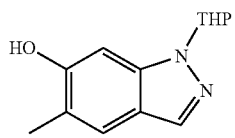

To a solution of 5-methyl-1-(tetrahydro-2H-pyran-2-yl)-6-(4,4,5,5-tetramethyl-1,3,2-dioxaborolan-2-yl)-1H-indazole (2.70 g, 7.89 mmol) in THF (80 mL) and NaOH aqueous solution (1 N, 40 mL) was added H$_2$O$_2$ aqueous (37%, 4.48 g, 39.5 mmol) at 0-15° C. The mixture was diluted with sat. NaHSO$_3$ (100 mL) and extracted with EtOAc (3×50 mL). The combined organic layers were washed with brine, dried over Na$_2$SO$_4$ and concentrated under vacuum. The residue was purified by silica column (PE:EtOAc=6:1) and the crude was slurried with PE (3.5 mL) to give the desired product (1.70 g, yield 94%) as a yellow solid.

$^1$H NMR (300 MHz, CDCl$_3$): δ 7.85 (s, 1H), 7.42 (s, 1H), 6.93 (s, 1H), 5.58 (dd, J=9.6, 2.7 Hz, 1H), 5.44 (s, 1H), 4.04-3.99 (m, 1H), 3.75-3.66 (m, 1H), 2.60-2.47 (m, 1H), 2.32 (s, 3H), 2.17-2.01 (m, 2H), 1.81-1.63 (m, 3H).

LC-MS [mobile phase: from 90% water (0.02% NH$_4$OAc) and 10% ACN to 5% water (0.02% NH$_4$OAc) and 95% ACN in 4 min]: Rt=2.113 min, MS Calcd.: 232, MS Found: 233 [M+H]$^+$.

Description 60

Tetrahydrofuran-3-yl Methanesulfonate (D60)

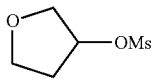

To a solution of tetrahydrofuran-3-ol (500 mg, 5.68 mmol) and Et$_3$N (860 mg, 8.52 mmol) in CH$_2$Cl$_2$ (10 mL) at 0° C. was added MsCl (842 mg, 7.39 mmol) dropwise. The reaction was stirred at room temperature for 4 hours. The reaction mixture was diluted with CH$_2$Cl$_2$ (150 mL), washed with sat. NaHCO$_3$ (50 mL), dried over Na$_2$SO$_4$ and concentrated to give the title compound (700 mg, 74%) as yellow oil.

$^1$H NMR (300 MHz, CDCl$_3$): δ 5.36-5.31 (m, 1H), 4.06-3.86 (m, 4H), 3.06 (s, 3H), 2.29-2.22 (m, 2H).

Description 61

5-methyl-1-(tetrahydro-2H-pyran-2-yl)-6-((tetrahydrofuran-3-yl)oxy)-1H-indazole (D61)

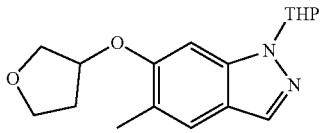

A mixture of 5-methyl-1-(tetrahydro-2H-pyran-2-yl)-1H-indazol-6-ol (150 mg, 0.65 mmol), tetrahydrofuran-3-yl methanesulfonate (129 mg, 0.78 mmol) and K$_2$CO$_3$ (180 mg, 1.3 mmol) in DMF (2.0 mL) was stirred at 80° C. overnight under N$_2$ atmosphere. The reaction was dilute with water (50 mL), extracted with EtOAc (150 mL×2), washed with brine (50 mL), dried over Na$_2$SO$_4$, filtered and concentrated. The residue was purified by silica gel chromatography (Petroleum ether:EtOAc=3:1) to give the title compound (150 mg, 77%) as a yellow oil.

$^1$H NMR (300 MHz, CDCl$_3$): δ 7.86 (s, 1H), 7.44 (s, 1H), 6.82 (s, 1H), 5.66 (dd, J=9.3, 2.1 Hz, 1H), 5.09-5.04 (m, 1H), 4.14-3.96 (m, 5H), 3.79-3.71 (m, 1H), 2.63-2.51 (m, 1H), 2.28 (s, 3H), 2.17-2.04 (m, 4H), 1.81-1.69 (m, 3H).

Description 62

5-methyl-6-((tetrahydrofuran-3-yl)oxy)-1H-indazole (D62)

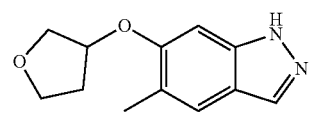 [SMILES: Cc1cc2cn[nH]c2cc1OC1CCOC1]

To a solution of 5-methyl-1-(tetrahydro-2H-pyran-2-yl)-6-((tetrahydrofuran-3-yl)oxy)-1H-indazole (150 mg, 0.5 mmol) in DCM (2 mL) was added TFA (2 mL). The resulting mixture was stirred at room temperature for 5 hours. The reaction was dilute with DCM (100 mL), washed with brine (100 mL), dried over Na$_2$SO$_4$, filtered and concentrated. The residue was purified by silica gel chromatography (Petroleum ether:EtOAc=2:3) to give the title compound (95 mg, 86%) as yellow solid.

$^1$H NMR (300 MHz, CDCl$_3$): δ7.92 (s, 1H), 7.48 (s, 1H), 6.74 (s, 1H), 5.02-4.96 (m, 1H), 4.13-3.93 (m, 4H), 2.29 (s, 3H), 2.27-2.20 (m, 2H).

Description 63

Tert-butyl 4-(1-(6-(((1R,4R)-2-oxa-5-azabicyclo[2.2.1]heptan-5-yl)-2-methylpyrimidin-4-yl)-5-methyl-1H-indazol-6-yl)piperidine-1-carboxylate (D63)

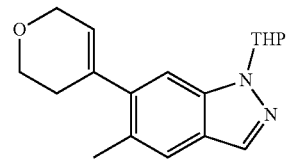

To a mixture of 2-(3,6-dihydro-2H-pyran-4-yl)-4,4,5,5-tetramethyl-1,3,2-dioxaborolane (939 mg, 4.47 mmol), 6-bromo-5-methyl-1-(tetrahydro-2H-pyran-2-yl)-1H-indazole (1200 mg, 4.07 mmol), PdCl$_2$(dppf)-CH$_2$Cl$_2$adduct (332 mg, 0.407 mmol) and tripotassium phosphate (2589 mg, 12.20 mmol) was added DMF (10 mL) and water (2.500 mL). The reaction mixture was heated to 100° C. for 3 h. The reaction mixture was diluted with ethyl acetate, after filtration, the filtrate was concentrated and purified by silica column (30% EA in PE) to give 6-(3,6-dihydro-2H-pyran-4-yl)-5-methyl-1-(tetrahydro-2H-pyran-2-yl)-1H-indazole (610 mg, 2.044 mmol, 50.3% yield).

MS: 299.0 [M+H]$^+$.

Description 64

5-methyl-1-(tetrahydro-2H-pyran-2-yl)-6-(tetrahydro-2H-pyran-4-yl)-1H-indazole (D64)

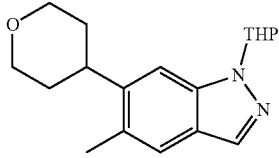

A mixture of 6-(3,6-dihydro-2H-pyran-4-yl)-5-methyl-1-(tetrahydro-2H-pyran-2-yl)-1H-indazole (610 mg, 2.044 mmol), Pd—C (435 mg, 0.409 mmol, 10%) and methanol (10 mL) was stirred under hydrogen balloon atmosphere at rt for 16 h. After filtration, the filtrate was concentrated to afford a crude 5-methyl-1-(tetrahydro-2H-pyran-2-yl)-6-(tetrahydro-2H-pyran-4-yl)-1H-indazole (614 mg, 2.044 mmol, 100% yield).
MS: 301.1 [M+H]$^+$.

Description 65

5-Methyl-6-(tetrahydro-2H-pyran-4-yl)-1H-indazole (D65)

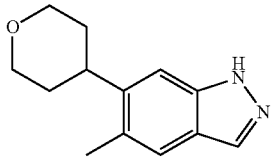 [SMILES: Cc1cc2cn[nH]c2cc1C1CCOCC1]

A solution of 5-methyl-1-(tetrahydro-2H-pyran-2-yl)-6-(tetrahydro-2H-pyran-4-yl)-1H-indazole (610 mg, 2.031 mmol), HCl (4.06 mL, 20.31 mmol) and methanol (5 mL) was stirred at rt for 16 h. The reaction solution was neutralized by aq. NaHCO$_3$ to pH=7, and extracted with ethyl acetate. The combined organic phases were dried and concentrated to give 5-methyl-6-(tetrahydro-2H-pyran-4-yl)-1H-indazole (430 mg, 1.988 mmol, 98% yield).
MS: 217.1 [M+H]$^+$.

Description 66

1-bromo-2-chloro-4-methyl-5-nitrobenzene (D66)

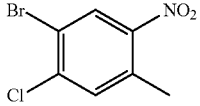

Con.HNO$_3$ (15 mL) was added to the solution of 1-bromo-2-chloro-4-methylbenzene (20 g, 100 mmol) in con.H$_2$SO$_4$ (65 mL) at −20° C. slowly. The reaction was stirred for 5 mins and then poured into ice-water (500 g). Then, the mixture was filtered and the solid was washed by water and dried to give the crude product as a yellow solid. (23 g, 95% yield).

Description 67

5-bromo-4-chloro-2-methylaniline (D67)

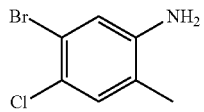

Con.HCl was slowly added to the stirred mixture of Fe (22.4 g, 400 mmol) and 1-bromo-2-chloro-4-methyl-5-nitrobenzene (20 g, 80 mmol) in THF (100 mL) at rt until the reaction completed (The temperature of the reaction rise to −60° C.). Then the reaction mixture was poured into K$_2$CO$_3$ (200 g) and EtOAc (500 mL) and the mixture was stirred for 0.5 hour. The mixture was filtered and the solution was washed with sat. NaHCO$_3$ (2×200 mL). Then the solution was dried and concentrated. The residue was purified by chromatography (EtOAc/PE=1/10) to give 5-bromo-4-chloro-2-methylaniline as a yellow solid (11 g, 62% yield).

Description 68

6-Bromo-5-chloro-1H-indazole (D68)

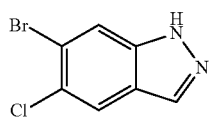

A solution of NaNO$_2$ (3.04 g, 44 mmol) in water (10 mL) was added to the solution of 5-bromo-4-chloro-2-methylaniline (9.3 g, 40 mmol) in HOAc (50 mL) at rt and the mixture was refluxed for 2 hours. The reaction was then concentrated and the residue was diluted with EtOAc (200 mL). The mixture was washed with sat. NaHCO$_3$ (2×100 mL) and dried. Then the solution was filtered and concentrated to give the crude product as a brown solid (4.7 g, 50% yield).

Description 69

6-Bromo-5-chloro-1-(tetrahydro-2H-pyran-2-yl)-1H-indazole (D69)

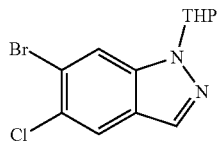

The solution of 6-bromo-5-chloro-1H-indazole (4.7 g, 20 mmol), DHP (4.7 mL) and p-TsOH (30 mg) in THF (50 mL) was refluxed for 2 hours. The reaction was diluted with EtOAc (50 mL) and washed with sat. NaHCO$_3$ (2×100 mL). Then the solution was dried and concentrated. The residue was purified by silica gel column (PE/EtOAc=10/1) to give 6-bromo-5-chloro-1-(tetrahydro-2H-pyran-2-yl)-1H-indazole as a yellow solid (2.5 g, 40% yield).

Description 70

Tert-butyl 4-(5-chloro-1H-indazol-6-yl)-5,6-dihydropyridine-1(2H)-carboxylate (D70)

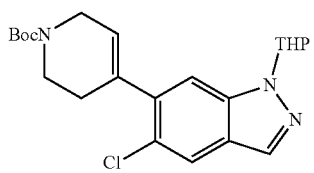

A mixture of 6-bromo-5-chloro-1-(tetrahydro-2H-pyran-2-yl)-1H-indazole) (6.7 g, 21.2 mmol), tert-butyl 4-(4,4,5,5-tetramethyl-1,3,2-dioxaborolan-2-yl)-5,6-dihydropyridine-1(2H)-carboxylate (7.3 g, 23.4 mmol), Na$_2$CO$_3$ (5 g, 46.7 mmol) and Pd(dppf)Cl$_2$ (1.5 g, 2.1 mmol) in dioxane/H$_2$O (70 mL/18 mL) was heated to 100° C. for 15 h. The reaction mixture was diluted with water (50 mL) and extracted with EtOAc (50 mL). The combined organic solution was washed with brine (50 mL), dried over anhydrous Na$_2$SO$_4$ and filtered. The filtrate was concentrated and the residue was purified by column chromatography (PE:EtOAc=20:1 to 5:1) to give desired product as a yellow oil (8.5 g 95% yield).

LC-MS [mobile phase: from 40% water (0.1% FA) and 60% ACN (0.1% FA) to 5% water (0.1% FA) and 95% ACN (0.1% FA) in 2.0 min]: Rt=1.60 min; MS Calcd: 417.2, MS Found: 418.4 [M+H]$^+$.

Description 71

5-Chloro-1-(tetrahydro-2H-pyran-2-yl)-6-(4,4,5,5-tetramethyl-1,3,2-dioxaborolan-2-yl)-1H-indazole (D71)

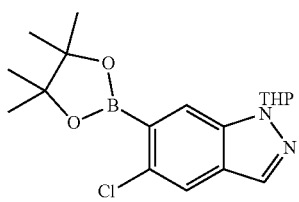

A solution of 6-bromo-5-chloro-1-(tetrahydro-2H-pyran-2-yl)-1H-indazole (400 mg, 1.26 mmol, 1.0 eq), bis(pinacolato)diboron (481 mg, 1.89 mmol, 1.5 eq) and KOAc (483 mg, 5.04 mmol, 4.0 eq) in dioxane (15 mL) was degassed and refilled with Ar for 3 times with water pump. Pd(dppf)Cl$_2$ (96 mg, 0.126 mmol, 0.1 eq) was added quickly in one portion under Ar. After being degassed for another 3 times with water pump, the reaction was stirred at 90° C. for 5 h. 30 mL H$_2$O was added and extracted with DCM three times. The organic phase was combined and dried over Na$_2$SO$_4$. Flash chromatography with PE:EtOAc=10:1 gave compound 5-chloro-1-(tetrahydro-2H-pyran-2-yl)-6-(4,4,5,5-tetramethyl-1,3,2-dioxaborolan-2-yl)-1H-indazole as a yellow solid (220 mg, yield 48%).

$^1$H NMR (400 MHz, CDCl$_3$) δ 7.96 (s, 1H), 7.89 (s, 1H), 7.71 (s, 1H), 5.75 (d, J=9.1 Hz, 1H), 4.01 (m, 1H), 3.77 (t, J=10.6 Hz, 1H), 2.57 (d, J=11.1 Hz, 1H), 2.16 (s, 1H), 2.03 (d, J=11.6 Hz, 1H), 1.88-1.54 (m, 3H), 1.41 (s, 12H).

Description 72

1-(5-chloro-1-(tetrahydro-2H-pyran-2-yl)-1H-indazol-6-yl)-4-methylpiperidin-4-ol (D72)

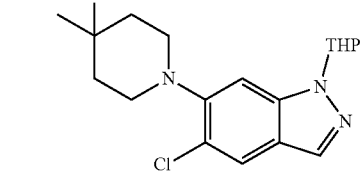

To a solution of 6-bromo-5-chloro-1-(tetrahydro-2H-pyran-2-yl)-1H-indazole (2.52 g, 8.00 mmol), 4-methylpiperidin-4-ol hydrochloride (1.45 g, 9.60 mmol), xphos (380 mg, 0.8 mmol), Pd$_2$(dba)$_3$ (748 mg, 0.8 mmol), t-BuONa (1.54 g, 16 mmol) in toluene (16 ml). The mixture was stirred at 100° C. under microwave for 2 hours. The residue was concentrated. And the residue was purified by silica gel chromatography (Petroleum ether:EtOAc=4:1 to 1:2) to give the title compound as a yellow solid (1.67 g, 60%).

LC-MS [method: 4MIN-40-95-POS, 40-95% positive, flow rate: 1.5 mL/min, stop time 4.0 min]: Rt=1.492 min, MS Calcd.: 349, MS Found: 350 [M+H]$^+$.

Description 73

1-(5-chloro-1H-indazol-6-yl)-4-methylpiperidin-4-ol (D73)

To a solution of 1-(5-chloro-1-(tetrahydro-2H-pyran-2-yl)-1H-indazol-6-yl)-4-methylpiperidin-4-ol (0.6 g, 1.72 mmol) in DCM/TFA (5 mL/5 mL) was stirred at 40° C. for 2 hours. The reaction solution was concentrated in vacuo. The residue was purified by silica gel chromatography (Petroleum ether:EtOAc=2:1) to give the title compound (305 mg, 67%) as a yellow solid.

LC-MS [method: 2.5MIN-05-95 05-95% positive, flow rate: 1.5 mL/min, stop time 2.5 min]: Rt=1.42 min, MS Calcd.: 265, MS Found: 266 [M+H]$^+$.

Description 74

5-bromo-2-methyl-4-nitroaniline (D74)

To a stirred solution of 5-bromo-2-methylaniline (5.0 g, 27 mmol) in conc.H₂SO₄ (40 ml) was added KNO₃ (2.7 g, 27 mmol) in portions and kept the internal temperature below 5° C. The resulting mixture was stirred for 2 hours under ice bath. The resulting mixture was poured into ice water and stirred for 10 min. The mixture was filtered and the filter cake was washed with water (100 ml). The filter cake was purified by column chromatography (PE:EtOAc from 20:1 to 10:1) to give the title compound (3.1 g, yield: 50%).

¹H NMR (300 MHz, CDCl₃) δ 7.88 (s, 1H), 6.91 (s, 1H), 4.25 (br, 2H), 2.16 (s, 3H).

Description 75

1-(6-bromo-5-nitro-1H-indazol-1-yl)ethanone (D75)

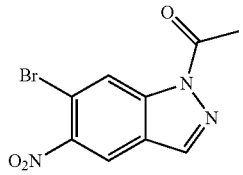 [SMILES: CC(=O)n1ncc2cc([N+](=O)[O-])c(Br)cc21]

To a solution of 5-bromo-2-methyl-4-nitroaniline (3.1 g, 13 mmol) in CHCl₃ (50 ml) was added Ac₂O (5.5 g, 54 mmol) under ice bath. Then KOAc (2.6 g, 27 mmol), 18-crown-6 (1.1 g, 4.1 mmol) and isoamyl nitrite (3.2 g, 27 mmol) was added. The resulting mixture was refluxed overnight. The reaction mixture was washed with water (100 ml) and the aqueous layer was extracted with DCM (200 ml). The organic layer was concentrated and the residue was purified by column chromatography (PE:EtOAc=10:1) to give the title compound (2.2 g, yield: 58%) as a brown solid.

¹H NMR (300 MHz, CDCl₃) δ 8.90 (s, 1H), 8.29 (s, 1H), 8.24 (s, 1H), 2.82 (s, 3H).

Description 76

6-bromo-5-nitro-1H-indazole (D76)

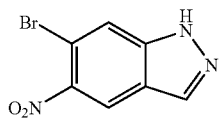

To a solution of 1-(6-bromo-5-nitro-1H-indazol-1-yl) ethanone (2.2 g, 7.8 mmol) in THF (10 ml) was added aqueous NaOH (5 M, 6 ml). The resulting mixture was stirred at room temperature for 1 hour. DCM (100 mL) was added to extract the desired compound. The organic solution was washed with water (30 mL) and brine, dried over Na₂SO₄ and concentrated to give the title compound (1.0 g, yield: 53%) as a brown solid which was used for next step directly.

¹H NMR (300 MHz, DMSO-d₆) δ 13.74 (s, 1H), 8.63 (s, 1H), 8.35 (s, 1H), 8.07 (s, 1H).

Description 77

6-bromo-5-nitro-1-(tetrahydro-2H-pyran-2-yl)-1H-indazole (D77)

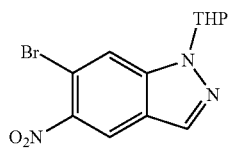

To a suspension of 6-bromo-5-nitro-1H-indazole (1.03 g, 4.26 mmol) and DHP (717 mg, 8.54 mmol) in DCM (10 mL) was added TsOH.H₂O (146 mg, 0.77 mmol) at rt. The resulting mixture was stirred at rt (25° C.) for 20 min. The reaction mixture was diluted with DCM (50 mL) and then washed with sat.Na₂CO₃ (30 mL) and brine, dried over MgSO₄ and concentrated. The crude product was purified by column chromatography (PE:EtOAc=5:1) to give the title compound (1.08 g, yield: 78%) as an orange solid.

¹H NMR (300 MHz, CDCl₃) δ 8.35 (s, 1H), 8.14 (s, 1H), 8.00 (s, 1H), 5.75-5.71 (m, 1H), 4.04-3.99 (m 1H), 3.82-3.74 (m, 1H), 2.54-2.41 (m, 1H), 2.21-2.08 (m, 2H), 1.85-1.66 (m, 3H).

Description 78

Tert-butyl 4-(5-nitro-1-(tetrahydro-2H-pyran-2-yl)-1H-indazol-6-yl)-5,6-dihydropyridine-1(2H)-carboxylate (D78)

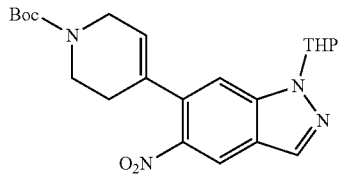

To a suspension of 6-bromo-5-nitro-1-(tetrahydro-2H-pyran-2-yl)-1H-indazole (1.08 g, 3.31 mmol), tert-butyl 4-(4,4,5,5-tetramethyl-1,3,2-dioxaborolan-2-yl)-5,6-dihydropyridine-1(2H)-carboxylate (1.08 g, 3.48 mmol) and Na₂CO₃ (878 mg, 8.28 mmol) in 1,4-dioxane (12 mL) and water (2.5 mL) was added Pd(dppf)Cl₂ (121 mg, 0.166 mmol) at room temperature. The resulting mixture was stirred at 100° C. under N₂ atmosphere overnight. The reaction mixture was cooled and filtered. The filtrate was concentrated and the crude product was purified by column chromatography (PE:EtOAc=5:1) to give the title compound (1.2 g, yield: 85%) as an orange solid.

¹H NMR (300 MHz, CDCl₃) δ 8.48 (s, 1H), 8.17 (s, 1H), 7.43 (s, 1H), 5.76-5.61 (m, 2H), 4.13-4.01 (m 3H), 3.83-3.74 (m, 1H), 3.72-3.65 (m, 2H), 2.58-2.45 (m, 1H), 2.41-2.28 (m, 2H), 2.22-2.06 (m, 2H), 1.85-1.65 (m, 3H), 1.51 (s, 9H).

Description 79

Tert-butyl 4-(5-amino-1-(tetrahydro-2H-pyran-2-yl)-1H-indazol-6-yl)piperidine-1-carboxylate (D79)

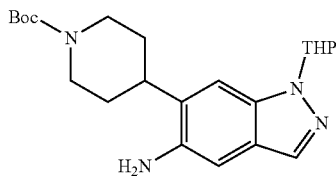

To a solution of tert-butyl 4-(5-nitro-1-(tetrahydro-2H-pyran-2-yl)-1H-indazol-6-yl)-5,6-dihydropyridine-1(2H)-carboxylate (1.0 g, 2.3 mmol) in MeOH (15 mL) was added Pd/C (10%, 100 mg) at room temperature. The resulting mixture was stirred at 50° C. under $H_2$ atmosphere (1 atm) for 3 hours. The reaction mixture was cooled and filtered. The filtrate was concentrated to give the title compound (876 mg, yield: 94%) as a white solid.

$^1$H NMR (300 MHz, CDCl$_3$) δ 7.82 (s, 1H), 7.28 (s, 1H), 6.98 (s, 1H), 5.66-5.62 (m, 1H), 4.41-4.24 (m, 2H), 4.07-4.01 (m 1H), 3.79-3.71 (m, 1H), 3.57 (s, 2H), 2.92-2.75 (m, 3H), 2.64-2.48 (m, 1H), 2.20-2.10 (m, 1H), 2.07-1.93 (m, 3H), 1.83-1.63 (m, 5H), 1.50 (s, 9H).

Description 80

5-chloro-6-(piperidin-4-yl)-1H-indazole (D80)

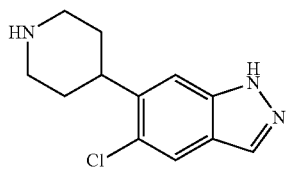 [SMILES: Clc1cc2cn[nH]c2cc1C1CCNCC1]

A solution of NaNO$_2$ (165 mg, 2.39 mmol) in water (5 mL) was added dropwise to a solution of tert-butyl 4-(5-amino-1-(tetrahydro-2H-pyran-2-yl)-1H-indazol-6-yl)piperidine-1-carboxylate (870 mg, 2.17 mmol) in conc. HCl (3 mL) under ice bath (0-5° C.). Then the resulting mixture was stirred for additional 15 min under ice bath. Then the mixture was added to a suspension of CuCl (387 mg, 3.91 mmol) in water (5 mL) at 60° C. in one portion. The resulting mixture was stirred for 30 min at 60° C. The reaction mixture was cooled and gradually added to sat. Na$_2$CO$_3$ (50 mL) and stirred for 15 min. Aq. ammonia (30%, 5 mL) was added to the mixture and stirred for 5 min. Then the mixture was extracted with EtOAc (30 mL×3) and the combined organic layers were washed with brine, dried over MgSO$_4$ and concentrated to give the title compound (400 mg, yield: 78%) as a pale yellow solid.

$^1$H NMR (300 MHz, DMSO-d$_6$) δ 13.15 (br 1H), 8.01 (s, 1H), 7.86 (s, 1H), 7.43 (s, 1H), 3.10-3.06 (m, 3H), 2.69-2.62 (m, 2H), 1.81-1.77 (m, 2H), 1.62-1.47 (m, 2H).

Description 81

5-chloro-6-(1-(oxetan-3-yl)piperidin-4-yl)-1H-indazole (D81)

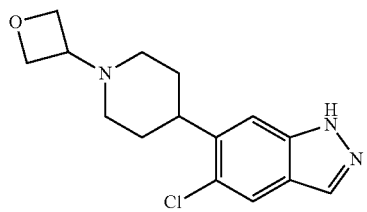 [SMILES: Clc1cc2cn[nH]c2cc1C1CCN(C2COC2)CC1]

To a solution of 5-chloro-6-(piperidin-4-yl)-1H-indazole (350 mg, 1.48 mmol) and oxetan-3-one (534 mg, 7.40 mmol) in DCE (10 mL) and MeOH (2 mL) was added HCl/MeOH (8 M, two drops) at room temperature. After the resulting mixture was stirred for 20 min, NaBH$_3$CN (279 mg, 4.44 mmol) was added in portions and the mixture was stirred for 3 hours. The reaction mixture was poured into sat. Na$_2$CO$_3$ (50 mL) and the resultant was extracted with DCM (3×30 mL). The combined organic layers were washed with brine, dried over Na$_2$SO$_4$ and concentrated. The crude product was purified by column chromatography (DCM: MeOH=20:1) to give the title compound (160 mg, yield: 37%) as a white solid.

$^1$H NMR (400 MHz, CDCl$_3$) δ 10.39 (br 1H), 7.99 (s, 1H), 7.78 (s, 1H), 7.43 (s, 1H), 4.77-4.68 (m, 4H), 3.61-3.54 (m, 1H), 3.20-3.10 (m, 1H), 2.96-2.93 (m, 2H), 2.09-1.99 (m, 4H), 1.84-1.74 (m, 2H).

Description 82

Tert-butyl 4-(5-chloro-1-(tetrahydro-2H-pyran-2-yl)-1H-indazol-6-yl)piperidine-1-carboxylate (D82)

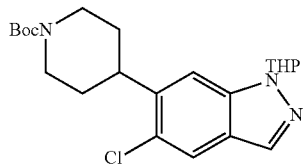

To a solution of tert-butyl 4-(5-chloro-1-(tetrahydro-2H-pyran-2-yl) 1H-indazol-6-yl)-5,6-dihydropyridine-1(2H)-carboxylate (350 mg, 0.84 mmol) in EtOAc (2 mL) was added PtO$_2$ (95 mg, 0.42 mmol). The mixture was stirred at room temperature for 5 h under H$_2$. The reaction mixture was filtered and the residue was washed by EtOAc (20 mL). The filtrate was concentrated and purified by column (PE: EtOAc=8:1-6:1) to get desired product as white solid (213 mg, 61% yield)

LC-MS [mobile phase: from 30% water (0.1% FA) and 70% ACN (0.1% FA) to 5% water (0.1% FA) and 95% ACN (0.1% FA) in 2.0 min]: Rt=0.74 min; MS Calcd: 419, MS Found: 420 [M+H]$^+$.

Description 83

5-chloro-6-(1-(tetrahydrofuran-3-yl)piperidin-4-yl)-1H-indazole (D83)

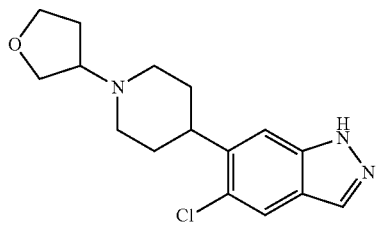 [SMILES: Clc1cc2cn[nH]c2cc1C1CCN(C2CCOC2)CC1]

To a solution of 5-chloro-6-(piperidin-4-yl)-1H-indazole (2.51 g, 10.66 mmol), oxolan-3-one (4.58 g, 53.25 mmol) and 5 mL of AcOH in DCM (80 mL) was added NaBH₃CN (1.34 g, 21.32 mmol). The mixture was stirred for 3 hours. The reaction mixture was concentrated. The crude was purified by column chromatography on silica gel (DCM/MeOH=30/1) to give the title compound (844 mg, yield 26%) as yellow oil.

LCMS [$C_{18}$; column size: 4.6×30 mm 5 μm; Dikwa Diamonsil plus; mobile phase: B (ACN): A1 (0.02% NH₄Oac+5% ACN); gradient (B %) in 4 min-05-95-POS; 5-95% positive, flow rate: 1.5 mL/min, stop time 4 min]: Rt=1.936 min; MS Calcd.: 305, MS Found: 306 [M+H]⁺.

Description 84

1-(5-chloro-1-(tetrahydro-2H-pyran-2-yl)-1H-indazol-6-yl)-3-methylpyrrolidin-3-ol (D84)

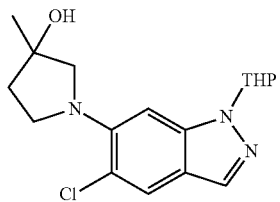

A mixture of 6-bromo-5-chloro-1-(tetrahydro-2H-pyran-2-yl)-1H-indazole (384 mg, 1.2 mmol), 3-methylpyrrolidin-3-ol hydrochloride (200 mg, 1.44 mmol), xphos (56 mg, 0.12 mmol), Pd₂(dba)₃ (112 mg, 0.12 mmol) and t-BuONa (232 mg, 2.4 mmol) in toluene (5.0 mL) was stirred at 120° C. under microwave for 5 hours. The mixture was diluted with H₂O (20 mL) and extracted with EtOAc (20 mL×3). The extracts were combined and dried over Na₂SO₄. The organic phase was filtered and concentrated. The residue was purified by silica gel chromatography column (Petroleum ether:EtOAc=5:1 to 2:1) to give the title compound (300 mg, 75%) as yellow oil.

¹H NMR (400 MHz, CDCl₃) δ 7.85 (s, 1H), 7.66 (s, 1H), 6.98 (d, J=5.6 Hz, 1H), 5.62 (dd, J=8.8 Hz, 2.4 Hz, 1H), 4.01 (d, J=11.2 Hz, 1H), 3.89-3.72 (m, 2H), 3.43-3.22 (m, 3H), 2.56 (br 1H), 2.17-2.07 (m, 3H), 1.78-1.60 (m, 5H), 1.50 (s, 3H).

LC-MS [4 min-05-95-POS; 5-95% positive, flow 1.5 mL/min, stop time 6.5 min]: Rt=2.592 min; MS Calcd.: 335, MS Found: 336 [M+H]+.

Description 85

1-(5-chloro-1H-indazol-6-yl)-3-methylpyrrolidin-3-ol (D85)

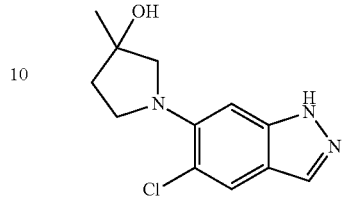

To a solution of 1-(5-chloro-1-(tetrahydro-2H-pyran-2-yl)-1H-indazol-6-yl)-3-methylpyrrolidin-3-ol (300 mg, 0.9 mmol) in DCM (3 mL) was added TFA (3.0 mL) and the mixture was stirred at room temperature for 2 hours. The mixture was diluted with DCM (20 mL) and washed with sat. NaHCO₃. The organic phase was dried over Na₂SO₄, filtered and concentrated. The residue was purified by silica gel chromatography column (Petroleum ether:EtOAc=1:1 to 1:2) to give the title compound (120 mg, 53%) as yellow oil.

¹H NMR (400 MHz, CDCl3) δ 7.90 (s, 1H), 7.71 (s, 1H), 6.92 (s, 1H), 4.13-4.08 (m, 1H), 3.86-3.78 (m, 1H), 3.37 (s, 2H), 3.25-3.16 (m, 1H), 2.09-2.02 (m, 2H), 1.50 (s, 3H).

Description 86 & D87

1-(5-chloro-1H-indazol-6-yl)-3-methylpyrrolidin-3-ol (Isomer 1, D86 and Isomer 2, D87)

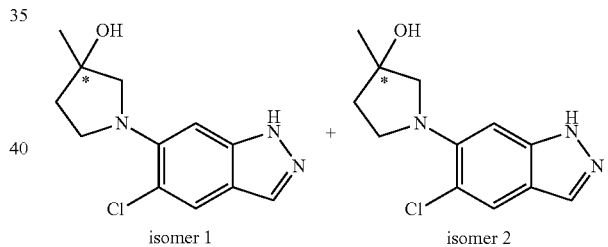

isomer 1    isomer 2

1-(5-chloro-1H-indazol-6-yl)-3-methylpyrrolidin-3-ol (120 mg) was separated to 1-(5-chloro-1H-indazol-6-yl)-3-methylpyrrolidin-3-ol (34 mg, 28%, Rt=5.40 min, isomer 1) and 1-(5-chloro-1H-indazol-6-yl)-3-methylpyrrolidin-3-ol (34 mg, 28%, Rt=8.62 min, isomer 2) by Chiral HPLC method: Chiralpak IF 5 μm 4.6×250 mm; Phase: Hex: EtOH=70:30; Flow rate: 1.0 mL/min; Wave length: 230 nm; Temperature: 30° C.).

Description 88

6-bromo-1-(tetrahydro-2H-pyran-2-yl)-1H-indazole (D88)

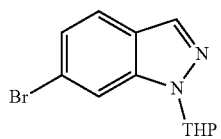

A mixture of 6-bromo-1H-indazole (10 g, 52 mmol), dihydropyran (5.5 g, 66 mmol) and p-TsOH (775 mg, 4.1 mmol) in THF (100 mL) was refluxed for 3 hours. The reaction mixture was diluted with H$_2$O (200 mL), extracted with EtOAc (150 mL×2), dried over Na$_2$SO$_4$ and concentrated. The residue was purified by flash chromatography column (petroleum ether/EtOAc=15/1) to afford the title compound (7.0 g, 49%) as a light yellow solid.

$^1$H NMR (400 MHz, CDCl$_3$): δ 7.98 (s, 1H), 7.79 (s, 1H), 7.58 (d, J=8.4 Hz, 1H), 7.27 (d, J=8.4 Hz, 1H), 5.66 (dd, J=9.2, 2.4 Hz, 1H), 4.05-4.01 (m, 1H), 3.78-3.72 (m, 1H), 2.58-2.48 (m, 1H), 2.17-2.05 (m, 2H), 1.81-1.67 (m, 3H).

Description 89

1-(tetrahydro-2H-pyran-2-yl)-6-(4,4,5,5-tetramethyl-1,3,2-dioxaborolan-2-yl)-1H-indazole (D89)

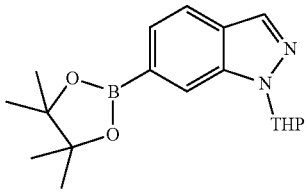

To a solution of 6-bromo-1-(tetrahydro-2H-pyran-2-yl)-1H-indazole (3.5 g, 10.7 mmol), 4,4,4',4',5,5,5',5'-octamethyl-2,2'-bi(1,3,2-dioxaborolane) (3.25 g, 12.8 mmol) and KOAc (4.82 g, 49.2 mmol) in dioxane (50 mL) was added Pd(dppf)Cl$_2$ (630 mg, 0.86 mmol). The reaction mixture was refluxed for 2 hours. The reaction mixture was filtered, and the filtrate was concentrated, purified by silica gel chromatography column (petroleum ether/EtOAc=10/1) to afford the title compound (3.8 g, 93%) as a yellow solid.

$^1$H NMR (300 MHz, CDCl$_3$): δ 8.06 (s, 2H), 7.73 (d, J=8.1 Hz, 1H), 7.60 (d, J=8.1 Hz, 1H), 5.81 (dd, J=9.6, 2.4 Hz, 1H), 4.10-4.05 (m, 1H), 3.84-3.77 (m, 1H), 2.71-2.58 (m, 1H), 2.21-2.16 (m, 1H), 2.06-2.01 (m, 1H), 1.83-1.69 (m, 3H), 1.40 (s, 12H).

Description 90

1-(tetrahydro-2H-pyran-2-yl)-1H-indazol-6-ol (D90)

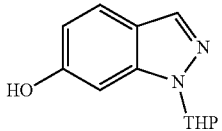

A mixture of 1-(tetrahydro-2H-pyran-2-yl)-6-(4,4,5,5-tetramethyl-1,3,2-dioxaborolan-2-yl)-1H-indazole (3.8 g, 11.6 mmol), H$_2$O$_2$ (12 mL, 30% solution in H$_2$O) and HOAc (10 mL) in THF (100 mL) was stirred at room temperature overnight. The reaction mixture was diluted with EtOAc (200 mL), washed with brine (100 mL), saturated NaHCO$_3$ (100 mL×2), brine (100 mL), dried over Na$_2$SO$_4$, concentrated and purified by silica gel chromatography column (petroleum ether/EtOAc=3/1) to afford the title compound (2.3 g, 91%) as a yellow solid.

$^1$H NMR (300 MHz, CDCl$_3$): δ 7.93 (s, 1H), 7.56 (d, J=8.7 Hz, 1H), 6.97 (s, 1H), 6.76 (d, J=8.7 Hz, 1H), 5.80 (s, 1H), 5.61 (dd, J=9.6, 2.7 Hz, 1H), 4.06-4.02 (m, 1H), 3.77-3.69 (m, 1H), 2.61-2.50 (m, 1H), 2.19-2.10 (m, 2H), 1.78-1.67 (m, 3H).

Description 91

Methyl 4-bromo-2-((1-(tetrahydro-2H-pyran-2-yl)-1H-indazol-6-yl)oxy)butanoate (D91)

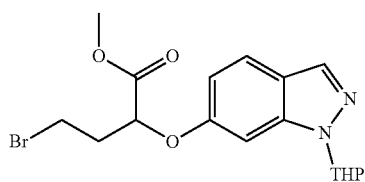

To a solution of 1-(tetrahydro-2H-pyran-2-yl)-1H-indazol-6-ol (1.0 g, 4.6 mmol) in DMF (8 mL) was added Cs$_2$CO$_3$ (1.94 g, 6.0 mmol) and methyl 2,4-dibromobutanoate (1.56 g, 6.0 mmol). The reaction mixture was stirred at room temperature for 3 hours. The reaction was diluted with saturated NH$_4$Cl (50 mL), extracted with EtOAc (100 mL×2). The combined organic layers were washed with brine (100 mL), dried over Na$_2$SO$_4$, concentrated and purified by silica gel chromatography (Petroleum ether: EtOAc=5:1) to give the title compound (1.2 g, 66%) as a light yellow oil.

$^1$H NMR (400 MHz, CDCl$_3$): δ 7.92 (s, 1H), 7.60 (d, J=8.4 Hz, 1H), 7.02 (s, 1H), 6.87 (dd, J=8.4, 2.4 Hz, 1H), 5.65-5.60 (m, 1H), 5.00-4.96 (m, 1H), 4.03-4.00 (m, 1H), 3.78-3.62 (m, 6H), 2.57-2.47 (m, 3H), 2.15-2.04 (m, 2H), 1.78-1.67 (m, 3H).

Description 92

Methyl 1-((1-(tetrahydro-2H-pyran-2-yl)-1H-indazol-6-yl)oxy)cyclopropanecarboxylate (D92)

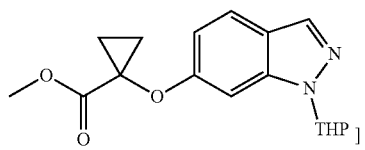

To a solution of methyl 4-bromo-2-((1-(tetrahydro-2H-pyran-2-yl)-1H-indazol-6-yl)oxy)butanoate (1.2 g, 3.03 mmol) in THF (8 mL) was added t-BuOK (345 mg, 3.03 mmol). The reaction mixture was stirred at room temperature for 3 hours. The reaction was diluted with saturated NH$_4$Cl (50 mL), extracted with EtOAc (50 mL×2), dried over Na$_2$SO$_4$, concentrated to give crude title compound (850 mg, 89%) as light yellow oil.

$^1$H NMR (400 MHz, CDCl$_3$): δ 7.93 (s, 1H), 7.58 (d, J=8.4 Hz, 1H), 7.02 (s, 1H), 6.84 (dd, J=8.8, 2.4 Hz, 1H), 5.63-5.58 (m, 1H), 4.02-3.93 (m, 2H), 3.73 (s, 3H), 2.56-2.43 (m, 1H), 2.15-2.03 (m, 2H), 1.88-1.68 (m, 5H), 1.40-1.38 (m, 2H).

Description 93

(1-((1-(tetrahydro-2H-pyran-2-yl)-1H-indazol-6-yl)oxy)cyclopropyl)methanol (D93)

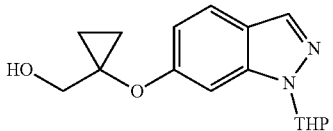

To a solution of methyl 1-((1-(tetrahydro-2H-pyran-2-yl)-1H-indazol-6-yl)oxy)cyclopropanecarboxylate (850 mg, 2.68 mmol) in THF (10 mL) at 0° C. was added LiAlH$_4$ (204 mg, 5.36 mmol) slowly. The reaction mixture was stirred at 0° C. for 1.5 hours. The reaction was quenched by dropwise addition of H$_2$O (0.5 mL), diluted with EtOAc (50 mL), stirred at room temperature for 30 minutes, dried over Na$_2$SO$_4$, filtered through celite, concentrated and purified by silica gel chromatography (Petroleum ether:EtOAc=3:1) to give the title compound (550 mg, 71%) as a colorless oil.

$^1$H NMR (400 MHz, CDCl$_3$): δ 7.92 (s, 1H), 7.57 (d, J=8.4 Hz, 1H), 7.18 (s, 1H), 6.91 (dd, J=8.8, 2.0 Hz, 1H), 5.64 (dd, J=8.8, 2.8 Hz, 1H), 4.02-3.99 (m, 1H), 3.91 (s, 2H), 3.76-3.71 (m, 1H), 2.60-2.53 (m, 1H), 2.18-2.06 (m, 2H), 1.77-1.67 (m, 3H), 1.15-1.13 (m, 2H), 1.00-0.95 (m, 2H).

Description 94

6-(1-(iodomethyl)cyclopropoxy)-1-(tetrahydro-2H-pyran-2-yl)-1H-indazole (D94)

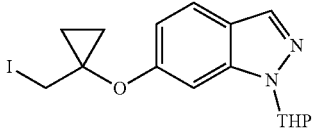

To a solution of PPh$_3$ (383 mg, 1.46 mmol) in DCM (6 mL) at 0° C. was added imidazole (100 mg, 1.46 mmol) and I$_2$ (371 mg, 1.46 mmol). The reaction mixture was added to a solution of (1-((1-(tetrahydro-2H-pyran-2-yl)-1H-indazol-6-yl)oxy)cyclopropyl)methanol (350 mg, 1.22 mmol) in DCM (2 mL) and then stirred at 0° C. for 2 hours under N$_2$ atmosphere. The reaction was concentrated and the residue was purified by silica gel chromatography (Petroleum ether:EtOAc=5:1) to give the title compound (300 mg, 62%) as a white solid.

$^1$H NMR (400 MHz, CDCl$_3$): δ 7.93 (s, 1H), 7.61 (d, J=8.8 Hz, 1H), 7.16 (d, J=2.0 Hz, 1H), 6.94 (dd, J=8.4, 2.0 Hz, 1H), 5.65 (dd, J=8.8, 2.4 Hz, 1H), 4.03-3.99 (m, 1H), 3.77-3.71 (m, 1H), 3.65-3.59 (m, 2H), 2.58-2.54 (m, 1H), 2.17-2.06 (m, 2H), 1.80-1.67 (m, 3H), 1.51-1.47 (m, 2H), 1.08-1.05 (m, 2H).

Description 95

6-(1-methylcyclopropoxy)-1-(tetrahydro-2H-pyran-2-yl)-1H-indazole (D95)

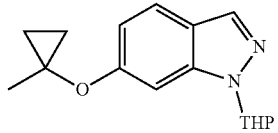

To a solution of 6-(1-(iodomethyl)cyclopropoxy)-1-(tetrahydro-2H-pyran-2-yl)-1H-indazole (500 mg, 1.26 mmol) in DMSO (5.0 mL) was added NaBH$_4$ (95 mg, 2.51 mmol). The reaction mixture was stirred at 90° C. for 1 hour. The reaction was diluted H$_2$O (50 mL), extracted with EtOAc (50 mL×2). The combined organic layers were washed with brine (50 mL×2), dried over Na$_2$SO$_4$ and concentrated to give the title compound (343 mg, 100%) as light yellow oil.

$^1$H NMR (400 MHz, CDCl$_3$): δ 7.91 (s, 1H), 7.56 (d, J=8.8 Hz, 1H), 7.14 (d, J=2.0 Hz, 1H), 6.88 (dd, J=8.4, 2.0 Hz, 1H), 5.64 (dd, J=9.2, 2.8 Hz, 1H), 4.05-4.01 (m, 1H), 3.77-3.71 (m, 1H), 2.62-2.53 (m, 1H), 2.19-2.06 (m, 2H), 1.80-1.67 (m, 3H), 1.61 (s, 3H), 1.08-1.05 (m, 2H), 0.77-0.74 (m, 2H).

Description 96

6-(1-methylcyclopropoxy)-1H-indazole (D96)

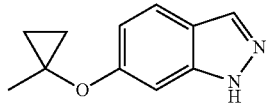

To a solution of 6-(1-methylcyclopropoxy)-1-(tetrahydro-2H-pyran-2-yl)-1H-indazole (340 mg, 1.25 mmol) in DCM (1 mL) was added TFA (5 mL). The reaction mixture was stirred at room temperature for 4 hours. The reaction solution was concentrated in vacuo. The residue was added EtOAc (50 mL), basified with saturated NaHCO$_3$ (30 mL), extracted with EtOAc (50 mL×2), concentrated and the residue was purified by silica gel chromatography (Petroleum ether:EtOAc=10:1 to 1:1) to give the title compound (215 mg, 91%) as a yellow solid.

$^1$H NMR (400 MHz, CDCl$_3$): δ 7.96 (s, 1H), 7.59 (d, J=8.8 Hz, 1H), 7.10 (s, 1H), 6.82 (dd, J=8.8, 2.0 Hz, 1H), 1.60 (s, 3H), 1.07-1.04 (m, 2H), 0.77-0.74 (m, 2H).

Description 97

Tert-butyl 5-methyl-4-(((trifluoromethyl)sulfonyl)oxy)-5,6-dihydropyridine-1(2H)-carboxylate (D97)

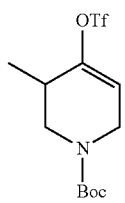

To a solution of tert-butyl 3-methyl-4-oxopiperidine-1-carboxylate (3.2 g, 15 mmol) in tetrahydrofuran (60 mL) was added lithium bis(trimethylsilyl)amide solution in tetrahydrofuran (13.9 mL, 18 mmol, 1.3 M in THF) slowly at −78° C. The mixture was stirred at −78° C. for 1.5 hours and then a solution of N-phenyl trifluoromethanesulfonimide (6.4 g, 18 mmol) in tetrahydrofuran (30 mL) was added slowly. The reaction mixture was stirred at −78° C. for 0.5 hour, then slowly warm up to room temperature and stirred for 2 hours. The reaction mixture was diluted with H₂O (50 mL), extracted with EtOAc (100 mL×2), dried over Na₂SO₄, concentrated and the residue was purified by silica gel chromatography column (petroleum ether/EtOAc=50/1) to afford crude product (5.0 g, 97%) as yellow oil.

¹H NMR (400 MHz, CDCl₃): δ 5.72 (s, 1H), 4.18-3.91 (m, 2H), 3.68-3.57 (m, 1H), 3.42-3.34 (m, 1H), 2.65-2.58 (m, 1H), 1.47 (s, 9H), 1.15 (d, J=7.2 Hz, 3H).

Description 98

Tert-butyl 5-methyl-4-(4,4,5,5-tetramethyl-1,3,2-dioxaborolan-2-yl)-5,6-dihydropyridine-1(2H)-carboxylate (D98)

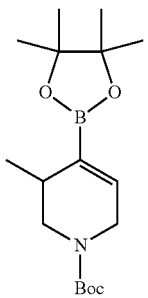

A mixture of tert-butyl 5-methyl-4-(((trifluoromethyl)sulfonyl)oxy)-5,6-dihydropyridine-1(2H)-carboxylate (5.0 g, 14.5 mmol), bis(pinacolato)diboron (4.1 g, 15.9 mmol), KOAc (5.0 g, 50.8 mmol), Pd(dppf)Cl₂ (409 mg, 0.56 mmol) and dppf (241 mg, 0.43 mmol) in 1,4-dioxane (50 mL) was stirred at reflux for 3 hours. The reaction mixture was diluted with H₂O (100 mL), extracted with EtOAc (100 mL×2), dried over Na₂SO₄, concentrated and purified by column chromatography on silica gel (petroleum ether/EtOAc=50/1) to afford the product (3.2 g, 68%) as a colorless oil.

¹H NMR (400 MHz, CDCl₃): δ 6.40 (s, 1H), 4.22-4.06 (m, 1H), 3.78-3.72 (m, 1H), 3.58-3.53 (m, 1H), 3.17-3.13 (m, 1H), 2.49-2.41 (m, 1H), 1.44 (s, 9H), 1.26 (s, 12H), 1.03 (d, J=7.2 Hz, 3H).

Description 99

Tert-butyl 5-methyl-4-(5-methyl-1H-indazol-6-yl)-5,6-dihydropyridine-1(2H)-carboxylate (D99)

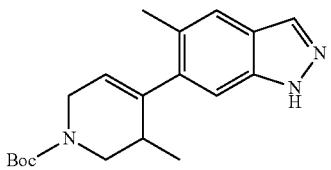 [SMILES: Cc1cc2cn[nH]c2cc1C1=CCN(C(=O)OC(C)(C)C)CC1C]

A mixture of tert-butyl 5-methyl-4-(4,4,5,5-tetramethyl-1,3,2-dioxaborolan-2-yl)-5,6-dihydropyridine-1(2H)-carboxylate (1.53 g, 4.74 mmol), 6-bromo-5-methyl-1H-indazole (500 mg, 2.37 mmol), Cs₂CO₃ (1.54 g, 4.74 mmol) and Pd(dppf)Cl₂ (171 mg, 0.24 mmol) in 1,4-dioxane/H₂O (10 mL, v/v=3/1) was stirred at 120° C. for 4 hours under microwave. The reaction mixture was diluted with H₂O (50 mL), extracted with EtOAc (50 mL×2), dried over Na₂SO₄, concentrated and the residue was purified by column chromatography on silica gel (petroleum ether/EtOAc=3/1) to afford the product (500 mg, 65%) as a yellow solid.

¹H NMR (400 MHz, CDCl₃): δ 7.98 (s, 1H), 7.53 (s, 1H), 7.16 (s, 1H), 5.52 (s, 1H), 4.30-4.20 (m, 1H), 4.30-4.20 (m, 1H), 3.99-3.88 (m, 1H), 3.64-3.46 (m, 2H), 2.67-2.55 (m, 1H), 2.34 (s, 3H), 1.51 (s, 9H), 0.91 (d, J=7.2 Hz, 3H).

Description 100

Tert-butyl 3-methyl-4-(5-methyl-1H-indazol-6-yl)piperidine-1-carboxylate (D100)

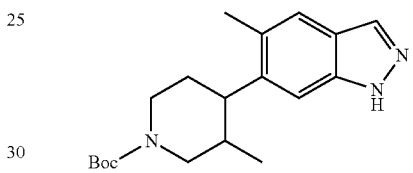

A mixture of tert-butyl 5-methyl-4-(5-methyl-1H-indazol-6-yl)-5,6-dihydropyridine-1(2H)-carboxylate (500 mg, 1.53 mmol) and Pd/C (50 mg, 10% w/t) in MeOH (20 mL) was stirred at 50° C. for 40 hours under H₂ atmosphere (50 psi). The reaction mixture was filtered through celite and washed with MeOH (20 mL). The filtrate was concentrated to afford the product (450 mg, 89%) as colorless oil.

LC-MS [mobile phase: from 90% water (0.1% FA) and 10% ACN (0.1% FA) to 5% water (0.1% FA) and 95% ACN (0.1% FA) in 10 min]: Rt=2.442 min; MS Calcd.: 329, MS Found: 274 [M+H−56]+.

Description 101

5-methyl-6-(3-methylpiperidin-4-yl)-1H-indazole (D101)

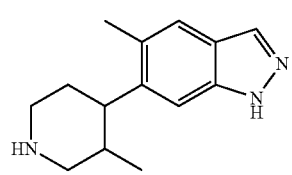 [SMILES: Cc1cc2cn[nH]c2cc1C1CCNCC1C]

To a solution of tert-butyl 3-methyl-4-(5-methyl-1H-indazol-6-yl)piperidine-1-carboxylate (450 mg, 1.37 mmol) in DCM (6 mL) was added TFA (3 mL). The reaction mixture was stirred at room temperature for 1 hour. The reaction mixture was basified with NaHCO₃ (30 mL), extracted with DCM (100 mL×2), dried over Na₂SO₄, and concentrated to afford the product (280 mg, 89%) as a white solid.

LC-MS [mobile phase: from 90% water (0.1% FA) and 10% ACN (0.1% FA) to 5% water (0.1% FA) and 95% ACN (0.1% FA) in 10 min]: Rt=2.480 min; MS Calcd.: 229, MS Found: 230 [M+H]⁺.

Description 102

5-methyl-6-(3-methyl-1-(oxetan-3-yl)piperidin-4-yl)-1H-indazole (D102)

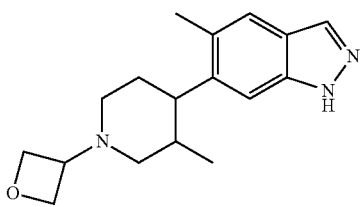 [SMILES: Cc1cc2cn[nH]c2cc1C1CCN(C2COC2)CC1C]

To a mixture of 5-methyl-6-(3-methylpiperidin-4-yl)-1H-indazole (260 mg, 1.14 mmol), oxetan-3-one (245 mg, 3.41 mmol) and HOAc (5 drops) in DCM (10 mL) was added NaBH₃CN (143 mg, 2.28 mmol). The reaction mixture was stirred at room temperature for 3 hours. The reaction mixture was added MeOH (3 mL), stirred at room temperature for 10 minutes, concentrated and the residue was purified by silica gel chromatography column (DCM/MeOH=30/1) to afford the product (48 mg, 15%) as a white solid.

¹H NMR (400 MHz, CDCl₃): δ 8.04 (s, 1H), 7.55 (s, 1H), 7.47 (s, 1H), 7.75-7.71 (brs, 4H), 3.58-3.52 (m, 1H), 2.93-2.89 (m, 2H), 2.56-2.48 (m, 1H), 2.34 (s, 3H), 2.38-2.22 (m, 2H), 1.99-1.94 (m, 1H), 1.76-1.65 (m, 2H), 0.69 (d, J=6.4 Hz, 3H).

Description 103

Tert-butyl 4-(1-(6-(((1R,4R)-2-oxa-5-azabicyclo[2.2.1]heptan-5-yl)-2-methoxypyrimidin-4-yl)-5-methyl-1H-indazol-6-yl)piperidine-1-carboxylate (D103)

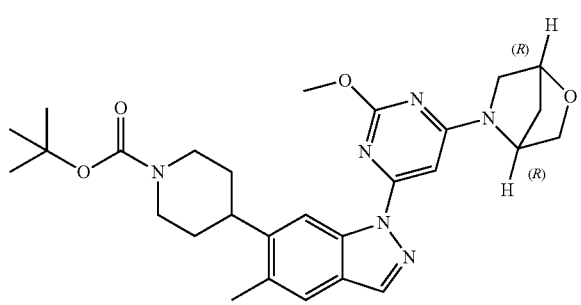

DMEDA (64 mg, 0.72 mmol) was added to a mixture of (1R,4R)-5-(6-iodo-2-methoxypyrimidin-4-yl)-2-oxa-5-azabicyclo[2.2.1]heptane (331 mg, 1 mmol), tert-butyl 4-(5-methyl-1H-indazol-6-yl)piperidine-1-carboxylate (113 mg, 0.36 mmol), CuI (68 mg, 0.36 mmol) and K₃PO₄ (230 mg, 1.08 mmol) in toluene (4 ml) under Ar. The reaction was stirred at 100° C. for 3 h. The cooled reaction mixture was filtered and the filtrate was concentrated. The residue was purified by silica gel chromatography (eluent: CH₂Cl₂: MeOH=50:1) to give desired product as white solid (130 mg, yield: 69%).

¹H NMR (400 MHz, CDCl₃) δ 8.73 (s, 1H), 8.07 (s, 1H), 7.52 (s, 1H), 6.56 (br 1H), 5.29 (br 1H), 4.74 (s, 1H), 4.28 (br 2H), 4.12 (s, 3H), 3.90 (dd, J=12.8, 9.6 Hz, 2H), 3.55-3.46 (m, 2H), 2.99-2.76 (m, 2H), 2.47 (s, 3H), 2.01-1.95 (m, 2H), 1.87 (d, J=13.2 Hz, 2H), 1.69-1.62 (m, 2H), 1.50 (s, 9H).

Description 104

Tert-butyl 4-(1-(6-(((1S,4S)-2-oxa-5-azabicyclo[2.2.1]heptan-5-yl)-2-methoxypyrimidin-4-yl)-5-methyl-1H-indazol-6-yl)piperidine-1-carboxylate (D104)

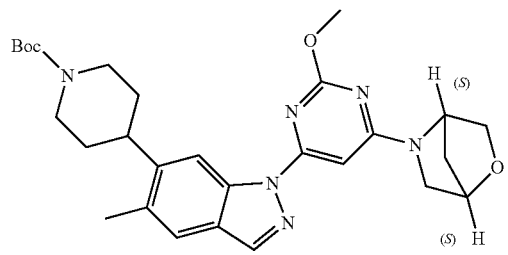

A mixture of tert-butyl 4-(5-methyl-1H-indazol-6-yl)piperidine-1-carboxylate (85 mg, 0.270 mmol), (1S,4S)-5-(6-iodo-2-methoxypyrimidin-4-yl)-2-oxa-5-azabicyclo[2.2.1]heptane (99 mg, 0.297 mmol), N,N'-dimethylcyclohexane-1,2-diamine (77 mg, 0.540 mmol), K₃PO₄ (114 mg, 0.540 mmol) and CuI (51 mg, 0.270 mmol) in toluene (3 mL) was stirred at 100° C. for 2 hours under N₂. The reaction was diluted with EtOAc (50 mL), washed with brine (50 mL), dried over Na₂SO₄, filtered and concentrated. The residue was purified by column chromatography on silica gel (petroleum ether/EtOAc=3/1) to give the title compound (70 mg, 50%) as yellow oil.

¹HNMR (400 MHz, CDCl₃): δ 8.72 (s, 1H), 8.05 (s, 1H), 7.49 (s, 1H), 6.54 (br 1H), 4.75-4.72 (m, 1H), 4.28 (br 2H), 4.12 (s, 3H), 4.09-4.02 (m, 2H), 3.92-3.86 (m, 3H), 3.04-2.93 (m, 1H), 2.86 (br 2H), 2.46 (s, 3H), 1.98-1.94 (m, 2H), 1.88-1.86 (m, 2H), 1.72-1.61 (m, 2H), 1.50 (s, 9H).

Description 105

Ethyl 2-(4-(1-(6-(((1S,4S)-2-oxa-5-azabicyclo[2.2.1]heptan-5-yl)-2-methoxypyrimidin-4-yl)-5-methyl-1H-indazol-6-yl)piperidin-1-yl)acetate (D105)

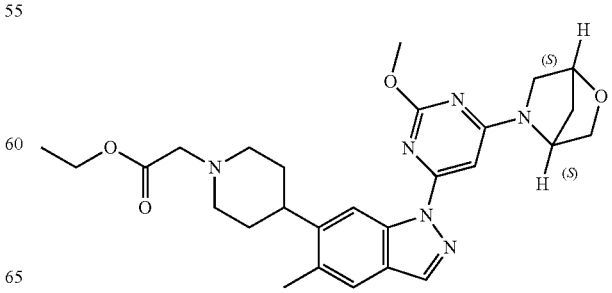

Step 1

(1S,4S)-5-(2-methoxy-6-(5-methyl-6-(piperidin-4-yl)-1H-indazol-1-yl)pyrimidin-4-yl)-2-oxa-5-azabicyclo[2.2.1]heptane Hydrochloride

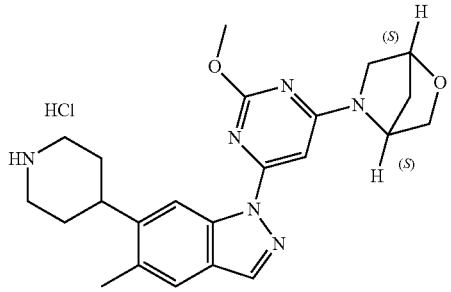

A mixture of tert-butyl 4-(1-(6-(((1S,4S)-2-oxa-5-azabicyclo[2.2.1]heptan-5-yl)-2-methoxypyrimidin-4-yl)-5-methyl-1H-indazol-6-yl)piperidine-1-carboxylate (280 mg, 0.54 mmol) in HCl/EtOAc (2 M, 5 mL) was stirred at rt for 30 min. The reaction mixture was concentrated to give crude product as a white solid. (260 mg, crude).

Step 2

Ethyl 2-(4-(1-(6-(((1S,4S)-2-oxa-5-azabicyclo[2.2.1]heptan-5-yl)-2-methoxypyrimidin-4-yl)-5-methyl-1H-indazol-6-yl)piperidin-1-yl)acetate

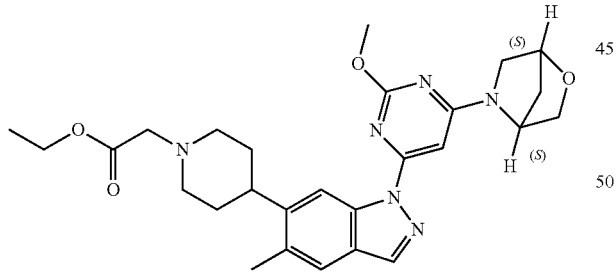

Ethyl 2-bromoacetate (89 mg, 0.54 mmol) was slowly added to the solution of (1S,4S)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride (120 mg, 0.27 mmol) and Et$_3$N (0.3 mL) in DMF (5 mL) and the reaction was stirred at rt overnight. The reaction was then diluted with EtOAc (30 mL) and washed with brine (50 mL×2). The solution was dried and concentrated. The residue was purified by prep-TLC (THF/EtOAc/PE=1/1/1) to give the product as a white solid. (103 mg, 75% yield).

Description 106

Tert-butyl 4-(1-(6-(((1R,4R)-2-oxa-5-azabicyclo[2.2.1]heptan-5-yl)-2-methoxypyrimidin-4-yl)-5-methyl-1H-indazol-6-yl)piperidine-1-carboxylate (D106)

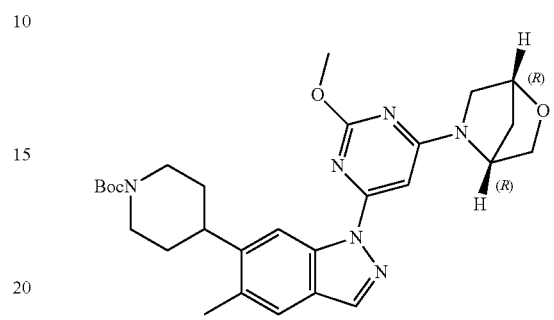

To a mixture of (1R,4R)-5-(6-iodo-2-methoxypyrimidin-4-yl)-2-oxa-5-azabicyclo[2.2.1]heptane (233 mg, 0.7 mmol), tert-butyl 4-(5-methyl-1H-indazol-6-yl)piperidine-1-carboxylate (200 mg, 0.63 mmol), CuI (120 mg) and K$_3$PO$_4$ (267 mg, 1.26 mmol) in toluene (5 mL) was added N$^1$,N$^2$-dimethylethane-1,2-diamine (111 mg) at rt under N$_2$ protection. The mixture was warmed at 90° C. for 2 h under N$_2$. The reaction mixture was poured into water (50 mL) and the mixture was extracted with EtOAc (3×50 mL). The organic solution was washed with brine (100 mL) and concentrated and the residue was purified by chromatography (EtOAc/PE=1/5) to give the product as a white solid (280 mg, yield: 85%).

Description 107

(1R,4R)-5-(2-methoxy-6-(5-methyl-6-(piperidin-4-yl)-1H-indazol-1-yl)pyrimidin-4-yl)-2-oxa-5-azabicyclo[2.2.1]heptane Hydrochloride (D107)

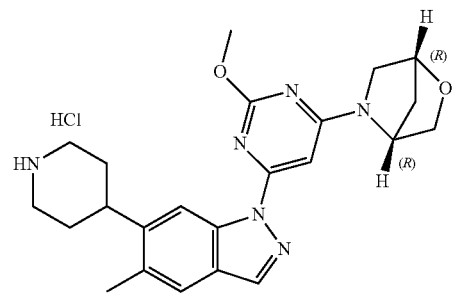

To a solution of tert-butyl 4-(1-(6-(((1R,4R)-2-oxa-5-azabicyclo[2.2.1]heptan-5-yl)-2-methoxypyrimidin-4-yl)-5-methyl-1H-indazol-6-yl)piperidine-1-carboxylate (280 mg, 0.54 mmol) in EtOAc (2 mL) was added HCl/EtOAc (2 M, 2 mL). The reaction was stirred at Rt for 30 min. The reaction mixture was concentrated to give crude product as a white solid. (250 mg, crude), which was used in next step without further purifications.

Description 108

Ethyl 2-(4-(1-(6-((1R,4R)-2-oxa-5-azabicyclo[2.2.1]heptan-5-yl)-2-methoxypyrimidin-4-yl)-5-methyl-1H-indazol-6-yl)piperidin-1-yl)acetate (D108)

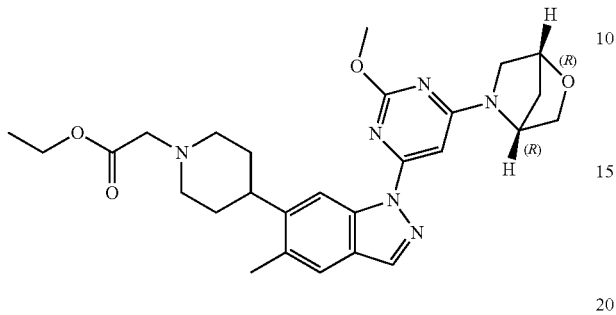

Ethyl 2-bromoacetate (124 mg, 0.74 mmol) was slowly added to the solution of (1R,4R)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride (100 mg, 0.22 mmol) and Et₃N (125 mg, 1.24 mmol) in DMF (2 mL) and the reaction was stirred at rt for 2 h. The reaction was then diluted with EtOAc (15 mL) and washed with brine (50 mL). The solution was dried and concentrated to give the product as a white solid. (82 mg).

LC-MS [mobile phase: from 90% water (0.1% FA) and 10% ACN (0.1% FA) to 5% water (0.1% FA) and 95% ACN (0.1% FA) in 2.0 min]: Rt=1.29 min; MS Calcd.: 506, MS Found: 507 [M+H]⁺.

Description 109

Tert-Butyl 4-(1-(6-(6-oxa-3-azabicyclo[3.1.1]heptan-3-yl)-2-methylpyrimidin-4-yl)-5-methyl-1H-indazol-6-yl)piperidine-1-carboxylate (D109)

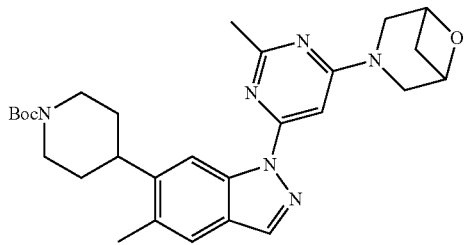 [SMILES: Cc1nc(N2CC3CC(C2)O3)cc(-n2ncc3cc(C)c(C4CCN(C(=O)OC(C)(C)C)CC4)cc32)n1]

To a solution of tert-butyl 4-(5-methyl-1H-indazol-6-yl)piperidine-1-carboxylate (100 mg, 0.317 mmol) in toluene (5 mL) was added 3-(6-iodo-2-methylpyrimidin-4-yl)-6-oxa-3-azabicyclo[3.1.1]heptane (111 mg, 0.349 mmol), CuI (60 mg, 0.32 mmol), K₃PO₄ (212 mg, 1.00 mmol) and N,N'-dimethyl-cyclohexane-1,2-diamine (45 mg, 0.51 mmol). The resulting mixture was refluxed for 3 hrs. After cooling to rt, the mixture was filtered. The filtrates were concentrated and the residue was purified by prep-TLC (DCM:ethyl acetate=5:1) to give the title compound (100 mg, yield 63%) as white solid.

¹H NMR (300 MHz, CDCl₃): δ 8.79 (s, 1H), 8.07 (s, 1H), 7.52 (s, 1H), 6.89 (s, 1H), 4.79-4.77 (m, 2H), 4.39-4.34 (m, 2H), 4.25-3.66 (m, 4H), 3.34-3.27 (m, 1H), 3.02-2.84 (m, 3H), 2.65 (s, 3H), 2.48 (s, 3H), 1.93-1.73 (m, 5H), 1.51 (s, 9H).

Description 110

Tert-Butyl 4-(1-(6-(8-oxa-3-azabicyclo[3.2.1]octan-3-yl)-2-methylpyrimidin-4-yl)-5-methyl-1H-indazol-6-yl)piperidine-1-carboxylate (D110)

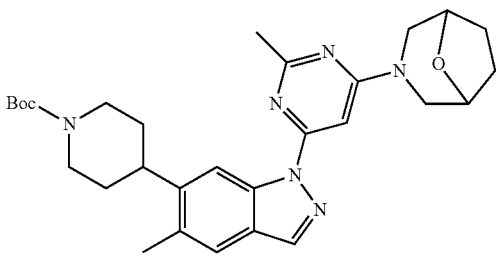 [SMILES: Cc1nc(N2CC3CCC(C2)O3)cc(-n2ncc3cc(C)c(C4CCN(C(=O)OC(C)(C)C)CC4)cc32)n1]

To a solution of tert-butyl 4-(5-methyl-1H-indazol-6-yl)piperidine-1-carboxylate (80 mg, 0.25 mmol) and 3-(6-iodo-2-methylpyrimidin-4-yl)-8-oxa-3-azabicyclo[3.2.1]octane (84 mg, 0.25 mmol) in toluene (5 mL) was added CuI (143 mg, 0.753 mmol), K₃PO₄ (159 mg, 0.750 mmol) and N,N'-dimethyl-cyclohexane-1,2-diamine (107 mg, 0.754 mmol). The resulting mixture was stirred at 120° C. for 3 hrs. The mixture was poured into ammonia hydrate (30%, 20 mL) and extracted with EtOAc (50 mL). The organic layer was concentrated and the residue was purified by prep-HPLC to give the title compound (90 mg, yield 69%) as a white solid.

¹H NMR (300 MHz, CDCl₃): δ 8.67 (s, 1H), 8.09 (s, 1H), 7.52 (s, 1H), 6.95 (s, 1H), 4.52 (br 2H), 4.33-4.29 (m, 2H), 4.06-4.02 (m, 2H), 3.34-3.29 (m, 2H), 2.97-2.84 (m, 3H), 2.69 (s, 3H), 2.47 (s, 3H), 2.02-1.99 (m, 2H), 1.94-1.85 (m, 4H), 1.78-1.69 (m, 2H), 1.51 (s, 9H).

Description 111

Tert-Butyl 4-(1-(6-iodo-2-methylpyrimidin-4-yl)-5-methyl-1H-indazol-6-yl)piperidine-1-carboxylate (D111)

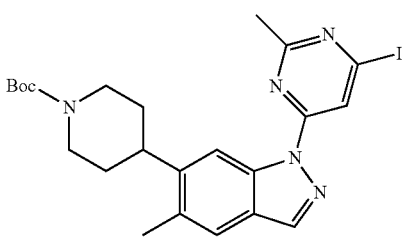 [SMILES: Cc1nc(I)cc(-n2ncc3cc(C)c(C4CCN(C(=O)OC(C)(C)C)CC4)cc32)n1]

To a mixture of tert-butyl 4-(5-methyl-1H-indazol-6-yl)piperidine-1-carboxylate (780 mg, 2.48 mmol) in toluene (20 mL) was added 4,6-diiodo-2-methylpyrimidine (1.10 g, 3.22 mmol), K₃PO₄ (2.60 g, 12.40 mmol), CuI (476 mg, 2.50 mmol) and N,N'-dimethyl-cyclohexane-1,2-diamine (298 mg, 2.09 mmol). The reaction mixture was heated to 100° C. and stirred for 3 hrs. The reaction mixture was cooled to room temperature and poured into water (100 mL). The desired was extracted with EtOAc (50 mL×3). The combined organic layers were washed with brine (30 mL), dried over Na₂SO₄ and concentrated. The residue was purified by column (PE:EtOAc=12:1) to give the title compound (800 mg, yield 62%) as a white solid.

¹H NMR (300 MHz, CDCl₃): δ 8.65 (s, 1H), 8.26 (s, 1H), 8.11 (s, 1H), 7.53 (s, 1H), 4.39-4.24 (m, 2H), 2.99-2.81 (m, 3H), 2.77 (s, 3H), 2.49 (s, 3H), 1.90-1.1.79 (m, 2H), 1.77-1.63 (m, 2H), 1.51 (s, 9H).

Description 112

Tert-Butyl 4-(1-(6-(8-oxa-3-azabicyclo[3.2.1]octan-3-yl)-2-methoxypyrimidin-4-yl)-5-methyl-1H-indazol-6-yl)piperidine-1-carboxylate (D112)

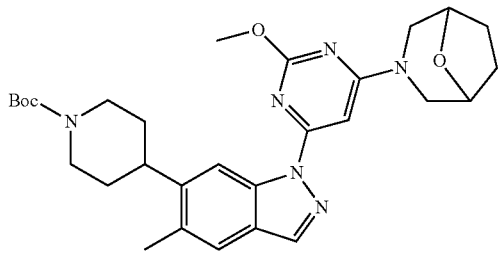 [SMILES: COc1nc(N2CC3CCC(C2)O3)cc(-n2ncc3cc(C)c(C4CCN(C(=O)OC(C)(C)C)CC4)cc32)n1]

To a solution of tert-butyl 4-(5-methyl-1H-indazol-6-yl)piperidine-1-carboxylate (80 mg, 0.25 mmol) and 3-(6-iodo-2-methoxypyrimidin-4-yl)-8-oxa-3-azabicyclo[3.2.1]octane (87 mg, 0.25 mmol) in toluene (5 mL) was added CuI (143 mg, 0.753 mmol), K₃PO₄ (159 mg, 0.750 mmol) and N,N'-dimethyl-cyclohexane-1,2-diamine (107 mg, 0.754 mmol). The resulting mixture was stirred at 120° C. for 3 hrs. TLC showed the reaction was completed. The mixture was poured into ammonia hydrate (30%, 20 mL) and extracted with EtOAc (50 mL). The organic layer was concentrated and the residue was purified by prep-HPLC to give the title compound (70 mg, yield 52%) as a white solid.

¹H NMR (300 MHz, CDCl₃): δ 8.71 (s, 1H), 8.07 (s, 1H), 7.52 (s, 1H), 6.77 (s, 1H), 4.48 (br 2H), 4.31-4.27 (m, 2H), 4.10 (s, 3H), 4.07-4.00 (m, 2H), 3.28-3.24 (m, 2H), 3.02-2.82 (m, 3H), 2.47 (s, 3H), 1.98-1.96 (m, 2H), 1.89-1.82 (m, 4H), 1.74-1.64 (m, 2H), 1.50 (s, 9H).

Description 113

Tert-Butyl 4-(1-(6-(6-oxa-3-azabicyclo[3.1.1]heptan-3-yl)-2-methoxypyrimidin-4-yl)-5-methyl-1H-indazol-6-yl)piperidine-1-carboxylate (D113)

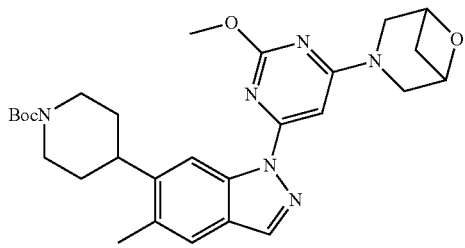 [SMILES: COc1nc(N2CC3CC(C2)O3)cc(-n2ncc3cc(C)c(C4CCN(C(=O)OC(C)(C)C)CC4)cc32)n1]

To a solution of tert-butyl 4-(5-methyl-1H-indazol-6-yl)piperidine-1-carboxylate (100 mg, 0.317 mmol) in toluene (5 mL) was added 3-(6-iodo-2-methoxypyrimidin-4-yl)-6-oxa-3-azabicyclo[3.1.1]heptane (105 mg, 0.317 mmol), CuI (60 mg, 0.32 mmol) and K₃PO₄ (212 mg, 1.00 mmol) and N,N'-dimethyl-cyclohexane-1,2-diamine (45 mg, 0.32 mmol). The resulting mixture was refluxed for 4 hrs. After cooled the mixture was filtered. The filtrates were concentrated and the residue was dissolved in EtOAc (20 mL). The solution was washed with NH₃.H₂O (30%, 10 mL×2), water (10 mL) and brine (10 mL), dried over Na₂SO₄ and concentrated. The residue was triturated with CH₃OH (5 mL) to give the title compound (100 mg, yield 61%) as white solid.

¹H NMR (300 MHz, CDCl₃): δ 8.75 (s, 1H), 8.08 (s, 1H), 7.52 (s, 1H), 6.80 (s, 1H), 4.77-4.75 (m, 2H), 4.39-4.25 (m, 2H), 4.14-4.02 (m, 4H), 3.89-3.86 (m, 2H), 3.75-3.63 (m, 1H), 3.35-3.28 (m, 1H), 2.99-2.85 (m, 3H), 2.48 (s, 3H), 1.97-1.86 (m, 3H), 1.75-1.72 (m, 2H), 1.51 (s, 9H).

Description 114

4-(1,4-dioxaspiro[4.5]decan-8-yl)morpholine (D114)

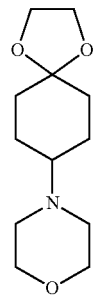

To a solution of 1,4-dioxaspiro[4.5]decan-8-one (5.00 g, 32.0 mmol), morpholine (5.7 g, 64.0 mmol) and acetic acid (1.9 g, 32.0 mmol) in CH₂Cl₂ (100 mL) was added NaBH₃CN (4.0 g, 64.0 mmol). The reaction mixture was stirred at room temperature overnight. The mixture was added H₂O (100 mL), extracted with DCM (100 mL×2), washed with water (100 mL×2), dried over Na₂SO₄, filtered and concentrated to afford the title compound (7.1 g, 98%) as a white solid.

¹H NMR (400 MHz, CDCl₃): δ 3.94 (s, 4H), 3.71 (t, J=4.8 Hz, 4H), 2.55 (t, J=4.8 Hz, 4H), 2.32-2.27 (m, 1H), 1.83-1.80 (m, 4H), 1.61-1.54 (m, 4H).

Description 115

4-morpholinocyclohexanone (D115)

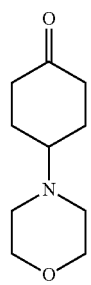

To a solution of 4-(1,4-dioxaspiro[4.5]decan-8-yl)morpholine (7.0 g, 30.8 mmol) in THF (150 mL) was added 7 N aqueous HCl (60 mL). The reaction mixture was stirred at room temperature for 17 hours and then 80° C. for 4 hours. The reaction mixture was treated with saturated aqueous NaHCO₃ (500 mL) to adjust pH=8, extracted with EtOAc (200 mL×3), dried Na₂SO₄ and concentrated. The residue was purified by silica gel chromatography column (DCM/MeOH=30/1) to afford the title compound (4.2 g, 75%) as yellow oil.

$^1$H NMR (400 MHz, CDCl₃): δ 3.74 (t, J=4.8 Hz, 4H), 2.64-2.47 (m, 7H), 2.34-2.27 (m, 2H), 2.07-1.99 (m, 2H), 1.92-1.83 (m, 2H).

Description 116

4-morpholinocyclohex-1-en-1-yl Trifluoromethanesulfonate (D116)

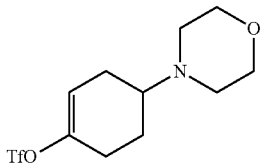 [SMILES: O=S(=O)(OC1=CCC(N2CCOCC2)CC1)C(F)(F)F]

To a solution of 4-morpholinocyclohexanone (3.2 g, 17.49 mmol) in THF (50 mL) was added a solution of LiHMDS (1.0 M in THF, 21 mL, 20.99 mmol) dropwise at −78° C. The mixture was stirred at −78° C. for 1 hour. 1,1,1-trifluoro-N-phenyl-N-((trifluoromethyl)sulfonyl)methanesulfonamide (6.87 g, 19.24 mmol) was added to the mixture at −78° C. The mixture was stirred at −78° C. for 1 hour and warmed to room temperature overnight. The reaction mixture was diluted with H₂O (100 mL), extracted with EtOAc (100 mL×3). The organic layer was concentrated. The residue was purified by column chromatography on silica gel (DCM/MeOH=40/1) to give the title compound (4.42 g, 80%) as yellow oil.

$^1$H NMR (300 MHz, CDCl₃): δ 5.74-5.72 (m, 1H), 3.74 (t, J=4.5 Hz, 4H), 2.66-2.51 (m, 5H), 2.46-2.32 (m, 3H), 2.26-2.02 (m, 2H), 1.74-1.61 (m, 1H).

Description 117

4-(4-(4,4,5,5-tetramethyl-1,3,2-dioxaborolan-2-yl)cyclohex-3-en-1-yl)morpholine (D117)

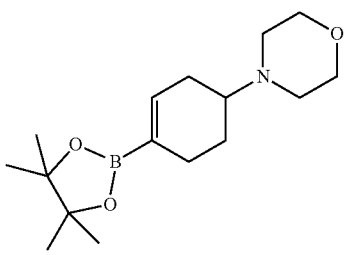 [SMILES: CC1(C)OB(C2=CCC(N3CCOCC3)CC2)OC1(C)C]

A mixture of 4-morpholinocyclohex-1-en-1-yl trifluoromethanesulfonate (4.42 g, 14.03 mmol), 4,4,4',4',5,5,5',5'-octamethyl-2,2'-bi(1,3,2-dioxaborolane) (4.28 g, 16.84 mmol), Pd(dppf)Cl₂ (1.03 g, 1.40 mmol) and KOAc (4.12 g, 42.09 mmol) in 1,4-dioxane (100 mL) was stirred at 110° C. overnight under N₂. The mixture was cooled to room temperature and filtered, concentrated. The residue was purified by column chromatography on silica gel (DCM/MeOH=80/1) to give the title compound (1.68 g, 41%) as a brown solid.

$^1$H NMR (400 MHz, CDCl₃): δ 6.49-6.50 (m, 1H), 3.78 (t, J=4.4 Hz, 4H), 2.80-2.52 (m, 5H), 2.38-2.33 (m, 2H), 2.18-1.98 (m, 4H), 1.27 (s, 12H).

Description 118

4-(4-(5-methyl-1H-indazol-6-yl)cyclohex-3-en-1-yl)morpholine (D118)

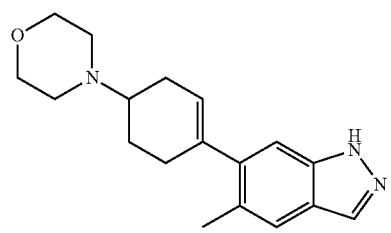 [SMILES: Cc1cc2cn[nH]c2cc1C1=CCC(N2CCOCC2)CC1]

A mixture of 4-(4-(4,4,5,5-tetramethyl-1,3,2-dioxaborolan-2-yl)cyclohex-3-en-1-yl)morpholine (1.0 g, 3.41 mmol), 6-bromo-5-methyl-1-(tetrahydro-2H-pyran-2-yl)-1H-indazole (657 mg, 3.1 mmol), K₂CO₃ (1.28 g, 9.3 mmol) and Pd(dppf)Cl₂ (227 mg, 0.31 mmol) in 1,4-dioxane (15 mL) and H₂O (1.5 mL) was stirred at 100° C. overnight under N₂. The mixture was filtered and concentrated. The residue was purified by column chromatography on silica gel (DCM/MeOH=30/1) to give the title compound (484 mg, 48%) as a yellow oil.

$^1$H NMR (400 MHz, CDCl₃): δ 7.97 (s, 1H), 7.50 (s, 1H), 7.18 (s, 1H), 5.57-5.56 (m, 1H), 3.79 (t, J=4.8 Hz, 4H), 2.71-2.60 (m, 5H), 2.51-2.38 (m, 2H), 2.35 (s, 3H), 2.26-2.11 (m, 2H), 1.72-1.61 (m, 2H).

Description 119 & 120

4-(4-(5-methyl-1H-indazol-6-yl)cyclohexyl)morpholine (D119, Isomer 1; D120, Isomer 2)

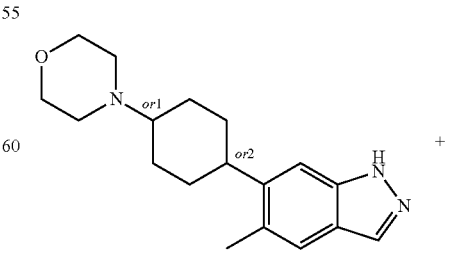

isomer 1

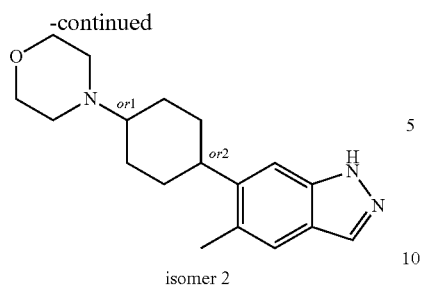

isomer 2

A mixture of 4-(4-(5-methyl-1H-indazol-6-yl)cyclohex-3-en-1-yl)morpholine (484 mg, 1.63 mmol) and Pd/C (10%, 200 mg) in MeOH (15 mL) was stirred at 50° C. for 5 days under H$_2$ (50 Psi). The mixture was filtered and concentrated. The residue was purified by column chromatography on silica gel (DCM/MeOH=40/1) to give the title isomer 1 (65 mg, 13%) and isomer 2 (80 mg, 16%) as a yellow solid.

Isomer 1:
$^1$H NMR (400 MHz, CDCl$_3$): δ 7.94 (s, 1H), 7.50 (s, 1H), 7.41 (s, 1H), 3.79 (t, J=4.8 Hz, 4H), 2.94-2.89 (m, 1H), 2.51 (br 4H), 2.44 (s, 3H), 2.28 (s, 1H), 2.14-2.10 (m, 2H), 1.93-1.84 (m, 2H), 1.61-1.52 (m, 4H).

LCMS [column: C$_{18}$; column size: 4.6×30 mm 5 μm; Dikwa Diamonsil plus; mobile phase: B (ACN): A1 (0.02% NH$_4$OAc+ 5% ACN); gradient (B %) in 4 mins-05-95-POS; flow rate: 1.5 ml/min]: Rt=2.283 min; MS Calcd.: 299, MS Found: 300 [M+H]$^+$.

Isomer 2:
$^1$H NMR (400 MHz, CDCl$_3$): δ 7.95 (s, 1H), 7.52 (s, 1H), 7.32 (s, 1H), 3.79 (br 4H), 2.81-2.62 (m, 5H), 2.43-2.39 (m, 4H), 2.14-2.09 (m, 2H), 2.04-2.00 (m, 2H), 1.56-1.43 (m, 4H).

LCMS [column: C$_{18}$; column size: 4.6×30 mm 5 μm; Dikwa Diamonsil plus; mobile phase: B (ACN): A1 (0.02% NH$_4$OAc+ 5% ACN); gradient (B %) in 4 mins-05-95-POS; flow rate: 1.5 ml/min]: Rt=1.904 min; MS Calcd.: 299, MS Found: 300 [M+H]$^+$.

Description 121

1,4-dioxaspiro[4.5]dec-7-en-8-yl trifluoromethanesulfonate (D121)

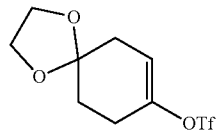 [SMILES: O=S(=O)(OC1=CCC2(CC1)OCCO2)C(F)(F)F]

To a solution of 1,4-dioxaspiro[4.5]decan-8-one (10 g, 64.1 mmol) and N,N-Bis(trifluoromethylsulfonyl)aniline (25.2 g, 70.5 mmol) in THF (150 mL) was added LiHMDS (70.5 mL, 70.5 mmol) drop-wise under N$_2$ at −78° C. The mixture was stirred at −78° C. for 30 min and warmed to room temperature. The reaction was quenched with aq.NH$_4$Cl (150 mL) and the mixture was extracted with EtOAc (150 mL×3). The combined organic layers were washed with brine (150 mL×3), dried over anhydrous Na$_2$SO$_4$ and concentrated to dryness. The residue was purified by silica gel chromatography (PE→PE:EtOAc=10:1) to give the product 1,4-dioxaspiro[4.5]dec-7-en-8-yltrifluoromethanesulfonate as a light yellow oil. (22.9 g, quantitative).

$^1$H NMR (400 MHz, CDCl$_3$): δ 5.66 (t, J=4.0 Hz, 1H), 3.99 (br, 4H), 2.53 (t, J=6.0 Hz, 2H), 2.41 (s, 2H), 1.91 (t, J=6.4 Hz, 2H).

Description 122

5-methyl-6-(1,4-dioxaspiro[4.5]dec-7-en-8-yl)-1-(tetrahydro-2H-pyran-2-yl)-1H-indazole (D122)

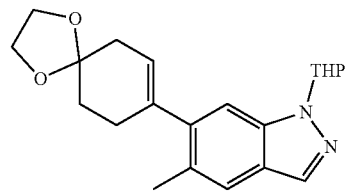

To a solution of 5-methyl-1-(tetrahydro-2H-pyran-2-yl)-6-(4,4,5,5-tetramethyl-1,3,2-dioxaborolan-2-yl)-1H-indazole (3.0 g, 8.77 mmol), 1,4-dioxaspiro[4.5]dec-7-en-8-yl trifluoromethanesulfonate (3.0 g, 10.52 mmol) and K$_2$CO$_3$ (3.6 g, 26.30 mmol) in 1,4-dioxane/H$_2$O (50 mL/10 mL) was added Pd(dppf)Cl$_2$ (642 mg, 0.88 mmol). The mixture was stirred at 100° C. for 4 hrs under N$_2$. The reaction mixture was poured into water (300 mL) and the mixture was extracted with EtOAc (100 mL×3). The combined organic layers were washed with brine (100 mL), dried over anhydrous Na$_2$SO$_4$, filtered and concentrated to dryness. The residue was purified by silica gel chromatography eluted with EtOAc:Petroleum Ether=1:10 to 1:3 to give the product (2.3 g, 74.0% yield) as a white solid.

LC-MS [mobile phase: from 90% water (0.1% FA) and 10% ACN (0.1% FA) to 5% water (0.1% FA) and 95% ACN (0.1% FA) in 2.5 min]: Rt=1.30 min; MS Calcd.: 354; MS Found: 355 [M+H]$^+$.

Description 123

5-methyl-6-(1,4-dioxaspiro[4.5]decan-8-yl)-1-(tetrahydro-2H-pyran-2-yl)-1H-indazole (D123)

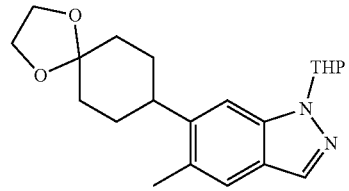

A mixture of 5-methyl-6-(1,4-dioxaspiro[4.5]dec-7-en-8-yl)-1-(tetrahydro-2H-pyran-2-yl)-1H-indazole (2.3 g, 6.49 mmol) and 10% Pd/C (230 mg) in MeOH (30 mL) was stirred at room temperature overnight under H$_2$. The reaction mixture was filtered and the filtered cake was washed with MeOH (30 mL×3). The filtrate was concentrated to dryness to give the product (1.8 g, 77.6% yield) as a white solid.

LC-MS [mobile phase: from 90% water (0.1% FA) and 10% ACN (0.1% FA) to 5% water (0.1% FA) and 95% ACN (0.1% FA) in 2.5 min]: Rt=1.295 min; MS Calcd: 356, MS Found: 357 [M+H]$^+$.

Description 124

4-(5-methyl-1H-indazol-6-yl)cyclohexanone (D124)

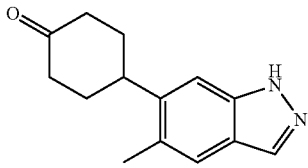 [SMILES: Cc1cc2cn[nH]c2cc1C1CCC(=O)CC1]

To a solution of 5-methyl-6-(1,4-dioxaspiro[4.5]decan-8-yl)-1-(tetrahydro-2H-pyran-2-yl)-1H-indazole (120 mg, 0.34 mmol) in CH$_2$Cl$_2$ (10 mL) was added TFA (4 mL). The reaction mixture was stirred at room temperature overnight. The reaction was concentrated to dryness, the residue was dissolved in CH$_2$Cl$_2$ (100 mL). The solution was washed with sat. NaHCO$_3$ (50 mL) and brine (50 mL), dried over anhydrous Na$_2$SO$_4$ and filtered. The filtrate was concentrated to dryness. The residue was purified by silica gel chromatography (eluted with EtOAc:Petroleum Ether=1:10 to 1:2) to give the product 4-(5-methyl-1H-indazol-6-yl)cyclohexanone (60 mg, 77.3% yield) as a yellow oil.

$^1$H NMR (400 MHz, CDCl$_3$): δ 7.97 (s, 1H), 7.56 (s, 1H), 7.32 (s, 1H), 3.36~3.28 (m, 1H), 2.59~2.55 (m, 4H), 2.51 (s, 3H), 2.26~2.21 (m, 2H), 1.96~1.89 (m, 2H).

LC-MS [mobile phase: from 90% water (0.1% FA) and 10% ACN (0.1% FA) to 5% water (0.1% FA) and 95% ACN (0.1% FA) in 2.5 min), Rt=1.23 min; MS Calcd.: 228; MS Found: 229 [M+H]$^+$.

Description 125

4-(1-(6-iodo-2-methylpyrimidin-4-yl)-5-methyl-1H-indazol-6-yl)cyclohexanone (D125)

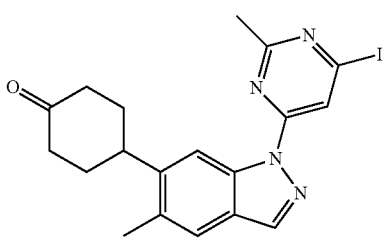 [SMILES: Cc1nc(I)cc(-n2ncc3cc(C)c(C4CCC(=O)CC4)cc32)n1]

A solution of 4-(5-methyl-1H-indazol-6-yl)cyclohexanone (7.0 g, 30.7 mmol), 4,6-diiodo-2-methylpyrimidine (20.0 g, 57.8 mmol) in THF (500 mL) was degassed and then CuI (2.0 g, 10.5 mmol) and K$_3$PO$_4$ (21.2 g, 100.00 mmol) were added. The mixture was degassed and N$^1$,N$^2$-dimethylethane-1,2-diamine (2 g, 22.7 mmol) was added. The reaction was stirred at rt overnight and then the reaction was diluted with EtOAc (500 mL). The mixture was washed with aq. NH$_4$Cl (200 mL×2) and brine (200 mL). The solution was dried and concentrated. The residue was purified by chromatography (silica EtOAc:DCM=0:100~5:100) to give a white solid. The solid was re-crystallized with DMF/water to give the product as a white solid. (4.5 g, 33% yield)

$^1$H NMR (400 MHz, CDCl$_3$): δ 8.70 (s, 1H), 8.27 (s, 1H), 8.13 (s, 1H), 7.57 (s, 1H), 3.37 (t, J=12.0 Hz, 1H), 2.76 (s, 3H), 2.62~2.59 (m, 4H), 2.55 (s, 3H), 2.30~2.26 (m, 2H), 2.09~1.98 (m, 2H).

Description 126

4-(1-(6-((1R,4R)-2-oxa-5-azabicyclo[2.2.1]heptan-5-yl)-2-methylpyrimidin-4-yl)-5-methyl-1H-indazol-6-yl)cyclohexanone (D126)

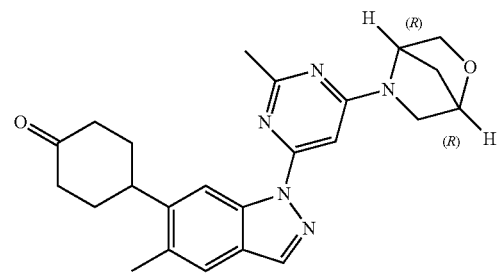

4-(1-(6-iodo-2-methylpyrimidin-4-yl)-5-methyl-1H-indazol-6-yl)cyclohexanone (200 mg, 0.45 mmol), (1R,4R)-2-oxa-5-azabicyclo[2.2.1]heptane (134 mg, 1.35 mmol) and DIPEA (580 mg, 4.49 mmol) in NMP (3 mL) was stirred at 10° C. for 15 hrs. Then the reaction was poured into water (30 mL) and extracted with EtOAc (3×30 mL). The organic phase was washed with brine (2×80 mL), dried over Na$_2$SO$_4$ and concentrated to obtain the crude. The crude was purified by silica gel chromatography (eluted with EtOAc in PE 10%-40%) to afford the title product (84 mg, yield 45%) as a white solid.

LC-MS [mobile phase: from 70% water (0.1% FA) and 30% ACN (0.1% FA) to 5% water (0.1% FA) and 95% ACN (0.1% FA) in 2.5 min]: Rt=1.406 min; MS Calcd.: 417; MS Found: 418 [M+H]$^+$.

Description 127

4-(1-(6-((1S,4S)-2-oxa-5-azabicyclo[2.2.1]heptan-5-yl)-2-methylpyrimidin-4-yl)-5-methyl-1H-indazol-6-yl)cyclohexanone (D127)

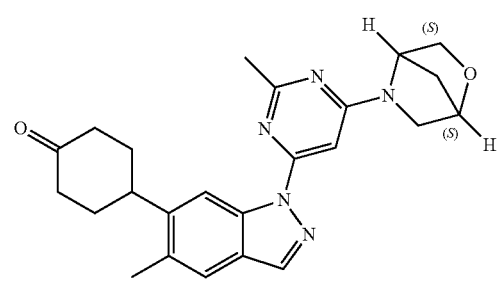

To a solution of 4-(1-(6-iodo-2-methylpyrimidin-4-yl)-5-methyl-1H-indazol-6-yl)cyclohexanone (223 mg, 0.50 mmol), (1S,4S)-2-oxa-5-azabicyclo[2.2.1]heptane hydrochloride (102 mg, 0.75 mmol) in NMP (5.0 mL) added DIPEA (0.5 mL), then the reaction mixture was stirred at 50° C. overnight. The reaction mixture was poured into brine (30 mL) and the mixture was extracted with EtOAc (30 mL×3).

The organic layers were dried over Na$_2$SO$_4$ and concentrated by vacuum. The crude was purified by silica gel (silica del: 10 g, CH$_2$Cl$_2$:CH$_3$OH=15:1) to give a white solid (166 mg, yield=79.6%).

LC-MS [mobile phase: from 95% water (0.1% FA) and 5% ACN (0.1% FA) to 5% water (0.1% FA) and 95% ACN (0.1% FA) in 10 min]: purity: 65.4%; Rt=1.567 min; MS Calcd: 417, MS Found: 418.0 [M+H]$^+$.

Descriptions 128 and 129

Cis-4-(1-(6-iodo-2-methylpyrimidin-4-yl)-5-methyl-1H-indazol-6-yl)-1-methylcyclohexanol (D128, RT: 2.153 min; D129, RT: 2.027 min)

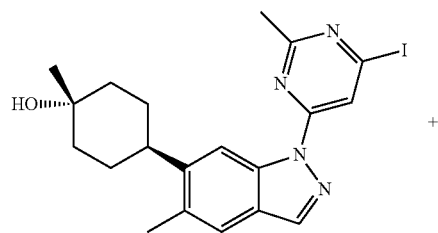

+

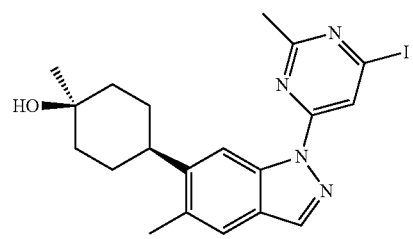

MeMgBr (0.4 mL, 1.2 mmol) was added to the solution of 4-(1-(6-iodo-2-methylpyrimidin-4-yl)-5-methyl-1H-indazol-6-yl)cyclohexanone (223 mg, 0.5 mmol) in THF (5 mL) at rt and the reaction was stirred at rt for 10 min. The reaction was quenched with sat. NH$_4$Cl (20 mL) and the mixture was extracted with EtOAc (2×20 mL). The solution was dried and concentrated. The residue was purified by chromatography (EtOAc:PE=1:3, 15 g of silica gel) to give two white solids.

Peak 1: 99 mg, 43% yield

LC-MS [mobile phase: from 70% water (0.1% FA) and 30% ACN (0.1% FA) to 5% water (0.1% FA) and 95% ACN (0.1% FA) in 10 min]: Rt=2.153 min; MS Calcd: 462, MS Found: 463 [M+H]$^+$.

Peak 2: 80 mg, 35% yield

LC-MS [mobile phase: from 70% water (0.1% FA) and 30% ACN (0.1% FA) to 5% water (0.1% FA) and 95% ACN (0.1% FA) in 10 min]: Rt=2.027 min; MS Calcd: 462, MS Found: 463 [M+H]$^+$.

Description 130

Trans-(1R,4R)-tert-butyl 5-(6-(6-(4-hydroxy-4-methylcyclohexyl)-5-methyl-1H-indazol-1-yl)-2-methylpyrimidin-4-yl)-2,5-diazabicyclo[2.2.1]heptane-2-carboxylate (D130)

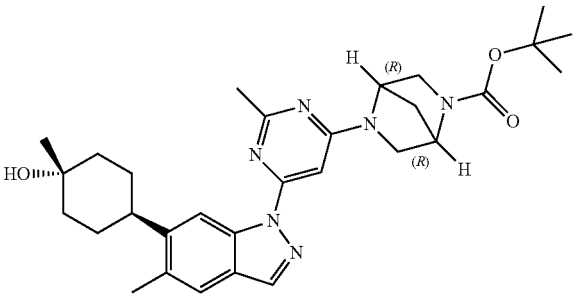

Trans-4-(1-(6-iodo-2-methylpyrimidin-4-yl)-5-methyl-1H-indazol-6-yl)-1-methylcyclohexanol (100 mg, 0.22 mmol), (1R,4R)-tert-butyl 2,5-diazabicyclo[2.2.1]heptane-2-carboxylate (128 mg, 0.66 mmol) and Et$_3$N (111 mg, 1.11 mmol) in NMP (3 mL) was stirred at 50° C. for 2 hours. Then the reaction mixture was poured into water (30 mL) and extracted with EtOAc (3×20 mL). The organic phase was washed with brine (3×50 mL), dried over Na$_2$SO$_4$ and concentrated. The crude was stirred with a solution of PE:EtOAc=10:1 (10 mL) and filtered to afford the title product (100 mg, yield 86%) as a white solid, LC-MS [mobile phase: from 80% water (0.1% FA) and 20% ACN (0.1% FA) to 5% water (0.1% FA) and 95% ACN (0.1% FA) in 2.5 min]: Rt=1.830 min; MS Calcd: 532, MS Found: 533 [M+H]$^+$.

Description 131

Cis-(1R,4R)-tert-butyl 5-(6-(6-(4-hydroxy-4-methylcyclohexyl)-5-methyl-1H-indazol-1-yl)-2-methylpyrimidin-4-yl)-2,5-diazabicyclo[2.2.1]heptane-2-carboxylate (D131)

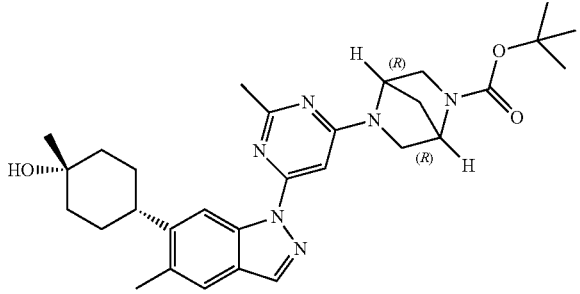

cis-4-(1-(6-iodo-2-methylpyrimidin-4-yl)-5-methyl-1H-indazol-6-yl)-1-methylcyclohexanol (100 mg, 0.22 mmol), (1R,4R)-tert-butyl 2,5-diazabicyclo[2.2.1]heptane-2-carboxylate (128 mg, 0.66 mmol), and Et$_3$N (111 mg, 1.11 mmol) in NMP (3 mL) was stirred at 50° C. for 2 hours. Then the reaction was poured into water (30 mL) and the mixture was extracted with EtOAc (3×20 mL). The organic phase was washed with brine (3×50 mL), dried over Na$_2$SO$_4$ and concentrated. The crude was stirred with a solution of PE:EtOAc=10:1 (10 mL) and filtered to afford the title product (90 mg, yield 78%) as a white solid.

LC-MS [mobile phase: from 70% water (0.1% FA) and 30% ACN (0.1% FA) to 5% water (0.1% FA) and 95% ACN (0.1% FA) in 2.5 min]: Rt=1.940 min; MS Calcd: 532, MS Found: 533 [M+H]$^+$.

Description 132

Cis-(1S,4S)-tert-butyl 5-(6-(6-(4-hydroxy-4-methyl-cyclohexyl)-5-methyl-1H-indazol-1-yl)-2-methylpyrimidin-4-yl)-2,5-diazabicyclo[2.2.1]heptane-2-carboxylate (D132)

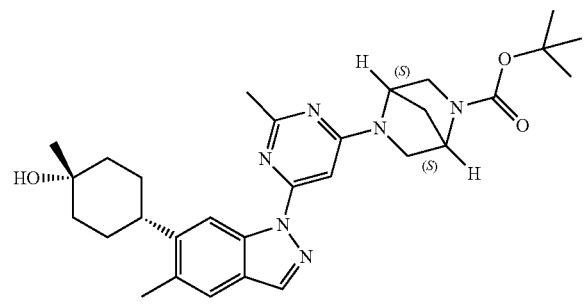

Cis-4-(1-(6-iodo-2-methylpyrimidin-4-yl)-5-methyl-1H-indazol-6-yl)-1-methylcyclohexanol (75 mg, 0.162 mmol), (1S,4S)-tert-butyl 2,5-diazabicyclo[2.2.1]heptane-2-carboxylate (96 mg, 0.487 mmol) and DIPEA (210 mg, 1.621 mmol) in NMP (7 mL) was stirred at 50° C. over weekend. Then the reaction was poured into water (40 mL) and extracted with EtOAc (3×40 mL). The organic phase was washed with brine (3×120 mL), dried over Na$_2$SO$_4$ and concentrated. The crude was stirred with a solution of PE:EtOAc=10:1 (5 mL) and filtered to afford the title product (85 mg, yield 98%) as a white solid.

LC-MS [mobile phase: from 60% water (0.1% FA) and 40% ACN (0.1% FA) to 5% water (0.1% FA) and 95% ACN (0.1% FA) in 2.0 min]: Rt=1.66 min; MS Calcd: 532, MS Found: 533 [M+H]$^+$.

Description 133

Trans-tert-butyl 5-(6-(6-(cis-4-hydroxy-4-methylcyclohexyl)-5-methyl-1H-indazol-1-yl)-2-methylpyrimidin-4-yl)-2,5-diazabicyclo[2.2.1]heptane-2-carboxylate (D133)

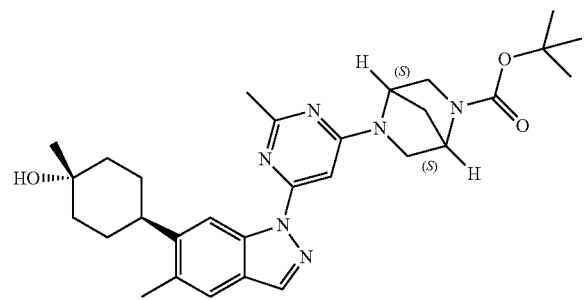

A solution of trans-4-(1-(6-iodo-2-methylpyrimidin-4-yl)-5-methyl-1H-indazol-6-yl)-1-methyl cyclohexanol (35 mg, 0.076 mmol), (1S,4S)-tert-butyl 2,5-diazabicyclo[2.2.1]heptane-2-carboxylate (60 mg, 0.3 mmol), Et$_3$N (0.5 mL) in NMP (5 mL) was stirred at 50° C. overnight. The reaction was diluted with EtOAc (50 mL) and the solution was washed with brine (3×50 mL). The organic solution was dried and concentrated to give the crude product as an off-white solid (40 mg, 99% yield) which was used directly into next step without further purification.

LC-MS [mobile phase: from 70% water (0.1% TFA) and 30% ACN (0.1% TFA) to 5% water (0.1% TFA) and 95% ACN (0.1% TFA) in 2 min]: Rt=1.61 min; MS Calcd.: 532, MS Found: 533 [M+H]$^+$.

Description 134

4-(1-(6-Iodo-2-methoxypyrimidin-4-yl)-5-methyl-1H-indazol-6-yl)cyclohexanone (D134)

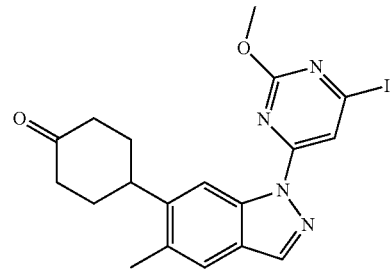 [SMILES: COc1nc(I)cc(-n2ncc3cc(C)c(C4CCC(=O)CC4)cc32)n1]

To a suspension of 4-(5-methyl-1H-indazol-6-yl)cyclohexanone (500 mg, 2.19 mmol), 4,6-diiodo-2-methoxypyrimidine (1.19 g, 3.29 mmol), CuI (250 mg, 1.31 mmol) and K$_3$PO$_4$ (1.86 g, 8.76 mmol) in THF (10 mL) was added N$^1$,N$^2$-dimethylethane-1,2-diamine (0.25 mL). The resulting mixture was degassed with N$_2$ three times and stirred at room temperature overnight. The reaction suspension was poured into aq. 10% NH$_3$—H$_2$O (50 mL). The resulting mixture was extracted with CH$_2$Cl$_2$ (2×40 mL). The combined organic layers were washed with brine (2×30 mL), dried over anhydrous Na$_2$SO$_4$ and concentrated. The residue was purified by silica gel chromatography (eluted with PE:EtOAc=4:1, 20 g of silica gel) to give product (370 mg, yield 36.5%) as a white solid.

$^1$H NMR (400 MHz, CDCl$_3$): δ 8.66 (s, 1H), 8.13 (s, 1H), 8.10 (s, 1H), 7.57 (s, 1H), 4.12 (s, 3H), 3.39~3.33 (m, 1H), 2.60~2.55 (m, 4H), 2.55 (s, 3H), 2.29~2.25 (m, 2H), 2.03~1.96 (m, 2H).

Description 135

4-(1-(6-(((1R,4R)-2-oxa-5-azabicyclo[2.2.1]heptan-5-yl)-2-methoxypyrimidin-4-yl)-5-methyl-1H-indazol-6-yl)cyclohexanone (D135)

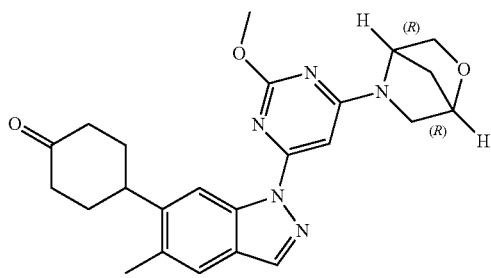

To a solution of 4-(1-(6-iodo-2-methoxypyrimidin-4-yl)-5-methyl-1H-indazol-6-yl)cyclohexanone (200 mg, 0.43 mmol) and (1R,4R)-2-oxa-5-azabicyclo[2.2.1]heptane hydrochloride (117 mg, 0.86 mmol) in DMF (10 mL) was added DIPEA (222 mg, 1.72 mmol) at room temperature. The reaction mixture was stirred at room temperature overnight. The reaction mixture was poured into water (50 mL) and extracted with EtOAc (30 mL×3). The combined organic layers were washed with brine (50 mL), dried over anhydrous $Na_2SO_4$, filtered and concentrated to dryness. The residue was purified by silica gel chromatography eluted with (EtOAc:Petroleum Ether=1:2, 10 g of silica gel) to give the product (120 mg, 64% yield) as a yellow solid.

LC-MS [mobile phase: from 90% water (0.1% FA) and 10% ACN (0.1% FA) to 5% water (0.1% FA) and 95% ACN (0.1% FA) in 2.5 min]: Rt=1.701 min; MS Calcd: 433, MS Found: 434 [M+H]$^+$.

Description 136

Tert-butyl 4-(1-(6-(((1R,4R)-2-oxa-5-azabicyclo[2.2.1]heptan-5-yl)-2-methylpyrimidin-4-yl)-5-methyl-1H-indazol-6-yl)piperidine-1-carboxylate (D136)

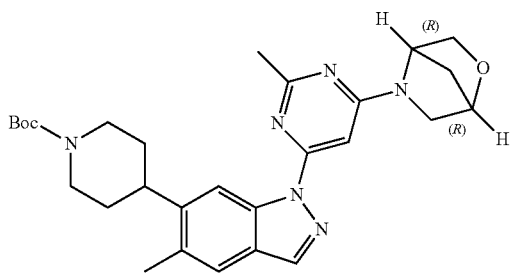

To a solution of tert-butyl 4-(5-methyl-1H-indazol-6-yl)piperidine-1-carboxylate (200 mg, 0.634 mmol) and (1R,4R)-5-(6-iodo-2-methylpyrimidin-4-yl)-2-oxa-5-azabicyclo[2.2.1]heptane (200 mg, 0.630 mmol) in toluene (30 ml) were added CuI (180 mg, 0.94 mmol), $K_3PO_4$ (267 mg, 1.26 mmol) and N,N'-dimethylethylenediamine (111 mg, 1.26 mmol). The reaction mixture was stirred at 100° C. for 4 h, filtered and concentrated to dryness. The residue was purified by silica gel chromatography eluted with $CH_2Cl_2$:MeOH=20:1 to give desired product as a yellow solid (260 mg, yield: 81%).

LC-MS [mobile phase: from 50% water (0.1% FA) and 50% ACN (0.1% FA) to 5% water (0.1% FA) and 95% ACN (0.1% FA) in 2.6 min]: Rt=1.97 min; MS Calcd: 504, MS Found: 505 [M+H]$^+$.

Description 137

Tert-butyl 4-(1-(6-(((1S,4S)-2-oxa-5-azabicyclo[2.2.1]heptan-5-yl)-2-methylpyrimidin-4-yl)-5-methyl-1H-indazol-6-yl)piperidine-1-carboxylate (D137)

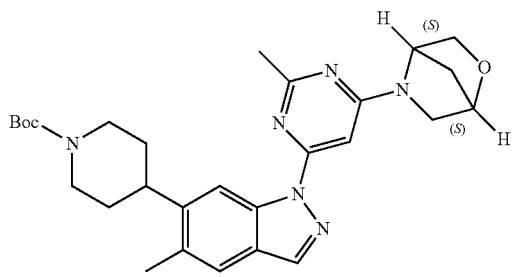

To a solution of tert-butyl 4-(5-methyl-1H-indazol-6-yl)piperidine-1-carboxylate (200 mg, 0.634 mmol) and (1S,4S)-5-(6-iodo-2-methylpyrimidin-4-yl)-2-oxa-5-azabicyclo[2.2.1]heptane (200 mg, 0.631 mmol) in toluene (30 ml) were added CuI (180 mg, 0.94 mmol), $K_3PO_4$ (267 mg, 1.26 mmol) and N,N'-dimethylethylenediamine (111 mg, 1.26 mmol). The reaction mixture was stirred at 100° C. for 4 h. The cooled reaction mixture was filtered and the filtrate was concentrated to dryness. The residue was purified by silica gel chromatography eluted with $CH_2Cl_2$:MeOH=20:1 to give desired product as a yellow solid (271 mg, yield: 85%).

LC-MS [mobile phase: from 50% water (0.1% FA) and 50% ACN (0.1% FA) to 5% water (0.1% FA) and 95% ACN (0.1% FA) in 2.6 min]: Rt=1.93 min; MS Calcd: 504, MS Found: 505 [M+H]$^+$.

Description 138

2-(4-(1-(6-(((1S,4S)-2-oxa-5-azabicyclo[2.2.1]heptan-5-yl)-2-methylpyrimidin-4-yl)-5-methyl-1H-indazol-6-yl)piperidin-1-yl)acetate (D138)

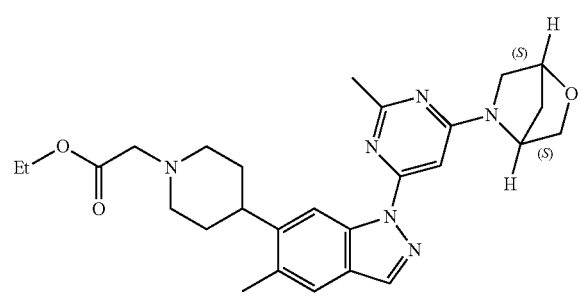

109

Step 1

Synthesis of (1S,4S)-5-(2-methyl-6-(5-methyl-6-(piperidin-4-yl)-1H-indazol-1-yl)pyrimidin-4-yl)-2-oxa-5-azabicyclo[2.2.1]heptane Hydrochloride

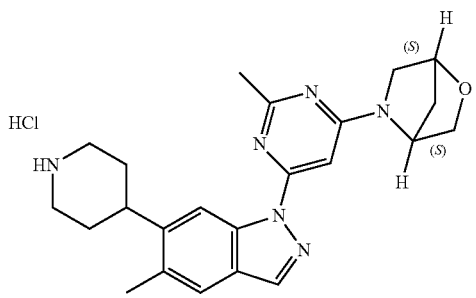

A mixture of tert-butyl 4-(1-(6-((1S,4S)-2-oxa-5-azabicyclo[2.2.1]heptan-5-yl)-2-methylpyrimidin-4-yl)-5-methyl-1H-indazol-6-yl)piperidine-1-carboxylate (280 mg, 0.54 mmol) in HCl/EtOAc (2 M, 5 mL) was stirred at Rt for 30 min. The reaction mixture was concentrated to give crude product as a white solid. (240 mg, crude).

Step 2

Synthesis of ethyl 2-(4-(1-(6-((1S,4S)-2-oxa-5-azabicyclo[2.2.1]heptan-5-yl)-2-methylpyrimidin-4-yl)-5-methyl-1H-indazol-6-yl)piperidin-1-yl)acetate

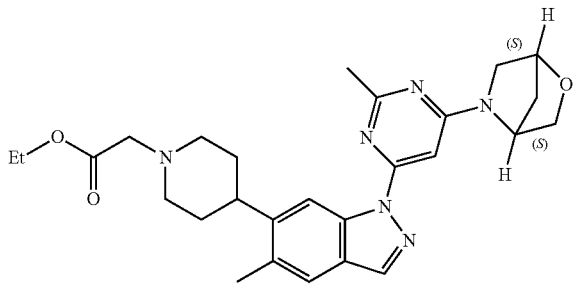

Ethyl 2-bromoacetate (89 mg, 0.54 mmol) was slowly added to the solution of (1S,4S)-5-(2-methyl-6-(5-methyl-6-(piperidin-4-yl)-1H-indazol-1-yl)pyrimidin-4-yl)-2-oxa-5-azabicyclo[2.2.1]heptane hydrochloride (120 mg, 0.27 mmol) and Et$_3$N (0.3 mL) in DMF (5 mL) and the reaction was stirred at rt overnight. The reaction was then diluted with EtOAc (30 mL) and washed with brine (50 mL×2). The solution was dried and concentrated. The residue was purified by prep-TLC (EtOAc/PE=2/1) to give the product as a white solid (75 mg, 57% yield).

110

Description 139

Step 1

(1R,4R)-5-(2-methyl-6-(5-methyl-6-(piperidin-4-yl)-1H-indazol-1-yl)pyrimidin-4-yl)-2-oxa-5-azabicyclo[2.2.1]heptane Hydrochloride

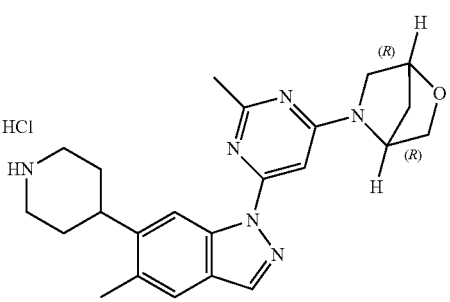

A mixture of tert-butyl 4-(1-(6-((1R,4R)-2-oxa-5-azabicyclo[2.2.1]heptan-5-yl)-2-methylpyrimidin-4-yl)-5-methyl-1H-indazol-6-yl)piperidine-1-carboxylate (270 mg, 0.41 mmol) in HCl/EtOAc (2 M, 2 mL) was stirred at Rt for 30 min. The reaction mixture was concentrated to give crude product, HCl salt, as a white solid. (250 mg, crude), which was used in next step without further purifications.

Step 2

Ethyl 2-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)acetate

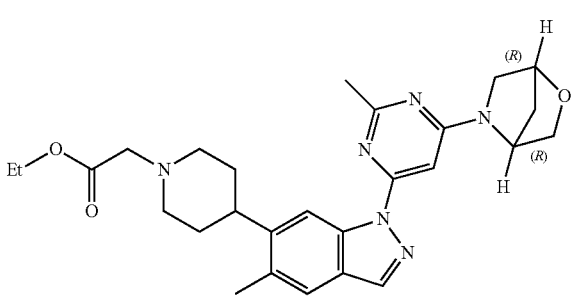

Ethyl 2-bromoacetate (248 mg, 1.48 mmol) was slowly added to the solution of (1R,4R)-5-(2-methyl-6-(5-methyl-6-(piperidin-4-yl)-1H-indazol-1-yl)pyrimidin-4-yl)-2-oxa-5-azabicyclo[2.2.1]heptane hydrochloride (200 mg, 0.45 mmol) and Et$_3$N (250 mg, 2.47 mmol) in DMF (3 mL) and the reaction was stirred at rt for 2 h. The reaction was then diluted with EtOAc (20 mL) and washed with brine (50 mL), dried and concentrated. The residue was purified by prep-TLC (PE/EtOAc=1/1) to give the product as a white solid. (55 mg, 23% yield).

LC-MS [mobile phase: from 80% water (0.1% FA) and 20% ACN (0.1% FA) to 5% water (0.1% FA) and 95% ACN (0.1% FA) in 2.0 min]: Rt=1.29 min; MS Calcd.: 490, MS Found: 491 [M+H]$^+$.

Description 140

Tert-butyl 4-(1-(6-(2-oxa-5-azabicyclo[2.2.2]octan-5-yl)-2-methoxypyrimidin-4-yl)-5-methyl-1H-indazol-6-yl)piperidine-1-carboxylate (D140)

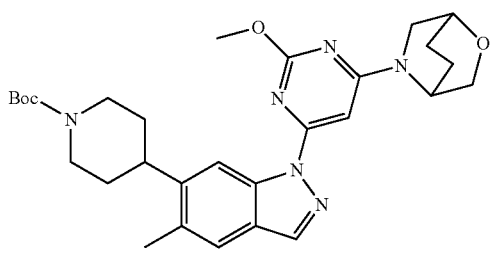 [SMILES: COc1nc(N2CC3CCC2CO3)cc(-n2ncc3cc(C)c(C4CCN(C(=O)OC(C)(C)C)CC4)cc32)n1]

A mixture of tert-butyl 4-(5-methyl-1H-indazol-6-yl)piperidine-1-carboxylate (50 mg, 0.16 mmol), 5-(6-iodo-2-methoxypyrimidin-4-yl)-2-oxa-5-azabicyclo[2.2.2]octane (65 mg, 0.19 mmol), N,N'-dimethylcyclohexane-1,2-diamine (45 mg, 0.32 mmol), CuI (30 mg, 0.16 mmol) and $K_3PO_4$ (68 mg, 0.32 mmol) in toluene (3 mL) was stirred at 100° C. for 2 hours. The mixture was diluted with EtOAc (30 mL), washed with brine (30 mL), dried over $Na_2SO_4$, filtered and concentrated. The residue was purified by silica gel chromatography column (petroleum ether/EtOAc=1:1) to give the title compound (64 mg) as colorless oil.

$^1$H-NMR (CDCl$_3$, 400 MHz): δ 8.73 (s, 1H), 8.07 (s, 1H), 7.51 (s, 1H), 6.61 (s, 1H), 4.98 (s, 1H), 4.31-4.29 (m, 2H), 4.22-4.09 (m, 4H), 3.93 (s, 1H), 3.02-2.86 (m, 3H), 2.47 (s, 3H), 2.11-1.98 (m, 5H), 1.89-1.85 (m, 2H), 1.80-1.63 (m, 4H), 1.50 (s, 9H).

Description 141

4,6-diiodo-2-(methylthio)pyrimidine (D141)

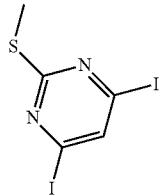

A mixture of 4,6-dichloro-2-(methylthio)pyrimidine (2.0 g, 10.25 mmol) and NaI (2.0 g, 13.33 mmol) in HI (55%, 20 mL) was stirred at 40° C. overnight. The reaction suspension was poured into ice water (50 mL). The resulting suspension was filtered. The filter cake was purified by silica gel chromatography (silica gel: 10 g, PE:EtOAc=8:1) to give product as a white solid (3.18 g, yield: 82%)

LC-MS [mobile phase: from 60% water (0.1% FA) and 40% ACN (0.1% FA) to 5% water (0.1% FA) and 95% ACN (0.1% FA) in 2.0 min]: Rt=1.18 min; MS Calcd.: 378, MS Found: 379 [M+H]$^+$.

Description 142

(1R,4R)-5-(6-iodo-2-(methylthio)pyrimidin-4-yl)-2-oxa-5-azabicyclo[2.2.1]heptane (D142)

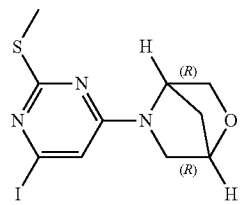

To a solution of 4,6-diiodo-2-(methylthio)pyrimidine (500 mg, 1.32 mmol) and (1R,4R)-2-oxa-5-azabicyclo[2.2.1]heptane (179 mg, 1.81 mmol) in i-PrOH (10 mL) and THF (10 mL) was added DIEA (513 mg, 3.97 mmol). The reaction was stirred at 50° C. overnight. The reaction solution was concentrated and the residue was diluted with EtOAc (30 mL). The resulting mixture was washed with brine (30 mL), dried over anhydrous $Na_2SO_4$ and concentrated. The residue was purified by silica gel chromatography (silica gel: 3 g, PE:EtOAc=3:1) to give product as a white solid (380 mg, yield: 82%)

LC-MS [mobile phase: from 60% water (0.1% FA) and 40% ACN (0.1% FA) to 5% water (0.1% FA) and 95% ACN (0.1% FA) in 2.0 min]: Rt=1.64 min; MS Calcd.: 349, MS Found: 350 [M+H]$^+$.

Description 143

(1R,4R)-5-(6-iodo-2-(methylsulfonyl)pyrimidin-4-yl)-2-oxa-5-azabicyclo [2.2.1]heptane (D143)

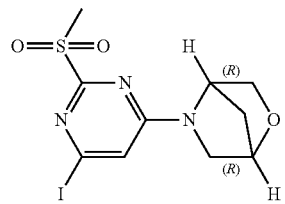

To a solution of (1R,4R)-5-(6-iodo-2-(methylthio)pyrimidin-4-yl)-2-oxa-5-azabicyclo[2.2.1]heptane (100 mg, 0.29 mmol) in $CH_2Cl_2$ (10 mL) was added m-CPBA (99 mg, 0.57 mmol). The reaction was stirred at room temperature overnight. PE (30 mL) was added and the resulting suspension was filtered. The filter cake was dissolved with EtOAc (20 mL). The resulting mixture was washed with sat. $NaHCO_3$ (20 mL) and brine (20 mL), dried over anhydrous and concentrated to give product as a white solid (85 mg, yield: 78%).

LC-MS [mobile phase: from 60% water (0.1% FA) and 40% ACN (0.1% FA) to 5% water (0.1% FA) and 95% ACN (0.1% FA) in 2.0 min]: Rt=0.89 min; MS Calcd.: 381, MS Found: 382 [M+H]$^+$.

Description 144

(1S,4S)-5-(6-iodo-2-(methylthio)pyrimidin-4-yl)-2-oxa-5-azabicyclo[2.2.1]heptane (D144)

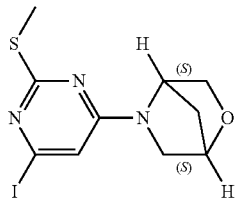

To a solution of 4,6-diiodo-2-(methylthio)pyrimidine (500 mg, 1.32 mmol) and (1S,4S)-2-oxa-5-azabicyclo[2.2.1]heptane (179 mg, 1.32 mmol) in i-PrOH (10 mL) and THF (10 mL) was added DIEA (513 mg, 3.97 mmol). The reaction was stirred at 50° C. overnight. The reaction solution was concentrated and the residue was diluted with EtOAc (30 mL). The resulting mixture was washed with brine (30 mL), dried over anhydrous $Na_2SO_4$ and concentrated. The residue was purified by silica gel chromatography (silica gel: 3 g, PE:EtOAc=3:1) to give product as a white solid (405 mg, yield: 88%)

LC-MS [mobile phase: from 60% water (0.1% FA) and 40% ACN (0.1% FA) to 5% water (0.1% FA) and 95% ACN (0.1% FA) in 2.0 min]: Rt=1.63 min; MS Calcd.: 349, MS Found: 350 $[M+H]^+$.

Description 145

(1S,4S)-5-(6-iodo-2-(methylsulfonyl)pyrimidin-4-yl)-2-oxa-5-azabicyclo[2.2.1]heptane (D145)

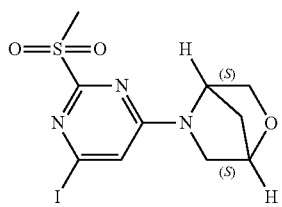

To a solution of (1S,4S)-5-(6-iodo-2-(methylthio)pyrimidin-4-yl)-2-oxa-5-azabicyclo[2.2.1] heptane (400 mg, 1.15 mmol) in $CH_2Cl_2$ (20 mL) was added m-CPBA (395 mg, 2.29 mmol).

The reaction was stirred at room temperature overnight. The reaction was quenched with sat.$Na_2S_2O_3$. The resulting mixture was washed with sat.$Na_2CO_3$ (20 mL) and brine (20 mL), dried over anhydrous and concentrated to give product as a white solid (310 mg, yield: 71%).

LC-MS [mobile phase: from 60% water (0.1% FA) and 40% ACN (0.1% FA) to 5% water (0.1% FA) and 95% ACN (0.1% FA) in 2.0 min]: Rt=0.92 min; MS Calcd.: 381, MS Found: 382 $[M+H]^+$.

Description 146

(1R,4R)-5-(6-(5-methyl-6-(1-(oxetan-3-yl)piperidin-4-yl)-1H-indazol-1-yl)-2-(methylsulfonyl)pyrimidin-4-yl)-2-oxa-5-azabicyclo[2.2.1]heptane (D146)

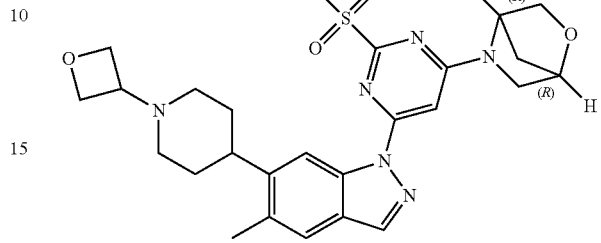

To a suspension of (1R,4R)-5-(6-iodo-2-(methylsulfonyl) pyrimidin-4-yl)-2-oxa-5-azabicyclo[2.2.1]heptane (80 mg, 0.21 mmol), 5-methyl-6-(1-(oxetan-3-yl)piperidin-4-yl)-1H-indazole (57 mg, 0.21 mmol), CuI (40 mg, 0.21 mmol) and $K_3PO_4$ (89 mg, 0.42 mmol) in toluene (4 mL) and THF (1 mL) was added $N^1,N^2$-dimethylethane-1,2-diamine (40 mg, 0.45 mmol). The resulting mixture was degassed with $N_2$ three times. The reaction was stirred at 80° C. for 2 h. EtOAc (20 mL) was added and the resulting mixture was washed with sat. $NH_4Cl$ (20 mL) and brine (20 mL), dried over anhydrous $Na_2SO_4$ and concentrated. The residue was purified by column (silica gel: 3 g, $CH_2Cl_2$:MeOH=20:1) to give product as a white solid (40 mg, yield: 36%).

LC-MS [mobile phase: from 60% water (0.1% FA) and 40% ACN (0.1% FA) to 5% water (0.1% FA) and 95% ACN (0.1% FA) in 2.0 min]: Rt=1.05 min; MS Calcd.: 524, MS Found: 525 $[M+H]^+$.

Description 147

(1S,4S)-5-(6-(5-methyl-6-(1-(oxetan-3-yl)piperidin-4-yl)-1H-indazol-1-yl)-2-(methylsulfonyl)pyrimidin-4-yl)-2-oxa-5-azabicyclo[2.2.1]heptane (D147)

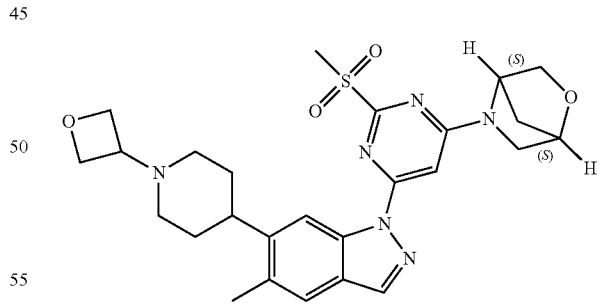

To a suspension of (1S,4S)-5-(6-iodo-2-(methylsulfonyl) pyrimidin-4-yl)-2-oxa-5-azabicyclo[2.2.1]heptane (112 mg, 0.29 mmol), 5-methyl-6-(1-(oxetan-3-yl)piperidin-4-yl)-1H-indazole (80 mg, 0.29 mmol), CuI (56 mg, 0.29 mmol) and $K_3PO_4$ (125 mg, 0.59 mmol) in toluene (8 mL) and THF (8 mL) was added $N^1,N^2$-dimethylethane-1,2-diamine (52 mg, 0.59 mmol). The resulting mixture was degassed with $N_2$ three times. The reaction was stirred at 80° C. for 2 h. EtOAc (30 mL) was added and the resulting mixture was washed with sat. $NH_4Cl$ (30 mL) and brine (30 mL), dried over anhydrous Na$_2$SO$_4$ and concentrated. The residue was purified by column (silica gel: 3 g, CH$_2$Cl$_2$:MeOH=20:1) to give the title product as a white solid (82 mg, yield: 53%).

LC-MS [mobile phase: from 60% water (0.1% FA) and 40% ACN (0.1% FA) to 5% water (0.1% FA) and 95% ACN (0.1% FA) in 2.0 min]: Rt=1.05 min; MS Calcd.: 524, MS Found: 525 [M+H]$^+$.

Description 148

2-azabicyclo[2.2.1]heptane-5-carboxylic Acid Hydrochloride (D148)

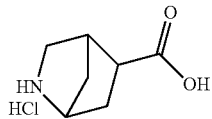

A mixture of 2-(tert-butoxycarbonyl)-2-azabicyclo[2.2.1]heptane-5-carboxylic acid (150 mg, 0.622 mmol) in HCl/EtOAc (3M, 1 mL) was stirred at rt for 2 h. The reaction was concentrated to give a pale yellow solid, which was used to next step without further purification. (15 mg, crude)

Description 149

Methyl 3-(6-iodo-2-methoxypyrimidin-4-yl)-3-azabicyclo[3.1.1]heptane-6-carboxylate (D149)

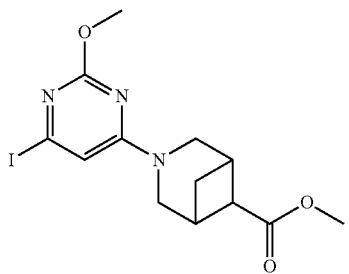 [SMILES: COC(=O)C1C2CC1CN(c1cc(I)nc(OC)n1)C2]

To a solution of methyl 3-azabicyclo[3.1.1]heptane-6-carboxylate hydrochloride (150 mg, 0.78 mmol) in isopropanol (6 mL) was added 4,6-diiodo-2-methoxypyrimidine (283 mg, 0.78 mmol) and TEA (236 mg, 2.34 mmol). The mixture was stirred at 40° C. for 2 hour. The mixture was diluted with H$_2$O (10 mL) and extracted with ethyl acetate (10 mL×3). The extracts were combined and dried over Na$_2$SO$_4$. The organic phase was filtered and concentrated. The residue was purified by silica gel chromatography column (Petroleum ether:EtOAc=20:1 to 5:1) to give the title compound (140 mg, 46%) as yellow solid.

$^1$H NMR (400 MHz, CDCl$_3$): δ 6.59 (s, 1H), 3.92 (s, 3H), 3.91-3.88 (m, 2H), 3.76 (s, 3H), 3.6 (s, 2H), 2.87 (d, J=5.6 Hz, 2H), 2.65-2.62 (m, 1H), 2.55 (d, J=5.6 Hz, 1H), 1.44-1.40 (m, 1H).

Description 150

Methyl 3-(6-(6-isopropoxy-5-methyl-1H-indazol-1-yl)-2-methoxypyrimidin-4-yl)-3-azabicyclo[3.1.1]heptane-6-carboxylate (D150)

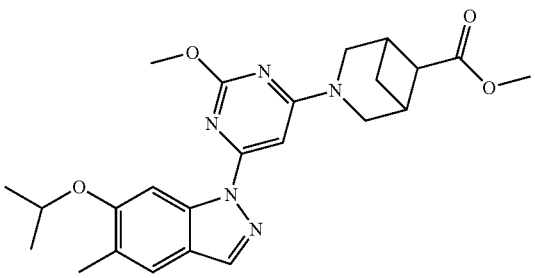 [SMILES: COC(=O)C1C2CC1CN(c1cc(-n3ncc4cc(C)c(OC(C)C)cc43)nc(OC)n1)C2]

A mixture of 6-isopropoxy-5-methyl-1H-indazole (53 mg, 0.28 mmol), methyl 3-(6-iodo-2-methoxypyrimidin-4-yl)-3-azabicyclo[3.1.1]heptane-6-carboxylate (120 mg, 0.31 mmol), K$_3$PO$_4$ (119 mg, 0.56 mmol), CuI (54 mg, 0.28 mmol) and N,N'-dimethyl-cyclohexane-1,2-diamine (80 mg, 0.56 mmol) in toluene (3.0 mL) was stirred at 110° C. for 2 hours. The reaction was diluted with EtOAc (100 mL), washed with brine (50 mL), dried over Na$_2$SO$_4$. The organic phase was filtered and concentrated, the residue was purified by prep-TLC (petroleum ether/EtOAc=8:1) to afford the title compound (100 mg, 79%) as a yellow solid.

$^1$H NMR (400 MHz, CDCl$_3$): δ 8.35 (s, 1H), 8.01 (s, 1H), 7.44 (s, 1H), 6.78 (s, 1H), 4.72-4.66 (m, 1H), 4.11 (s, 3H), 4.03-3.95 (m, 2H), 3.82-3.72 (m, 2H), 3.77 (s, 3H), 2.89 (d, J=2.8 Hz, 2H), 2.68-2.63 (m, 1H), 2.29 (s, 3H), 1.60 (d, J=5.6 Hz, 1H), 1.48-1.45 (m, 1H), 1.42 (d, J=6.0 Hz, 6H).

Description 151

2-{2-Methyl-6-[5-methyl-6-(tetrahydro-pyran-4-yl)-indazol-1-yl]-pyrimidin-4-yl}-2-aza-bicyclo[2.2.1]heptane-5-carboxylic Acid Methyl Ester (D151)

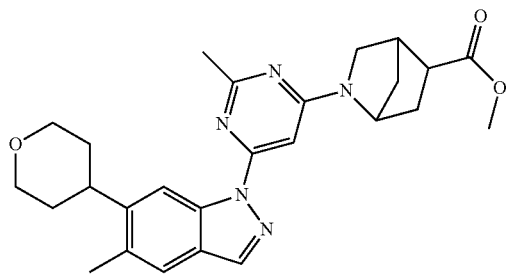 [SMILES: COC(=O)C1CC2CC1CN2c1cc(-n2ncc3cc(C)c(C4CCOCC4)cc32)nc(C)n1]

1-(6-Iodo-2-methyl-pyrimidin-4-yl)-5-methyl-6-(tetrahydro-pyran-4-yl)-1H-indazole (350 mg, 0.80 mmol), 2-Aza-bicyclo[2.2.1]heptane-5-carboxylic acid methyl ester (164 mg, 0.96 mmol) and DIPEA (280 mg, 2.164 mmol) in NMP (8 mL) was stirred at 50° C. for 3 days. Then the reaction was poured into water (30 mL) and extracted with EtOAc (30 mL×3). The organic phase was washed with brine (90 mL×3), dried over Na$_2$SO$_4$ and concentrated to obtain the crude compound (350 mg), which was used in next steps without further purifications.

Description 152

Cis-1-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 1) (D152)

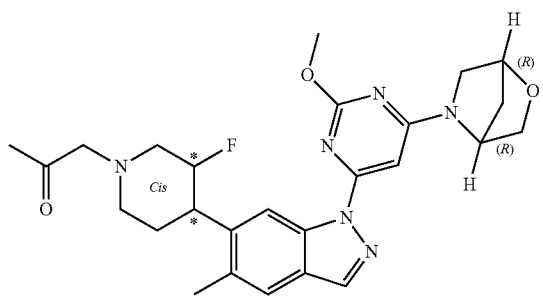

To a solution of cis-(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (from Peak 1, 140 mg, 0.32 mmol) in DMF (2 mL) was added Et$_3$N (162 mg, 1.60 mmol) followed by 1-bromopropan-2-one (131 mg, 0.96 mmol). The reaction was stirred at rt for 2 h. EtOAc (20 mL) was added and the resulting mixture was washed with brine (2×50 mL), dried over anhydrous Na$_2$SO$_4$ and concentrated to give target product as a yellow oil (148 mg, yield: 94%).

LC-MS [mobile phase: 80% water (0.1% FA) and 20% ACN (0.1% FA) to 5% water (0.1% FA) and 95% ACN (0.1% FA) in 9.0 min]: Rt=3.85 min; MS Calcd.: 494, MS Found: 495 [M+H]$^+$.

Description 153

Cis-1-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 2) (D153)

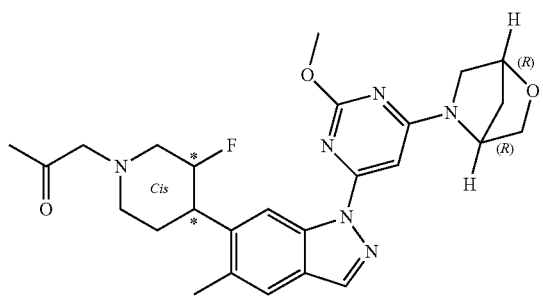

To a solution of cis-(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (from Peak 2, 145 mg, 0.33 mmol) in DMF (2 mL) was added Et$_3$N (167 mg, 1.65 mmol) followed by 1-bromopropan-2-one (136 mg, 0.99 mmol). The reaction was stirred at rt for 2 h. EtOAc (20 mL) was added and the resulting mixture was washed with brine (2×50 mL), dried over anhydrous Na$_2$SO$_4$ and concentrated to give the target product as a yellow oil (152 mg, yield: 93%).

LC-MS [mobile phase: 80% water (0.1% FA) and 20% ACN (0.1% FA) to 5% water (0.1% FA) and 95% ACN (0.1% FA) in 9.0 min]: Rt=3.86 min; MS Calcd.: 494.2, MS Found: 495.2 [M+H]$^+$.

Description 154

Cis-1-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 1) (D154)

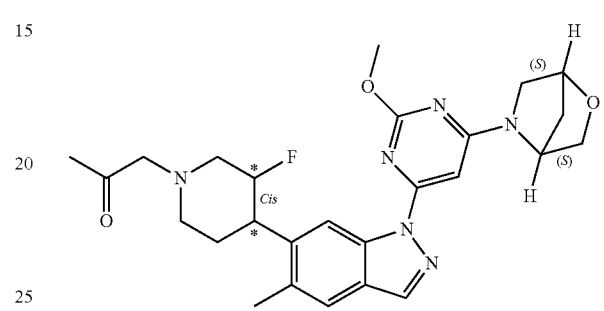

1-bromopropan-2-one (99 mg, 0.72 mmol) and Et$_3$N (0.3 mL) were slowly added to the solution of cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane hydrochloride (from Peak 1, 180 mg, 0.36 mmol) in DMF (5 mL) and the reaction was stirred at rt overnight. EtOAc (20 mL) was added and the resulting mixture was washed with brine (3×20 mL). The solution was dried and concentrated. The residue was purified by prep-TLC (EtOAc:PE=2:1) to give the product as a white solid (140 mg, yield: 78%).

LC-MS [mobile phase: from 90% water (0.1% FA) and 10% ACN (0.1% FA) to 5% water (0.1% FA) and 95% ACN (0.1% FA) in 2.0 min]: Rt=1.26 & 1.30 min; MS Calcd.: 494, MS Found: 495.4 [M+H]$^+$.

Description 155

Cis-1-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 2) (D155)

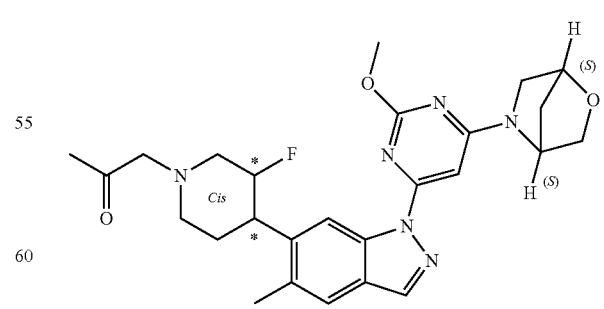

Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane hydrochloride (from Peak 2, 105 mg, 0.22 mmol) was dissolved in DMF (4 mL), Et$_3$N (120 mg, 1.1 mmol) and 1-bromopropan-2-one (75 mg, 0.55 mmol) were added to the solution at rt. The mixture was stirred at Rt for 3 hours. The reaction was diluted with EtOAc (50 mL). The solution was washed with sat. NH$_4$Cl (100 mL×2). The organic layer was concentrated to give title compound as a white oil (110 mg, crude)

LC-MS [mobile phase: 80% water (0.1% FA) and 20% ACN (0.1% FA) to 5% water (0.1% FA) and 95% ACN (0.1% FA) in 2.0 min]: Rt=1.16 min; MS Calcd.: 494, MS Found: 495 [M+H]$^+$.

Description 156

1-(6-chloro-2-methoxypyrimidin-4-yl)-5-methyl-6-(1-(oxetan-3-yl)piperidin-4-yl)-1H-indazole (D156)

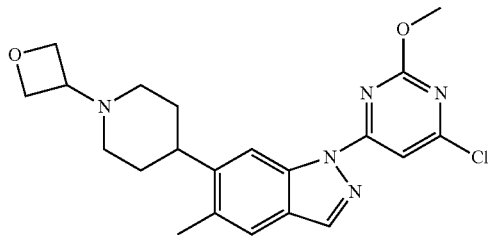 [SMILES: COc1nc(Cl)cc(-n2ncc3cc(C)c(C4CCN(C5COC5)CC4)cc32)n1]

To a solution of 5-methyl-6-(1-(oxetan-3-yl)piperidin-4-yl)-1H-indazole (200 mg, 0.74 mmol) and 4,6-dichloro-2-methoxypyrimidinein (132 mg, 0.74 mmol) in DMF (30 mL) was added Cs$_2$CO$_3$ (720 mg, 2.21 mmol). The reaction mixture was stirred at 50° C. for 2 h. The resulting mixture was diluted with water (100 mL) and extracted with EtOAc (2×100 mL). The combined organic layer was washed with water (3×100 mL) and brine (100 mL), dried over anhydrous Na$_2$SO$_4$, filtered and concentrated to give a residue. The residue was purified by silica gel column chromatography (PE:EtOAc=1:2) to give the title compound (120 mg, yield: 40%) as a white solid.

LC-MS [mobile phase: from 50% water (0.1% FA) and 50% ACN (0.1% FA) to 5% water (0.1% FA) and 95% ACN (0.1% FA) in 2.6 min]: Rt=0.801 min; MS Calcd: 413, MS Found: 414 [M+H]$^+$.

Description 157

Tert-butyl cis-4-(1-(6-chloro-2-methoxypyrimidin-4-yl)-5-methyl-1H-indazol-6-yl)-3-fluoropiperidine-1-carboxylate (from Peak 1) (D157)

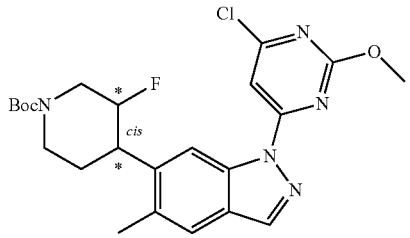 [SMILES: COc1nc(Cl)cc(-n2ncc3cc(C)c(C4CCN(C(=O)OC(C)(C)C)CC4F)cc32)n1]

A mixture of tert-butyl cis-3-fluoro-4-(5-methyl-1H-indazol-6-yl)piperidine-1-carboxylate (peak 1) (300 mg, 0.9 mmol), 4,6-dichloro-2-methoxypyrimidine (209 mg, 1.17 mmol) and Cs$_2$CO$_3$ (878 mg, 2.7 mmol) in DMF (5 mL) was stirred at 50° C. overnight. The reaction mixture was poured into water (50 mL) and the mixture was extracted with EtOAc (30 mL×3). The organic solution was dried over Na$_2$SO$_4$ and concentrated. The residue was purified by SGC (PE to PE:EtOAc=20:1) to give a white solid. (260 mg, yield: 60%).

LC-MS [mobile phase: from 50% water (0.1% NH$_3$H$_2$O) and 50% ACN (0.1% NH$_3$H$_2$O) to 5% water (0.1% NH$_3$H$_2$O) and 95% ACN (0.1% NH$_3$H$_2$O) in 2.6 min]: Rt=2.327 min; MS Calcd: 475; MS Found: 476 [M+H]$^+$.

Description 158

Cis-1-(6-chloro-2-methoxypyrimidin-4-yl)-6-(3-fluoropiperidin-4-yl)-5-methyl-1H-indazole Hydrochloride (from Peak 1) (D158)

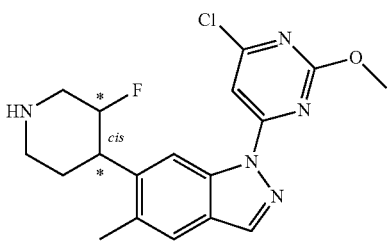 [SMILES: COc1nc(Cl)cc(-n2ncc3cc(C)c(C4CCNCC4F)cc32)n1]

To a solution of tert-butyl cis-4-(1-(6-chloro-2-methoxypyrimidin-4-yl)-5-methyl-1H-indazol-6-yl)-3-fluoropiperidine-1-carboxylate (from peak 1) (60 mg, 0.126 mmol) in EtOAc (2 mL) was added 3N HCl/EtOAc (1 mL). The mixture was stirred at rt for 0.5 h. The reaction mixture was concentrated to give the crude title compound (50 mg, crude) as a white solid.

LC-MS [mobile phase: from 70% water (0.1% FA) and 30% ACN (0.1% FA) to 5% water (0.1% FA) and 95% ACN (0.1% FA) in 2.6 min]: Rt=1.04 min; MS Calcd: 375; MS Found: 376 [M+H]$^+$.

Description 159

Cis-1-(6-chloro-2-methoxypyrimidin-4-yl)-6-(3-fluoro-1-(oxetan-3-yl)piperidin-4-yl)-5-methyl-1H-indazole (from Peak 1)(D159)

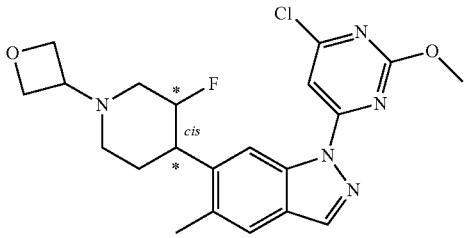 [SMILES: COc1nc(Cl)cc(-n2ncc3cc(C)c(C4CCN(C5COC5)CC4F)cc32)n1]

To a stirred mixture of cis-1-(6-chloro-2-methoxypyrimidin-4-yl)-6-(3-fluoropiperidin-4-yl)-5-methyl-1H-indazole hydrochloride (from peak 1) (50 mg, 0.12 mmol), oxetan-3-one (21 mg, 0.24 mmol), 4 Å molecular sieves (5 mg) in MeOH/CH$_2$Cl$_2$ (2 mL/2 mL) at 0° C. were added AcOH (2 mg, 0.033 mmol) and NaBH$_3$CN (15 mg, 0.24 mmol). The reaction was warmed to room temperature and stirred overnight. The reaction mixture was filtered and the solid was washed with CH$_2$Cl$_2$ (20 mL). The filtrate was washed with aqueous NaHCO$_3$ (10 mL), dried, filtered. The filtrate was concentrated and the residue was purified by column chromatography (eluent: CH$_2$Cl$_2$, followed by CH$_2$Cl$_2$: MeOH=40:1) afforded desired product as a white solid (40 mg, yield: 76%).

LC-MS [mobile phase: from 70% water (0.1% FA) and 30% ACN (0.1% FA) to 5% water (0.1% FA) and 95% ACN (0.1% FA) in 2.6 min]: Rt=1.43 min; MS Calcd: 431; MS Found: 432 [M+H]$^+$.

Description 160

Tert-butyl cis-4-(1-(6-chloro-2-methoxypyrimidin-4-yl)-5-methyl-1H-indazol-6-yl)-3-fluoropiperidine-1-carboxylate (from Peak 2) (D160)

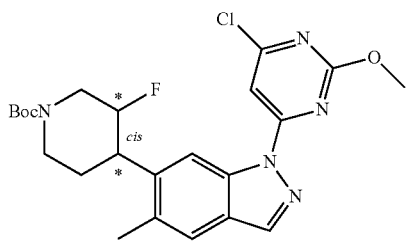 [SMILES: COc1nc(Cl)cc(-n2ncc3cc(C)c(C4CCN(C(=O)OC(C)(C)C)CC4F)cc32)n1]

A mixture of tert-butyl cis-3-fluoro-4-(5-methyl-1H-indazol-6-yl)piperidine-1-carboxylate (peak 2) (300 mg, 0.9 mmol), 4,6-dichloro-2-methoxypyrimidine (209 mg, 1.17 mmol) and Cs$_2$CO$_3$ (878 mg, 2.7 mmol) in DMF (5 mL) was stirred at 50° C. overnight. The reaction mixture was poured into water (50 mL) and the mixture was extracted with EtOAc (30 mL×3). The organic solution was dried over Na$_2$SO$_4$ and concentrated. The residue was purified by SGC (PE to PE:EtOAc=20:1) to give a white solid (260 mg, yield: 60%).

LC-MS [mobile phase: from 60% water (0.1% NH$_3$H$_2$O) and 40% ACN (0.1% NH$_3$H$_2$O) to 5% water (0.1% NH$_3$H$_2$O) and 95% ACN (0.1% NH$_3$H$_2$O) in 2.6 min]: Rt=2.3 min; MS Calcd: 475; MS Found: 476 [M+H]$^+$.

Description 161

Cis-1-(6-chloro-2-methoxypyrimidin-4-yl)-6-(3-fluoropiperidin-4-yl)-5-methyl-1H-indazole Hydrochloride (from Peak 2) (D161)

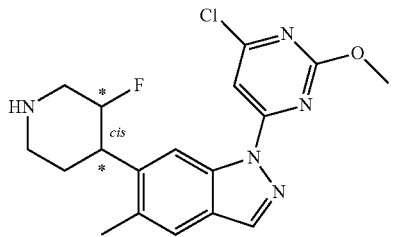

To a solution of tert-butyl cis-4-(1-(6-chloro-2-methoxypyrimidin-4-yl)-5-methyl-1H-indazol-6-yl)-3-fluoropiperidine-1-carboxylate (from peak 2) (60 mg, 0.126 mmol) in EtOAc (2 mL) was added 3 N HCl/EtOAc (1 mL). The mixture was stirred at rt for 0.5 h and concentrated to give the crude (50 mg, crude) as a white solid.

Description 162

Cis-1-(6-chloro-2-methoxypyrimidin-4-yl)-6-(3-fluoro-1-(oxetan-3-yl)piperidin-4-yl)-5-methyl-1H-indazole (from Peak 2) (D162)

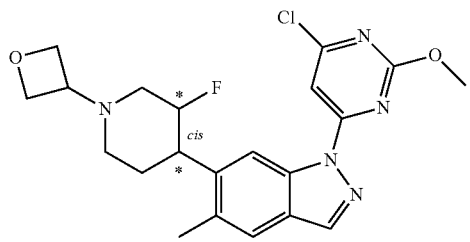 [SMILES: COc1nc(Cl)cc(-n2ncc3cc(C)c(C4CCN(C5COC5)CC4F)cc32)n1]

To a stirred mixture of cis-1-(6-chloro-2-methoxypyrimidin-4-yl)-6-(3-fluoropiperidin-4-yl)-5-methyl-1H-indazole hydrochloride (from peak 2) (50 mg, 0.12 mmol), oxetan-3-one (21 mg, 0.24 mmol), 4 Å molecular sieves (5 mg) in MeOH/CH$_2$Cl$_2$ (2 mL/2 mL) at 0° C. were added AcOH (2 mg, 0.033 mmol) and NaBH$_3$CN (15 mg, 0.24 mmol). The reaction was warmed to room temperature and stirred overnight. The reaction mixture was filtered and the solid was washed with CH$_2$Cl$_2$ (20 mL). The filtrate was washed with aqueous NaHCO$_3$ (10 mL), dried, filtered. The filtrate was concentrated and the residue was purified by column chromatography (eluent: CH$_2$Cl$_2$, followed by CH$_2$Cl$_2$: MeOH=40:1) afforded desired product as a white solid (40 mg, yield: 76%).

LC-MS [mobile phase: from 70% water (0.1% NH$_3$H$_2$O) and 30% ACN (0.1% NH$_3$H$_2$O) to 5% water (0.1% NH$_3$H$_2$O) and 95% ACN (0.1% NH$_3$H$_2$O) in 2.6 min]: Rt=2.51 min; MS Calcd: 431; MS Found: 432 [M+H]$^+$.

Description 163

Tert-butyl cis-4-(1-(6-chloro-2-methylpyrimidin-4-yl)-5-methyl-1H-indazol-6-yl)-3-fluoropiperidine-1-carboxylate (from Peak 1) (D163)

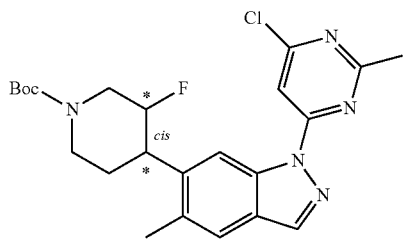 [SMILES: Cc1nc(Cl)cc(-n2ncc3cc(C)c(C4CCN(C(=O)OC(C)(C)C)CC4F)cc32)n1]

A mixture of tert-butyl cis-t3-fluoro-4-(5-methyl-1H-indazol-6-yl)piperidine-1-carboxylate (peak 1) (330 mg, 1 mmol), 4,6-dichloro-2-methylpyrimidine (178 mg, 1.1 mmol) and Cs$_2$CO$_3$ (652 mg, 2.0 mmol) in DMF (5 mL) was stirred at 50° C. overnight. The reaction mixture was poured into water (50 mL) and the mixture was extracted with EtOAc (30 mL×3). The organic solution was dried over Na₂SO₄ and concentrated. The residue was purified by SGC (PE to PE:EtOAc=20:1-10:1) to give a white solid. (220 mg, yield: 48%).

LC-MS [mobile phase: from 50% water (0.1% NH₃H₂O) and 50% ACN (0.1% NH₃H₂O) to 5% water (0.1% NH₃H₂O) and 95% ACN (0.1% NH₃H₂O) in 2.6 min]: Rt=2.306 min; MS Calcd: 459; MS Found: 460 [M+H]⁺.

Description 164

Cis-1-(6-chloro-2-methylpyrimidin-4-yl)-6-(3-fluoropiperidin-4-yl)-5-methyl-1H-indazole Hydrochloride (from Peak 1) (D164)

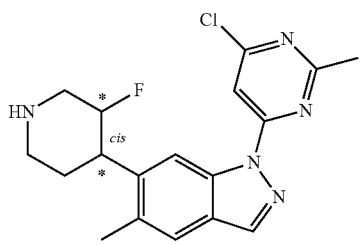 [SMILES: Cc1nc(Cl)cc(-n2ncc3cc(C)c(C4CCNCC4F)cc32)n1]

To the solution of tert-butyl cis-4-(1-(6-chloro-2-methylpyrimidin-4-yl)-5-methyl-1H-indazol-6-yl)-3-fluoropiperidine-1-carboxylate (from peak 1) (60 mg, 0.13 mmol) in EtOAc (5 mL) was added 3 N HCl/EtOAc (2 mL). The mixture was stirred at rt for 0.5 h. The reaction mixture was concentrated to give the crude title compound (50 mg, crude) as a white solid.

LC-MS [mobile phase: from 70% water (0.1% FA) and 30% ACN (0.1% FA) to 5% water (0.1% FA) and 95% ACN (0.1% FA) in 2.6 min]: Rt=0.95 min; MS Calcd: 359; MS Found: 360 [M+H]⁺.

Description 165

Cis-1-(6-chloro-2-methylpyrimidin-4-yl)-6-(3-fluoro-1-(oxetan-3-yl)piperidin-4-yl)-5-methyl-1H-indazole (from Peak 1) (D165)

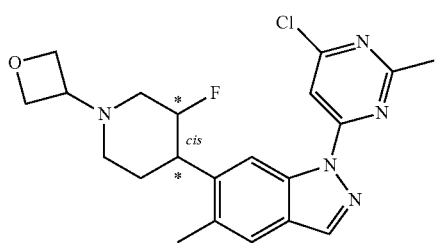 [SMILES: Cc1nc(Cl)cc(-n2ncc3cc(C)c(C4CCN(C5COC5)CC4F)cc32)n1]

To a stirred mixture of cis-1-(6-chloro-2-methylpyrimidin-4-yl)-6-(3-fluoropiperidin-4-yl)-5-methyl-1H-indazole hydrochloride (from peak 1) (50 mg, 0.126 mmol), oxetan-3-one (21 mg, 0.24 mmol), 4 Å molecular sieves (5 mg) in MeOH/CH₂Cl₂ (2 mL/2 mL) at 0° C. were added AcOH (2 mg, 0.033 mmol) and NaBH₃CN (15 mg, 0.24 mmol). The reaction mixture was warmed to room temperature and stirred overnight, filtered and washed with CH₂Cl₂ (20 mL). The organic part was washed with aqueous NaHCO₃ (10 mL), dried and filtered. The filtrate was concentrated and the residue was purified by column chromatography (eluent: CH₂Cl₂, followed by CH₂Cl₂:MeOH=40:1) afforded desired product as a white solid (40 mg, yield: 76%).

LC-MS [mobile phase: from 50% water (0.1% NH₃H₂O) and 50% ACN (0.1% NH₃H₂O) to 5% water (0.1% NH₃H₂O) and 95% ACN (0.1% NH₃H₂O) in 2.6 min]: Rt=1.816 min; MS Calcd: 415; MS Found: 416 [M+H]⁺.

Description 166

Tert-butyl cis-4-(1-(6-chloro-2-methylpyrimidin-4-yl)-5-methyl-1H-indazol-6-yl)-3-fluoropiperidine-1-carboxylate (from Peak 2) (D166)

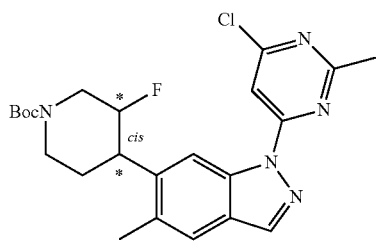 [SMILES: Cc1nc(Cl)cc(-n2ncc3cc(C)c(C4CCN(C(=O)OC(C)(C)C)CC4F)cc32)n1]

A mixture of tert-butyl cis-3-fluoro-4-(5-methyl-1H-indazol-6-yl)piperidine-1-carboxylate (peak 2) (300 mg, 0.9 mmol), 4,6-dichloro-2-methylpyrimidine (190 mg, 1.17 mmol) and Cs₂CO₃ (878 mg, 2.7 mmol) in DMF (5 mL) was stirred at 50° C. overnight. The reaction mixture was poured into water (50 mL) and the mixture was extracted with EtOAc (30 mL×3). The organic solution was dried over Na₂SO₄ and concentrated. The residue was purified by SGC (PE to PE:EtOAc=20:1) to give a white solid. (200 mg, yield: 48%).

LC-MS [mobile phase: from 50% water (0.1% NH₃H₂O) and 50% ACN (0.1% NH₃H₂O) to 5% water (0.1% NH₃H₂O) and 95% ACN (0.1% NH₃H₂O) in 2.6 min]: Rt=2.35 min; MS Calcd: 459; MS Found: 460 [M+H]⁺.

Description 167

Cis-1-(6-chloro-2-methylpyrimidin-4-yl)-6-(3-fluoropiperidin-4-yl)-5-methyl-1H-indazole Hydrochloride (from Peak 2) (D167)

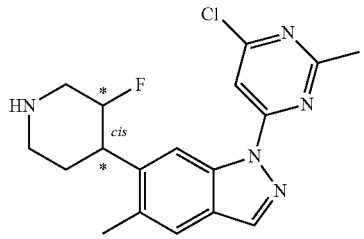 [SMILES: Cc1nc(Cl)cc(-n2ncc3cc(C)c(C4CCNCC4F)cc32)n1]

To a solution of cis-tert-butyl 4-(1-(6-chloro-2-methylpyrimidin-4-yl)-5-methyl-1H-indazol-6-yl)-3-fluoropiperidine-1-carboxylate (from peak 2) (60 mg, 0.13 mmol) in EtOAc (2 mL) was added 3 N HCl/EtOAc (1 mL). The mixture was stirred at rt for 0.5 h. The reaction mixture was concentrated to give the crude title compound (50 mg, crude) as a white solid.

Description 168

Cis-1-(6-chloro-2-methylpyrimidin-4-yl)-6-(3-fluoro-1-(oxetan-3-yl)piperidin-4-yl)-5-methyl-1H-indazole (from Peak 2) (D168)

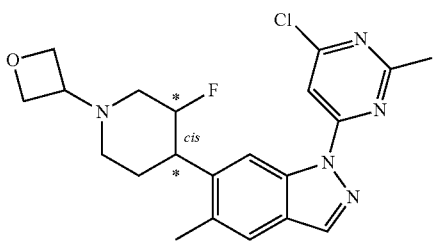 [SMILES: Cc1nc(Cl)cc(-n2ncc3cc(C)c(C4CCN(C5COC5)CC4F)cc32)n1]

To a stirred mixture of cis-1-(6-chloro-2-methylpyrimidin-4-yl)-6-(3-fluoropiperidin-4-yl)-5-methyl-1H-indazole hydrochloride (from peak 2) (50 mg, 0.126 mmol), oxetan-3-one (21 mg, 0.24 mmol), 4 Å molecular sieves (5 mg) in MeOH/CH$_2$Cl$_2$ (2 mL/2 mL) at 0° C. were added AcOH (2 mg, 0.033 mmol) and NaBH$_3$CN (15 mg, 0.24 mmol). The reaction was warmed to room temperature and stirred overnight. The reaction mixture was filtered and the solid was washed with CH$_2$Cl$_2$ (20 mL). The filtrate was washed with aqueous NaHCO$_3$ (10 mL), dried, filtered. The filtrate was concentrated and the residue was purified by column chromatography (eluent: CH$_2$Cl$_2$, followed by CH$_2$Cl$_2$:MeOH=40:1) afforded desired product as a white solid (40 mg, yield: 76%).

LC-MS [mobile phase: from 70% water (0.1% NH$_3$H$_2$O) and 30% ACN (0.1% NH$_3$H$_2$O) to 5% water (0.1% NH$_3$H$_2$O) and 95% ACN (0.1% NH$_3$H$_2$O) in 2.6 min]: Rt=2.43 min; MS Calcd: 415; MS Found: 416 [M+H]$^+$.

Description 169

Tert-butyl 4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (D169)

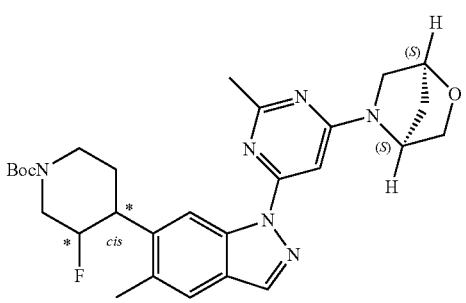

To a solution of tert-butyl 3-fluoro-4-(5-methyl-1H-indazol-6-yl)piperidine-1-carboxylate (peak 1) (50 mg, 0.15 mmol) and (1S,4S)-5-(6-iodo-2-methylpyrimidin-4-yl)-2-oxa-5-azabicyclo[2.2.1]heptane (48 mg, 0.15 mmol) in toluene (30 ml) were added CuI (44 mg, 0.23 mmol), K$_3$PO$_4$.3H$_2$O (80 mg, 0.30 mmol) and N,N'-dimethylethylenediamine (27 mg, 0.30 mmol). The reaction mixture was stirred at 100° C. for 4 h. The reaction mixture was concentrated. The residue was dissolved in EtOAc (50 mL) was added NH$_4$OH (20 mL). The organic layer was separated and the aq. layer was extracted with EtOAc (2×50 mL). The combined organic phases were washed with brine (50 mL), dried over anhydrous Na2SO4, and filtered. The filtrate was concentrated. The residue was purified by silica gel chromatography eluted with PE/EtOAc=10/1 to give desired product as a white solid (75 mg, yield: 96%).

LC-MS [mobile phase: from 50% water (0.1% FA) and 50% ACN (0.1% FA) to 5% water (0.1% FA) and 95% ACN (0.1% FA) in 2.6 min]: purity 91%, Rt=1.79 min; MS Calcd: 522, MS Found: 523 [M+H]$^+$.

Description 170

4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (D170)

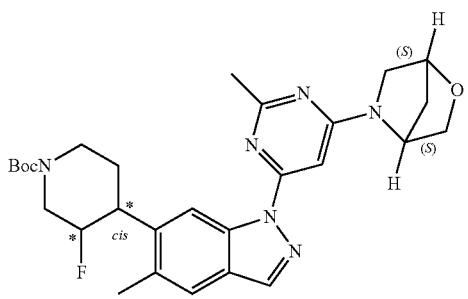

To a solution of tert-butyl 3-fluoro-4-(5-methyl-1H-indazol-6-yl)piperidine-1-carboxylate (peak 2) (50 mg, 0.15 mmol) and (1S,4S)-5-(6-iodo-2-methylpyrimidin-4-yl)-2-oxa-5-azabicyclo[2.2.1]heptane (48 mg, 0.15 mmol) in toluene (30 ml) were added CuI (44 mg, 0.23 mmol), K$_3$PO$_4$.3H$_2$O (80 mg, 0.30 mmol) and N,N'-dimethylethylenediamine (27 mg, 0.30 mmol). The reaction mixture was stirred at 100° C. for 4 h. The reaction mixture was concentrated. The residue was dissolved in EtOAc (50 mL) was added NH$_4$OH (20 mL). The organic layer was separated and the aq. layer was extracted with EtOAc (2×50 mL). The combined organic phases were washed with brine (50 mL), dried over anhydrous Na$_2$SO$_4$, and filtered. The filtrate was concentrated. The residue was purified by silica gel chromatography eluted with PE/EtOAc=2/1 to give desired product as a white solid (60 mg, yield: 76%).

LC-MS [mobile phase: from 50% water (0.1% FA) and 50% ACN (0.1% FA) to 5% water (0.1% FA) and 95% ACN (0.1% FA) in 2.6 min]: purity 88%]: Rt=1.80 min; MS Calcd: 522, MS Found: 523 [M+H]$^+$.

Description 171

3-(6-Iodo-2-methyl-pyrimidin-4-yl)-3-aza-bicyclo[3.1.1]heptane-6-carboxylic Acid Methyl Ester (D171)

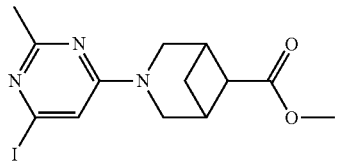 [SMILES: COC(=O)C1C2CC1CN(c1cc(I)nc(C)n1)C2]

To a solution of 4,6-diiodo-2-methylpyrimidine (345 mg, 1.0 mmol) in NMP (3 mL) was added 3-Aza-bicyclo[3.1.1]heptane-6-carboxylic acid methyl ester (150 mg, 1.0 mmol), TEA (874 mg, 8.65 mmol) at room temperature. The reaction mixture was stirred at 40° C. overnight. The reaction mixture was poured into water (10 mL), extracted with EtOAc (5 mL×3). The combined organic layers were washed with brine (5 mL), dried over anhydrous $Na_2SO_4$, filtered, concentrated. The residue was purified by SGC (PE:EtOAc=5:1) to give the title product as a yellow oil. (200 mg, yield: 52%) which was used directly.

Description 172

3-{2-Methyl-6-[5-methyl-6-(tetrahydro-pyran-4-yl)-indazol-1-yl]-pyrimidin-4-yl}-3-aza-bicyclo[3.1.1]heptane-6-carboxylic Acid Methyl Ester (D172)

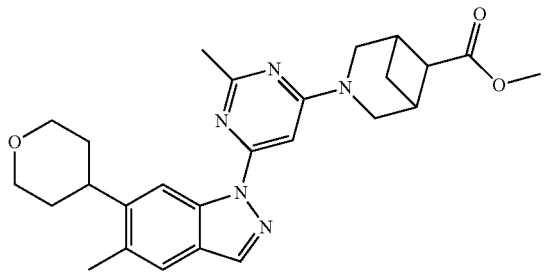 [SMILES: COC(=O)C1C2CC1CN(c1cc(-n3ncc4cc(C)c(C5CCOCC5)cc43)nc(C)n1)C2]

To a solution of 3-(6-Iodo-2-methyl-pyrimidin-4-yl)-3-aza-bicyclo[3.1.1]heptane-6-carboxylic acid methyl ester (160 mg, 0.49 mmol) and 5-Methyl-6-(tetrahydro-pyran-4-yl)-1H-indazole (150 mg, 0.69 mmol) in toluene (10 mL) was added CuI (132 mg, 0.69 mmol), $K_3PO_4$ (170 mg, 0.82 mmol) at room temperature. After addition, $N^1,N^2$-dimethylethane-1,2-diamine (72 mg, 0.82 mmol) was added under $N_2$ protection. The reaction mixture was stirred at 70° C. overnight. The reaction mixture was poured into water (20 mL), extracted with EtOAc (10 mL×3). The combined organic layers were washed with brine (20 mL), dried over anhydrous $Na_2SO_4$, filtered and concentrated to give a yellow oil. The residue was used to next step without further purification (250 mg, crude).

LC-MS [mobile phase: from 70% water (0.1% FA) and 30% ACN (0.1% FA) to 95% water (0.1% FA) and 5% ACN (0.1% FA) in 2.0 min, purity: 44%]: Rt=1.61 min; MS Calcd: 461, MS Found: 462 [M+H]+.

Description 173

2-{2-Methyl-6-[5-methyl-6-(tetrahydro-pyran-4-yl)-indazol-1-yl]-pyrimidin-4-yl}-2-aza-bicyclo[2.2.1]heptane-5-carboxylic Acid Methyl Ester (D173)

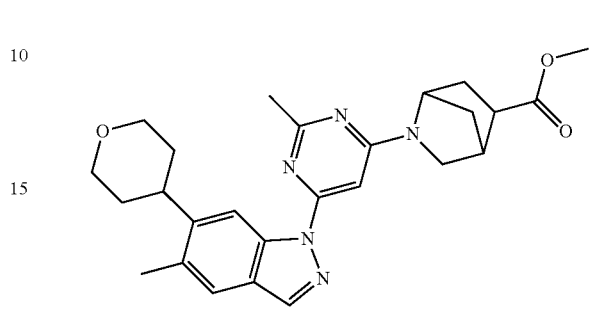

1-(6-Iodo-2-methyl-pyrimidin-4-yl)-5-methyl-6-(tetrahydro-pyran-4-yl)-1H-indazole (350 mg, 0.80 mmol), 2-Aza-bicyclo[2.2.1]heptane-5-carboxylic acid methyl ester (164 mg, 0.96 mmol) and DIPEA (280 mg, 2.164 mmol) in NMP (8 mL) was stirred at 50° C. for 3 days. Then the reaction was poured into water (30 mL) and extracted with EtOAc (30 mL×3). The organic phase was washed with brine (90 mL×3), dried over $Na_2SO_4$ and concentrated to obtain the crude compound (350 mg, yield %)

Description 174

6-(3,6-dihydro-2H-pyran-4-yl)-5-methyl-1-(tetrahydro-2H-pyran-2-yl)-1H-indazole (D174)

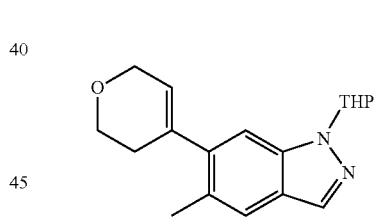

To a solution of 6-bromo-5-methyl-1-(tetrahydro-2H-pyran-2-yl)-1H-indazole (2 g, 6.78 mmol) and 2-(3,6-dihydro-2H-pyran-4-yl)-4,4,5,5-tetramethyl-1,3,2-dioxaborolane (1.7 g, 8.14 mmol) in 1,4-dioxane/$H_2O$ (50 mL/5 mL) was added $Na_2CO_3$ (2.8 g, 27.12 mmol) at room temperature. Then Pd(dppf)$Cl_2$ (240 mg, 0.339 mmol) was added under $N_2$ protection. The reaction mixture was heated to 90° C. overnight. The reaction mixture was poured into water (150 mL), extracted with EtOAc (50 mL×3). The combined organic layers were washed with brine (200 mL), dried over anhydrous $Na_2SO_4$, filtered, concentrated to dryness. The residue was purified by silica gel chromatography eluted with (EtOAc:Petroleum Ether=1:10) to give the product as a white solid (1.4 g, 70% yield).

LC-MS [mobile phase: from 40% water (0.1% FA) and 60% ACN (0.1% FA) to 5% water (0.1% FA) and 95% ACN (0.1% FA) in 2.5 min]: Rt=1.157 min; MS Calcd.: 298; MS Found: 299.0 [M+H]+.

Description 175

5-methyl-1-(tetrahydro-2H-pyran-2-yl)-6-(tetrahydro-2H-pyran-4-yl)-1H-indazole (D175)

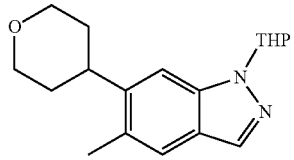

To a solution of 6-(3,6-dihydro-2H-pyran-4-yl)-5-methyl-1-(tetrahydro-2H-pyran-2-yl)-1H-indazole (700 mg, 2.35 mmol) in MeOH (5 mL) was added 10% Pd/C (50 mg). The mixture was stirred at rt overnight under $H_2$ atmosphere. The reaction mixture was filtered through a short of celite, washed with EtOAc (5 mL), the filtrate was concentrated to give the product as a white solid (600 mg, 85% yield).

LC-MS [mobile phase: from 40% water (0.1% FA) and 60% ACN (0.1% FA) to 5% water (0.1% FA) and 95% ACN (0.1% FA) in 2.5 min]: Rt=1.100 min; MS Calcd.: 300; MS Found: 301 $[M+H]^+$.

Description 176

5-methyl-6-(tetrahydro-2H-pyran-4-yl)-1H-indazole (D176)

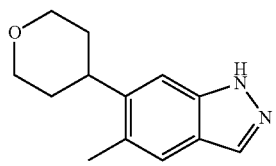 [SMILES: Cc1cc2cn[nH]c2cc1C1CCOCC1]

To a solution of 5-methyl-1-(tetrahydro-2H-pyran-2-yl)-6-(tetrahydro-2H-pyran-4-yl)-1H-indazole (600 mg, 2 mmol) in DCM (10 mL) was added TFA (5 mL) at room temperature. The reaction mixture was heated to 30° C. overnight. The reaction mixture was concentrated to dryness. The residue was dissolved in DCM (10 mL), washed with aq.NaHCO$_3$ (20 mL), brine (10 mL), dried over Na$_2$SO$_4$, filtered and concentrated, the residue was purified by silica gel chromatography eluted with (EtOAc:Petroleum Ether=1:1) to give the product as a white solid (300 mg, 70% yield).

LC-MS [mobile phase: from 60% water (0.1% FA) and 40% ACN (0.1% FA) to 5% water (0.1% FA) and 95% ACN (0.1% FA) in 2.5 min]: Rt=1.020 min; MS Calcd.: 216; MS Found: 217 $[M+H]^+$.

Description 177

1-(6-Iodo-2-methylpyrimidin-4-yl)-5-methyl-6-(tetrahydro-2H-pyran-4-yl)-1H-indazole (D177)

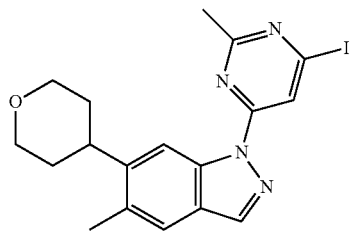 [SMILES: Cc1nc(I)cc(-n2ncc3cc(C)c(C4CCOCC4)cc32)n1]

To a solution of 5-methyl-6-(tetrahydro-2H-pyran-4-yl)-1H-indazole (340 mg, 1.57 mmol) and 4,6-diiodo-2-methylpyrimidine (1.63 g, 4.72 mmol) in THF (60 mL) was added CuI (299 mg, 1.57 mmol) followed by K$_3$PO$_4$ (1.33 g, 6.29 mmo) and $N^1,N^2$-dimethylethane-1,2-diamine (277 mg, 3.14 mmo). The resulting mixture was degassed with N$_2$ three times. The reaction was stirred at room temperature overnight. EtOAc (100 mL) was added and the resulting mixture was washed with brine (2×100 mL), dried over anhydrous Na$_2$SO$_4$ and concentrated. The residue was purified by silica gel chromatography (eluted with PE:EtOAc=4:1, 20 g of silica gel) to give product (640 mg, yield 93.7%) as a white solid.

LC-MS [mobile phase: from 90% water (0.1% FA) and 10% ACN (0.1% FA) to 5% water (0.1% FA) and 95% ACN (0.1% FA) in 2 min]: Rt=1.73 min; MS Calcd.: 434, MS Found: 435 $[M+H]^+$.

Description 178

(1S,4S)-tert-butyl 4-(1-(6-(2-oxa-5-azabicyclo[2.2.1]heptan-5-yl)-2-methylpyrimidin-4-yl)-5-chloro-1H-indazol-6-yl)piperidine-1-carboxylate (D178)

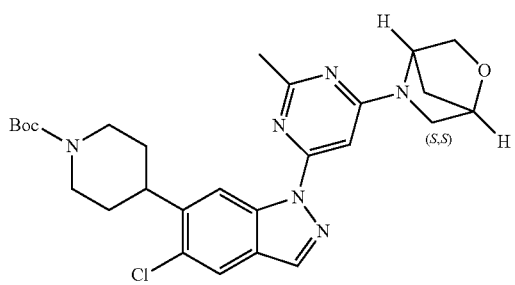

To a suspension of tert-butyl 4-(5-chloro-1H-indazol-6-yl)piperidine-1-carboxylate (150 mg, 0.45 mmol), (1S,4S)-5-(6-iodo-2-methylpyrimidin-4-yl)-2-oxa-5-azabicyclo[2.2.1]heptane (142 mg, 0.45 mmol), N,N'-dimethylcyclohexane-1,2-diamine (64 mg, 0.45 mmol), CuI (43 mg, 0.23 mmol) and K$_3$PO$_4$ (191 mg, 0.90 mmol) in toluene (4 mL) was stirred at 100° C. for 2 hours. Then the reaction mixture was diluted with 60 mL of EtOAc and washed with water (30 mL), NH$_3$.H$_2$O (2 mL) and brine (30 mL). The organic layer was dried over Na$_2$SO$_4$, filtered and concentrated. The residue was purified by flash chromatography (DCM/MeOH=40:1) to give compound (190 mg, 81%) as a yellow solid.

¹H NMR (400 MHz, CDCl₃): δ 8.87 (s, 1H), 8.08 (s, 1H), 7.75 (s, 1H), 6.67 (s, 1H), 5.36-5.30 (m, 1H), 4.75 (s, 1H), 4.33-4.29 (m, 1H), 3.93-3.88 (m, 2H), 3.56-3.48 (m, 1H), 3.28-3.26 (m, 1H), 2.94-2.88 (m, 2H), 2.60 (s, 3H), 2.05-1.95 (m, 4H), 1.70-1.67 (m, 2H), 1.65-1.63 (m, 2H), 1.47 (s, 9H).

Description 179

(1S,4S)-5-(6-(5-chloro-6-(piperidin-4-yl)-1H-indazol-1-yl)-2-methylpyrimidin-4-yl)-2-oxa-5-azabicyclo[2.2.1]heptane (D179)

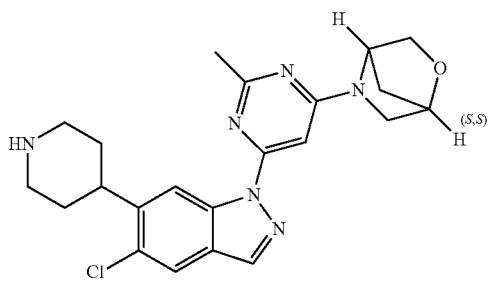

To a solution of (1S,4S)-tert-butyl 4-(1-(6-(2-oxa-5-azabicyclo[2.2.1]heptan-5-yl)-2-methylpyrimidin-4-yl)-5-chloro-1H-indazol-6-yl)piperidine-1-carboxylate (190 mg, 0.363 mmol) in DCM (4 mL) was added TFA (1 mL). The solution was stirred at room temperature for 1 hour. The reaction solution was diluted with DCM (30 mL) and water (20 mL), adjust pH>7 by sat. NaHCO₃, extracted with DCM (30 mL×2). The organic layer was washed with brine (30 mL), dried over Na₂SO₄, filtered and concentrated to give the title compound (153 mg, 100%) as a yellow solid.

¹H NMR (400 MHz, CDCl₃): δ 8.95 (s, 1H), 8.09 (s, 1H), 7.77 (s, 1H), 6.66 (s, 1H), 5.32 (s, 1H), 4.75 (s, 1H), 3.91-3.89 (m, 2H), 3.51-3.48 (m, 3H), 3.38-3.20 (m, 1H), 3.10-3.02 (m, 2H), 2.59 (s, 3H), 2.16-1.88 (m, 8H).

Description 180

(1S,4S)-ethyl 2-(4-(1-(6-(2-oxa-5-azabicyclo[2.2.1]heptan-5-yl)-2-methylpyrimidin-4-yl)-5-chloro-1H-indazol-6-yl)piperidin-1-yl)acetate (D180)

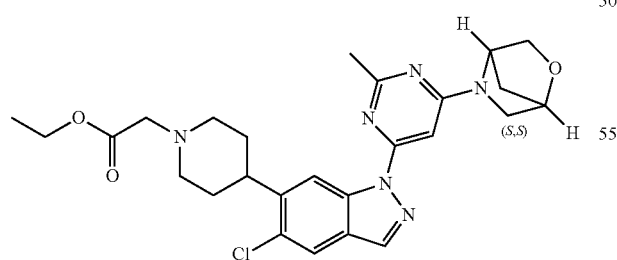

To a solution of (1S,4S)-5-(6-(5-chloro-6-(piperidin-4-yl)-1H-indazol-1-yl)-2-methylpyrimidin-4-yl)-2-oxa-5-azabicyclo[2.2.1]heptane (153 mg, 0.36 mmol) and TEA (181 mg, 1.8 mmol) in DMF (4 mL) was added ethyl bromoacetate (180 mg, 1.08 mmol) in DMF (0.5 mL) at 0° C. The solution was stirred at room temperature for 1 hour. The reaction solution was diluted with EtOAc (60 mL), washed with water (20 mL) and brine (20 mL). The organic layer was dried over Na₂SO₄, filtered and concentrated. The residue was purified by flash chromatography (DCM/MeOH=40:1) to give title product (165 mg, 89%) as a yellow solid.

¹H NMR (400 MHz, CDCl₃): δ 8.92 (s, 1H), 8.09 (s, 1H), 7.77 (s, 1H), 6.66 (s, 1H), 5.34 (s, 1H), 4.75 (s, 1H), 4.25-4.20 (m, 2H), 3.93-3.89 (m, 2H), 3.54-3.42 (m, 2H), 3.33-3.28 (m, 2H), 3.17-3.09 (m, 3H), 2.62 (s, 3H), 2.45-2.39 (m, 2H), 2.03-1.90 (m, 6H), 1.35-1.29 (m, 3H).

Description 181

3-trans-4-(5-methyl-1H-indazol-6-yl)piperidin-3-ol (D181)

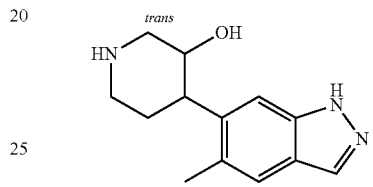

To a solution of 3-trans-tert-butyl 3-hydroxy-4-(5-methyl-1-(tetrahydro-2H-pyran-2-yl)-1H-indazol-6-yl)piperidine-1-carboxylate (1.0 g, 2.41 mmol) in MeOH (5.0 mL) was added HCl/1,4-dioxane (10 mL, 6 M). The reaction mixture was stirred at room temperature overnight. The reaction was concentrated. The residue was dissolved in MeOH (50 mL) and Amberlyst (R) A21 (3.0 g) was added. The resulting mixture was stirred at room temperature for 2 hours, filtered. The filtrate was concentrated to afford the title compound (510 mg, 67%) as a white solid. LCMS [column: C₁₈; column size: 4.6×30 mm 5 μm; Dikwa Diamonsil plus; mobile phase: B (ACN): A1 (0.02% NH₄OAc+ 5% ACN); gradient (B %) in 4 min-05-95-POS; flow rate: 1.5 mL/min]: Rt=1.321 min; MS Calcd.: 231, MS Found: 232 [M+H]⁺.

Description 182

3-trans-(1R,4R)-4-(1-(6-(2-oxa-5-azabicyclo[2.2.1]heptan-5-yl)-2-methoxypyrimidin-4-yl)-5-methyl-1H-indazol-6-yl)piperidin-3-ol (D182)

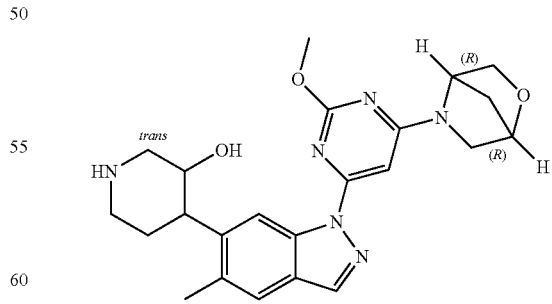

A mixture of 3-trans-4-(5-methyl-1H-indazol-6-yl)piperidin-3-ol (400 mg, 1.73 mmol), (1R,4R)-5-(6-iodo-2-methoxypyrimidin-4-yl)-2-oxa-5-azabicyclo[2.2.1]heptane (577 mg, 1.73 mmol), N,N'-dimethylcyclohexane-1,2-diamine (242 mg, 1.73 mmol), CuI (165 mg, 0.87 mmol) and K₃PO₄ (733 mg, 3.46 mmol) in toluene (10 mL) and DMSO (4 mL) was stirred at 100° C. for 3 hours. The reaction was diluted with EtOAc (100 mL), washed with NH₃.H₂O (30 mL×2), brine (30 mL), dried over Na₂SO₄, concentrated. The residue was purified by silica gel chromatography column (DCM/MeOH=10/1) to give the title compound (180 mg, 24%) as a white solid.

LCMS [column: C₁₈; column size: 4.6×30 mm 5 μm; Dikwa Diamonsil plus; mobile phase: B (ACN): A1 (0.02% NH₄OAc+ 5% ACN); gradient (B %) in 4 min-05-95-POS; flow rate: 1.5 mL/min]: Rt=1.836 min; MS Calcd.: 436, MS Found: 437 [M+H]⁺.

Description 183

(1R,4R)-tert-butyl 4-(1-(6-(2-oxa-5-azabicyclo [2.2.1]heptan-5-yl)-2-methoxypyrimidin-4-yl)-5-chloro-1H-indazol-6-yl)piperidine-1-carboxylate (D183)

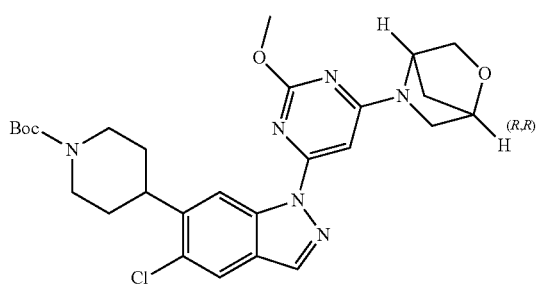

To a suspension of tert-butyl 4-(5-chloro-1H-indazol-6-yl)piperidine-1-carboxylate (150 mg, 0.44 mmol), (1R,4R)-5-(6-iodo-2-methoxypyrimidin-4-yl)-2-oxa-5-azabicyclo [2.2.1]heptane (178 mg, 0.53 mmol), N,N'-dimethyl-cyclohexane-1,2-diamine (62 mg, 0.44 mmol), CuI (44 mg, 0.23 mmol) and K₃PO₄ (188 mg, 0.89 mmol) in toluene (5 mL) was stirred at 100° C. under N₂ atmosphere for 2 hours. Then the reaction mixture was diluted with 150 mL of EtOAc and washed with brine (30 mL×3). The organic layers were dried over Na₂SO₄, filtered and concentrated. The residue was purified by flash chromatography (petroleum ether/EtOAc=2:1) to give compound (176 mg, 73%) as a yellow solid.

LC-MS [C₁₈; column size: 4.6×30 mm 5 μm; Dikwa Diamonsil plus; mobile phase: B (ACN): A1 (0.02% NH₄OAc+ 5% ACN); gradient (B %) in 4 min-05-95-POS; 5-95% positive, flow rate: 1.5 mL/min, stop time 4 min]: Rt=2.938 min; MS Calcd.: 540, MS Found: 541 [M+H]⁺.

Description 184

(1R,4R)-5-(6-(5-chloro-6-(piperidin-4-yl)-1H-indazol-1-yl)-2-methoxypyrimidin-4-yl)-2-oxa-5-azabicyclo[2.2.1]heptane (D184)

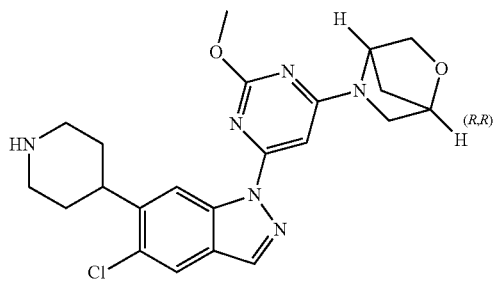

To a solution of (1R,4R)-tert-butyl 4-(1-(6-(2-oxa-5-azabicyclo[2.2.1]heptan-5-yl)-2-methoxypyrimidin-4-yl)-5-chloro-1H-indazol-6-yl)piperidine-1-carboxylate (176 mg, 0.32 mmol) in DCM (10 mL) was added TFA (1 mL). The mixture was stirred at room temperature for 6 hours. Sat-.NaHCO₃ was added to the mixture to adjust pH=7-8. The mixture was diluted with DCM (30 mL), washed with brine (10 mL×3). The organic layer was dried over Na₂SO₄, filtered and concentrated to give the title compound (139 mg, 95%) as a yellow solid.

LC-MS [C₁₈; column size: 4.6×30 mm 5 μm; Dikwa Diamonsil plus; mobile phase: B (ACN): A1 (0.02% NH₄OAc+ 5% ACN); gradient (B %) in 4 min-05-95-POS; 5-95% positive, flow rate: 1.5 mL/min, stop time 4 min]: Rt=1.996 min; MS Calcd.: 440, MS Found: 441 [M+H]⁺.

Description 185

(1R,4R)-ethyl 2-(4-(1-(6-(2-oxa-5-azabicyclo[2.2.1] heptan-5-yl)-2-methoxypyrimidin-4-yl)-5-chloro-1H-indazol-6-yl)piperidin-1-yl)acetate (D185)

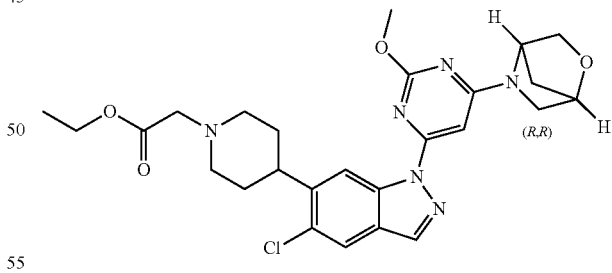

To a solution of (1R,4R)-5-(6-(5-chloro-6-(piperidin-4-yl)-1H-indazol-1-yl)-2-methoxypyrimidin-4-yl)-2-oxa-5-azabicyclo[2.2.1]heptane (136 mg, 0.31 mmol) in DMF (5 mL) was added ethyl bromoacetate (155 mg, 0.93 mmol) and TEA (156 mg, 1.55 mmol). The mixture was stirred at room temperature for 2 hours. The mixture was diluted with EtOAc (150 mL), washed with brine (30 mL×3). The organic layer was dried over Na₂SO₄, filtered and concentrated. The residue was purified by prep-TLC (petroleum ether/EtOAc=2:5) to give the title compound (43 mg, 26%) as a yellow oil.

LC-MS [C$_{18}$; column size: 4.6×30 mm 5 μm; Dikwa Diamonsil plus; mobile phase: B (ACN): A1 (0.02% NH$_4$OAc+ 5% ACN); gradient (B %) in 4 min-05-95-POS; 5-95% positive, flow rate: 1.5 mL/min, stop time 4 min]: Rt=2.735 min; MS Calcd.: 526, MS Found: 527 [M+H]$^+$.

Description 186

Tert-butyl 4-(5-chloro-1H-indazol-6-yl)piperidine-1-carboxylate (D186)

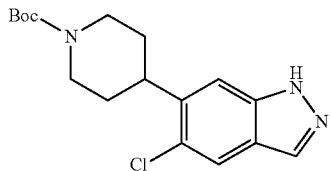 [SMILES: CC(C)(C)OC(=O)N1CCC(c2cc3[nH]ncc3cc2Cl)CC1]

To a solution of 5-chloro-6-(piperidin-4-yl)-1H-indazole (730 mg, 3 mmol) in MeOH (10 mL) was added KOH (506 mg, 9 mmol, in 10 mL of H$_2$O) and (Boc)$_2$O (809 mg, 3.71 mmol) under ice bath. The mixture was stirred at room temperature overnight. The reaction mixture was added H$_2$O (50 mL), extracted with EtOAc (30*3 mL). The combined organic layer was concentrated. The crude was purified by flash chromatography (petroleum ether/EtOAc=1:1) to title compound (545 mg, 52%) as a yellow solid.

$^1$H NMR (400 MHz, CDCl$_3$): δ 10.36 (br 1H), 8.00 (br, 1H), 7.79 (s, 1H), 7.36 (s, 1H), 4.28 (br, 2H), 3.30-3.22 (m, 1H), 2.89 (br, 2H), 1.96 (d, J=13.2 Hz, 2H), 1.64 (br, 2H), 1.50 (s, 9H).

Description 187

(1S,4S)-tert-butyl 4-(1-(6-(2-oxa-5-azabicyclo[2.2.1]heptan-5-yl)-2-methoxypyrimidin-4-yl)-5-chloro-1H-indazol-6-yl)piperidine-1-carboxylate (D187)

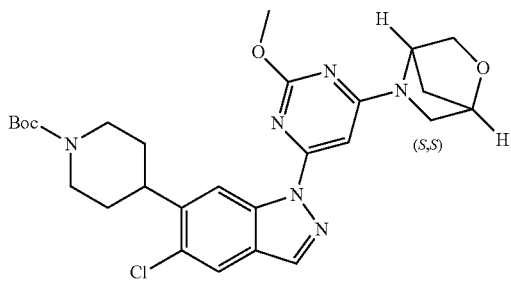 [SMILES: COc1nc(N2CC3CC2CO3)cc(-n2ncc3cc(Cl)c(C4CCN(C(=O)OC(C)(C)C)CC4)cc32)n1]

A mixture of tert-butyl 4-(5-chloro-1H-indazol-6-yl)piperidine-1-carboxylate (200 mg, 0.6 mmol) and (1S,4S)-5-(6-iodo-2-methoxypyrimidin-4-yl)-2-oxa-5-azabicyclo[2.2.1]heptane (217 mg, 0.65 mmol), CuI (57 mg, 0.3 mmol), K$_3$PO$_4$ (254 mg, 1.2 mmol) and N,N'-dimethylcyclohexane-1,2-diamine (85 mg, 0.6 mmol) in toluene (3 mL) was stirred at 100° C. for 3 hours. The mixture was diluted with 50 mL of EtOAc and washed with NH$_3$H$_2$O (30 mL×3). The organic layer was dried over Na$_2$SO$_4$, filtered and concentrated. The crude was purified by flash chromatography column (Petroleum ether/EtOAc=1/1) to give the title compound (263 mg, 81%) as a white solid.

$^1$HNMR (400 MHz, CDCl$_3$): δ 8.82 (s, 1H), 8.10 (s, 1H), 7.77 (s, 1H), 6.54 (br 1H), 5.26 (br, 1H), 4.75 (s, 1H), 4.30 (br, 2H), 4.11 (s, 3H), 3.91 (s, 2H), 3.54-3.47 (m, 2H), 3.32-3.26 (m, 1H), 2.90 (s, 2H), 1.98 (d, J=11.6 Hz, 4H), 1.61 (s, 2H), 1.50 (s, 9H).

Description 188

(1S,4S)-5-(6-(5-chloro-6-(piperidin-4-yl)-1H-indazol-1-yl)-2-methoxypyrimidin-4-yl)-2-oxa-5-azabicyclo[2.2.1]heptane (D188)

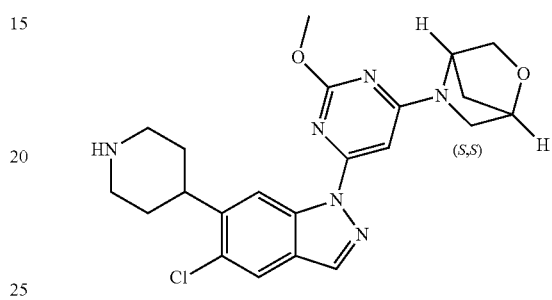

To a solution of (1S,4S)-tert-butyl 4-(1-(6-(2-oxa-5-azabicyclo[2.2.1]heptan-5-yl)-2-methoxypyrimidin-4-yl)-5-chloro-1H-indazol-6-yl)piperidine-1-carboxylate (263 mg, 0.48 mmol) in DCM (4 mL) was added TFA (1 mL). The mixture was stirred at room temperature for 2 hours. Sat-.NaHCO$_3$ was added to the mixture to adjust pH>7. The mixture was diluted with H$_2$O (50 mL), extracted with EtOAc (30 mL×3). The organic layer was dried over Na$_2$SO$_4$, filtered and concentrated to give the title compound (215 mg, 100%) as a white solid.

$^1$HNMR (400 MHz, CDCl$_3$): δ 8.88 (s, 1H), 8.12 (s, 1H), 7.80 (s, 1H), 6.55 (br, 1H), 5.28 (br, 1H), 4.75 (s, 1H), 4.13 (s, 3H), 3.93-3.88 (m, 2H), 3.59-3.55 (m, 5H), 3.15-3.09 (m, 2H), 2.21 (d, J=13.6 Hz, 2H), 2.07-2.00 (m, 5H).

Description 189

(1S,4S)-ethyl 2-(4-(1-(6-(2-oxa-5-azabicyclo[2.2.1]heptan-5-yl)-2-methoxypyrimidin-4-yl)-5-chloro-1H-indazol-6-yl)piperidin-1-yl)acetate (D189)

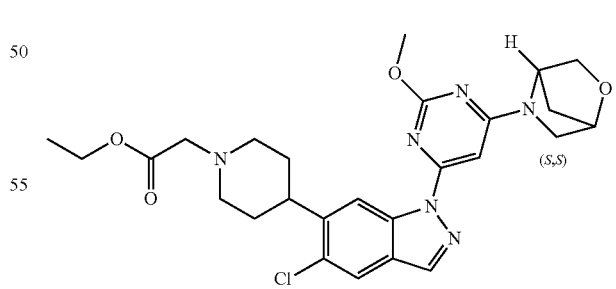

To a solution of (1S,4S)-5-(6-(5-chloro-6-(piperidin-4-yl)-1H-indazol-1-yl)-2-methoxypyrimidin-4-yl)-2-oxa-5-azabicyclo[2.2.1]heptane (215 mg, 0.49 mmol) in DMF (5 mL) was added ethyl bromoacetate (243 mg, 1.46 mmol) and TEA (245 mg, 2.43 mmol) at 0° C. The mixture was stirred at room temperature for 2 hours. The mixture was diluted with H$_2$O (50 mL) and extracted with EtOA (30 mL×3). The organic layer was dried over $Na_2SO_4$, filtered and concentrated. The residue was purified by flash chromatography column (petroleum ether/EtOAc=1/2) to give the title compound (181 mg, 70%) as a white solid.

$^1$HNMR (400 MHz, CDCl$_3$): δ 8.85 (s, 1H), 8.08 (s, 1H), 7.75 (s, 1H), 6.54 (br, 1H), 5.27 (br 1H), 4.74 (s, 1H), 4.21 (d, J=7.2 Hz, 2H), 4.13 (s, 3H), 3.93-3.88 (m, 2H), 3.53-3.44 (m, 2H), 3.30 (s, 2H), 3.13-3.10 (m, 3H), 2.43 (t, J=10.8 Hz, 2H), 2.03-1.87 (m, 6H), 1.30 (t, J=7.2 Hz, 3H).

Description 190

(1R,4R)-tert-butyl 4-(1-(6-(2-oxa-5-azabicyclo[2.2.1]heptan-5-yl)-2-methylpyrimidin-4-yl)-5-chloro-1H-indazol-6-yl)piperidine-1-carboxylate (D190)

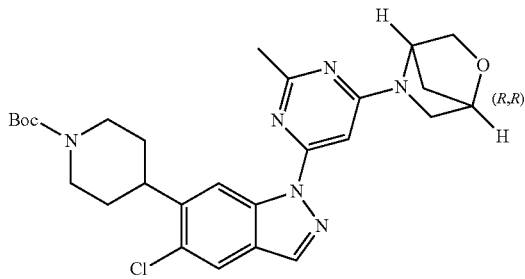 [SMILES: Cc1nc(N2CC3CC2CO3)cc(-n2ncc3cc(Cl)c(C4CCN(C(=O)OC(C)(C)C)CC4)cc32)n1]

To a suspension of tert-butyl 4-(5-chloro-1H-indazol-6-yl)piperidine-1-carboxylate ((200 mg, 0.59 mmol), (1R,4R)-5-(6-iodo-2-methylpyrimidin-4-yl)-2-oxa-5-azabicyclo[2.2.1]heptane (207 mg, 0.65 mmol), N,N'-dimethylcyclohexane-1,2-diamine (84 mg, 0.59 mmol), CuI (57 mg, 0.30 mmol) and $K_3PO_4$ (250 mg, 1.18 mmol) in toluene (3 mL) was stirred at 100° C. for 2 hrs. Then the reaction mixture was diluted with EtOAc (60 mL), washed with $NH_3.H_2O$ (30 mL) and brine (30 mL), dried over $Na_2SO_4$, filtered and concentrated. The residue was purified by flash chromatography (petroleum ether/EtOAc=1:1) to give compound (281 mg, 91%) as a yellow oil.

$^1$HNMR (400 MHz, CDCl$_3$): δ 8.91 (s, 1H), 8.12 (s, 1H), 7.79 (s, 1H), 6.68 (br 1H), 5.36 (br 1H), 4.79 (s, 1H), 4.41-4.29 (m, 2H), 3.97-3.92 (m, 2H), 3.64-3.49 (m, 2H), 3.34-3.27 (m, 1H), 3.02-2.88 (m, 2H), 2.65 (s, 3H), 2.05-1.98 (m, 4H), 1.78-1.68 (m, 2H), 1.54 (s, 9H).

Description 191

(1R,4R)-5-(6-(5-chloro-6-(piperidin-4-yl)-1H-indazol-1-yl)-2-methylpyrimidin-4-yl)-2-oxa-5-azabicyclo[2.2.1]heptane (D191)

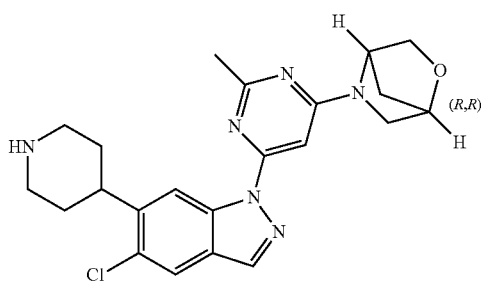 [SMILES: Cc1nc(N2CC3CC2CO3)cc(-n2ncc3cc(Cl)c(C4CCNCC4)cc32)n1]

A solution of (1R,4R)-tert-butyl 4-(1-(6-(2-oxa-5-azabicyclo[2.2.1]heptan-5-yl)-2-methylpyrimidin-4-yl)-5-chloro-1H-indazol-6-yl)piperidine-1-carboxylate (281 mg, 0.536 mmol) in TFA/DCM (6 mL, v/v=1/1) was stirred at room temperature for 1 hour. The mixture was diluted with Sat.NaHCO$_3$ to pH=7~8, extracted with DCM (20 mL×3). The organic layer was dried over $Na_2SO_4$, filtered and concentrated to give the crude compound (280 mg, 100%) as a yellow solid.

LC-MS [C$_{18}$; column size: 4.6×30 mm 5 μm; Dikwa Diamonsil plus; mobile phase: B (ACN): A1 (0.02% NH$_4$OAc+ 5% ACN); gradient (B %) in 4 min-05-95-POS; 5-95% positive, flow rate: 1.5 mL/min, stop time 4 min]: Rt=1.977 min; MS Calcd.: 424, MS Found: 425 [M+H]$^+$.

Description 192

(1R,4R)-ethyl 2-(4-(1-(6-(2-oxa-5-azabicyclo[2.2.1]heptan-5-yl)-2-methylpyrimidin-4-yl)-5-chloro-1H-indazol-6-yl)piperidin-1-yl)acetate (D192)

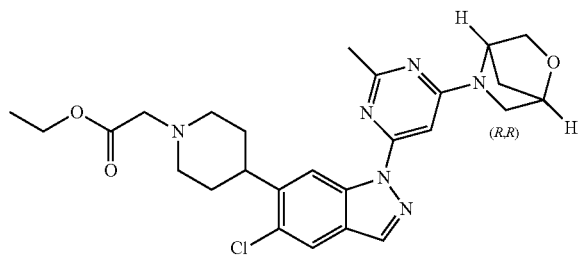 [SMILES: CCOC(=O)CN1CCC(c2cc3c(cnn3-c3cc(N4CC5CC4CO5)nc(C)n3)cc2Cl)CC1]

To a solution of (1R,4R)-5-(6-(5-chloro-6-(piperidin-4-yl)-1H-indazol-1-yl)-2-methylpyrimidin-4-yl)-2-oxa-5-azabicyclo[2.2.1]heptane (280 mg, 0.66 mmol) in DMF (5 mL) was added ethyl bromoacetate (330 mg, 1.98 mmol) and TEA (333 mg, 3.30 mmol) at 0° C. The mixture was stirred at room temperature for 2 hours. The mixture was diluted with H$_2$O (20 mL), extracted with EtOAc (50 mL×2). The combined organic layers were dried over $Na_2SO_4$, filtered and concentrated. The residue was purified by column chromatography on silica gel (DCM/MeOH=20:1) to give the title compound (188 mg, 56%) as a white solid.

$^1$H NMR (400 MHz, CDCl$_3$): δ 8.93 (s, 1H), 8.08 (s, 1H), 7.74 (s, 1H), 6.65 (br 1H), 5.33 (br 1H), 4.74 (s, 1H), 4.23 (q, J=7.2 Hz, 2H), 3.91 (t, J=8.4 Hz, 2H), 3.56-3.42 (m, 2H), 3.31 (s, 2H), 3.17-3.09 (m, 3H), 2.62 (s, 3H), 2.42 (t, J=10 Hz, 2H), 2.04-1.91 (m, 6H), 1.31 (t, J=7.2 Hz, 3H).

Description 193

9-(6-iodo-2-methoxypyrimidin-4-yl)-3,7-dioxa-9-azabicyclo[3.3.1]nonane (D193)

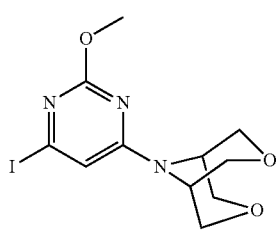 [SMILES: COc1nc(I)cc(N2C3COCC2COC3)n1]

A mixture of 3,7-dioxa-9-azabicyclo[3.3.1]nonane oxalate (100 mg, 0.775 mmol), 4,6-diiodo-2-methoxypyrimidine (280 mg, 3.33 mmol) and TEA (235 mg, 2.33 mmol) in 4 mL of i-PrOH and 2 mL of DMF was stirred at 35° C. for 12 hrs and 100° C. for 6 hrs. The solution was poured into H$_2$O (30 mL) and extracted with EtOAc (30 mL×2). The organic layer was washed with 30 mL of brine, dried over Na$_2$SO$_4$, filtered and concentrated. The residue was purified by column chromatography on silica gel (Petroleum ether/EtOAc=2/1) to give the title compound (100 mg, 35%) as yellow solid.

$^1$H NMR (300 MHz, CDCl$_3$): δ 6.58 (s, 1H), 4.13-4.10 (m, 5H), 3.94-3.89 (m, 8H).

Description 194

Tert-butyl 4-(1-(6-(3,7-dioxa-9-azabicyclo[3.3.1] nonan-9-yl)-2-methoxypyrimidin-4-yl)-5-methyl-1H-indazol-6-yl)piperidine-1-carboxylate (D194)

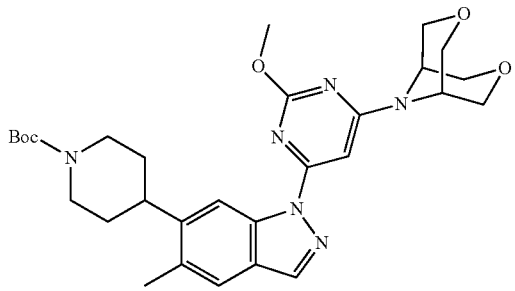 [SMILES: COc1nc(N2C3COCC2COC3)cc(-n2ncc3cc(C)c(C4CCN(C(=O)OC(C)(C)C)CC4)cc32)n1]

A mixture of tert-butyl-4-(5-methyl-1H-indazol-6-yl)piperidine-1-carboxylate (119 mg, 0.38 mmol), 9-(6-iodo-2-methoxypyrimidin-4-yl)-3,7-dioxa-9-azabicyclo[3.3.1]nonane (60 mg, 0.16 mmol) and CsCO$_3$ (124 mg, 0.38 mmol) in DMF (1.5 mL) was stirred at 85° C. for 5 hours. The mixture was added EtOAc (80 mL), washed with H$_2$O (30 mL×3). The organic phases was dried over Na$_2$SO$_4$, filtered and concentrated. The crude was purified by flash chromatography (petroleum ether/EtOAc=1:1) to give compound (40 mg, 38%) as a colorless oil.

LCMS [column: C$_{18}$; column size: 2.1×50 mm; Waters ACQUITY UPLC BEH; mobile phase: B (ACN); A (0.02% NH$_4$OAc+ 5% ACN); flow rate: 1.5 ml/min; gradient (B %) in 4 mins]: Rt=2.694 min; MS Calcd.: 550, MS Found: 551 [M+H]$^+$.

Description 195

9-(2-methoxy-6-(5-methyl-6-(piperidin-4-yl)-1H-indazol-1-yl)pyrimidin-4-yl)-3,7-dioxa-9-azabicyclo[3.3.1]nonane (D195)

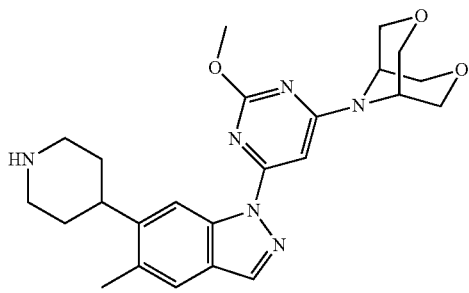 [SMILES: COc1nc(N2C3COCC2COC3)cc(-n2ncc3cc(C)c(C4CCNCC4)cc32)n1]

To a solution of tert-butyl 4-(1-(6-(3,7-dioxa-9-azabicyclo [3.3.1]nonan-9-yl)-2-methoxypyrimidin-4-yl)-5-methyl-1H-indazol-6-yl)piperidine-1-carboxylate (40 mg, 0.07 mmol) in TFA (1 mL) and DCM (4 mL) was stirred at room temperature overnight. The mixture was added H$_2$O (20 mL), extracted with EtOAc (30 mL×3). The combined organic layer was dried over Na$_2$SO$_4$, filtered and concentrated to give the compound (32 mg, 98%) as yellow solid.

LCMS [column: O$_{18}$; column size: 4.6×30 mm; Diamonsil plus; mobile phase: B (ACN); A (0.02% NH$_4$OAc+ 5% ACN); flow rate: 1.5 ml/min; gradient (B %) in 4 mins]: Rt=1.874 min; MS Calcd.: 450, MS Found: 451 [M+H]$^+$.

Description 196

8-(6-iodo-2-methoxypyrimidin-4-yl)-3-oxa-8-azabicyclo[3.2.1]octane (D196)

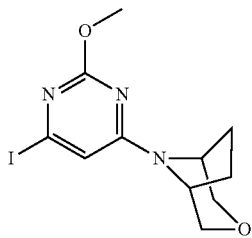

To a solution of 4,6-diiodo-2-methylpyrimidine (1.09 g, 3.33 mmol), 3-oxa-8-azabicyclo[3.2.1]octane (500 mg, 3.33 mmol) and TEA (1.35 g, 13.32 mmol) in i-PrOH (10 mL) and DMSO (4 mL) was stirred at 25° C. overnight. The mixture was diluted with H$_2$O (20 mL) and extracted with EtOAc (20 mL×3). The organic phase was dried over Na$_2$SO$_4$, filtered and concentrated. The residue was purified by silica gel chromatography column (petroleum ether/EtOAc=7/1) to give the title compound (930 mg, 78%) as yellow solid.

$^1$HNMR (400 MHz, CDCl$_3$): δ 6.55 (s, 1H), 3.90 (s, 3H), 3.74-3.71 (m, 3H), 3.63-3.60 (m, 3H), 2.12-2.10 (m, 2H), 2.05-2.00 (m, 2H).

Description 197

Tert-butyl 4-(1-(6-(3-oxa-8-azabicyclo[3.2.1]octan-8-yl)-2-methoxypyrimidin-4-yl)-5-methyl-1H-indazol-6-yl)piperidine-1-carboxylate (D197)

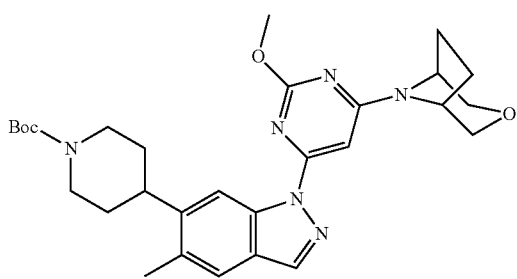 [SMILES: COc1nc(N2C3CCC2COC3)cc(-n2ncc3cc(C)c(C4CCN(C(=O)OC(C)(C)C)CC4)cc32)n1]

A mixture of 5-methyl-6-(1-(oxetan-3-yl)piperidin-4-yl)-1H-indazole (200 mg, 0.64 mmol), 8-(6-iodo-2-methoxypyrimidin-4-yl)-3-oxa-8-azabicyclo[3.2.1]octane (242 mg, 0.70 mmol), N,N'-dimethylcyclohexane-1,2-diamine (180 mg, 1.27 mmol), CuI (121 mg, 0.63 mmol) and $K_3PO_4$ (269 mg, 1.27 mmol) in toluene (8 mL) was stirred at 100° C. for 4 hours. The mixture was diluted with 15 mL of $H_2O$ and $NH_3H_2O$ (5 mL) and extracted with EtOAc (20 mL×2).

The organic layer was dried over $Na_2SO_4$, filtered and concentrated. The residue was purified by pre-TLC (petroleum ether/EtOAc=3/1) to give the title compound (269 mg, 79%) as a colorless oil.

LCMS [$C_{18}$; column size: 4.6×30 mm 5 μm; Dikwa Diamonsil plus; mobile phase: B (ACN): A1 (0.02% $NH_4OAc$+ 5% ACN); gradient (B %) in 4 mins. 05-95-POS; 5-95% positive, flow rate: 1.5 mL/min, stop time 4 min]: Rt=2.958 min; MS Calcd.: 534, MS Found: 535 [M+H]$^+$.

Description 198

8-(2-methoxy-6-(5-methyl-6-(piperidin-4-yl)-1H-indazol-1-yl)pyrimidin-4-yl)-3-oxa-8-azabicyclo[3.2.1]octane (D198)

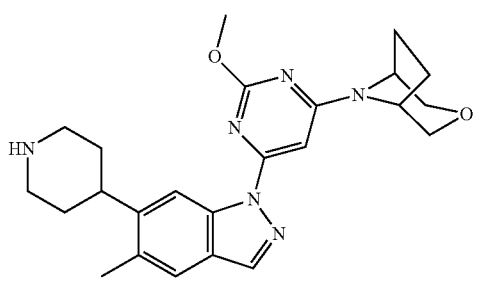 [SMILES: COc1nc(N2C3CCC2COC3)cc(-n2ncc3cc(C)c(C4CCNCC4)cc32)n1]

To a mixture of tert-butyl 4-(1-(6-(3-oxa-8-azabicyclo[3.2.1]octan-8-yl)-2-methoxypyrimidin-4-yl)-5-methyl-1H-indazol-6-yl)piperidine-1-carboxylate (269 mg, 0.504 mmol) in DCM (4 mL) was added $HCl/Et_2O$ (2 M, 2 mL). The mixture was stirred at room temperature for 5 hours. The reaction was concentrated. The residue was dissolved in 20 mL of MeOH and treated with Amberlyst A-21 resin for 15 minutes. The resin was filtered off and filtrate was concentrate to give the title compound (230 mg, 100%) as white solid.

LCMS [$C_{18}$; column size: 4.6×30 mm 5 μm; Dikwa Diamonsil plus; mobile phase: B (ACN): A1 (0.02% $NH_4OA$+5% ACN); gradient (B %) in 4 mins. 05-95-POS; 5-95% positive, flow 1.5 mL/min, stop time 4 min]: Rt=2.089 min; MS Calcd.: 434, MS Found: 435 [M+H]$^+$.

Description 199

5-chloro-1-(tetrahydro-2H-pyran-2-yl)-6-(4,4,5,5-tetramethyl-1,3,2-dioxaborolan-2-yl)-1H-indazole (D199)

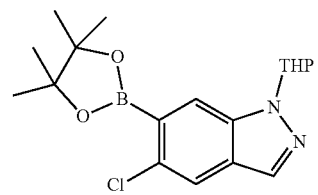

To a solution of 6-bromo-5-chloro-1-(tetrahydro-2H-pyran-2-yl)-1H-indazole (5 g, 15.87 mmol), 4,4,4',4',5,5,5',5'-octamethyl-2,2'-bi(1,3,2-dioxaborolane) (4.84 g, 19.04 mmol) and $CH_3COOK$ (6.23 g, 63.48 mmol) in (100 ml) of dioxane was added $Pd(dppf)Cl_2$ (1.17 g, 1.58 mmol). The mixture was heated to 90° C. for 2 hours. The mixture was concentrated in vacuo. The crude was purified by column chromatography on silica gel (petroleum ether/EtOAc=10/1) to afford the title compound (4.0 g, 70%) as a yellow solid.

$^1$H NMR (300 MHz, CDCl$_3$): δ 7.97 (s, 1H), 7.90 (s, 1H), 7.72 (s, 1H), 5.78-5.74 (m, 1H), 4.05-4.00 (m, 1H), 3.82-3.71 (m, 1H), 2.64-2.52 (m, 1H), 2.22-2.00 (m, 2H), 1.84-1.63 (m, 3H), 1.27 (s, 12H).

Description 200

5-chloro-1-(tetrahydro-2H-pyran-2-yl)-1H-indazol-6-ol (D200)

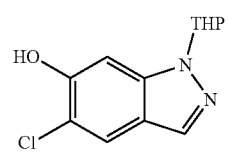

To a solution of 5-chloro-1-(tetrahydro-2H-pyran-2-yl)-6-(4,4,5,5-tetramethyl-1,3,2-dioxaborolan-2-yl)-1H-indazole (4.0 g, 11.02 mmol) in 12 mL of $H_2O_2$, was added 10 mL of acetic acid in 100 mL of THF. The reaction was stirred at room temperature for 18 hours. Water (20 mL) was added. The mixture was extracted with EtOAc (20 mL×2). The organic layer was washed with brine, dried over $Na_2SO_4$, filtered and concentrated. The residue was purified by column chromatography on silica gel (petroleum ether/EtOAc=5/1) to afford the title compound (2.51 g, 91%) as a yellow solid.

$^1$H NMR (300 MHz, CDCl$_3$): δ 7.90 (s, 1H), 7.70 (s, 1H), 7.20 (s, 1H), 5.63-5.59 (m, 2H), 4.06-4.01 (m, 1H), 3.78-3.69 (m, 1H), 2.58-2.47 (m, 1H), 2.17-2.03 (m, 2H), 1.79-1.65 (m, 3H).

Description 201

5-chloro-1-(tetrahydro-2H-pyran-2-yl)-6-(((S)-tetrahydrofuran-3-yl)oxy)-1H-indazole (D201)

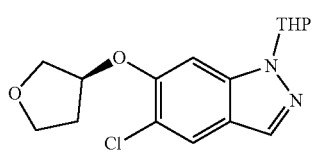

To a solution of 5-chloro-1-(tetrahydro-2H-pyran-2-yl)-1H-indazol-6-ol (450 mg, 1.8 mmol), (R)-tetrahydrofuran-3-ol (157 mg, 1.8 mmol) and PPh$_3$ (566 mg, 2.2 mmol) in THF (6 mL), was added DIAD (444 mg, 2.2 mmol). The mixture was stirred at 0° C. to room temperature overnight. The mixture was diluted with H$_2$O (30 mL) and extracted with EtOAc (30 mL×3). The extracts were combined and dried over Na$_2$SO$_4$. The organic phase was filtered and concentrated. The residue was purified by column chromatography on silica gel (petroleum ether/EtOAc=2/1) to give the title compound (400 mg, 69%) as yellow oil.

$^1$H NMR (300 MHz, CDCl$_3$): δ 7.89 (s, 1H), 7.73 (s, 1H), 6.98 (s, 1H), 5.88-5.86 (m, 1H), 5.07-4.97 (m, 1H), 4.15-3.99 (m, 5H), 3.80-3.71 (m, 1H), 2.58-2.48 (m, 1H), 2.79-2.15 (m, 4H), 1.75-1.71 (m, 3H).

Description 202

(S)-5-chloro-6-((tetrahydrofuran-3-yl)oxy)-1H-indazole (D202)

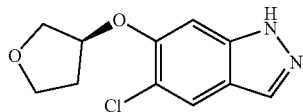 [SMILES: Clc1cc2cn[nH]c2cc1O[C@H]1CCOC1]

A mixture of 5-chloro-1-(tetrahydro-2H-pyran-2-yl)-6-(((S)-tetrahydrofuran-3-yl)oxy)-1H-indazole (300 mg, 0.93 mmol) in DCM (6 mL) and TFA (6 mL) was stirred at room temperature for 2 hours. The mixture was concentrated. The crude product was purified by prep-HPLC to give the title compound (45 mg, 20%) as yellow oil.

$^1$H NMR (DMSO-d$_6$, 400 MHz): δ 12.97 (br 1H), 7.95 (s, 1H), 7.85 (s, 1H), 7.09 (s, 1H), 5.19-5.16 (m, 1H), 3.97-3.76 (m, 4H), 2.30-2.25 (m, 1H), 2.07-2.03 (m, 1H).

Description 203

Methyl 2-(6-iodo-2-methoxypyrimidin-4-yl)-2-azabicyclo[2.2.1]heptane-5-carboxylate (D203)

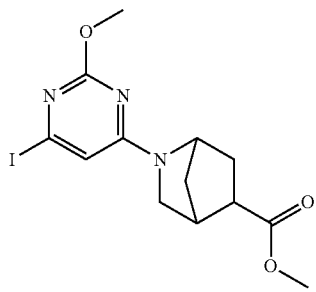 [SMILES: COC(=O)C1CC2CC1CN2c1cc(I)nc(OC)n1]

To a solution of 1 4,6-diiodo-2-methoxypyrimidine (750 mg, 2.07 mmol) and methyl 2-azabicyclo[2.2.1]heptane-5-carboxylate hydrochloride (398 mg, 2.07 mmol) in i-PrOH (12 mL) was added TEA (628 mg, 6.21 mmol). The mixture was stirred at room temperature overnight. The mixture was concentrated and purified by column chromatography on silica gel (petroleum ether/EtOAc=10/1 to 3/2) to give the title compound (639 mg, 78%) as yellow oil.

$^1$HNMR (300 MHz, CDCl$_3$): δ 6.52 (s, 0.4H), 6.31 (s, 0.6H), 4.88 (s, 1H), 4.16 (s, 1H), 3.91 (s, 3H), 3.72 (s, 3H), 3.53-3.33 (m, 1H), 2.97-2.90 (m, 1H), 2.61-2.56 (m, 1H), 2.05-2.03 (m, 2H), 1.80-1.60 (m, 2H).

Descriptions 204 and 205 methyl 2-(6-iodo-2-methoxypyrimidin-4-yl)-2-azabicyclo[2.2.1]heptane-5-carboxylate (D204, isomer 1; D205, isomer 2)

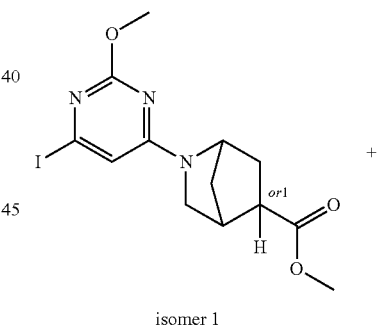

isomer 1

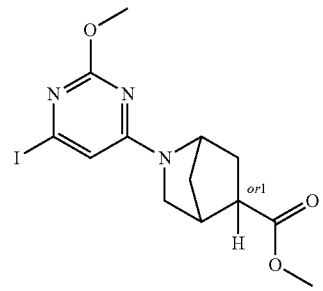

isomer 2 methyl 2-(6-iodo-2-methoxypyrimidin-4-yl)-2-azabicyclo[2.2.1]heptane-5-carboxylate (639 mg) was separated by chiral-prep-HPLC to afford isomer 1 (239 mg, 37%) and isomer 2 (215 mg, 34%).

Chiral pre-HPLC [column: Chiralpak IA; 5 μm 20×150 mm; Phase: CO$_2$:EtOH=90:10, flow rate: 10 mL/min; Wave length: 230 nm).

Isomer 1, D204

$^1$H NMR (400 MHz, CDCl$_3$): δ 6.51 (s, 0.4H), 6.29 (s, 0.6H), 4.87 (s, 1H), 4.14 (s, 1H), 3.92 (s, 3H), 3.71 (s, 3H), 3.49-3.28 (m, 1H), 2.95-2.91 (m, 1H), 2.59-2.58 (m, 1H), 2.03-1.99 (m, 2H), 1.79-1.76 (m, 2H).

Chiral HPLC (Chiralpak ID 5 μm 4.6×250 mm; Phase: Hex:EtOH=90:10; Flow rate: 1.0 mL/min; Wave length: 230 nm; Temperature: 30° C.): Rt=11.802 min.

Isomer 2, D205

$^1$H NMR (400 MHz, CDCl$_3$): δ 6.51 (s, 0.4H), 6.29 (s, 0.6H), 4.87 (s, 1H), 4.13 (s, 1H), 3.89 (s, 3H), 3.71 (s, 3H), 3.49-3.28 (m, 1H), 2.96-2.90 (m, 1H), 2.59-2.58 (m, 1H), 2.03-1.99 (m, 2H), 1.79-1.76 (m, 2H).

Chiral HPLC (Chiralpak ID 5 μm 4.6×250 mm; Phase: Hex:EtOH=90:10; Flow rate: 1.0 mL/min; Wave length: 230 nm; Temperature: 30° C.): Rt=13.409 min.

Description 206

Methyl 2-(6-(5-chloro-6-(((S)-tetrahydrofuran-3-yl)oxy)-1H-indazol-1-yl)-2-methoxypyrimidin-4-yl)-2-azabicyclo[2.2.1]heptane-5-carboxylate (Isomer 1) (D206)

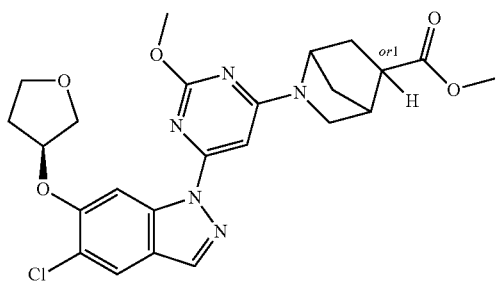

A mixture of (S)-5-chloro-6-((tetrahydrofuran-3-yl)oxy)-1H-indazole (45 mg, 0.19 mmol), (5R)-methyl 2-(6-iodo-2-methoxypyrimidin-4-yl)-2-azabicyclo[2.2.1]heptane-5-carboxylate (isomer 1) (82 mg, 0.21 mmol), N,N'-dimethylcyclohexane-1,2-diamine (54 mg, 0.38 mmol), CuI (36 mg, 0.19 mmol) and K$_3$PO$_4$ (81 mg, 0.38 mmol) in toluene (3 mL) was stirred at 100° C. for 2 hours. The mixture was diluted with EtOAc (100 mL), washed with brine (40 mL), dried over Na$_2$SO$_4$, filtered and concentrated. The residue was purified by column chromatography on silica gel (petroleum ether/EtOAc=4/1) to give the title compound (28 mg, 29%) as yellow oil.

$^1$HNMR (400 MHz, CDCl$_3$): δ 8.43 (s, 1H), 8.04 (s, 1H), 7.73 (s, 1H), 6.70-6.48 (m, 1H), 5.09 (br 1H), 4.13-3.94 (m, 7H), 3.72 (s, 3H), 3.55-3.43 (m, 1H), 2.96 (br 1H), 2.62 (t, J=7.6 Hz, 1H), 2.31-2.24 (m, 2H), 2.08-2.04 (m, 2H), 1.82-1.80 (m, 2H), 1.33-1.27 (m, 2H).

Description 207

5-chloro-1-(tetrahydro-2H-pyran-2-yl)-6-(((R)-tetrahydrofuran-3-yl)oxy)-1H-indazole (D207)

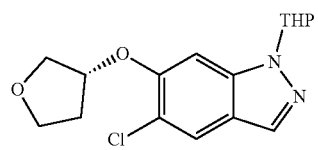

To a solution of 5-chloro-1-(tetrahydro-2H-pyran-2-yl)-1H-indazol-6-ol (450 mg, 1.8 mmol), (S)-tetrahydrofuran-3-ol (157 mg, 1.8 mmol), PPh$_3$ (566 mg, 2.2 mmol) in 6 mL of THF at 0° C. was added DIAD (444 mg, 2.2 mmol). The reaction was stirred at 0° C. to room temperature overnight. The mixture was diluted with EtOAc (50 mL), washed with water (50 mL×2), concentrated with silica gel. The crude product was purified by column chromatography on silica gel (petroleum ether/EtOAc=2/1) to afford the title compound (500 mg, 87%) as yellow oil.

$^1$H NMR (300 MHz, CDCl$_3$): δ 7.89 (s, 1H), 7.73 (s, 1H), 6.98 (s, 1H), 5.88-5.86 (m, 1H), 5.07-4.97 (m, 1H), 4.15-3.99 (m, 5H), 3.80-3.71 (m, 1H), 2.58-2.48 (m, 1H), 2.79-2.15 (m, 4H), 1.75-1.71 (m, 3H).

Description 208

(R)-5-chloro-6-((tetrahydrofuran-3-yl)oxy)-1H-indazole (D208)

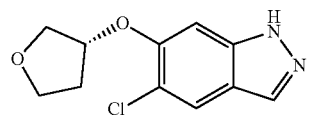 [SMILES: Clc1cc2cn[nH]c2cc1O[C@@H]1CCOC1]

A solution of 5-chloro-1-(tetrahydro-2H-pyran-2-yl)-6-(((R)-tetrahydrofuran-3-yl)oxy)-1H-indazole (500 mg, 1.55 mmol) in DCM (6 mL) was added TFA (6 mL) at room temperature. The mixture was stirred at room temperature for 3 hours. The mixture was concentrated and purified by prep-HPLC to afford the title compound (230 mg, 60%) as yellow oil.

$^1$HNMR (DMSO-d$_6$, 300 MHz): δ 12.99 (br 1H), 7.94 (s, 1H), 7.85 (s, 1H), 7.08 (s, 1H), 5.17-5.14 (m, 1H), 3.97-3.75 (m, 4H), 2.30-2.23 (m, 1H), 2.04-1.99 (m, 1H).

Description 209

Methyl 2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylate (Isomer 1) (D209)

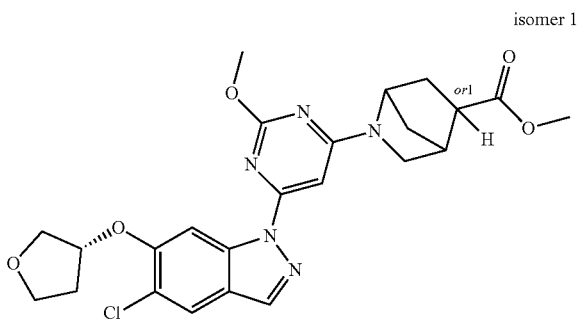 [SMILES: COC(=O)C1CC2CC1CN2c1cc(-n2ncc3cc(Cl)c(O[C@@H]4CCOC4)cc32)nc(OC)n1]

A mixture of methyl 2-(6-iodo-2-methoxypyrimidin-4-yl)-2-azabicyclo[2.2.1]heptane-5-carboxylate (isomer 1) (115 mg, 0.30 mmol), (R)-5-chloro-6-((tetrahydrofuran-3-yl)oxy)-1H-indazole (70 mg, 0.21 mmol), N,N'-dimethylcyclohexane-1,2-diamine (84 mg, 0.60 mmol), CuI (56 mg, 0.30 mmol) and $K_3PO_4$ (125 mg, 0.60 mmol) in toluene (3 mL) was stirred at 100° C. for 3 hours. The reaction was filtered and concentrated. The residue was diluted with EtOAc (20 mL), washed with $NH_3H_2O$ (10 mL), brine (10 mL), dried over $Na_2SO_4$, filtered and concentrated. The residue was purified by Prep-TLC (petroleum ether/EtOAc=2/1) to give the title compound (106 mg, 72%) as a colorless oil.

$^1$HNMR (400 MHz, $CDCl_3$): δ 8.42 (s, 1H), 8.03 (s, 1H), 7.73 (s, 1H), 6.69 (s, 0.4H), 6.47 (s, 0.6H)), 5.09 (br 1H), 4.13-3.94 (m, 7H), 3.71 (s, 3H), 3.57-3.42 (m, 1H), 3.10-2.98 (m, 1H), 2.63 (t, J=7.6 Hz, 1H), 2.34-2.20 (m, 2H), 2.07-2.04 (m, 2H), 1.82-1.80 (m, 2H), 1.33-1.25 (m, 2H).

Description 210

Methyl 2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylate (Isomer 2) (D210)

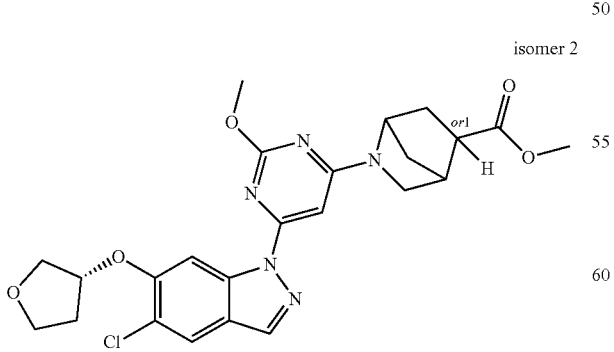

A mixture of methyl 2-(6-iodo-2-methoxypyrimidin-4-yl)-2-azabicyclo[2.2.1]heptane-5-carboxylate (isomer 2) (128 mg, 0.33 mmol), (R)-5-chloro-6-(((tetrahydrofuran-3-yl)oxy)-1H-indazole (70 mg, 0.30 mmol), N,N'-dimethylcyclohexane-1,2-diamine (85 mg, 0.60 mmol), CuI (57 mg, 0.30 mmol) and $K_3PO_4$ (127 mg, 0.60 mmol) in toluene (3 mL) was stirred at 100° C. for 2 hours. The reaction was filtered and concentrated. The residue was diluted with EtOAc (100 mL), washed with brine (50 mL), dried over $Na_2SO_4$, filtered and concentrated. The residue was purified by Prep-TLC (petroleum ether/EtOAc=4/1) to give the title compound (138 mg, 92%) as a yellow solid.

$^1$HNMR (400 MHz, $CDCl_3$): δ 8.42 (s, 1H), 8.03 (s, 1H), 7.73 (s, 1H), 6.69 (s, 0.4H), 6.47 (s, 0.6H)), 5.09 (br 1H), 4.13-3.94 (m, 7H), 3.71 (s, 3H), 3.57-3.42 (m, 1H), 3.10-2.98 (m, 1H), 2.63 (t, J=7.6 Hz, 1H), 2.34-2.20 (m, 2H), 2.07-2.04 (m, 2H), 1.82-1.80 (m, 2H), 1.33-1.25 (m, 2H).

Description 211

Cis-6-(3-fluoropiperidin-4-yl)-5-methyl-1H-indazole (from Peak 1) (D211)

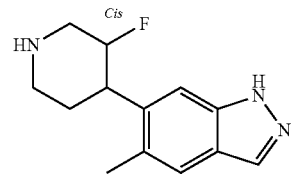 [SMILES: Cc1cc2cn[nH]c2cc1C1CCNCC1F]

To a solution of tert-butyl cis-3-fluoro-4-(5-methyl-1H-indazol-6-yl)piperidine-1-carboxylate (peak 1, 200 mg, 0.6 mmol) in DCM (4 mL) was added TFA (2 mL). The reaction mixture was stirred at rt overnight, concentrated, basified to pH>12 with $Na_2CO_3$ aq. and NaOH aq., filtered and dried to give the title product as a white solid. (150 mg, crude)

LC-MS [mobile phase: from 70% water (0.1% FA) and 30% ACN (0.1% FA) to 5% water (0.1% FA) and 95% ACN (0.1% FA) in 2.6 min]: Rt=0.757 min; MS Calcd.: 233, MS Found: 234 $[M+H]^+$.

Description 212

Cis-6-(3-fluoro-1-(tetrahydrofuran-3-yl)piperidin-4-yl)-5-methyl-1H-indazole (from Peak 1) (D212)

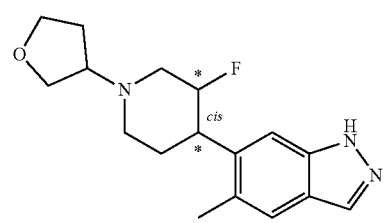 [SMILES: Cc1cc2cn[nH]c2cc1C1CCN(C2CCOC2)CC1F]

To a stirred mixture of cis-6-(3-fluoropiperidin-4-yl)-5-methyl-1H-indazole (from Peak 1) (150 mg, 0.64 mmol), dihydrofuran-3(2H)-one (110 mg, 1.28 mmol), 4 Å molecular sieves (50 mg) in MeOH/$CH_2Cl_2$ (2 mL/5 mL) at 0° C. were added AcOH (12 mg, 0.192 mmol) and $NaBH_3CN$ (80 mg, 1.28 mmol). The reaction was warmed to room temperature and stirred overnight. TLC showed the reaction was complete. The reaction mixture was filtered and the filtrate was washed with aqueous $NaHCO_3$ (10 mL), dried, filtered.

The filtrate was concentrated and the residue was purified by column chromatography (eluent: CH₂Cl₂, followed by CH₂Cl₂:MeOH=20:1) afforded desired product as a white solid (165 mg, yield: 85%).

LC-MS [mobile phase: from 80% water (0.1% FA) and 20% ACN (0.1% FA) to 5% water (0.1% FA) and 95% ACN (0.1% FA) in 2.0 min]: Rt=0.796 min; MS Calcd: 303; MS Found: 304 [M+H]⁺.

Description 213

Cis-6-(3-fluoropiperidin-4-yl)-5-methyl-1H-indazole (from Peak 2) (D213)

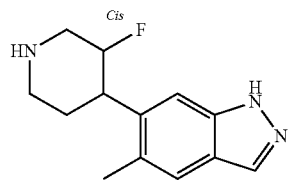

TFA (2 mL) was added to a solution of tert-butyl cis-3-fluoro-4-(5-methyl-1H-indazol-6-yl)piperidine-1-carboxylate (peak 2, 200 mg, 0.6 mmol) in DCM (4 mL). The reaction was stirred at rt overnight. The solution was concentrated and then Na₂CO₃ aq. and NaOH aq. were added until pH>12. The mixture was filtered and the solid was dried to give product as a white solid. (140 mg, crude)

LC-MS [mobile phase: from 70% water (0.1% FA) and 30% ACN (0.1% FA) to 5% water (0.1% FA) and 95% ACN (0.1% FA) in 2.6 min]: Rt=0.757 min; MS Calcd.: 233, MS Found: 234 [M+H]⁺.

Description 214

Cis-6-(3-fluoro-1-(tetrahydrofuran-3-yl)piperidin-4-yl)-5-methyl-1H-indazole) (from Peak 2) (D214)

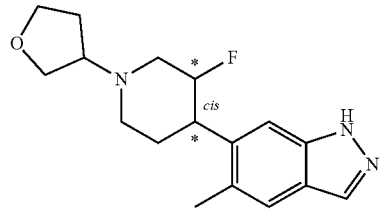 [SMILES: Cc1cc2cn[nH]c2cc1C1CCN(C2CCOC2)CC1F]

To a stirred mixture of cis-6-(3-fluoropiperidin-4-yl)-5-methyl-1H-indazole (from Peak 2) (140 mg, 0.6 mmol), dihydrofuran-3(2H)-one (103 mg, 1.2 mmol), 4 Å molecular sieves (50 mg) in MeOH/CH₂Cl₂ (2 mL/5 mL) at 0° C. were added HOAc (11 mg, 0.18 mmol) and NaBH₃CN (75 mg, 1.2 mmol). The reaction was warmed to room temperature and stirred overnight. TLC showed the reaction was complete. The reaction mixture was filtered and the filtrate was washed with aqueous NaHCO₃ (10 mL), dried, filtered. The filtrate was concentrated and the residue was purified by column chromatography (eluent: CH₂Cl₂, followed by CH₂Cl₂:MeOH=20:1) afforded desired product as a white solid (155 mg, yield: 86%).

LC-MS [mobile phase: from 80% water (0.1% FA) and 20% ACN (0.1% FA) to 5% water (0.1% FA) and 95% ACN (0.1% FA) in 2.0 min]: Rt=0.796 min; MS Calcd: 303; MS Found: 304 [M+H]⁺.

Description 215

Cis-tert-butyl 4-(5-methyl-1-(tetrahydro-2H-pyran-2-yl)-1H-indazol-6-yl)-3-((4-nitrobenzoyl)oxy)piperidine-1-carboxylate

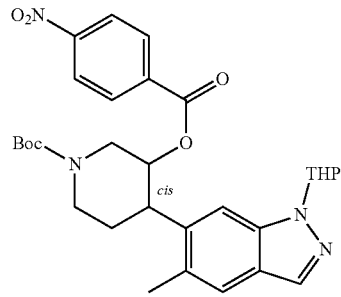

To a solution of trans tert-butyl 3-hydroxy-4-(5-methyl-1-(tetrahydro-2H-pyran-2-yl)-1H-indazol-6-yl)piperidine-1-carboxylate (2.50 g, 6.02 mmol), p-nitrobenzoic acid (1.51 g, 9.03 mmol) in THF (25 mL) was added PPh₃ (2.37 g, 9.03 mmol) and diisopropyl azodicarboxylate (1.82 g, 9.03 mmol) at 0° C. The reaction mixture was then stirred at room temperature overnight, concentrated and purified by silica gel chromatography column (Petroleum ether/EtOAc=5/1) to give the title product (1.50 g, yield 44.0%) as a light yellow solid.

LCMS [column: C₁₈; column size: 4.6×30 mm 5 μm; Dikwa Diamonsil plus; mobile phase: B (MeCN): A (0.02% NH₄OAc+ 5% MeCN); gradient (B %) in 4 min-05-95-POS; flow rate: 1.5 mL/min]: Rt=2.641 min; MS Calcd.: 564, MS Found: 565 [M+H]⁺.

Description 216

Cis-tert-butyl 3-hydroxy-4-(5-methyl-1-(tetrahydro-2H-pyran-2-yl)-1H-indazol-6-yl)piperidine-1-carboxylate

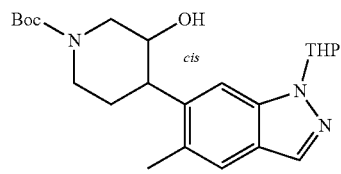

To a solution of Cis-tert-butyl 4-(5-methyl-1-(tetrahydro-2H-pyran-2-yl)-1H-indazol-6-yl)-3-((4-nitrobenzoyl)oxy) piperidine-1-carboxylate (1.50 g, 2.66 mmol) in MeOH (15 mL) was added K2CO₃ (550 mg, 3.99 mmol). The reaction mixture was then stirred at room temperature for 3 hours. The reaction mixture was diluted with EtOAc (100 mL), washed with saturated NaHCO₃ (30 mL), dried over Na₂SO₄, concentrated and the residue was purified by silica gel chromatography column (Petroleum ether/EtOAc=1/1) to give the title compound (1.05 g, yield 95%) as a white solid.

$^1$H NMR (400 MHz, CDCl$_3$): δ 7.92 (s, 1H), 7.52 (s, 1H), 7.46 (s, 1H), 6.36 (br, 1H), 5.77-5.68 (m, 1H), 5.00-4.94 (m, 1H), 4.45-4.31 (m, 2H), 4.08-4.03 (m, 1H), 3.96-3.89 (m, 1H), 3.77 (t, J=12.4 Hz, 1H), 3.17 (d, J=12.8 Hz, 1H), 3.07-3.01 (m, 1H), 2.94-2.85 (m, 1H), 2.64-2.55 (m, 1H), 2.48-2.38 (m, 1H), 2.43 (s, 3H), 2.18-2.10 (m, 1H), 2.06-2.02 (m, 1H), 1.82-1.75 (m, 3H), 1.51 (s, 9H).

Description 217

Cis-4-(5-methyl-1H-indazol-6-yl)piperidin-3-ol Hydrochloride

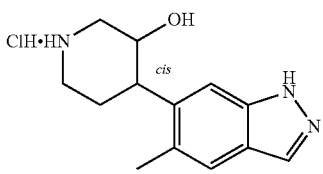

To a solution of cis-tert-butyl 3-hydroxy-4-(5-methyl-1-(tetrahydro-2H-pyran-2-yl)-1H-indazol-6-yl)piperidine-1-carboxylate (1.05 g, 2.53 mmol) in MeOH (5.0 mL) was added HCl/1,4-dioxane (10 mL, 6 M). The reaction mixture was stirred at room temperature for 18 hrs and concentrated to give the crude product (1.0 g) as a white solid, which was used directly for next step.

LCMS [column: O$_{18}$; column size: 4.6×30 mm 5 μm; Dikwa Diamonsil plus; mobile phase: B (MeCN): A (0.02% NH4OAc+ 5% MeCN in water); gradient (B %) in 4 min-05-95-POS; flow rate: 1.5 mL/min]: Rt=1.447 min; MS Calcd.: 231, MS Found: 232 [M+H]$^+$.

Description 218

Cis-tert-butyl 3-hydroxy-4-(5-methyl-1H-indazol-6-yl)piperidine-1-carboxylate

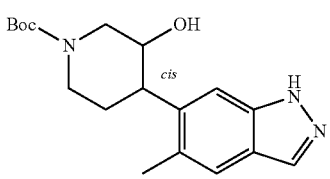 [SMILES: Cc1cc2cn[nH]c2cc1C1CCN(C(=O)OC(C)(C)C)CC1O]

To a solution of crude cis-4-(5-methyl-1H-indazol-6-yl)piperidin-3-ol hydrochloride (1.0 g, 2.53 mmol) in MeOH (16 mL) at 0° C. was added KOH (8.3 mL, 8.3 mmol, 1M in H$_2$O) and Boc$_2$O (724 mg, 3.32 mmol). The reaction mixture was stirred at room temperature for 30 hrs, diluted with H$_2$O (50 mL), extracted with EtOAc (50 mL×2). The organic layer was washed with brine (50 mL), dried over Na$_2$SO$_4$, concentrated. The residue was purified by silica gel chromatography column (Petroleum ether/EtOAc=1/1) to give the product (300 mg, 36%) as a white solid.

1H NMR (400 MHz, CDCl$_3$): δ 7.95 (s, 1H), 7.55 (s, 1H), 7.45 (s, 1H), 4.36-4.29 (m, 2H), 3.91 (br, 1H), 3.17-3.12 (m, 1H), 3.07-3.01 (m, 1H), 2.44 (s, 3H), 2.40-2.32 (m, 1H), 1.61-1.57 (m, 2H), 1.50 (s, 9H).

Description 219

Cis-tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-hydroxypiperidine-1-carboxylate

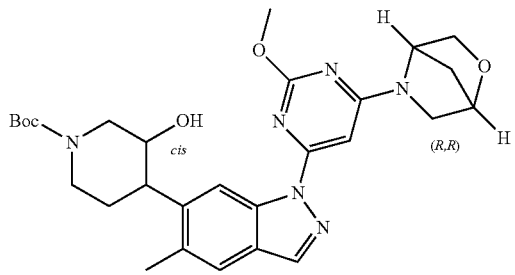

A mixture of cis-tert-butyl 3-hydroxy-4-(5-methyl-1H-indazol-6-yl)piperidine-1-carboxylate (300 mg, 0.91 mmol), (1R,4R)-5-(6-iodo-2-methoxypyrimidin-4-yl)-2-oxa-5-azabicyclo[2.2.1]heptanes (519 mg, 1.56 mmol), N,N'-dimethylcyclohexane-1,2-diamine (182 mg, 1.30 mmol), CuI (123 mg, 0.650 mmol) and K$_3$PO$_4$ (551 mg, 2.60 mmol) in toluene (5 mL) was stirred at 100° C. for 2 hrs, diluted with EtOAc (100 mL), washed with NH$_3$.H$_2$O (20 mL×2), brine (20 mL), dried over Na$_2$SO$_4$, and concentrated. The residue was purified by silica gel chromatography column (Petroleum ether/EtOAc=1/1) to give the title compound (300 mg, 62%) as a white solid.

$^1$H NMR (400 MHz, CDCl$_3$): δ 8.85 (s, 1H), 8.00 (s, 1H), 7.55 (s, 1H), 6.54 (br, 1H), 5.11 (s, 1H), 4.74 (s, 1H), 4.39-4.27 (m, 2H), 4.13 (s, 3H), 3.94-3.88 (m, 3H), 3.75-3.67 (m, 1H), 3.56-3.47 (m, 2H), 3.23-3.18 (m, 1H), 3.08-3.02 (m, 1H), 2.94-2.86 (m, 1H), 2.46 (s, 3H), 2.44-2.35 (m, 1H), 2.02-1.91 (m, 3H), 1.51 (s, 9H).

Description 220

Cis-4-(1-(6-((1R,4R)-2-oxa-5-azabicyclo[2.2.1]heptan-5-yl)-2-methoxypyrimidin-4-yl)-5-methyl-1H-indazol-6-yl)piperidin-3-ol

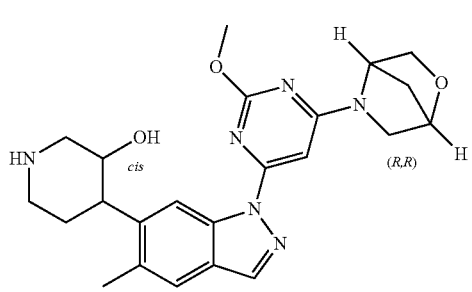

To a solution of cis-tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-hydroxypiperidine-1-carboxylate (300 mg, 0.56 mmol) in DCM (2 mL) was added TFA (2 mL). The reaction mixture was stirred at room temperature for 2 hrs, diluted with DCM (50 mL), basified with saturated Na$_2$CO$_3$ (30 mL) to adjust pH=9, extracted with DCM (50 mL×2). The combined organic layers were washed with brine (30 mL), dried over Na₂SO₄ and concentrated to give the title product (200 mg, 82%) as a white solid.

1H NMR (400 MHz, CDCl3): δ 8.83 (s, 1H), 8.06 (s, 1H), 7.54 (s, 1H), 6.54 (br, 1H), 5.26 (br, 1H), 4.74 (s, 1H), 4.13 (s, 3H), 3.94-3.86 (m, 4H), 3.56-3.49 (m, 1H), 3.46-3.42 (m, 1H), 3.29-3.17 (m, 3H), 3.00-2.92 (m, 1H), 2.85-2.80 (m, 1H), 2.46 (s, 3H), 2.34-2.27 (m, 1H), 2.04-1.92 (m, 3H).

Description 221

3-trans-4-(5-methyl-1H-indazol-6-yl)piperidin-3-ol

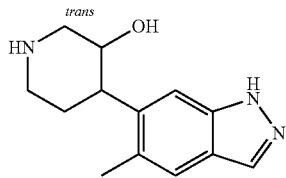 [SMILES: Cc1cc2cn[nH]c2cc1C1CCNCC1O]

To a solution of 3-trans-tert-butyl 3-hydroxy-4-(5-methyl-1-(tetrahydro-2H-pyran-2-yl)-1H-indazol-6-yl)piperidine-1-carboxylate (1.00 g, 2.41 mmol) in MeOH (5.0 mL) was added HCl/1,4-dioxane (10 mL, 6 M). The reaction mixture was stirred at room temperature overnight, concentrated, dissolved in MeOH (50 mL) and treated with Amberlyst (R) A21 (3.0 g). The resulting mixture was stirred at room temperature for 2 hrs and filtered. The filtrate was concentrated to afford the title product (510 mg, 67.0%) as a white solid.

LCMS [column: O₁₈; column size: 4.6×30 mm 5 μm; Dikwa Diamonsil plus; mobile phase: B (MeCN): A1 (0.02% NH4OAc+ 5% MeCN); gradient (B %) in 4 min-05-95-POS; flow rate: 1.5 mL/min]: Rt=1.321 min; MS Calcd.: 231, MS Found: 232 [M+H]⁺.

Description 222

3-trans-(1R,4R)-4-(1-(6-(2-oxa-5-azabicyclo[2.2.1]heptan-5-yl)-2-methoxypyrimidin-4-yl)-5-methyl-1H-indazol-6-yl)piperidin-3-ol

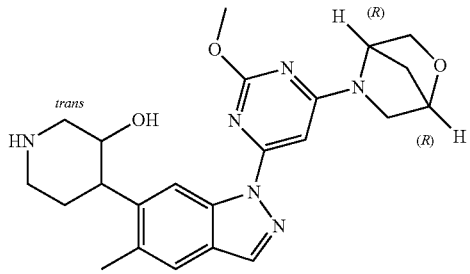

A mixture of 3-trans-4-(5-methyl-1H-indazol-6-yl)piperidin-3-ol (400 mg, 1.73 mmol), (1R,4R)-5-(6-iodo-2-methoxypyrimidin-4-yl)-2-oxa-5-azabicyclo[2.2.1]heptane (577 mg, 1.73 mmol), N,N'-dimethylcyclohexane-1,2-diamine (242 mg, 1.73 mmol), CuI (165 mg, 0.87 mmol) and K₃PO₄ (733 mg, 3.46 mmol) in toluene (10 mL) and DMSO (4 mL) was stirred at 100° C. for 3 hrs, diluted with EtOAc (100 mL), washed with NH₃H₂O (30 mL×2), brine (30 mL), dried over Na₂SO₄ and concentrated. The residue was purified by silica gel chromatography column (DCM/MeOH=10/1) to give the title compound (180 mg, 24.0%) as a white solid.

LCMS [column: C₁₈; column size: 4.6×30 mm 5 μm; Dikwa Diamonsil plus; mobile phase: B (MeCN): A1 (0.02% NH₄OAc+ 5% MeCN); gradient (B %) in 4 min-05-95-POS; flow rate: 1.5 mL/min]: Rt=1.836 min; MS Calcd.: 436, MS Found: 437 [M+H]⁺.

Description 223

Cis-tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-hydroxypiperidine-1-carboxylate

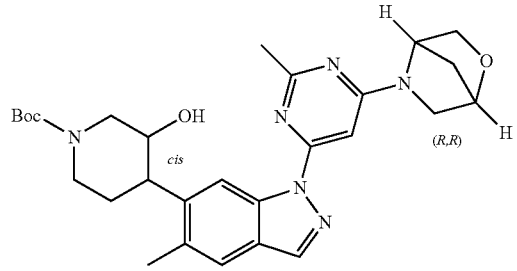

A mixture of cis-tert-butyl 3-hydroxy-4-(5-methyl-1H-indazol-6-yl)piperidine-1-carboxylate (1.67 g, 5.05 mmol), (1R,4R)-5-(6-iodo-2-methylpyrimidin-4-yl)-2-oxa-5-azabicyclo[2.2.1]heptane (1.60 g, 5.05 mmol), N,N'-dimethylcyclohexane-1,2-diamine (141 mg, 1.01 mmol), CuI (97.0 mg, 0.510 mmol) and K₃PO₄ (2.14 g, 10.1 mmol) in toluene (15 mL) was stirred at 100° C. for 4 hrs, then diluted with EtOAc (200 mL), washed with NH₃.H₂O (30 mL×2), brine (50 mL), dried over Na₂SO₄ and concentrated. The residue was purified by silica gel chromatography column (Petroleum ether/EtOAc=1/1) to give the title compound (2.40 g, 91.0%) as a white solid.

¹H NMR (400 MHz, CDCl₃): δ 8.87 (s, 1H), 8.04 (d, J=7.2 Hz, 1H), 7.53 (s, 1H), 6.64 (br, 1H), 5.31 (s, 1H), 4.74 (s, 1H), 4.43-4.33 (m, 2H), 3.96-3.88 (m, 3H), 3.64-3.42 (m, 2H), 3.18 (d, J=10.4 Hz, 1H), 3.07 (d, J=12.0 Hz, 1H), 2.94-2.88 (m, 1H), 2.59 (s, 3H), 2.54-2.40 (m, 1H), 2.46 (s, 3H), 2.00-1.95 (m, 2H), 1.84-1.78 (m, 1H), 1.73-1.62 (m, 1H), 1.51 (s, 9H).

Description 224

Cis-4-(1-(6-((1R,4R)-2-oxa-5-azabicyclo[2.2.1]heptan-5-yl)-2-methylpyrimidin-4-yl)-5-methyl-1H-indazol-6-yl)piperidin-3-ol

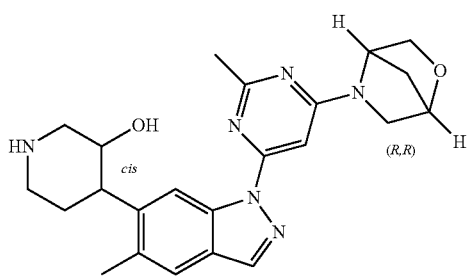

To a solution of cis-tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-hydroxypiperidine-1-carboxylate (2.40 g, 4.62 mmol) in DCM (10 mL) at 0° C. was added TFA (10 mL). The reaction mixture was stirred at room temperature for 2 hrs, poured into saturated NaHCO₃ (100 mL) at 0° C., extracted with DCM (100 mL×3). The organic layer was washed with brine (100 mL), dried over Na₂SO₄ and concentrated to give the title product (1.80 g, 93.0%) as a yellow solid.

¹H NMR (400 MHz, CDCl₃): δ 8.90 (s, 1H), 8.06 (s, 1H), 7.53 (s, 1H), 6.64 (br, 1H), 5.31 (s, 1H), 4.74 (s, 1H), 3.92-3.84 (m, 3H), 3.69-3.48 (m, 2H), 3.31-3.18 (m, 3H), 2.95 (d, J=12.8 Hz, 1H), 2.86-2.80 (m, 1H), 2.61 (s, 3H), 2.45-2.37 (m, 1H), 2.43 (s, 3H), 2.01-1.96 (m, 3H), 1.67-1.64 (m, 1H).

Description D225

Cis-tert-butyl 4-(1-(6-((1S,4S)-2-oxa-5-azabicyclo[2.2.1]heptan-5-yl)-2-methyl-pyrimidin-4-yl)-5-methyl-1H-indazol-6-yl)-3-hydroxypiperidine-1-carboxylate (D225)

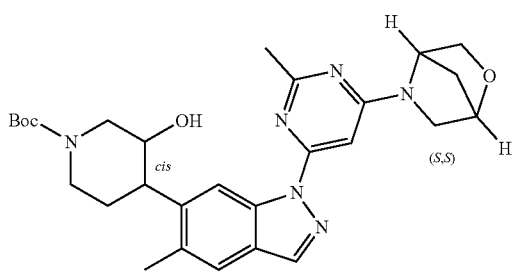 [SMILES: Cc1nc(N2CC3CC2CO3)cc(-n2ncc3cc(C)c(C4CCN(C(=O)OC(C)(C)C)CC4O)cc32)n1]

A mixture of cis-tert-butyl 3-hydroxy-4-(5-methyl-1H-indazol-6-yl)piperidine-1-carboxylate (1.00 g, 3.02 mmol), (1S,4S)-5-(6-iodo-2-methylpyrimidin-4-yl)-2-oxa-5-azabicyclo[2.2.1]heptane (1.05 g, 3.32 mmol), N,N'-dimethylcyclohexane-1,2-diamine (84.0 mg, 0.600 mmol), CuI (57.0 mg, 0.300 mmol) and K₃PO₄ (1.28 g, 6.04 mmol) in toluene (10 mL) was stirred at 100° C. for 4 hours. The reaction mixture was diluted with EtOAc (200 mL), washed with NH₃H₂O (30 mL×2), brine (50 mL), dried over Na₂SO₄ and concentrated. The residue was purified by silica gel chromatography column (Petroleum ether/EtOAc=1/1) to give the title compound (1.20 g, 76.0%) as a white solid.

¹H NMR (400 MHz, CDCl₃): δ 8.88 (s, 1H), 8.07 (s, 1H), 7.54 (s, 1H), 6.63 (br, 1H), 5.30 (s, 1H), 4.74 (s, 1H), 4.40-4.35 (m, 2H), 3.99-3.90 (m, 3H), 3.58-3.41 (m, 2H), 3.19 (d, J=10.8 Hz, 1H), 3.07 (d, J=14.4 Hz, 1H), 2.94-2.88 (m, 1H), 2.61 (s, 3H), 2.53-2.42 (m, 1H), 2.46 (s, 3H), 2.01-1.92 (m, 2H), 1.71-1.66 (m, 2H), 1.51 (s, 9H).

Description 226

Cis-4-(1-(6-((1S,4S)-2-oxa-5-azabicyclo[2.2.1]heptan-5-yl)-2-methylpyrimidin-4-yl)-5-methyl-1H-indazol-6-yl)piperidin-3-ol (D226)

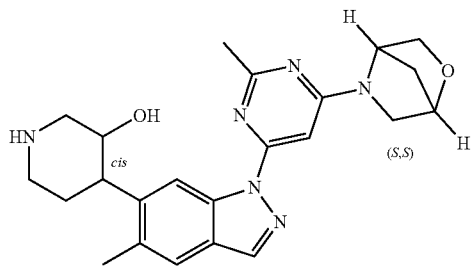 [SMILES: Cc1nc(N2CC3CC2CO3)cc(-n2ncc3cc(C)c(C4CCNCC4O)cc32)n1]

To a solution of cis-tert-butyl 4-(1-(6-((1S,4S)-2-oxa-5-azabicyclo[2.2.1]heptan-5-yl)-2-methylpyrimidin-4-yl)-5-methyl-1H-indazol-6-yl)-3-hydroxypiperidine-1-carboxylate (1.20 g, 2.31 mmol) in DCM (6 mL) at 0° C. was added TFA (6 mL). The reaction mixture was stirred at room temperature for 2 hours, poured into saturated NaHCO₃ (50 mL) at 0° C., extracted with DCM (50 mL×3). The combined organic layers were washed with brine (50 mL), dried over Na₂SO₄ and concentrated to give the product (950 mg, 98%) as a white solid.

¹H NMR (400 MHz, CDCl₃): δ 8.89 (s, 1H), 8.06 (s, 1H), 7.53 (s, 1H), 6.66 (br, 1H), 5.31 (s, 1H), 4.75 (s, 1H), 3.91-3.80 (m, 3H), 3.55-3.49 (m, 1H), 3.32-3.18 (m, 3H), 2.96 (d, J=10.0 Hz, 1H), 2.87-2.80 (m, 1H), 2.62 (s, 3H), 2.46 (s, 3H), 2.42-2.35 (m, 1H), 2.02-1.95 (m, 3H), 1.78-1.65 (m, 1H).

Description D227

(1R,4R)-2-oxa-5-azabicyclo[2.2.1]heptan-1-yl-methanol Hydrochloride (D227)

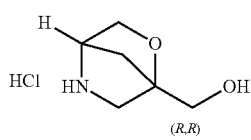

To a solution of (1R,4R)-tert-butyl 1-(hydroxymethyl)-2-oxa-5-azabicyclo[2.2.1]heptane-5-carboxylate (580 mg, 2.53 mmol) in MeOH (4 mL) was added HCl/MeOH (2 M, 2.5 mL).

The reaction mixture was stirred at room temperature for 4 hours, then concentrated to give the title product (418 mg, 100%) as a yellow oil.

¹H NMR (400 MHz, DMSO-d₆): δ 9.78 (s, 1H), 9.53 (s, 1H), 4.32 (s, 1H), 4.10-4.06 (m, 1H), 3.96 (br, 1H), 3.83-3.66 (m, 3H), 3.21-3.06 (m, 2H), 1.93-1.81 (m, 2H).

Description 228

((1R,4R)-5-(6-iodo-2-methylpyrimidin-4-yl)-2-oxa-5-azabicyclo[2.2.1]heptan-1-yl)methanol (D228)

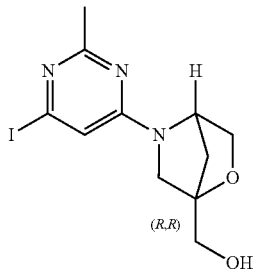 [SMILES: Cc1nc(I)cc(N2CC3(CO)CC2CO3)n1]

A mixture of 4,6-diiodo-2-methylpyrimidine (875 mg, 2.53 mmol), (1R,4R)-2-oxa-5-azabicyclo[2.2.1]heptan-1-yl-methanol hydrochloride (418 mg, 2.53 mmol) and K₂CO₃ (1.40 g, 10.1 mmol) in DMF (20 mL) was stirred at room temperature for 16 hours, then concentrated. The residue was purified by silica gel chromatography column (Petroleum ether/EtOAc=4/1 to DCM/MeOH=40/1) to give the title compound (610 mg, 69%) as a yellow oil.

¹H NMR (300 MHz, CDCl₃): δ 6.55 (br, 1H), 5.24 (br, 1H), 4.00-3.89 (m, 4H), 3.42-3.31 (m, 2H), 2.48 (s, 3H), 2.11-1.66 (m, 3H).

Description 229

Tert-butyl 4-(1-(6-((1R,4R)-1-(hydroxymethyl)-2-oxa-5-azabicyclo[2.2.1]heptan-5-yl)-2-methylpyrimidin-4-yl)-5-methyl-1H-indazol-6-yl)piperidine-1-carboxylate (D229)

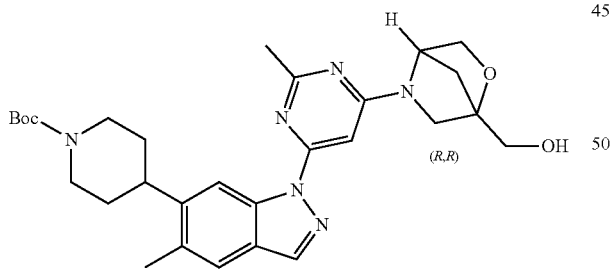

A mixture of ((1R,4R)-5-(6-iodo-2-methylpyrimidin-4-yl)-2-oxa-5-azabicyclo[2.2.1]heptan-1-yl)methanol (200 mg, 0.580 mmol), tert-butyl 4-(5-methyl-1H-indazol-6-yl)piperidine-1-carboxylate (183 mg, 0.580 mmol), N,N'-dimethylcyclohexane-1,2-diamine (82.0 mg, 0.580 mmol), CuI (55.0 mg, 0.290 mmol) and K₃PO₄ (246 mg, 1.16 mmol) in toluene (8 mL) was stirred at 100° C. for 4 hours. The reaction mixture was diluted with EtOAc (60 mL), washed with NH₃·H₂O (4 mL) and H₂O (10 mL), brine (20 mL). The organic phase was dried over Na₂SO₄ and concentrated. The residue was purified by silica gel chromatography column (DCM/MeOH=80/1 to DCM/MeOH=40/1) to give the title compound (220 mg, 71%) as a white solid.

¹H NMR (400 MHz, CDCl₃): δ 8.76 (s, 1H), 8.05 (s, 1H), 7.50 (s, 1H), 6.71 (br, 1H), 5.30 (br, 1H), 4.32-4.29 (m, 2H), 4.05-3.96 (m, 4H), 3.58-3.54 (m, 2H), 2.98-2.85 (m, 3H), 2.60 (s, 3H), 2.45 (s, 3H), 2.05-1.73 (m, 7H), 1.50 (s, 9H).

Description 230

((1R,4R)-5-(2-methyl-6-(5-methyl-6-(piperidin-4-yl)-1H-indazol-1-yl)pyrimidin-4-yl)-2-oxa-5-azabicyclo[2.2.1]heptan-1-yl)methanol (D230)

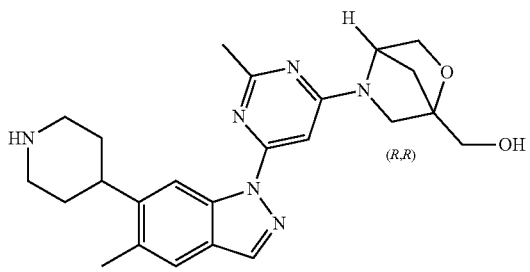 [SMILES: Cc1nc(N2CC3(CO)CC2CO3)cc(-n2ncc3cc(C)c(C4CCNCC4)cc32)n1]

To a solution of tert-butyl 4-(1-(6-((1R,4R)-1-(hydroxymethyl)-2-oxa-5-azabicyclo[2.2.1]heptan-5-yl)-2-methylpyrimidin-4-yl)-5-indazol-6-yl)piperidine-1-(220 mg, 0.410 mmol) in MeOH (2 mL) was added HCl/MeOH (2 M, 2 mL). The reaction mixture was stirred at room temperature for 2 hours, then concentrated. The residue was dissolved in DCM/MeOH=10/1 (20 mL) and H₂O (5 mL), adjusted to pH>7.0 with saturated NaHCO₃ and extracted with DCM/MeOH=10/1 (20 mL×5). The combined organic layers were concentrated to give the title product (178 mg, 100%) as a yellow solid.

¹H NMR (400 MHz, DMSO-d₆): δ 8.75 (s, 1H), 8.31 (s, 1H), 7.62 (s, 1H), 6.91-6.58 (m, 1H), 5.15-4.80 (m, 2H), 3.90 (d, J=6.8 Hz, 1H), 3.81-3.72 (m, 3H), 3.57 (d, J=10.0 Hz, 1H), 3.48-3.44 (m, 1H), 3.33-3.29 (m, 3H), 3.07-3.01 (m, 1H), 2.91-2.85 (m, 2H), 2.55 (s, 3H), 2.44 (s, 3H), 1.87-1.71 (m, 6H).

Description 231

(1S,4S)-2-oxa-5-azabicyclo[2.2.1]heptan-1-ylmethanol Hydrochloride (D231)

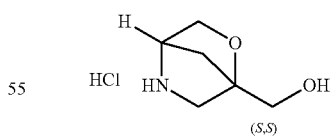

To a solution of (1S,4S)-tert-butyl 1-(hydroxymethyl)-2-oxa-5-azabicyclo[2.2.1]heptane-5-carboxylate (540 mg, 2.36 mmol) in MeOH (4 mL) was added HCl/MeOH (2 M, 2.5 mL). The reaction mixture was stirred at room temperature for 16 hours and concentrated to give the product (389 mg, 100%) as yellow oil.

¹H NMR (400 MHz, DMSO-d₆): δ 9.81 (s, 1H), 9.54 (s, 1H), 4.32 (s, 1H), 4.09-4.07 (m, 1H), 3.77-3.66 (m, 3H), 3.21-3.06 (m, 2H), 1.93-1.81 (m, 2H).

Description 232

((1S,4S)-5-(6-iodo-2-methylpyrimidin-4-yl)-2-oxa-5-azabicyclo[2.2.1]heptan-1-yl)methanol (D232)

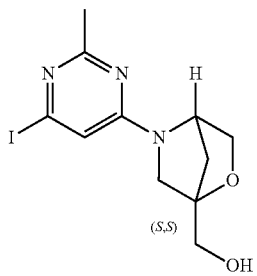 [SMILES: Cc1nc(I)cc(N2CC3(CO)CC2CO3)n1]

The title compound was prepared by a procedure similar to that described for D228 starting from a mixture of 4,6-diiodo-2-methylpyrimidine, (1S,4S)-2-oxa-5-azabicyclo[2.2.1]heptan-1-ylmethanol hydrochloride and $K_2CO_3$ in DMF at room temperature for 16 hours.

$^1$H NMR (300 MHz, CDCl$_3$): δ 6.55 (br, 1H), 5.24 (br, 1H), 4.00-3.89 (m, 4H), 3.42-3.31 (m, 2H), 2.48 (s, 3H), 2.11-1.66 (m, 3H).

Description 233

Tert-butyl 4-(1-(6-((1S,4S)-1-(hydroxymethyl)-2-oxa-5-azabicyclo[2.2.1]heptan-5-yl)-2-methylpyrimidin-4-yl)-5-methyl-1H-indazol-6-yl)piperidine-1-carboxylate (D233)

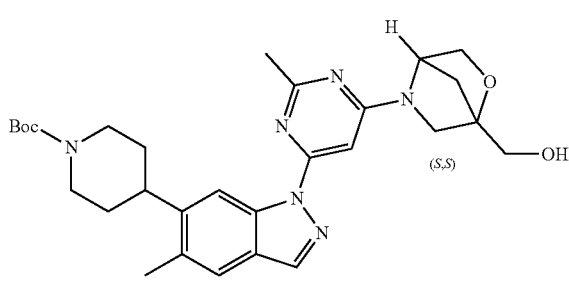 [SMILES: Cc1nc(N2CC3(CO)CC2CO3)cc(-n2ncc3cc(C)c(C4CCN(C(=O)OC(C)(C)C)CC4)cc32)n1]

The title compound was prepared by a procedure similar to that described for D229 starting from a mixture of ((1S,4S)-5-(6-iodo-2-methylpyrimidin-4-yl)-2-oxa-5-azabicyclo[2.2.1]heptan-1-yl)methanol, tert-butyl 4-(5-methyl-1H-indazol-6-yl)piperidine-1-carboxylate, N,N'-dimethylcyclohexane-1,2-diamine, CuI and $K_3PO_4$ in toluene at 100° C. for 4 hours.

$^1$H NMR (400 MHz, CDCl$_3$): δ 8.76 (s, 1H), 8.05 (s, 1H), 7.50 (s, 1H), 6.71 (br, 1H), 5.30 (br, 1H), 4.31-4.30 (m, 2H), 4.01-3.96 (m, 4H), 3.58-3.54 (m, 2H), 2.98-2.85 (m, 3H), 2.60 (s, 3H), 2.45 (s, 3H), 2.05-1.73 (m, 7H), 1.50 (s, 9H).

Description 234

((1S,4S)-5-(2-methyl-6-(5-methyl-6-(piperidin-4-yl)-1H-indazol-1-yl)pyrimidin-4-yl)-2-oxa-5-azabicyclo[2.2.1]heptan-1-yl)methanol (D234)

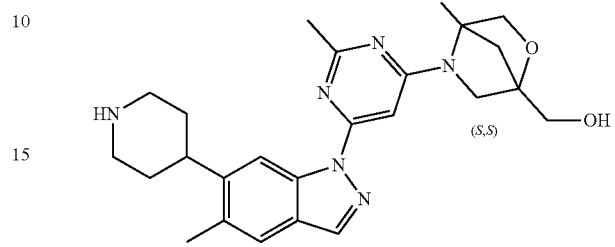

The title compound was prepared by a procedure similar to that described for D230 starting from a solution of tert-butyl 4-(1-(6-((1S,4S)-1-(hydroxymethyl)-2-oxa-5-azabicyclo[2.2.1]heptan-5-yl)-2-methylpyrimidin-4-yl)-5-methyl-1H-indazol-6-yl)piperidine-1-carboxylate in MeOH and HCl/MeOH (2 M) at room temperature for 4 hours.

$^1$H NMR (400 MHz, DMSO-d$_6$): δ 8.74 (s, 1H), 8.29 (s, 1H), 7.60 (s, 1H), 6.91-6.58 (m, 1H), 5.15-4.79 (m, 2H), 3.91-3.89 (m, 1H), 3.78-3.73 (m, 3H), 3.59-3.56 (m, 1H), 3.37-3.32 (m, 2H), 3.09-3.06 (m, 2H), 2.92-2.86 (m, 1H), 2.73-2.61 (m, 2H), 2.55 (s, 3H), 2.44 (s, 3H), 1.92-1.73 (m, 4H), 1.59-1.51 (m, 2H).

Description 235

Tert-butyl 4-(5-methyl-1-(tetrahydro-2H-pyran-2-yl)-1H-indazol-6-yl)-3-oxopiperid-ine-1-carboxylate (D235)

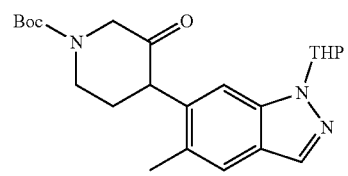

To a mixture of trans-tert-butyl 3-hydroxy-4-(5-methyl-1-(tetrahydro-2H-pyran-2-yl)-1H-indazol-6-yl)piperidine-1-carboxylate (4.9 g, 11.8 mmol) in DCM (100 mL) was added DMP (7.00 g, 16.5 mmol) in portions. The reaction mixture was stirred at 0° C. under $N_2$ for 30 minutes and then stirred at 20° C. for 24 hours, then cooled to 0° C. and treated with sat. NaHCO$_3$ (60 mL) and sat. Na$_2$SO$_3$ (60 mL). The mixture was stirred at 0° C. for 30 minutes and extracted with DCM (100 mL×2). The combined organic layers were washed with brine (100 mL), dried over Na$_2$SO$_4$ and concentrated in vacuo. The residue was purified by silica gel chromatography column (Petroleum ether/EtOAc=2/1) to give the title compound (2.53 g, 52%) as a white solid.

$^1$H NMR (400 MHz, CDCl$_3$): δ 7.93 (d, J=3.6 Hz, 1H), 7.54 (s, 1H), 7.27 (d, J=14.4 Hz, 1H), 5.68-5.65 (m, 1H), 4.36-4.29 (m, 1H), 4.15-4.09 (m, 1H), 4.01-3.88 (m, 2H), 3.75-3.70 (m, 1H), 3.56-3.51 (m, 1H), 2.55-2.53 (m, 1H), 2.36-2.31 (m, 5H), 2.16-2.13 (m, 1H), 2.06-2.01 (m, 1H), 1.77-1.66 (m, 2H), 1.60-1.55 (m, 2H), 1.49 (s, 9H).

Description 236

Tert-butyl 3-hydroxy-3-methyl-4-(5-methyl-1-(tetrahydro-2H-pyran-2-yl)-1H-indazol-6-yl)piperidine-1-carboxylate (D236)

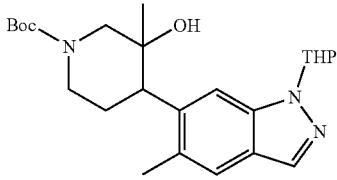

To a solution of tert-butyl 4-(5-methyl-1-(tetrahydro-2H-pyran-2-yl)-1H-indazol-6-yl)-3-oxopiperidine-1-carboxylate (1.00 g, 2.40 mmol) in THF (16 mL) was added dropwised methyl-magnesiumbromide (3M in diethyl ether, 3.2 mL, 9.6 mmol) at −25° C. under N₂. The reaction mixture was warmed to room temperature and stirred for 3 hours. The reaction mixture was cooled to 0° C., quenched with saturated NH₄Cl (15 mL) and extracted with EtOAc (60 mL×2). The combined organic layers were concentrated to give the product (950 mg, 91.0%) as a yellow oil.

LC-MS [column: C₁₈; column size: 4.6×50 mm; mobile phase: B (MeCN) A (0.02% NH4OAc); gradient (B %) in 4 min-05-95-POS]: Rt=2.370 min; MS Calcd.: 429, MS Found: 430 [M+H]⁺.

Description 237

3-methyl-4-(5-methyl-1H-indazol-6-yl)piperidin-3-ol Hydrochloride (D237)

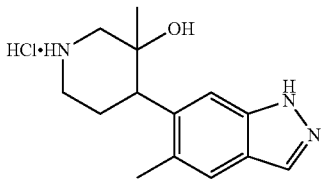

To a solution of tert-butyl 3-hydroxy-3-methyl-4-(5-methyl-1-(tetrahydro-2H-pyran-2-yl)-1H-indazol-6-yl)piperidine-1-carboxylate (950 mg, 2.21 mmol) in MeOH (10 mL) was added HCl/MeOH (2 M, 10 mL). The reaction mixture was stirred at room temperature for 16 hours and concentrated to give the title product (700 mg, 100%) as a brown oil.

LC-MS [column: C₁₈; column size: 4.6×50 mm; mobile phase: B (MeCN) A (0.02% NH₄OAc); gradient (B %) in 4 min-05-95-POS]: Rt=1.252 min; MS Calcd.: 245, MS Found: 246 [M+H]⁺; Rt=1.231 min and 1.382 min; MS Calcd.: 245, MS Found: 246 [M+H]⁺.

Description 238

Tert-butyl 3-hydroxy-3-methyl-4-(5-methyl-1H-indazol-6-yl)piperidine-1-carboxylate (D238)

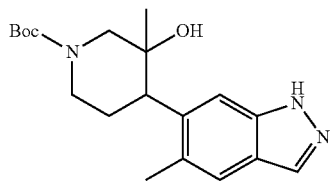 [SMILES: Cc1cc2cn[nH]c2cc1C1CCN(C(=O)OC(C)(C)C)CC1(C)O]

To a solution of 3-methyl-4-(5-methyl-1H-indazol-6-yl)piperidin-3-ol hydrochloride (700 mg, 2.21 mmol) in MeOH (10 mL) was added KOH (495 mg, 8.84 mmol) in H₂O (6 mL). After the reaction mixture was stirred at 0° C. for 10 minutes, Boc₂O (573 mg, 2.65 mmol) was added. The reaction mixture was stirred at room temperature for 6 hours, diluted with water (20 mL) and extracted with DCM (50 mL×2). The combined organic layers were concentrated in vacuo and purified by silica gel chromatography column (Petroleum ether/EtOAc=2/1 to 1/1) to give the title compound (200 mg, 26.0%) as a colorless oil.

LC-MS [column: C₁₈; column size: 4.6×50 mm; mobile phase: B (MeCN) A (0.02% NH₄OAc); gradient (B %) in 4 min-05-95-POS]: Rt=2.035 min; MS Calcd.: 345, MS Found: 290 [M+H−56]⁺; Rt=2.012 min and 2.140 min; MS Calcd.: 345, MS Found: 290 [M+H−56]⁺.

Description 239

Tert-butyl 4-(1-(6-(((1R,4R)-2-oxa-5-azabicyclo[2.2.1]heptan-5-yl)-2-methylpyrimid-in-4-yl)-5-methyl-1H-indazol-6-yl)-3-hydroxy-3-methylpiperidine-1-carboxylate (D239)

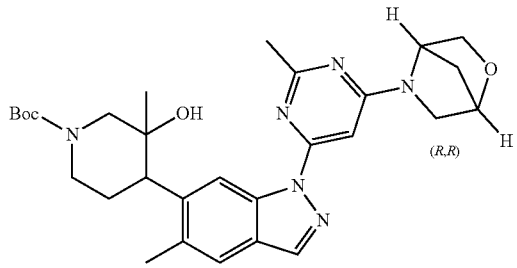 [SMILES: Cc1nc(N2CC3CC2CO3)cc(-n2ncc3cc(C)c(C4CCN(C(=O)OC(C)(C)C)CC4(C)O)cc32)n1]

The title compound was prepared by a procedure similar to that described for D229 starting from a mixture of tert-butyl 3-hydroxy-3-methyl-4-(5-methyl-1H-indazol-6-yl)piperidine-1-carboxylate, (1R,4R)-5-(6-iodo-2-methylpyrimidin-4-yl)-2-oxa-5-azabicyclo[2.2.1]hep-tane, CuI and K₃PO₄ in toluene at 100° C. under N₂ for 4 hours.

¹H NMR (400 MHz, CDCl₃): δ 9.14-8.83 (m, 1H), 8.07 (s, 1H), 7.51 (s, 1H), 6.63 (br, 1H), 5.30 (s, 1H), 4.74 (s, 1H), 4.32-4.09 (m, 2H), 3.87-3.85 (m, 2H), 3.52-3.32 (m, 2H), 2.98-2.84 (m, 2H), 2.57-2.27 (m, 7H), 2.06-1.91 (m, 3H), 1.61-1.59 (m, 2H), 1.51 (s, 9H), 1.30 (s, 1H), 1.05 (s, 2H).

Description 240

4-(1-(6-((1R,4R)-2-oxa-5-azabicyclo[2.2.1]heptan-5-yl)-2-methylpyrimidin-4-yl)-5-methyl-1H-indazol-6-yl)-3-methylpiperidin-3-ol (D240)

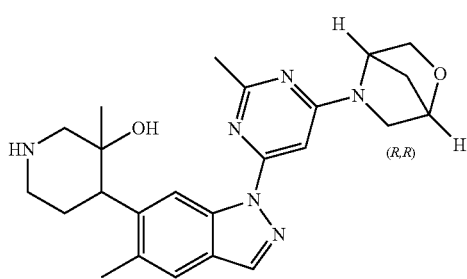

To a solution of tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-hydroxy-3-methylpiperidine-1-carboxylate (400 mg, 0.75 mmol) in MeOH (6 mL) was added HCl/MeOH (2 M, 8 mL). The reaction mixture was stirred at room temperature for 6 hour, concentrated, dissolved in DCM (60 mL), adjusted to pH>7 with saturated NaHCO$_3$. The aqueous was extracted with DCM (30 mL×2). The combined organic layers were concentrated to give the title product (320 mg, 100%) as a yellow solid.

$^1$H NMR (400 MHz, CDCl$_3$): 9.20-8.88 (m, 1H), 8.07-8.05 (m, 1H), 7.53-7.49 (m, 1H), 6.65 (br, 1H), 5.29 (s, 1H), 4.74 (s, 1H), 3.89 (s, 2H), 3.54-3.52 (m, 2H), 3.21-3.17 (m, 2H), 2.98-2.45 (m, 9H), 2.25-1.95 (m, 3H), 1.65-1.62 (m, 2H), 1.37 (s, 1H), 0.98 (s, 2H).

Description 241

2-oxa-5-azabicyclo[2.2.1]heptan-1-ylmethanol Trifluoroacetic Salts (D241)

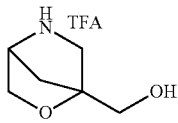

To a solution of tert-butyl 1-(hydroxymethyl)-2-oxa-5-azabicyclo[2.2.1]heptane-5-carboxylate (290 mg, 1.26 mmol) in CH$_2$Cl$_2$ (20 mL) was added TFA (1.44 g, 10.0 mmol) at rt. The reaction mixture was stirred at rt overnight and concentrated to give the crude product (492 mg) as a white solid.

LC-MS [mobile phase: from 50% water (0.1% FA) and 50% MeCN (0.1% FA) to 5% water (0.1% FA) and 95% MeCN (0.1% FA) in 2.6 min]: Rt=0.32 min; MS Calcd: 129.08, MS Found: 130.2 [M+H]$^+$.

Description 242

(5-(6-iodo-2-methylpyrimidin-4-yl)-2-oxa-5-azabicyclo[2.2.1]heptan-1-yl)methanol (D242)

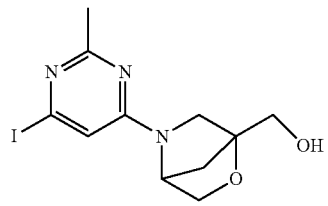 [SMILES: Cc1nc(I)cc(N2CC3(CO)CC2CO3)n1]

To a solution of 2-oxa-5-azabicyclo[2.2.1]heptan-1-ylmethanol trifluoroacetic salts (492 mg, 2.00 mmol) and 4,6-diiodo-2-methylpyrimidine (769 mg, 2.20 mmol) in DMF (20 mL) was added DIEA (1.05 g, 8.10 mmol) at rt. The reaction mixture was stirred at 50° C. for 6 h, diluted with water (50 mL) and extracted with EtOAc (3×200 mL). The combined organic layers were washed with water (3×150 mL) and brine (300 mL), dried over anhydrous Na$_2$SO$_4$, filtered and concentrated to give a residue. The residue was purified by silica gel column chromatography (PE:EtOAc=1:1) to give title product (350 mg, yield 50%) as pale yellow oil.

LC-MS [mobile phase: from 50% water (0.1% FA) and 50% MeCN (0.1% FA) to 5% water (0.1% FA) and 95% MeCN (0.1% FA) in 2.0 min]: Rt=0.28 min; MS Calcd: 347.01, MS Found: 348.2 [M+H]$^+$.

Description 243

Tert-butyl 4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (D243)

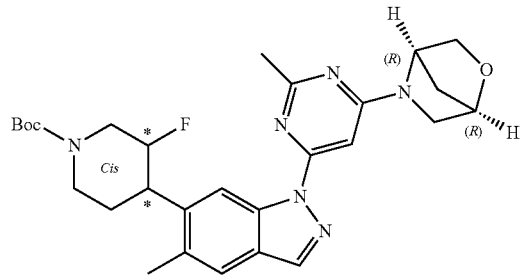

To a suspension of cis-tert-butyl 3-fluoro-4-(5-methyl-1H-indazol-6-yl)piperidine-1-carboxylate (D30, Peak 1, 100 mg, 0.300 mmol), (1R,4R)-5-(6-iodo-2-methylpyrimidin-4-yl)-2-oxa-5-azabicyclo[2.2.1]heptane (95.0 mg, 0.300 mmol), CuI (57.0 mg, 0.300 mmol), K$_3$PO$_4$ (127 mg, 0.6 mmol) in toluene (10 mL) was added DMEDA (53.0 mg, 0.600 mmol). The resulting mixture was degassed, then stirred at 90° C. for 2 h, poured into water (100 ml) and extracted with EtOAc (100 mL×2). The combined organic phase was washed with brine (100 mL), dried and concentrated. The residue was purified by SGC (PE→PE:EtOAc=10:1) to give the product as a white solid (117 mg, yield: 75%).

LC-MS [mobile phase: from 80% water (0.1% FA) and 20% MeCN (0.1% FA) to 5% water (0.1% FA) and 95% MeCN (0.1% FA) in 2.6 min]: Rt=1.927 min; MS Calcd.: 522, MS Found: 523.3 [M+H]⁺.

Description 244

(1R,4R)-5-(6-(6-(3-fluoropiperidin-4-yl)-5-methyl-1H-indazol-1-yl)-2-methylpyrimi-din-4-yl)-2-oxa-5-azabicyclo[2.2.1]heptane (D244)

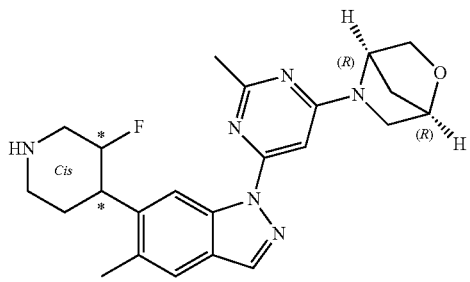

To a solution of tert-butyl cis-4-(1-(6-(((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (1, 117 mg, 0.22 mmol) in EtOAc (3 mL) was added HCl/EtOAc (3 N, 2 mL). The reaction mixture was stirred at rt for 0.5 hours, concentrated, diluted in DCM (100 mL), washed with aq. NaHCO₃ (100 mL) and brine (100 mL), dried over Na₂SO₄, filtered and concentrated to give the product as a white solid (100 mg, >100% yield). The crude solid was directly used into next step.

Description 245

Methyl 3-(4-(1-(6-(((1R,4R)-2-oxa-5-azabicyclo[2.2.1]heptan-5-yl)-2-methylpyrimi-din-4-yl)-5-methyl-1H-indazol-6-yl)-3-fluoropiperidin-1-yl)propanoate (D245)

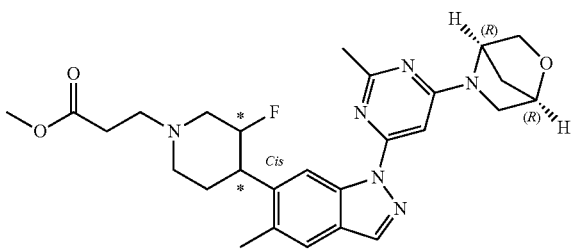

A mixture of (1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane (D244, 100 mg, 0.240 mmol) and methyl acrylate (41.0 mg, 0.480 mmol) in MeOH (5 mL) was stirred at 70° C. for 2 h and concentrated. The residue was purified by SGC (DCM→DCM:MeOH=30:1) to give the product as a white solid (100 mg, yield: 83%).

LC-MS [mobile phase: from 80% water (0.1% FA) and 20% MeCN (0.1% FA) to 5% water (0.1% FA) and 95% MeCN (0.1% FA) in 2.6 min]: Rt=0.950 min; MS Calcd.: 508, MS Found: 509.3 [M+H]⁺.

Description 246

Methyl 3-(4-(1-(6-(((1R,4R)-2-oxa-5-azabicyclo[2.2.1]heptan-5-yl)-2-methylpyrimid-in-4-yl)-5-methyl-1H-indazol-6-yl)-3-fluoropiperidin-1-yl)propanoate (D246)

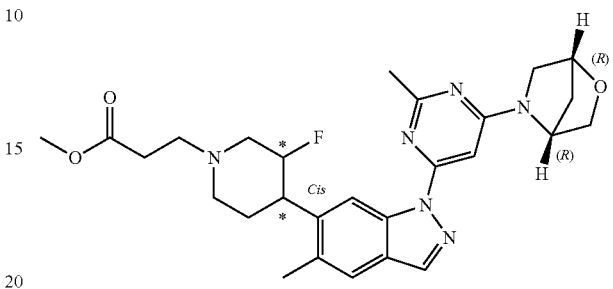

To a solution of cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptanes hydrochloride (D31, from Peak 2, 115 mg, 0.27.0 mmol) in MeOH (10 mL) was added methyl acrylate (0.5 mL). The resulting mixture was refluxed for 2 h, then concentrated. The residue was purified by prep-TLC(CH₂Cl₂:MeOH=20:1) to give product (125 mg, yield: 90%) as a white solid.

LC-MS [mobile phase: from 80% water (0.1% FA) and 20% MeCN (0.1% FA) to 5% water (0.1% FA) and 95% MeCN (0.1% FA) in 2.0 min]: Rt=1.08 min; MS Calcd.: 508.3, MS Found: 509.4 [M+H]⁺.

Description 247

Cis-tert-butyl 4-(1-(6-(((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (D247)

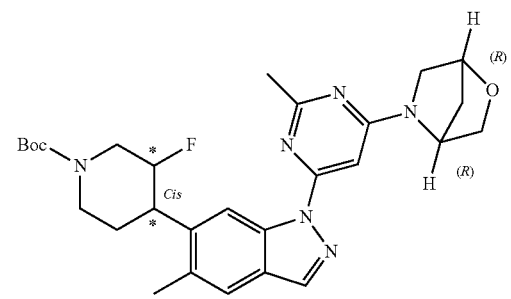

A mixture of cis-tert-butyl 3-fluoro-4-(5-methyl-1H-indazol-6-yl)piperidine-1-carboxylate (50 mg, 0.15 mmol), (1R,4R)-5-(6-iodo-2-methylpyrimidin-4-yl)-2-oxa-5-azabicyclo[2.2.1]heptane (70 mg, 0.22 mmol), CuI (10 mg), K₃PO₄ (212 mg, 1.0 mmol) in toluene/THF (10 mL) was degassed before DMEDA (10 mg) was added. The reaction mixture was stirred at 90° C. for 1 h, then concentrated. The residue was purified by silica gel chromatography eluted with (EtOAc:Petroleum Ether=1:3) to give the product as a white solid (85 mg).

Description 248

Cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hydrochloride (D248)

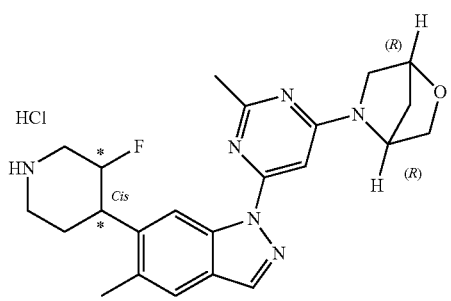

A solution of cis-(tert-butyl 4-(1-(6-(((1R,4R)-2-oxa-5-azabicyclo[2.2.1]heptan-5-yl)-2-methylpyrimidin-4-yl)-5-methyl-1H-indazol-6-yl)-3-fluoropiperidine-1-carboxylate (85 mg, 0.15 mmol) in HCl/EtOAc (5 mL, 1 N) was stirred at rt for 4 hours, then concentrated to give the product as an off-white solid (65 mg).

Description 249

Cis-tert-butyl 4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (D249)

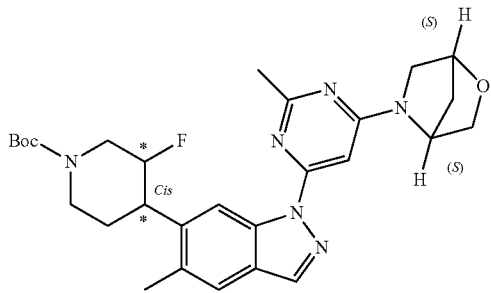

The title compound was prepared by a procedure similar to that described for D229 starting from a mixture of cis-tert-butyl 3-fluoro-4-(5-methyl-1H-indazol-6-yl)piperidine-1-carboxylate (D30), (1S,4S)-5-(6-iodo-2-methylpyrimidin-4-yl)-2-oxa-5-azabicyclo[2.2.1]-heptane, K$_3$PO$_4$ in toluene/THF (5 mL/1 mL), DMEDA at 80° C. for 3 hour.

LC-MS [mobile phase: from 90% water (0.1% FA) and 10% MeCN (0.1% TFA) to 5% water (0.1% FA) and 95% MeCN (0.1% FA) in 9.0 min]: Rt=6.67 min; MS Calcd.: 522, MS Found: 523 [M+H]$^+$.

Description 250

Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hydrochloride (D250)

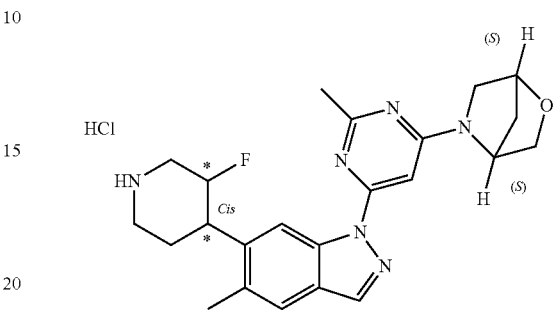

The title compound was prepared by a procedure similar to that described for D230 starting from a solution of cis-(tert-butyl-4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate in EtOAc (4 mL) and HCl/EtOAc (3 N) at rt for 60 min.

LC-MS [mobile phase: from 90% water (0.1% FA) and 10% MeCN (0.1% FA) to 5% water (0.1% FA) and 95% MeCN (0.1% FA) in 2.0 min]: Rt=1.11 min; MS Calcd.: 422, MS Found: 423. [M+H]$^+$.

Description 251

Methyl 3-(4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)propanoate (D251)

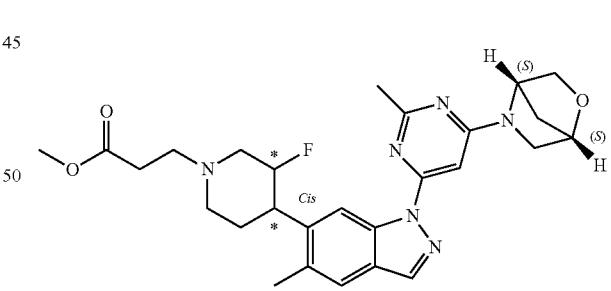

A mixture of (1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane (D250, 100 mg, 0.24 mmol) and methyl acrylate (41 mg, 0.48 mmol) in MeOH (5 mL) was stirred at 70° C. for 2 h and concentrated. The residue was purified by SGC (DCM→DCM:MeOH=30:1) to give the product as a white solid (100 mg, yield: 83%).

LC-MS [mobile phase: from 80% water (0.1% FA) and 20% MeCN (0.1% FA) to 5% water (0.1% FA) and 95% MeCN (0.1% FA) in 2.6 min]: Rt=0.948 min; MS Calcd.: 508, MS Found: 509.3 [M+H]$^+$.

Description 252

Cis-tert-butyl 4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (D252)

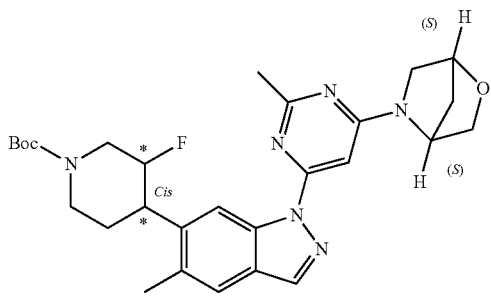

The title compound was prepared by a procedure similar to that described for D229 starting from a mixture of cis-tert-butyl 3-fluoro-4-(5-methyl-1H-indazol-6-yl)piperidine-1-carboxylate (D30), (1S,4S)-5-(6-iodo-2-methylpyrimidin-4-yl)-2-oxa-5-azabicyclo[2.2.1]-heptane, CuI and $K_3PO_4$ in toluene/THF and DMEDA at 80° C. for 3 hour.

LC-MS [mobile phase: from 90% water (0.1% FA) and 10% MeCN (0.1% FA) to 5% water (0.1% FA) and 95% MeCN (0.1% FA) in 2.0 min]: Rt=1.62 min; MS Calcd.: 522, MS Found: 523 $[M+H]^+$.

Description 252

Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane Hydrochloride (D252)

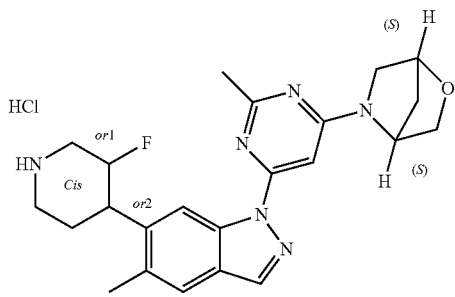

The title compound was prepared by a procedure similar to that described for D230 starting from a solution of cis-(tert-butyl-4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (D251) in EtOAc and HCl/EtOAc (3 N) at rt for 60 min.

LC-MS [mobile phase: from 90% water (0.1% FA) and 10% MeCN (0.1% FA) to 5% water (0.1% FA) and 95% MeCN (0.1% FA) in 2.0 min]: Rt=0.91 min; MS Calcd.: 422, MS Found: 423 $[M+H]^+$.

Description 253

Methyl 3-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)propanoate (D253)

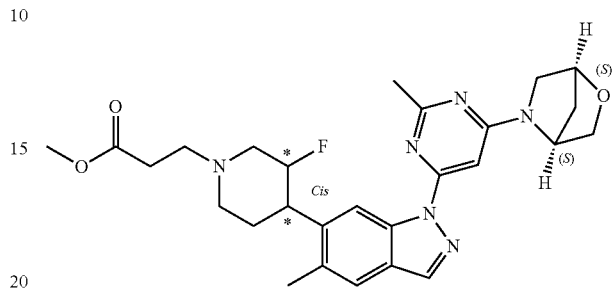

The title compound was prepared by a procedure similar to that described for D251 starting from a solution of cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptanes hydrochloride (D252) in MeOH and methyl acrylate at refluxed for 2 h.

LC-MS [mobile phase: from 80% water (0.1% FA) and 20% MeCN (0.1% FA) to 5% water (0.1% FA) and 95% MeCN (0.1% FA) in 2.0 min]: Rt=1.09 min; MS Calcd.: 508.3, MS Found: 509.4 $[M+H]^+$.

Description 254

Tert-butyl 4-(1-(6-((1R,4R)-2-oxa-5-azabicyclo[2.2.1]heptan-5-yl)-2-methoxypyrim-idin-4-yl)-5-methyl-1H-indazol-6-yl)-3-fluoropiperidine-1-carboxylate (D254)

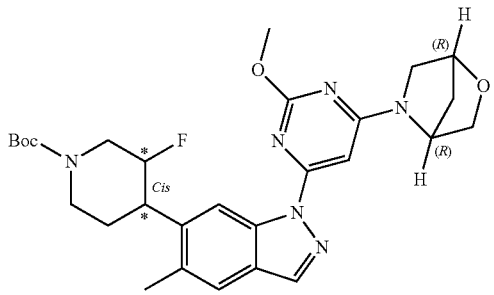

The title compound was prepared by a procedure similar to that described for D229 starting from a mixture of tert-butyl 3-fluoro-4-(5-methyl-1H-indazol-6-yl)piperidine-1-carboxylate (D30, Peak 1) and (1R,4R)-5-(6-iodo-2-methoxypyrimid in-4-yl)-2-oxa-5-azabicyclo[2.2.1]heptane in toluene/THF and $N^1,N^2$-dimethylethane-1,2-diamine, CuI and $K_3PO_4$ at 90° C. for 2 hours under $N_2$.

LC-MS [mobile phase: 40% water (0.1% FA) and 60% MeCN (0.1% FA) to 5% water (0.1% FA) and 95% MeCN (0.1% FA) in 2.0 min]: Rt=1.71 min; MS Calcd.: 538, MS Found: 539 $[M+H]^+$.

Description 255

(1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane HCl Salt (D255)

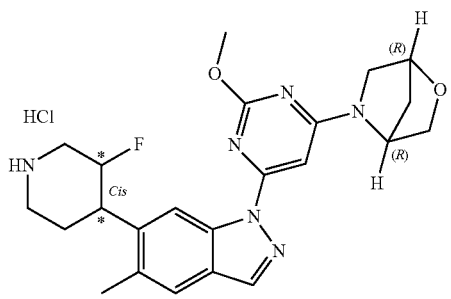

The title compound was prepared by a procedure similar to that described for D230 starting from a solution of tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidine-1-carboxylate (D254) in EtOAc and HCl.EtOAc.

LC-MS [mobile phase: 70% water (0.1% FA) and 30% MeCN (0.1% FA) to 5% water (0.1% FA) and 95% MeCN (0.1% FA) in 2.0 min]: Rt=0.67 min; MS Calcd.: 438, MS Found: 439 [M+H]$^+$.

Description 256

Methyl 3-(4-(1-(6-((1R,4R)-2-oxa-5-azabicyclo[2.2.1]heptan-5-yl)-2-methoxypyrimid-in-4-yl)-5-methyl-1H-indazol-6-yl)-3-fluoropiperidin-1-yl)propanoate (D256)

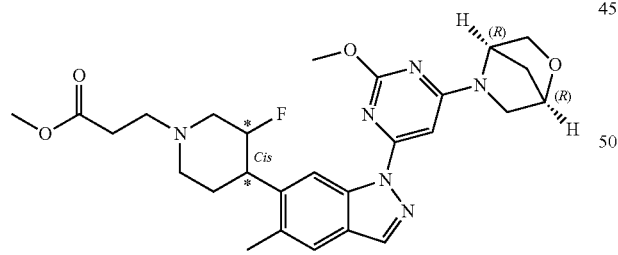

The title compound was prepared by a procedure similar to that described for D245 starting from a mixture of (1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (D255) and methyl acrylate in MeOH at 70° C. for 2 h.

LC-MS [mobile phase: from 80% water (0.1% FA) and 20% MeCN (0.1% FA) to 5% water (0.1% FA) and 95% MeCN (0.1% FA) in 2.6 min]: Rt=1.028 min; MS Calcd.: 524, MS Found: 525.3 [M+H]$^+$.

Description 257

Tert-butyl 4-(1-(6-((1R,4R)-2-oxa-5-azabicyclo[2.2.1]heptan-5-yl)-2-methoxypyrimi-din-4-yl)-5-methyl-1H-indazol-6-yl)-3-fluoropiperidine-1-carboxylate (D257)

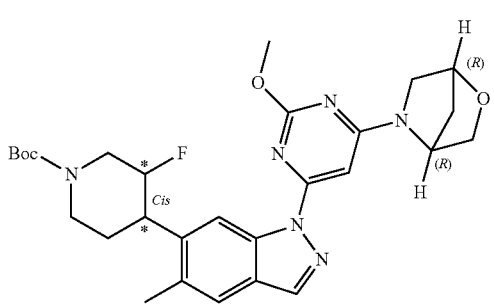

The title compound was prepared by a procedure similar to that described for D229 starting from a mixture of Pert-butyl 3-fluoro-4-(5-methyl-1H-indazol-6-yl)piperidine-1-carboxylate (D31, Peak 2) and (1R,4R)-5-(6-iodo-2-methoxypyrimidin-4-yl)-2-oxa-5-azabicyclo[2.2.1]heptane in toluene/THF, N$^1$,N$^2$-dimethylethane-1,2-diamine, CuI and K$_3$PO$_4$ at 90° C. for 2 hours under N$_2$.

LC-MS [mobile phase: 40% water (0.1% FA) and 60% MeCN (0.1% FA) to 5% water (0.1% FA) and 95% MeCN (0.1% FA) in 2.0 min]: Rt=1.71 min; MS Calcd.: 538, MS Found: 539 [M+H]$^+$.

Description 258

(1R,4R)-5-(6-(6-(3-fluoropiperidin-4-yl)-5-methyl-1H-indazol-1-yl)-2-methoxypyrim-idin-4-yl)-2-oxa-5-azabicyclo[2.2.1]heptane HCl (D258)

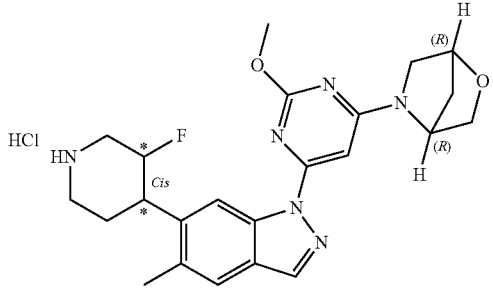

The title compound was prepared by a procedure similar to that described for D230 starting from a mixture of tert-butyl 4-(1-(6-((1R,4R)-2-oxa-5-azabicyclo[2.2.1]heptan-5-yl)-2-methoxypyrim-idin-4-yl)-5-methyl-1H-indazol-6-yl)-3-fluoropiperidine-1-carboxylate (D257) in EtOAc and HCl.EtOAc at rt for 30 min.

LC-MS [mobile phase: 70% water (0.1% FA) and 30% MeCN (0.1% FA) to 5% water (0.1% FA) and 95% MeCN (0.1% FA) in 2.0 min]: Rt=0.76 min; MS Calcd.: 438, MS Found: 439 [M+H]$^+$.

Description 259

Methyl 3-(4-(1-(6-(((1R,4R)-2-oxa-5-azabicyclo[2.2.1]heptan-5-yl)-2-methoxypyrimid-in-4-yl)-5-methyl-1H-indazol-6-yl)-3-fluoropiperidin-1-yl)propanoate (D259)

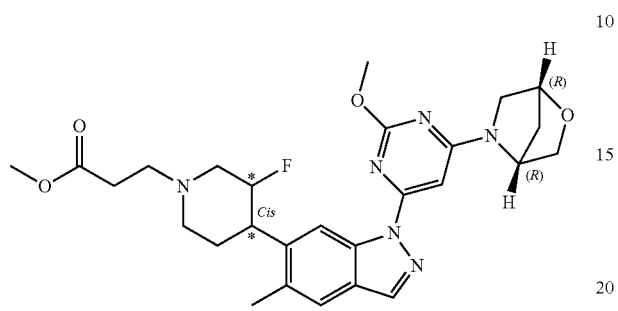

The title compound was prepared by a procedure similar to that described for D245 starting from a solution of (1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (D258) in MeOH and methyl acrylate at reflux for 2 h.

LC-MS [mobile phase: from 80% water (0.1% FA) and 20% MeCN (0.1% FA) to 5% water (0.1% FA) and 95% MeCN (0.1% FA) in 9.0 min]: Rt=6.36 min; MS Calcd.: 524.3, MS Found: 525.3 [M+H]+.

Description 260

Tert-butyl 4-(1-(6-((1S,4S)-2-oxa-5-azabicyclo[2.2.1]heptan-5-yl)-2-methoxypyrimi-din-4-yl)-5-methyl-1H-indazol-6-yl)-3-fluoropiperidine-1-carboxylate (D260)

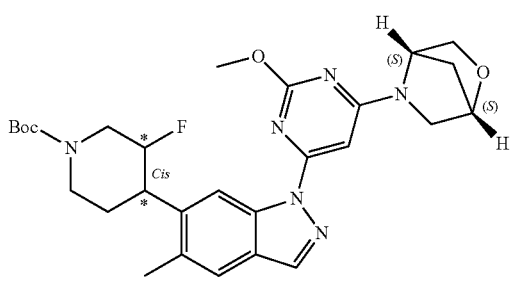

The title compound was prepared by a procedure similar to that described for D229 starting from a suspension of cis-tert-butyl 3-fluoro-4-(5-methyl-1H-indazol-6-yl)piperidine-1-carboxylate (D30, Peak 1), (1S,4S)-5-(6-iodo-2-methoxypyrimidin-4-yl)-2-oxa-5-azabicyclo[2.2.1]heptane, CuI, K$_3$PO$_4$ in toluene and DMEDA at 90° C. for 2 h.

LC-MS [mobile phase: from 80% water (0.1% FA) and 20% MeCN (0.1% FA) to 5% water (0.1% FA) and 95% MeCN (0.1% FA) in 2.6 min]: Rt=1.944 min; MS Calcd.: 538, MS Found: 539.3 [M+H]+.

Description 261

(1S,4S)-5-(6-(6-(3-fluoropiperidin-4-yl)-5-methyl-1H-indazol-1-yl)-2-methoxypyri-midin-4-yl)-2-oxa-5-azabicyclo[2.2.1]heptane (D261)

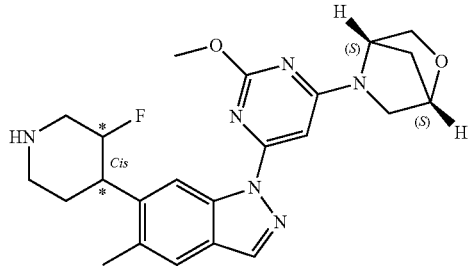

The title compound was prepared by a procedure similar to that described for D230 starting from a solution of tert-butyl cis-4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (D260) in EtOAc and HCl/EtOAc (3 N) at rt for 0.5 hours.

LC-MS [mobile phase: from 80% water (0.1% FA) and 20% MeCN (0.1% FA) to 5% water (0.1% FA) and 95% MeCN (0.1% FA) in 2.6 min]: Rt=0.927 min; MS Calcd.: 438, MS Found: 439.3 [M+H]+.

Description 262

Methyl 3-(4-(1-(6-((1S,4S)-2-oxa-5-azabicyclo[2.2.1]heptan-5-yl)-2-methoxypyrimidi-n-4-yl)-5-methyl-1H-indazol-6-yl)-3-fluoropiperidin-1-yl)propanoate (D262)

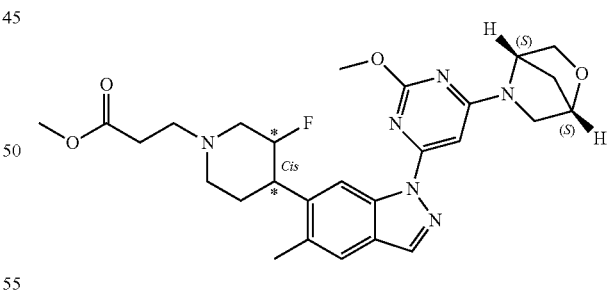

The title compound was prepared by a procedure similar to that described for D245 starting from a mixture of (1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (D261) and methyl acrylate in MeOH at 70° C. for 2 h.

LC-MS [mobile phase: from 80% water (0.1% FA) and 20% MeCN (0.1% FA) to 5% water (0.1% FA) and 95% MeCN (0.1% FA) in 2.6 min]: Rt=1.03 min; MS Calcd.: 524, MS Found: 525.3 [M+H]+.

Description 263

Cis-tertbutyl 4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (D263)

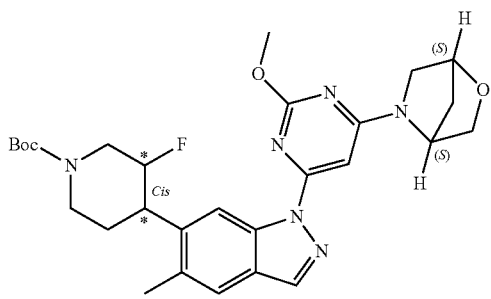

The title compound was prepared by a procedure similar to that described for D229 starting from a mixture of cis-tert-butyl 3-fluoro-4-(5-methyl-1H-indazol-6-yl)piperidine-1-carboxylate (D31, Peak 2), (1S,4S)-5-(6-iodo-2-methoxypyrimidin-4-yl)-2-oxa-5-azabicyclo[2.2.1]heptane, CuI and $K_3PO_4$ in toluene/THF and DMEDA at 80° C. for 3 hour.

LC-MS [mobile phase: from 90% water (0.1% FA) and 10% MeCN (0.1% FA) to 5% water (0.1% FA) and 95% MeCN (0.1% FA) in 2.0 min]: Rt=1.64 min; MS Calcd.: 538, MS Found: 539 [M+H]⁺.

Description 264

Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane Hydrochloride (D264)

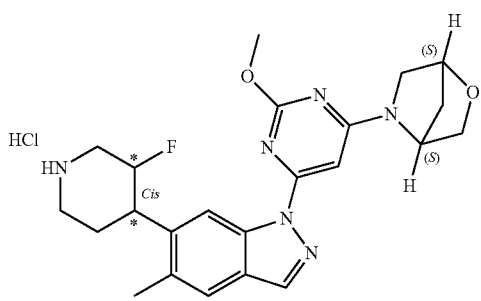

The title compound was prepared by a procedure similar to that described for D230 starting from a solution of cis-(tert-butyl-4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidine-1-carboxylate (D31, Peak 2) in EtOAc and HCl/EtOAc (3 N) at rt for 60 min.

LC-MS [mobile phase: from 90% water (0.1% FA) and 10% MeCN (0.1% FA) to 5% water (0.1% FA) and 95% MeCN (0.1% FA) in 2.0 min]: Rt=0.99 min; MS Calcd.: 438, MS Found: 439 [M+H]⁺.

Description 265

Methyl 3-(4-(1-(6-((1S,4S)-2-oxa-5-azabicyclo[2.2.1]heptan-5-yl)-2-methoxypyrimi-din-4-yl)-5-methyl-1H-indazol-6-yl)-3-fluoropiperidin-1-yl)propanoate (D265)

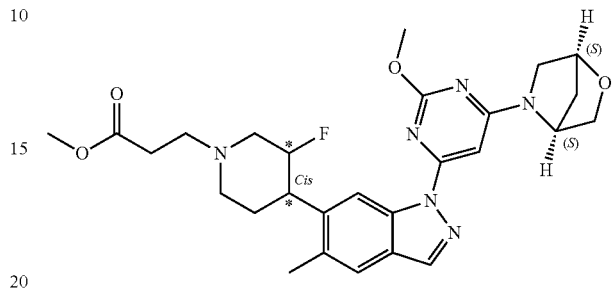

The title compound was prepared by a procedure similar to that described for D245 starting from a solution of (1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane (D264) in MeOH and methyl acrylate at reflux for 2 h.

LC-MS [mobile phase: from 80% water (0.1% FA) and 20% MeCN (0.1% FA) to 5% water (0.1% FA) and 95% MeCN (0.1% FA) in 9.0 min]: Rt=6.86 min; MS Calcd.: 524.3, MS Found: 525.3 [M+H]⁺.

Description 266

(R)-tetrahydrofuran-3-yl Methanesulfonate (D266)

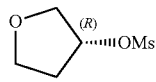

To a solution of (R)-tetrahydrofuran-3-ol (1.50 g, 17.0 mmol) and TEA (3.43 g, 34.0 mmol) in DCM (10 mL) was added MsCl (2.54 g, 22.1 mmol) at 0° C. The reaction mixture was stirred at room temperature for 3 hours, then diluted with $H_2O$ (30 mL), extracted with DCM (30 mL×2). The combined organic layers were concentrated to give the title compound (2.5 g, 90%) as a yellow oil.

¹H-NMR (CDCl₃, 400 MHz): δ 5.32 (br, 1H), 4.05-3.88 (m, 4H), 3.05 (s, 3H), 2.27-2.23 (m, 2H).

Description 267

(S)-tetrahydrofuran-3-yl Methanesulfonate (D267)

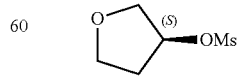

The title compound was prepared by a procedure similar to that described for D266 starting from a solution of (S)-tetrahydrofuran-3-ol and TEA in DCM and MsCl at 0° C. then room temperature for 2 hours.

$^1$H-NMR (CDCl$_3$, 300 MHz): δ 5.32 (br, 1H), 4.06-3.89 (m, 4H), 3.05 (s, 3H), 2.28-2.23 (m, 2H).

Description 268

Methyl 3-(4-(1-(6-((1R,4R)-2-oxa-5-azabicyclo [2.2.1]heptan-5-yl)-2-methylpyrimidin-4-yl)-5-methyl-1H-indazol-6-yl)piperidin-1-yl)propanoate (D268)

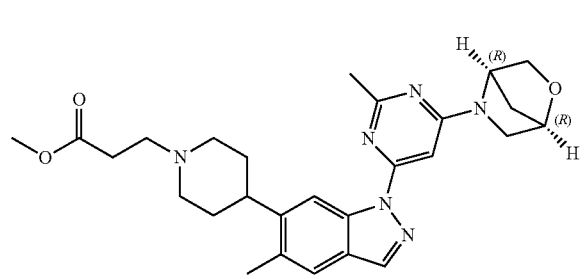

The title compound was prepared by a procedure similar to that described for D245 starting from a solution of (1R,4R)-5-(2-methyl-6-(5-methyl-6-(piperidin-4-yl)-1H-indazol-1-yl)pyrimidin-4-yl)-2-oxa-5-azabicyclo[2.2.1]heptane (D130) in MeOH and methyl acrylate at rt then 70° C. for 3 h.

LC-MS [mobile phase: from 90% water (0.1% FA) and 10% MeCN (0.1% FA) to 5% water (0.1% FA) and 95% MeCN (0.1% FA) in 2.0 min]: Rt=1.211 min; MS Calcd.: 490.60, MS Found: 491.2 [M+H]$^+$.

Description 269

Methyl 3-(4-(1-(6-((1R,4R)-2-oxa-5-azabicyclo [2.2.1]heptan-5-yl)-2-methoxypyrim-idin-4-yl)-5-methyl-1H-indazol-6-yl)piperidin-1-yl)propanoate (D269)

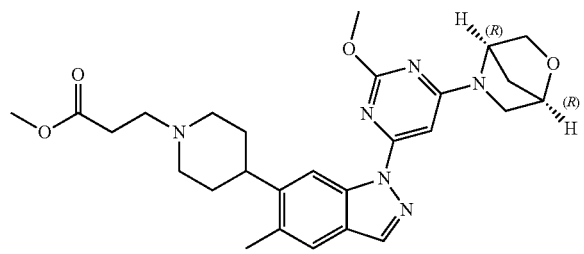

The title compound was prepared by a procedure similar to that described for D245 starting from a solution of (1R,4R)-5-(2-methyl-6-(5-methoxy-6-(piperidin-4-yl)-1H-indazol-1-yl)pyrimidin-4-yl)-2-oxa-5-azabicyclo[2.2.1]heptane (D107) in MeOH and methyl acrylate at rt then 70° C. for 3 h.

LC-MS [mobile phase: from 90% water (0.1% FA) and 10% MeCN (0.1% FA) to 5% water (0.1% FA) and 95% MeCN (0.1% FA) in 2.0 min]: Rt=1.252 min; MS Calcd.: 506.26, MS Found: 507.2 [M+H]$^+$.

Description 270

Methyl 3-(4-(1-(6-((1S,4S)-2-oxa-5-azabicyclo [2.2.1]heptan-5-yl)-2-methoxypyrimi-din-4-yl)-5-methyl-1H-indazol-6-yl)piperidin-1-yl)propanoate (D270)

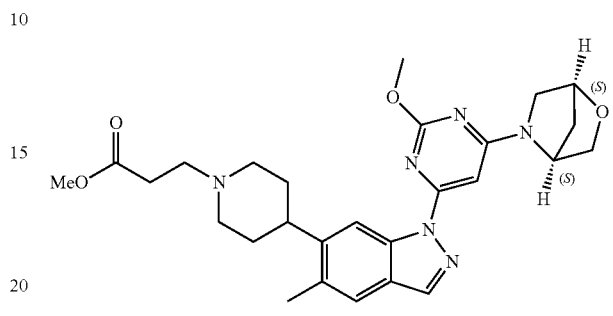

The title compound was prepared by a procedure similar to that described for D245 starting from a solution of (1S,4S)-5-(2-methoxy-6-(5-methyl-6-(piperidin-4-yl)-1H-indazol-1-yl)pyrimidin-4-yl)-2-oxa-5-azabicyclo[2.2.1]heptane (D105, step 1) in MeOH and methyl acrylate at rt then reflux for 2 h.

Description 271

(5-(6-iodo-2-methoxypyrimidin-4-yl)-2-oxa-5-azabicyclo[2.2.1]heptan-1-yl)methanol (D271)

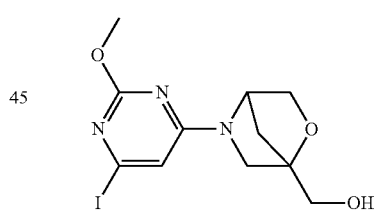

To a solution of 2-oxa-5-azabicyclo[2.2.1]heptan-1-yl-methanol trifluoroacetic salts (214 mg, 0.880 mmol) and 4,6-diiodo-2-methoxypyrimidine (318 mg, 0.880 mmol) in THF/EtOH=1/1 (40 ml) was added DIEA (568 mg, 4.40 mmol) at rt. The reaction mixture was stirred at 50° C. for 5 h, then concentrated to give a residue. The residue was purified by silica gel column chromatography (PE: EtOAc=1:2) to give title product as a white solid (200 mg, yield 62%).

LC-MS [mobile phase: from 50% water (0.1% FA) and 50% MeCN (0.1% FA) to 5% water (0.1% FA) and 95% MeCN (0.1% FA) in 2.6 min]: Rt=0.88 min; MS Calcd: 363.1, MS Found: 364.0 [M+H]$^+$.

Description 272

4-(5-methyl-1-(tetrahydro-2H-pyran-2-yl)-1H-indazol-6-yl)tetrahydro-2H-pyran-3-ol (trans) (D272)

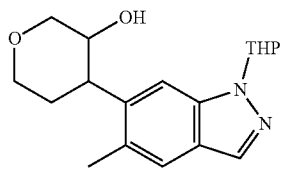

To a mixture of 6-(3,6-dihydro-2H-pyran-4-yl)-5-methyl-1-(tetrahydro-2H-pyran-2-yl)-1H-indazole (D63, 1.1 g, 3.7 mmol) in THF (20 mL) was added BH$_3$/THF (8 mL) at 0° C. The reaction mixture was stirred at 0° C. for 30 min, then allowed to rt and stirred overnight. Aq.

NaOH (8 mL) was added dropwise into the reaction mixture at 0° C. followed by H$_2$O$_2$ solution (3 mL). The reaction mixture was stirred at rt for 2 h, diluted with water and extracted with EtOAc (100 mL×3). The combined organic layers were washed with brine, dried over anhydrous Na$_2$SO$_4$, filtered and concentrated to give a residue. The residue was purified by column (PE:EtOAc=5:1-1:1) to give the title product as a white solid (540 mg, 46% yield).

LC-MS [mobile phase: from 50% water (0.1% FA) and 50% MeCN (0.1% FA) to 5% water (0.1% FA) and 95% MeCN (0.1% FA) in 2.6 min]: Rt=0.84 min and 0.95 min; MS Calcd.: 316.18, MS Found: 317.3 [M+H]$^+$.

Description 273

4-(5-methyl-1-(tetrahydro-2H-pyran-2-yl)-1H-indazol-6-yl)dihydro-2H-pyran-3(4H)-one (D273)

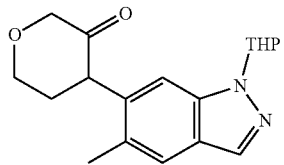

To a mixture of 4-(5-methyl-1-(tetrahydro-2H-pyran-2-yl)-1H-indazol-6-yl)tetrahydro-2H-pyran-3-ol (D272, 680 mg, 2.15 mmol) in CH$_2$Cl$_2$ (20 mL) was added dess-matin peroxidant (3.60 g, 9.61 mmol) at 0° C. The reaction mixture was stirred at 0° C. for 5 min, allowed to rt and stirred for 2 h, washed with sat. NaHCO$_3$ and Na$_2$S$_2$O$_3$. The organic layer was separated and the aqueous layer was extracted with CH$_2$Cl$_2$ (100 mL). The combined organic layer was washed with brine and dried over anhydrous Na$_2$SO$_4$, filtered and concentrated to give a residue. The residue was purified by column (PE:EtOAc=6:1) to give the title product as a white solid (540 mg, 79% yield).

LC-MS [mobile phase: from 50% water (0.1% FA) and 50% MeCN (0.1% FA) to 5% water (0.1% FA) and 95% MeCN (0.1% FA) in 2.6 min]: Rt=1.17 min; MS Calcd.: 314.16, MS Found: 315.3 [M+H]$^+$.

Description 274

4-(5-methyl-1-(tetrahydro-2H-pyran-2-yl)-1H-indazol-6-yl)tetrahydro-2H-pyran-3-ol (cis) (D274)

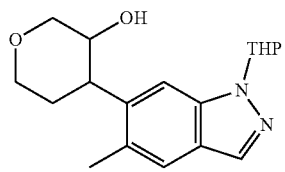

To a mixture of 4-(5-methyl-1-(tetrahydro-2H-pyran-2-yl)-1H-indazol-6-yl)dihydro-2H-pyran-3(4H)-one (540 mg, 1.72 mmol) in MeOH (20 mL) was added NaBH$_4$ (260 mg, 6.88 mmol) at 0° C. Then the reaction mixture was allowed to rt and stirred for 2 h, diluted with water and extracted with CH$_2$Cl$_2$ (100 mL×2). The combined organic layers were washed with brine, dried over anhydrous Na$_2$SO$_4$, filtered and concentrated to give a residue. The residue was purified by column (PE:EtOAc=1:1) to give the title product as a white solid (460 mg, 86% yield).

LC-MS [mobile phase: from 60% water (0.1% FA) and 40% MeCN (0.1% FA) to 5% water (0.1% FA) and 95% MeCN (0.1% FA) in 2.6 min]: Rt=1.30 min and 1.35 min; MS Calcd.: 316.18, MS Found: 317.3 [M+H]$^+$.

Description 275

4-(5-methyl-1H-indazol-6-yl)tetrahydro-2H-pyran-3-ol (cis) (D275)

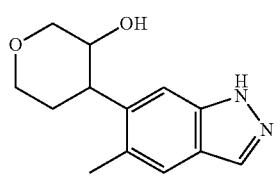 [SMILES: Cc1cc2cn[nH]c2cc1C1CCOCC1O]

To a mixture of 4-(5-methyl-1-(tetrahydro-2H-pyran-2-yl)-1H-indazol-6-yl)tetrahydro-2H-pyran-3-ol (D88, 460 mg, 1.45 mmol) in CH$_2$Cl$_2$ (15 mL) was added TFA (2 ml). The reaction mixture was stirred at rt overnight, washed with sat. NaHCO$_3$ and brine, dried over anhydrous Na$_2$SO$_4$, filtered and concentrated to give a residue. The residue was purified by column (PE:EtOAc=1:3) to give a white solid (200 mg, 60% yield).

LC-MS [mobile phase: from 50% water (0.1% FA) and 50% MeCN (0.1% FA) to 5% water (0.1% FA) and 95% MeCN (0.1% FA) in 2.6 min]: Rt=0.75 min; MS Calcd.: 232.12, MS Found: 233.3 [M+H]$^+$.

Description 276

5-methyl-6-(piperidin-4-yl)-1-(tetrahydro-2H-pyran-2-yl)-1H-indazole (D276)

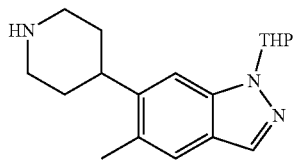

To a suspension of 5-methyl-6-(piperidin-4-yl)-1H-indazole (10.0 g, 46.5 mmol) and DHP (7.80 g, 93.0 mmol) in THF (200 mL) was added in one portion p-TsOH (884 mg, 4.70 mmol). The reaction mixture was stirred at 60° C. overnight and concentrated. The residue was re-dissolved in DCM (1.5 L), washed with sat. NaHCO$_3$ and brine, dried over Na$_2$SO$_4$ and concentrated. The residue was purified by chromatography (MeOH/DCM=1/15) to give the product as a brown solid. (6.7 g, 48% yield)

LC-MS [mobile phase: from 95% water (0.1% FA) and 5% MeCN (0.1% FA) to 5% water (0.1% FA) and 95% MeCN (0.1% FA) in 2.6 min]: Rt=1.108 min; MS Calcd.: 299.20, MS Found: 300.4 [M+H]$^+$.

Description 277 trans-4-(4-(5-methyl-1-(tetrahydro-2H-pyran-2-yl)-1H-indazol-6-yl)piperidin-1-yl)tetrahydrofuran-3-ol (D277)

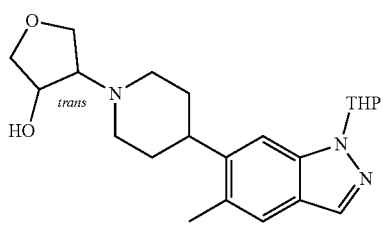

To a solution of 5-methyl-6-(piperidin-4-yl)-1-(tetrahydro-2H-pyran-2-yl)-1H-indazole (D276, 1.20 g, 4.01 mmol) in DMF (15 mL) was added Cs$_2$CO$_3$ (3.90 g, 12.0 mmol) and 3,6-dioxabicyclo[3.1.0]hexane (1.38 g, 16.0 mmol). The reaction mixture was stirred at 80° C. for 18 hrs, cooled, diluted with water (150 mL) and extracted with EtOAc (40 mL×3). The combined organic layers were washed with brine (100 mL×2), dried over Na$_2$SO$_4$ and concentrated. The residue was purified by chromatography (MeOH/DCM=1/100-1/10) to give the product as a yellow solid (660 mg, 43% yield).

LC-MS [mobile phase: from 60% water (0.1% FA) and 40% MeCN (0.1% FA) to 5% water (0.1% FA) and 95% MeCN (0.1% FA) in 2.0 min]: Rt=0.52 min; MS Calcd.: 385.24, MS Found: 386.4 [M+H]$^+$.

Description 278

4-(4-(5-methyl-1-(tetrahydro-2H-pyran-2-yl)-1H-indazol-6-yl)piperidin-1-yl)dihydrofuran-3(2H)-one

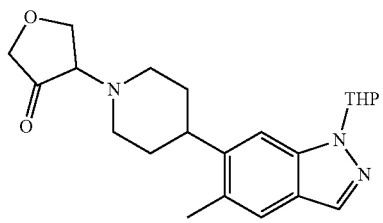

To a solution of DMSO (1.50 g, 19.5 mmol) in CH$_2$Cl$_2$ (30 mL) was added dropwise a solution of oxalyl chloride (1.20 g, 9.34 mmol) in CH$_2$Cl$_2$ (5 mL) at −65° C. under N$_2$. The reaction mixture was stirred at −65° C.~−60° C. for 20 min and a solution of 4-(4-(5-methyl-1-(tetrahydro-2H-pyran-2-yl)-1H-indazol-6-yl)piperidin-1-yl)tetrahydrofuran-3-ol (3.00 g, 7.78 mmol) in CH$_2$Cl$_2$ (5 mL) was added dropwise. The reaction mixture was stirred at −60° C.~−55° C. for 20 min and Et$_3$N (3.90 g, 38.9 mmol) was added dropwise. The reaction mixture was stirred at −55° C. for 20 min, quenched with water, diluted with CH$_2$Cl$_2$ (60 mL), and washed with brine (2×60 mL). The separated organic layer was dried over anhydrous Na$_2$SO$_4$ and concentrated. The residue was purified by silica gel column (CH$_2$Cl$_2$:MeOH=80:1) to give the product (2.0 g, yield: 67%) as a pale yellow solid.

LC-MS [mobile phase: from 70% water (0.1% FA) and 30% MeCN (0.1% FA) to 5% water (0.1% FA) and 95% MeCN (0.1% FA) in 2.0 min]: Rt=0.96 min; MS Calcd: 383.2, MS Found: 384.4 [M+H]$^+$.

Description 279

Cis-4-(4-(5-methyl-1-(tetrahydro-2H-pyran-2-yl)-1H-indazol-6-yl)piperidin-1-yl)tetrahydrofuran-3-ol (D279)

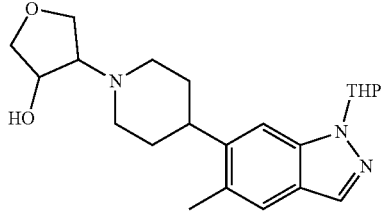

To a solution of 4-(4-(5-methyl-1-(tetrahydro-2H-pyran-2-yl)-1H-indazol-6-yl)piperidin-1-yl) dihydrofuran-3(2H)-one (D278, 2.00 g, 5.22 mmol) in MeOH (20 mL) was added NaBH$_4$ (592 mg, 15.65 mmol). The reaction mixture was stirred at room temperature for 60 min, quenched with aq. 1 N HCl, diluted with CH$_2$Cl$_2$ (100 mL), washed with sat. NaHCO$_3$ (100 mL) and brine (100 mL). The organic solution was dried over anhydrous Na$_2$SO$_4$ and concentrated. The residue was purified by silica gel column (CH$_2$Cl$_2$:MeOH=10:1) to give the title product (1.6 g, yield: 80%) as a white solid.

183

LC-MS [mobile phase: from 70% water (0.1% FA) and 30% MeCN (0.1% FA) to 5% water z (0.1% FA) and 95% MeCN (0.1% FA) in 2.0 min]: Rt=0.68 min; MS Calcd: 385.2, MS Found: 386.5 [M+H]⁺.

Description 280

Cis-4-(4-(5-methyl-1H-indazol-6-yl)piperidin-1-yl) tetrahydrofuran-3-ol

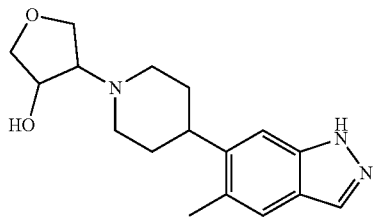 [SMILES: Cc1cc2cn[nH]c2cc1C1CCN(C2COCC2O)CC1]

To a solution of 4-(4-(5-methyl-1-(tetrahydro-2H-pyran-2-yl)-1H-indazol-6-yl)piperidin-1-yl) tetrahydrofuran-3-ol (D279, 400 mg, 1.04 mmol) in $CH_2Cl_2$ (10 mL) was added dropwise TFA (2 mL). The reaction mixture was stirred at room temperature overnight, concentrated, diluted with EtOAc (20 mL), washed with sat. sat. $NaHCO_3$ (2×20 mL) and brine (20 mL). The organic solution was dried over anhydrous $Na_2SO_4$ and concentrated. The residue was purified by silica gel column ($CH_2Cl_2$:MeOH=10:1) to give the product (250 mg, yield: 80%) as a pale yellow solid.

LC-MS [mobile phase: from 70% water (0.1% FA) and 30% MeCN (0.1% FA) to 5% water (0.1% FA) and 95% MeCN (0.1% FA) in 9.0 min]: Rt=3.48 min; MS Calcd: 301.2, MS Found: 302.2[M+H]⁺.

Description 281

1-benzyl-1H-pyrrole-2,5-dione (D281)

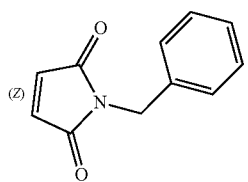 [SMILES: O=C1C=CC(=O)N1Cc1ccccc1]

To a stirred solution of furan-2,5-dione (20.0 g, 204.0 mmol) in $Et_2O$ (500.0 ml) was added dropwise phenylmethanamine (32.8 g, 306.0 mmol) in $Et_2O$ (50 ml) at 5-10° C. The reaction mixture was stirred at room temperature for 16 h. The crystallized acid was filtered and washed with $Et_2O$, then added to a mixture of acetic anhydride (40 ml) and $CH_3COOK$ (4.0 g). The suspension was heated on a steam bath (70° C.) for 16 h, dissolved in $CH_2Cl_2$ (400 ml), washed with aq.$NaHCO_3$ (2×500 ml) and concentrated. The residue was purified by column chromatography (PE/EtOAc=10/1) to give the desired product as a white solid (12.6 g, yield: 33%).

¹H NMR (400 MHz, $CDCl_3$) 7.35~7.28 (m, 5H), 6.70 (s, 2H), 4.67 (s, 2H),

184

Description 282

5-methyl-1-(tetrahydro-2H-pyran-2-yl)-1H-indazole-6-carbaldehyde (D282)

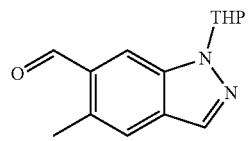

To a stirred solution of 6-bromo-5-methyl-1-(tetrahydro-2H-pyran-2-yl)-1H-indazole (24.0 g, 81.6 mmol) in dry THF (300 ml) was added dropwise n-BuLi (163 mmol, 102 ml, 1.6 M in THF) at −78° C. The reaction mixture was stirred at −78° C. for 2 h. Then dry DMF (12.0 g, 163.2 mmol) was added to the mixture. The reaction mixture was stirred at −78° C. for 4 hrs, poured into water (400 ml), extracted with EtOAc (2×400 mL), washed with brine, dried over $Na_2SO_4$ and concentrated to give the crude compound as a brown oil. The residue was purified by column chromatography (PE:EtOAc=10:1) to give the desired product as a yellow solid (10.5 g, yield: 53%).

LC-MS [mobile phase: from 50% water (0.1% FA) and 50% MeCN (0.1% FA) to 5% water (0.1% FA) and 95% MeCN (0.1% FA) in 2.6 min]: Rt=1.40 min; MS Calcd: 244.12; MS Found: 245.2 [M+H]⁺.

Description 283

(Z)-6-(hydrazonomethyl)-5-methyl-1-(tetrahydro-2H-pyran-2-yl)-1H-indazole (D283)

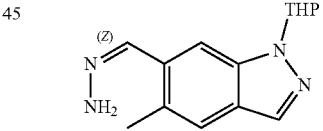

To a stirred solution of $N_2H_4.H_2O$ (43.1 g, 860.0 mmol) in ethanol (50 ml) was added dropwise 6-bromo-5-methyl-1-(tetrahydro-2H-pyran-2-yl)-1H-indazole (10.5 g, 43.0 mmol) in ethanol (650 ml) under $N_2$. The reaction mixture was stirred at room temperature for 16 h, diluted with water (200 ml), concentrated under vacuum to remove solvent, extracted with $CH_2Cl_2$ (2×300 ml), washed with brine, dried over $Na_2SO_4$ and concentrated to give the target compound as a yellow solid. (10.5 g, yield: 99%).

LC-MS [mobile phase: from 50% water (0.1% FA) and 50% MeCN (0.1% FA) to 5% water (0.1% FA) and 95% MeCN (0.1% FA) in 2.6 min]: Rt=0.93 min; MS Calcd: 258.15; MS Found: 259.3 [M+H]⁺.

Description 284

5-benzyl-3-(5-methyl-1-(tetrahydro-2H-pyran-2-yl)-1H-indazol-6-yl)-3,3a-dihydropyrrolo[3,4-c]pyrazole-4,6(5H,6H)-dione (D284)

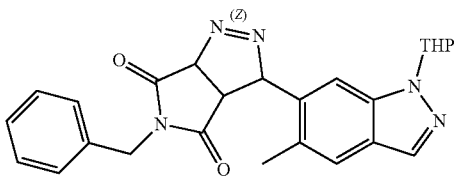

To a mixture of 6-bromo-5-methyl-1-(tetrahydro-2H-pyran-2-yl)-1H-indazole (10.5 g, 40.7 mmol) in 1,4-dioxane (400 ml) was added manganese dioxide (70.7 g, 814.0 mmol). The reaction mixture was stirred at room temperature for 2 hrs, then filtered, directly added into a solution of 1-benzyl-1H-pyrrole-2,5-dione in 1,4-dioxane (100 ml). The reaction mixture was stirred at room temperature for 16 h, concentrated and purified by flash chromatography ($C_{18}$, 330 g, $H_2O$/MeCN=0/100) to give the desired product as a yellow oil (9.5 g, yield: 53%).

LC-MS [mobile phase: from 50% water (0.1% FA) and 50% MeCN (0.1% FA) to 5% water (0.1% FA) and 95% MeCN (0.1% FA) in 2.6 min]: Rt=1.55 min; MS Calcd: 443.20; MS Found: 444.2 $[M+H]^+$.

Description 285

3-benzyl-6-(5-methyl-1-(tetrahydro-2H-pyran-2-yl)-1H-indazol-6-yl)-3-azabicyclo-[3.1.0]hexane-2,4-dione (D285)

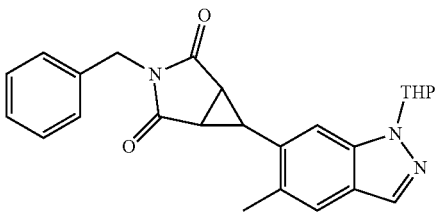

A mixture of 5-benzyl-3-(5-methyl-1-(tetrahydro-2H-pyran-2-yl)-1H-indazol-6-yl)-3,3a-dihydropyrrolo[3,4-c]pyrazole-4,6(5H,6H)-dione (9.5 g, 21.4 mmol) in 1,4-dioxane (200 ml) was stirred at 70° C. for 16 h and concentrated to give the target compound as a yellow oil. (8.7 g, yield: 97%).

LC-MS [mobile phase: from 50% water (0.1% FA) and 50% MeCN (0.1% FA) to 5% water (0.1% FA) and 95% MeCN (0.1% FA) in 2.6 min]: Rt=1.59 min; MS Calcd: 415.19; MS Found: 416.1 $[M+H]^+$.

Description 286

6-(3-benzyl-3-azabicyclo[3.1.0]hexan-6-yl)-5-methyl-1-(tetrahydro-2H-pyran-2-yl)-1H-indazole (D286)

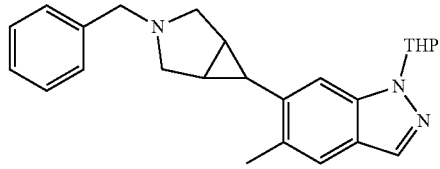

To a stirred solution of 3-benzyl-6-(5-methyl-1-(tetrahydro-2H-pyran-2-yl)-1H-indazol-6-yl)-3-azabicyclo[3.1.0]hexane-2,4-dione (7.2 g, 17.3 mmol) in dry THF (160 ml) was added LAH (5.3 g, 138.8 mmol) at 0° C. Then the reaction mixture was stirred at room temperature for 3 h, quenched with $Na_2SO_4.10H_2O$ (120.0 g), filtered and extracted with EtOAc (2×200 ml). The combined organic layers were washed with brine, dried over $Na_2SO_4$ and concentrated.

The residue was purified by column chromatography (PE:EtOAc=10:1) to give the desired product as a yellow oil (2.3 g, yield: 34%).

LC-MS [mobile phase: from 50% water (0.1% FA) and 50% MeCN (0.1% FA) to 5% water (0.1% FA) and 95% MeCN (0.1% FA) in 2.6 min]: Rt=0.83 min; MS Calcd: 387.23; MS Found: 388.4 $[M+H]^+$.

Description 287

6-(3-azabicyclo[3.1.0]hexan-6-yl)-5-methyl-1-(tetrahydro-2H-pyran-2-yl)-1H-indazole (D287)

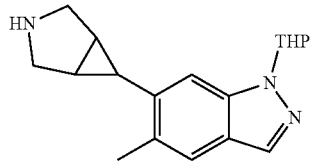

To a stirred solution of 6-(3-benzyl-3-azabicyclo[3.1.0]hexan-6-yl)-5-methyl-1-(tetrahydro-2H-pyran-2-yl)-1H-indazole (1.1 g, 2.8 mmol) in methanol (40 ml) was added Pd/C (300 mg, 10%) under $H_2$. The reaction mixture was stirred at room temperature for 16 hrs, filtered and concentrated to give the desired product as a pale yellow oil (600 mg, yield: 71%).

LC-MS [mobile phase: from 50% water (0.1% FA) and 50% MeCN (0.1% FA) to 5% water (0.1% FA) and 95% MeCN (0.1% FA) in 2.6 min]: Rt=0.76 min; MS Calcd: 297.18; MS Found: 298.4 $[M+H]^+$.

Description 288

5-methyl-1-(tetrahydro-2H-pyran-2-yl)-6-(3-((S)-tetrahydrofuran-3-yl)-3-azabicyclo[3.1.0]hexan-6-yl)-1H-indazole (D288)

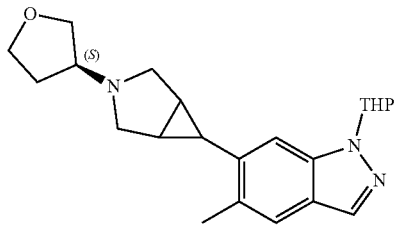

To a stirred solution of 6-(3-azabicyclo[3.1.0]hexan-6-yl)-5-methyl-1-(tetrahydro-2H-pyran-2-yl)-1H-indazole (300 mg, 1.0 mmol) in MeCN (40 ml) were added (R)-tetrahydrofuran-3-yl 4-methylbenzenesulfonate (726 mg, 3.0 mmol) and $K_2CO_3$ (342 mg, 3.0 mmol). Then the reaction mixture was stirred at 110° C. for 16 h, filtered and extracted with EtOAc (2×50 ml). The combined organic layers were washed with brine, dried over $Na_2SO_4$ and concentrated. The residue was purified by column chromatography (EtOAc:PE=2:1) to give the desired product as a pale yellow oil (150 mg, yield: 40%).

LC-MS [mobile phase: from 60% water (0.1% FA) and 40% MeCN (0.1% FA) to 5% water (0.1% FA) and 95% MeCN (0.1% FA) in 2.6 min]: Rt=0.79 min; MS Calcd: 367.23; MS Found: 368.3 [M+H]$^+$.

Description 289

5-methyl-6-(3-((S)-tetrahydrofuran-3-yl)-3-azabicyclo[3.1.0]hexan-6-yl)-1H-indazole (D289)

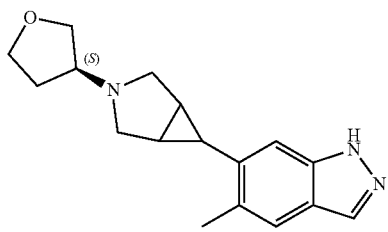

To a stirred solution of 5-methyl-1-(tetrahydro-2H-pyran-2-yl)-6-(3-((S)-tetrahydrofuran-3-yl)-3-azabicyclo[3.1.0]hexan-6-yl)-1H-indazole (150 mg, 0.4 mmol) in methanol (15 ml) was added a solution of HCl (g).in MeOH (5.0 ml, 15.0 mmol, 3 M). Then the reaction mixture was stirred at room temperature for 16 h, basified with aq.NaHCO$_3$ to pH 8-9, extracted with CH$_2$Cl$_2$ (2×50 ml). The combined organic layers were washed with brine, dried over Na$_2$SO$_4$ and concentrated. The residue was purified by column chromatography (pure EtOAc) to give the desired product as a yellow solid (100 mg, yield: 86%).

LC-MS [mobile phase: from 60% water (0.1% FA) and 40% MeCN (0.1% FA) to 5% water (0.1% FA) and 95% MeCN (0.1% FA) in 2.6 min]: Rt=0.68 min; MS Calcd: 283.17; MS Found: 284.2[M+H]$^+$.

Description 290

1-(oxiran-2-yl)prop-2-en-1-ol (D290)

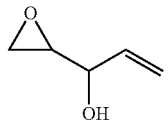

To a solution of penta-1,4-dien-3-ol (4.2 g, 50 mmol) in DCM (50 mL) was slowly added m-CPBA (11.5 g, 75%, 50 mmol) at −20° C. The reaction mixture was stirred at rt overnight, filtered, washed with aq. K$_2$CO$_3$ (20 mL), dried over Na$_2$SO$_4$ and concentrated. The residue was purified by column chromatography (EtOAc/PE=1/5) to give the title product as a colorless oil (2.6 g, yield 52%).

$^1$H NMR (400 MHz, CDCl$_3$): δ 5.99~5.81 (m, 1H), 5.43~5.38 (m, 1H), 5.29~5.25 (m, 1H), 4.36~4.34 (m, 0.4H), 4.03~4.01 (m, 0.5H), 3.12~3.05 (m, 1H), 2.85~2.75 (m, 2H), 2.03~1.98 (m, 1H).

Description 291

1-aminopent-4-ene-2,3-diol (D291)

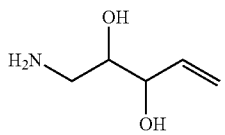

A mixture of 1-(oxiran-2-yl)prop-2-en-1-ol (1.2 g, 12.0 mmol) in NH$_3$.H$_2$O (28/%, 20 mL) was stirred at rt for 3 days. The obtained solution was concentrated to give the crude product as a light brown oil (1.4 g, yield 100%).

$^1$H NMR (400 MHz, CDCl$_3$): δ 5.96~5.84 (m, 1H), 5.24~5.02 (m, 2H), 3.95~3.82 (m, 1H), 3.45~3.16 (m, 3H), 2.62~2.40 (m, 3H).

Description 292

N-(2,3-dihydroxypent-4-en-1-yl)-4-methylbenzenesulfonamide (D292)

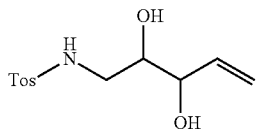

To a solution of 1-aminopent-4-ene-2,3-diol (235 mg, 2.0 mmol) and pyridine (480 mg, 6.0 mmol) in DCM (8 mL) was slowly added a solution of TosCl (380 mg, 2.0 mmol) in DCM (2 mL) at 0° C. The reaction mixture was stirred at rt overnight, then concentrated. The residue was purified by silico gel chromatography (MeOH/EtOAC=1/20~1/3) to give the title product as a yellow oil (120 mg, yield 22%).

$^1$H NMR (400 MHz, CDCl$_3$): δ 7.73 (d, J=8.0 Hz, 2H), 7.29 (d, J=8.0 Hz, 2H), 5.83~5.78 (m, 1H), 5.60 (br, 1H), 5.34~5.18 (m, 2H), 4.20~4.05 (m, 1H), 3.71~3.61 (m, 1H), 3.13~2.95 (m, 2H), 2.41 (s, 3H).

Description 293

2-(bromomethyl)-1-tosylpyrrolidine-3,4-diol (D293)

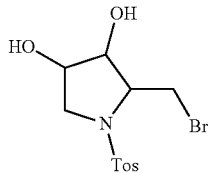

To a solution of N-(2,3-dihydroxypent-4-en-1-yl)-4-methylbenzenesulfonamide (135 mg, 0.5 mmol) in DME (4 mL) and water (1 mL) was added NBS (84 mg, 0.5 mmol) at 0° C. The reaction mixture was stirred at 0° C. for 2 hrs, then concentrated. The residue was purified by reverse column (MeCN/H$_2$O=5/95-80/20) to give the title product as a white solid (120 mg, yield 69%).

$^1$H NMR (400 MHz, CDCl$_3$): δ 7.68~7.64 (m, 2H), 7.30~7.19 (m, 2H), 4.17~3.27 (m, 7H), 2.68~2.50 (m, 1H), 2.38~2.30 (m, 3H), 1.60 (br, 1H).

Description 294

5-tosyl-2-oxa-5-azabicyclo[2.2.1]heptan-7-ol (D294)

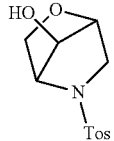

A mixture of 2-(bromomethyl)-1-tosylpyrrolidine-3,4-diol (120 mg, 0.34 mmol) in aq.NaOH (2 M, 2 mL) was stirred at rt overnight, then purified by reverse column (MeCN/H$_2$O=5/95-80/20) to give the title product as a colorless oil (85 mg, yield 93%).

$^1$H NMR (400 MHz, CDCl$_3$): δ 7.74~7.70 (m, 2H), 7.35~7.31 (m, 2H), 5.13~5.11 (m, 0.5H), 4.87~4.85 (m, 0.5H), 4.70~4.66 (m, 0.5H), 4.25~3.81 (m, 4.5H), 3.40~3.38 (m, 1H), 2.45~2.43 (m, 3H).

LC-MS [mobile phase: from 80% water (0.1% FA) and 20% MeCN (0.1% FA) to 5% water (0.1% FA) and 95% MeCN (0.1% FA) in 9.0 min]: Rt=3.61 min & 3.77 min; MS Calcd.: 269.07, MS Found: 270.2 [M+H]$^+$.

Description 295

2-oxa-5-azabicyclo[2.2.1]heptan-7-ol (D295)

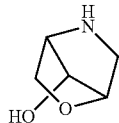

To a solution of naphthalene (952 mg, 7.43 mmol) in DME (10 mL) was added sodium (342 mg, 14.85 mmol) at room temperature under N$_2$. The resulting mixture was stirred at room temperature for 3 h. Then 5-tosyl-2-oxa-5-azabicyclo[2.2.1]heptan-7-ol (1.0 g, 3.71 mmol) was dissolved in dry DME (10 mL) and cooled to −70° C. The above naphthalide solution was added dropwise. Addition continued until a persistent and green color was maintained. The reaction mixture was allowed to room temperature, then quenched with $^i$PrOH, concentrated and purified by silica gel chromatography (CH$_2$Cl$_2$:MeOH=5:1) to give the title product (410 mg, yield 96%) as a yellow solid.

LC-MS [mobile phase: from 80% water (0.1% FA) and 20% MeCN (0.1% FA) to 5% water (0.1% FA) and 95% MeCN (0.1% FA) in 2.0 min]: Rt=0.24 min; MS Calcd.: 115.1, MS Found: 116.2 [M+H]$^+$.

Description 296

5-(6-iodo-2-methylpyrimidin-4-yl)-2-oxa-5-azabicyclo[2.2.1]heptan-7-ol (D296)

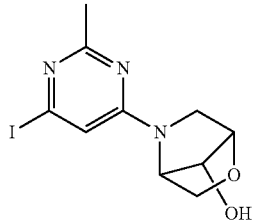 [SMILES: Cc1nc(I)cc(N2CC3OCC2C3O)n1]

To a mixture of 4,6-diiodo-2-methylpyrimidine (1.20 g, 3.47 mmol) and 2-oxa-5-azabicyclo[2.2.1]heptan-7-ol (400 mg, 3.47 mmol) in i-PrOH (10 mL) and THF (10 mL) was added Et$_3$N (1.05 g, 10.42 mmol). The reaction mixture was stirred at 50° C. overnight, cooled to room temperature, diluted with EtOAc (30 mL) and water (30 mL). The organic part was purified by C$_{18}$ column (eluant: MeCN/H$_2$O=5/95 to 95/5) to give the title product (400 mg, yield: 35%) as a pale yellow solid.

LC-MS [mobile phase: from 90% water (0.1% FA) and 10% MeCN (0.1% FA) to 5% water (0.1% FA) and 95% MeCN (0.1% FA) in 12.0 min]: Rt=4.267 min & 4.630 min; MS Calcd.: 333.0, MS Found: 334.2 [M+H]$^+$.

Description 297

(((1R,4R)-5-(6-iodo-2-methoxypyrimidin-4-yl)-2-oxa-5-azabicyclo[2.2.1]heptan-1-yl)methanol (D297)

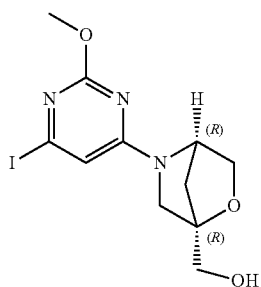

To a suspension of 4,6-diiodo-2-methoxypyrimidine (510 mg, 1.42 mmol) and (1R,4R)-2-oxa-5-azabicyclo[2.2.1]heptan-1-ylmethanol trifluoroacetate salts (400 mg, 1.42 mmol) in DMF (20 mL) was added DIPEA (735 mg, 5.7 mmol). The reaction mixture was stirred at 50° C. for 6 h. The reaction mixture was diluted with EtOAc (100 mL), then washed with water (50 mL×3) and brine (50 mL). The organic layer was dried over anhydrous $Na_2SO_4$, filtered, concentrated and purified by silica gel column chromatography (PE:EtOAc=2:1) to give the title product (250 mg, yield 49%) as a colorless oil.

LC-MS [mobile phase: from 50% water (0.1% FA) and 50% MeCN (0.1% FA) to 5% water (0.1% FA) and 95% MeCN (0.1% FA) in 2.6 min]: Rt=0.968 min; MS Calcd: 363.01, MS Found: 364.2 $[M+H]^+$.

Description 298

6-(3-benzyl-3-azabicyclo[3.1.0]hexan-6-yl)-5-methyl-1H-indazole (D298)

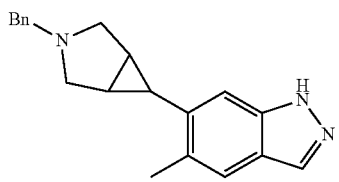 [SMILES: Cc1cc2cn[nH]c2cc1C1C2CN(Cc3ccccc3)CC21]

To a solution of 6-(3-benzyl-3-azabicyclo[3.1.0]hexan-6-yl)-5-methyl-1-(tetrahydro-2H-pyran-2-yl)-1H-indazole (400 mg, 1.03 mmol) in MeOH (20 ml) was added HCl/MeOH (3M, 20 mL) at rt. The reaction mixture was stirred at rt for 16 hrs and concentrated to give the product as a yellow solid (340 mg, crude).

LC-MS [mobile phase: from 50% water (0.1% FA) and 50% MeCN (0.1% FA) to 5% water (0.1% FA) and 95% MeCN (0.1% FA) in 2.6 min]: Rt=0.783 min; MS Calcd: 303.17, MS Found: 304.4 $[M+H]^+$.

Description 299

(1R,4R)-5-(6-(6-(3-benzyl-3-azabicyclo[3.1.0]hexan-6-yl)-5-methyl-1H-indazol-1-yl)-2-methylpyrimidin-4-yl)-2-oxa-5-azabicyclo[2.2.1]heptane (D299)

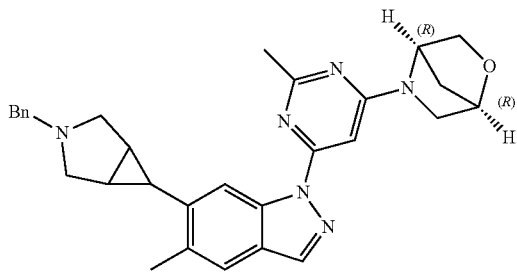

To a solution of 6-(3-benzyl-3-azabicyclo[3.1.0]hexan-6-yl)-5-methyl-1H-indazole (340 mg, 1.12 mmol) and (1R,4R)-5-(6-iodo-2-methylpyrimidin-4-yl)-2-oxa-5-azabicyclo[2.2.1]heptane (355 mg, 1.12 mmol) in toluene (30 ml) were added CuI (320 mg, 1.68 mmol), $K_3PO_4$ (475 mg, 2.24 mmol) and N,N'-dimethylethylenediamine (200 mg, 2.24 mmol). The reaction mixture was stirred at 100° C. for 4 h, cooled to rt, treated with $NH_4OH$ and extracted with EtOAc (2×50 mL). The combined organic parts were washed with brine (2×50 mL), dried over anhydrous $Na_2SO_4$, filtered and concentrated. The residue was purified by silica gel chromatography eluted with PE/EtOAc=2/1 to give the desired product as a white solid (290 mg, yield: 57%).

LC-MS [mobile phase: from 50% water (0.1% FA) and 50% MeCN (0.1% FA) to 5% water (0.1% FA) and 95% MeCN (0.1% FA) in 2.6 min]: Rt=0.843 min; MS Calcd: 492.26, MS Found: 493.4 $[M+H]^+$.

Description 300

(1R,4R)-5-(6-(6-(3-azabicyclo[3.1.0]hexan-6-yl)-5-methyl-1H-indazol-1-yl)-2-methylpyrimidin-4-yl)-2-oxa-5-azabicyclo[2.2.1]heptane (D300)

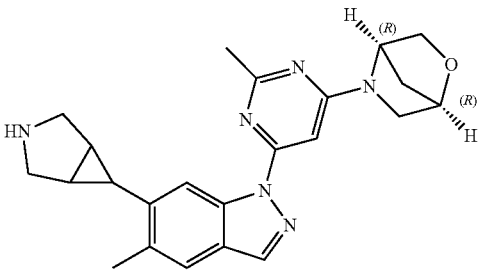

To a solution of (1R,4R)-5-(6-(6-(3-benzyl-3-azabicyclo[3.1.0]hexan-6-yl)-5-methyl-1H-indazol-1-yl)-2-methylpyrimidin-4-yl)-2-oxa-5-azabicyclo[2.2.1]heptane (290 mg, 0.59 mmol) in MeOH (20 mL) was added 10% Pd/C (290 mg) at rt under $H_2$. The reaction mixture was stirred at rt overnight, filtered and concentrated to give the title product as a white solid (220 mg, yield: 92%).

LC-MS [mobile phase: from 90% water (0.1% FA) and 10% MeCN (0.1% FA) to 5% water (0.1% FA) and 95% MeCN (0.1% FA) in 2.6 min]: Rt=1.213 min; MS Calcd: 402.22, MS Found: 403.4 $[M+H]^+$.

Example 1

(1R,4R)-5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.1]heptane

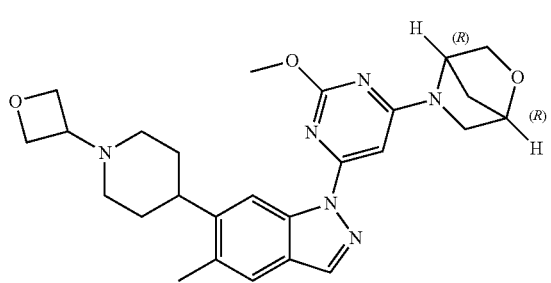

5-methyl-6-(1-(oxetan-3-yl)piperidin-4-yl)-1H-indazole (100 mg, 0.368 mmol), (1R,4R)-5-(6-iodo-2-methoxypyrimidin-4-yl)-2-oxa-5-azabicyclo[2.2.1]heptane (122.7 mg, 0.368 mmol), CuI (70.2 mg, 0.368 mmol), K$_3$PO$_4$ (156.4 mg, 0.737 mmol), N$^1$,N$^2$-dimethylethane-1,2-diamine (64.9 mg, 0.737 mmol) in toluene (5 mL) was stirred at 100° C. for 4 h. Then the mixture was cooled down to r.t. The organic phase was diluted with EtOAc (20 mL) and filtered through a pad of celite. The filtrate was concentrated to obtain the crude product, which was re-dissolved in DCM (5 mL) and further purified with prep-TLC to get the title product as a white solid (90 mg, yield 51%)

$^1$H NMR (400 MHz, CDCl$_3$): δ 8.77 (s, 1H), 8.07 (s, 1H), 7.51 (s, 1H), 6.54 (s, 1H), 5.30-5.27 (s, 1H), 4.74-4.68 (m, 5H), 4.16 (s, 3H), 3.94-3.88 (q, J=7.6 Hz, 2H), 3.57-3.45 (m, 4H), 2.94-2.91 (d, J=10.8 Hz, 2H), 2.86-2.80 (m, 1H), 2.45 (s, 3H), 2.04-1.82 (m, 7H).

LC-MS [mobile phase: from 80% water (0.1% TFA) and 20% ACN (0.1% TFA) to 20% water (0.1% TFA) and 80% ACN (0.1% TFA) in 10 min]: Rt=4.72 min; MS Calcd.: 476, MS Found: 477 [M+H]$^+$.

Example 2

(1S,4S)-5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.1]heptane

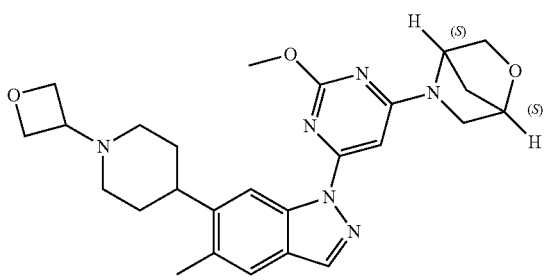

5-methyl-6-(1-(oxetan-3-yl)piperidin-4-yl)-1H-indazole (80 mg, 0.294 mmol), (1S,4S)-5-(6-iodo-2-methoxypyrimidin-4-yl)-2-oxa-5-azabicyclo[2.2.1]heptane (98.2 mg, 0.294 mmol), CuI (70.2 mg, 0.368 mmol,), K$_3$PO$_4$ (125.2 mg, 0.589 mmol), N$^1$,N$^2$-dimethylethane-1,2-diamine (52.9 mg, 0.589 mmol) in toluene (5 mL) was stirred at 100° C. for 4 h. Then the mixture was cooled down to rt. The organic phase was diluted with EtOAc (20 mL) and filtered through a pad of celite. The filtrate was concentrated to obtain the crude. The crude was re-dissolved in DCM (5 mL) and further purified with prep-TLC to get the title product as a white solid (90 mg, yield 64%)

$^1$H NMR (400 MHz, CDCl$_3$): δ 8.77 (s, 1H), 8.07 (s, 1H), 7.51 (s, 1H), 6.54 (s, 1H), 5.30-5.27 (s, 1H), 4.74-4.68 (m, 5H), 4.16 (s, 3H), 3.97-3.88 (q, J=7.6 Hz, 2H), 3.57-3.45 (m, 4H), 2.94-2.91 (d, J=9.6 Hz, 2H), 2.86-2.80 (m, 1H), 2.45 (s, 3H), 2.04-1.82 (m, 7H).

LC-MS [mobile phase: from 90% water (0.1% TFA) and 10% ACN (0.1% TFA) to 10% water (0.1% TFA) and 90% ACN (0.1% TFA) in 10 min]: Rt=5.71 min; MS Calcd.: 476, MS Found: 477 [M+H]$^+$.

Example 3

(1R,4R)-5-(2-methoxy-6-(6-(1-methylcyclopropoxy)-1H-indazol-1-yl)pyrimidin-4-yl)-2-oxa-5-azabicyclo[2.2.1]heptane

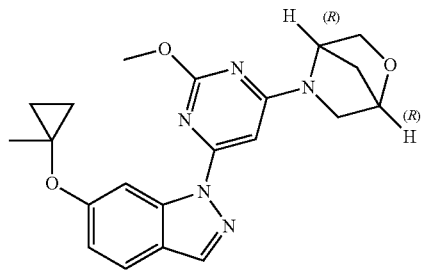

A mixture of 6-(1-methylcyclopropoxy)-1H-indazole (50 mg, 0.25 mmol,), (1R,4R)-5-(6-iodo-2-methoxypyrimidin-4-yl)-2-oxa-5-azabicyclo[2.2.1]heptane (91 mg, 0.27 mmol), CuI (47 mg, 0.25 mmol), K$_3$PO$_4$ (106 mg, 0.5 mmol) and N,N'-dimethylcyclohexane-1,2-diamine (71 mg, 0.5 mmol) in toluene (3.0 mL) was stirred at 100° C. for 4 hours. The mixture was diluted with EtOAc (100 mL), washed with brine (50 mL), dried over Na$_2$SO$_4$, filtered and concentrated to give the title compound (36 mg, 34%) as a white solid.

$^1$HNMR (400 MHz, DMSO-d$_6$): δ 8.44 (d, J=2 Hz, 1H), 8.33 (s, 1H), 7.74 (d, J=8.8 Hz, 1H), 6.93-6.90 (m, 1H), 4.72 (s, 1H), 4.00 (s, 3H), 3.81 (d, J=6 Hz, 1H), 3.70 (d, J=7.2 Hz, 1H), 3.54-3.52 (m, 2H), 3.45-3.32 (m, 2H), 1.89 (s, 2H), 1.57 (s, 3H), 0.99-0.96 (m, 2H), 0.79-0.76 (m, 2H).

LC-MS [column: C$_{18}$; column size: 4.6×50 mm; mobile phase: B (ACN): A (0.02% NH$_4$OAc); gradient (B %) in 6 min]: Rt=3.616 min, MS Calcd.: 393, MS Found: 394 [M+H]$^+$.

Example 4

(1S,4S)-5-(2-methoxy-6-(6-(1-methylcyclopropoxy)-1H-indazol-1-yl)pyrimidin-4-yl)-2-oxa-5-azabicyclo[2.2.1]heptane

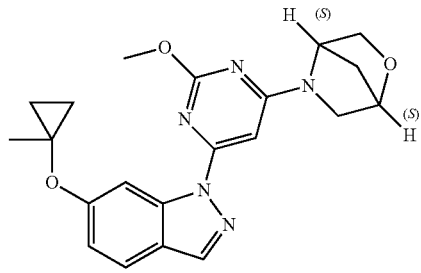

A mixture of (1S,4S)-5-(6-iodo-2-methoxypyrimidin-4-yl)-2-oxa-5-azabicyclo[2.2.1]heptane (98 mg, 0.293 mmol), 6-(1-methylcyclopropoxy)-1H-indazole (50 mg, 0.266 mmol), CuI (51 mg, 0.266 mmol), K$_3$PO$_4$ (113 mg, 0.532 mmol) and N,N'-dimethylcyclohexane-1,2-diamine (76 mg, 0.532 mmol) in toluene (3 mL) was stirred at 100° C. for 2 hours under N$_2$. The reaction was diluted with EtOAc (50 mL), washed with brine (50 mL×3), dried over Na$_2$SO$_4$, filtered and concentrated, the residue was purified by chiral- HPLC (column: Chiralpak IC; 5 μm 20×150 mm; Phase: Hex:EtOH=70:30, flow rate: 15 mL/min; wave length: 230 nm) to give the title compound (27 mg, 26%) as a white solid.

¹HNMR (400 MHz, CDCl₃): δ 8.50 (d, J=2.4 Hz, 1H), 8.07 (d, J=0.8 Hz, 1H), 7.59 (d, J=8.8 Hz, 1H), 6.91 (dd, J=2.4 Hz, J=8.8 Hz, 1H), 6.60 (dr s, 1H), 5.25 (dr s, 1H), 4.77-4.71 (m, 1H), 4.11 (s, 3H), 3.93-3.88 (m, 2H), 3.62-3.43 (m, 2H), 2.04-1.90 (s, 2H), 1.64 (s, 3H), 1.12-1.04 (m, 2H), 0.75-0.68 (m, 2H).

LC-MS [column: C₁₈; column size: 4.6×50 mm; mobile phase: B (ACN): A (0.02% NH₄OAc); gradient (B %) in 6 min]: Rt=4.083 min; MS Calcd.: 393, MS Found: 394 [M+H]⁺.

Example 5

(1R,4R)-5-(6-(5-chloro-6-(1-(oxetan-3-yl)piperidin-4-yl)-1H-indazol-1-yl)-2-methoxypyrimidin-4-yl)-2-oxa-5-azabicyclo[2.2.1]heptane

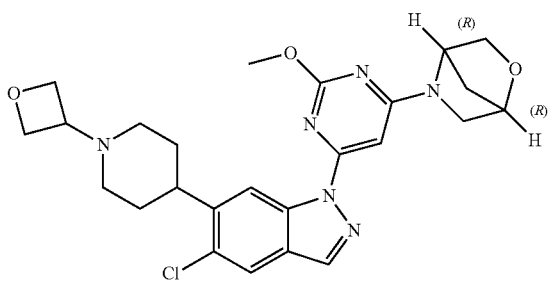

DMEDA (59 uL, 0.54 mmol) was added to a solution of 5-chloro-6-(1-(oxetan-3-yl)piperidin-4-yl)-1H-indazole (80 mg, 0.27 mmol), (1R,4R)-5-(6-iodo-2-methoxypyrimidin-4-yl)-2-oxa-5-azabicyclo[2.2.1]heptane (100 mg, 0.30 mmol), CuI (52 mg, 0.27 mmol) and K3PO4 (117 mg, 0.54 mmol) in toluene (5 mL) under Ar. The reaction was stirred at 100° C. for 3.5 h. The mixture was filtered and the filtrate was concentrated. The residue was purified by column chromatography (DCM:MeOH=50:1) to give product as a white solid (35 mg, yield: 26%).

LC-MS [mobile phase: from 80% water (0.1% FA) and 20% ACN (0.1% FA) to 5% water (0.1% FA) and 95% ACN (0.1% FA) in 10.0 min]: Rt=5.217 min; MS Calcd: 496.2, MS Found: 497.7 [M+H]⁺.

¹H NMR (400 MHz, CDCl₃) δ 8.86 (s, 1H), 8.09 (s, 1H), 7.75 (s, 1H), 6.56 (br 1H), 5.27 (br 1H), 4.75 (s, 1H), 4.72-4.55 (m, 4H), 4.14 (s, 3H), 4.00-3.80 (m, 2H), 3.66-3.36 (m, 3H), 3.13 (t, J=12.0 Hz, 1H), 2.93 (d, J=10.6 Hz, 2H), 2.05-1.78 (m, 8H).

Example 6

(1S,4S)-5-(6-(5-chloro-6-(1-(oxetan-3-yl)piperidin-4-yl)-1H-indazol-1-yl)-2-methoxypyrimidin-4-yl)-2-oxa-5-azabicyclo[2.2.1]heptane

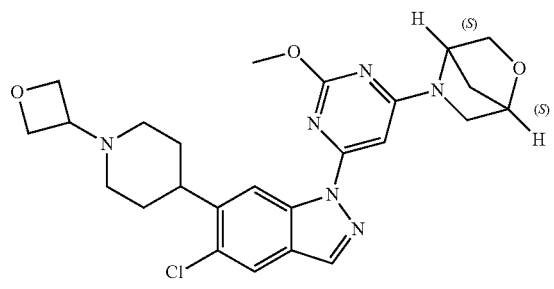

To a solution of 5-chloro-6-(1-(oxetan-3-yl)piperidin-4-yl)-1H-indazole (80 mg, 0.27 mmol), (1S,4S)-5-(6-iodo-2-methoxypyrimidin-4-yl)-2-oxa-5-azabicyclo[2.2.1]heptane (100 mg, 0.27 mmol), CuI (52 mg, 0.27 mmol) and K₃PO₄ (117 mg, 0.54 mmol) in dry toluene (5 mL) was added N,N-dimethyl-1,2-ethanediamine (59 mg, 0.54 mmol). The suspension was degassed with Ar and refluxed at 90° C. for 3 hours. After the reaction was cooled to room temperature, the mixture was filtered. The residue was wash with DCM (20 mL). Then the filtrate's solvent was removed under vacuum and the residue was purified by column chromatography (DCM:MeOH=10:1) to give the title product (80 mg, yield: 58.7%) as a white solid.

¹H NMR (400 MHz, CDCl₃) δ 8.86 (s, 1H), 8.08 (s, 1H), 7.75 (s, 1H), 6.56 (br 1H), 5.26 (br 1H), 4.75 (s, 1H), 4.70-4.50 (m, 4H), 4.14 (s, 3H), 4.00-3.80 (m, 2H), 3.59-3.47 (m, 3H), 3.13 (t, J=12.0 Hz, 1H), 2.93 (d, J=11.2 Hz, 2H), 2.08-1.79 (m, 8H).

LC-MS [mobile phase: from 80% water (0.1% FA) and 20% ACN (0.1% FA) to 5% water (0.1% FA) and 95% ACN (0.1% FA) in 10.0 min]: Rt=5.04 min; MS Calcd: 496, MS Found: 497 [M+H]⁺.

Examples 7 and 8

A solution of 4-(1-(6-((1S,4S)-2-oxa-5-azabicyclo[2.2.1]heptan-5-yl)-2-methyl-pyrimidin-4-yl)-5-methyl-1H-indazol-6-yl)cyclohexanone (166 mg, 0.40 mmol) in dry THF (5.0 mL) was cooled to −20° C. and methylmagnesium bromide (2.0 mL, 2.0 mmol) was added dropwise. Then the reaction mixture was stirred at room temperature for 2 h. The reaction mixture was quenched with brine (15 mL) at 0° C. and the mixture was extracted with EtOAc (30 mL×3). The organic layers were dried over Na₂SO₄ and concentrated by vacuum. The crude was purified by pre-HPLC to give two white solids:

Example 7

Cis-4-(1-(6-((1S,4S)-2-oxa-5-azabicyclo[2.2.1]heptan-5-yl)-2-methylpyrimidin-4-yl)-5-methyl-1H-indazol-6-yl)-1-methylcyclohexanol (34 mg, Yield=19.7%)

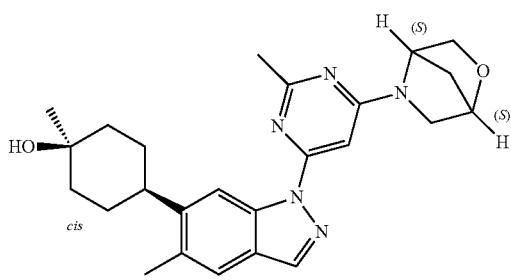

$^1$H NMR (400 MHz, CDCl$_3$): δ 8.86 (s, 1H), 8.05 (s, 1H), 7.49 (s, 1H), 6.66 (s, 1H), 5.35-5.30 (m, 1H), 4.74 (s, 1H), 3.90 (s, 2H), 3.54 (s, 2H), 2.78 (m, 1H), 2.61 (s, 3H), 2.45 (m, 3H), 1.98-1.96 (m, 4H), 1.87-1.80 (m, 4H), 1.77-1.63 (m, 6H).

LC-MS [mobile phase: from 70% water (0.1% FA) and 30% ACN (0.1% FA) to 5% water (0.1% FA) and 95% ACN (0.1% FA) in 10 min]: Rt=8.49 min; MS Calcd: 433.55, MS Found: 434.6 [M+H]$^+$.

Example 8

Trans-4-(1-(6-((1S,4S)-2-oxa-5-azabicyclo[2.2.1]heptan-5-yl)-2-methylpyrimidin-4-yl)-5-methyl-1H-indazol-6-yl)-1-methylcyclohexanol (21 mg, Yield=12.1%)

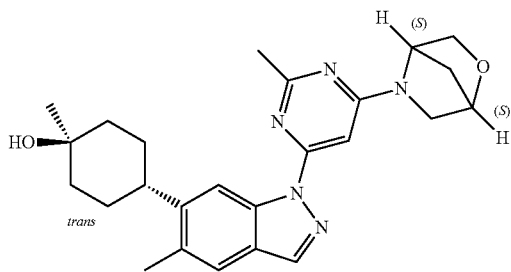

$^1$H NMR (400 MHz, CDCl$_3$): δ8.85 (s, 1H), 8.05 (s, 1H), 7.49 (s, 1H), 6.67 (s, 1H), 5.36-5.31 (m, 1H), 4.74 (s, 1H), 3.90 (s, 2H), 3.54 (s, 2H), 2.87 (m, 1H), 2.61 (s, 3H), 2.46 (m, 3H), 1.92-1.91 (m, 4H), 1.71-1.69 (m, 4H), 1.60-1.59 (m, 6H).

LC-MS [mobile phase: from 70% water (0.1% FA) and 30% ACN (0.1% FA) to 5% water (0.1% FA) and 95% ACN (0.1% FA) in 10 min]: Rt=7.36 min; MS Calcd: 433, MS Found: 434 [M+H]$^+$.

Waters 2767/Qda; 1 Waters XBridge 30×150 mm 5 μm; flow rate: 20 ml/min; wave length: 214 nm/254 nm;

A: H$_2$O, B: ACN

Method:

| Time | B % |
|---|---|
| 0 | 10 |
| 2 | 60 |
| 12 | 90 |
| 12.5 | 95 |
| 15 | 95 |
| 15.2 | 10 |
| 18 | 10 |
| 0 | 10 |

Examples 9 and 10

A solution of 4-(1-(6-((1R,4R)-2-oxa-5-azabicyclo[2.2.1]heptan-5-yl)-2-methylpyrimidin-4-yl)-5-methyl-1H-indazol-6-yl)cyclohexanone (120 mg, 0.29 mmol) in THF (5 mL) was drop-wised added to methyl magnesium bromide (1 N in THF, 15 mL, 15 mmol) at −20° C. with stirring. Then the reaction was allowed warm to 25° C. with stirring for 3 hours. Then the reaction was quenched with sat.NH$_4$Cl (20 mL) and the mixture was extracted with EtOAc (2×20 mL). The organic phase was washed with brine (2×50 mL), dried over Na$_2$SO$_4$ and concentrated to obtain the crude. The crude was purified by Prep-HPLC to obtain two white solid:

Example 9

Cis-4-(1-(6-((1R,4R)-2-oxa-5-azabicyclo[2.2.1]heptan-5-yl)-2-methylpyrimidin-4-yl)-5-methyl-1H-indazol-6-yl)-1-methylcyclohexanol (Single Unknown Isomer 1, Rt=7.266 min) as a White Solid (23 mg, Yield 18.4%)

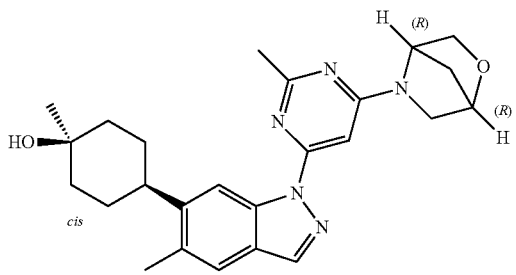

$^1$H NMR (400 MHz, CDCl$_3$): δ 8.86 (s, 1H), 8.05 (s, 1H), 7.49 (s, 1H), 6.66 (br, 1H), 5.30 (br, 1H), 4.74 (s, 1H), 3.90 (s, 2H), 3.54-3.53 (m, 2H), 2.81-2.75 (t, 1H), 2.61 (s, 3H), 2.45 (s, 3H), 1.98-1.93 (m, 4H), 1.87-1.77 (m, 4H), 1.67-1.60 (m, 2H), 1.32 (s, 3H), 1.32 (m, 1H).

LC-MS [mobile phase: from 70% water (0.1% TFA) and 30% ACN (0.1% TFA) to 30% water (0.1% TFA) and 70% ACN (0.1% TFA) in 10 min]: Rt=7.27 min; MS Calcd.: 433, MS Found: 434 [M+H]$^+$.

Example 10

Trans-4-(1-(6-((1R,4R)-2-oxa-5-azabicyclo[2.2.1]heptan-5-yl)-2-methylpyrimidin-4-yl)-5-methyl-1H-indazol-6-yl)-1-methylcyclohexanol (Single Unknown Enantiomer 2, Rt=5.939 min) as a White Solid (23 mg, Yield 18.4%)

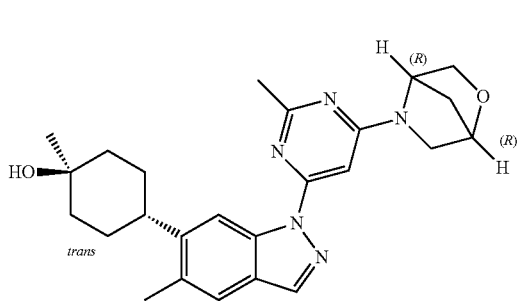

$^1$H NMR (400 MHz, CDCl$_3$): δ 8.85 (s, 1H), 8.05 (s, 1H), 7.49 (s, 1H), 6.67 (s, 1H), 5.28 (brs, 1H), 4.74 (s, 1H), 3.90 (s, 2H), 3.53 (s, 2H), 2.87 (s, 1H), 2.61 (s, 3H), 2.46 (s, 3H), 1.98-1.91 (m, 6H), 1.77-1.69 (m, 4H), 1.43 (s, 3H).

LC-MS [mobile phase: from 70% water (0.1% TFA) and 30% ACN (0.1% TFA) to 30% water (0.1% TFA) and 70% ACN (0.1% TFA) in 10 min]: purity 99.1%, Rt=5.94 min; MS Calcd.: 433, MS Found: 434 [M+H]$^+$.

Waters 2767/Qda; Waters XBridge 30×150 mm 5 μm; flow rate: 20 ml/min; wave length: 214 nm/254 nm; Trigger: 254 nm, A: H$_2$O, B: ACN Method:

| Time | B % |
| --- | --- |
| 0 | 10 |
| 2 | 60 |
| 12 | 90 |
| 12.5 | 95 |
| 15 | 95 |
| 15.2 | 10 |
| 18 | 10 |

Examples 11 and 12

To a solution of MeMgBr (3.0 mol/L in Et$_2$O, 0.28 mL, 0.84 mmol) in THF (10 mL) was added 4-(1-(6-((1R,4R)-2-oxa-5-azabicyclo[2.2.1]heptan-5-yl)-2-methoxypyrimidin-4-yl)-5-methyl-1H-indazol-6-yl)cyclohexanone (120 mg, 0.28 mmol) drop-wise at −20° C. The mixture was warmed at room temperature overnight under N$_2$. The reaction mixture was poured into sat.NH$_4$Cl (50 mL) and the mixture was extracted with EtOAc (50 mL×3). The combined organic layers were washed with brine (50 mL), dried over anhydrous Na$_2$SO$_4$, filtered and concentrated to dryness. The residue was purified by prep-HPLC (Waters 2767/Qda; Waters XBridge 30×150 mm 5 μm; flow rate: 20 ml/min; wave length: 214 nm/254 nm; Trigger: 254 nm, H$_2$O (0.05% TFA): acetonitrile=90:10~10:90) to give two white solids.

Example 11

Cis-4-(1-(6-((1R,4R)-2-oxa-5-azabicyclo[2.2.1]heptan-5-yl)-2-methoxypyrimidin-4-yl)-5-methyl-1H-indazol-6-yl)-1-methylcyclohexanol (Single Unknown Enantiomer 2, Rt=1.848 min) (18 mg, 14% Yield)

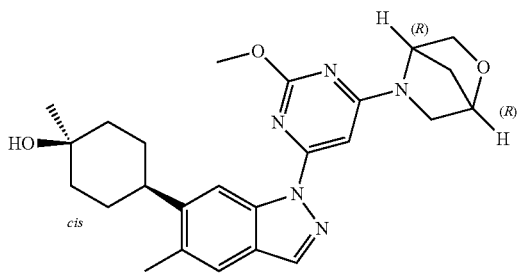

$^1$H NMR (400 MHz, CDCl$_3$): δ 8.879 (s, 1H), 8.064 (s, 1H), 7.497 (s, 1H), 6.534 (s, 0.6H), 5.256 (s, 0.5H), 4.735 (s, 1H), 4.178 (s, 3H), 3.911-3.890 (d, J=8.4 Hz, 2H), 3.540-3.464 (d, J=30.4 Hz, 2H), 2.822-2.768 (m, 1H), 2.457 (s, 3H), 1.974-1.940 (m, 4H), 1.602-1.569 (m, 4H), 1.308 (s, 3H), 0.880-0.836 (m, 4H).

LC-MS [mobile phase: from 90% water (0.1% FA) and 10% ACN (0.1% FA) to 5% water (0.1% FA) and 95% ACN (0.1% FA) in 2.5 min]: Rt=1.848 min; MS Calcd: 449, MS Found: 450[M+H]$^+$.

Example 12

Trans-4-(1-(6-((1R,4R)-2-oxa-5-azabicyclo[2.2.1]heptan-5-yl)-2-methoxypyrimidin-4-yl)-5-methyl-1H-indazol-6-yl)-1-methylcyclohexanol (Single Unknown Enantiomer 1, Rt=1.631 min) (9 mg, 7% Yield)

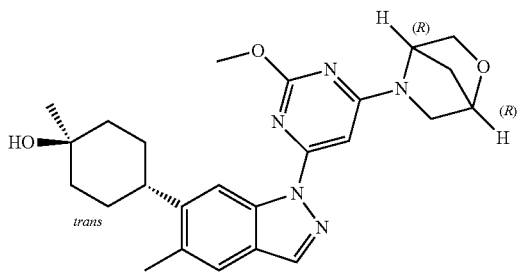

$^1$H NMR (400 MHz, CDCl$_3$): δ 8.776 (s, 1H), 8.070 (s, 1H), 7.510 (s, 1H), 6.557 (s, 0.6H), 5.249 (s, 0.5H), 4.741 (s, 1H), 4.164 (s, 3H), 3.911-3.895 (d, J=6.4 Hz, 2H), 3.552-3.481 (d, J=28.4 Hz, 2H), 2.876-2.856 (m, 1H), 2.461 (s, 3H), 1.924~1.866 (m, 4H), 1.694~1.658 (m, 4H), 1.559 (s, 3H), 0.880-0.835 (m, 4H).

LC-MS [mobile phase: from 90% water (0.1% FA) and 10% ACN (0.1% FA) to 5% water (0.1% FA) and 95% ACN (0.1% FA) in 2.5 min]: Rt=1.631 min; MS Calcd: 449, MS Found: 450 [M+H]$^+$.

Examples 13 and 14

(1R,4R)-5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.1]heptane

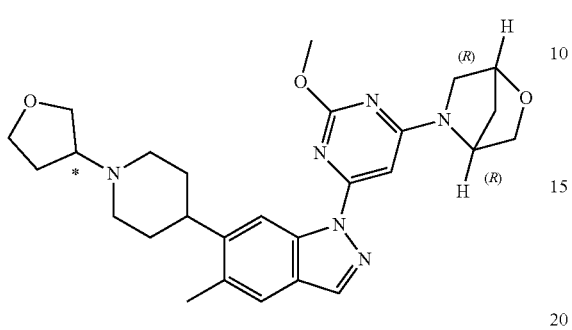

To a mixture of 5-methyl-6-(1-(tetrahydrofuran-3-yl)piperidin-4-yl)-1H-indazole (100 mg, 0.35 mmol), (1R,4R)-5-(6-iodo-2-methoxypyrimidin-4-yl)-2-oxa-5-azabicyclo[2.2.1]heptane (130 mg, 0.39 mmol), CuI (67 mg, 0.35 mmol) and $K_3PO_4$ (150 mg, 0.7 mmol) in toluene (5 mL) was added $N^1,N^2$-dimethylethane-1,2-diamine (62 mg, 0.7 mmol) at rt under $N_2$ protection. The mixture was warmed to 90° C. for 2 h under $N_2$. The reaction mixture was poured into water (30 mL) and the mixture was extracted with EtOAc (20 mL×3). The combined organic layers were washed with brine (30 mL), dried over anhydrous $Na_2SO_4$, filtered and concentrated to give crude product as a white solid. (100 mg, yield: 58%). The compound was chirally separated by KERMANDA.

Chiral prep-HPLC: AD-H, 0.46 cm I.D.×15 cm L, Phase: $CO_2$:EtOH (0.1% $NH_3.H_2O$)=60/40, Flow rate: 0.5 mL/min, Wave length: 254 nm, Temperature: 25° C.

Single Unknown Enantiomer 1 (E13, Rt=3.147 min)

$^1$H NMR (400 MHz, CDCl$_3$): δ 8.75 (s, 1H), 8.05 (s, 1H), 7.50 (s, 1H), 6.50 (s, 1H), 5.35 (s, 0.7H), 4.73 (s, 1H), 4.13 (s, 3H), 3.99~3.98 (m, 4H), 3.85~3.79 (m, 1H), 3.69~3.62 (m, 1H), 3.54~3.42 (m, 1H), 3.16~3.13 (m, 1H), 3.06~3.05 (m, 1H), 2.99~2.94 (m, 1H), 2.85~2.83 (m, 1H), 2.45 (s, 3H), 2.27~2.21 (m, 2H), 2.15~2.11 (m, 1H), 2.00~1.98 (s, 8H).

LC-MS [mobile phase: from 70% water (0.1% FA) and 30% ACN (0.1% FA) to 5% water (0.1% FA) and 95% ACN (0.1% FA) in 10 min]: Rt=1.98 min; MS Calcd: 490, MS Found: 491 [M+H]$^+$.

Chiral HPLC [AD-H, 0.46 cm I.D.×15 cm L, Phase: $CO_2$:EtOH (0.1% $NH_3H_2O$)=60/40, Flow rate: 0.5 mL/min, Wave length: 254 nm, Temperature: 25° C.]: Rt: 3.147 min; ee: 100% Single Unknown Enantiomer 2 (E14, Rt=5.410 min):

$^1$H NMR (400 MHz, CDCl$_3$): δ 8.75 (s, 1H), 8.05 (s, 1H), 7.50 (s, 1H), 6.50 (s, 1H), 5.35 (s, 0.7H), 4.73 (s, 1H), 4.13 (s, 3H), 3.99~3.96 (m, 4H), 3.87~3.79 (m, 1H), 3.69~3.62 (m, 1H), 3.54~3.42 (m, 1H), 3.16~3.12 (m, 1H), 3.06~3.05 (m, 1H), 2.98~2.94 (m, 1H), 2.85~2.83 (m, 1H), 2.45 (s, 3H), 2.27~2.21 (m, 2H), 2.15~2.11 (m, 1H), 2.00~1.98 (s, 8H).

LC-MS [mobile phase: from 90% water (0.1% FA) and 10% ACN (0.1% FA) to 5% water (0.1% FA) and 95% ACN (0.1% FA) in 10 min]: Rt=4.67 min; MS Calcd: 490 MS Found: 491 [M+H]$^+$.

Chiral HPLC [AD-H, 0.46 cm I.D.×15 cm L, Phase: HEP:EtOH (0.1% DEA)=60/40, Flow rate: 0.5 mL/min, Wave length: 254 nm, Temperature: 25° C.]: Rt: 5.410 min; ee: 100%

Examples 15 and 16

(1S,4S)-5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.1]heptane

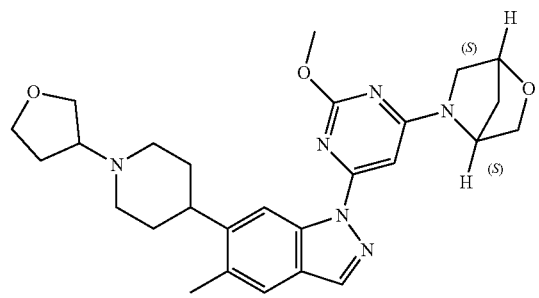

To a mixture of 5-methyl-6-(1-(tetrahydrofuran-3-yl)piperidin-4-yl)-1H-indazole (100 mg, 0.35 mmol), (1S,4S)-5-(6-iodo-2-methoxypyrimidin-4-yl)-2-oxa-5-azabicyclo[2.2.1]heptane (130 mg, 0.39 mmol), CuI (67 mg, 0.35 mmol) and $K_3PO_4$ (150 mg, 0.7 mmol) in toluene (5 mL) was added N1,N2-dimethylethane-1,2-diamine (62 mg, 0.7 mmol) at rt under $N_2$ protection. The mixture was warmed to 90° C. for 2 h under $N_2$. The reaction mixture was poured into water (30 mL) and the mixture was extracted with EtOAc (20 mL×3). The combined organic layers were washed with brine (30 mL), dried over anhydrous $Na_2SO_4$, filtered and concentrated to give crude product as a white solid. (67 mg, yield: 39%). The compound was chiral separated by KERMANDA.

Chiral method: AD-H, 0.46 cm I.D.*15 cm L, Phase: $CO_2$:EtOH (0.1% $NH_3H_2O$)=60/40, Flow rate: 0.5 mL/min, Wave length: 254 nm, Temperature: 25° C.

Example 15

(1S,4S)-5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.1]heptane, (Single Unknown Enantiomer 1, Rt=5.712 min)

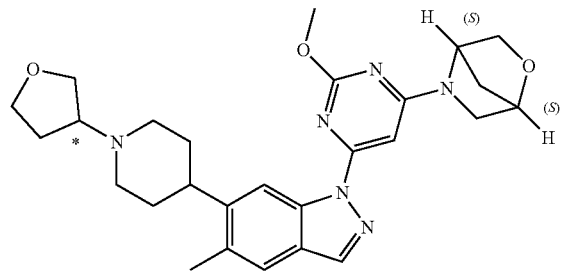

White solid. (12 mg, 7% yield)

$^1$H NMR (400 MHz, CDCl$_3$): δ 8.75 (s, 1H), 8.06 (s, 1H), 7.50 (s, 1H), 6.50 (s, 0.9H), 5.35 (s, 0.6H), 4.73 (s, 1H), 4.13

(s, 3H), 3.99~3.98 (m, 4H), 3.85~3.79 (m, 1H), 3.69~3.62 (m, 1H), 3.54~3.42 (m, 1H), 3.16~3.13 (m, 1H), 3.06~3.05 (m, 1H), 2.99~2.94 (m, 1H), 2.85~2.83 (m, 1H), 2.45 (s, 3H), 2.27~2.21 (m, 2H), 2.15~2.11 (m, 1H), 2.00~1.98 (s, 8H).

LC-MS [mobile phase: from 70% water (0.1% FA) and 30% ACN (0.1% FA) to 5% water (0.1% FA) and 95% ACN (0.1% FA) in 10 min]: Rt=2.11 min; MS Calcd: 490, MS Found: 491 [M+H]$^+$.

Chiral HPLC [AD-H, 0.46 cm I.D.×15 cm L, Phase: HEP:EtOH (0.1% DEA)=60/40, Flow rate: 0.5 mL/min, Wave length: 254 nm, Temperature: 25° C.]: Rt: 5.712 min; ee: 100%

Example 16

(1S,4S)-5-(2-methoxy-6-(5-methyl-6-(1-(tetrahydro-furan-3-yl)piperidin-4-yl)-1H-indazol-1-yl)pyrimi-din-4-yl)-2-oxa-5-azabicyclo[2.2.1]heptane, (Single Unknown Enantiomer 2, Rt=6.709 min)

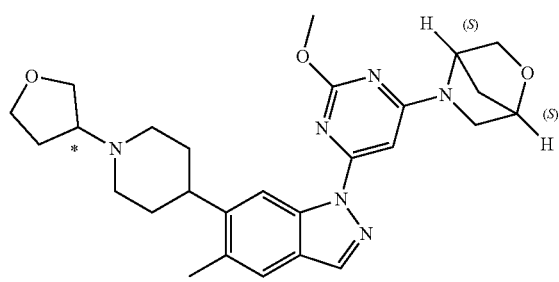

White solid. (11 mg, 6% yield)

$^1$H NMR (400 MHz, CDCl$_3$): δ 8.75 (s, 1H), 8.06 (s, 1H), 7.50 (s, 1H), 6.50 (s, 0.9H), 5.35 (s, 0.7H), 4.73 (s, 1H), 4.13 (s, 3H), 3.99~3.96 (m, 4H), 3.87~3.79 (m, 1H), 3.69~3.62 (m, 1H), 3.54~3.42 (m, 1H), 3.16~3.12 (m, 1H), 3.06~3.05 (m, 1H), 2.98~2.94 (m, 1H), 2.85~2.83 (m, 1H), 2.45 (s, 3H), 2.27~2.21 (m, 2H), 2.15~2.11 (m, 1H), 2.00~1.98 (s, 8H).

LC-MS [mobile phase: from 70% water (0.1% FA) and 30% ACN (0.1% FA) to 5% water (0.1% FA) and 95% ACN (0.1% FA) in 10 min]: Rt=2.10 min; MS Calcd: 490.6, MS Found: 491.3 [M+H]$^+$.

Chiral HPLC [AD-H, 0.46 cm I.D.×15 cm L, Phase: HEP:EtOH (0.1% DEA)=60/40, Flow rate: 0.5 mL/min, Wave length: 254 nm, Temperature: 25° C.]: Rt: 6.709 min; ee: 100%

Example 17

2-(4-(1-(6-(((1R,4R)-2-oxa-5-azabicyclo[2.2.1]hep-tan-5-yl)-2-methoxypyrimidin-4-yl)-5-methyl-1H-indazol-6-yl)-3-fluoropiperidin-1-yl)ethanol (Single Unknown Enantiomer 1, Rt=11.593 min) (from Peak 1)

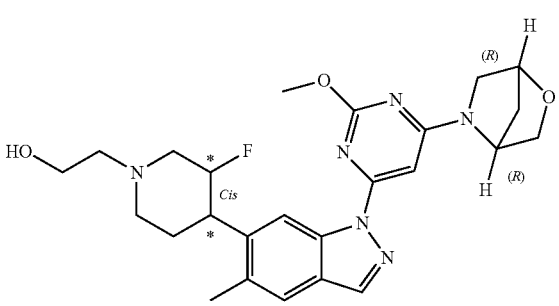

To a mixture of ethyl 2-(4-(1-(6-((1R,4R)-2-oxa-5-azabi-cyclo[2.2.1]heptan-5-yl)-2-methoxypyrimidin-4-yl)-5-methyl-1H-indazol-6-yl)-3-fluoropiperidin-1-yl)acetate (from Peak 1, 60 mg, 0.11 mmol) was dissolved in dry THF (3 mL) was added LiAlH$_4$ (22 mg, 0.55 mmol). The mixture was stirred at rt for 30 min, quenched with EtOAc (20 mL), filtered and concentrated. The residue was purified by C$_{18}$ column eluted with MeCN/H$_2$O (0.1% NH$_3$H$_2$O, from 5/95 to 90/10) to give the target product as a white solid (29 mg, yield: 55%).

$^1$H NMR (400 MHz, CDCl$_3$): δ 8.83 (s, 1H), 8.08 (s, 1H), 7.54 (s, 1H), 6.53 (br, 0.7H), 5.26 (s, 1H), 4.87 (s, 1H), 4.73 (br, 1H), 3.98 (s, 3H), 3.91~3.89 (m, 2H), 3.68~3.66 (m, 2H), 3.58~3.53 (m, 1H), 3.41~3.39 (m, 1H), 3.14~3.02 (m, 1H), 3.01~2.99 (m, 1H), 2.71~2.68 (m, 2H), 2.48 (s, 3H), 2.36~2.23 (m, 2H), 1.94~1.82 (m, 3H), 1.58~1.57 (m, 2H).
$^{19}$F NMR (376 MHz, CDCl$_3$): δ −183.92 (s)

LC-MS [mobile phase: 80% water (0.1% FA) and 20% ACN (0.1% FA) to 5% water (0.1% FA) and 95% ACN (0.1% FA) in 10.0 min]: Rt=3.80 min; MS Calcd.: 482, MS Found: 483 [M+H]$^+$.

Chiral HPLC [AD 4.6×250 mm, 5 μm (Daicel) (CA-HPLC-023), Phase: Hexane/EtOH (0.2% DEA)=60/40, flowrate: 1 mL/min, temperature: 35° C.]: Rt: 11.625 min, 100% ee.

Example 18

2-(4-(1-(6-(((1R,4R)-2-oxa-5-azabicyclo[2.2.1]hep-tan-5-yl)-2-methoxypyrimidin-4-yl)-5-methyl-1H-indazol-6-yl)-3-fluoropiperidin-1-yl)ethane (Single Unknown Enantiomer 2, Rt=18.919 min) (from Peak 2)

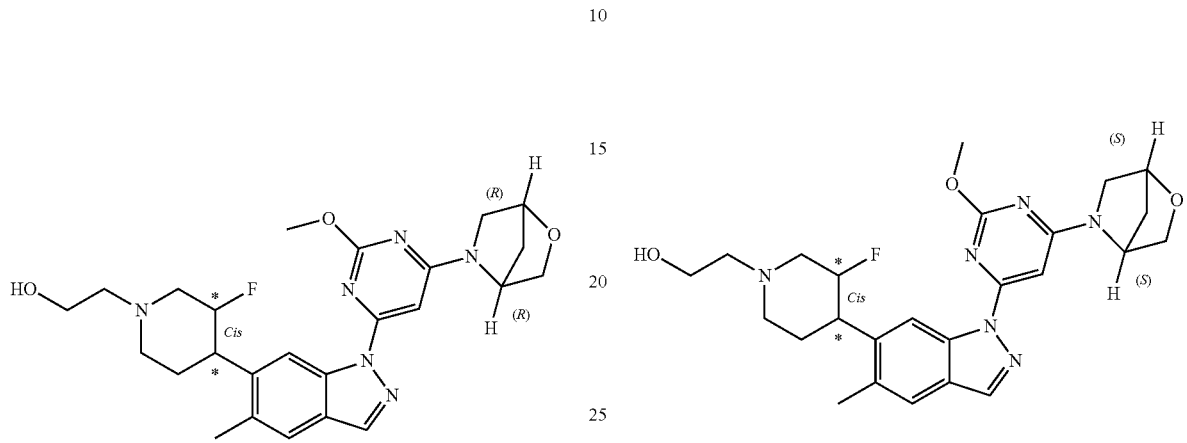

Ethyl 2-(4-(1-(6-(((1R,4R)-2-oxa-5-azabicyclo[2.2.1]hep-tan-5-yl)-2-methoxypyrimidin-4-yl)-5-methyl-1H-indazol-6-yl)-3-fluoropiperidin-1-yl)acetate (from Peak 2, 80 mg, 0.15 mmol) was dissolved in dried THF (3 mL), LiAlH$_4$ (30 mg, 0.75 mmol) was added to the solution and the mixture was stirred at Rt for 30 min. The reaction mixture was quenched with EtOAc (20 mL) and filtered. The filtrate was concentrated and the residue was purified by C$_{15}$ column eluting with MeCN/H$_2$O (0.1% NH$_3$H$_2$O, from 5/95 to 90/10) to give target product as a white solid (30 mg, yield: 40%).

$^1$H NMR (400 MHz, CDCl$_3$): δ 8.88 (s, 1H), 8.08 (s, 1H), 7.54 (s, 1H), 6.55 (br, 0.7H), 5.26 (br, 0.6H), 4.95~4.91 (m, 1H), 4.73 (s, 1H), 4.12 (s, 3H), 3.93~3.88 (m, 2H), 3.74~3.72 (m, 2H), 3.51~3.49 (m, 3H), 3.15~3.14 (m, 2H), 2.79~2.78 (m, 2H) 2.48 (s, 3H), 2.42~2.36 (m, 3H), 2.01~1.88 (m, 4H).

$^{19}$F NMR (376 MHz, CDCl$_3$): δ −183.92 (s)

LC-MS [mobile phase: 80% water (0.1% FA) and 20% ACN (0.1% FA) to 5% water (0.1% FA) and 95% ACN (0.1% FA) in 10.0 min]: Rt=3.83 min; MS Calcd.: 482, MS Found: 483 [M+H]$^+$.

Chiral HPLC [AD 4.6×250 mm, 5 μm (Daicel) (CA-HPLC-023), Phase: Hexane/EtOH (0.2% DEA)=60/40, flowrate: 1 mL/min, temperature: 35° C.]: Rt: 18.919 min, 95.3% ee.

Example 19

2-(4-(1-(6-(((1S,4S)-2-oxa-5-azabicyclo[2.2.1]hep-tan-5-yl)-2-methoxypyrimidin-4-yl)-5-methyl-1H-indazol-6-yl)-3-fluoropiperidin-1-yl)ethanol (from Peak 1) (Single Unknown Enantiomer 1)

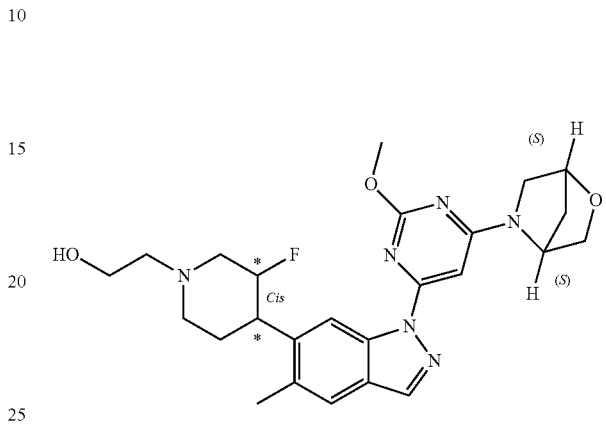

LiAlH$_4$ (19 mg, 0.50 mmol) was added to the solution of Cis-ethyl 2-(4-(1-(6-(((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)acetate (from Peak 1, 52 mg, 0.10 mmol) in THF (2 mL) and the reaction was stirred at rt for 60 min. The reaction was then quenched with EtOAc and sat. NH$_4$Cl. Then the mixture was filtered and the filtrate was concentrated and the residue was purified by C$_{18}$ flash column (acetonitrile:water=5:95-90:10) to give the product as a white solid (29 mg, yield: 61%).

$^1$H NMR (400 MHz, CDCl$_3$): δ 8.88 (s, 1H), 8.08 (s, 1H), 7.54 (s, 1H), 6.57 (br, 0.9H), 5.24 (br, 0.4H), 4.91~4.85 (m, 0.5H), 4.79~4.74 (m, 0.5H), 4.74 (s, 1H), 4.12 (s, 3H), 3.93~3.86 (m, 2H), 3.68 (t, J=5.2 Hz, 2H), 3.59~3.39 (m, 3H), 3.18~3.08 (m, 1H), 3.02 (d, J=10.4 Hz, 1H), 2.73~2.66 (m, 2H), 2.56~2.52 (m, 1H), 2.48 (s, 3H), 2.37 (dd, J=9.6, 4.0 Hz, 1H), 2.29 (dd, J=11.6, 2.0 Hz, 1H), 2.00~1.84 (m, 4H).

$^{19}$F NMR (376 MHz, CDCl$_3$): δ −183.91 (s)

LC-MS [mobile phase: from 90% water (0.1% FA) and 10% ACN (0.1% FA) to 5% water (0.1% FA) and 95% ACN (0.1% FA) in 9 min]: purity 100%, Rt=4.76 min; MS Calcd: 482, MS Found: 483 [M+H]$^+$.

Chiral HPLC [Column: AD Column size: 0.46 cm I.D.× 25 cm, 5 μm (Daicel) (CA-HPLC-023). Injection: 10 μl, Mobile phase: Hexane:EtOH (0.2% DEA)=70:30, Flow rate: 1 ml/min, Wave length: UV 254 nm, Temperature: 35° C.]: Rt: 13.088 min, ee: 100%

Example 20

2-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)ethanol (from Peak 2) (Single Unknown Enantiomer 2)

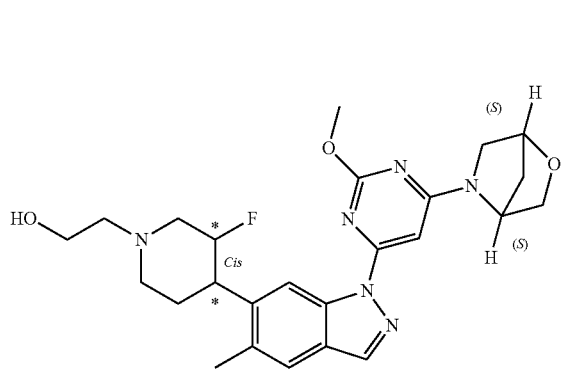

LiAlH$_4$ (19 mg, 0.50 mmol) was added to the solution of Cis-ethyl 2-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)acetate (from Peak 2, 53 mg, 0.10 mmol) in THF (2 mL) and the reaction was stirred at Rt for 60 min. The reaction was then quenched with EtOAc and sat. NH$_4$Cl.

Then the mixture was filtered and the filtrate was concentrated and the residue was purified by C$_{18}$ flash column (acetonitrile:water=5:95~90:10) to give the product as a white solid (36 mg, yield: 74%).

$^1$H NMR (400 MHz, CDCl$_3$): δ 8.88 (s, 1H), 8.08 (s, 1H), 7.54 (s, 1H), 6.56 (br, 0.9H), 5.26 (br, 0.4H), 4.92~4.86 (m, 0.5H), 4.80~4.74 (m, 0.5H), 4.74 (s, 1H), 4.12 (s, 3H), 3.93~3.88 (m, 2H), 3.68 (t, J=4.8 Hz, 2H), 3.59~3.40 (m, 3H), 3.18~3.08 (m, 1H), 3.03 (d, J=10.8 Hz, 1H), 2.73~2.66 (m, 2H), 2.56~2.52 (m, 1H), 2.49 (s, 3H), 2.38 (dd, J=9.6, 4.0 Hz, 1H), 2.30 (m, 1H), 2.01~1.84 (m, 4H).

$^{19}$F NMR (376 MHz, CDCl$_3$): δ −183.94 (s)

LC-MS [mobile phase: from 90% water (0.1% FA) and 10% ACN (0.1% FA) to 5% water (0.1% FA) and 95% ACN (0.1% FA) in 9 min]: Rt=4.77 min; MS Calcd: 482, MS Found: 483 [M+H]$^+$.

Chiral HPLC [Column: AD Column size: 0.46 cm I.D.× 25 cm, 5 μm (Daicel) (CA-HPLC-023). Injection: 10 μl, Mobile phase: Hexane:EtOH (0.2% DEA)=70:30, Flow rate: 1 ml/min, Wave length: UV 254 nm, Temperature: 35° C.]: Rt: 16.844 min, ee: 96.5%

Example 21

2-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)ethanol (from Peak 1, Single Unknown Enantiomer 1)

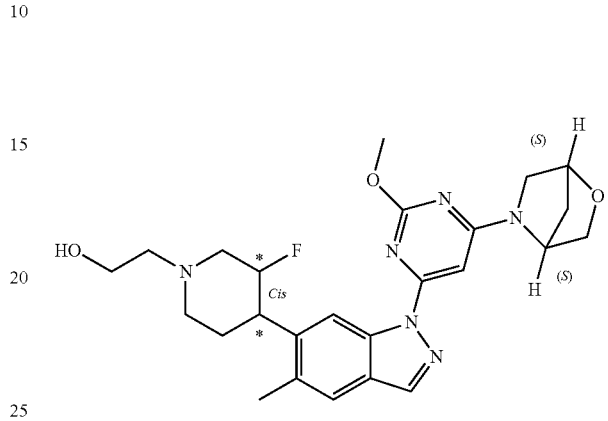

LiAlH$_4$ (21 mg, 0.56 mmol) was added to the solution of Cis-ethyl 2-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)acetate (from Peak 1, 57 mg, 0.11 mmol) in THF (2 mL) and the reaction was stirred at Rt for 60 min. The reaction was then quenched with EtOAc and sat. NH$_4$Cl. Then the mixture was filtered and the filtrate was concentrated and the residue was purified by C$_{18}$ flash column (acetonitrile:water=5:95~90:10) to give the product as a white solid (37 mg, yield: 71%).

$^1$H NMR (400 MHz, CDCl$_3$): δ 8.91 (s, 1H), 8.07 (s, 1H), 7.53 (s, 1H), 6.68 (br, 0.9H), 5.31 (br, 0.4H), 4.97~4.89 (m, 0.5H), 4.84~4.74 (m, 0.5H), 4.74 (s, 1H), 3.91 (brs, 2H), 3.71~3.66 (m, 2H), 3.56~3.43 (m, 3H), 3.18~3.08 (m, 1H), 3.05 (d, J=10.4 Hz, 1H), 2.73~2.69 (m, 2H), 2.61 (brs, 4H), 2.48 (s, 3H), 2.38 (dd, J=10.0, 4.4 Hz, 1H), 2.30 (dd, J=12.0, 2.0 Hz, 1H), 2.00~1.84 (m, 4H).

$^{19}$F NMR (376 MHz, CDCl$_3$): δ −183.88 (s)

LC-MS [mobile phase: from 90% water (0.1% FA) and 10% ACN (0.1% FA) to 5% water (0.1% FA) and 95% ACN (0.1% FA) in 9 min]: Rt=4.43 min; MS Calcd: 466, MS Found: 467 [M+H]$^+$.

Chiral HPLC [Column: AD Column size: 0.46 cm I.D.× 25 cm, 5 μm (Daicel) (CA-HPLC-023). Injection: 10 μl, Mobile phase: Hexane:EtOH (0.2% DEA)=70:30, Flow rate: 1 ml/min, Wave length: UV 254 nm, Temperature: 35° C.]: Rt: 8.762 min, ee: 100%

Example 22

2-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)ethanol (from Peak 2) (Single Unknown Enantiomer 2)

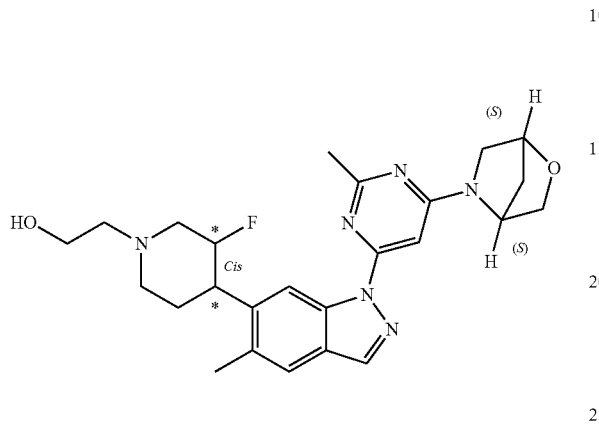

LiAlH$_4$ (19 mg, 0.51 mmol) was added to the solution of Cis-ethyl 2-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)acetate (from Peak 2, 52 mg, 0.10 mmol) in THF (2 mL) and the reaction was stirred at Rt for 60 min. The reaction was then quenched with EtOAc and sat. NH$_4$Cl. Then the mixture was filtered and the filtrate was concentrated and the residue was purified by C$_{18}$ flash column (acetonitrile:water=5:95-90:10) to give the product as a white solid (30 mg, yield: 63%).

$^1$H NMR (400 MHz, CDCl$_3$): δ 8.92 (s, 1H), 8.07 (s, 1H), 7.53 (s, 1H), 6.68 (br, 0.9H), 5.29 (br, 0.4H), 4.96~4.90 (m, 0.5H), 4.84~4.78 (m, 0.5H), 4.74 (s, 1H), 3.91 (brs, 2H), 3.71~3.66 (m, 2H), 3.56~3.43 (m, 3H), 3.18~3.08 (m, 1H), 3.05 (d, J=10.8 Hz, 1H), 2.73~2.69 (m, 2H), 2.61 (s, 4H), 2.48 (s, 3H), 2.38 (dd, J=10.0, 4.0 Hz, 1H), 2.30 (dd, J=12.0, 2.0 Hz, 1H), 2.01~1.88 (m, 4H).

$^{19}$F NMR (376 MHz, CDCl$_3$): δ −183.88 (s)

LC-MS [mobile phase: from 90% water (0.1% FA) and 10% ACN (0.1% FA) to 5% water (0.1% FA) and 95% ACN (0.1% FA) in 9 min]: purity 100%, Rt=4.46 min; MS Calcd: 466, MS Found: 467 [M+H]$^+$.

Chiral HPLC [Column: AD Column size: 0.46 cm I.D.× 25 cm, 5 μm (Daicel) (CA-HPLC-023).

Injection: 10 μl, Mobile phase: Hexane:EtOH (0.2% DEA)=70:30, Flow rate: 1 ml/min, Wave length: UV 254 nm, Temperature: 35° C.]: Rt: 10.654 min, ee: 97.4%

Example 23

Cis-2-(4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidin-1-yl)ethanol (Single Unknown Enantiomer 1, Rt=9.718 min)

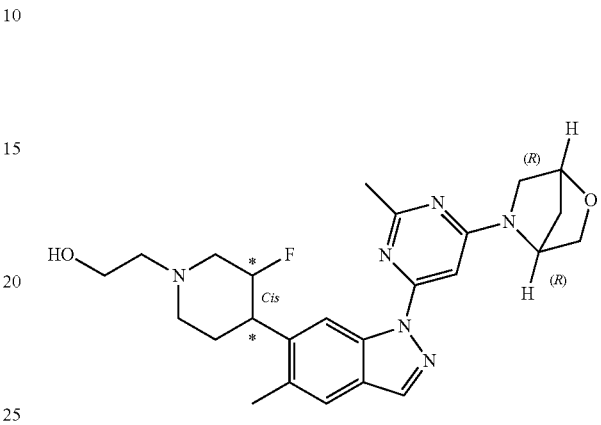

LiAlH$_4$ (12 mg, 0.32 mmol) was added to the solution of Cis-ethyl 2-(4-(1-(6-((1R,4R)-2-oxa-5-azabicyclo[2.2.1]heptan-5-yl)-2-methylpyrimidin-4-yl)-5-1H-indazol-6-yl)-3-(from Peak 1, 60 mg, 0.12 mmol) in THF (5 mL) and the reaction was stirred at rt for 10 min. The reaction was then quenched with sat. NH$_4$Cl (0.5 mL). Then the mixture was filtered and the filtrate was concentrated and the residue was purified by C$_{18}$ flash column (acetonitrile:water=5:95~90:10) to give the product as an off-white solid. (16 mg, 29% yield)

$^1$H NMR (400 MHz, CDCl$_3$): δ 8.92 (s, 1H), 8.07 (s, 1H), 7.53 (s, 1H), 6.70 (br, 0.9H), 5.35~5.29 (m, 0.3H), 4.94~4.79 (m, 1H), 4.74 (br, 1H), 3.91 (s, 2H), 3.72~3.69 (m, 2H), 3.55~3.42 (m, 3H), 3.15~3.02 (m, 2H), 2.73~2.69 (m, 2H), 2.61 (s, 3H), 2.48 (s, 3H), 2.35~2.21 (m, 2H), 1.99~1.92 (m, 4H).

$^{19}$F NMR (376 MHz, CDCl$_3$): δ −183.89 (s)

LC-MS [mobile phase: from 90% water (0.1% FA) and 10% ACN (0.1% FA) to 5% water (0.1% FA) and 95% ACN (0.1% FA) in 10 min]: Rt=4.33 min; MS Calcd: 466, MS Found: 467 [M+H]+.

Chiral HPLC [Column: AD Column size: 0.46 cm I.D.× 25 cm, 5 μm (Daicel) (CA-HPLC-023).

Injection: 10 μl, Mobile phase: Hexane:EtOH (0.2% DEA)=70:30, Flow rate: 1 ml/min, Wave length: UV 254 nm, Temperature: 35° C.]: Rt: 9.718 min, ee: 97.5%

Example 24

Cis-2-(4-(1-(6-((1R,4R)-2-oxa-5-azabicyclo[2.2.1]
heptan-5-yl)-2-methylpyrimidin-4-yl)-5-methyl-1H-
indazol-6-yl)-3-fluoropiperidin-1-yl)ethanol (Single
Unknown Enantiomer 2, Rt=13.492 min)

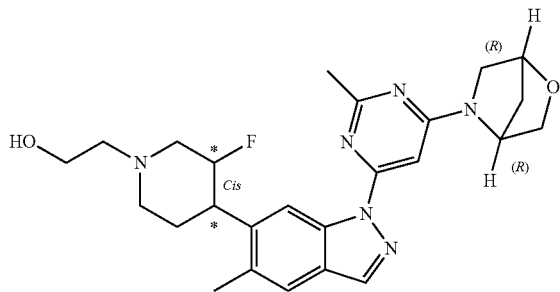

LiAlH₄ (7.6 mg, 0.2 mmol) was added to the solution of Cis-ethyl 2-(4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidin-1-yl)acetate (from Peak 2, 51 mg, 0.1 mmol) in THF (5 mL) and the reaction was stirred at Rt for 10 min. The reaction was then quenched with sat. NH₄Cl (0.5 mL). Then the mixture was filtered and the filtrate was concentrated and the residue was purified by C₁₈ flash column (acetonitrile:water=5:95~90:10) to give the product as an off-white solid. (11 mg, 24% yield)

$^1$H NMR (400 MHz, CDCl₃): δ 8.92 (s, 1H), 8.07 (s, 1H), 7.53 (s, 1H), 6.68 (br, 0.7H), 5.28 (br, 0.2H), 4.94~4.81 (m, 1H), 4.74 (br, 1H), 3.91 (s, 2H), 3.71 (m, 2H), 3.54~3.44 (m, 3H), 3.15~3.11 (m, 1H), 3.04 (m, 1H), 2.71 (m, 2H), 2.61 (s, 3H), 2.48 (s, 3H), 2.37~2.24 (m, 2H), 2.01~1.99 (m, 4H).

$^{19}$F NMR (376 MHz, CDCl₃): δ −183.89 (s)

LC-MS [mobile phase: from 90% water (0.1% FA) and 10% ACN (0.1% FA) to 5% water (0.1% FA) and 95% ACN (0.1% FA) in 10 min]: Rt=4.41 min; MS Calcd: 466.3, MS Found: 467.4[M+H]+.

Chiral HPLC [Column: AD Column size: 0.46 cm I.D.× 25 cm, 5 μm (Daicel) (CA-HPLC-023).

Injection: 10 μl, Mobile phase: Hexane:EtOH (0.2% DEA)=70:30, Flow rate: 1 ml/min, Wave length: UV 254 nm, Temperature: 35° C.]: Rt: 13.492 min, ee: 94.6%

To a mixture of 5-chloro-6-(1-(oxetan-3-yl)piperidin-4-yl)-1H-indazole (80 mg, 0.274 mmol), (1R,4R)-5-(6-iodo-2-methylpyrimidin-4-yl)-2-oxa-5-azabicyclo[2.2.1]heptane (87 mg, 0.274 mmol), CuI (52 mg, 0.273 mmol) and K₃PO₄ (175 mg, 0.824 mmol) under argon at room temperature was added dry toluene (3.0 ml), followed by addition of N,N′ dimethylethylenedia-mine (48 mg, 0.544 mmol) via syringe. The reaction was stirred under argon at 100° C. for 2.5 hours.

The reaction mixture was concentrated to dryness and the residue was purified by silica gel chromatography eluted with DCM/MeOH=50/1 afforded impure desired product as yellow solid (80 mg, confirmed by TLC). The obtained product was further purified by preparative HPLC (acidic conditions). The fractions were concentrated to dryness afforded TFA salt of desired product as white solid. The white solid was suspended in water (5 ml) and aq. NH₃.H₂O (2 ml) was added. The resultant was filtered and the filter cake was suspended in water (10 ml) with addition of a small amount of MeOH (ca. 1 ml). Further drying under lyophilizer afforded pure desired product as white solid (47 mg, Yield: 35%).

$^1$H NMR (400 MHz, CDCl₃) δ 8.94 (s, 1H), 8.07 (s, 1H), 7.74 (s, 1H), 6.68 (br 1H), 5.30 (br 1H), 4.75-4.71 (m, 5H), 3.91 (s, 2H), 3.59-3.40 (m, 3H), 3.14 (t, J=11.8 Hz, 1H), 2.97 (d, J=10.0 Hz, 2H), 2.63 (s, 3H), 2.08-1.85 (m, 8H).

LC-MS [mobile phase: from 90% water (0.1% FA) and 10% ACN (0.1% FA) to 5% water (0.1% FA) and 95% ACN (0.1% FA) in 10 min]: Rt=5.64 min; MS Calcd: 480, MS Found: 481 [M+H]+.

Prep-HPLC:

Instrument: Gilson 281, Column: YMC-Actus Triart Prep C18-S 250×20 mm 10 μm

Flow rate: 20 ml/min, Wavelength: 214 nm/254 nm, Trigger: 254 nm

Mobile phase A: H₂O (0.05% TFA), Mobile phase B: ACN

Gradient Method:

| Time | B % |
|---|---|
| 0 | 20 |
| 15.2 | 40 |
| 15.5 | 95 |
| 17.5 | 95 |
| 17.7 | 10 |
| 20 | 10 |

Example 25

(1R,4R)-5-(6-(5-chloro-6-(1-(oxetan-3-yl)piperidin-4-yl)-1H-indazol-1-yl)-2-methylpyrimidin-4-yl)-2-oxa-5-azabicyclo[2.2.1]heptane

Example 26

(1S,4S)-5-(6-(5-chloro-6-(1-(oxetan-3-yl)piperidin-4-yl)-1H-indazol-1-yl)-2-methylpyrimidin-4-yl)-2-oxa-5-azabicyclo[2.2.1]heptane

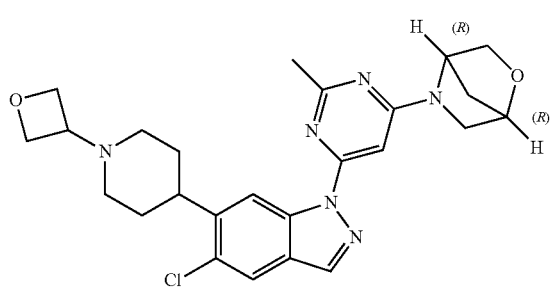

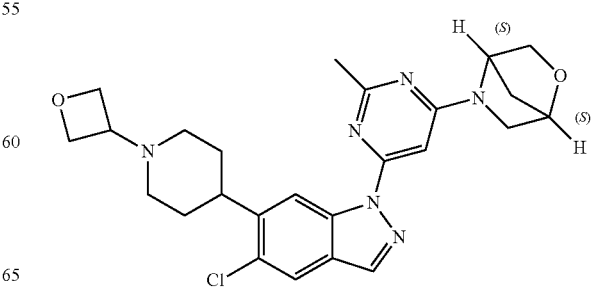

To a mixture of 5-chloro-6-(1-(oxetan-3-yl)piperidin-4-yl)-1H-indazole (80 mg, 0.274 mmol), (1S,4S)-5-(6-iodo-2-methylpyrimidin-4-yl)-2-oxa-5-azabicyclo[2.2.1]heptane (87 mg, 0.274 mmol), CuI (52 mg, 0.273 mmol) and $K_3PO_4$ (175 mg, 0.824 mmol) under argon at room temperature was added dry toluene (3.0 ml), followed by addition of N,N'-dimethylethylenediamine (48 mg, 0.544 mmol) via syringe. The reaction was stirred under argon at 100° C. for 4 hours.

The reaction mixture was concentrated to dryness and the residue was purified by silica gel chromatography eluted with DCM/MeOH=30/1 afforded impure desired product as yellow solid. The obtained product was further purified by silica gel chromatography eluted with DCM/MeOH=40/1 afforded a light yellow solid. The solid was dissolved in MeCN (2 ml) and water (6 ml) was added, white solid precipitated. The resultant was filtered and the filter cake was washed by water (10 ml), dried under infrared lamp and collected to give pure desired product as white solid (51 mg, Yield: 38%).

$^1$H NMR (400 MHz, CDCl$_3$) δ 8.94 (s, 1H), 8.07 (s, 1H), 7.74 (s, 1H), 6.68 (br 1H), 5.35 (br 1H), 4.75-4.70 (m, 5H), 3.91 (s, 2H), 3.60-3.40 (m, 3H), 3.16-3.10 (m, 1H), 2.97 (d, J=10.8 Hz, 2H), 2.63 (s, 3H), 2.06-1.84 (m, 8H).

LC-MS [mobile phase: from 90% water (0.1% FA) and 10% ACN (0.1% FA) to 5% water (0.1% FA) and 95% ACN (0.1% FA) in 10 min]: purity: 97% @ 254 nm; R.T.=5.47 min; MS Calcd: 480.20, MS Found: 481.7 [M+H]$^+$.

Example 27

2-(4-(1-(6-((1R,4R)-2-oxa-5-azabicyclo[2.2.1]heptan-5-yl)-2-methoxypyrimidin-4-yl)-5-methyl-1H-indazol-6-yl)piperidin-1-yl)ethanol

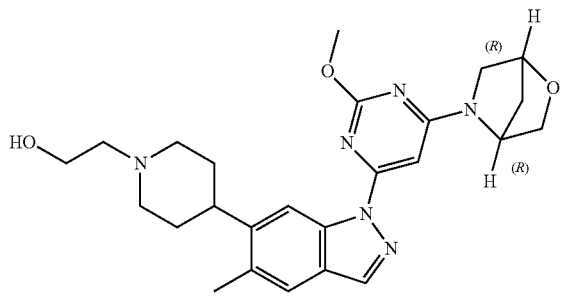

LiAlH$_4$ (30 mg, 0.79 mmol) was added to the solution of ethyl 2-(4-(1-(6-((1R,4R)-2-oxa-5-azabicyclo[2.2.1]heptan-5-yl)-2-methoxypyrimidin-4-yl)-5-methyl-1H-indazol-6-yl)piperidin-1-yl)acetate (80 mg, 0.16 mmol) in THF (5 mL) and the reaction was stirred at Rt for 0.5 hour. The reaction was then quenched with EtOAc. Then the mixture was filtered and the filtrate was concentrated and the residue was purified by C18 flash column (acetonitrile:water=5:95~100:0) to give the product as a brown solid (24 mg, yield: 33%).

$^1$H NMR (400 MHz, CDCl$_3$): δ 8.78 (s, 1H), 8.06 (s, 1H), 7.51 (s, 1H), 6.56 (br, 1H), 5.28 (br, 0.5H), 4.74 (br, 1H), 4.15 (s, 3H), 3.93 (dd, J=13.6, 7.6 Hz, 2H), 3.66 (t, J=5.2 Hz, 2H), 3.55~3.48 (m, 2H), 3.11 (d, J=11.2 Hz, 2H), 2.90~2.81 (m, 1H), 2.62 (t, J=5.2 Hz, 2H), 2.46 (s, 3H), 2.28 (t, J=11.2 Hz, 2H), 2.00~1.75 (m, 7H).

LC-MS [mobile phase: from 90% water (0.1% FA) and 10% ACN (0.1% FA) to 5% water (0.1% FA) and 95% ACN (0.1% FA) in 9 min]: Rt=3.69 min; MS Calcd: 464, MS Found: 465 [M+H]$^+$.

Example 28

2-(4-(1-(6-((1S,4S)-2-oxa-5-azabicyclo[2.2.1]heptan-5-yl)-2-methoxypyrimidin-4-yl)-5-methyl-1H-indazol-6-yl)piperidin-1-yl)ethanol

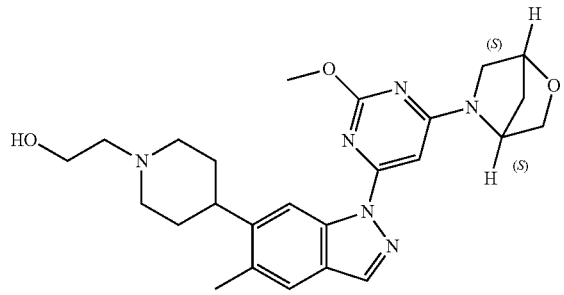

LiAlH$_4$ (19 mg, 0.5 mmol) was added to the solution of ethyl 2-(4-(1-(6-((1S,4S)-2-oxa-5-azabicyclo[2.2.1]heptan-5-yl)-2-methoxypyrimidin-4-yl)-5-methyl-1H-indazol-6-yl)piperidin-1-yl)acetate (103 mg, 0.2 mmol) in THF (5 mL) and the reaction was stirred at Rt for 0.5 hour. The reaction was then quenched with sat. NH$_4$Cl (0.5 mL). Then the mixture was filtered and the filtrate was concentrated and the residue was purified by C$_{18}$ flash column (acetonitrile:water=5:95~100:0) to give the product as a brown solid. (47 mg, 50% yield)

$^1$H NMR (400 MHz, CDCl$_3$): δ 8.78 (s, 1H), 8.07 (s, 1H), 7.51 (s, 1H), 6.56 (br, 0.9H), 5.26 (br, 0.6H), 4.74 (br, 1H), 4.15 (s, 3H), 3.92~3.89 (m, 2H), 3.69~3.65 (m, 2H), 3.55~3.47 (m, 2H), 3.14~3.10 (m, 2H), 2.87 (t, J=11.2 Hz, 1H), 2.65~2.62 (m, 2H), 2.46 (s, 3H), 2.30~2.27 (m, 2H), 1.99~1.75 (m, 6H).

LC-MS [mobile phase: from 90% water (0.1% FA) and 10% ACN (0.1% FA) to 5% water (0.1% FA) and 95% ACN (0.1% FA) in 10 min]: Rt=4.53 min; MS Calcd: 464.3, MS Found: 465.4 [M+H]$^+$.

Example 29

Step 1

Cis-4-(1-(6-((1R,4R)-2,5-diazabicyclo[2.2.1]heptan-2-yl)-2-methylpyrimidin-4-yl)-5-methyl-1H-indazol-6-yl)-1-methylcyclohexanol

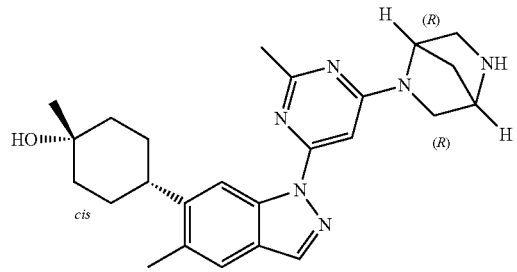

Cis-(1R,4R)-tert-butyl 5-(6-(6-(4-hydroxy-4-methylcyclohexyl)-5-methyl-1H-indazol-1-yl)-2-methylpyrimidin-4-yl)-2,5-diazabicyclo[2.2.1]heptane-2-carboxylate (90 mg, 0.07 mmol) and TFA (2 mL) in DCM (5 mL) was stirred at rt for 3 hours. The reaction was concentrated. The solid was diluted with MeOH (20 mL) and basified to pH of 8-9. The mixture was filtered, the filtrate was concentrated to obtain cis-4-(1-(6-((1R,4R)-2,5-diazabicyclo[2.2.1]heptan-2-yl)-2-methylpyrimidin-4-yl)-5-methyl-1H-indazol-6-yl)-1-methylcyclohexanol (80 mg, crude) as a yellow solid.

LC-MS [mobile phase: from 80% water (0.1% FA) and 20% ACN (0.1% FA) to 5% water (0.1% FA) and 95% ACN (0.1% FA) in 2.5 min], purity: 88.4%; Rt=1.008 min; MS Calcd: 432, MS Found: 433.3[M+H]⁺.

Step 2

Synthesis of Cis-1-methyl-4-(5-methyl-1-(2-methyl-6-((1R,4R)-5-(oxetan-3-yl)-2,5-diazabicyclo[2.2.1]heptan-2-yl)pyrimidin-4-yl)-1H-indazol-6-yl)cyclohexanol (Rt=5.35 min)

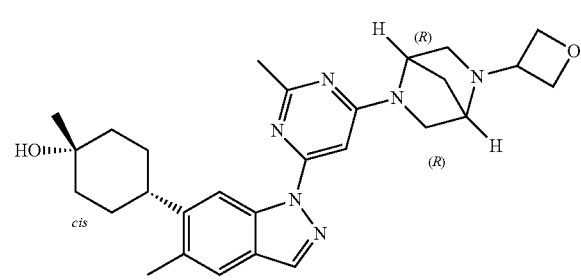

Cis-4-(1-(6-((1R,4R)-2,5-diazabicyclo[2.2.1]heptan-2-yl)-2-methylpyrimidin-4-yl)-5-methyl-1H-indazol-6-yl)-1-methylcyclohexanol (80 mg, 0.18 mmol) and oxetan-3-one (40 mg, 0.53 mmol) in DCE (10 mL) was stirred at rt for 15 h. Then the NaBH₃CN (70 mg, 1.11 mmol) was added to the mixture and stirred 40° C. for 2 days. The reaction was quenched with MeOH (10 mL) and water (0.5 mL) before concentrated. The crude was purified by Prep-HPLC to afford the desired product (Rt=5.35 min) as a white solid (13 mg, yield 14%)

¹H NMR (400 MHz, CDCl3): δ 8.85 (s, 1H), 8.05 (s, 1H), 7.49 (s, 1H), 6.62 (brs, 1H), 5.14 (brs, 1H), 4.72-4.66 (m, 2H), 4.56-4.53 (t, 1H), 4.49 (s, 1H), 4.01-3.95 (m, 1H), 3.60 (s, 1H), 3.40 (brs, 2H), 3.02-3.00 (d, 1H), 2.85-2.74 (m, 2H), 2.60 (s, 3H), 2.45 (s, 3H), 2.01-1.92 (m, 3H), 1.86-1.77 (m, 5H), 1.66-1.60 (m, 2H), 1.32 (s, 4H).

LC-MS [mobile phase: from 70% water (0.1% TFA) and 30% ACN (0.1% TFA) to 30% water (0.1% TFA) and 70% ACN (0.1% TFA) in 10 min]: Rt=5.53 min; MS Calcd.: 488.6, MS Found: 489.6 [M+H]⁺.

Waters 2767/Qda; Waters XBridge 30×150 mm 5 μm; Flow rate: 20 ml/min; wave length: 214 nm/254 nm; Trigger: 254 nm
A: H₂O
B: ACN
Method:

| Time | B % |
|---|---|
| 0 | 10 |
| 2 | 45 |
| 12 | 65 |
| 12.5 | 95 |
| 15 | 95 |

-continued

| Time | B % |
|---|---|
| 15.2 | 10 |
| 18 | 10 |

Example 30

Trans-1-methyl-4-(5-methyl-1-(2-methyl-6-((1S,4S)-5-(oxetan-3-yl)-2,5-diazabicyclo[2.2.1]heptan-2-yl)pyrimidin-4-yl)-1H-indazol-6-yl)cyclohexanol

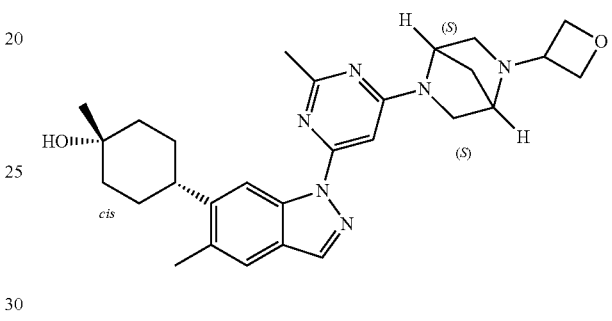

Step 1

Cis-4-(1-(6-((1S,4S)-2,5-diazabicyclo[2.2.1]heptan-2-yl)-2-methylpyrimidin-4-yl)-5-methyl-1H-indazol-6-yl)-1-methylcyclohexanol

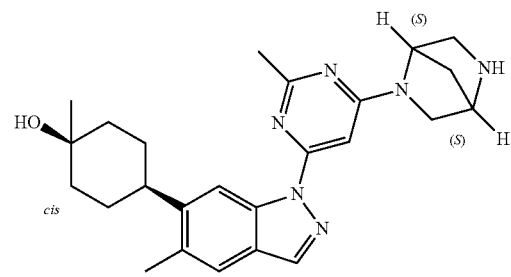

Cis-(1S,4S)-tert-butyl 5-(6-(6-(4-hydroxy-4-methylcyclohexyl)-5-methyl-1H-indazol-1-yl)-2-methylpyrimidin-4-yl)-2,5-diazabicyclo[2.2.1]heptane-2-carboxylate (85 mg, 0.16 mmol) and TFA (2 mL) in DCM (8 mL) was stirred at rt for 3 hours. The reaction was concentrated. The solid was diluted with MeOH (3 mL) and basified to a pH of 9-10. The mixture was filtered, the filtrate was concentrated to obtain cis-4-(1-(6-((1S,4S)-2,5-diazabicyclo[2.2.1]heptan-2-yl)-2-methylpyrimidin-4-yl)-5-methyl-1H-indazol-6-yl)-1-methylcyclohexanol (100 mg) as a yellow solid. The solid was used in next step directly.

Step 2

Cis-1-methyl-4-(5-methyl-1-(2-methyl-6-((1S,4S)-5-(oxetan-3-yl)-2,5-diazabicyclo[2.2.1]heptan-2-yl)pyrimidin-4-yl)-1H-indazol-6-yl)cyclohexanol (Rt=5.41 min)

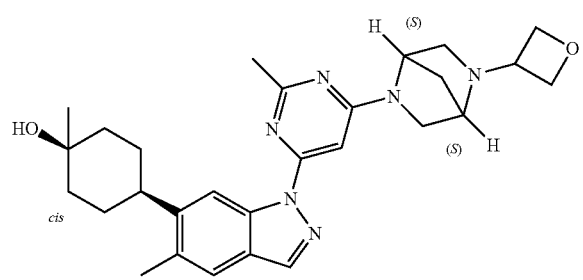

Cis-4-(1-(6-((1S,4S)-2,5-diazabicyclo[2.2.1]heptan-2-yl)-2-methylpyrimidin-4-yl)-5-methyl-1H-indazol-6-yl)-1-methylcyclohexanol (100 mg), and oxetan-3-one (50 mg, 0.69 mmol) in DCE (10 mL) was stirred at rt for 15 h. Then the Na(CN)BH$_3$ (145 mg, 2.31 mmol) was added to the mixture and stirred 25° C. for 1 day. The reaction was quenched with MeOH (10 mL) and water (0.5 mL), then concentrated. The crude was purified by Prep-HPLC to afford the title product as a white solid (10 mg, yield 10%)

$^1$H NMR (400 MHz, CDCl$_3$): δ 8.85 (s, 1H), 8.05 (s, 1H), 7.49 (s, 1H), 6.59 (br, 0.9H), 5.15 (br, 0.3H), 4.72-4.66 (m, 2H), 4.56-4.53 (t, J=6.0 Hz, 1H), 4.50 (br, 1H), 3.99-3.96 (m, 1H), 3.60 (s, 1H), 3.45-3.31 (m, 2H), 3.02 (d, J=8.0 Hz, 1H), 2.84 (d, J=10.0 Hz, 1H), 2.88 (t, J=11.6 Hz, 1H), 2.61 (s, 3H), 2.45 (s, 3H), 2.01-1.76 (m, 9H), 1.63-1.57 (m, 2H), 1.32 (s, 3H).

LC-MS [mobile phase: from 70% water (0.1% TFA) and 30% ACN (0.1% TFA) to 30% water (0.1% TFA) and 70% ACN (0.1% TFA) in 10 min]: Rt=5.41 min; MS Calcd.: 488, MS Found: 489 [M+H]$^+$.

Waters 2767/Qda; Waters XBridge 30×150 mm 5 μm; flow rate: 20 ml/min; wave length: 214 nm/254 nm; Trigger: 254 nm

A: H$_2$O B: ACN

Method:

| Time | B % |
| --- | --- |
| 0 | 10 |
| 2 | 45 |
| 12 | 65 |
| 12.5 | 95 |
| 15 | 95 |
| 15.2 | 10 |
| 18 | 10 |

Example 31

Step 1

Synthesis of Trans-4-(1-(6-((1R,4R)-2,5-diazabicyclo[2.2.1]heptan-2-yl)-2-methylpyrimidin-4-yl)-5-methyl-1H-indazol-6-yl)-1-methylcyclohexanol

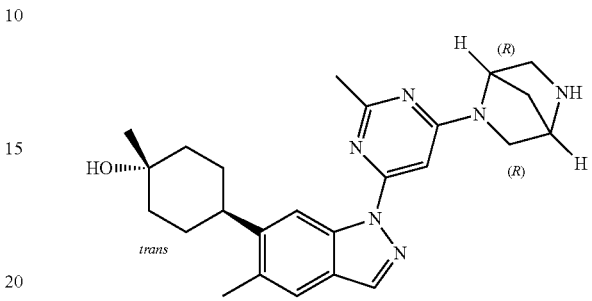

Trans-(1R,4R)-tert-butyl 5-(6-(6-(4-hydroxy-4-methylcyclohexyl)-5-methyl-1H-indazol-1-yl)-2-methylpyrimidin-4-yl)-2,5-diazabicyclo[2.2.1]heptane-2-carboxylate (100 mg, 0.19 mmol) and TFA (2 mL) in DCM (5 mL) was stirred at rt for 3 hours. The reaction was concentrated. The solid was diluted with MeOH (20 mL) and basified to pH of 8-9. The mixture was filtered, the filtrate was concentrated to obtain trans-4-(1-(6-((1R,4R)-2,5-diazabicyclo[2.2.1]heptan-2-yl)-2-methylpyrimidin-4-yl)-5-methyl-1H-indazol-6-yl)-1-methylcyclohexanol (70 mg, yield 87%) as a yellow solid.

LC-MS [mobile phase: from 80% water (0.1% FA) and 20% ACN (0.1% FA) to 5% water (0.1% FA) and 95% ACN (0.1% FA) in 2.5 min]: purity: 87.5%; Rt=0.920 min; MS Calcd: 432, MS Found: 433.5[M+H]$^+$.

Step 2

Trans-1-methyl-4-(5-methyl-1-(2-methyl-6-((1R,4R)-5-(oxetan-3-yl)-2,5-diazabicyclo[2.2.1]heptan-2-yl)pyrimidin-4-yl)-1H-indazol-6-yl)cyclohexanol (Rt=4.79 min)

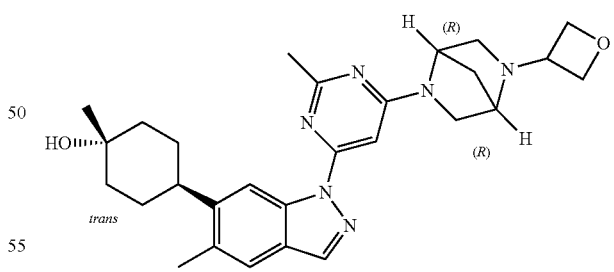

The solution of trans-4-(1-(6-((1R,4R)-2,5-diazabicyclo[2.2.1]heptan-2-yl)-2-methylpyrimidin-4-yl)-5-methyl-1H-indazol-6-yl)-1-methylcyclohexanol (70 mg, 0.18 mmol) and oxetan-3-one (40 mg, 0.53 mmol) in DCE (10 mL) was stirred at rt for 15 h. Then the NaBH$_3$CN (70 mg, 1.11 mmol) was added to the mixture and stirred 40° C. for 2 days. The reaction was quenched with MeOH (10 mL) and water (0.5 mL) before concentrated. The crude was purified by Prep-HPLC to obtain trans-1-methyl-4-(5-methyl-1-(2-methyl-6-((1R,4R)-5-(oxetan-3-yl)-2,5-diazabicyclo[2.2.1]

heptan-2-yl)pyrimidin-4-yl)-1H-indazol-6-yl)cyclohexanol (Rt=4.79 min) as a white solid (8 mg, yield 10%)

¹H NMR (400 MHz, CDCl₃): δ 8.85 (s, 1H), 8.05 (s, 1H), 7.49 (s, 1H), 6.59 (brs, 1H), 5.13 (brs, 1H), 4.72-4.66 (m, 2H), 4.56-4.53 (t, 1H), 4.49 (s, 1H), 4.01-3.95 (m, 1H), 3.60 (s, 1H), 3.41 (brs, 2H), 3.03-3.00 (d, 1H), 2.87-2.84 (d, 2H), 2.60 (s, 3H), 2.45 (s, 3H), 2.00-1.90 (m, 6H), 1.77-1.65 (m, 5H), 1.43 (s, 3H).

LC-MS [mobile phase: from 70% water (0.1% TFA) and 30% ACN (0.1% TFA) to 30% water (0.1% TFA) and 70% ACN (0.1% TFA) in 10 min]: purity 92.3%, Rt=4.79 min; MS Calcd.: 488.6, MS Found: 489.6 $[M+H]^+$.

Prep-HPLC:

Waters 2767/Qda; Waters XBridge 30×150 mm 5 μm; flow rate: 20 ml/min; wave length: 214 nm/254 nm; Trigger: 254 nm A: H₂O
B: ACN
Method:

| Time | B % |
|---|---|
| 0 | 10 |
| 2 | 45 |
| 12 | 65 |
| 12.5 | 95 |
| 15 | 95 |
| 15.2 | 10 |
| 18 | 10 |

Example 32

Trans-1-methyl-4-(5-methyl-1-(2-methyl-6-((1S,4S)-5-(oxetan-3-yl)-2,5-diazabicyclo[2.2.1]heptan-2-yl) pyrimidin-4-yl)-1H-indazol-6-yl)cyclohexanol

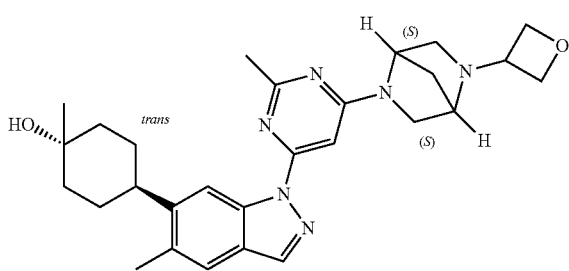

TFA (1 mL) was added to the solution of trans-(1S,4S)-tert-butyl 5-(6-(6-(4-hydroxy-4-methylcyclohexyl)-5-methyl-1H-indazol-1-yl)-2-methylpyrimidin-4-yl)-2,5-diazabicyclo[2.2.1]heptane-2-carboxylate (40 mg, 0.075 mmol) in DCM (3 mL) at rt and stirred for 1 hour. The reaction was then concentrated to give a brown oil and the residue was used directly. The solution of the brown oil and oxetan-3-one (14 mg, 0.2 mmol) in DCM was stirred at rt overnight. To the reaction NaBH₃CN (13 mg, 0.2 mmol) was added and stirred for 2 days. Then more oxetan-3-one (14 gm, 0.2 mmol) was added and the reaction was stirred for 1 more day and then diluted with water (3 mL). The mixture was extracted with DCM (3×10 mL) and the solution was dried and concentrated. The residue was purified by prep-HPLC to give the title product with TFA salt (15 mg, 33% yield) as a white solid.

¹H NMR (400 MHz, CDCl₃): δ 8.85 (s, 1H), 8.05 (s, 1H), 7.49 (s, 1H), 6.65 (br, 0.9H), 5.14 (br, 0.5H), 4.73~4.66 (m, 2H), 4.57~4.53 (m, 2H), 4.00~3.96 (m, 1H), 3.60 (s, 1H), 3.41 (br, 1H), 3.01 (d, J=8.8 Hz, 2H), 2.88~2.84 (m, 2H), 2.60 (s, 3H), 2.46 (s, 3H), 1.98~1.91 (m, 6H), 1.78~1.69 (m, 5H), 1.43 (s, 3H).

LC-MS [mobile phase: from 80% water (0.1% FA) and 20% ACN (0.1% FA) to 5% water (0.1% FA) and 95% ACN (0.1% FA) in 10 min]: Rt=4.83 min; MS Calcd: 488, MS Found: 489 $[M+H]^+$.

Prep-HPLC:
Waters 2767/Qda
Waters XBridge 30×150 mm 5 μm
flow rate: 20 ml/min
A: H₂O (0.1% NH₄OH)
B: ACN
Method:

| Time | B % |
|---|---|
| 0 | 20 |
| 2 | 40 |
| 12 | 60 |
| 12.5 | 95 |
| 15 | 95 |
| 15.2 | 10 |
| 18 | 10 |

Example 33

1-(1-(6-((1S,4S)-2-oxa-5-azabicyclo[2.2.1]heptan-5-yl)-2-methylpyrimidin-4-yl)-5-chloro-1H-indazol-6-yl)-4-methylpiperidin-4-ol

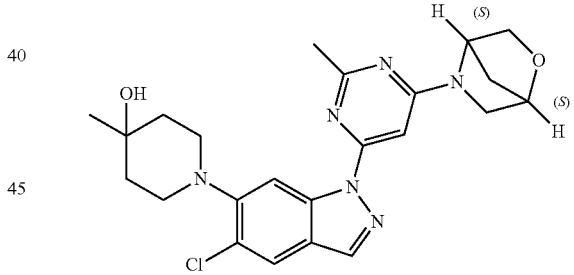

To a solution of 1-(5-chloro-1H-indazol-6-yl)-4-methylpiperidin-4-ol (50 mg, 0.19 mmol) (1S,4S)-5-(6-iodo-2-methylpyrimidin-4-yl)-2-oxa-5-azabicyclo[2.2.1]heptane (66 mg, 0.21 mmol), CuI (36 mg, 0.19 mmol), K₃PO₄ (80 mg, 0.38 mmol) in toluene (3 ml) was added N, N'-Dimethyl-cyclohexane-1,2-diamine (54 mg, 0.38 mmol). The mixture was stirred at 110° C. for 2 hour. The mixture was cooled to room temperature. The residue was poured into water (2 ml) and extracted with EtOAc (2 mL×2). The combined organic layers were washed with brine, dried over Na₂SO₄, filtered and concentrated. The residue was purified by Pre-HPLC (gilson-2 T3 C₁₈ 5 μm 19×150 mm 20-60% B, A: H₂O (0.1% HCl), B: ACN, UV: 214 nm, Flow rate: 15 ml/min) to give the title compound as a white solid (17 mg, 20%).

¹H NMR (400 MHz, CD₃OD): δ 8.64 (d, J=2.8 Hz, 1H), 8.11 (d, J=3.2 Hz, 1H), 7.79 (d, J=3.2 Hz, 1H), 6.71 (br 1H), 4.75 (s, 1H), 3.86 (dd, J=24.4, 7.6 Hz, 2H), 3.57-3.55 (d, J=10 Hz, 1H), 3.17-3.12 (m, 4H), 2.54 (s, 3H), 2.03-1.75 (m, 7H), 1.31-1.29 (m, 4H).

LC-MS [column: $C_{18}$; column size: 4.6×50 mm; mobile phase: B (ACN): A (0.02% $NH_4OAc$); gradient (B %) in 6 min]: Rt=4.202 min; MS Calcd.: 454, MS Found: 455 $[M+H]^+$.

Example 34

1-(1-(6-((1R,4R)-2-oxa-5-azabicyclo[2.2.1]heptan-5-yl)-2-methylpyrimidin-4-yl)-5-chloro-1H-indazol-6-yl)-4-methylpiperidin-4-ol

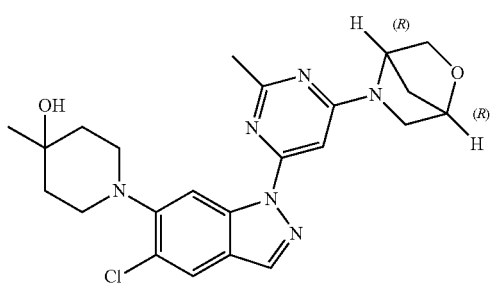

To a solution of 1-(5-chloro-1H-indazol-6-yl)-4-methylpiperidin-4-ol (50 mg, 0.189 mmol), (1R,4R)-5-(6-iodo-2-methylpyrimidin-4-yl)-2-oxa-5-azabicyclo[2.2.1]heptane (66 mg, 0.208 mmol), CuI (36 mg, 0.189 mmol), $K_3PO_4$ (80 mg, 0.378 mmol) in toluene (3 ml) was added N,N'-Dimethyl-cyclohexane-1,2-diamine (54 mg, 0.378 mmol). The mixture was stirred at 110° C. for 2 hours. The mixture was cooled to room temperature. The residue was poured into water (2 ml) and extracted with EtOAc (2 mL×2). The combined organic layers were washed with brine, dried over $Na_2SO_4$, filtered and concentrated. It was purified by Prep-HPLC (waters-1 $C_{18}$ 5 μm 19×150 mm-11212, 20-75% B, A: $H_2O$ (0.1% $NH_4HCO_3$), B: ACN, 214, flow rate: 15 ml/min, GT12 mins-18 min) to give the title compound as a white solid (20 mg, 23%).

$^1$H NMR (400 MHz, $CD_3OD$): δ 8.64 (d, J=2.8 Hz, 1H), 8.11 (d, J=3.2 Hz, 1H), 7.79 (d, J=3.2 Hz, 1H), 6.71 (s, 1H), 4.75 (s, 1H), 3.90-3.83 (m, 2H), 3.57-3.55 (dd, J=24, 6.8 Hz, 1H), 3.17-3.12 (m, 4H), 2.54 (s, 3H), 2.03-1.75 (m, 7H), 1.31-1.29 (m, 4H).

LC-MS [column: $C_{18}$; column size: 4.6×50 mm; mobile phase: B(ACN), A (0.02% $NH_4OAc$), gradient (B %), stop time 6.0 min]: Rt=4.204 min, MS Calcd.: 454, MS Found: 455 $[M+H]^+$.

Example 35

Step 1

(1R,4R)-5-(2-methoxy-6-(5-methyl-6-(piperidin-4-yl)-1H-indazol-1-yl)pyrimidin-4-yl)-2-oxa-5-azabicyclo[2.2.1]heptane Hydrochloride

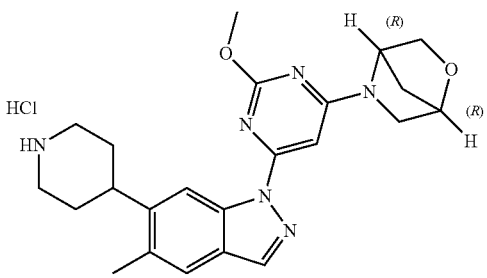

A mixture of tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)piperidine-1-carboxylate (280 mg, 0.54 mmol) in HCl/EtOAc (2M/L, 2 mL) was stirred at Rt for 30 min. The reaction mixture was concentrated to give crude product (1R,4R)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride as a white solid. (250 mg, crude)

Step 2

(1R,4R)-5-(2-methoxy-6-(6-(1-(2-methoxyethyl)piperidin-4-yl)-5-methyl-1H-indazol-1-yl)pyrimidin-4-yl)-2-oxa-5-azabicyclo[2.2.1]heptane To a mixture of (1R,4R)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride (50 mg, 0.11 mmol) and $K_2CO_3$ (46 mg, 0.33 mmol) in ACN (5 mL) was added 1-bromo-2-methoxyethane (17 mg, 0.121 mmol), the reaction was stirred at 80° C. overnight. The reaction mixture was filtered and the filtrate was concentrated. The residue was purified by Prep-HPLC (A: $H_2O$ (0.1% TFA), B: CAN, A:B=80:20 to A:B=5:95) to give product as a white solid. (15 mg, yield 28%).

$^1$H NMR (400 MHz, $CDCl_3$): δ 8.76 (s, 1H), 8.07 (s, 1H), 7.53 (s, 1H), 6.55 (s, 0.6H), 5.25 (s, 0.4H), 4.73 (s, 1H), 4.16 (s, 3H), 3.93~3.89 (m, 4H), 3.80~3.78 (m, 2H), 3.54~3.47 (m, 3H), 3.46 (s, 3H), 3.30~3.28 (m, 2H), 3.03~2.94 (m, 3H), 2.46 (s, 3H), 2.28~2.15 (m, 2H), 2.10~2.07 (m, 2H), 1.97~1.79 (m, 2H).

$^{19}$F NMR (376 MHz, CDCl$_3$): δ −75.4 (s)

LC-MS [mobile phase: from 70% water (0.1% FA) and 30% ACN (0.1% FA) to 5% water (0.1% FA) and 95% ACN (0.1% FA) in 12 min]: Rt=2.12 min; MS Calcd: 478, MS Found: 479 [M+H]$^+$.

Example 36

Step 1

(1S,4S)-5-(2-methoxy-6-(5-methyl-6-(piperidin-4-yl)-1H-indazol-1-yl)pyrimidin-4-yl)-2-oxa-5-azabicyclo[2.2.1]heptane Hydrochloride

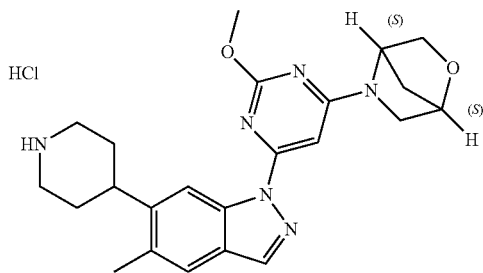

A mixture of tert-butyl 4-(1-(6-(((1S,4S)-2-oxa-5-azabicyclo[2.2.1]heptan-5-yl)-2-methoxypyrimidin-4-yl)-5-methyl-1H-indazol-6-yl)piperidine-1-carboxylate (280 mg, 0.54 mmol) in HCl/EtOAc (2M/L, 2 mL) was stirred at rt for 30 min. The reaction mixture was concentrated to give crude product H-hydrochloride as a white solid. (260 mg, crude).

Step 2

(1S,4S)-5-(2-methoxy-6-(6-(1-(2-methoxyethyl)piperidin-4-yl)-5-methyl-1H-indazol-1-yl)pyrimidin-4-yl)-2-oxa-5-azabicyclo[2.2.1]heptane

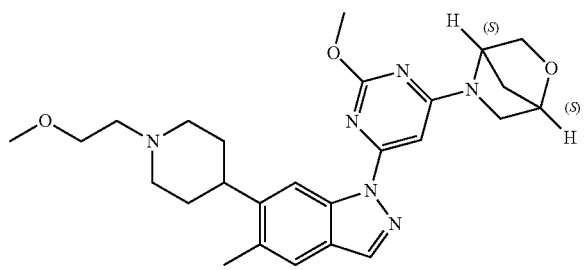

To a mixture of (1S,4S)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride (80 mg, 0.18 mmol) and K$_2$CO$_3$ (75 mg, 0.54 mmol) in ACN (8 mL) was added 1-bromo-2-methoxyethane (28 mg, 0.2 mmol), the reaction was stirred at 80° C. overnight. The reaction mixture was filtered and the filtrate was concentrated. the residue was purified by Prep-HPLC (A: H$_2$O (0.1% TFA), B: CAN, A:B=80:20 to A:B=5:95) to give the title product as a white solid. (24 mg, yield 28%).

$^1$H NMR (400 MHz, CDCl$_3$): δ 8.72 (s, 1H), 8.09 (s, 1H), 7.54 (s, 1H), 6.56 (s, 0.7H), 5.26 (s, 0.3H), 4.74 (s, 1H), 4.14 (s, 3H), 3.93~3.89 (m, 4H), 3.80~3.78 (m, 2H), 3.54~3.47 (m, 3H), 3.46 (s, 3H), 3.30~3.28 (m, 2H), 3.03~2.94 (m, 3H), 2.46 (s, 3H), 2.29~2.26 (m, 2H), 2.09~2.01 (m, 2H), 1.99~1.96 (m, 2H).

$^{19}$F NMR (376 MHz, CDCl$_3$): δ −75.7 (s)

LC-MS [mobile phase: from 80% water (0.1% FA) and 80% ACN (0.1% FA) to 5% water (0.1% FA) and 95% ACN (0.1% FA) in 12 min]: Rt=4.08 min; MS Calcd: 478, MS Found: 479 [M+H]$^+$.

Example 37

(1R,4R)-5-(6-(6-(1-(2-fluoroethyl)piperidin-4-yl)-5-methyl-1H-indazol-1-yl)-2-methoxypyrimidin-4-yl)-2-oxa-5-azabicyclo[2.2.1]heptane

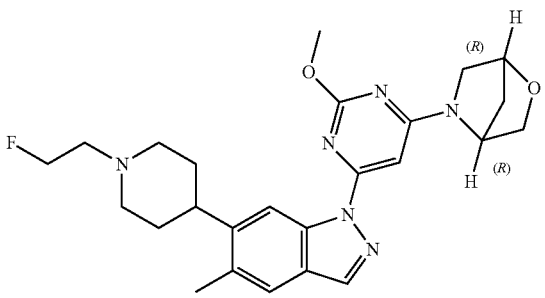

To a solution of (1R,4R)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride (100 mg, 0.22 mmol) in DMF (5 mL) was added Et$_3$N (120 mg, 1.19 mmol) followed by 1-fluoro-2-iodoethane (124 mg, 0.71 mmol). The reaction was stirred at room temperature overnight. The reaction solution directly was purified by prep-HPLC (Waters 2767/Qda, Waters sunfire C$_{18}$ 20×250 mm 10 μm, Mobile Phase: MeCN/H$_2$O (0.1% TFA): 25-95%, Flow rate: 30 mL/min, Trigger: 254 nm) to give the titlebproduct, TFA salt, as a white solid (72 mg)

$^1$H NMR (400 MHz, CDCl$_3$): δ 8.72 (s, 1H), 8.10 (s, 1H), 7.55 (s, 1H), 6.56 (br, 0.9H), 5.29 (br, 0.6H), 4.96 (br, 1H), 4.84 (br, 1H), 4.75 (s, 1H), 4.15 (s, 3H), 3.94~3.88 (m, 4H), 3.76~3.71 (m, 1H), 3.54~3.47 (br, 3H), 3.11~2.99 (m, 4H), 2.46 (s, 3H), 2.35~2.23 (m, 2H), 2.16~2.13 (m, 2H), 2.03~1.96 (m, 2H).

$^{19}$F NMR (376 MHz, CDCl$_3$): δ −75.747 (s), δ −215.641 (s).

LC-MS [mobile phase: from 90% water (0.1% FA) and 10% ACN (0.1% FA) to 5% water (0.1% FA) and 95% ACN (0.1% FA) in 9 min]: purity: 100%, Rt=3.73 min; MS Calcd: 466, MS Found: 467 [M+H]$^+$.

Example 38

(1S,4S)-5-(6-(6-(1-(2-fluoroethyl)piperidin-4-yl)-5-methyl-1H-indazol-1-yl)-2-methoxypyrimidin-4-yl)-2-oxa-5-azabicyclo[2.2.1]heptane

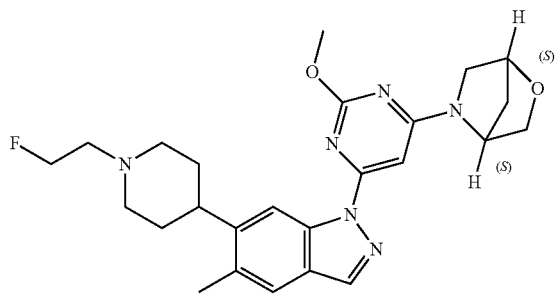

To a solution of (1S,4S)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride (100 mg, 0.22 mmol) in DMF (5 mL) was added Et₃N (120 mg, 1.19 mmol) followed by 1-fluoro-2-iodoethane (124 mg, 0.71 mmol). The reaction was stirred at room temperature overnight. The reaction solution was directly purified by prep-HPLC (Waters 2767/Qda, Waters sunfire C₁₈ 20×250 mm 10 μm, Mobile Phase: MeCN/H₂O (0.1% TFA): 25-95%, Flow rate: 30 mL/min, Trigger: 254 nm) to give the title product, TFA salt, as a white solid (55 mg).

¹H NMR (400 MHz, CDCl₃): δ 8.72 (s, 1H), 8.10 (s, 1H), 7.55 (s, 1H), 6.56 (br, 0.9H), 5.29 (br, 0.6H), 4.96 (br, 1H), 4.84 (br, 1H), 4.75 (s, 1H), 4.15 (s, 3H), 3.96~3.88 (m, 5H), 3.54~3.47 (br, 3H), 3.11~2.99 (m, 4H), 2.47 (s, 3H), 2.31~2.23 (m, 2H), 2.16~2.13 (m, 2H), 2.03~1.96 (m, 2H).

¹⁹F NMR (376 MHz, CDCl₃): δ75.755 (s), 6-215.688 (s).

LC-MS [mobile phase: from 90% water (0.1% FA) and 10% ACN (0.1% FA) to 5% water (0.1% FA) and 95% ACN (0.1% FA) in 9 min]: purity: 100%, Rt=3.71 min; MS Calcd: 466, MS Found: 467 [M+H]+.

Example 39

(1R,4R)-5-(2-methyl-6-(5-methyl-6-(1-(oxetan-3-yl)piperidin-4-yl)-1H-indazol-1-yl)pyrimidin-4-yl)-2-oxa-5-azabicyclo[2.2.1]heptane

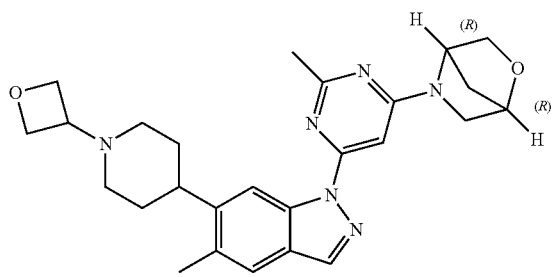

To a suspension of 5-methyl-6-(1-(oxetan-3-yl)piperidin-4-yl)-1H-indazole (64 mg, 0.24 mmol), (1R,4R)-5-(6-iodo-2-methylpyrimidin-4-yl)-2-oxa-5-azabicyclo[2.2.1]heptane (75 mg, 0.24 mmol), CuI (45 mg, 0.24 mmol) and K₃PO₄ (100 mg, 0.48 mmol) in dry toluene (2 mL) was added N,N'-dimethyl-1,2-ethanediamine (45 mg, 0.51 mmol). The suspension was degassed with N₂ and refluxed for 2 h. The solvent was removed under vacuum and the residue was purified by silica gel chromatography (eluted with DCM/MeOH=30:1) to give product (38 mg, yield 35%) as a yellow solid.

¹H NMR (400 MHz, DMSO) δ 8.75 (s, 1H), 8.31 (s, 1H), 7.62 (s, 1H), 6.90-6.60 (br, 1H), 5.18 (s, 1H), 4.72 (s, 1H), 4.53 (dt, J=12.1, 6.3 Hz, 4H), 3.82 (d, J=7.2 Hz, 1H), 3.69 (d, J=7.3 Hz, 1H), 3.53 (d, J=9.8 Hz, 1H), 3.49-3.39 (m, 2H), 2.90-2.79 (m, 3H), 2.55 (s, 3H), 2.42 (s, 3H), 2.06-1.78 (m, 6H), 1.75-1.66 (m, 2H).

LC-MS [mobile phase: from 90% water (0.1% FA) and 10% ACN (0.1% FA) to 5% water (0.1% FA) and 95% ACN (0.1% FA) in 10 min]: purity 95.80%, Rt=7.32 min; MS Calcd.: 460.26, MS Found: 461.6 [M+H]+.

Example 40

(1S,4S)-5-(2-methyl-6-(5-methyl-6-(1-(oxetan-3-yl)piperidin-4-yl)-1H-indazol-1-yl)pyrimidin-4-yl)-2-oxa-5-azabicyclo[2.2.1]heptane

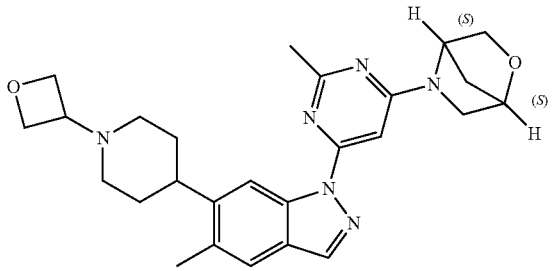

To a suspension of 5-methyl-6-(1-(oxetan-3-yl)piperidin-4-yl)-1H-indazole (64 mg, 0.24 mmol), (1S,4S)-5-(6-iodo-2-methylpyrimidin-4-yl)-2-oxa-5-azabicyclo[2.2.1]heptane (75 mg, 0.24 mmol), CuI (45 mg, 0.24 mmol) and K₃PO₄ (100 mg, 0.48 mmol) in dry toluene (2 mL) was added N,N'-dimethyl-1,2-ethanediamine (45 mg, 0.51 mmol). The suspension was degassed with N₂ and refluxed for 2 h. The solvent was removed under vacuum and the residue was purified by silica gel chromatography (eluted with DCM/MeOH=30:1) to give product (76 mg, yield 70%) as a white solid.

¹H NMR (400 MHz, DMSO) δ 8.75 (s, 1H), 8.31 (s, 1H), 7.62 (s, 1H), 6.90~6.60 (br, 1H), 5.18 (s, 1H), 4.72 (s, 1H), 4.53 (dt, J=12.1, 6.3 Hz, 4H), 3.82 (d, J=7.2 Hz, 1H), 3.69 (d, J=7.3 Hz, 1H), 3.53 (d, J=9.8 Hz, 1H), 3.49~3.39 (m, 2H), 2.90~2.79 (m, 3H), 2.55 (s, 3H), 2.42 (s, 3H), 2.06~1.78 (m, 6H), 1.74~1.65 (m, 2H).

LC-MS [mobile phase: from 90% water (0.1% FA) and 10% ACN (0.1% FA) to 5% water (0.1% FA) and 95% ACN (0.1% FA) in 10 min]: Rt=5.24 min; MS Calcd.: 460, MS Found: 461 [M+H]⁺.

Example 41

Step 1

3-(2-Methoxy-6-(5-methyl-6-(piperidin-4-yl)-1H-indazol-1-yl)pyrimidin-4-yl)-8-oxa-3-azabicyclo[3.2.1]octane 2,2,2-trifluoroacetate

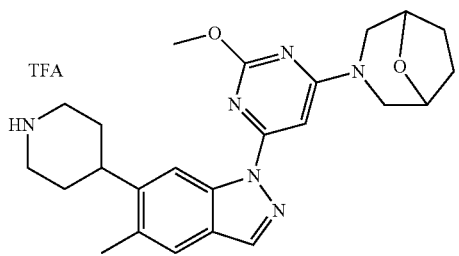 [SMILES: COc1nc(N2CC3CCC(C2)O3)cc(-n2ncc3cc(C)c(C4CCNCC4)cc32)n1]

To a solution of tert-butyl 4-(1-(6-(8-oxa-3-azabicyclo[3.2.1]octan-3-yl)-2-methoxypyrimidin-4-yl)-5-methyl-1H-indazol-6-yl)piperidine-1-carboxylate (70 mg, 0.13 mmol) in DCM (4 mL) was added TFA (0.5 mL). The resulting mixture was stirred at rt for 1 h. TLC showed the reaction was completed. The mixture was concentrated to give the crude product (90 mg, yield >100%) as white solid which was used for next step directly.

LCMS: 5-95% ACN in 3 min]: Rt=1.73 min, MS Calcd.: 434, MS Found: 435 [M+H]$^+$.

Step 2

3-(2-Methoxy-6-(5-methyl-6-(1-(oxetan-3-yl)piperidin-4-yl)-1H-indazol-1-yl)pyrimidin-4-yl)-8-oxa-3-azabicyclo[3.2.1]octane

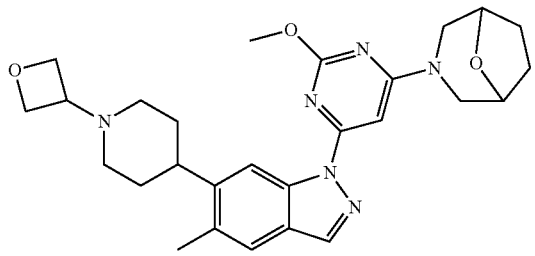 [SMILES: COc1nc(N2CC3CCC(C2)O3)cc(-n2ncc3cc(C)c(C4CCN(C5COC5)CC4)cc32)n1]

To a solution of 3-(2-methoxy-6-(5-methyl-6-(piperidin-4-yl)-1H-indazol-1-yl)pyrimidin-4-yl)-8-oxa-3-azabicyclo[3.2.1]octane 2,2,2-trifluoroacetate (90 mg of crude, 0.16 mmol) in ClCH$_2$CH$_2$Cl (5 mL) was added oxetan-3-one (0.5 mL). The mixture was stirred at rt for 30 min. Then NaBH$_3$CN (50 mg, 0.80 mmol) was added and the resulting reaction mixture was stirred at rt for 2 hrs. TLC showed the reaction was completed. The mixture was partitioned with water (20 mL) and EtOAc (50 mL). The organic layer was concentrated and the residue was purified by prep-TLC (DCM:MeOH=13:1) to give the title compound (22 mg) as a white solid.

$^1$H NMR (300 MHz, CDCl$_3$): δ 8.76 (s, 1H), 8.06 (s, 1H), 7.51 (s, 1H), 6.77 (s, 1H), 4.70-4.68 (m, 4H), 4.49 (br 2H), 4.14 (s, 3H), 4.05-3.97 (m, 2H), 3.57-3.52 (m, 1H), 3.28-3.24 (m, 2H), 2.95-2.91 (m, 2H), 2.85-2.80 (m, 1H), 2.46 (s, 3H), 2.04-1.81 (m, 10H).

LC-MS [mobile phase: from 95% water (0.02% NH$_4$OAc) and 5% ACN to 5% water (0.02% NH$_4$OAc) and 95% ACN in 6.5 min]: Rt=4.401 min; MS Calcd.: 490, MS Found: 491 [M+H]$^+$.

Example 42

Step 1

3-(2-Methyl-6-(5-methyl-6-(piperidin-4-yl)-1H-indazol-1-yl)pyrimidin-4-yl)-8-oxa-3-azabicyclo[3.2.1]octane 2,2,2-trifluoroacetate

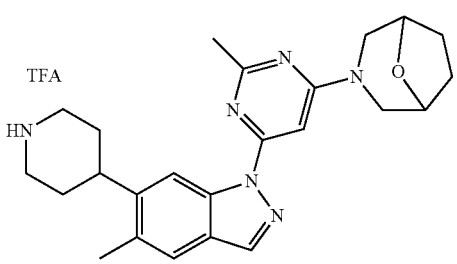 [SMILES: Cc1nc(N2CC3CCC(C2)O3)cc(-n2ncc3cc(C)c(C4CCNCC4)cc32)n1]

To a solution of tert-butyl 4-(1-(6-(8-oxa-3-azabicyclo[3.2.1]octan-3-yl)-2-methylpyrimidin-4-yl)-5-methyl-1H-indazol-6-yl)piperidine-1-carboxylate (90 mg, 0.17 mmol) in DCM (4 mL) was added TFA (0.5 mL). The resulting mixture was stirred at rt for 1 h. TLC showed the reaction was completed. The mixture was concentrated to give the crude product (100 mg, yield >100%) as white solid which was used for next step directly.

LCMS [5-95% ACN in 3 min]: Rt=1.71 min, MS Calcd.: 418, MS Found: 419 [M+H]$^+$.

Step 2

3-(2-Methyl-6-(5-methyl-6-(1-(oxetan-3-yl)piperidin-4-yl)-1H-indazol-1-yl)pyrimidin-4-yl)-8-oxa-3-azabicyclo[3.2.1]octane

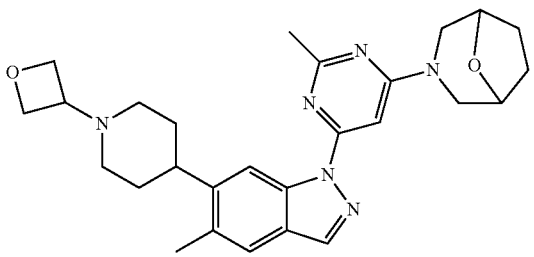 [SMILES: Cc1nc(N2CC3CCC(C2)O3)cc(-n2ncc3cc(C)c(C4CCN(C5COC5)CC4)cc32)n1]

To a solution of 3-(2-methyl-6-(5-methyl-6-(piperidin-4-yl)-1H-indazol-1-yl)pyrimidin-4-yl)-8-oxa-3-azabicyclo[3.2.1]octane 2,2,2-trifluoroacetate (100 mg of crude, 0.17 mmol) in ClCH$_2$CH$_2$Cl (5 mL) was added oxetan-3-one (0.5 mL). The mixture was stirred at rt for 30 min. Then NaBH$_3$CN (60 mg, 0.96 mmol) was added and the resulting reaction mixture was stirred at rt for 2 hrs. TLC showed the reaction was completed. The mixture was partitioned with water (20 mL) and EtOAc (50 mL). The organic layer was concentrated and the residue was purified by prep-TLC (DCM:MeOH=13:1) to give the title compound (30 mg) as a white solid.

¹H NMR (300 MHz, CDCl₃): δ 8.82 (s, 1H), 8.05 (s, 1H), 7.50 (s, 1H), 6.88 (s, 1H), 4.73-4.71 (m, 4H), 4.50 (br 2H), 4.10-4.00 (m, 2H), 3.58-3.54 (m, 1H), 3.25-3.21 (m, 2H), 2.99-2.96 (m, 2H), 2.86-2.80 (m, 1H), 2.64 (s, 3H), 2.45 (s, 3H), 2.07-1.81 (m, 10H).

LC-MS [mobile phase: from 95% water (0.02% NH₄OAc) and 5% ACN to 5% water (0.02% NH₄OAc) and 95% ACN in 6.5 min]: Rt=4.425 min; MS Calcd.: 474; MS Found: 475 [M+H]⁺.

Example 43

Step 1

3-(2-Methoxy-6-(5-methyl-6-(piperidin-4-yl)-1H-indazol-1-yl)pyrimidin-4-yl)-6-oxa-3-azabicyclo[3.1.1]heptane 2,2,2-trifluoroacetate

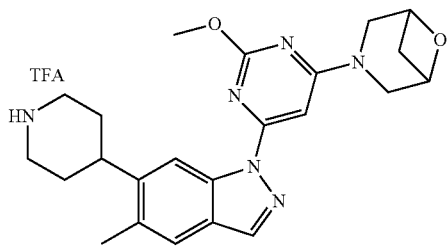 [SMILES: COc1nc(N2CC3CC(C2)O3)cc(-n2ncc3cc(C)c(C4CCNCC4)cc32)n1]

To a solution of tert-butyl 4-(1-(6-(6-oxa-3-azabicyclo[3.1.1]heptan-3-yl)-2-methoxypyrimidin-4-yl)-5-methyl-1H-indazol-6-yl)piperidine-1-carboxylate (70 mg, 0.14 mmol) in DCM (5 mL) was added TFA (0.5 mL). The mixture was stirred at rt for 30 min. TLC showed the reaction was completed. The mixture was concentrated to give the title compound (80 mg, yield >100%) as white solid.

LC-MS [mobile phase: from 95% water and 5% ACN to 5% water and 95% ACN in 3 min]: Rt=1.62 min; MS Calcd.: 420, MS Found: 421 [M+H]⁺.

Step 2

3-(2-Methoxy-6-(5-methyl-6-(1-(oxetan-3-yl)piperidin-4-yl)-1H-indazol-1-yl)pyrimidin-4-yl)-6-oxa-3-azabicyclo[3.1.1]heptane

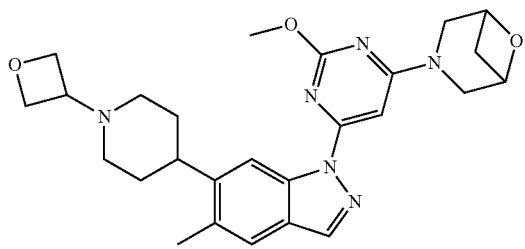 [SMILES: COc1nc(N2CC3CC(C2)O3)cc(-n2ncc3cc(C)c(C4CCN(C5COC5)CC4)cc32)n1]

To a solution of 3-(2-methoxy-6-(5-methyl-6-(piperidin-4-yl)-1H-indazol-1-yl)pyrimidin-4-yl)-6-oxa-3-azabicyclo[3.1.1]heptane 2,2,2-trifluoroacetate (80 mg of crude, 0.14 mmol) in DCE (5 mL) was added CH₃OH (1 mL) and oxetan-3-one (0.5 mL). The mixture was stirred at rt for 30 min. To the mixture was added NaBH₃CN (62 mg, 1.0 mmol). The mixture was stirred at rt for 2 hrs. To the mixture was added sat. Na₂CO₃ solution (20 mL). After stirred at rt for 10 min DCM (10 mL×2) was added to extract the desired compound. The combined organic layers were washed with brine (20 mL), dried over Na₂SO₄ and concentrated. The residue was purified by prep-TLC (DCM:CH₃OH=15:1) to give the title compound (40 mg, yield 54%) as a white solid.

¹H NMR (300 MHz, CDCl₃): δ 8.80 (s, 1H), 8.08 (s, 1H), 7.52 (s, 1H), 6.79 (s, 1H), 4.78-4.69 (m, 6H), 4.25-4.06 (m, 4H), 3.91-3.86 (m, 2H), 3.71-3.55 (m, 2H), 3.35-3.28 (m, 1H), 2.95-2.79 (m, 3H), 2.46 (s, 3H), 2.04-1.94 (m, 7H).

LC-MS [mobile phase: from 95% water (0.1% TFA) and 5% ACN to 5% water (0.1% TFA) and 95% ACN in 6.5 min]: Rt=3.167 min; MS Calcd.: 476, MS Found: 477 [M+H]⁺.

Example 44

Step 1

3-(2-Methyl-6-(5-methyl-6-(piperidin-4-yl)-1H-indazol-1-yl)pyrimidin-4-yl)-6-oxa-3-azabicyclo[3.1.1]heptane 2,2,2-trifluoroacetate

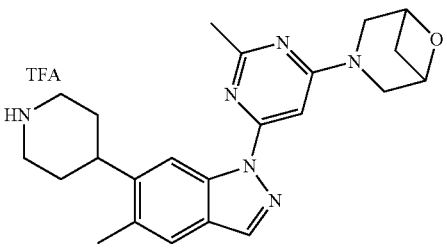 [SMILES: Cc1nc(N2CC3CC(C2)O3)cc(-n2ncc3cc(C)c(C4CCNCC4)cc32)n1]

To a solution of tert-butyl 4-(1-(6-(6-oxa-3-azabicyclo[3.1.1]heptan-3-yl)-2-methylpyrimidin-4-yl)-5-methyl-1H-indazol-6-yl)piperidine-1-carboxylate (90 mg, 0.18 mmol) in DCM (5 mL) was added TFA (1 mL). The mixture was stirred at rt for 1 h. TLC showed the reaction was completed. The mixture was concentrated to give the title compound (100 mg, yield >100%) as a white solid.

¹H NMR (300 MHz, DMSO-d₆): δ 8.75 (s, 1H), 8.71-8.64 (m, 1H), 8.50-8.42 (m, 1H), 8.33 (s, 1H), 7.65 (s, 1H), 6.87 (s, 1H), 4.72-4.70 (m, 2H), 4.00-3.87 (m, 1H), 3.71-3.64 (m, 2H), 3.46-3.41 (m, 2H), 3.21-3.05 (m, 4H), 2.59 (s, 3H), 2.44 (s, 3H), 2.00-1.84 (m, 6H).

Step 2

3-(2-Methyl-6-(5-methyl-6-(1-(oxetan-3-yl)piperidin-4-yl)-1H-indazol-1-yl)pyrimidin-4-yl)-6-oxa-3-azabicyclo[3.1.1]heptane

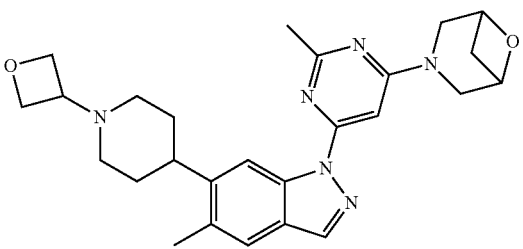 [SMILES: Cc1nc(N2CC3CC(C2)O3)cc(-n2ncc3cc(C)c(C4CCN(C5COC5)CC4)cc32)n1]

To a solution of 3-(2-methyl-6-(5-methyl-6-(piperidin-4-yl)-1H-indazol-1-yl)pyrimidin-4-yl)-6-oxa-3-azabicyclo[3.1.1]heptane 2,2,2-trifluoroacetate (100 mg of crude, 0.18 mmol) in DCE (5 mL) was added CH$_3$OH (1 mL) and oxetan-3-one (0.5 mL). After the mixture was stirred at rt for 20 min. Then NaBH$_3$CN (62 mg, 1.0 mmol) was added. The resulting mixture was stirred at rt for 2 hrs. To the mixture was added sat. Na$_2$CO$_3$ solution (20 mL). The mixture was stirred at rt for 10 min and extracted with DCM (10 mL×2). The combined organic layers were washed with water (10 mL), brine (40 mL), dried over Na$_2$SO$_4$ and concentrated. The residue was purified by prep-TLC (DCM:CH$_3$OH=15:1) to give the title compound (50 mg) as a white solid.

$^1$H NMR (400 MHz, CDCl$_3$): δ 8.50 (s, 1H), 8.06 (s, 1H), 7.51 (s, 1H), 6.89 (s, 1H), 4.78-4.71 (m, 6H), 4.02-3.72 (m, 4H), 3.58-3.55 (m, 1H), 3.33-3.28 (m, 1H), 2.99-2.96 (m, 2H), 2.88-2.81 (m, 1H), 2.69 (s, 3H), 2.46 (s, 3H), 2.05-1.96 (m, 7H).

LC-MS [mobile phase: from 95% water (0.02% NH$_4$OAc) and 5% ACN to 5% water (0.02% NH$_4$OAc) and 95% ACN in 6.5 min]: Rt=4.091 min; MS Calcd.: 460, MS Found: 461 [M+H]$^+$.

Example 45

8-(2-methyl-6-(5-methyl-6-(1-(oxetan-3-yl)piperidin-4-yl)-1H-indazol-1-yl)pyrimidin-4-yl)-3-oxa-8-azabicyclo[3.2.1]octane

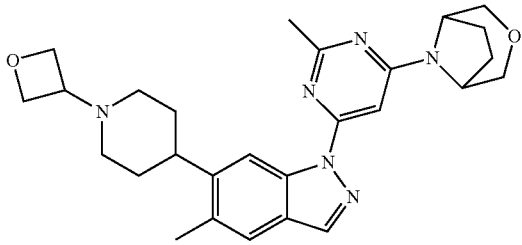 [SMILES: Cc1nc(N2C3CCC2COC3)cc(-n2ncc3cc(C)c(C4CCN(C5COC5)CC4)cc32)n1]

A mixture of 8-(6-iodo-2-methylpyrimidin-4-yl)-3-oxa-8-azabicyclo[3.2.1]octane (200 mg, 0.6 mmol) and 5-methyl-6-(1-(oxetan-3-yl)piperidin-4-yl)-1H-indazole (164 mg, 0.6 mmol) in toluene (10 mL) was added K$_3$PO$_4$ (254 mg, 1.2 mmol), CuI (114 mg, 0.6 mmol) and N$^1$,N$^2$-dimethylethane-1,2-diamine (53 mg, 0.6 mmol). The mixture was degassed, then stirred at 100° C. overnight under Ar and filtered. The filtrate was concentrated and purified by prep-HPLC to give title compound as a yellow solid (TFA salt) (41 mg, 14% yield).

$^1$H NMR (400 MHz, DMSO-d$_6$): δ 10.74 (s, 1H), 8.74 (s, 1H), 8.35 (s, 1H), 7.68 (s, 1H), 3.92 (s, 1H), 4.86-4.78 (m, 4H), 4.62-4.50 (m, 3H), 3.65-3.58 (m, 6H), 3.24-3.07 (m, 3H), 2.58 (s, 3H), 2.47 (s, 3H), 2.27-1.93 (m, 8H).

$^{19}$F NMR (400 MHz, DMSO-d6): δ -74.47

LC-MS [mobile phase: from 80% water (0.1% FA) and 20% ACN (0.1% FA) to 5% water (0.1% FA) and 95% ACN (0.1% FA) in 10 min]: Rt=5.05 min; MS Calcd: 474, MS Found: 475 [M+H]$^+$.

Instrument: Waters 2767/Qda

Column: Waters sunfire C$_{18}$ 20×250 mm 10 μm Flow rate: 30 ml/min,

Wavelength: 214 nm/254 nm, Trigger: 254 nm

Mobile Phase A: H$_2$O (0.1% TFA), Mobile Phase B: ACN

Gradient Method:

| Time | B % |
|------|-----|
| 0    | 15  |
| 10   | 30  |
| 10.2 | 95  |
| 13.2 | 95  |
| 13.5 | 10  |
| 15   | 10  |

Example 46

9-(2-methyl-6-(5-methyl-6-(1-(oxetan-3-yl)piperidin-4-yl)-1H-indazol-1-yl)pyrimidin-4-yl)-3,7-dioxa-9-azabicyclo[3.3.1]nonane

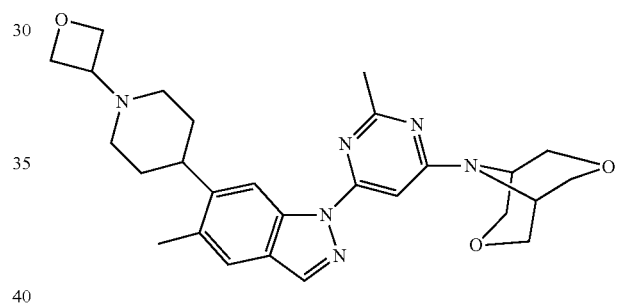

A mixture of 9-(6-iodo-2-methylpyrimidin-4-yl)-3,7-dioxa-9-azabicyclo[3.3.1]nonane (40 mg, 0.12 mmol), 5-methyl-6-(1-(oxetan-3-yl)piperidin-4-yl)-1H-indazole (35 mg, 0.13 mmol), N,N'-dimethylcyclohexane-1,2-diamine (34 mg, 0.24 mmol), CuI (23 mg, 0.12 mmol) and K$_3$PO$_4$ (51 mg, 0.24 mmol) in toluene (3 mL) was stirred at 100° C. for 2 hours. The mixture was diluted with EtOAc (100 mL), washed with brine (50 mL), dried over Na$_2$SO$_4$. The organic phase was filtered and concentrated. The residue was purified by silica gel chromatography column (petroleum ether/EtOAc=10:1 to 1:1) to give the title compound (18 mg, 31%) as a yellow oil.

$^1$HNMR (400 MHz, CDCl$_3$): δ 8.83 (s, 1H), 8.05 (s, 1H), 7.50 (s, 1H), 6.89 (s, 1H), 4.71 (d, J=6.4, 4H), 4.15 (d, J=10.8, 4H), 3.98 (d, J=8.8, 4H), 3.58-3.55 (m, 1H), 2.98 (d, J=10.4, 2H). 2.88-2.81 (m, 1H), 2.65 (s, 3H), 2.46 (s, 3H), 2.07-1.93 (m, 5H), 1.67 (br 3H).

LC-MS [mobile phase: from 90% water (0.1% FA) and 10% ACN (0.1% FA) to 5% water (0.1% FA) and 95% ACN (0.1% FA) in 10 min]: Rt=2.885 min; MS Calcd.: 490, MS Found: 491 [M+H]$^+$.

Example 47

1-(1-(6-(((1S,4S)-2-oxa-5-azabicyclo[2.2.1]heptan-5-yl)-2-methylpyrimidin-4-yl)-5-chloro-1H-indazol-6-yl)-3-methylpyrrolidin-3-ol

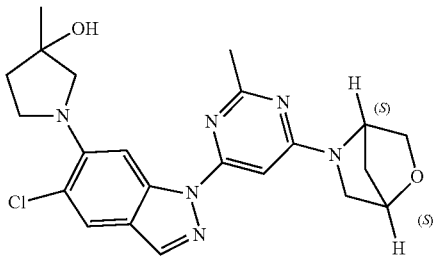

isomer 2

A mixture of 1-(5-chloro-1H-indazol-6-yl)-3-methylpyrrolidin-3-ol (40 mg, 0.16 mmol), (1S,4S)-5-(6-iodo-2-methylpyrimidin-4-yl)-2-oxa-5-azabicyclo[2.2.1]heptane (56 mg, 0.18 mmol), N,N'-dimethylcyclohexane-1,2-diamine (45 mg, 0.32 mmol), CuI (31 mg, 0.16 mmol) and $K_3PO_4$ (65 mg, 0.32 mmol) in toluene (3 mL) was stirred at 110° C. for 2 hours. The mixture was diluted with EtOAc (10 mL) and washed with $NH_3H_2O$ (10 mL×3). The organic phase was dried over $Na_2SO_4$, filtered and concentrated. The residue was purified by pre-HPLC (waters-1 $C_{18}$ 5 µm 19×150 mm 20-50% B, A: $H_2O$ (0.1% TFA), B: ACN, MS, Flowrate: 15 ml/min) to give the title compound (17 mg, 24%) as a yellow solid.

$^1$HNMR (300 MHz, $CDCl_3$): δ 8.22 (s, 1H), 8.02 (s, 1H), 7.65 (s, 1H), 6.77 (br 1H), 5.58 (br 1H) 4.81 (s, 1H), 3.96-3.86 (m, 4H), 3.63-3.37 (m, 5H), 2.76 (s, 3H), 2.16-2.01 (m, 4H), 1.54 (s, 3H).

LC-MS [column: $C_{18}$; column size: 4.6×50 mm; mobile phase: B (ACN): A (0.02% $NH_4OAc$); gradient (B %) in 6 min]: Rt=4.347 min; MS Calcd.: 440, MS Found: 441 [M+H]$^+$.

Example 48

1-(1-(6-((1S,4S)-2-oxa-5-azabicyclo[2.2.1]heptan-5-yl)-2-methylpyrimidin-4-yl)-5-chloro-1H-indazol-6-yl)-3-methylpyrrolidin-3-ol

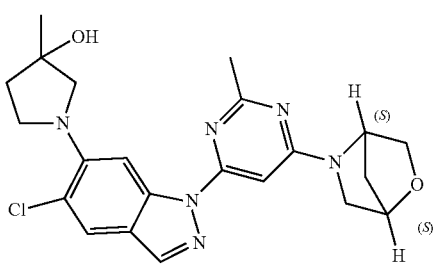

isomer 1

A mixture of 1-(5-chloro-1H-indazol-6-yl)-3-methylpyrrolidin-3-ol (40 mg, 0.16 mmol), (1S,4S)-5-(6-iodo-2-methylpyrimidin-4-yl)-2-oxa-5-azabicyclo[2.2.1]heptane (56 mg, 0.18 mmol), N,N'-dimethylcyclohexane-1,2-diamine (44 mg, 0.32 mmol), CuI (31 mg, 0.16 mmol) and $K_3PO_4$ (65 mg, 0.32 mmol) in toluene (3 mL) was stirred at 110° C. for 2 hours. The mixture was diluted with EtOAc (10 mL) and washed with $NH_3$—$H_2O$ (10 mL×3). The organic phase was dried over $Na_2SO_4$, filtered and concentrated. The residue was purified by pre-HPLC (waters-1 $C_{18}$ 5 µm 19×150 mm 20-50% B, A: $H_2O$ (0.1% TFA), B: ACN, MS, flow rate: 15 ml/min) to give the title compound (15 mg, 21%) as a yellow solid.

$^1$HNMR (300 MHz, $CDCl_3$): δ 8.26 (s, 1H), 8.04 (s, 1H), 7.66 (s, 1H), 6.81 (br 1H), 5.60 (br 1H) 4.81 (s, 1H), 3.95-3.86 (m, 4H), 3.61-3.34 (m, 5H), 2.76 (s, 3H), 2.15-2.05 (m, 4H), 1.53 (s, 3H).

LC-MS [column: $C_{18}$; column size: 4.6×50 mm; mobile phase: B (ACN): A (0.02% $NH_4OAc$); gradient (B %) in 6 min]: Rt=4.355 min, MS Calcd.: 440, MS Found: 441 [M+H]$^+$.

Example 49

1-(1-(6-(((1R,4R)-2-oxa-5-azabicyclo[2.2.1]heptan-5-yl)-2-methylpyrimidin-4-yl)-5-chloro-1H-indazol-6-yl)-3-methylpyrrolidin-3-ol

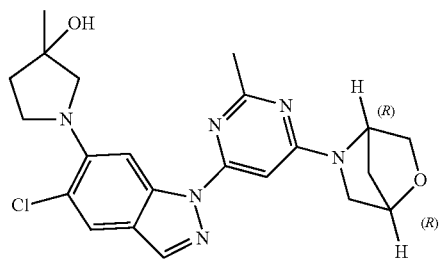

isomer 2

A mixture of 1-(5-chloro-1H-indazol-6-yl)-3-methylpyrrolidin-3-(34 mg, 0.13 mmol), (1R,4R)-5-(6-iodo-2-methylpyrimidin-4-yl)-2-oxa-5-azabicyclo[2.2.1]heptane (48 mg, 0.15 mmol), N,N'-dimethylcyclohexane-1,2-diamine (37 mg, 0.26 mmol), CuI (26 mg, 0.13 mmol) and $K_3PO_4$ (55 mg, 0.26 mmol) in toluene (3 mL) was stirred at 110° C. for 2 hours. The mixture was diluted with EtOAc (10 mL) and washed with $NH_3$—$H_2O$ (10 mL×3). The organic phase was dried over $Na_2SO_4$, filtered and concentrated. The residue was purified by pre-HPLC (gilson-2 $C_{18}$ 5 µm 19×150 mm; 40-55% B, A: $H_2O$ (0.1% $NH_4HCO_3$), B: ACN, UV: 254 nm, flow rate: 15 ml/min) to give the title compound (14 mg, 25%) as a yellow solid.

$^1$HNMR (300 MHz, $CDCl_3$): δ 8.52 (s, 1H), 7.99 (s, 1H), 7.67 (s, 1H), 6.67 (s, 1H), 4.74 (s, 1H), 3.90 (s, 3H), 3.56-3.47 (m, 4H), 3.44-3.33 (m, 2H), 2.59 (s, 3H), 2.12-2.02 (m, 2H), 1.99-1.96 (m, 2H), 1.52 (s, 3H).

LC-MS [column: $C_{18}$; column size: 4.6×50 mm; mobile phase: B (ACN): A (0.02% $NH_4OAc$); gradient (B %) in 6 min]: Rt=3.504 min; MS Calcd.: 440, MS Found: 441 [M+H]$^+$.

Example 50

1-(1-(6-(((1R,4R)-2-oxa-5-azabicyclo[2.2.1]heptan-5-yl)-2-methylpyrimidin-4-yl)-5-chloro-1H-indazol-6-yl)-3-methylpyrrolidin-3-ol isomer 1

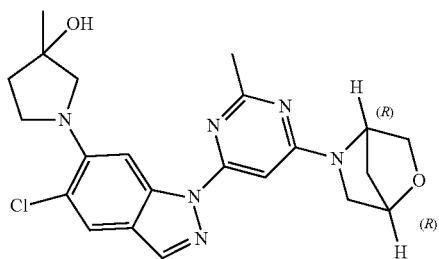

A mixture of 1-(5-chloro-1H-indazol-6-yl)-3-methylpyrrolidin-3-ol (34 mg, 0.13 mmol), (1R,4R)-5-(6-iodo-2-methylpyrimidin-4-yl)-2-oxa-5-azabicyclo[2.2.1]heptane (48 mg, 0.15 mmol), N,N'-dimethylcyclohexane-1,2-diamine (37 mg, 0.26 mmol), CuI (26 mg, 0.13 mmol) and $K_3PO_4$ (55 mg, 0.26 mmol) in toluene (3 mL) was stirred at 110° C. for 2 hrs. The mixture was diluted with EtOAc (10 mL) and washed with $NH_3 \cdot H_2O$ (10 mL×3). The organic phase was dried over $Na_2SO_4$, filtered and concentrated. The residue was purified by pre-HPLC (waters-1 Xbridge $C_{18}$ 5 μm 19×150 mm; 30-70% B, A: $H_2O$ (0.1% $NH_4HCO_3$), B: ACN, UV: 214 nm, flow rate: 15 ml/min) to give the title compound (19 mg, 33%) as a yellow solid.

¹HNMR (300 MHz, CDCl₃): δ 8.52 (s, 1H), 7.99 (s, 1H), 7.67 (s, 1H), 6.66 (s, 1H), 4.74 (s, 1H), 3.90 (s, 3H), 3.54-3.47 (m, 4H), 3.37-3.30 (m, 2H), 2.59 (s, 3H), 2.10-2.08 (m, 2H), 1.99-1.95 (m, 2H), 1.52 (s, 3H).

LC-MS [column: $C_{18}$; column size: 4.6×50 mm; mobile phase: B (ACN): A (0.02% $NH_4OAc$); gradient (B %) in 6 min]: Rt=3.338 min; MS Calcd.: 440, MS Found: 441 [M+H]⁺.

Example 51

2-(4-(1-(6-(((1R,4R)-2-oxa-5-azabicyclo[2.2.1]heptan-5-yl)-2-methylpyrimidin-4-yl)-5-methyl-1H-indazol-6-yl)piperidin-1-yl)ethanol

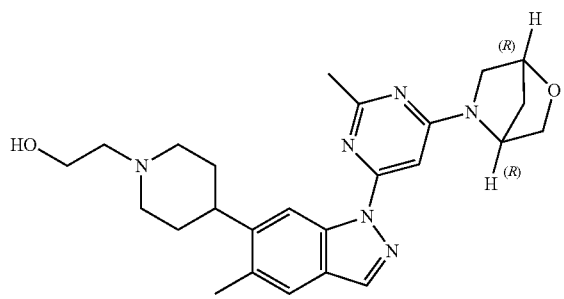

LiAlH₄ (20 mg, 0.53 mmol) was added to the solution of ethyl 2-(4-(1-(6-(((1R,4R)-2-oxa-5-azabicyclo[2.2.1]heptan-5-yl)-2-methylpyrimidin-4-yl)-5-methyl-1H-indazol-6-yl)piperidin-1-yl)acetate (52 mg, 0.106 mmol) in THF (5 mL) and the reaction was stirred at rt for 2 h. The reaction was then quenched with EtOAc. Then the mixture was filtered and the filtrate was concentrated and the residue was purified by $C_{18}$ flash column (acetonitrile:water=5:95-100:0) to give the title product as a white solid (25 mg, yield: 53%).

¹H NMR (400 MHz, CDCl₃): δ 8.82 (s, 1H), 8.05 (s, 1H), 7.49 (s, 1H), 6.67 (br, 0.9H), 5.30 (br, 0.5H), 4.74 (br, 1H), 3.90 (s, 2H), 3.68 (t, J=5.2 Hz, 2H), 3.53 (br, 2H), 3.15 (d, J=11.2 Hz, 2H), 2.88~2.81 (m, 1H), 2.65~2.63 (m, 2H), 2.63 (s, 3H), 2.46 (s, 3H), 2.32~2.26 (m, 2H), 2.01~1.95 (m, 7H).

LC-MS [mobile phase: from 90% water (0.1% FA) and 10% ACN (0.1% FA) to 5% water (0.1% FA) and 95% ACN (0.1% FA) in 9 min]: Rt=3.18 min; MS Calcd: 448, MS Found: 449 [M+H]⁺.

Example 52

2-(4-(1-(6-(((1S,4S)-2-oxa-5-azabicyclo[2.2.1]heptan-5-yl)-2-methylpyrimidin-4-yl)-5-methyl-1H-indazol-6-yl)piperidin-1-yl)ethanol

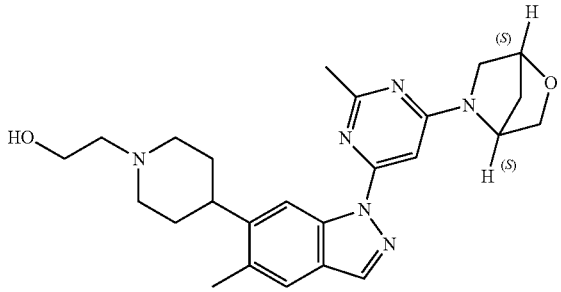

LiAlH₄ (19 mg, 0.5 mmol) was added to the solution of ethyl 2-(4-(1-(6-(((1S,4S)-2-oxa-5-azabicyclo[2.2.1]heptan-5-yl)-2-methylpyrimidin-4-yl)-5-methyl-1H-indazol-6-yl)piperidin-1-yl)acetate (75 mg, 0.153 mmol) in THF (5 mL) and the reaction mixture was stirred at rt for 0.5 hour. The reaction was then quenched with sat. NH₄Cl (0.5 mL). Then the mixture was filtered and the filtrate was concentrated and the residue was purified by C18 flash column (acetonitrile:water=5:95-100:0) to give the product as an off-white solid. (45 mg, 65% yield)

¹H NMR (400 MHz, CDCl₃): δ 8.83 (s, 1H), 8.06 (s, 1H), 7.50 (s, 1H), 6.68 (br, 0.7H), 5.27 (br, 0.5H), 4.74 (br, 1H), 3.91 (s, 2H), 3.74~3.71 (m, 2H), 3.54~3.46 (m, 2H), 3.23~3.20 (m, 2H), 2.87 (t, J=11.2 Hz, 1H), 2.70 (br, 2H), 2.64 (s, 3H), 2.46 (s, 3H), 2.37 (t, J=12.0 Hz, 2H), 2.01~1.95 (m, 6H).

LC-MS [mobile phase: from 90% water (0.1% FA) and 10% ACN (0.1% FA) to 5% water (0.1% FA) and 95% ACN (0.1% FA) in 10 min]: Rt=4.21 min; MS Calcd: 448, MS Found: 449 [M+H]⁺.

Example 53

Step 1

(1R,4R)-5-(2-methyl-6-(5-methyl-6-(piperidin-4-yl)-1H-indazol-1-yl)pyrimidin-4-yl)-2-oxa-5-azabicyclo[2.2.1]heptane

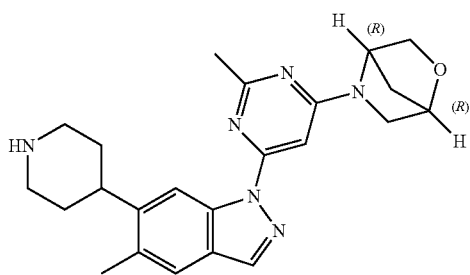

To a stirred solution of tert-butyl 4-(1-(6-((1R,4R)-2-oxa-5-azabicyclo[2.2.1]heptan-5-yl)-2-methylpyrimidin-4-yl)-5-methyl-1H-indazol-6-yl)piperidine-1-carboxylate (260 mg, 0.515 mmol) in CH$_2$Cl$_2$ (10 mL) at room temperature was added trifluoroacetic acid (5 mL). The reaction mixture was stirred at room temperature overnight. The reaction mixture was concentrated and the residue was dissolved in CH$_2$Cl$_2$ (50 mL). Aq. NH$_3$H$_2$O (10 mL) was added and the organic layer was separated. The aqueous layer was extracted with CH$_2$Cl$_2$ (50 mL) and the combined organic layers were washed with brine, dried over anhydrous Na$_2$SO$_4$, filtered. The filtrate was concentrated to dryness and the residue was purified by silica gel chromatography eluted with CH$_2$Cl$_2$:MeOH=20:1 to give desired product as a yellow solid (180 mg, yield: 86%).

LC-MS [mobile phase: from 50% water (0.1% FA) and 50% ACN (0.1% FA) to 5% water (0.1% FA) and 95% ACN (0.1% FA) in 2.6 min]: Rt=0.78 min; MS Calcd: 404, MS Found: 405 [M+H]$^+$.

Step 2

Synthesis of 1-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)-2-hydroxyethanone

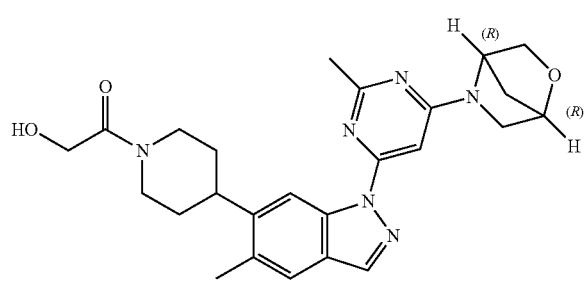

To a stirred solution of (1R,4R)-5-(2-methyl-6-(5-methyl-6-(piperidin-4-yl)-1H-indazol-1-yl)pyrimidin-4-yl)-2-oxa-5-azabicyclo[2.2.1]heptane (180 mg, 0.445 mmol), 2-hydroxyacetic acid (33.9 mg, 0.44 mmol) and HATU (254 mg, 0.668 mmol) in DMF (20 mL) at room temperature was added DIPEA (172 mg, 1.3 mmol). The reaction mixture was stirred at room temperature overnight. The reaction mixture was diluted with EtOAc (50 mL) and H$_2$O (50 mL). The organic layer was separated and the aqueous layer was extracted with EtOAc (2×50 mL). The combined organic layers were washed with water (2×50 mL), brine, dried over anhydrous Na$_2$SO$_4$ and filtered. The filtrate was concentrated to dryness. The residue was purified by silica gel chromatography eluted with CH$_2$Cl$_2$:MeOH=20:1 to give the desired product as a white solid (36 mg, yield: 17%).

$^1$H NMR (400 MHz, CDCl$_3$) δ 8.75 (s, 1H), 8.06 (s, 1H), 7.52 (s, 1H), 6.67 (br 1H), 5.29 (br 1H), 4.83 (d, J=10.4 Hz, 1H), 4.74 (s, 1H), 4.30-4.19 (m, 2H), 3.90 (s, 2H), 3.74-3.67 (m, 2H), 3.53 (br 2H), 3.21-3.15 (m, 1H), 3.12-3.09 (m, 1H), 2.90-2.84 (m, 1H), 2.60 (s, 3H), 2.48 (s, 3H), 2.02-1.95 (m, 4H), 1.82-1.72 (m, 2H).

LC-MS [mobile phase: from 60% water (0.1% FA) and 40% ACN (0.1% FA) to 5% water (0.1% FA) and 95% ACN (0.1% FA) in 10.0 min]: Rt=4.13 min; MS Calcd: 462, MS Found: 463 [M+H]$^+$.

Example 54

Step 1

(1S,4S)-5-(2-methyl-6-(5-methyl-6-(piperidin-4-yl)-1H-indazol-1-yl)pyrimidin-4-yl)-2-oxa-5-azabicyclo[2.2.1]heptane

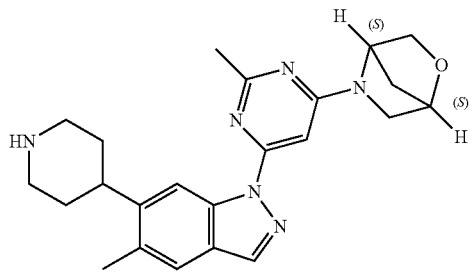

To a stirred solution of tert-butyl 4-(1-(6-((1S,4S)-2-oxa-5-azabicyclo[2.2.1]heptan-5-yl)-2-methylpyrimidin-4-yl)-5-methyl-1H-indazol-6-yl)piperidine-1-carboxylate (271 mg, 0.537 mmol) in CH$_2$Cl$_2$ (10 mL) at room temperature was added trifluoroacetic acid (5 mL). The reaction mixture was stirred at room temperature overnight. The reaction mixture was concentrated and the residue was dissolved in CH$_2$Cl$_2$ (50 mL). Aq. NH$_3$.H$_2$O (10 mL) was added and the organic layer was separated. The aqueous layer was extracted with CH$_2$Cl$_2$ (50 mL) and the combined organic layers were washed with brine, dried over anhydrous Na$_2$SO$_4$, filtered. The filtrate was concentrated to dryness. The residue was purified by silica gel chromatography eluted with CH$_2$Cl$_2$:MeOH=20:1 to give the desired product as a yellow solid (190 mg, yield: 87%).

LC-MS [mobile phase: from 50% water (0.1% FA) and 50% ACN (0.1% FA) to 5% water (0.1% FA) and 95% ACN (0.1% FA) in 2.6 min]: Rt=0.78 min; MS Calcd: 404, MS Found: 405 [M+H]$^+$.

Step 2

1-(4-(1-(6-((1S,4S)-2-oxa-5-azabicyclo[2.2.1]heptan-5-yl)-2-methylpyrimidin-4-yl)-5-methyl-1H-indazol-6-yl)piperidin-1-yl)-2-hydroxyethanone

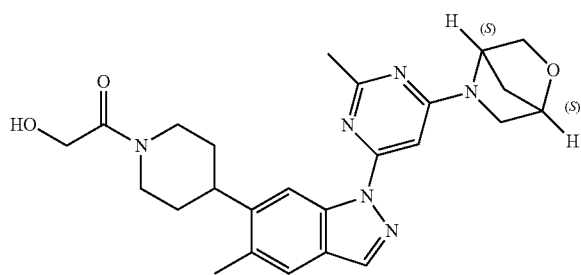

To a stirred solution of (1S,4S)-5-(2-methyl-6-(5-methyl-6-(piperidin-4-yl)-1H-indazol-1-yl)pyrimidin-4-yl)-2-oxa-5-azabicyclo[2.2.1]heptane (180 mg, 0.445 mmol), 2-hydroxyacetic acid (33.9 mg, 0.44 mmol) and HATU (254 mg, 0.668 mmol) in DMF (20 mL) at room temperature was added DIPEA (172 mg, 1.3 mmol). The reaction mixture was stirred at room temperature overnight. The reaction mixture was diluted with EtOAc (50 mL) and H₂O (50 mL) was added. The organic layer was separated and the aqueous layer was extracted with EtOAc (2×50 mL). The combined organic layers were washed with water (2×50 mL), brine, dried over anhydrous Na₂SO₄ and filtered. The filtrate was concentrated to dryness and the residue was purified by silica gel chromatography eluted with CH₂Cl₂:MeOH=20:1 to give the desired product as a white solid (38 mg, yield: 18%).

$^1$H NMR (400 MHz, CDCl₃) δ 8.75 (s, 1H), 8.06 (s, 1H), 7.52 (s, 1H), 6.67 (br 1H), 5.29 (br 1H), 4.84 (d, J=12.4 Hz, 1H), 4.74 (s, 1H), 4.30-4.19 (m, 2H), 3.90 (s, 2H), 3.74-3.67 (m, 2H), 3.52 (br 2H), 3.22-3.15 (m, 1H), 3.12-3.09 (m, 1H), 2.90-2.87 (m, 1H), 2.60 (s, 3H), 2.48 (s, 3H), 2.02-1.95 (m, 4H), 1.81-1.72 (m, 2H).

LC-MS [mobile phase: from 60% water (0.1% FA) and 40% ACN (0.1% FA) to 5% water (0.1% FA) and 95% ACN (0.1% FA) in 10.0 min]: Rt=3.99 min; MS Calcd: 462.24, MS Found: 463.5 [M+H]⁺.

Example 55

(1R,4R)-5-(2-methyl-6-(5-methyl-6-(3-methyl-1-(oxetan-3-yl)piperidin-4-yl)-1H-indazol-1-yl)pyrimidin-4-yl)-2-oxa-5-azabicyclo[2.2.1]heptane

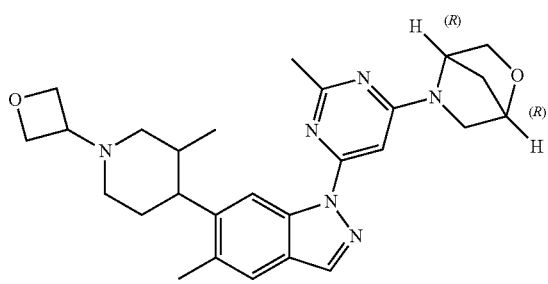

A mixture of 5-methyl-6-(3-methyl-1-(oxetan-3-yl)piperidin-4-yl)-1H-indazole (45 mg, 0.16 mmol), (1R,4R)-5-(6-iodo-2-methylpyrimidin-4-yl)-2-oxa-5-azabicyclo[2.2.1]heptane (57 mg, 0.18 mmol), N,N'-dimethylcyclohexane-1,2-diamine (45 mg, 0.32 mmol), CuI (30 mg, 0.16 mmol) and K₃PO₄ (68 mg, 0.32 mmol) in toluene (3 mL) was stirred at 100° C. for 2 hours. The mixture was diluted with EtOAc (100 mL), washed with brine (50 mL), dried over Na₂SO₄, filtered and concentrated. The residue was purified by prep-HPLC ((waters-1 C₁₈ 5 μm 19×150 mm-11212; 20-75% B, A: H₂O (0.1% NH₄HCO₃), B: ACN, 214, flow rate 15 ml/min, GT12 mins-18 min) to give the title compound (10 mg, 13%) as a yellow solid.

$^1$HNMR (400 MHz, CDCl₃): δ 8.77 (s, 1H), 8.06 (s, 1H), 7.50 (s, 1H), 6.67 (br 1H), 5.35 (br 1H), 4.74-4.70 (m, 5H), 3.91 (s, 2H), 3.58-3.52 (m, 2H), 2.93-2.90 (m, 2H), 2.64 (s, 3H), 2.56-2.52 (m, 1H), 2.43 (s, 3H), 2.23-2.21 (m, 1H), 2.00-1.93 (m, 3H), 1.82 (s, 2H), 1.30-1.26 (m, 2H), 0.79-0.76 (m, 3H).

LC-MS [mobile phase: from 90% water (0.1% FA) and 10% ACN (0.1% FA) to 5% water (0.1% FA) and 95% ACN (0.1% FA) in 10 min]: Rt=4.389 min; MS Calcd.: 474, MS Found: 475 [M+H]⁺.

Example 56

(1R,4R)-5-(6-(6-(1-(3-deuterooxetan-3-yl)piperidin-4-yl)-5-methyl-1H-indazol-1-yl)-2-methoxypyrimidin-4-yl)-2-oxa-5-azabicyclo[2.2.1]heptane

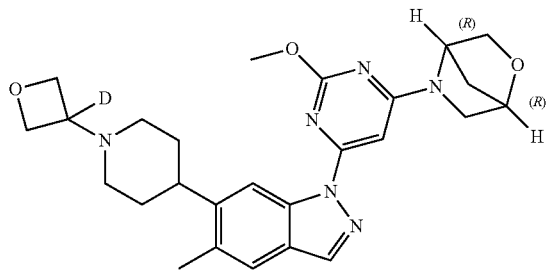

To a mixture of (1R,4R)-5-(6-iodo-2-methoxypyrimidin-4-yl)-2-oxa-5-azabicyclo[2.2.1]heptane (90 mg, 0.270 mmol) and 6-(1-(3-deuterooxetan-3-yl)piperidin-4-yl)-5-methyl-1H-indazole (73 mg, 0.268 mmol) in toluene (20 mL) were added CuI (77 mg, 0.41 mmol), K₃P₄.3H₂O (209 mg, 0.89 mmol) and N,N'-dimethylethylenediamine (48 mg, 0.54 mmol). The reaction mixture was stirred at 100° C. for 4 h. LC-MS showed the reaction was complete. The reaction mixture was diluted with EtOAc (50 mL) and filtered. The filtrate was concentrated and the residue was purified by silica gel column chromatography, followed by prep-TLC (EtOAc/PE=1/1) to give the title product as a white solid (62 mg). The white solid was slurred in EtOAc for 2 h and filtered to give pure desired product as a white solid (35 mg, yield: 27%).

$^1$H NMR (400 MHz, CDCl₃) δ 8.77 (s, 1H), 8.06 (s, 1H), 7.51 (s, 1H), 6.56 (br 1H), 5.26 (br 1H), 4.74 (s, 1H), 4.68 (s, 4H), 4.12 (s, 3H), 3.92-3.90 (m, 2H), 3.55-3.48 (m, 2H), 2.94-2.80 (m, 3H), 2.45 (s, 3H), 2.03-1.85 (m, 8H).

LC-MS [mobile phase: from 90% water (0.1% FA) and 10% ACN (0.1% FA) to 5% water (0.1% FA) and 95% ACN (0.1% FA) in 10.0 min]: Rt=4.24 min; MS Calcd: 477, MS Found: 478 [M+H]⁺; 500 [M+Na]⁺.

Example 57

(1S,4S)-5-(6-(6-(1-(3-deuterooxetan-3-yl)piperidin-4-yl)-5-methyl-1H-indazol-1-yl)-2-methoxypyrimidin-4-yl)-2-oxa-5-azabicyclo[2.2.1]heptane

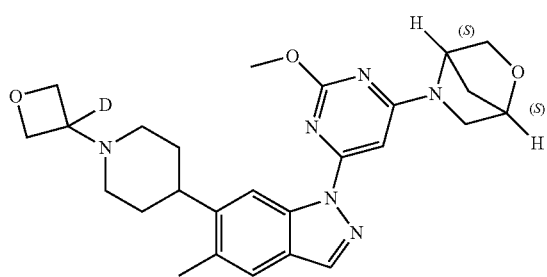

To a solution of (1S,4S)-5-(6-iodo-2-methoxypyrimidin-4-yl)-2-oxa-5-azabicyclo[2.2.1]heptane (90 mg, 0.270 mmol) and 6-(1-(3-deuterooxetan-3-yl)piperidin-4-yl)-5-methyl-1H-indazole (75 mg, 0.275 mmol) in toluene (20 mL) were added CuI (75 mg, 0.41 mmol), $K_3PO_4 \cdot 3H_2O$ (220 mg, 0.94 mmol) and N,N'-dimethylethylenediamine (49 mg, 0.54 mmol). The reaction mixture was stirred at 100° C. for 4 h. LC-MS showed the reaction was complete. The reaction mixture was diluted with EtOAc (100 mL) and filtered. The filtrate was concentrated and the residue was purified by silica gel column chromatography, followed by prep-TLC (EtOAc/PE=1/1) to give pure desired product as white solid (75 mg, yield: 58%).

$^1$H NMR (400 MHz, CDCl$_3$) δ 8.77 (s, 1H), 8.06 (s, 1H), 7.51 (s, 1H), 6.56 (br 1H), 5.30 (br 1H), 4.74 (s, 1H), 4.69 (s, 4H), 4.11 (s, 3H), 3.92-3.90 (m, 2H), 3.54-3.43 (m, 2H), 2.93 (d, J=10.8 Hz, 2H), 2.90-2.80 (m, 1H), 2.45 (s, 3H), 2.03-1.86 (m, 8H).

LC-MS [mobile phase: from 90% water (0.1% FA) and 10% ACN (0.1% FA) to 5% water (0.1% FA) and 95% ACN (0.1% FA) in 10.0 min]: Rt=4.21 min; MS Calcd: 477, MS Found: 478 [M+H]$^+$; 500 [M+Na]$^+$.

Example 58

(1R,4R)-5-(2-methoxy-6-(5-methyl-6-(piperidin-4-yl)-1H-indazol-1-yl)pyrimidin-4-yl)-2-oxa-5-azabicyclo[2.2.1]heptane

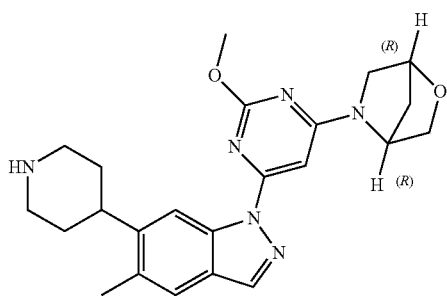

HCl/MeOH (5 M, 4 ml) was dropwise added to a solution of tert-butyl 4-(1-(6-((1R,4R)-2-oxa-5-azabicyclo[2.2.1]heptan-5-yl)-2-methoxypyrimidin-4-yl)-5-methyl-1H-indazol-6-yl)piperidine-1-carboxylate (94 mg, 0.18 mmol) in methanol (4 ml) under Ar. The reaction was stirred at room temperature for 1 h. The reaction mixture was dropwise added to an ice cooled aq. $Na_2CO_3$ (30 ml) (pH equals 10). The resultant was concentrated to remove MeOH and extracted with $CH_2Cl_2$ (6×100 ml). The combined organics were washed with brine (25 ml), dried over anhydrous $Na_2SO_4$, filtered and concentrated. The residue was purified by column chromatography (eluent: $CH_2Cl_2$:MeOH=10:1) to give desired product as crude white solid (48 mg, yield: 63%).

Part of the obtained desired product (33 mg) was further purified by prep-HPLC (basic conditions). The fractions were concentrated and then dried under lyophilizer afforded pure desired product as yellow solid (20 mg).

LC-MS [mobile phase: from 90% water (0.1% FA) and 10% ACN (0.1% FA) to 5% water (0.1% TFA) and 95% ACN (0.1% TFA) in 10.0 min]: Rt=5.57 min; MS Calcd: 420, MS Found: 421 [M+H]$^+$.

$^1$H NMR (400 MHz, CDCl$_3$) δ 8.76 (s, 1H), 8.06 (s, 1H), 7.51 (s, 1H), 6.56 (br 1H), 5.25 (br 1H), 4.73 (s, 1H), 4.16 (s, 3H), 3.90 (q, J=7.3 Hz, 2H), 3.55-3.49 (m, 2H), 3.27-3.24 (m, 2H), 2.99-2.93 (m, 1H), 2.86-2.80 (m, 2H), 2.47 (s, 3H), 2.00-1.89 (m, 4H), 1.74-1.69 (m, 2H).

Example 59

(1S,4S)-5-(2-methoxy-6-(5-methyl-6-(piperidin-4-yl)-1H-indazol-1-yl)pyrimidin-4-yl)-2-oxa-5-azabicyclo[2.2.1]heptane

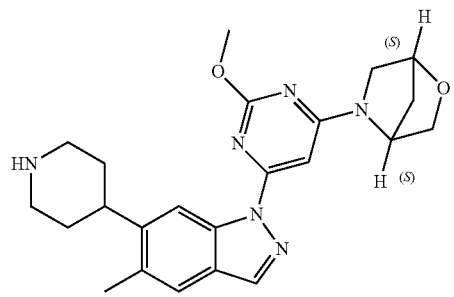

To a solution of tert-butyl 4-(1-(6-((1S,4S)-2-oxa-5-azabicyclo[2.2.1]heptan-5-yl)-2-methoxypyrimidin-4-yl)-5-methyl-1H-indazol-6-yl)piperidine-1-carboxylate (65 mg, 0.125 mmol) in 2 mL of DCM was added 0.5 mL of TFA dropwise. The reaction was stirred at room temperature for 2 hours. The reaction was added sat. NaHCO$_3$ to adjust pH=8-9 and extracted with DCM (50 mL×2). The combined organic layer was dried over Na$_2$SO$_4$, filtered and concentrated. The residue was purified by chiral-HPLC (IB, hex:EtOH:DEA=50:50:0.3; flow rate: 10 mL/min, wave length: 230 nm) to afford the title compound (14 mg, 27%) as a white solid.

$^1$HNMR (400 MHz, CDCl$_3$): δ 8.75 (s, 1H), 8.06 (s, 1H), 7.50 (s, 1H), 6.55 (br 1H), 5.24 (br 1H), 4.73 (s, 1H), 4.15 (s, 3H), 3.97-3.87 (m, 2H), 3.68-3.41 (m, 2H), 3.26-3.23 (m, 2H), 2.95 (t, J=14.4 Hz, 1H), 2.82 (t, J=11.2 Hz, 2H), 2.46 (s, 3H), 2.00-1.71 (m, 5H), 1.64-1.60 (m, 2H).

LC-MS [mobile phase: from 90% water (0.1% FA) and 10% ACN (0.1% FA) to 5% water (0.1% FA) and 95% ACN (0.1% FA) in 10 min]: Rt=3.057 min; MS Calcd.: 420, MS Found: 421 [M+H]$^+$.

Example 60

3-(2-methoxy-6-(5-methyl-6-(piperidin-4-yl)-1H-indazol-1-yl)pyrimidin-4-yl)-6-oxa-3-azabicyclo[3.1.1]heptane 2,2,2-trifluoroacetate

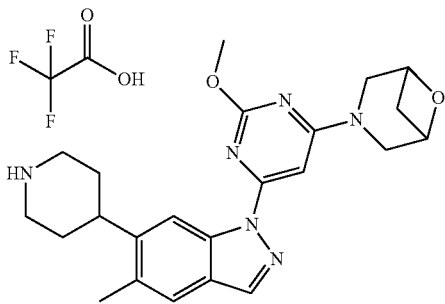

To a solution of tert-butyl 4-(1-(6-(6-oxa-3-azabicyclo[3.1.1]heptan-3-yl)-2-methoxypyrimidin-4-yl)-5-methyl-1H-indazol-6-yl)piperidine-1-carboxylate (44 mg, 0.085 mmol) in DCM (5 mL) was added TFA (1 mL). The mixture was stirred at rt for 4 hrs. Then TLC indicated that the reaction is completed. The mixture was concentrated to give the desired product (40 mg) as a yellow solid.

$^1$H NMR (300 MHz, CD$_3$OD): δ 8.73 (s, 1H), 8.19 (m, 1H), 7.64 (m, 1H), 6.86 (s, 1H), 4.83-4.75 (m, 2H), 4.12 (s, 3H), 4.08-3.92 (m, 1H), 3.86-3.67 (m, 3H), 3.61-3.50 (m, 2H), 3.38-3.16 (m, 3H), 2.52 (s, 3H), 2.21-1.89 (m, 6H).

$^{19}$F NMR (376 MHz, CD$_3$OD): δ −77.58 (s, 3F).

LC-MS [mobile phase: from 95% water (0.02% NH$_4$OAc) and 5% ACN to 5% water (0.02% NH$_4$OAc) and 95% ACN in 6.5 min]: Rt=3.311 min, MS Calcd.: 534, MS Found: 421 [M −114+H]$^+$.

Example 61

3-(2-methyl-6-(5-methyl-6-(piperidin-4-yl)-1H-indazol-1-yl)pyrimidin-4-yl)-6-oxa-3-azabicyclo[3.1.1]heptane 2,2,2-trifluoroacetate

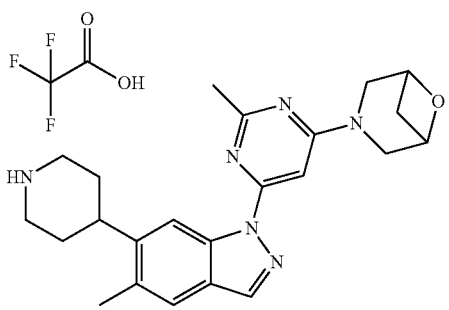

To a solution of tert-butyl 4-(1-(6-(6-oxa-3-azabicyclo[3.1.1]heptan-3-yl)-2-methylpyrimidin-4-yl)-5-methyl-1H-indazol-6-yl)piperidine-1-carboxylate (48 mg, 0.095 mmol) in DCM (5 mL) was added TFA (1 mL). The mixture was stirred at r.t for 4 hrs. Then LCMS indicated that the reaction was completed. The mixture was concentrated to give the desired product (50 mg, yield 100%) as a white solid.

$^1$H NMR (300 MHz, CD$_3$OD): δ 8.75 (s, 1H), 8.26 (m, 1H), 7.67 (m, 1H), 7.11 (s, 1H), 4.85-4.79 (m, 2H), 4.11-3.77 (m, 4H), 3.63-3.53 (m, 2H), 3.39-3.33 (m, 1H), 3.27-3.16 (m, 2H), 2.73 (s, 3H), 2.53 (s, 3H), 2.22-1.91 (m, 6H).

$^{19}$F NMR (376 MHz, CD$_3$OD): δ −77.38 (s, 3F).

LC-MS [mobile phase: from 95% water (0.02% NH$_4$OAc) and 5% ACN to 5% water (0.02% NH$_4$OAc) and 95% ACN in 6.5 min]: Rt=3.278 min, MS Calcd.: 518, MS Found: 405 [M-114+H]$^+$.

Example 62

3-(2-methoxy-6-(5-methyl-6-(piperidin-4-yl)-1H-indazol-1-yl)pyrimidin-4-yl)-8-oxa-3-azabicyclo[3.2.1]octane 2,2,2-trifluoroacetate

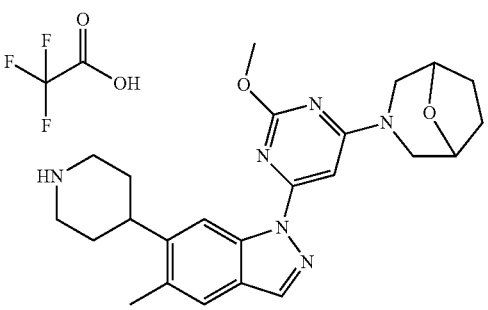

To a solution of tert-butyl 4-(1-(6-(8-oxa-3-azabicyclo[3.2.1]octan-3-yl)-2-methoxypyrimidin-4-yl)-5-methyl-1H-indazol-6-yl)piperidine-1-carboxylate (70 mg, 0.13 mmol) in DCM (5 mL) was added TFA (0.5 mL). The resulting mixture was stirred at rt overnight. TLC showed the reaction was completed. The mixture was concentrated to give the title compound (66 mg, yield 93%) as a yellow oil.

$^1$H NMR (400 MHz, DMSO-d$_6$): δ 8.76 (br 1H), 8.63 (s, 1H), 8.54 (br 1H), 8.35 (s, 1H), 7.67 (s, 1H), 6.80 (s, 1H), 4.45 (s, 2H), 4.01 (br 5H), 3.46-3.43 (m, 2H), 3.22-3.09 (m, 5H), 2.46 (s, 3H), 2.00-1.97 (m, 2H), 1.86-1.78 (m, 4H), 1.73-1.70 (m, 2H).

$^{19}$F NMR (376 MHz, DMSO-d$_6$): δ −74.79 (s, 3F).

LC-MS [mobile phase: from 95% water (0.1% TFA) and 5% ACN to 5% water (0.1% TFA) and 95% ACN in 6.5 min), Rt=3.562 min, MS Calcd.: 548, MS Found: 435 [M −114+H]$^+$.

Example 63

3-(2-methyl-6-(5-methyl-6-(piperidin-4-yl)-1H-indazol-1-yl)pyrimidin-4-yl)-8-oxa-3-azabicyclo[3.2.1]octane 2,2,2-trifluoroacetate

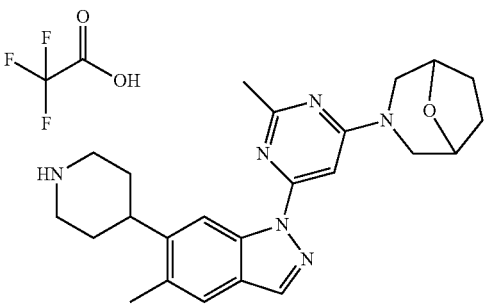

To a solution of tert-butyl 4-(1-(6-(8-oxa-3-azabicyclo[3.2.1]octan-3-yl)-2-methylpyrimidin-4-yl)-5-methyl-1H-indazol-6-yl)piperidine-1-carboxylate (80 mg, 0.15 mmol) in DCM (5 mL) was added TFA (0.5 mL). The resulting mixture was stirred at r.t overnight. TLC showed the reaction was completed. The mixture was concentrated to give the title compound (80 mg, yield 100%) as a white solid.

$^1$H NMR (400 MHz, DMSO-$d_6$): δ 8.80 (br 1H), 8.74 (s, 1H), 8.62 (br 1H), 8.34 (s, 1H), 7.66 (s, 1H), 6.92 (s, 1H), 4.46 (s, 2H), 4.02 (br 2H), 3.48-3.45 (m, 2H), 3.23-3.09 (m, 5H), 2.57 (s, 3H), 2.46 (s, 3H), 2.01-1.97 (m, 2H), 1.91-1.85 (m, 4H), 1.72-1.70 (m, 2H). $^{19}$F NMR (376 MHz, DMSO-$d_6$): δ −74.75 (s, 3F).

LC-MS [mobile phase: from 95% water (0.1% TFA) and 5% ACN to 5% water (0.1% TFA) and 95% ACN in 6.5 min]: Rt=3.305 min, MS Calcd.: 532, MS Found: 419 [M−114+H]$^+$.

Examples 64, 65 and 66

Step 1

5-(2-methoxy-6-(5-methyl-6-(piperidin-4-yl)-1H-indazol-1-yl)pyrimidin-4-yl)-2-oxa-5-azabicyclo[2.2.2]octane Hydrochloride

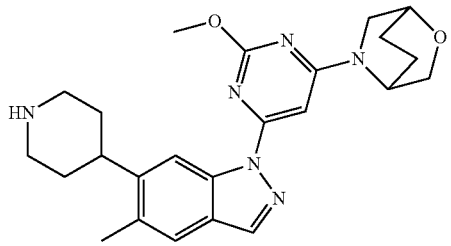 [SMILES: COc1nc(N2CC3CCC2CO3)cc(-n2ncc3cc(C)c(C4CCNCC4)cc32)n1]

To a solution of tert-butyl 4-(1-(6-(2-oxa-5-azabicyclo[2.2.2]octan-5-yl)-2-methoxypyrimidin-4-yl)-5-methyl-1H-indazol-6-yl)piperidine-1-carboxylate (64 mg, 0.12 mmol) in MeOH (2 mL) was added HCl/dioxane (1 mL). The mixture was stirred at room temperature for 2 hours. The mixture was concentrated to give the compound (47 mg, 87%) as a yellow oil.

LCMS [column: $C_{18}$; column size: 4.6×30 mm 5 μm; Dikwa Diamonsil plus; mobile phase: B (ACN): A1 (0.02% NH$_4$OAc+ 5% ACN); gradient (B %) in 4 mins. 10-95-POS; flow rate: 1.5 ml/min]: Rt=1.910 min; MS Calcd.: 434, MS Found: 435 [M+H]$^+$.

Step 2

5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.2]octane

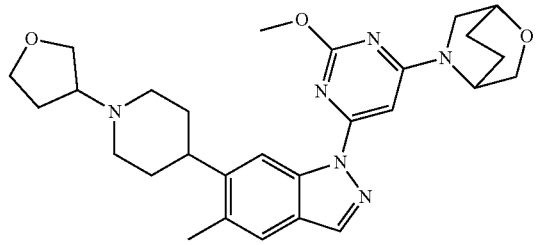 [SMILES: COc1nc(N2CC3CCC2CO3)cc(-n2ncc3cc(C)c(C4CCN(C5CCOC5)CC4)cc32)n1]

To a solution of 5-(2-methoxy-6-(5-methyl-6-(piperidin-4-yl)-1H-indazol-1-yl)pyrimidin-4-yl)-2-oxa-5-azabicyclo[2.2.2]octane hydrochloride (47 mg, 0.10 mmol), dihydrofuran-3(2H)-one (49 mg, 0.56 mmol) and AcOH (2 drop) in DCM (5 mL) was added NaBH$_3$CN (14 mg, 0.22 mmol). The mixture was stirred at room temperature for 20 hours. sat. NaHCO$_3$ (3 drops) was added to the mixture. The mixture was concentrated and purified by silica gel chromatography column (DCM/MeOH=15/1) to give the title compound (40 mg, 73%) as a colorless oil.

LCMS [column: $C_{18}$; column size: 4.6×30 mm 5 μm; Dikwa Diamonsil plus; mobile phase: B (ACN): A1 (0.02% NH$_4$OAc+ 5% ACN); gradient (B %) in 4 mins. 10-95-POS; flow rate: 1.5 ml/min]: Rt=2.382 min; MS Calcd.: 504, MS Found: 505 [M+H]$^+$.

5-(2-methoxy-6-(5-methyl-6-(1-(tetrahydrofuran-3-yl)piperidin-4-yl)-1H-indazol-1-yl)pyrimidin-4-yl)-2-oxa-5-azabicyclo[2.2.2]octane (40 mg, 0.08 mmol) was separated by chiral-HPLC to give E64, (2 mg, 5%), E65, (7 mg, 17%) and E66 (5 mg, 12%).

Chiral pre-HPLC: column: Chiralpak ID 5 μm 20×150 mm; Phase: ACN:IPA:NH$_3$.H$_2$O=80:20:0.3, Flow rate: 13 mL/min; Wave length: 254 nm.

E64 (Mixture, Isomer 1 and Isomer 2)

$^1$H NMR (400 MHz, CDCl$_3$): δ 8.76 (s, 1H), 8.07 (s, 1H), 7.51 (s, 1H), 6.60 (s, 1H), 4.98 (br 1H), 4.13 (s, 3H), 4.09-3.91 (m, 3H), 3.85-3.79 (m, 1H), 3.70 (br 1H), 3.54-3.52 (m, 1H), 3.17-2.84 (m, 3H), 2.46 (s, 3H), 2.33-2.21 (m, 3H), 2.08-1.92 (m, 6H), 1.79-1.58 (m, 7H).

Chiral-HPLC [Column: Chiralpak ID 250 mm×4.6 mm 5 μm; Mobile phase: ACN:IPA:DEA=80:20:0.2; Flow rate: 1 ml/min; Wave length: 230 nm; Temperature: ambient]: Rt=5.191 min and 5.305 min.

LC-MS [column: $C_{18}$; column size: 4.6×50 mm; mobile phase: B (ACN) A (0.02% NH$_4$OAc); gradient (B %)]: Rt=3.987 min, MS Calcd.: 504, MS Found: 505 [M+H]$^+$.

E65 (Isomer 3)

$^1$H NMR (400 MHz, CDCl$_3$): δ 8.76 (s, 1H), 8.06 (s, 1H), 7.51 (s, 1H), 6.60 (s, 1H), 4.98 (br 1H), 4.18-4.11 (m, 4H), 4.07-3.91 (m, 4H), 3.85-3.79 (m, 1H), 3.72-3.68 (m, 1H), 3.54-3.49 (m, 1H), 3.16 (d, J=10.8 MHz, 1H), 3.06-2.81 (m, 3H), 2.46 (s, 3H), 2.29-2.20 (m, 3H), 2.14-1.73 (m, 10H).

Chiral-HPLC [Column: Chiralpak ID 250 mm×4.6 mm 5 μm; Mobile phase: ACN:IPA:DEA=80:20:0.2; Flow rate: 1 ml/min; Wave length: 230 nm; Temperature: ambient]: Rt=6.742 min.

LC-MS [column: $C_{18}$; column size: 4.6×50 mm; mobile phase: B (ACN) A (0.02% $NH_4OAc$); gradient (B %)]: Rt=3.915 min, MS Calcd.: 504, MS Found: 505 $[M+H]^+$.

E66 (Isomer 4)

$^1$H NMR (400 MHz, $CDCl_3$): δ 8.69 (s, 1H), 8.00 (s, 1H), 7.44 (s, 1H), 6.53 (s, 1H), 4.91 (br 1H), 4.06 (s, 3H), 4.00-3.84 (m, 4H), 3.78-3.72 (m, 1H), 3.47-3.44 (m, 1H), 3.14-2.75 (m, 3H), 2.39 (s, 3H), 2.26-2.15 (m, 3H), 2.02-1.77 (m, 6H), 1.72-1.58 (m, 7H).

Chiral-HPLC [Column: Chiralpak ID 250 mm×4.6 mm 5 µm; Mobile phase: ACN:IPA:DEA=80:20:0.2; Flow rate: 1 ml/min; Wave length: 230 nm; Temperature: ambient]: Rt=8.435 min.

LC-MS [column: $C_{18}$; column size: 4.6×50 mm; mobile phase: B (ACN) A (0.02% $NH_4OAc$); gradient (B %)]: Rt=3.911 min, MS Calcd.: 504, MS Found: 505 $[M+H]^+$.

Examples 67 and 68

(1R,4R)-5-(6-(5-chloro-6-(1-(tetrahydrofuran-3-yl)piperidin-4-yl)-1H-indazol-1-yl)-2-methoxypyrimidin-4-yl)-2-oxa-5-azabicyclo[2.2.1]heptane

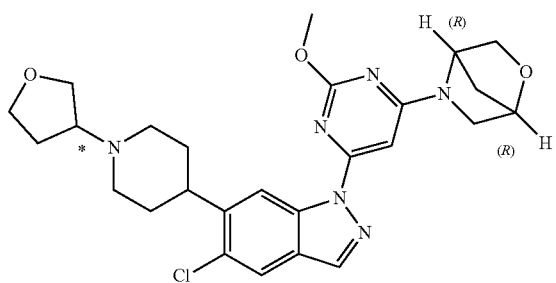

To a solution of 5-chloro-6-(1-(tetrahydrofuran-3-yl)piperidin-4-yl)-1H-indazole (200 mg, 0.65 mmol), (1R,4R)-5-(6-iodo-2-methoxypyrimidin-4-yl)-2-oxa-5-azabicyclo[2.2.1]heptane (240 mg, 0.72 mmol), CuI (125 mg, 0.65 mmol), $K_3PO_4$ (278 mg, 1.3 mmol) and N,N'-dimethylcyclohexane-1,2-diamine (186 mg, 1.3 mmol) in toluene (3 mL) and DMSO (1 mL) was stirred at 100° C. for 4 hours. The mixture was diluted with EtOAc (5 mL×2), washed with brine, dried over $Na_2SO_4$, filtered and concentrated. The crude was purified by prep-TLC (DCM/MeOH=10/1) to give the mixture compound (62 mg, 18%) as a white solid.

LCMS [column: $C_{18}$; column size: 2.1×50 mm; Waters ACQUITY UPLC BEH; mobile phase: B (ACN); A (0.02% $NH_4OAc$+ 5% ACN); flow rate: 0.5 ml/min; gradient (B %) in 3 mins]: Rt=1.91 min; MS Calcd.: 510, MS Found: 511 $[M+H]^+$.

The mixture (62 mg, 0.12 mmol) was separated by chiral-HPLC to afford crude E67 (28 mg, 45%) and E68 (28 mg, 45%).

Chiral pre-HPLC: column: Chiralpak ID; 5 µm 20×150 mm; Phase: $CO_2$:EtOH=50:50; Flow rate: 9 ml/min, Wave length: 254 nm E67 (Isomer 1)

Crude Isomer 1 (28 mg) was purified by prep-HPLC (x-bridge $C_{18}$, 5 µm, 21.2×150 mm, 50-80% ACN—$H_2O$ (0.1% $NH_4HCO_3$), flow rate: 15 ml/min, GT7.5 mins.) to give isomer 1 (9 mg) as a yellow oil.

$^1$HNMR (400 MHz, $CD_3OD$): δ 8.84 (s, 1H), 8.20 (s, 1H), 7.85 (s, 1H), 6.59 (s, 1H), 4.75 (s, 1H), 4.10 (s, 3H), 3.99-3.67 (m, 7H), 3.59-3.57 (m, 1H), 3.23-3.17 (m, 3H), 3.09-2.96 (m, 2H), 2.36-2.29 (m, 2H), 2.18-2.14 (m, 1H), 2.01 (s, 4H), 1.93-1.78 (m, 3H).

Chiral-HPLC [column: chiral pak IE, 5 µm 250 mm×4.6 mm; mobile phase: Hex:IPA=50:50; flow rate: 1 mL/min; wave length: 230 nm; temperature: 30° C.]: Rt=12.995 min.

LCMS column [$C_{18}$; column size: 4.6×50 mm; mobile phase: B (ACN): A (0.02% $NH_4OAc$); gradient (B %) in 6 mins]: Rt=3.554 min, MS Calcd.: 510, MS Found: 511 $[M+H]^+$.

E68 (Isomer 2)

Crude Isomer 2 (28 mg) was purified by prep-HPLC (x-bridge $C_{18}$, 5 µm, 19×150 mm, 40-75% ACN—$H_2O$ (0.1% $NH_4HCO_3$), flow rate: 15 ml/min, GT12 mins) to give pure isomer 2 (10 mg) as a yellow oil.

$^1$H NMR (400 MHz, $CD3OD$): δ 8.84 (s, 1H), 8.20 (s, 1H), 7.85 (s, 1H), 6.59 (s, 1H), 4.75 (s, 1H), 4.10 (s, 3H), 3.99-3.67 (m, 7H), 3.59-3.57 (m, 1H), 3.23-3.17 (m, 3H), 3.09-2.96 (m, 2H), 2.36-2.29 (m, 2H), 2.18-2.14 (m, 1H), 2.01 (s, 4H), 1.93-1.78 (m, 3H).

Chiral-HPLC [column: chiral pak IE, 5 µm 250 mm×4.6 mm; mobile phase: Hex:IPA=50:50; flow rate: 1 mL/min; wave length: 230 nm; temperature: 30° C.]: Rt=15.944 min.

LCMS column [$C_{18}$; column size: 4.6×50 mm; mobile phase: B (ACN): A (0.02% $NH_4OAc$); gradient (B %) in 6 mins]: Rt=4.071 min; MS Calcd.: 510, MS Found: 511 $[M+H]^+$.

Examples 69 and 70

(1S,4S)-5-(6-(5-chloro-6-(1-(tetrahydrofuran-3-yl)piperidin-4-yl)-1H-indazol-1-yl)-2-methoxypyrimidin-4-yl)-2-oxa-5-azabicyclo[2.2.1]heptane

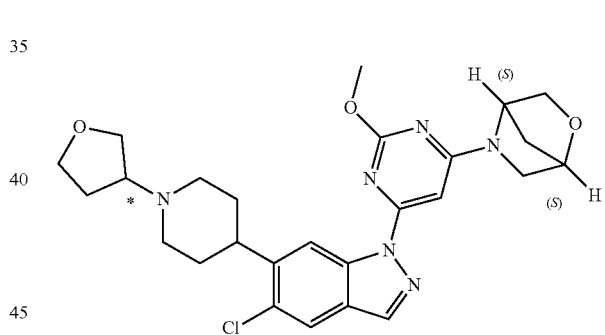

To a suspension of 5-chloro-6-(1-(tetrahydrofuran-3-yl)piperidin-4-yl)-1H-indazole (150 mg, 0.49 mmol), (1S,4S)-5-(6-iodo-2-methoxypyrimidin-4-yl)-2-oxa-5-azabicyclo[2.2.1]heptane (180 mg, 0.54 mmol), N,N'-dimethylcyclohexane-1,2-diamine (140 mg, 0.98 mmol), CuI (93 mg, 0.49 mmol) and $K_3PO_4$ (208 mg, 0.98 mmol) in toluene (2 mL) and DMSO (2 mL) was was stirred at 100° C. under $N_2$ atmosphere for 2 hrs. Then the reaction mixture was diluted with 15 mL water and 3 mL of $NH_3H_2O$, extracted with EtOAc (30 mL×3). The organic layer was dried over $Na_2SO_4$, filtered and concentrated. The crude was purified by column chromatography on silica gel (DCM/MeOH=15/1) to give the title compound (50 mg, yield 20%) as a yellow oil.

To a suspension of 5-chloro-6-(1-(tetrahydrofuran-3-yl)piperidin-4-yl)-1H-indazole (200 mg, 0.66 mmol), (1S,4S)-5-(6-iodo-2-methoxypyrimidin-4-yl)-2-oxa-5-azabicyclo[2.2.1]heptane (240 mg, 0.72 mmol), N,N'-dimethylcyclohexane-1,2-diamine (186 mg, 1.31 mmol), CuI (125 mg, 0.66 mmol) and $K_3PO_4$ (278 mg, 1.31 mmol) in toluene (3 mL) and DMF (1 mL) was was stirred at 100° C. under N₂ atmosphere for 4 hours. Then the reaction mixture was diluted with 15 mL water and 3 mL of NH₃H₂O and extracted with EtOAc (30 mL×3). The organic layer was washed with brine (15 mL), dried over Na₂SO₄, filtered and concentrated. The crude was purified by column chromatography on silica gel (DCM/MeOH=15/1) to give the mixture compound (65 mg, yield 19%) as a yellow oil.

LC-MS [C₁₈; column size: 4.6×30 mm 5 μm; Dikwa Diamonsil plus; mobile phase: B (ACN): A1 (0.02% NH₄OAc+ 5% ACN); gradient (B %) in 4 min-05-95-POS; 5-95% positive, flow rate: 1.5 mL/min, stop time 4 min]: Rt=2.490 min; MS Calcd.: 510, MS Found: 511 [M+H]⁺. The mixture compound (110 mg) was separated by chiral HPLC to afford isomer 1 (10 mg, 9%) as yellow oil and isomer 2 (13 mg, 12%) as a yellow oil.

Chiral pre-HPLC: column: Chiralpak IC; 5 μm 20×150 mm; Phase: MeOH:DCM:NH₃H₂O=80:20:0.3; flow rate: 12 ml/min, wave length: 254 nm E69 (Isomer 1)

Chiral-HPLC [column: chiral pak IC, 5 μm 250 mm×4.6 mm; mobile phase: MeOH:DCM:DEA=80:20:0.2; flow rate: 1 mL/min; wave length: 230 nm; temperature: 30° C.]: Rt=16.364 min.

¹HNMR (400 MHz, CDCl₃): δ 8.85 (s, 1H), 8.09 (s, 1H), 7.75 (s, 1H), 6.54 (br 1H), 5.28-5.25 (m, 1H), 4.75 (s, 1H), 4.12 (s, 3H), 4.01-3.89 (m, 4H), 3.83 (q, J=8.0 Hz, 1H), 3.70 (t, J=8.0 Hz, 1H), 3.54-3.35 (m, 2H), 3.16-3.02 (m, 3H), 2.95-2.92 (m, 1H), 2.27 (q, J=12 Hz, 2H), 2.13-1.89 (m, 6H), 1.87-1.76 (m, 2H).

LCMS [column: Phenomenex Kinetex 5 μm EVO, C₁₈; column size: 4.6×50 mm; mobile phase: B (ACN): A (0.02% NH₄OAc); gradient (B %) in 6 mins]: Rt=3.911 min, MS Calcd.: 510, MS Found: 511 [M+H]⁺.

E70 (Isomer 2)

Chiral-HPLC [column: chiral pak IC, 5 μm 250 mm×4.6 mm; mobile phase: MeOH:DCM:DEA=80:20:0.2; flow rate: 1 mL/min; wave length: 230 nm; temperature: 30° C.]: Rt=18.717 min.

¹H NMR (400 MHz, CDCl₃): δ 8.84 (s, 1H), 8.07 (s, 1H), 7.75 (s, 1H), 6.54 (br 1H), 5.27 (br 1H), 4.75 (s, 1H), 4.12 (s, 3H), 4.01-3.89 (m, 4H), 3.83 (q, J=8.0 Hz, 1H), 3.70 (t, J=7.6 Hz, 1H), 3.55-3.40 (m, 2H), 3.17-3.02 (m, 3H), 2.95-2.92 (m, 1H), 2.27 (q, J=12 Hz, 2H), 2.13-1.89 (m, 6H), 1.87-1.76 (m, 2H).

LCMS [column: Phenomenex Kinetex 5 μm EVO, O₁₈; column size: 4.6×50 mm; mobile phase: B (ACN): A (0.02% NH₄OAc); gradient (B %) in 6 mins]: Rt=3.908 min; MS Calcd.: 510, MS Found: 511 [M+H]⁺.

Example 71

(1R,4R)-5-(2-methoxy-6-(5-methyl-6-(4-morpholinocyclohexyl)-1H-indazol-1-yl)pyrimidin-4-yl)-2-oxa-5-azabicyclo[2.2.1]heptane

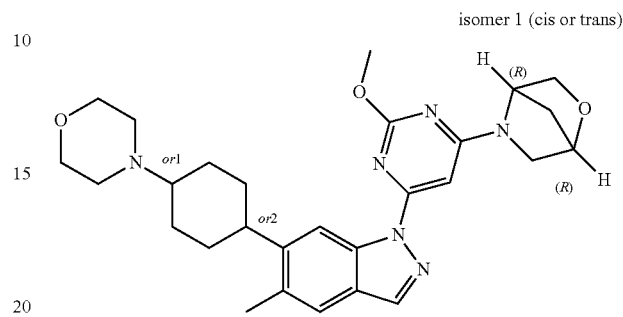

isomer 1 (cis or trans)

To a solution of 4-(4-(5-methyl-1H-indazol-6-yl)cyclohexyl)morpholine (isomer 2) (40 mg, 0.13 mmol), (1R,4R)-5-(6-iodo-2-methoxypyrimidin-4-yl)-2-oxa-5-azabicyclo [2.2.1]heptane (53 mg, 0.16 mmol), CuI (25 mg, 0.13 mmol), K₃PO₄ (55 mg, 0.26 mmol) and N,N'-dimethylcyclohexane-1,2-diamine (37 mg, 0.26 mmol) in toluene (2.5 mL) and DMSO (0.5 mL) was stirred at 100° C. for 4 hours. The mixture was diluted with EtOAc (30 mL×3), washed with brine (30 mL×2), dried over Na₂SO₄, filtered and concentrated. The crude was purified by prep-HPLC (x-bridge C₁₈, 5 μm, 19×150 mm, 30-95% ACN—H₂O (0.1% NH₄HCO₃), flow rate: 15 ml/min, GT12 mins.) to give compound (10 mg, 15%) as a white solid.

¹HNMR (400 MHz, CD₃OD): δ 8.66 (s, 1H), 8.11 (s, 1H), 7.53 (s, 1H), 6.54 (br 1H), 5.14 (br 1H), 4.74 (s, 1H), 4.09 (s, 3H), 3.90-3.83 (m, 2H), 2.74-2.72 (m, 4H), 3.57-3.55 (m, 1H), 3.35 (s, 1H), 2.87-2.81 (m, 1H), 2.66-2.64 (m, 4H), 2.44 (s, 3H), 2.38-2.33 (m, 1H), 2.14-2.11 (m, 2H), 1.99 (s, 4H), 1.61-1.42 (m, 4H).

LCMS [column: C₁₈; column size: 4.6×50 mm; mobile phase: B (ACN): A (0.1% TFA); gradient (B %) in 6 mins]: Rt=3.004 min, MS Calcd.: 504, MS Found: 505 [M+H]⁺.

Example 72

(1R,4R)-5-(6-(5-methyl-6-(1-(oxetan-3-yl)piperidin-4-yl)-1H-indazol-1-yl)-2-(trideuteriummethoxy)pyrimidin-4-yl)-2-oxa-5-azabicyclo[2.2.1]heptane

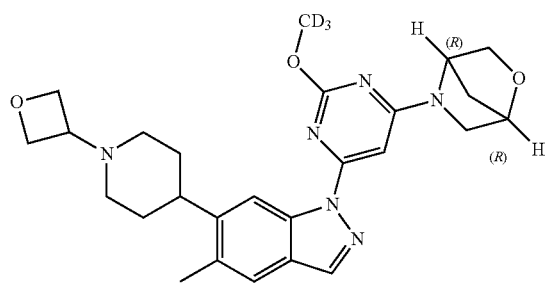

To a solution of (1R,4R)-5-(6-(5-methyl-6-(1-(oxetan-3-yl)piperidin-4-yl)-1H-indazol-1-yl)-2-(methylsulfonyl)pyrimidin-4-yl)-2-oxa-5-azabicyclo[2.2.1]heptane (40 mg, 0.08 mmol) in DMF (2 mL) was added NaH (60%, 15 mg, 0.38 mmol) and MeOD-d$_4$ (0.5 mL) at 0° C. under N$_2$. The reaction was stirred at room temperature overnight. The reaction was quenched with sat. NH$_4$Cl. The resulting mixture was purified by C$_{18}$ column eluting with MeCN/H$_2$O (0.1% TFA, from 5/95 to 95/5) to give the title product as a white solid (24 mg, yield: 66%).

$^1$H NMR (400 MHz, CDCl$_3$): δ 8.77 (s, 1H), 8.07 (s, 1H), 7.51 (s, 1H), 6.54 (br, 0.5H), 5.26 (br, 0.5H), 4.74~4.69 (m, 5H), 3.94 (q, J=7.6 Hz, 2H), 3.58~3.42 (m, 3H), 2.97~2.82 (m, 3H), 2.46 (s, 3H), 2.04~1.87 (m, 9H).

LC-MS [mobile phase: from 90% water (0.1% FA) and 10% ACN (0.1% FA) to 5% water (0.1% FA) and 95% ACN (0.1% FA) in 9 min]: Rt=3.29 min; MS Calcd: 479.3, MS Found: 480.3 [M+H]$^+$.

Example 73

(1S,4S)-5-(6-(5-methyl-6-(1-(oxetan-3-yl)piperidin-4-yl)-1H-indazol-1-yl)-2-(trideuteriummethoxy)pyrimidin-4-yl)-2-oxa-5-azabicyclo[2.2.1]heptane

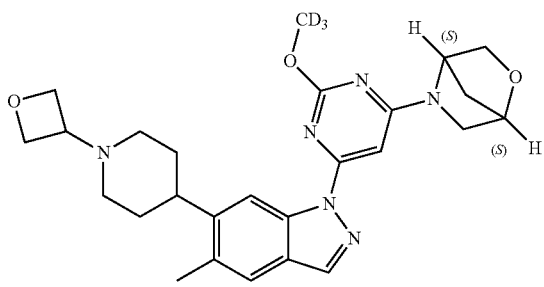

To a solution of (1S,4S)-5-(6-(5-methyl-6-(1-(oxetan-3-yl)piperidin-4-yl)-1H-indazol-1-yl)-2-(methylsulfonyl)pyrimidin-4-yl)-2-oxa-5-azabicyclo[2.2.1]heptane (80 mg, 0.15 mmol) in DMF (10 mL) was added NaH (60%, 30 mg, 0.76 mmol) and MeOD-d$_4$ (0.5 mL) at 0° C. under N$_2$. The reaction mixture was stirred at room temperature for 3 h. The reaction was quenched with sat. NH$_4$Cl. The resulting mixture was purified by C$_{18}$ column eluting with MeCN/H$_2$O (0.1% TFA): from 5/95 to 95/5 to give product, TFA salt, as a white solid (60 mg, yield: 82%).

$^1$H NMR (400 MHz, CDCl$_3$): δ 8.73 (s, 1H), 8.09 (s, 1H), 7.55 (s, 1H), 6.56 (br, 0.5H), 5.28 (br, 0.5H), 5.09 (t, J=7.2 Hz, 2H), 4.82 (t, J=7.6 Hz, 2H), 4.75 (s, 1H), 4.27 (s, 1H), 3.94~3.88 (m, 2H), 3.75~3.72 (m, 2H), 3.56~3.42 (m, 3H), 3.08 (t, J=8.0 Hz, 1H), 2.86~2.80 (m, 2H), 2.46 (s, 3H), 2.35~2.25 (m, 2H), 2.19~1.94 (m, 4H).

$^{19}$F NMR (376 MHz, CDCl$_3$): δ −75.69 (s)

LC-MS [mobile phase: from 90% water (0.1% FA) and 10% ACN (0.1% FA) to 5% water (0.1% FA) and 95% ACN (0.1% FA) in 9 min]: Rt=3.23 min; MS Calcd: 479, MS Found: 480 [M+H]$^+$.

Example 74

2-(6-(6-(cis-4-hydroxy-4-methylcyclohexyl)-5-methyl-1H-indazol-1-yl)-2-methylpyrimidin-4-yl)-2-azabicyclo[2.2.1]heptane-5-carboxylic Acid
(Rt=3.23 min)

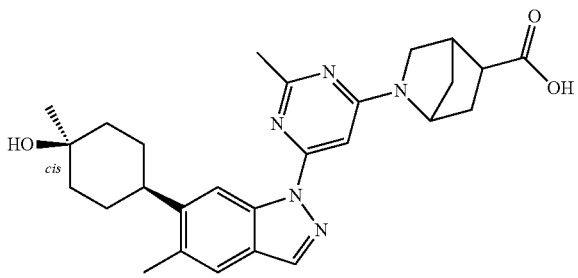 [SMILES: Cc1nc(N2CC3CC2CC3C(=O)O)cc(-n2ncc3cc(C)c([C@H]4CC[C@@](C)(O)CC4)cc32)n1]

To a solution of cis-4-(1-(6-iodo-2-methylpyrimidin-4-yl)-5-methyl-1H-indazol-6-yl)-1-methylcyclohexanol (160 mg, 0.34 mmol), 2-azabicyclo[2.2.1]heptane-5-carboxylic acid hydrochloride (182 mg, 1.02 mmol) in NMP (4 mL) was added Et$_3$N (344 mg, 3.4 mmol), stirred at 70° C. overnight. The reaction was pour into water (10 mL) and extracted with EA (10 mL×3), washed with brine (10 mL) and concentrated. The combined organic parts were dried, concentrated and purified by prep-HPLC to give the desired product as a white solid. (100 mg, yield: 60%)

$^1$H NMR (400 MHz, CD$_3$OD): δ 8.667 (s, 1H), 8.268 (s, 1H), 7.604 (s, 1H), 7.144 (s, 1H), 3.634 (s, 4H), 2.900 (s, 1H), 2.856~2.843 (m, 1H), 2.732 (s, 3H), 2.473 (s, 3H), 2.189-2.165 (m, 2H), 2.099-2.035 (m, 2H), 1.894-1.820 (m, 4H), 1.334-1.312 (m, 4H 1.274 (s, 3H).

$^{19}$F NMR (376 MHz, CD$_3$OD): δ −77.148 TFA salt

LC-MS [mobile phase: from 50% water (0.1% TFA) and 50% ACN (0.1% TFA) to 95% water (0.1% TFA) and 5% ACN (0.1% TFA) in 10 min]: Rt=3.23 min; MS Calcd.: 475, MS Found: 476 [M+H]$^+$.

Prep-HPLC:

Waters 2767/Qda

Waters sunfire C$_{18}$ 20×250 mm 10 μm

Flow rate: 30 ml/min

A: H$_2$O (0.1% TFA)

B: ACN

| Time | B % |
| --- | --- |
| 0 | 35 |
| 10 | 50 |
| 10.2 | 95 |
| 13.2 | 95 |
| 13.5 | 10 |
| 15 | 10 |

Example 75

2-(6-(6-(cis-4-hydroxy-4-methylcyclohexyl)-5-methyl-1H-indazol-1-yl)-2-methylpyrimidin-4-yl)-2-azabicyclo[2.2.1]heptane-5-carboxylic Acid (Rt=3.57 min)

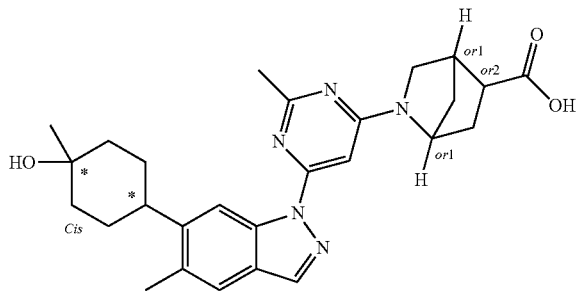 [SMILES: Cc1nc(N2CC3CC2CC3C(=O)O)cc(-n2ncc3cc(C)c(C4CCC(C)(O)CC4)cc32)n1]

To a solution of cis-4-(1-(6-iodo-2-methylpyrimidin-4-yl)-5-methyl-1H-indazol-6-yl)-1-methylcyclohexanol (160 mg, 0.34 mmol), 2-azabicyclo[2.2.1]heptane-5-carboxylic acid hydrochloride (182 mg, 1.02 mmol) in NMP (4 mL) was added Et$_3$N (344 mg, 3.4 mmol), stirred at 70° C. overnight. The reaction was poured into water (10 mL) and extracted with EA (10 mL×3), washed with brine (10 mL), concentrated, purified by Prep. HPLC [Waters sunfire, C$_{18}$, 20×250 mm, 10 μm, 35-95% B, A: H$_2$O (0.1% TFA), B: ACN; UV: 214 nm; flow rate: 30 ml/min] to give the title product as a white solid (13 mg, yield 8%).

$^1$H NMR (400 MHz, CD$_3$OD): δ 8.789 (s, 1H), 8.100 (s, 1H), 7.525 (s, 1H), 6.778 (s, 1H), 3.631~3.505 (m, 2H), 2.963 (s, 1H), 2.860~2.800 (m, 1H), 2.555 (s, 4H), 2.448 (s, 3H), 2.065-2.000 (m, 4H), 1.854-1.823 (m, 4H), 1.711-1.582 (m, 5H), 1.268 (s, 3H).

LCMS [mobile phase: from 50% water (0.1% TFA) and 50% ACN (0.1% TFA) to 95% water (0.1% TFA) and 5% ACN (0.1% TFA) in 10 min]: Rt=3.57 min; MS Calcd.: 475, MS Found: 476 [M+H]$^+$.

Chiral HPLC [Chiralpak AD-H 0.46 cm I.D×15 cm L, HEP/IPA (0.1% DEA)=60:40 (V/V), Flow Rate: 0.5 ml/min, Wave length: 254 nm, Temperature: 25° C.]: Rt=3.391 min.

Example 76

2-(6-(6-(cis-4-hydroxy-4-methylcyclohexyl)-5-methyl-1H-indazol-1-yl)-2-methylpyrimidin-4-yl)-2-azabicyclo[2.2.1]heptane-5-carboxylic Acid, TFA Salt (Rt=3.63 min)

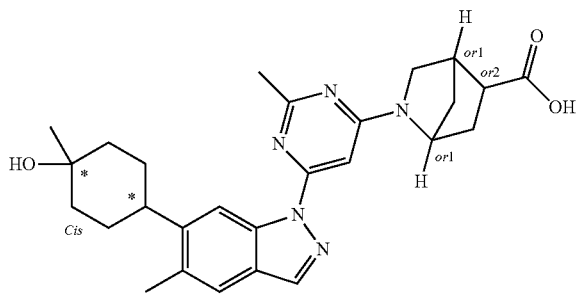 [SMILES: Cc1nc(N2CC3CC2CC3C(=O)O)cc(-n2ncc3cc(C)c(C4CCC(C)(O)CC4)cc32)n1]

To a solution of cis-4-(1-(6-iodo-2-methylpyrimidin-4-yl)-5-methyl-1H-indazol-6-yl)-1-methylcyclohexanol (160 mg, 0.34 mmol), 2-azabicyclo[2.2.1]heptane-5-carboxylic acid hydrochloride (182 mg, 1.02 mmol) in NMP (4 mL) was added Et$_3$N (344 mg, 3.4 mmol), stirred at 70° C. overnight. The reaction was poured into water (10 mL) and extracted with EA (10 mL×3), washed with brine (10 mL), concentrated and purified by Prep. HPLC [Waters sunfire, C$_{18}$, 20×250 mm, 10 μm, 35-95% B, A: H$_2$O (0.1% TFA), B: ACN; UV: 214 nm; flow rate: 30 ml/min] to give the title product as a white solid (13 mg, yield 8%).

$^1$H NMR (400 MHz, CD$_3$OD): δ 8.743 (s, 1H), 8.161 (s, 1H), 7.556 (s, 1H), 6.884 (s, 1H), 3.631~3.564 (m, 2H), 3.016 (s, 1H), 2.843 (m, 1H), 2.687 (s, 1H), 2.617 (s, 3H), 2.458 (s, 3H), 2.098-2.021 (m, 4H), 1.854-1.823 (m, 4H), 1.765-1.588 (m, 5H), 1.274 (s, 3H).

LCMS [mobile phase: from 50% water (0.1% TFA) and 50% ACN (0.1% TFA) to 95% water (0.1% TFA) and 5% ACN (0.1% TFA) in 10 min]: purity 96.9%, Rt=3.63 min; MS Calcd.: 475.5, MS Found: 476.7 [M+H]$^+$.

Chiral HPLC [Chiralpak AD-H 0.46 cm I.D×15 cm L, HEP/IPA (0.1% DEA)=60:40 (V/V), Flow Rate: 0.5 mL/min, Wave length: 254 nm, Temperature: 25° C.]: Rt=2.45 min.

Example 77

Cis-3-{6-[6-(4-Hydroxy-4-methyl-cyclohexyl)-5-methyl-indazol-1-yl]-2-methyl-pyrimidin-4-yl}-3-aza-bicyclo[3.1.1]heptane-6-carboxylic Acid (Rt=3.23 min)

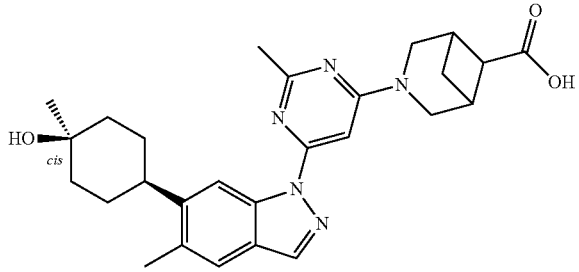 [SMILES: Cc1nc(N2CC3CC(C2)C3C(=O)O)cc(-n2ncc3cc(C)c([C@H]4CC[C@@](C)(O)CC4)cc32)n1]

To a solution of cis-4-(1-(6-iodo-2-methylpyrimidin-4-yl)-5-methyl-1H-indazol-6-yl)-1-methylcyclohexanol (160 mg, 0.34 mmol), 3-Aza-bicyclo[3.1.1]heptane-6-carboxylic acid methyl ester (182 mg, 1.02 mmol) in NMP (4 mL) was added Et$_3$N (344 mg, 3.4 mmol), stirred at 70° C. overnight. The reaction mixture was poured into water (100 mL), extracted with EtOAc (50 mL×3). The combined organic layers were washed with brine (50 mL), dried over anhydrous Na$_2$SO$_4$ and concentrated to dryness. The residue was added in THF (10 ml) and added LiOH (53 mg) the solution was stirred at room temperature for 3 hr, then TLC shown the reaction was completed, the solution was concentrated to dryness and purified by prep-HPLC to give the product (100 mg, yield: 60%)

$^1$H NMR (400 MHz, CD$_3$OD): δ 8.667 (s, 1H), 8.268 (s, 1H), 7.604 (s, 1H), 7.144 (s, 1H), 3.96 (m, 4H), 2.900 (m, 3H), 2.75~2.67 (m, 5H), 2.47 (s, 3H), 2.02-1.99 (m, 2H), 1.86-1.82 (m, 2H), 1.71-1.53 (m, 5H), 1.274 (s, 3H).

$^{19}$F NMR (376 MHz, CD$_3$OD): δ −77.148 TFA salt

LC-MS [mobile phase: from 50% water (0.1% TFA) and 50% ACN (0.1% TFA) to 95% water (0.1% TFA) and 5% ACN (0.1% TFA) in 10 min]: Rt=3.23 min; MS Calcd.: 475, MS Found: 476 [M+H]$^+$.

Prep-HPLC:
Waters 2767/Qda Waters sunfire C₁₈ 20×250 mm 10 μm
Flow rate: 30 ml/min
A: H₂O (0.1% TFA) B: ACN

| Time | B % |
|------|-----|
| 0    | 35  |
| 10   | 50  |
| 10.2 | 95  |
| 13.2 | 95  |
| 13.5 | 10  |
| 15   | 10  |

Example 78

Cis-3-{6-[6-(4-Hydroxy-4-methyl-cyclohexyl)-5-methyl-indazol-1-yl]-2-methyl-pyrimidin-4-yl}-3-aza-bicyclo[3.1.1]heptane-6-carboxylic Acid (Isomer 1, Rt=3.57 min)

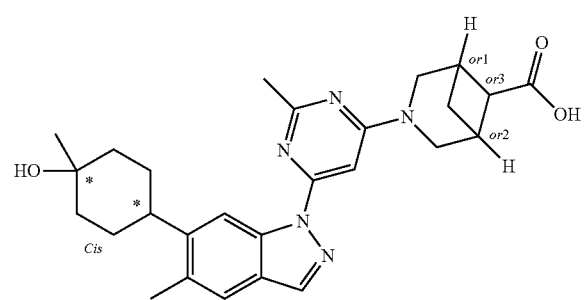 [SMILES: Cc1nc(N2CC3CC(C2)C3C(=O)O)cc(-n2ncc3cc(C)c(C4CCC(C)(O)CC4)cc32)n1]

To a solution of cis-4-(1-(6-iodo-2-methylpyrimidin-4-yl)-5-methyl-1H-indazol-6-yl)-1-methylcyclohexanol (160 mg, 0.34 mmol), 3-Aza-bicyclo[3.1.1]heptane-6-carboxylic acid methyl ester (182 mg, 1.02 mmol) in NMP (4 mL) was added Et₃N (344 mg, 3.4 mmol), stirred at 70° C. overnight. The reaction mixture was poured into water (100 mL), extracted with EtOAc (50 mL×3). The combined organic layers were washed with brine (50 mL), dried over anhydrous Na₂SO₄ and concentrated to dryness. The residue was added in THF (10 ml) and added LiOH (53 mg) the solution was stirred at room temperature for 3 hr. The solution was concentrated to dryness and purified by Prep. HPLC [Waters sunfire, C₁₈, 20×250 mm, 10 μm, 35-95% B, A: H₂O (0.1% TFA), B: ACN; UV: 214 nm; flow rate: 30 ml/min] to give the product (30 mg, yield 18%).

¹H NMR (400 MHz, CD₃OD): δ 8.80 (s, 1H), 8.09 (s, 1H), 7.53 (s, 1H), 6.84 (s, 1H), 4.25~4.23 (m, 1H), 4.06~4.03 (m, 1H), 3.69~3.67 (m, 1H), 3.50~3.45 (m, 1H), 3.02~2.99 (m, 1H), 2.87~2.77 (m, 3H), 2.56 (s, 3H), 2.46 (s, 3H), 2.11~1.97 (m, 3H), 1.86-1.82 (m, 2H), 1.71-1.59 (m, 4H), 1.35-1.27 (m, 1H), 1.24 (s, 3H).

LC-MS [mobile phase: from 50% water (0.1% TFA) and 50% ACN (0.1% TFA) to 95% water (0.1% TFA) and 5% ACN (0.1% TFA) in 10 min]: Rt=3.57 min; MS Calcd.: 475, MS Found: 476 [M+H]⁺.

Chiral HPLC [Chiralpak AD-H 0.46 cm I.D×15 cm L, HEP/IPA (0.1% DEA)=60:40 (V/V), Flow Rate: 0.5 mL/min, Wave length: 254 nm, Temperature: 25° C.]: Rt=3.391 min.

Example 79

Cis-3-{6-[6-(4-Hydroxy-4-methyl-cyclohexyl)-5-methyl-indazol-1-yl]-2-methyl-pyrimidin-4-yl}-3-aza-bicyclo[3.1.1]heptane-6-carboxylic Acid (Isomer 2, Rt=3.63 min)

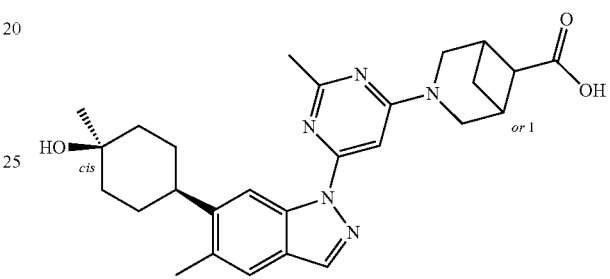

To a solution of cis-4-(1-(6-iodo-2-methylpyrimidin-4-yl)-5-methyl-1H-indazol-6-yl)-1-methylcyclohexanol (160 mg, 0.34 mmol), 3-Aza-bicyclo[3.1.1]heptane-6-carboxylic acid methyl ester (182 mg, 1.02 mmol) in NMP (4 mL) was added Et₃N (344 mg, 3.4 mmol), stirred at 70° C. overnight. The reaction mixture was poured into water (100 mL), extracted with EtOAc (50 mL×3). The combined organic layers were washed with brine (50 mL), dried over anhydrous Na₂SO₄ and concentrated to dryness. The residue was added in THF (10 ml) and added LiOH (53 mg) the solution was stirred at room temperature for 3 hr. The solution was concentrated to dryness and purified by Prep. HPLC [Waters sunfire, O₁₈, 20×250 mm, 10 μm, 35-95% B, A: H₂O (0.1% TFA), B: ACN; UV: 214 nm; flow rate: 30 ml/min] to give the product (6 mg, yield 3.6%)

¹H NMR (400 MHz, CD₃OD): δ 8.82 (s, 1H), 8.09 (s, 1H), 7.52 (s, 1H), 6.87 (s, 1H), 3.93~3.72 (m, 4H), 2.85~2.80 (m, 3H), 2.65~2.59 (m, 1H), 2.59 (s, 3H), 2.49~2.44 (m, 1H), 2.44 (s, 3H), 2.7~1.97 (m, 2H), 1.86-1.82 (m, 2H), 1.72-1.57 (m, 4H), 1.44-1.39 (m, 1H), 1.27 (s, 3H).

LC-MS [mobile phase: from 50% water (0.1% TFA) and 50% ACN (0.1% TFA) to 95% water (0.1% TFA) and 5% ACN (0.1% TFA) in 10 min]: Rt=3.63 min; MS Calcd.: 475.5, MS Found: 476.7 [M+H]⁺.

Chiral condition [Chiralpak AD-H 0.46 cm I.D×15 cm L, HEP/IPA (0.1% DEA)=60:40 (V/V), Flow Rate: 0.5 mL/min, Wave length: 254 nm, Temperature=25° C.]: Rt=2.45 min, 98.496% ee

Example 80

3-{2-Methyl-6-[5-methyl-6-(tetrahydro-pyran-4-yl)-indazol-1-yl]-pyrimidin-4-yl}-3-aza-bicyclo[3.1.1]heptane-6-carboxylic Acid

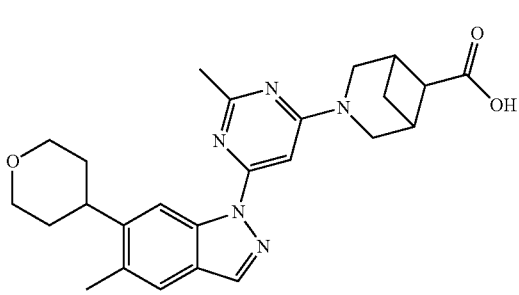 [SMILES: Cc1nc(N2CC3CC(C2)C3C(=O)O)cc(-n2ncc3cc(C)c(C4CCOCC4)cc32)n1]

To a solution of 3-{2-Methyl-6-[5-methyl-6-(tetrahydro-pyran-4-yl)-indazol-1-yl]-pyrimidin-4-yl}-3-aza-bicyclo[3.1.1]heptane-6-carboxylic acid methyl ester (200 mg, 0.43 mmol) in MeOH/THF (3 mL/3 mL) was added 2 N LiOH (1.72 mL, 3.43 mmol) at rt. The mixture was warmed to 40° C. overnight. TLC showed the reaction was completed. The reaction mixture was concentrated, dissolved in water (10 mL), washed with Et$_2$O (10 mL×2), water phases were adjust to PH=2~3 with aq. KHSO$_4$ (2 mL) and concentrated. The residue was purified by Prep-HPLC to give a white solid. (110 mg, 75% yield)

$^1$H NMR (400 MHz, CD$_3$OD): δ 8.64 (s, 1H), 8.25 (s, 1H), 7.58 (s, 1H), 7.08 (s, 1H), 4.13 (m, 2H), 3.95~3.93 (brs, 4H), 3.70~3.63 (m, 2H), 3.33~3.31 (m, 1H), 2.95~2.70 (m, 2H), 2.74 (s, 3H), 2.70~2.60 (m, 2H), 2.501 (s, 3H), 1.90~1.82 (m, 4H), 1.54~1.50 (m, 1H).

$^{19}$F NMR (376 MHz, CD$_3$OD): δ −77.155 TFA salt

LC-MS [mobile phase: from 50% water (0.1% FA) and 50% ACN (0.1% FA) to 95% water (0.1% FA) and 5% ACN (0.1% FA) in 10 min]: Rt=5.55 min; MS Calcd: 447, MS Found: 448 [M+H]$^+$.

Prep-HPLC method:

Waters 2767/Qda Waters sunfire O$_{18}$ 20×250 mm 10 μm Flow rate: 30 ml/min

A: H$_2$O (0.1% TFA) B: ACN

| Time | B % |
| --- | --- |
| 0 | 35 |
| 10 | 50 |
| 10.2 | 95 |
| 12.2 | 95 |
| 13.5 | 10 |
| 15 | 10 |

Example 81

3-(6-(6-isopropoxy-5-methyl-1H-indazol-1-yl)-2-methoxypyrimidin-4-yl)-3-azabicyclo[3.1.1]heptane-6-carboxylic Acid

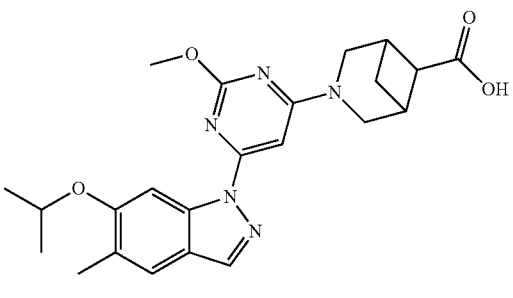 [SMILES: COc1nc(N2CC3CC(C2)C3C(=O)O)cc(-n2ncc3cc(C)c(OC(C)C)cc32)n1]

To a solution of methyl 3-(6-(6-isopropoxy-5-methyl-1H-indazol-1-yl)-2-methoxypyrimidin-4-yl)-3-azabicyclo[3.1.1]heptane-6-carboxylate (100 mg, 0.22 mmol) in THF (2 mL) was added a solution of LiOH in H$_2$O (2 mL, 4.0 mmol, 2 N in H$_2$O). The resulting mixture was stirred at room temperature for 2 hours. The reaction was acidified with 1 N HCl solution to adjust pH=6~7, extracted with EtOAc (30 mL×2), dried over Na$_2$SO$_4$. The organic phase was filtered and concentrated, the residue was purified by prep-HPLC to afford the title compound (40 mg, 42%) as white solid.

$^1$H NMR (400 MHz, DMSO-d$_6$): δ 8.31 (s, 1H), 8.23 (s, 1H), 7.58 (s, 1H), 6.72 (s, 1H), 4.70-4.64 (m, 1H), 4.00 (s, 3H), 3.88-3.79 (m, 2H), 3.70 (s, 2H), 2.77 (br 2H), 2.53-2.50 (m, 1H), 2.46-2.43 (m, 1H), 2.23 (s, 3H), 1.38 (d, J=6.0 Hz, 6H), 1.37-1.34 (m, 1H).

Examples 82 and 83

2-{2-Methyl-6-[5-methyl-6-(tetrahydro-pyran-4-yl)-indazol-1-yl]-pyrimidin-4-yl}-2-aza-bicyclo[2.2.1]heptane-5-carboxylic Acid

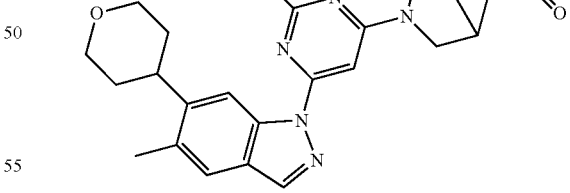

To a solution of 2-{2-Methyl-6-[5-methyl-6-(tetrahydro-pyran-4-yl)-indazol-1-yl]-pyrimidin-4-yl}-2-aza-bicyclo[2.2.1]heptane-5-carboxylic acid methyl ester (350 mg, 0.73 mmol) in MeOH/THF (3 mL/3 mL) was added 2 N LiOH (1.72 mL, 3.43 mmol) at rt. The mixture was warmed to 40° C. overnight. The reaction mixture was concentrated, dissolved in water (10 mL), washed with Et$_2$O (10 mL×2), water phases were adjust to pH=2-3 with aq. KHSO$_4$ (2 mL) and concentrated. The residue was purified by prep-HPLC to give a white solid. (110 mg, 45% yield)

Prep-HPLC:

Waters 2767/Qda; Waters XBridge 30×150 mm 5 µm; 20 ml/min; 214 nm/254 nm;

Trigger: 254 nm

A: H₂O B: ACN

Method:

| Time | B % |
|------|-----|
| 0    | 10  |
| 2    | 45  |
| 12   | 65  |
| 12.5 | 95  |
| 15   | 95  |
| 15.2 | 10  |
| 18   | 10  |

Example 82 (Single Unknown Isomer 1, Rt=3.920 Min)

¹H NMR (400 MHz, DMSO-d₆): δ12.29 (s, 1H), 8.73 (s, 1H), 8.29 (s, 1H), 7.62 (s, 1H), 7.02-6.52 (d, 1H), 4.88~4.10 (m, 1H), 4.08~3.99 (m, 2H), 3.56~3.41 (m, 3H), 3.22~3.07 (m, 3H), 2.62~2.60 (m, 4H), 2.45 (s, 3H), 1.98~1.96 (m, 1H), 1.91~1.62 (m, 7H).

LC-MS [mobile phase: from 70% water (0.1% TFA) and 30% ACN (0.1% TFA) to 30% water (0.1% TFA) and 70% ACN (0.1% TFA) in 10 min]: Rt=5.25 min; MS Calcd.: 447, MS Found: 448 [M+H]⁺.

Chiral HPLC [Column: AD-H; Column size: 0.46 cm I.D.×15 cm L Injection: 2 µl Mobile phase: HEP:EtOH (0.1% DEA)=70:30 Flow rate: 0.5 ml/min, Wave length: UV 254 nm, Temperature: 25° C., Sample solution in EtOH Example 83 (Single Unknown Isomer 2, Rt=4.377 min)

¹H NMR (400 MHz, DMSO-d₆): δ12.29 (s, 1H), 8.73 (s, 1H), 8.29 (s, 1H), 7.62 (s, 1H), 7.02-6.52 (d, 1H), 4.88~4.10 (m, 1H), 4.08~3.99 (m, 2H), 3.56~3.41 (m, 3H), 3.22~3.07 (m, 3H), 2.62~2.60 (m, 4H), 2.45 (s, 3H), 1.98~1.96 (m, 1H), 1.91~1.62 (m, 7H).

LC-MS [mobile phase: from 70% water (0.1% TFA) and 30% ACN (0.1% TFA) to 30% water (0.1% TFA) and 70% ACN (0.1% TFA) in 10 min]: Rt=5.25 min; MS Calcd.: 447, MS Found: 448 [M+H]⁺.

Chiral HPLC [Column: AD-H; Column size: 0.46 cm I.D.×15 cm L Injection: 2 µl Mobile phase: HEP:EtOH (0.1% DEA)=70:30 Flow rate: 0.5 ml/min, Wave length: UV 254 nm, Temperature: 25° C.; Sample solution in EtOH Example 84

2-(6-(5-chloro-6-(((S)-tetrahydrofuran-3-yl)oxy)-1H-indazol-1-yl)-2-methoxypyrimidin-4-yl)-2-azabicyclo[2.2.1]heptane-5-carboxylic Acid (Isomer 1)

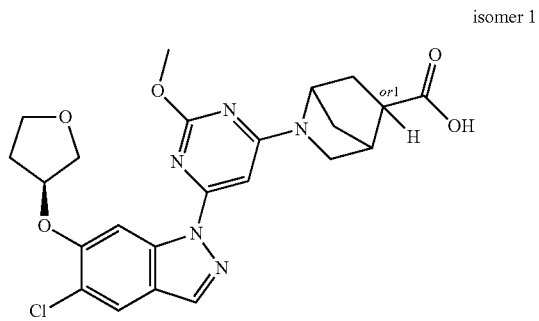 [SMILES: COc1nc(N2CC3CC2CC3C(=O)O)cc(-n2ncc3cc(Cl)c(O[C@H]4CCOC4)cc32)n1]

isomer 1

To a solution of methyl 2-(6-(5-chloro-6-(((S)-tetrahydrofuran-3-yl)oxy)-1H-indazol-1-yl)-2-methoxypyrimidin-4-yl)-2-azabicyclo[2.2.1]heptane-5-carboxylate (28 mg, 0.06 mmol) in THF (3 mL) was added a solution of LiOH in H₂O (0.5 mL, 0.12 mmol, 2 N in H₂O). The mixture was stirred at room temperature for 2 hours. The reaction was acidified with 1N HCl solution to adjust pH=3-4, extracted with EtOAc, dried over Na₂SO₄, filtered and concentrated. The residue was purified by prep-HPLC (waters-1 C₁₈ 5 µm 19×150 mm-11212; 10-45% B, A: H₂O (0.1% NH₄HCO₃), B: ACN, 214 nm, Flow rate: 15 ml/min, GT12 mins) to give the title compound (26 mg, 89%) as a white solid.

¹H NMR (400 MHz, DMSO-d₆): δ 8.40 (s, 1H), 8.33 (s, 1H), 8.01 (s, 1H), 6.70-6.43 (m, 1H), 5.18 (s, 1H), 4.79-4.43 (m, 1H), 3.99-3.81 (m, 7H), 3.45-3.42 (m, 1H), 3.24-3.21 (m, 2H), 2.89-2.83 (m, 1H), 2.34-2.09 (m, 3H), 1.97-1.81 (m, 2H), 1.65-1.59 (m, 1H).

LCMS [column: Phenomenex Kinetex 5 µm EVO, C₁₈; column size: 4.6×50 mm; mobile phase: B (ACN): A (0.1% TFA); gradient (B %) in 6 mins]: Rt=4.182 min, MS Calcd.: 485, MS Found: 486 [M+H]⁺.

Example 85

2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylic Acid (Isomer 1)

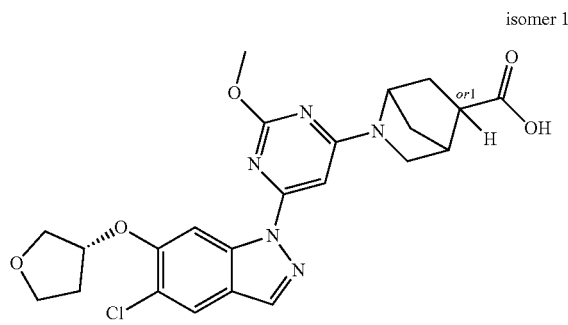 [SMILES: COc1nc(N2CC3CC2CC3C(=O)O)cc(-n2ncc3cc(Cl)c(O[C@@H]4CCOC4)cc32)n1]

isomer 1

To a solution of methyl 2-(6-(5-chloro-6-(((R)-tetrahydrofuran-3-yl)oxy)-1H-indazol-1-yl)-2-methoxypyrimidin-4- yl)-2-azabicyclo[2.2.1]heptane-5-carboxylate (isomer 1) (105 mg, 0.21 mmol) in THF (4 mL) was added a solution of LiOH in H$_2$O (0.5 mL, 0.42 mmol, 2 N in H$_2$O). The mixture was stirred at room temperature for 2 hours. The reaction was acidified with 1N HCl solution to adjust pH=3-4, extracted with EtOAc and dried over Na$_2$SO$_4$, filtered and concentrated. The crude was purified by prep-HPLC (waters-1 C$_{18}$ 5 μm 19×150 mm-11212; 10-45% B, A: H$_2$O (0.1% NH$_4$HCO$_3$), B: ACN, 214, Flow rate: 15 ml/min, GT12 mins) to give the title compound (32 mg, 31%) as a white solid.

$^1$HNMR (400 MHz, DMSO-d$_6$): δ 8.39 (s, 1H), 8.32 (s, 1H), 7.99 (s, 1H), 6.68-6.44 (m, 1H), 5.17 (s, 1H), 4.78-4.41 (m, 1H), 3.98 (s, 3H), 3.94-3.81 (m, 4H), 3.43-3.28 (m, 2H), 3.13-3.05 (m, 1H), 2.88-2.82 (m, 1H), 2.38-1.76 (m, 4H), 1.71-1.61 (m, 2H).

LCMS [column: Phenomenex Kinetex 5 μm EVO, C$_{18}$; column size: 4.6×50 mm; mobile phase: B (ACN): A (0.1% TFA); gradient (B %) in 6 mins]: Rt=4.291 min, MS Calcd.: 485, MS Found: 486 [M+H]$^+$.

Example 86

2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylic Acid (Isomer 2)

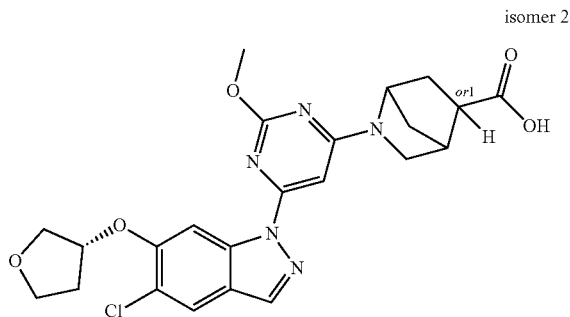 [SMILES: COc1nc(N2CC3CC2CC3C(=O)O)cc(-n2ncc3cc(Cl)c(O[C@@H]4CCOC4)cc32)n1]

isomer 2

To a solution of methyl 2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylate (isomer 2) (135 mg, 0.27 mmol) in THF (4 mL) was added a solution of LiOH in H$_2$O (0.5 mL, 0.54 mmol, 2 N in H$_2$O). The mixture was stirred at room temperature for 2 hours. The reaction was acidified with 1N HCl solution to adjust pH=3-4, extracted with EtOAc (30 mL×2), dried over Na$_2$SO$_4$, filtered and concentrated. The crude was purified by prep-HPLC (waters-1 C$_{18}$ 5 μm 19×150 mm-11212; 10-45% B, A: H$_2$O (0.1% NH$_4$HCO$_3$), B: CAN, 214, Flow rate 15 ml/min, GT12 mins-18MIN) to give the title compound (45 mg, 34%) as a white solid.

$^1$HNMR (400 MHz, DMSO-d$_6$): δ 8.38 (s, 1H), 8.32 (s, 1H), 7.99 (s, 1H), 6.68-6.42 (m, 1H), 5.17 (s, 1H), 4.78-4.43 (m, 1H), 3.98-3.79 (m, 7H), 3.47-3.40 (m, 2H), 3.16-3.11 (m, 1H), 2.89-2.84 (m, 1H), 2.30-2.09 (m, 1H), 1.97-1.81 (m, 2H), 1.70-1.60 (m, 2H).

LCMS [column: Phenomenex Kinetex 5 μm EVO, C$_{18}$; column size: 4.6×50 mm; mobile phase: B (ACN): A (0.1% TFA); gradient (B %) in 6 mins]: Rt=4.296 min, MS Calcd.: 485, MS Found: 486 [M+H]$^+$.

Examples 87 and 88

Cis-1-(4-(1-(6-(((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-ol (from Peak 1) (from Peak 1) (Single Unknown Isomer 1, Rt=4.556 Min; Single Unknown Isomer 2, Rt=5.225 Min)

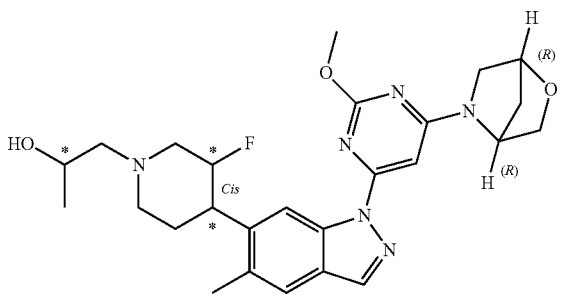

To a solution of cis-1-(4-(1-(6-(((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 1, 148 mg, 0.30 mmol) in MeOH (5 mL) was added NaBH$_4$ (34 mg, 0.90 mmol). The reaction was stirred at Rt for 60 min. The reaction was quenched with sat.NH$_4$Cl. The resulting mixture was filtered and the filtrate was concentrated. The residue was purified by Prep-HPLC (Gilson 281, YMC-Actus Triart Prep C$_{18}$-S 250×20 mm 10 μm, Mobile phase: MeCN/H$_2$O (0.05% TFA): from 30/70 to 95/5, Flow rate: 20 mL/min, Wave length: 254 nm) to give target product as a white solid (130 mg, yield: 87%).

LC-MS [mobile phase: 80% water (0.1% FA) and 20% ACN (0.1% FA) to 5% water (0.1% FA) and 95% ACN (0.1% FA) in 9 min]: Rt=3.59 min; MS Calcd.: 496, MS Found: 497 [M+H]$^+$.

The compound cis-1-(4-(1-(6-(((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-ol (from Peak 1, 130 mg, 0.26 mmol) was purified by chiral prep-HPLC (AD-H, 0.46 cm I.D.×15 cm L, Mobile phase: CO$_2$:EtOH (0.1% NH$_3$H$_2$O)=60:40, Flow rate: 0.5 mL/min, Wave length: UV 254 nm, Temperature: 25° C.) to give the title products (mixture) as a white solid.

E87 (Single Unknown Isomer 1, Rt=4.556 Min, from Peak 1) (45 mg, Yield: 35%).

$^1$H NMR (400 MHz, CDCl$_3$): δ 8.89 (s, 1H), 8.08 (s, 1H), 7.54 (s, 1H), 6.55 (br, 0.6H), 5.26 (br, 0.5H), 4.90 (td, J=10.0, 4.8 Hz, 0.5H), 4.78 (td, J=10.0, 5.2 Hz, 0.5H), 4.74 (s, 1H), 4.13 (s, 3H), 3.93~3.87 (m, 3H), 3.59~3.46 (m, 2H), 3.33~3.22 (m, 2H), 3.17~3.08 (m, 2H), 2.56~2.48 (m, 2H), 2.48 (s, 3H), 2.34 (t, J=11.2 Hz, 1H), 2.14~2.08 (m, 1H), 2.01~1.92 (m, 3H), 1.84~1.74 (m, 1H), 1.19 (d, J=6.0 Hz, 3H).

$^{19}$F NMR (376 MHz, CDCl$_3$): δ −183.97 (s)

LC-MS [mobile phase: 80% water (0.1% FA) and 20% ACN (0.1% FA) to 5% water (0.1% FA) and 95% ACN (0.1% FA) in 9.0 min]: purity 100%, Rt=3.47 min; MS Calcd.: 496, MS Found: 497 [M+H]$^+$.

Chiral HPLC [AD 4.6×250 mm, 5 μm (Daicel) (CA-HPLC-023), Phase: Hexane/EtOH (0.2% DEA)=60/40, flow rate: 1 mL/min, temperature: 35° C.]: Rt: 4.556 min, ee: 100%.

E88 (Single Unknown Isomer 2, Rt=5.225 Min, from Peak 1)

(45 mg, yield: 35%).

$^1$H NMR (400 MHz, CDCl$_3$): δ 8.89 (s, 1H), 8.08 (s, 1H), 7.54 (s, 1H), 6.55 (br, 0.6H), 5.26 (br, 0.4H), 4.86 (td, J=10.0, 4.4 Hz, 0.5H), 4.74 (td, J=10.0, 5.2 Hz, 0.5H), 4.74 (s, 1H), 4.12 (s, 3H), 3.93~3.86 (m, 3H), 3.61~3.46 (m, 3H), 3.25~3.09 (m, 2H), 2.91 (d, J=11.8 Hz, 1H), 2.48 (s, 3H), 2.48~2.32 (m, 3H), 2.21 (td, J=10.4, 4.4 Hz, 1H), 1.98~1.83 (m, 4H), 1.19 (d, J=6.4 Hz, 3H)

$^{19}$F NMR (376 MHz, CDCl$_3$): δ -183.91 (s)

LC-MS [mobile phase: 80% water (0.1% FA) and 20% ACN (0.1% FA) to 5% water (0.1% FA) and 95% ACN (0.1% FA) in 9.0 min]: purity 100%, Rt=3.49 min; MS Calcd.: 496, MS Found: 497 [M+H]$^+$.

Chiral HPLC [AD 4.6×250 mm, 5 μm (Daicel) (CA-HPLC-023), Phase: Hexane/EtOH (0.2% DEA)=60/40, flow rate: 1 mL/min, temperature: 35° C.]: Rt: 5.225 min, ee: 99.53%.

Examples 89 and 90

Cis-1-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-ol (from Peak 2) (Single Unknown Isomer 1, Rt=4.787 min; Single Unknown Isomer 2, Rt=5.624 min)

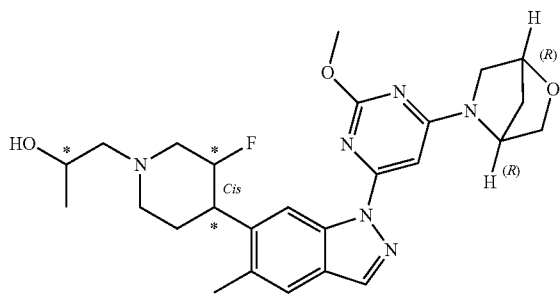

To a solution of cis-1-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 2, 152 mg, 0.31 mmol) in MeOH (5 mL) was added NaBH$_4$ (35 mg, 0.92 mmol). The reaction was stirred at Rt for 60 min. The reaction was quenched with sat.NH$_4$Cl. The resulting mixture was filtered and the filtrate was concentrated. The residue was purified by Prep-HPLC (Gilson 281, YMC-Actus Triart Prep C$_{18}$-S 250×20 mm 10 μm, Mobile phase: MeCN/H$_2$O (0.05% TFA): from 30/70 to 95/5, Flow rate: 20 mL/min, wave length: 254 nm) to give target product as a white solid (130 mg, yield: 85%).

LC-MS [mobile phase: 80% water (0.1% FA) and 20% ACN (0.1% FA) to 5% water (0.1% FA) and 95% ACN (0.1% FA) in 9 min]: Rt=3.54 min; MS Calcd.: 496, MS Found: 497 [M+H]$^+$.

The compound cis-1-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-ol (from Peak 8, 130 mg, 0.26 mmol) was purified by chiral prep-HPLC (AD-H, 0.46 cm I.D.×15 cm L, Mobile phase: CO$_2$:EtOH (0.1% NH$_3$.H$_2$O)=60:40, Flow rate: 0.5 mL/min, Wave length: UV 254 nm, Temperature: 25° C.) to give the title products, TFA salt, as pale yellow solids.

E89 (Single Unknown Isomer 1, Rt=4.787 Min, from Peak 2) (40 mg, Yield: 31%).

$^1$H NMR (400 MHz, CDCl$_3$): δ 8.89 (s, 1H), 8.09 (s, 1H), 7.55 (s, 1H), 6.55 (br, 0.5H), 5.26 (br, 0.5H), 4.92~4.86 (m, 0.5H), 4.79~4.74 (m, 0.5H), 4.74 (s, 1H), 4.12 (s, 3H), 3.93~3.87 (m, 3H), 3.54~3.48 (m, 3H), 3.19~2.98 (m, 2H), 2.56~2.42 (m, 3H), 2.49 (s, 3H), 2.28~2.21 (m, 1H), 2.00~1.93 (m, 5H), 1.19 (d, J=6.0 Hz, 3H).

$^{19}$F NMR (376 MHz, CDCl$_3$): δ -75.443 (s), -184.03 (s)

LC-MS [mobile phase: 80% water (0.1% FA) and 20% ACN (0.1% FA) to 5% water (0.1% FA) and 95% ACN (0.1% FA) in 9.0 min]: Rt=3.45 min; MS Calcd.: 496.2, MS Found: 497.2 [M+H]$^+$.

Chiral HPLC [AD 4.6×250 mm, 5 μm (Daicel) (CA-HPLC-023), Phase: Hexane/EtOH (0.2% DEA)=60/40, flow rate: 1 mL/min, temperature: 35° C.]: Rt: 4.787 min, ee: 100%.

Example 90 (Single Unknown Isomer 2, Rt=5.624 Min, from Peak 2) (40 mg, Yield: 31%)

$^1$H NMR (400 MHz, CDCl$_3$): δ 8.89 (s, 1H), 8.09 (s, 1H), 7.55 (s, 1H), 6.55 (br, 0.5H), 5.26 (br, 0.5H), 4.99~4.92 (m, 0.5H), 4.88~4.79 (m, 0.5H), 4.74 (s, 1H), 4.13 (s, 3H), 3.96~3.87 (m, 3H), 3.59~3.41 (m, 3H), 3.20~3.14 (m, 2H), 2.62~2.54 (m, 2H), 2.49~2.42 (m, 1H), 2.49 (s, 3H), 2.24~2.18 (m, 1H), 2.01~1.86 (m, 5H), 1.21 (d, J=6.0 Hz, 3H)

$^{19}$F NMR (376 MHz, CDCl$_3$): δ -75.44 (s), -184.16 (s)

LC-MS [mobile phase: 80% water (0.1% FA) and 20% ACN (0.1% FA) to 5% water (0.1% FA) and 95% ACN (0.1% FA) in 9.0 min]: Rt=3.48 min; MS Calcd.: 496.2, MS Found: 497.3 [M+H]$^+$.

Chiral HPLC [AD 4.6×250 mm, 5 μm (Daicel) (CA-HPLC-023), Phase: Hexane/EtOH (0.2% DEA)=60/40, flow rate: 1 mL/min, temperature: 35° C.]: Rt: 5.624 min, ee: 99.81%.

Examples 91 and 92

Cis-1-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-ol (from Peak 1) (Single Unknown Isomer 1, Rt=4.424 min; Single Unknown Isomer 2, Rt=4.974 min)

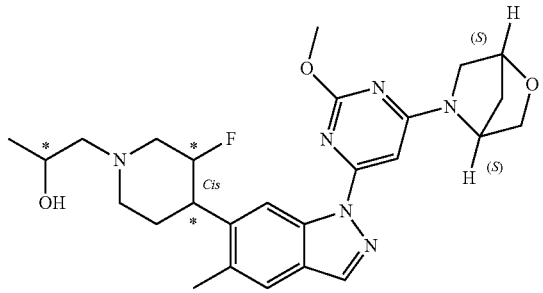

NaBH$_4$ (38 mg, 1.0 mmol) was added to the solution of cis-1-(4-(1-(6-((1S,4S)-2-oxa-5-azabicyclo[2.2.1]heptan-5-yl)-2-methoxypyrimidin-4-yl)-5-methyl-1H-indazol-6-yl)-

3-fluoropiperidin-1-yl)propan-2-one (from Peak 1, 140 mg, 0.28 mmol) in MeOH (10 mL) and the reaction was stirred at Rt for 60 min. The reaction was then diluted with EtOAc and then washed with brine (10 mL). The solution was dried and concentrated. The residue was purified by prep-HPLC (Waters 2767/Qda, Waters sunfire $C_{18}$ 20×250 mm 10 µm, 30 mL/min, $H_2O$ (0.1% TFA):acetonitrile=80:20-95:5) to give the desired product with TFA salt as a white solid (140 mg, yield: 83%).

LC-MS [mobile phase: from 90% water (0.1% FA) and 10% ACN (0.1% FA) to 5% water (0.1% FA) and 95% ACN (0.1% FA) in 9.0 min]: purity 100%; Rt=4.38 min; MS Calcd.: 496, MS Found: 497 [M+H]$^+$.

The compound was chiral separated by Kermanda to give two yellow solids

Example 91, Peak 1: (52 mg, Yield: 37%)

$^1$H NMR (400 MHz, CDCl$_3$): δ 8.89 (s, 1H), 8.09 (s, 1H), 7.56 (s, 1H), 6.55 (brs, 0.7H), 5.25 (br, 0.4H), 5.07~4.92 (m, 1H), 4.74 (s, 1H), 4.12 (s, 3H), 4.12~4.04 (m, 1H), 3.92~3.89 (m, 2H), 3.71~3.25 (m, 5H), 3.21~3.18 (m, 1H), 2.69 (br, 2H), 2.49 (s, 3H), 2.09~1.98 (m, 5H), 1.24 (d, J=6.4 Hz, 3H), $^{19}$F NMR (376 MHz, CDCl$_3$): δ −75.47 (s), −183.35 (s) TFA salt LC-MS [mobile phase: from 80% water (0.1% FA) and 20% ACN (0.1% FA) to 5% water (0.1% FA) and 95% ACN (0.1% FA) in 9 min]: Rt=3.44 min; MS Calcd: 496, MS Found: 497 [M+H]$^+$.

Chiral HPLC [Column: AD Column size: 0.46 cm I.D.× 15 cm L. Injection: 2 µl Mobile phase: HEP:IPA (0.1% DEA)=60:40, Flow rate: 0.5 mL/min, Wave length: UV 254 nm, Temperature: 25° C.]: Rt: 4.424 min, ee: 100%

Example 92, Peak 2: (58 mg, Yield: 42%)

$^1$H NMR (400 MHz, CDCl$_3$): δ 8.87 (s, 1H), 8.10 (s, 1H), 7.58 (s, 1H), 6.55 (brs, 0.8H), 5.27 (br, 0.6H), 5.27~5.11 (m, 1H), 4.74 (s, 1H), 4.32 (br, 1H), 4.13 (s, 3H), 4.10 (br, 1H), 3.94~3.81 (m, 3H), 3.55~3.48 (m, 2H), 3.33~3.30 (m, 1H), 3.19~3.15 (m, 1H), 3.03~2.90 (m, 2H), 2.49 (s, 3H), 2.40~2.20 (m, 2H), 2.00~1.97 (m, 2H), 1.31 (d, J=6.4 Hz, 3H), $^{19}$F NMR (376 MHz, CDCl$_3$): δ −75.43 (s), −183.31 (s) TFA salt LC-MS [mobile phase: from 80% water (0.1% FA) and 20% ACN (0.1% FA) to 5% water (0.1% FA) and 95% ACN (0.1% FA) in 9 min]: Rt=3.43 min; MS Calcd: 496, MS Found: 497.3 [M+H]$^+$.

Chiral HPLC [Column: AD Column size: 0.46 cm I.D.× 15 cm L. Injection: 2 µl Mobile phase:

HEP:IPA (0.1% DEA)=60:40, Flow rate: 0.5 mL/min, Wave length: UV 254 nm,

Temperature: 25° C.]: Rt: 4.974 min, ee: 98.85%

Example 93

Cis-1-(4-(1-(6-((1S,4S)-2-oxa-5-azabicyclo[2.2.1] heptan-5-yl)-2-methoxypyrimidin-4-yl)-5-methyl-1H-indazol-6-yl)-3-fluoropiperidin-1-yl)propan-2-ol (from Peak 2)

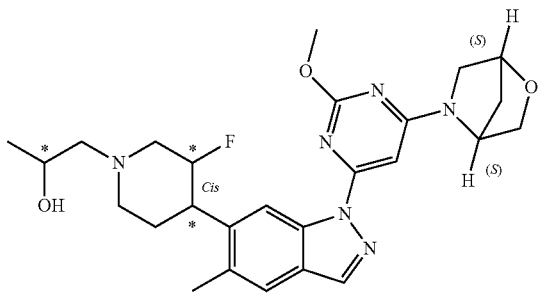

Cis-1-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propan-2-one (from Peak 2, 110 mg, 0.22 mmol) was dissolved in MeOH (5 mL), NaBH$_4$ (56 mg, 1.3 mmol) was added to the solution. The mixture was stirred at Rt for 20 min. The reaction was diluted with sat. NH$_4$Cl (50 mL), the mixture was extracted with EtOAc (50 mL×3). The organic layer was concentrated and the residue was purified by prep HPLC (Gilson ZYMC-Ac+US Triad; $C_{18}$-s 250×20 mm, 10 µm; Mobile phase: MeCN/H$_2$O (0.1% TFA) from 20/80 to 95/5, Flow rate: 20 mL/min. Trigser: 254 nm) to give the mixture product as a white solid (98 mg, yield: 85%)

LC-MS [mobile phase: 90% water (0.1% FA) and 10% ACN (0.1% FA) to 5% water (0.1% FA) and 95% ACN (0.1% FA) in 10.0 min]: Rt=4.38 min; MS Calcd.: 496.6, MS Found: 497.3 [M+H]$^+$.

The mixture was purified by chiral prep-HPLC [AD-H, 0.46 cm I.D.×15 cm L, Mobile phase: CO$_2$:EtOH (0.1% NH$_3$.H$_2$O)=60:40, Flow rate: 0.5 mL/min, Wave length: 254 nm, Temperature: 25° C.] to give one isomer as a white solid (25 mg, yield 25%).

$^1$H NMR (400 MHz, CDCl$_3$): δ 8.89 (s, 1H), δ 8.04 (s, 1H), δ 7.54 (s, 1H), δ 6.56 (s, 1H), δ 5.27 (s, 1H), δ 4.93~4.82 (m, 1H), δ 4.74 (s, 1H), δ 4.13 (s, 3H), δ 3.91~3.39 (m, 3H), δ 3.54~3.52 (m, 2H), δ 3.44 (s, 2H), δ 3.16~3.11 (d, J=16 Hz, 2H), δ 2.55~2.53 (m, 2H), δ 2.48 (s, 3H), δ 2.33 (s, 1H), δ 2.15 (s, 1H), δ 1.98 (s, 3H), δ 1.56 (s, 1H), δ 1.19~1.18 (d, J=4 Hz 3H).

$^{19}$F NMR (376.5 MHz, CDCl$_3$): δ −184.00 (s)

LC-MS [mobile phase: 90% water (0.1% FA) and 10% ACN (0.1% FA) to 5% water (0.1% FA) and 95% ACN (0.1% FA) in 10.0 min]: Rt=4.34 min; MS Calcd.: 496, MS Found: 497 [M+H]$^+$.

Chiral HPLC: Rt: 5.182 min, ee: 100%

Chiral method: Column: AD Column size: 0.46 cm I.D.× 15 cm L. Injection: 2 µl Mobile phase: HEP:EtOH (0.1% DEA)=60:40, Flow rate: 0.5 mL/min, Wave length: UV 254 nm, Temperature: 25° C.

Examples 94 and 95

5-(2-methoxy-6-(5-methyl-6-(1-(oxetan-3-yl)piperidin-4-yl)-1H-indazol-1-yl)pyrimidin-4-yl)-2-oxa-5-azabicyclo[2.2.2]octane (Single Unknown Isomer 1, Rt=5.871 min; Single Unknown Isomer 2, Rt=6.524 min)

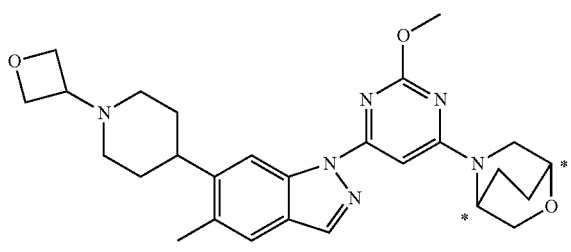 [SMILES: COc1nc(N2CC3CCC2CO3)cc(-n2ncc3cc(C)c(C4CCN(C5COC5)CC4)cc32)n1]

To a suspension of 1-(6-chloro-2-methoxypyrimidin-4-yl)-5-methyl-6-(1-(oxetan-3-yl)piperidin-4-yl)-1H-indazole (120 mg, 0.29 mmol) and 2-oxa-5-azabicyclo[2.2.2]octane hydrochloride (92 mg, 0.58 mmol) in DMF (20 mL) was added DIPEA (188 mg, 1.45 mmol). The resulting mixture was stirred at 80° C. overnight. The resulting mixture was diluted with water (50 mL) and extracted with EtOAc (3×100 mL). The combined organic layer was washed with water (3×100 mL) and brine (100 mL), dried over anhydrous Na$_2$SO$_4$, filtered and concentrated to give a residue. The residue was purified by silica gel column chromatography (EtOAc) to give the mixture compound (60 mg, yield: 42%) as white solid.

LC-MS [mobile phase: from 50% water (0.1% FA) and 50% ACN (0.1% FA) to 5% water (0.1% FA) and 95% ACN (0.1% FA) in 2.6 min]: Rt=0.791 min; MS Calcd: 490, MS Found: 491 [M+H]$^+$.

Chiral Separation of Racemates:

Method: Column: AD-H; Column size: 0.46 cm I.D.×15 cm L; Mobile phase: CO$_2$:EtOH (0.1% NH$_3$.H$_2$O)=60:40; Flow rate: 0.5 mL/min; Wave length: UV 254 nm; Temperature: 25° C.; Sample solution in EtOH E94 white solid (Rt=5.871 min, 12 mg, yield: 8%)

$^1$H NMR (400 MHz, CDCl$_3$) δ 8.78 (s, 1H), 8.07 (s, 1H), 7.51 (s, 1H), 6.61 (m, 1H), 4.99 (m, 1H), 4.69~4.68 (d, J=6.4 Hz, 4H), 4.16 (m, 1H), 4.15 (s, 3H), 4.11 (m, 1H), 4.07~4.05 (m, 1H), 3.96~3.92 (m, 1H), 3.57~3.52 (m, 2H), 2.94-2.91 (m, 2H), 2.85~2.82 (m, 1H), 2.46 (s, 3H), 2.25~2.21 (m, 1H), 2.08-1.99 (m, 4H), 1.94~1.85 (m, 4H), 1.81~1.74 (m, 1H).

LC-MS [mobile phase: from 80% water (0.1% FA) and 20% ACN (0.1% FA) to 5% water (0.1% FA) and 95% ACN (0.1% FA) in 10.0 min]; Rt=3.81 min; MS Calcd: 490, MS Found: 491 [M+H]$^+$, 514 [M+Na]$^+$.

Chiral HPLC: Rt: 871 min, ee 100%;

E95 white solid (Rt=6.524 min, 12 mg, yield: 8).

$^1$H NMR (400 MHz, CDCl$_3$) δ 8.78 (s, 1H), 8.07 (s, 1H), 7.51 (s, 1H), 6.61 (m, 1H), 4.98 (m, 1H), 4.69~4.68 (d, J=6.4 Hz, 4H), 4.18 (m, 1H), 4.15 (s, 3H), 4.12 (m, 1H), 4.07~4.05 (m, 1H), 3.94~3.92 (m, 1H), 3.59~3.52 (m, 2H), 2.94~2.91 (m, 2H), 2.85~2.82 (m, 1H), 2.46 (s, 3H), 2.28~2.22 (m, 1H), 2.08~1.99 (m, 4H), 1.94~1.88 (m, 4H), 1.81~1.73 (m, 1H).

LC-MS [mobile phase: from 80% water (0.1% FA) and 20% ACN (0.1% FA) to 5% water (0.1% FA) and 95% ACN (0.1% FA) in 10.0 min]: Rt=3.81 min; MS Calcd: 490, MS Found: 491 [M+H]', 514 [M+Na].

Chiral HPLC: Rt: 6.524 min, ee 100%;

Example 96

Cis-(1R,4R)-5-(6-(6-(3-fluoro-1-(oxetan-3-yl)piperidin-4-yl)-5-methyl-1H-indazol-1-yl)-2-methoxypyrimidin-4-yl)-2-oxa-5-azabicyclo[2.2.1]heptane (Single Unknown Enantiomer 1, Rt=1.853 min, from Peak 1)

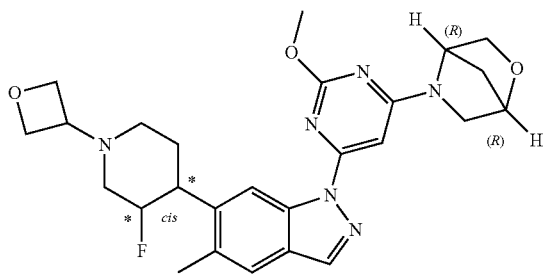

A mixture of cis-1-(6-chloro-2-methoxypyrimidin-4-yl)-6-(3-fluoro-1-(oxetan-3-yl)piperidin-4-yl)-5-methyl-1H-indazole (from peak 1) (20 mg, 0.046 mmol), (1R,4R)-2-oxa-5-azabicyclo[2.2.1]heptane (13 mg, 0.092 mmol) and DIEA (18 mg, 0.138 mmol) in DMF (1 mL) was stirred at 60° C. for 3 h. The reaction mixture was purified by Prep-HPLC (A: water, B: ACN, A:B=80:20 to A:B=5:95) to give a white solid. (13 mg, yield 56%).

$^1$H NMR (400 MHz, CDCl$_3$): δ 8.88 (s, 1H), 8.08 (s, 1H), 7.54 (s, 1H), 6.54 (br 0.7H), 5.25 (br 0.5H), 4.93~4.90 (m, 1H), 4.78~4.62 (m, 6H), 4.15 (s, 3H), 3.94~3.88 (m, 2H), 3.69~3.46 (m, 3H), 3.24~3.08 (m, 2H), 2.82~2.80 (m, 1H), 2.47 (s, 3H), 2.13~1.64 (m, 6H).

$^{19}$F NMR (376 MHz, CDCl3): δ −183.97.

LC-MS [mobile phase: from 50% water (0.1% NH$_3$H$_2$O) and 50% ACN (0.1% NH$_3$H$_2$O) to 5% water (0.1% NH$_3$H$_2$O) and 95% ACN (0.1% NH$_3$H$_2$O) in 12 min]: Rt=5.356 min; MS Calcd: 494, MS Found: 495 [M+H]$^+$.

Chiral method: Phase: CO$_2$: MeOH (0.03% DEA)=70/30, F: 1.8 mL/min, W: 254 nm, Rt: 1.853 min, 100% ee.

Example 97

Cis-(1R,4R)-5-(6-(6-(3-fluoro-1-(oxetan-3-yl)piperidin-4-yl)-5-methyl-1H-indazol-1-yl)-2-methoxypyrimidin-4-yl)-2-oxa-5-azabicyclo[2.2.1]heptane (Single Unknown Enantiomer 2, Rt=2.594 min, from Peak 2)

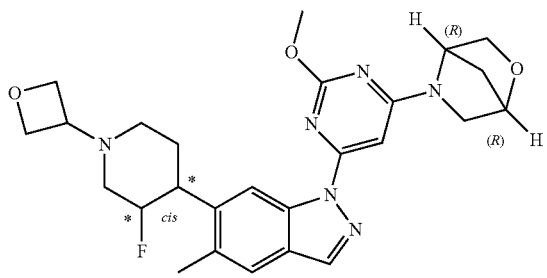

A mixture of cis-1-(6-chloro-2-methoxypyrimidin-4-yl)-6-(3-fluoro-1-(oxetan-3-yl)piperidin-4-yl)-5-methyl-1H-indazole (from peak 2) (20 mg, 0.046 mmol), (1R,4R)-2-oxa-5-azabicyclo[2.2.1]heptane (13 mg, 0.092 mmol) and DIEA (18 mg, 0.138 mmol) in DMF (1 mL) was stirred at rt overnight. The reaction mixture was purified by Prep-HPLC (A: water, B:

ACN, A:B=80:20 to A:B=5:95) to give a white solid. (7 mg, yield 30%).

$^1$H NMR (400 MHz, CDCl3): δ 8.88 (s, 1H), 8.08 (s, 1H), 7.54 (s, 1H), 6.54 (s, 0.6H), 5.25 (s, 0.4H), 4.93~4.90 (m, 1H), 4.78~4.62 (m, 6H), 4.15 (s, 3H), 3.94~3.88 (m, 2H), 3.67~3.65 (m, 1H), 3.55~3.51 (m, 2H), 3.21~3.19 (m, 1H), 3.13~3.09 (m, 1H), 2.82~2.80 (m, 1H), 2.47 (s, 3H), 2.10~2.09 (m, 1H), 2.05~1.96 (m, 4H), 1.87~1.64 (m, 1H).

$^{19}$F NMR (376 MHz, CDCl$_3$): δ −183.97.

LC-MS [mobile phase: from 50% water (0.1% NH$_3$H$_2$O) and 50% ACN (0.1% NH$_3$H$_2$O) to 5% water (0.1% NH$_3$H$_2$O) and 95% ACN (0.1% NH$_3$H$_2$O) in 12 min]: Rt=5.36 min; MS Calcd: 494, MS Found: 495 [M+H]$^+$.

Chiral method: Phase: CO$_2$: MeOH (0.03% DEA)=70/30, F: 1.8 mL/min, W: 254 nm, Rt:
2.594 min, 100% ee.

Example 98

Cis-(1S,4S)-5-(6-(6-(3-fluoro-1-(oxetan-3-yl)piperidin-4-yl)-5-methyl-1H-indazol-1-yl)-2-methoxypyrimidin-4-yl)-2-oxa-5-azabicyclo[2.2.1]heptane
(Single Unknown Enantiomer 1, Rt=3.622 min, from Peak 1)

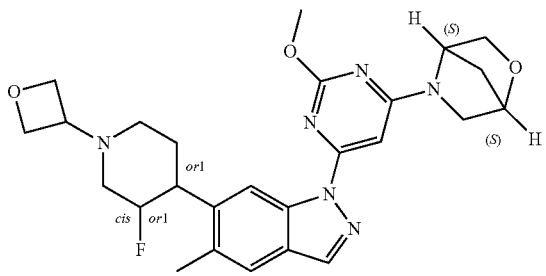

A mixture of cis-1-(6-chloro-2-methoxypyrimidin-4-yl)-6-(3-fluoro-1-(oxetan-3-yl)piperidin-4-yl)-5-methyl-1H-indazole (from peak 1) (20 mg, 0.046 mmol), (1S,4S)-2-oxa-5-azabicyclo[2.2.1]heptane (13 mg, 0.092 mmol) and DIEA (18 mg, 0.138 mmol) in DMF (1 mL) was stirred at 60° C. for 3 h. The reaction mixture was purified by Prep-HPLC (A: water, B: ACN, A:B=80:20 to A:B=5:95) to give a white solid. (9 mg, yield 40%).

$^1$H NMR (400 MHz, CDCl$_3$): δ 8.88 (s, 1H), 8.08 (s, 1H), 7.54 (s, 1H), 6.54 (br 0.7H), 5.25 (br 0.5H), 4.93~4.90 (m, 1H), 4.78~4.62 (m, 6H), 4.15 (s, 3H), 3.94~3.88 (m, 2H), 3.69~3.46 (m, 3H), 3.24~3.08 (m, 2H), 2.82~2.80 (m, 1H), 2.47 (s, 3H), 2.13~1.64 (m, 6H).

$^{19}$F NMR (376 MHz, CDCl3): δ −183.97.

LC-MS [mobile phase: from 50% water (0.1% NH$_3$H$_2$O) and 50% ACN (0.1% NH$_3$H$_2$O) to 5% water (0.1% NH$_3$H$_2$O) and 95% ACN (0.1% NH$_3$H$_2$O) in 12 min]: Rt=5.36 min; MS Calcd: 494, MS Found: 495 [M+H]$^+$.

Chiral HPLC [Phase: CO$_2$: MeOH (0.03% DEA)=70/30, Flow rate: 1.8 mL/min, Wave length: 254 nm]: Rt: 3.622 min, 100% ee.

Example 99

Cis-(1S,4S)-5-(6-(6-(3-fluoro-1-(oxetan-3-yl)piperidin-4-yl)-5-methyl-1H-indazol-1-yl)-2-methoxypyrimidin-4-yl)-2-oxa-5-azabicyclo[2.2.1]heptane
(Single Unknown Enantiomer 2, Rt=4.377 min, from Peak 2)

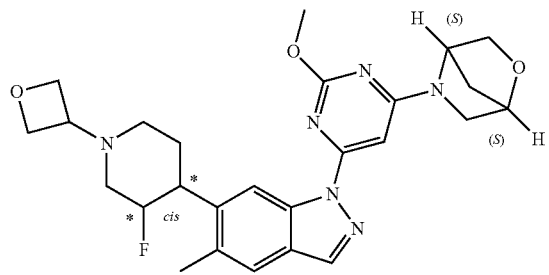

A mixture of cis-1-(6-chloro-2-methoxypyrimidin-4-yl)-6-(3-fluoro-1-(oxetan-3-yl)piperidin-4-yl)-5-methyl-1H-indazole (from peak 2) (20 mg, 0.046 mmol), (1S,4S)-2-oxa-5-azabicyclo[2.2.1]heptane (13 mg, 0.092 mmol) and DIEA (18 mg, 0.138 mmol) in DMF (1 mL) was stirred at rt overnight. The reaction mixture was purified by Prep-HPLC (A: water, B: ACN, A:B=80:20 to A:B=5:95) to give a white solid. (17 mg, yield 64%).

1H NMR (400 MHz, CDCl3): δ 8.88 (s, 1H), 8.08 (s, 1H), 7.54 (s, 1H), 7.54 (s, 0.6H), 5.25 (s, 0.4H), 4.93~4.90 (m, 1H), 4.78~4.62 (m, 6H), 4.15 (s, 3H), 3.94~3.88 (m, 2H), 3.67~3.65 (m, 1H), 3.55~3.51 (m, 2H), 3.21~3.19 (m, 1H), 3.13~3.09 (m, 1H), 2.82~2.80 (m, 1H), 2.47 (s, 3H), 2.10~2.09 (m, 1H), 2.05~1.96 (m, 4H), 1.87~1.64 (m, 1H).

$^{19}$F NMR (376 MHz, CDCl3): δ −183.97.

LC-MS [mobile phase: from 95% water (0.1% FA) and 5% ACN (0.1% FA) to 5% water (0.1% FA) and 95% ACN (0.1% FA) in 9 min]: Rt=5.26 min; MS Calcd: 494, MS Found: 495 [M+H]$^+$.

Chiral HPLC [Phase: CO$_2$: MeOH (0.02% DEA)=80/20, Flow rate: 1.8 mL/min, Wave length: 254 nm]: Rt: 4.377 min, 100% ee.

Example 100

Cis-(1R,4R)-5-(6-(6-(3-fluoro-1-(oxetan-3-yl)piperidin-4-yl)-5-methyl-1H-indazol-1-yl)-2-methylpyrimidin-4-yl)-2-oxa-5-azabicyclo[2.2.1]heptane
(Single Unknown Enantiomer 1, Rt=7.192 min, from Peak 1)

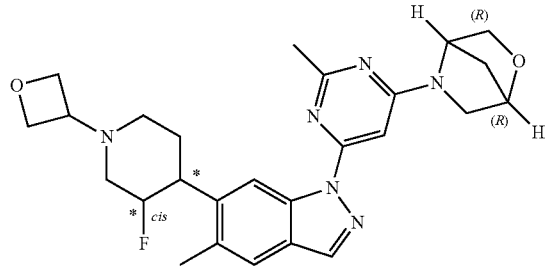

A mixture of cis-1-(6-chloro-2-methylpyrimidin-4-yl)-6-(3-fluoro-1-(oxetan-3-yl)piperidin-4-yl)-5-methyl-1H-indazole (from peak 1) (20 mg, 0.048 mmol), (1R,4R)-2-oxa-5-azabicyclo[2.2.1]heptane (13 mg, 0.096 mmol) and DIEA (19 mg, 0.144 mmol) in DMF (1 mL) was stirred at 60° C. for 3 h. The reaction mixture was purified by Prep-HPLC (A: water, B: ACN, A:B=80:20 to A:B=5:95) to give a white solid. (10 mg, yield 40%).

$^1$H NMR (400 MHz, CDCl$_3$): δ 8.91 (s, 1H), 8.07 (s, 1H), 7.53 (s, 1H), 6.67 (br 0.8H), 5.25 (s, 0.4H), 4.97~4.85 (m, 1H), 4.78~4.67 (m, 6H), 3.91 (s, 2H), 3.89~3.48 (m, 3H), 3.28~3.25 (m, 1H), 3.12~3.10 (m, 1H), 2.88~2.85 (m, 1H), 2.64 (s, 3H), 2.47 (s, 3H), 2.15~1.94 (m, 6H).

$^{19}$F NMR (376 MHz, CDCl$_3$): δ −183.94.

LC-MS [mobile phase: from 70% water (0.1% NH$_3$H$_2$O) and 30% ACN (0.1% NH$_3$H$_2$O) to 5% water (0.1% NH$_3$H$_2$O) and 95% ACN (0.1% NH$_3$H$_2$O) in 12 min]: Rt=7.99 min; MS Calcd: 478, MS Found: 479 [M+H]$^+$.

Chiral HPLC [Phase: CO$_2$:MeOH (0.03% DEA)=70/30, Flow rate: 1.8 mL/min, Wave length: 254 nm]: Rt: 7.192 min, 100% ee.

Example 101

Cis-(1R,4R)-5-(6-(6-(3-fluoro-1-(oxetan-3-yl)piperidin-4-yl)-5-methyl-1H-indazol-1-yl)-2-methylpyrimidin-4-yl)-2-oxa-5-azabicyclo[2.2.1]heptane (Single Unknown Enantiomer 2, Rt=8.287 min, from Peak 2)

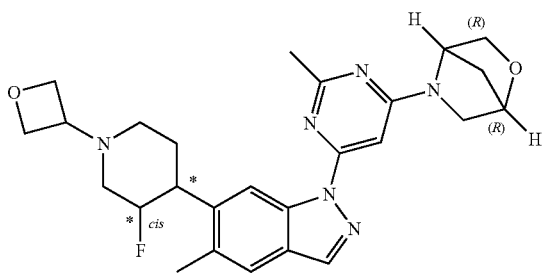

A mixture of cis-1-(6-chloro-2-methylpyrimidin-4-yl)-6-(3-fluoro-1-(oxetan-3-yl)piperidin-4-yl)-5-methyl-1H-indazole (from peak 2) (20 mg, 0.048 mmol), (1R,4R)-2-oxa-5-azabicyclo[2.2.1]heptane (13 mg, 0.096 mmol) and DIEA (19 mg, 0.144 mmol) in DMF (1 mL) was stirred at rt overnight. The reaction mixture was purified by Prep-HPLC (A: water, B: ACN, A:B=80:20 to A:B=5:95) to give a white solid. (5 mg, yield 21%).

1H NMR (400 MHz, CDCl3): δ 8.91 (s, 1H), 8.07 (s, 1H), 7.53 (s, 1H), 6.54 (s, 0.6H), 5.25 (s, 0.4H), 4.97~4.90 (m, 1H), 4.78~4.62 (m, 6H), 3.91 (s, 2H), 3.68~3.65 (m, 1H), 3.53~3.48 (m, 2H), 3.28~3.25 (m, 1H), 3.12~3.08 (m, 1H), 2.88~2.85 (m, 1H), 2.64 (s, 3H), 2.47 (s, 3H), 2.22~2.14 (m, 1H), 2.05~1.96 (m, 5H).

$^{19}$F NMR (376 MHz, CDCl$_3$): δ −183.94.

LC-MS [mobile phase: from 70% water (0.1% NH$_3$H$_2$O) and 30% ACN (0.1% NH$_3$H$_2$O) to 5% water (0.1% NH$_3$H$_2$O) and 95% ACN (0.1% NH$_3$H$_2$O) in 12 min]: Rt=7.99 min; MS Calcd: 478, MS Found: 479 [M+H]$^+$.

Chiral HPLC [Phase: CO$_2$: MeOH (0.03% DEA)=70/30, Flow rate: 1.8 mL/min, Wave length:: 254 nm]: Rt: 8.287 min, 100% ee.

Example 102

Cis-(1S,4S)-5-(6-(6-(3-fluoro-1-(oxetan-3-yl)piperidin-4-yl)-5-methyl-1H-indazol-1-yl)-2-methylpyrimidin-4-yl)-2-oxa-5-azabicyclo[2.2.1]heptane (Single Unknown Enantiomer 1, Rt=5.285 min, from Peak 1)

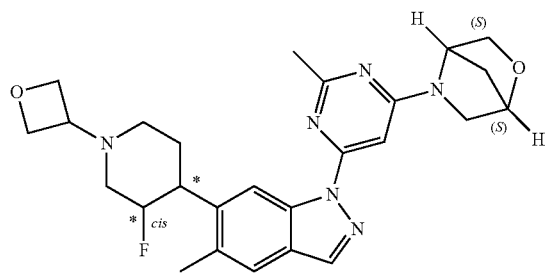

A mixture of cis-1-(6-chloro-2-methylpyrimidin-4-yl)-6-(3-fluoro-1-(oxetan-3-yl)piperidin-4-yl)-5-methyl-1H-indazole (from peak 1) (20 mg, 0.048 mmol), (1S,4S)-2-oxa-5-azabicyclo[2.2.1]heptane (13 mg, 0.096 mmol) and DIEA (19 mg, 0.144 mmol) in DMF (1 mL) was stirred at 60° C. for 3 h. The reaction mixture was purified by Prep-HPLC (A: water, B: ACN, A:B=80:20 to A:B=5:95) to give a white solid. (10 mg, yield 42%).

$^1$H NMR (400 MHz, CDCl$_3$): δ 8.91 (s, 1H), 8.07 (s, 1H), 7.53 (s, 1H), 6.67 (br 0.8H), 5.25 (s, 0.4H), 4.97~4.85 (m, 1H), 4.78~4.67 (m, 6H), 3.91 (s, 2H), 3.89~3.48 (m, 3H), 3.28~3.25 (m, 1H), 3.12~3.10 (m, 1H), 2.88~2.85 (m, 1H), 2.64 (s, 3H), 2.47 (s, 3H), 2.15~1.94 (m, 6H).

$^{19}$F NMR (376 MHz, CDCl$_3$): δ −183.94.

LC-MS [mobile phase: from 70% water (0.1% NH$_3$H$_2$O) and 30% ACN (0.1% NH$_3$H$_2$O) to 5% water (0.1% NH$_3$H$_2$O) and 95% ACN (0.1% NH$_3$H$_2$O) in 12 min]: Rt=7.99 min; MS Calcd: 478, MS Found: 479 [M+H]$^+$.

Chiral method: Phase: CO$_2$: MeOH (0.03% DEA)=70/30, F: 1.8 mL/min, W: 254 nm, Rt: 5.285 min, 100% ee.

Example 103

Cis-(1S,4S)-5-(6-(6-(3-fluoro-1-(oxetan-3-yl)piperidin-4-yl)-5-methyl-1H-indazol-1-yl)-2-methylpyrimidin-4-yl)-2-oxa-5-azabicyclo[2.2.1]heptane (Single Unknown Enantiomer 2, Rt=7.705 min, from Peak 2)

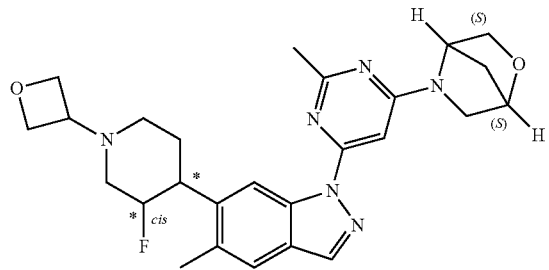

A mixture of cis-1-(6-chloro-2-methylpyrimidin-4-yl)-6-(3-fluoro-1-(oxetan-3-yl)piperidin-4-yl)-5-methyl-1H-indazole (from peak 2) (20 mg, 0.048 mmol), (1S,4S)-2-oxa-5- azabicyclo[2.2.1]heptane (13 mg, 0.096 mmol) and DIEA (19 mg, 0.144 mmol) in DMF (1 mL) was stirred at rt overnight. The reaction mixture was purified by Prep-HPLC (A: water, B: ACN, A:B=80:20 to A:B=5:95) to give a white solid. (12 mg, yield 52%).

$^1$H NMR (400 MHz, CDCl$_3$): δ 8.91 (s, 1H), 8.07 (s, 1H), 7.53 (s, 1H), 6.54 (s, 0.6H), 5.25 (s, 0.4H), 4.97~4.90 (m, 1H), 4.78~4.62 (m, 6H), 3.91 (s, 2H), 3.68~3.65 (m, 1H), 3.53~3.48 (m, 2H), 3.28~3.25 (m, 1H), 3.12~3.08 (m, 1H), 2.88~2.85 (m, 1H), 2.64 (s, 3H), 2.47 (s, 3H), 2.22~2.14 (m, 1H), 2.05~1.96 (m, 5H).

$^{19}$F NMR (376 MHz, CDCl$_3$): δ −183.94.

LC-MS [mobile phase: from 95% water (0.1% FA) and 5% ACN (0.1% FA) to 5% water (0.1% FA) and 95% ACN (0.1% FA) in 9 min]: Rt=4.83 min; MS Calcd: 478, MS Found: 479 [M+H]$^+$.

Chiral HPLC [Phase: CO$_2$: EtOH:ACN (0.025% DEA) =75/21/9, Flow rate: 3.0 mL/min, Wave length: 254 nm]: Rt: 7.705 min, 100% ee.

Example 104

(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane (from Peak 1)

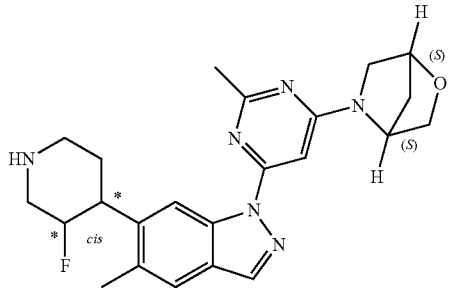

To a solution of cis-tert-butyl 4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (75 mg, 0.144 mmol) (from peak 1) in CH$_2$Cl$_2$ (20 mL) was added TFA (2 mL) at rt. The reaction was stirred at r.t overnight. The solution was concentrated and then sat. NaHCO$_3$ (20 mL) was added. The mixture was extracted with EtOAc (3×20 mL). The combined organic was washed with water (50 mL), brine (50 mL), dried over anhydrous Na$_2$SO$_4$, filtered. The filtrate was concentrated and purified by prep-TLC (EtOAc/MeOH=10/1) to give the product as a white solid (49 mg, 81% yield).

$^1$H NMR (400 MHz, CDCl$_3$): δ 8.94 (s, 1H), 8.07 (s, 1H), 7.53 (s, 1H), 6.68 (s, 1H), 5.29 (s, 1H), 5.28~4.74 (m, 2H), 3.90 (s, 2H), 3.61~3.52 (m, 3H), 3.23~3.20 (m, 2H), 2.86~2.78 (m, 2H), 2.62 (s, 3H), 2.49 (s, 3H), 2.07~1.87 (m, 4H).

$^{19}$F NMR (376 MHz, CDCl$_3$): δ −183.009 (s)

LC-MS [mobile phase: from 50% water (0.1% FA) and 50% ACN (0.1% FA) to 5% water (0.1% FA) and 95% ACN (0.1% FA) in 2.0 min]: Rt=0.78 min; MS Calcd.: 422, MS Found: 423 [M+H]$^+$.

Example 105

(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane (from Peak 2)

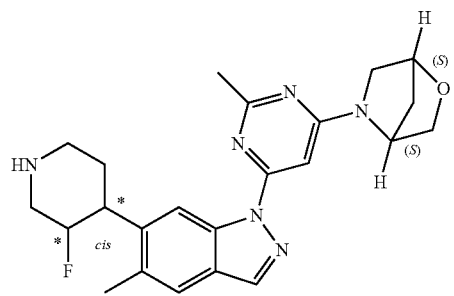

To a solution of cis-tert-butyl 4-(1-(6-(((1S,4S)-2-oxa-5-azabicyclo[2.2.1]heptan-5-yl)-2-methylpyrimidin-4-yl)-5-methyl-1H-indazol-6-yl)-3-fluoropiperidine-1-carboxylate (from Peak 2, 60 mg, 0.11 mmol) in CH$_2$Cl$_2$ (20 mL) was added TFA (2 mL) at rt. The reaction was stirred at rt overnight. The solution was concentrated and then NH$_4$OH (10 mL) was added. The mixture was extracted with EtOAc (3×50 mL). The combined organic was washed with water (50 mL), brine (50 mL), dried over anhydrous Na$_2$SO$_4$ and filtered. The filtrate was concentrated and purified by prep-TLC (EtOAc/MeOH=5/1) to give the product as a white solid (21 mg, 43% yield)

$^1$H NMR (400 MHz, CDCl$_3$): δ 8.93 (s, 1H), 8.07 (s, 1H), 7.53 (s, 1H), 6.68 (s, 1H), 5.29 (s, 1H), 4.74 (m, 2H), 3.90 (s, 2H), 3.61~3.52 (m, 3H), 3.23~3.20 (m, 2H), 2.86~2.78 (m, 2H), 2.62 (s, 3H), 2.49 (s, 3H), 2.07~1.87 (m, 5H).

$^{19}$F NMR (376 MHz, CDCl$_3$): δ −182.777 (s)

LC-MS [mobile phase: from 50% water (0.1% FA) and 50% ACN (0.1% FA) to 5% water (0.1% FA) and 95% ACN (0.1% FA) in 2.0 min]: Rt=0.78 min; MS Calcd.: 422, MS Found: 423 [M+H]$^+$.

Examples 106 and 107

(1S,4S)-5-(6-(5-chloro-6-(1-(tetrahydrofuran-3-yl)piperidin-4-yl)-1H-indazol-1-yl)-2-methylpyrimidin-4-yl)-2-oxa-5-azabicyclo[2.2.1]heptane (Single Unknown Isomer 1, Rt=4.877 min; Single Unknown Isomer 2, Rt=4.877 min)

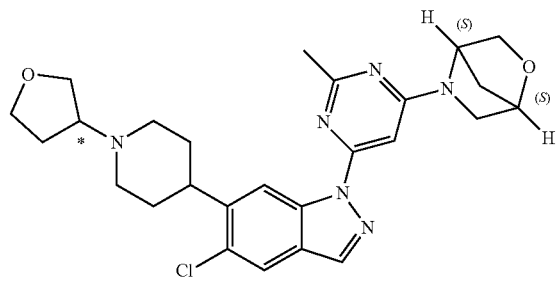

A mixture of 5-chloro-6-(1-(tetrahydrofuran-3-yl)piperidin-4-yl)-1H-indazole (200 mg, 0.65 mmol), (1S,4S)-5-(6-iodo-2-methylpyrimidin-4-yl)-2-oxa-5-azabicyclo[2.2.1]

heptane (228 mg, 0.72 mmol), N,N'-dimethylcyclohexane-1,2-diamine (93 mg, 0.64 mmol), CuI (62 mg, 0.33 mmol) and $K_3PO_4$ (277 mg, 1.31 mmol) in toluene (3 mL) was stirred at 100° C. for 4 hours. The mixture was diluted with EtOAc (40 mL), washed with $NH_3.H_2O$ (10 mL×2), brine (10 mL×3), dried over $Na_2SO_4$, filtered and concentrated. The residue was purified by pre-TLC (DCM/MeOH=20/1) to give the title compound (180 mg, 56%) as a white solid.

$^1$HNMR (400 MHz, $CDCl_3$): δ 8.93 (s, 1H), 8.07 (s, 1H), 7.74 (s, 1H), 6.64 (s, 1H), 5.35 (br 1H), 4.74 (s, 1H), 4.03-3.80 (m, 6H), 3.52-3.48 (m, 2H), 3.15-3.04 (m, 4H), 2.63 (s, 3H), 2.42-3.38 (m, 2H), 2.17-1.95 (m, 8H).

LC-MS [Phenomenex Kinetex 5 μm EVO $C_{18}$, 50×4.6 mm; mobile phase: B (ACN): A (0.02% $NH_4OAc$); gradient (B %) in 6 min]: Rt=3.953 min; MS Calcd.: 494, MS Found: 495 $[M+H]^+$.

Chiral Separation of Racemates:

Method: Column: OZ-H; Column size: 0.46 cm I.D.×15 cm L; Injection: 2 μl; Mobile phase: HEP:EtOH (0.1% DEA)=60:40; Flow rate: 0.5 mL/min; Wave length: UV 254 nm;

Temperature: 25° C.; Sample solution in EtOH

E106

35 mg, 35% yield $^1$H NMR (400 MHz, $CDCl_3$): δ 8.93 (s, 1H), 8.07 (s, 1H), 7.74 (s, 1H), 6.67 (br, 0.75H), 5.35 (br, 0.69H), 4.74 (s, 1H), 3.99~3.96 (m, 1H), 3.91 (s, 3H), 3.85~3.82 (m, 1H), 3.74~3.69 (m, 1H), 3.54~3.50 (m, 2H), 3.21~1.95 (m, 4H), 2.62 (s, 3H), 2.33~1.83 (m, 10H).

LC-MS [mobile phase: from 80% water (0.1% FA) and 20% ACN (0.1% FA) to 5% water (0.1% FA) and 95% ACN (0.1% FA) in 9.0 min], Rt=3.57 min; MS Calcd: 494, MS Found: 495 $[M+H]^+$.

Chiral HPLC: Rt: 6.604 min, ee: 100%

E107

30 mg, 30% yield $^1$H NMR (400 MHz, $CDCl_3$): δ 8.93 (s, 1H), 8.07 (s, 1H), 7.74 (s, 1H), 6.67 (br, 0.77H), 5.35 (br, 0.57H), 4.74 (s, 1H), 4.02~3.96 (m, 1H), 3.91 (s, 3H), 3.85~3.82 (m, 1H), 3.74~3.69 (m, 1H), 3.54~3.43 (m, 2H), 3.21~1.95 (m, 4H), 2.62 (s, 3H), 2.33~1.85 (m, 10H).

LC-MS [mobile phase: from 80% water (0.1% FA) and 20% ACN (0.1% FA) to 5% water (0.1% FA) and 95% ACN (0.1% FA) in 9.0 min]: Rt=3.58 min; MS Calcd: 494, MS Found: 495 $[M+H]^+$.

Chiral HPLC: Rt: 8.036 min, ee: 98.1%

Examples 108 and 109

(1R,4R)-5-(6-(5-chloro-6-(1-(tetrahydrofuran-3-yl)piperidin-4-yl)-1H-indazol-1-yl)-2-methylpyrimidin-4-yl)-2-oxa-5-azabicyclo[2.2.1]heptane

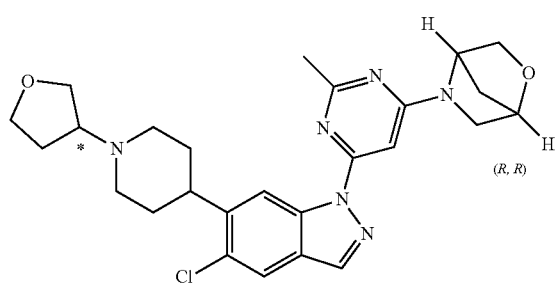

A mixture of 5-chloro-6-(1-(tetrahydrofuran-3-yl)piperidin-4-yl)-1H-indazole (200 mg, 0.66 mmol), (1R,4R)-5-(6-iodo-2-methylpyrimidin-4-yl)-2-oxa-5-azabicyclo[2.2.1]heptane (229 mg, 0.72 mmol), CuI (125 mg, 0.66 mmol), $K_3PO_4$ (280 mg, 1.32 mmol) and N,N'-dimethyl-cyclohexane-1,2-diamine (187 mg, 1.32 mmol) in toluene (3 mL) was stirred at 100° C. for 3 hours. The mixture was added EtOAc (80 mL), washed with $NH_3.H_2O$ (10%, 30×3 mL). The organic phases was dried over $Na_2SO_4$, filtered and concentrated. The crude was purified by flash chromatography (DCM/MeOH=15:1) to give the mixture compound (80 mg, 24%) as colorless oil.

LC-MS [column: $C_{18}$; column size: 4.6×50 mm; mobile phase: B (ACN) A (0.02% $NH_4OAc$); gradient (B %)]: Rt=2.491 min, MS Calcd.: 494, MS Found: 495 $[M+H]^+$.

The mixture (80 mg, 0.16 mmol) was separated by chiral-HPLC to afford isomer 1 (9 mg, 11%) and isomer 2 (30 mg, 37%).

Chiral pre-HPLC: column: Superchiral S-OD, 2 cm I.D.× 25 cm Length, 5 μm; Phase:

$CO_2$/MeOH/DEA=70/3010.05; 3.0 ml/min, 254 nm.

Example 108

$^1$H NMR (400 MHz, $CDCl_3$): δ 8.92 (s, 1H), 8.07 (s, 1H), 7.74 (s, 1H), 6.65 (br 1H), 5.33 (br 1H), 4.75 (s, 1H), 4.02-3.85 (m, 5H), 3.74-3.70 (m, 1H), 3.52 (br 2H), 3.21-2.96 (m, 4H), 2.62 (s, 3H), 2.33-2.22 (m, 2H), 2.16-1.76 (m, 8H).

Chiral-HPLC [column: Superchiral S-OD, 2 cm I.D.×25 cm Length, 5 μm; mobile phase: $CO_2$/MeOH/DEA=70/30/0.05; flow rate: 3.0 mL/min; 254 nm; T: 35° C.]: Rt=4.873 min.

LC-MS [column: $C_{18}$; column size: 4.6×50 mm; mobile phase: B (ACN) A (0.02% $NH_4OAc$); gradient (B %)]: Rt=3.961 min, MS Calcd.: 494, MS Found: 495 $[M+H]^+$.

Example 109

$^1$H NMR (400 MHz, $CDCl_3$): δ 8.92 (s, 1H), 8.07 (s, 1H), 7.74 (s, 1H), 6.65 (br 1H), 5.33 (br 1H), 4.75 (s, 1H), 4.15-3.81 (m, 5H), 3.74-3.70 (m, 1H), 3.52 (br 2H), 3.25-2.93 (m, 4H), 2.62 (s, 3H), 2.47-2.42 (m, 2H), 2.12-1.85 (m, 8H).

Chiral-HPLC [column: Superchiral S-OD, 2 cm I.D.×25 cm Length, 5 μm; mobile phase: $CO_2$/MeOH/DEA=70/30/0.05; flow rate: 3.0 mL/min; 254 nm; T: 35° C.]: Rt=5.001 min.

LC-MS [column: $C_{18}$; column size: 4.6×50 mm; mobile phase: B (ACN) A (0.02% $NH_4OAc$); gradient (B %)]: Rt=3.949 min, MS Calcd.: 494, MS Found: 495 $[M+H]^+$.

Example 110

(1S,4S)-2-(4-(1-(6-(2-oxa-5-azabicyclo[2.2.1]heptan-5-yl)-2-methylpyrimidin-4-yl)-5-chloro-1H-indazol-6-yl)piperidin-1-yl)ethanol

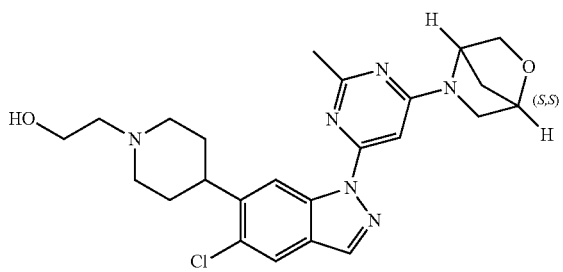

To a solution of (1S,4S)-ethyl 2-(4-(1-(6-(2-oxa-5-azabicyclo[2.2.1]heptan-5-yl)-2-methylpyrimidin-4-yl)-5-chloro-1H-indazol-6-yl)piperidin-1-yl)acetate (165 mg, 0.32 mmol) in dry THF (4 mL) was added LiAlH$_4$ (0.67 mL, 1.60 mmol, 2.4 M in THF) at 0° C. After stirring for 1 hour at 0° C., the reaction mixture was diluted with THF (60 mL), and quenched with H$_2$O (0.1 mL) followed by 15% aq.NaOH (0.1 mL), H$_2$O (0.3 mL). MgSO$_4$ was added to the mixture and stirred for 30 minutes. The mixture was filtered and the filtrate was concentrated. The residue was purified by prep-HPLC (watersgilson-1 X-bridge C$_{18}$ 5 μm 19×150 mm 25-70% B, A: H$_2$O (0.1% NH$_4$HCO$_3$), B: ACN, UV: 254 nm, Flowrate: 15 ml/min, GT: 12 mins) to give the title compound (45 mg, 30%) as a colorless oil.

$^1$H NMR (400 MHz, CDCl$_3$): δ 8.92 (s, 1H), 8.08 (s, 1H), 7.73 (s, 1H), 6.65 (s, 1H), 5.30 (br 1H), 4.75 (s, 1H), 3.93-3.88 (m, 2H), 3.69-3.67 (m, 2H), 3.53-3.44 (m, 2H), 3.16-3.11 (m, 3H), 2.64-2.62 (m, 5H), 2.33-2.28 (m, 2H), 2.05-1.96 (m, 4H), 1.88-1.78 (m, 2H).

LCMS [column: Phenomenex Kinetex 5 μm EVO, C18; column size: 4.6×50 mm; mobile phase: B (ACN): A (0.01% TFA); gradient (B %) in 6 mins]: Rt=3.147 min, MS Calcd.: 468, MS Found: 469 [M+H]$^+$.

Examples 111 and 112

3-trans-(1R,4R)-4-(1-(6-(2-oxa-5-azabicyclo[2.2.1]heptan-5-yl)-2-methoxypyrimidin-4-yl)-5-methyl-1H-indazol-6-yl)-1-(oxetan-3-yl)piperidin-3-ol
(Single Known Isomer 1, Single Known Isomer 2)

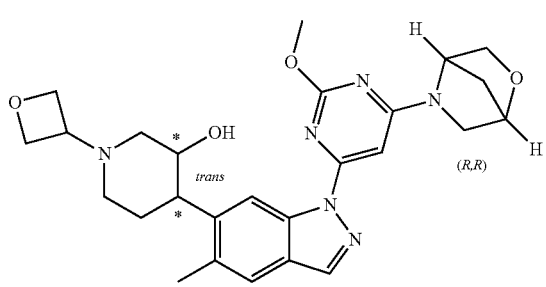

To a stirred mixture of 3-trans-(1R,4R)-4-(1-(6-(2-oxa-5-azabicyclo[2.2.1]heptan-5-yl)-2-methoxypyrimidin-4-yl)-5-methyl-1H-indazol-6-yl)piperidin-3-ol (180 mg, 0.41 mmol), oxetan-3-one (119 mg, 1.65 mmol) in MeOH/DCM (2 mL/5 mL) at were added AcOH solution (2 drops, from 1 drop HOAc in 1 mL DCM) and NaBH$_3$CN (52 mg, 0.82 mmol). The reaction was stirred at room temperature for 5 hours. The reaction mixture was diluted with DCM (30 mL), washed with aqueous NaHCO$_3$ (10 mL), dried over Na$_2$SO$_4$, concentrated. The residue was purified by Prep-TLC (DCM/MeOH=20/1) to give the mixture compound (58 mg, 29%) as a white solid.

LCMS [column: C$_{18}$, column size: 4.6×30 mm 5 μm; Dikwa Diamonsil plus; mobile phase: B (ACN): A1 (0.02% NH$_4$OAc+ 5% ACN); gradient (B %) in 4 min-05-95-POS; flow rate: 1.5 ml/min]: Rt=1.993 min; MS Calcd.: 492, MS Found: 493 [M+H]$^+$.

The mixture (55 mg) was separated by chiral-prep-HPLC to give isomer 1 (17 mg, 31%) as a white solid and isomer 2 (16 mg, 29%) as a white solid.

Chiral Pre-HPLC:

column: Superchiral S-AD; 2 cm I.D.×25 cm L, 5 μm; mobile phase: CO$_2$/IPA/DEA=60/40/0.05; flow rate: 30 mL/min, 254 nm, T: 35° C.

Example 111

$^1$H NMR (400 MHz, CDCl$_3$): δ 8.78 (s, 1H), 8.00 (s, 1H), 7.51 (s, 1H), 6.41 (b rs, 1H), 5.11 (s, 1H), 4.70~4.63 (m, 5H), 4.15~4.07 (m, 4H), 3.93~3.80 (m, 2H), 3.66~3.36 (m, 3H), 3.10~3.07 (m, 1H), 2.92~2.79 (m, 2H), 2.48 (s, 3H), 2.04~1.68 (m, 7H).

Chiral HPL [column: Superchiral S-AD; 0.46 cm I.D.×15 cm L, 5 μm; mobile phase: CO$_2$/IPA/DEA=60/40/0.05; flow rate: 3 mL/min, 254 nm, T: 35° C.]: Rt=4.809 min.

LC-MS [column: C$_{18}$; column size: 4.6×50 mm; mobile phase: B (ACN) A (0.02% NH$_4$OAc); gradient (B %) in 6 min-05-95-POS; flow rate: 1.5 ml/min]: Rt=3.259 min; MS Calcd.: 492, MS Found: 493 [M+H]$^+$.

Example 112

$^1$H NMR (400 MHz, CDCl$_3$): δ 8.82 (s, 1H), 8.05 (s, 1H), 7.54 (s, 1H), 6.51 (b rs, 1H), 5.26 (s, 1H), 4.74~4.62 (m, 5H), 4.16~4.06 (m, 4H), 3.94~3.88 (m, 2H), 3.64~3.45 (m, 3H), 3.11~3.08 (m, 1H), 2.92~2.80 (m, 2H), 2.48 (s, 3H), 2.00~1.88 (m, 5H), 1.81~1.71 (m, 2H).

Chiral HPL [column: Superchiral S-AD; 0.46 cm I.D.×15 cm L, 5 μm; mobile phase: CO$_2$/IPA/DEA=60/40/0.05; flow rate: 3 mL/min, 254 nm, T: 35° C.]: Rt=5.179 min.

LC-MS [column: C$_{18}$; column size: 4.6×50 mm; mobile phase: B (ACN) A (0.02% NH$_4$OAc); gradient (B %) in 6 min-05-95-POS; flow rate: 1.5 ml/min]: Rt=3.285 min; MS Calcd.: 492, MS Found: 493 [M+H]$^+$.

Example 113

(1R,4R)-2-(4-(1-(6-(2-oxa-5-azabicyclo[2.2.1]heptan-5-yl)-2-methoxypyrimidin-4-yl)-5-chloro-1H-indazol-6-yl)piperidin-1-yl)ethanol

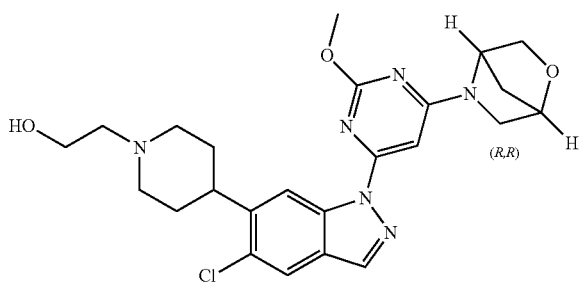

To a solution of (1R,4R)-ethyl 2-(4-(1-(6-(2-oxa-5-azabicyclo[2.2.1]heptan-5-yl)-2-methoxypyrimidin-4-yl)-5-chloro-1H-indazol-6-yl)piperidin-1-yl)acetate (43 mg, 0.08 mmol) in THF (3 mL) was added LiAlH$_4$ (0.17 mL, 0.41 mmol, 2.4 M in THF) at 0° C. After stirring for 1 hour at 0° C., the reaction was quenched with H$_2$O (4 drops) followed by 15% aq.NaOH (4 drops), H$_2$O (12 drops). The mixture was diluted with EtOAc and dried over Na$_2$SO$_4$. The mixture was stirred for 1 hour and filtered. The filtrate was concentrated. The residue was purified by prep-HPLC (Kinete EVO C18 SN H16-100024 phenomenex; waters-2 Kinete EVO C$_{18}$ 5 μm 21.2×150 mm 20-70% B, A: H$_2$O (0.1% NH$_4$HCO$_3$), B: CAN, UV: 254 nm, Flow rate 15 ml/min, 15 min-GT 10 mins) to give the title compound (22 mg, 56%) as a white solid.

$^1$HNMR (400 MHz, CDCl$_3$): δ 8.87 (s, 1H), 8.10 (s, 1H), 7.76 (s, 1H), 6.55 (s, 1H), 5.27 (s, 1H), 4.75 (s, 1H), 4.14 (s, 3H), 3.93-3.89 (m, 2H), 3.69-3.47 (m, 4H), 3.20-3.09 (m, 3H), 2.63 (t, J=5.2 Hz, 2H), 2.32 (t, J=12 Hz, 2H), 2.05-1.94 (m, 4H), 1.80 (q, J=12 Hz, 2H).

LCMS [column: Phenomenex Kinetex 5 μm EVO, C$_{18}$; column size: 4.6×50 mm; mobile phase: B (ACN): A (0.1% TFA); gradient (B %) in 6 mins]: Rt=2.819 min, MS Calcd.: 484, MS Found: 485 [M+H]$^+$.

Example 114

(1S,4S)-2-(4-(1-(6-(2-oxa-5-azabicyclo[2.2.1]heptan-5-yl)-2-methoxypyrimidin-4-yl)-5-chloro-1H-indazol-6-yl)piperidin-1-yl)ethanol

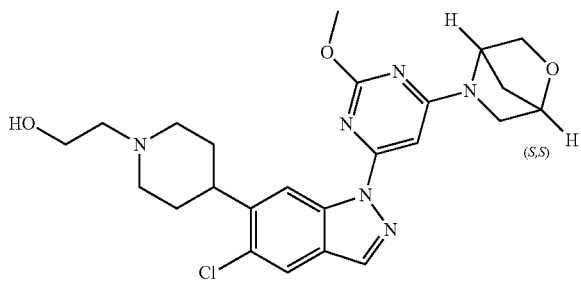

To a solution of (1S,4S)-ethyl 2-(4-(1-(6-(2-oxa-5-azabicyclo[2.2.1]heptan-5-yl)-2-methoxypyrimidin-4-yl)-5-chloro-1H-indazol-6-yl)piperidin-1-yl)acetate (181 mg, 0.34 mmol) in THF (5 mL) was added LiAlH$_4$ (0.72 mL, 1.72 mmol, 2.4 M in THF) at 0° C. After stirring for 1 hour at 0° C., the reaction was quenched with H$_2$O (2 mL) followed by 2 M aq.NaOH (2 mL), H$_2$O (6 mL) and Na$_2$SO$_4$ (300 mg). The mixture was filtered and the filtrate was concentrated. The residue was purified by flash chromatography column (DCM/MeOH=40/1) to give the title compound (97 mg, 59%) as a white solid.

$^1$HNMR (400 MHz, CDCl$_3$): δ 8.88 (s, 1H), 8.09 (s, 1H), 7.78 (s, 1H), 6.54 (br 1H), 5.26 (br 1H), 4.74 (s, 1H), 4.15 (s, 3H), 3.90 (dd, J=10.4, 8.0 Hz, 2H), 3.83-3.71 (m, 5H), 3.43 (d, J=12.0 Hz, 2H), 3.42-3.21 (m, 1H), 2.84 (t, J=13.2 Hz, 2H), 2.55 (t, J=11.6 Hz, 2H), 2.01-2.01 (m, 6H).

LCMS [column: Phenomenex Kinetex 5 μm EVO, C$_{18}$; column size: 4.6×50 mm; mobile phase: B (ACN): A (0.1% TFA); gradient (B %) in 6 mins]: Rt=2.928 min, MS Calcd.: 484, MS Found: 485 [M+H]$^+$.

Example 115

(1R,4R)-2-(4-(1-(6-(2-oxa-5-azabicyclo[2.2.1]heptan-5-yl)-2-methylpyrimidin-4-yl)-5-chloro-1H-indazol-6-yl)piperidin-1-yl)ethanol

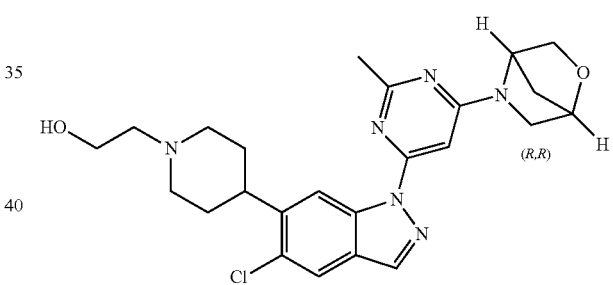

To a solution of (1R,4R)-ethyl 2-(4-(1-(6-(2-oxa-5-azabicyclo[2.2.1]heptan-5-yl)-2-methylpyrimidin-4-yl)-5-chloro-1H-indazol-6-yl)piperidin-1-yl)acetate (188 mg, 0.37 mmol) in THF (5 mL) was added LiAlH$_4$ (0.77 mL, 1.84 mmol, 2.4 M in THF) at 0° C. The mixture was stirred at 0° C. for 1 hour. The mixture was quenched with H$_2$O (8 drops) followed by 15% aq.NaOH (8 drops), H$_2$O (24 drops). The mixture was diluted with EtOAc and dried over Na$_2$SO$_4$. The mixture was stirred for 1 hour and filtered. The filtrate was concentrated. The residue was purified by triturated with MeOH (3 mL) and filtered. The filter cake was dried to give the title compound (110 mg, 63%) as a white solid.

$^1$HNMR (400 MHz, CDCl$_3$): δ 8.92 (s, 1H), 8.08 (s, 1H), 7.74 (s, 1H), 6.68 (br 1H), 5.34-5.29 (m, 1H), 4.75 (s, 1H), 3.93-3.89 (m, 2H), 3.69-3.43 (m, 4H), 3.17-3.10 (m, 3H), 2.64-2.59 (m, 5H), 2.31 (t, J=10.4 Hz, 2H), 2.05-1.94 (m, 4H), 1.92-1.79 (m, 2H).

LCMS [column: Phenomenex Kinetex 5 μm EVO, C$_{18}$; column size: 4.6×50 mm; mobile phase: B (ACN): A (0.1% TFA); gradient (B %) in 6 mins. Rt=2.286 min, MS Calcd.: 468, MS Found: 469 [M+H]$^+$.

Examples 116 and 117

(1R,4R)-5-(6-(5-chloro-6-(1-(tetrahydrofuran-3-yl)piperidin-4-yl)-1H-indazol-1-yl)-2-methoxypyrimidin-4-yl)-2-oxa-5-azabicyclo[2.2.1]heptane (Single Unknown Isomer 1 and Single Unknown Isomer 2)

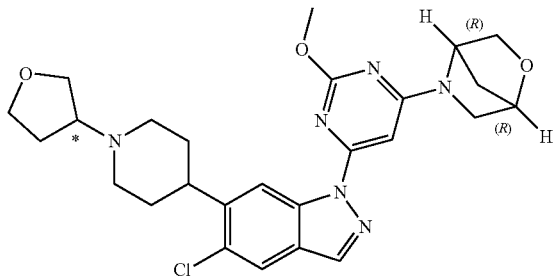

To a solution of 5-chloro-6-(1-(tetrahydrofuran-3-yl)piperidin-4-yl)-1H-indazole (200 mg, 0.65 mmol), (1R,4R)-5-(6-iodo-2-methoxypyrimidin-4-yl)-2-oxa-5-azabicyclo[2.2.1]heptane (240 mg, 0.72 mmol), CuI (125 mg, 0.65 mmol), $K_3PO_4$ (278 mg, 1.3 mmol) and N,N'-dimethylcyclohexane-1,2-diamine (186 mg, 1.3 mmol) in toluene (3 mL) and DMSO (1 mL) was stirred at 100° C. for 4 hours. The mixture was diluted with EtOAc (5 mL×2), washed with brine, dried over $Na_2SO_4$, filtered and concentrated. The crude was purified by prep-TLC (DCM/MeOH=10/1) to give the mixture compound (62 mg, 18%) as a white solid.

LCMS [column: $C_{18}$; column size: 2.1×50 mm; Waters ACQUITY UPLC BEH; mobile phase: B (ACN) A (0.02% $NH_4OAc$+ 5% ACN); flow rate: 0.5 ml/min; gradient (B %) in 3 mins]: Rt=1.91 min; MS Calcd.: 510, MS Found: 511 $[M+H]^+$.

The mixture (62 mg, 0.12 mmol) was separated by chiral-HPLC to afford isomer 1 (28 mg, 45%) and isomer 2 (28 mg, 45%).

Chiral pre-HPLC: column: Chiralpak ID; 5 μm 20×150 mm; Phase: $CO_2$:EtOH=50:50; 9 ml/min, 254 nm

E116 (Single Unknown Isomer 1)

Chiral-HPLC [column: chiral pak 1E, 5 μm 250 mm×4.6 mm; mobile phase: Hex:IPA=50:50; flow rate: 1 mL/min; 230 nm; T: 30° C.]: Rt=12.925 min.

Isomer 1 (28 mg, 45%) was purified by prep-HPLC (x-bridge $C_{18}$, 5 μm, 21.2×150 mm, 50-80% ACN—$H_2O$ (0.1% $NH_4HCO_3$), flow rate: 15 ml/min, GT7.5 mins.) to give isomer 1 (9 mg, 14%) as a yellow oil.

$^1$HNMR (400 MHz, $CD_3OD$): δ 8.84 (s, 1H), 8.20 (s, 1H), 7.85 (s, 1H), 6.59 (s, 1H), 4.75 (s, 1H), 4.10 (s, 3H), 3.99-3.67 (m, 7H), 3.59-3.57 (m, 1H), 3.23-3.17 (m, 3H), 3.09-2.96 (m, 2H), 2.36-2.29 (m, 2H), 2.18-2.14 (m, 1H), 2.01 (s, 4H), 1.93-1.78 (m, 3H).

Chiral-HPLC [column: chiral pak 1E, 5 μm 250 mm×4.6 mm; mobile phase: Hex:IPA=50:50; flow rate: 1 mL/min; 230 nm; T: 30° C.]: Rt=12.995 min.

LCMS [column: $C_{18}$; column size: 4.6×50 mm; mobile phase: B (ACN): A (0.02% $NH_4OAc$); gradient (B %) in 6 mins]: Rt=3.554 min, MS Calcd.: 510, MS Found: 511 $[M+H]^+$.

E117 (Single Unknown Isomer 2)

Chiral-HPLC [column: chiral pak 1E, 5 μm 250 mm×4.6 mm; mobile phase: Hex:IPA=50:50; flow rate: 1 mL/min; 230 nm; T: 30° C.]: Rt=16.121 min.

Isomer 2 (28 mg, 45%) was purified by prep-HPLC (x-bridge $C_{18}$, 5 μm, 19×150 mm, 40-75% ACN—$H_2O$ (0.1% $NH_4HCO_3$), flow rate: 15 ml/min, GT12 mins.) isomer 2 (10 mg, 16%) as a yellow oil.

$^1$HNMR (400 MHz, $CD_3OD$): δ 8.84 (s, 1H), 8.20 (s, 1H), 7.85 (s, 1H), 6.59 (s, 1H), 4.75 (s, 1H), 4.10 (s, 3H), 3.99-3.67 (m, 7H), 3.59-3.57 (m, 1H), 3.23-3.17 (m, 3H), 3.09-2.96 (m, 2H), 2.36-2.29 (m, 2H), 2.18-2.14 (m, 1H), 2.01 (s, 4H), 1.93-1.78 (m, 3H).

Chiral-HPLC [column: chiral pak IE, 5 μm 250 mm×4.6 mm; mobile phase: Hex:IPA=50:50; flow rate: 1 mL/min; 230 nm; T: 30° C.]: Rt=15.944 min.

LCMS [column: $C_{18}$; column size: 4.6×50 mm; mobile phase: B (ACN): A (0.02% $NH_4OAc$); gradient (B %) in 6 mins]: Rt=4.071 min; MS Calcd.: 510, MS Found: 511 $[M+H]^+$.

Example 118

9-(2-methoxy-6-(5-methyl-6-(1-(oxetan-3-yl)piperidin-4-yl)-1H-indazol-1-yl)pyrimidin-4-yl)-3,7-dioxa-9-azabicyclo[3.3.1]nonane

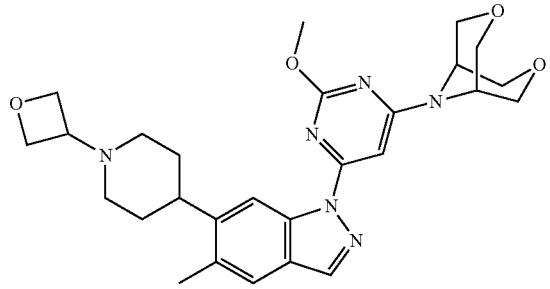 [SMILES: COc1nc(N2C3COCC2COC3)cc(-n2ncc3cc(C)c(C4CCN(C5COC5)CC4)cc32)n1]

To a mixture of 9-(2-methoxy-6-(5-methyl-6-(piperidin-4-yl)-1H-indazol-1-yl)pyrimidin-4-yl)-3,7-dioxa-9-azabicyclo[3.3.1]nonane (32 mg, 0.07 mmol), oxetan-3-one (26 mg, 0.35 mmol), Na(CN)BH$_3$ (9 mg, 0.14 mmol) in DCM (2 mL), was added catalyst AcOH. After stirring at room temperature overnight, the mixture was concentrated. The crude was purified by prep-HPLC (x-bridge $C_{18}$, 5 μm, 19×150 mm, 15-80% ACN—$H_2O$ (0.1% $NH_4HCO_3$), flow rate: 15 ml/min, GT 7 mins.) to give compound (8 mg, 22%) as white solid.

$^1$H NMR (400 MHz, $CDCl_3$): δ 8.76 (s, 1H), 8.06 (s, 1H), 7.51 (s, 1H), 6.78 (s, 1H), 4.82 (br 1H), 4.68 (d, J=6.4 Hz, 4H), 4.16 (s, 3H), 4.15-4.13 (m, 4H), 4.00-3.95 (m, 4H), 3.82 (br 1H), 3.57-3.53 (m, 1H), 2.93 (d, J=10.8 Hz, 2H), 2.85-2.83 (m, 1H), 2.46 (s, 3H), 2.02 (d, J=12.0 Hz, 2H), 1.95-1.88 (m, 4H).

LC-MS: Phenomenex Kinetex 5 μm EVO $C_{18}$, 50×4.6 mm; mobile phase: B (ACN): A (0.02% $NH_4OAc$); gradient (B %) in 6 min]: Rt=4.217 min; MS Calcd.: 506, MS Found: 507 $[M+H]^+$.

Example 119

8-(2-methoxy-6-(5-methyl-6-(1-(oxetan-3-yl)piperidin-4-yl)-1H-indazol-1-yl)pyrimidin-4-yl)-3-oxa-8-azabicyclo[3.2.1]octane

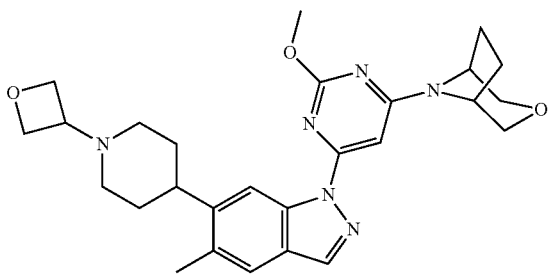 [SMILES: COc1nc(N2C3CCC2COC3)cc(-n2ncc3cc(C)c(C4CCN(C5COC5)CC4)cc32)n1]

To a solution of 8-(2-methoxy-6-(5-methyl-6-(piperidin-4-yl)-1H-indazol-1-yl)pyrimidin-4-yl)-3-oxa-8-azabicyclo[3.2.1]octane (230 mg, 0.53 mmol), oxetan-3-one (191 mg, 2.65 mmol) and NaBH₃CN (67 mg, 1.06 mmol) in DCM (10 mL) was added AcOH (1 drop). The mixture was stirred at room temperature for 18 hours. The mixture was concentrated. The residue was dissolved in 50 mL of EtOAc, washed with 25 mL of H₂O. The organic layer was dried over Na₂SO₄, filtered and concentrated. purified by prep-HPLC: (Kinete EVO C$_{18}$ SN H16-100024 phenomenex; gilson-2 Kinete EVO C$_{18}$ 5 μm 21.2×150 mm 4 5-95% B, A: H₂O (0.1% NH₄HCO₃), B: ACN, UV: 214 nm, flowrate 20 ml/min, GT 12 mins) to give the title compound (50 mg, 19%) as a yellow oil.

¹HNMR (400 MHz, CDCl₃): δ 8.78 (s, 1H), 8.07 (s, 1H), 7.51 (s, 1H), 6.73 (s, 1H), 4.80-4.73 (m, 1H), 4.70 (d, J=6.8 Hz, 4H), 4.65-4.50 (m, 1H), 4.16 (s, 3H), 3.84-3.82 (m, 2H), 3.65-3.62 (m, 2H), 3.56 (t, J=7.2 Hz, 1H), 2.95-2.92 (m, 2H), 2.85 (t, J=7.2 Hz, 1H), 2.46 (s, 3H), 2.16-2.11 (m, 2H), 2.08-1.99 (m, 4H), 1.97-1.86 (m, 4H).

LC-MS [Phenomenex Kinetex 5 μm EVO C$_{18}$, 50×4.6 mm; mobile phase: B (ACN): A (0.02% NH₄OAc); gradient (B %) in 6 min]: Rt=4.309 min; MS Calcd.: 490, MS Found: 491 [M+H]⁺.

Examples 120 and 121

Cis-(1R,4R)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1]heptane (from Peak 1) (Single Unknown Enantiomer 1, Rt=2.246 min; Single Unknown Enantiomer 2, Rt=3.058 min)

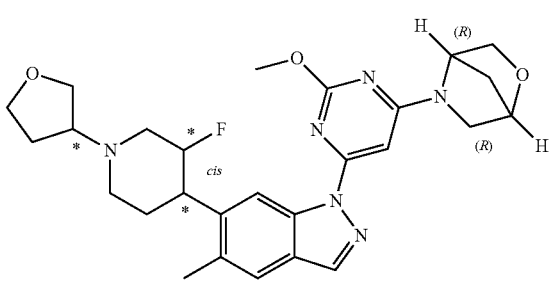

To a suspension of cis-6-(3-fluoro-1-(tetrahydrofuran-3-yl)piperidin-4-yl)-5-methyl-1H-indazole (from Peak 1, 100 mg, 0.33 mmol), (1R,4R)-5-(6-iodo-2-methoxypyrimidin-4-yl)-2-oxa-5-azabicyclo[2.2.1]heptane (120 mg, 0.36 mmol), CuI (63 mg, 0.33 mmol) and K₃PO₄ (140 mg, 0.66 mmol) in toluene (10 mL) and THF (2 mL) was added N₁,N₂-dimethylethane-1,2-diamine (58 mg, 0.66 mmol). The resulting mixture was degassed with N₂ three times. The mixture was warmed at 80° C. for 2 h under N₂. EtOAc (20 mL) was added and the resulting mixture was washed with sat. NH₄Cl (20 mL) and brine (20 mL), dried over anhydrous Na₂SO₄ and concentrated. The residue was purified by prep-TLC (CH₂Cl₂: EtOAc=1:1) to give the product (145 mg, yield: 86%) as a white solid.

LC-MS [mobile phase: from 70% water (0.1% FA) and 30% ACN (0.1% FA) to 5% water (0.1% FA) and 95% ACN (0.1% FA) in 2.0 min]: Rt=1.13 min; MS Calcd: 508, MS Found: 509 [M+H]⁺.

The compound cis-(1R,4R)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1]heptane (from peak 1, 140 mg, 0.28 mmol) was purified by chiral prep-HPLC (AD-H, 0.46 cm I.D.×15 cm L, Mobile phase: CO₂:EtOH (0.1% DEA)=60:40, Flow rate: 0.5 mL/min, Wave length: UV 254 nm, Temperature: 25° C.) to give the mixture product as two white solids.

E120 (from Peak 1) (Single Unknown Enantiomer 1, Rt=2.246 min)

(64 mg, yield: 46%).

¹H NMR (400 MHz, CDCl₃): δ 8.87 (s, 1H), 8.08 (s, 1H), 7.54 (s, 1H), 6.55 (br, 0.5H), 5.26 (br, 0.5H), 4.91~4.74 (m, 1H), 4.74 (s, 1H), 4.13 (s, 3H), 3.99~3.72 (m, 6H), 3.56~3.46 (m, 2H), 3.25~3.02 (m, 4H), 2.48 (s, 3H), 2.32~2.06 (m, 3H), 1.96~1.86 (m, 6H).

¹⁹F NMR (376 MHz, CDCl₃): δ −183.33.

LC-MS [mobile phase: from 90% water (0.1% FA) and 10% ACN (0.1% FA) to 5% water (0.1% FA) and 95% ACN (0.1% FA) in 9 min]: Rt=3.78 min; MS Calcd: 508, MS Found: 509[M+H]⁺.

Chiral HPLC [AD-H 4.6×250 mm, 5 μm (Daicel) (CA-HPLC-023), Phase: Hexane/EtOH (0.2% DEA)=60/40, flow rate: 0.5 mL/min, temperature: 35° C.]: Rt: 2.246 min, ee: 100%

E121 (from Peak 1) (Single Unknown Enantiomer 2, Rt=3.058 min)

(69 mg, yield: 49%)

¹H NMR (400 MHz, CDCl₃): δ 8.87 (s, 1H), 8.08 (s, 1H), 7.54 (s, 1H), 6.54 (br, 0.5H), 5.25 (br, 0.5H), 4.92~4.86 (m, 0.5H), 4.80~4.74 (m, 0.5H), 4.74 (s, 1H), 4.12 (s, 3H), 4.02~3.96 (m, 1H), 3.93~3.88 (m, 3H), 3.85~3.78 (m, 1H), 3.71~3.66 (m, 1H), 3.55~3.42 (m, 3H), 3.19~3.05 (m, 2H), 2.83 (d, J=10.8 Hz, 1H), 2.48 (s, 3H), 2.29~2.19 (m, 2H), 2.14~2.05 (m, 1H), 2.00~1.76 (m, 6H).

¹⁹F NMR (376 MHz, CDCl₃): δ −183.22.

LC-MS [mobile phase: from 90% water (0.1% FA) and 10% ACN (0.1% FA) to 5% water (0.1% FA) and 95% ACN (0.1% FA) in 9 min]: Rt=3.25 min; MS Calcd: 508, MS Found: 509 [M+H]⁺.

Chiral HPLC [AD-H 4.6×250 mm, 5 μm (Daicel) (CA-HPLC-023), Phase:

Hexane/EtOH (0.2% DEA)=60/40, flow rate: 0.5 mL/min, temperature: 35° C.]: Rt: 3.058 min, ee: 99.80%

Examples 122 and 123

Cis-(1R,4R)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1]heptane (from Peak 2) (Single Unknown Enantiomer 1, Rt=1.563 min; Single Unknown Enantiomer 2, Rt=2.418 min)

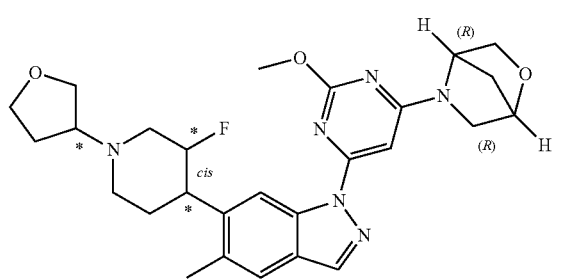

The mixture of cis-6-(3-fluoro-1-(tetrahydrofuran-3-yl)piperidin-4-yl)-5-methyl-1H-indazole (100 mg, 0.33 mmol) and (1R,4R)-5-(6-iodo-2-methoxypyrimidin-4-yl)-2-oxa-5-azabicyclo[2.2.1]heptane (110 mg, 0.33 mmol), CuI (30 mg), K₃PO₄ (212 mg, 1.0 mmol) in toluene (20 ml) was degassed before N,N'-dimethylethylenediamine (30 mg) was added. The reaction mixture was stirred at 90° C. for 1 h. The reaction mixture was concentrated. The residue was purified by silica gel chromatography eluted with EtOAc/PE=1/3 to give a crude product as a white solid which was further purified by prep-TLC (EtOAc/PE=1/2) to give the desired product as a white solid (80 mg, yield: 48%).

LC-MS [mobile phase: from 80% water (0.1% FA) and 20% ACN (0.1% FA) to 5% water (0.1% FA) and 95% ACN (0.1% FA) in 2.0 min]: purity 98%, Rt=1.22 min; MS Calcd: 508, MS Found: 509 [M+H]⁺.

The mixture (80 mg) was purified by prep-HPLC (Method: Column: AD-H; Column size: 0.46 cm I.D.×15 cm L; Injection: 2 μl; Mobile phase: CO₂:IPA (0.1% NH₃.H₂O) =60:40; Flow rate: 0.5 mL/min; Wave length: UV 254 nm; Temperature: 25° C.; Sample solution in EtOH) afforded two white solids:

Example 122

White solid (Rt=1.563 min, 20.7 mg, 26% yield)

$^1$H NMR (400 MHz, CDCl3) δ 8.87 (s, 1H), 8.08 (s, 1H), 7.54 (s, 1H), 6.55 (br, 0.87H), 5.26 (br, 0.68H), 4.91~4.77 (m, 1H), 4.74 (s, 1H), 4.12 (s, 3H), 4.00~3.98 (m, 1H), 3.94~3.89 (m, 3H), 3.83~3.80 (m, 1H), 3.71~3.66 (m, 1H), 3.55~3.42 (m, 3H), 3.18~3.14 (m, 2H), 2.83~2.80 (m, 1H), 2.48 (s, 3H), 2.27~2.23 (m, 2H), 2.14~2.07 (m, 1H), 1.99~1.74 (m, 5H).

19F NMR (376 MHz, CDCl3) δ −183.22 (s, 1F),

LC-MS [mobile phase: from 90% water (0.1% FA) and 10% ACN (0.1% FA) to 5% water (0.1% FA) and 95% ACN (0.1% FA) in 2.0 min]: Rt=1.27 min; MS Calcd: 508, MS Found: 509 [M+H]⁺.

Chiral HPLC: 1.563 min, ee 100%;

Example 123

White solid (Rt=2.418 min, 23.0 mg, 29% yield)

$^1$H NMR (400 MHz, CDCl₃) δ 8.87 (s, 1H), 8.08 (s, 1H), 7.54 (s, 1H), 6.55 (br, 0.97H), 5.26 (br, 0.67H), 4.89~4.74 (m, 1H), 4.74 (s, 1H), 4.14 (s, 3H), 4.00~3.46 (m, 9H), 3.25~3.01 (m, 5H), 2.48 (s, 3H), 2.31~1.74 (m, 6H).

$^{19}$F NMR (376 MHz, CDCl₃) δ −183.33 (s, 1F), LC-MS [mobile phase: from 90% water (0.1% FA) and 10% ACN (0.1% FA) to 5% water (0.1% FA) and 95% ACN (0.1% FA) in 2.0 min]: Purity: 100% @ 254 nm; Rt=1.27 min; MS Calcd: 508, MS Found: 509 [M+H]⁺.

Chiral HPLC: Rt: 2.418 min, ee 99.3%;

Examples 124 and 125

(1S,4S)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1]heptane (from Peak 1)

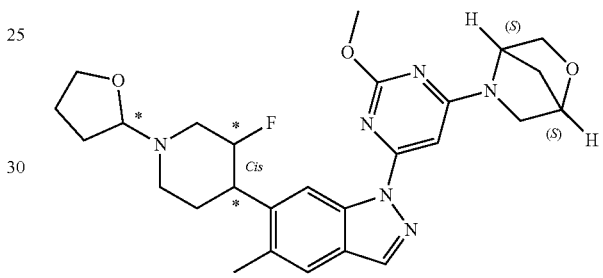

The mixture of Cis-4-(6-(6-(3-fluoro-1-(tetrahydrofuran-3-yl)piperidin-4-yl)-5-methyl-1H-indazol-1-yl)-2-methoxy-pyrimidin-4-yl)morpholine (from Peak 1, 100 mg, 0.33 mmol), (1S,4S)-5-(6-iodo-2-methoxypyrimidin-4-yl)-2-oxa-5-azabicyclo[2.2.1]heptane (117 mg, 0.36 mmol), CuI (63 mg, 0.33 mmol), K₃PO₄ (140 mg, 0.66 mmol) in toluene/THF (8 mL/3 mL) was degassed before DMEDA (38 mg, 0.43 mmol) was added. The resulting mixture was degassed with N₂ three times. The reaction was then stirred at 80° C. for 2 hour. EtOAc (60 mL) was added and the resulting mixture was washed with sat. NH₄Cl (20 mL) and brine (20 mL). The organic solution was dried over anhydrous Na₂SO₄ and concentrated. The residue was purified by chromatography (PE:EtOAc:CH₂Cl₂=1:1:1) to give the product as a white solid (140 mg, yield: 87%).

LC-MS [mobile phase: from 50% water (0.1% NH₄OH) and 50% ACN (0.1% NH₄OH) to 5% water (0.1% NH₄OH) and 95% ACN (0.1% NH₄OH) in 2.0 min]: Rt=1.29 min; MS Calcd.: 508, MS Found: 509 [M+H]⁺.

Cis-(1S,4S)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1]heptane (from Peak 1) (140 mg) was purified by chiral prep-HPLC (AD-H, 0.46 cm I.D.×15 cm L, Mobile phase: CO₂:EtOH (0.1% NH₃.H₂O) =60:40, Flow rate: 0.5 mL/min, 254 nm, Temperature: 25° C.) to give product as two white solids.

Example 124 Peak 1: (34 mg, Yield 23%)

$^1$H NMR (400 MHz, CDCl₃): δ 8.86 (s, 1H), 8.07 (s, 1H), 7.53 (s, 1H), 6.56 (br, 1H), 5.26 (br, 0.5H), 4.86~4.74 (m, 1H), 4.73 (s, 1H), 4.12 (s, 3H), 3.98 (br, 1H), 3.91~3.90 (m,

3H), 3.89~3.80 (m, 1H), 3.72 (br, 1H), 3.55~3.50 (m, 2H), 3.23~3.00 (m, 4H), 2.48 (s, 3H), 2.31 (br, 1H), 2.21~2.20 (m, 1H), 1.99~1.83 (m, 6H).

$^{19}$F NMR (376.5 MHz, CDCl$_3$): δ −183.3

LC-MS [mobile phase: 95% water (0.1% FA) and 5% ACN (0.1% FA) to 5% water (0.1% FA) and 95% ACN (0.1% FA) in 10.0 min]: Rt=4.84 min; MS Calcd.: 508, MS Found: 509 [M+H]$^+$.

Chiral HPLC: Rt: 10.349 min, ee: 100%

Chiral method: Column: AD Column size: 0.46 cm I.D.× 15 cm L. Injection: 2 μl Mobile phase: HEP: EtOH (0.1% DEA)=60:40, Flow rate: 0.5 mL/min, Wave length: UV 254 nm, Temperature: 25° C., Rt: 10.349 min, ee: 100%

Example 125

Peak 2: (30 mg, yield 22%).

$^1$H NMR (400 MHz, CDCl$_3$): δ 8.86 (s, 1H), 8.07 (s, 1H), 7.53 (s, 1H), 6.54 (br, 1H), 5.25 (br, 0.5H), 4.90~4.74 (m, 1H), 4.73 (s, 1H), 4.12 (s, 3H), 3.99~3.98 (m, 1H), 3.94~3.88 (m, 3H), 3.83~3.80 (m, 1H), 3.70~3.67 (m, 1H), 3.55~3.42 (m, 3H), 3.23~3.00 (m, 2H), 2.82~2.80 (m, 1H), 2.48 (s, 3H), 2.26~2.23 (m, 2H), 2.10~1.82 (m, 6H).

$^{19}$F NMR (376.5 MHz, CDCl$_3$): δ −183.21 (s)

LC-MS [mobile phase: 95% water (0.1% FA) and 5% ACN (0.1% FA) to 5% water (0.1% FA) and 95% ACN (0.1% FA) in 10.0 min]: Rt=4.81 min; MS Calcd.: 508, MS Found: 509 [M+H]$^+$.

Chiral HPLC: Rt: 15.150 min, ee: 100%

Chiral method: Column: AD Column size: 0.46 cm I.D.× 15 cm L. Injection: 2 μl Mobile phase: HEP: EtOH (0.1% DEA)=60:40, Flow rate: 0.5 mL/min, Wave length: UV 254 nm, Temperature: 25° C., Rt: 15.150 min, ee: 100%

Examples 126 and 127

Cis-(1S,4S)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1] heptane (from Peak 2) (Single Unknown Enantiomer 1, Rt=1.568 min; Single Unknown Enantiomer 2, Rt=2.174 min)

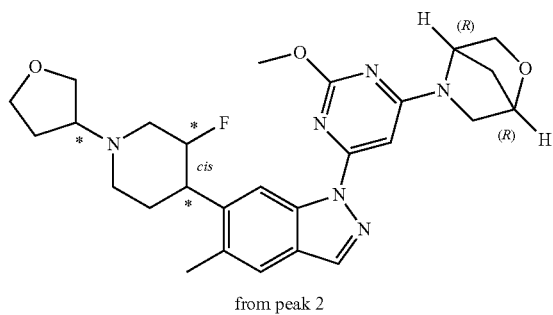

from peak 2

The mixture of cis-6-(3-fluoro-1-(tetrahydrofuran-3-yl) piperidin-4-yl)-5-methyl-1H-indazole (100 mg, 0.33 mmol) and (1S,4S)-5-(6-iodo-2-methoxypyrimidin-4-yl)-2-oxa-5-azabicyclo[2.2.1]heptane (110 mg, 0.33 mmol), CuI (30 mg), K$_3$PO$_4$ (212 mg, 1.0 mmol) in toluene (20 ml) was degassed before N,N'-dimethylethylenediamine (30 mg) was added. The reaction mixture was stirred at 90° C. for 1 h. The reaction mixture was concentrated. The residue was purified by silica gel chromatography eluted with EtOAc/ PE=1/3 to give a crude product as a white solid which was further purified by prep-TLC (EtOAc/PE=1/2) to give the mixture product as a white solid (75 mg, yield: 45%).

LC-MS [mobile phase: from 80% water (0.1% FA) and 20% ACN (0.1% FA) to 5% water (0.1% FA) and 95% ACN (0.1% FA) in 2.0 min]: purity 82%, Rt=1.23 min; MS Calcd: 508, MS Found: 509 [M+H]$^+$.

The mixture cis-(1S,4S)-5-(6-(6-(3-fluoro-1-(tetrahydrofuran-3-yl)piperidin-4-yl)-5-methyl-1H-indazol-1-yl)-2-methoxypyrimidin-4-yl)-2-oxa-5-azabicyclo[2.2.1]heptane (80 mg) was purified by chiral prep-HPLC (Method: Column: AD-H; Column size: 0.46 cm I.D.×15 cm L;

Injection: 2 μl; Mobile phase: CO$_2$:IPA (0.1% NH$_3$H$_2$O) =60:40; Flow rate: 0.5 mL/min; Wave length: UV 254 nm; Temperature: 25° C.; Sample solution in EtOH) to afford two white solids Example 126

White solid (Rt=1.568 min, 30.1 mg, 41% yield)

$^1$H NMR (400 MHz, CDCl$_3$) δ 8.87 (s, 1H), 8.08 (s, 1H), 7.54 (s, 1H), 6.55 (br, 0.80H), 5.26 (br, 0.47H), 4.91~4.77 (m, 1H), 4.74 (s, 1H), 4.12 (s, 3H), 4.00~3.98 (m, 1H), 3.94~3.89 (m, 3H), 3.83~3.80 (m, 1H), 3.71~3.66 (m, 1H), 3.55~3.42 (m, 3H), 3.18~3.14 (m, 2H), 2.83~2.80 (m, 1H), 2.48 (s, 3H), 2.27~2.23 (m, 2H), 2.14~2.07 (m, 1H), 1.99~1.74 (m, 5H).

$^{19}$F NMR (376 MHz, CDCl$_3$) δ −183.21 (s, 1F),

LC-MS [mobile phase: from 95% water (0.1% FA) and 5% ACN (0.1% FA) to 5% water (0.1% FA) and 95% ACN (0.1% FA) in 9.0 min]: Rt=4.97 min; MS Calcd: 508, MS Found: 509 [M+H]$^+$.

Chiral HPLC: Rt: 1.568 min, ee 100%;

Example 127

White solid (Rt=2.174 min, 25.6 mg, 34% yield)

$^1$H NMR (400 MHz, CDCl$_3$) δ 8.87 (s, 1H), 8.08 (s, 1H), 7.54 (s, 1H), 6.55 (br, 0.70H), 5.27 (br, 0.35H), 4.89~4.77 (m, 1H), 4.74 (s, 1H), 4.14 (s, 3H), 4.04~3.99 (m, 1H), 3.92~3.89 (m, 4H), 3.83~3.70 (m, 3H), 3.56~3.46 (m, 3H), 3.25~3.02 (m, 3H), 2.48 (s, 3H), 2.33~1.56 (m, 6H).

$^{19}$F NMR (376 MHz, CDCl$_3$) δ −183.33 (s, 1F),

LC-MS [mobile phase: from 95% water (0.1% FA) and 5% ACN (0.1% FA) to 5% water (0.1% FA) and 95% ACN (0.1% FA) in 9.0 min]: Rt=4.95 min; MS Calcd: 508, MS Found: 509 [M+H]$^+$.

Chiral HPLC: Rt: 2.174 min, ee 100%;

Examples 128 and 129

Cis-(1R,4R)-5-(6-(6-(3-fluoro-1-(tetrahydrofuran-3-yl)piperidin-4-yl)-5-methyl-1H-indazol-1-yl)-2-methylpyrimidin-4-yl)-2-oxa-5-azabicyclo[2.2.1]heptane (from peak 1) (Single Unknown Enantiomer 1, Rt=7.568 min; Single Unknown Enantiomer 2, Rt=8.695 min)

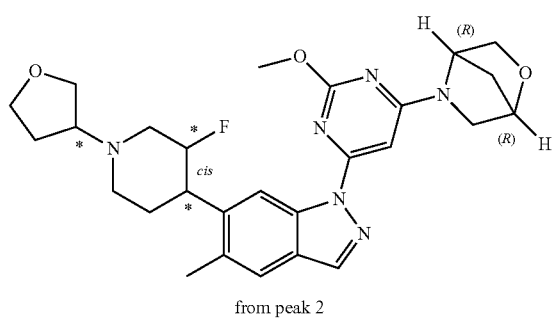

from peak 2

To a suspension of cis-6-(3-fluoro-1-(tetrahydrofuran-3-yl)piperidin-4-yl)-5-methyl-1H-indazole (from Peak 1, 100 mg, 0.33 mmol), (1R,4R)-5-(6-iodo-2-methylpyrimidin-4-yl)-2-oxa-5-azabicyclo[2.2.1]heptane (115 mg, 0.36 mmol), CuI (63 mg, 0.33 mmol) and $K_3PO_4$ (140 mg, 0.66 mmol) in toluene (10 mL) and THF (2 mL) was added $N_1,N_2$-dimethylethane-1,2-diamine (58 mg, 0.66 mmol). The resulting mixture was degassed with $N_2$ three times. The mixture was warmed at 80° C. for 2 h under $N_2$. EtOAc (20 mL) was added and the resulting mixture was washed with sat. NH4Cl (20 mL) and brine (20 mL), dried over anhydrous $Na_2SO_4$ and concentrated. The residue was purified by prep-HPLC (Gilson 281, YMC-Actus Triart Prep C18-S 250×20 mm 10 μm, Mobile phase: MeCN/$H_2O$ (0.05% TFA): from 15/85 to 95/5, Flow rate: 20 ml/min, 254 nm) to give the product as a white solid (145 mg, yield: 89%).

LC-MS [mobile phase: from 70% water (0.1% FA) and 30% ACN (0.1% FA) to 5% water (0.1% FA) and 95% ACN (0.1% FA) in 2.0 min]: Rt=1.13 min; MS Calcd: 492, MS Found: 493 [M+H]$^+$.

The compound cis-(1R,4R)-5-(6-(6-(3-fluoro-1-(tetrahydrofuran-3-yl)piperidin-4-yl)-5-methyl-1H-indazol-1-yl)-2-methylpyrimidin-4-yl)-2-oxa-5-azabicyclo[2.2.1]heptane (from peak 1, 140 mg, 0.28 mmol) was purified by chiral prep-HPLC (OZ-H, 0.46 cm I.D.×15 cm L, Mobile phase: $CO_2$:EtOH (0.1% $NH_3.H_2O$)=60:40, Flow rate: 0.5 mL/min, Wave length: UV 254 nm, Temperature: 25° C.) to give product as two white solids.

Example 128 (from peak 1) (Single Unknown Enantiomer 1, Rt=7.568 min)

(53 mg, yield: 38%)

$^1$H NMR (400 MHz, CDCl$_3$): δ 8.90 (s, 1H), 8.06 (s, 1H), 7.53 (s, 1H), 6.68 (br, 0.8H), 5.28 (br, 0.2H), 4.98~4.90 (m, 0.5H), 4.86~4.79 (m, 0.5H), 4.74 (s, 1H), 4.03~3.71 (m, 6H), 3.53~3.46 (m, 3H), 3.19~3.09 (m, 2H), 2.87 (d, J=9.2 Hz, 1H), 2.63 (s, 3H), 2.48 (s, 3H), 2.31~2.21 (m, 2H), 2.13~2.09 (m, 1H), 1.98~1.86 (m, 5H).

$^{19}$F NMR (376 MHz, CDCl$_3$): δ −183.16.

LC-MS [mobile phase: from 90% water (0.1% FA) and 10% ACN (0.1% FA) to 5% water (0.1% FA) and 95% ACN (0.1% FA) in 9 min]: purity 100%, Rt=3.26 min; MS Calcd: 492, MS Found: 493 [M+H]$^+$.

Chiral HPLC: OZ-H 4.6×250 mm, 5 μm (Daicel) (CA-HPLC-023), Phase: Hexane/EtOH (0.2% DEA)=60/40, flow rate: 0.5 mL/min, temperature: 35° C., Rt: 7.568 min, ee: 100%

Example 129 (from peak 1) (Single Unknown Enantiomer 1, Rt=8.695 min)

(44 mg, yield: 31%).

$^1$H NMR (400 MHz, CDCl$_3$): δ 8.90 (s, 1H), 8.06 (s, 1H), 7.53 (s, 1H), 6.68 (br, 0.8H), 5.30 (br, 0.2H), 4.96~4.91 (m, 0.5H), 4.84~4.78 (m, 0.5H), 4.74 (s, 1H), 4.03~3.73 (m, 6H), 3.53~3.44 (m, 2H), 3.29~3.04 (m, 4H), 2.63 (s, 3H), 2.48 (s, 3H), 2.36~2.28 (m, 1H), 2.25~2.19 (m, 1H), 2.11~2.06 (m, 1H), 1.98~1.81 (m, 5H).

$^{19}$F NMR (376 MHz, CDCl$_3$): δ −183.27.

LC-MS [mobile phase: from 90% water (0.1% FA) and 10% ACN (0.1% FA) to 5% water (0.1% FA) and 95% ACN (0.1% FA) in 9 min]: Rt=3.25 min; MS Calcd: 492, MS Found: 493 [M+H]$^+$.

Chiral HPLC [OZ-H 4.6×250 mm, 5 μm (Daicel) (CA-HPLC-023), Phase: Hexane/EtOH (0.2% DEA)=60/40, flow rate: 0.5 mL/min, temperature: 35° C.]: Rt: 8.695 min, ee: 99.78%

Examples 130 and 131

Cis-(1S,4S)-5-(6-(6-(3-fluoro-1-(tetrahydrofuran-3-yl)piperidin-4-yl)-5-methyl-1H-indazol-1-yl)-2-methylpyrimidin-4-yl)-2-oxa-5-azabicyclo[2.2.1]heptane (from peak 1) (Single Unknown Enantiomer 1, Rt=7.955 min; Single Unknown Enantiomer 2, Rt=9.311 min)

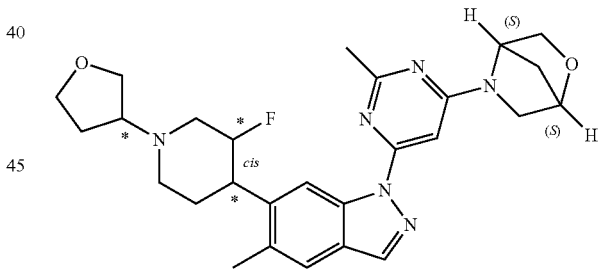

To a suspension of cis-6-(3-fluoro-1-(tetrahydrofuran-3-yl)piperidin-4-yl)-5-methyl-1H-indazole (from Peak 1, 100 mg, 0.33 mmol), (1S,4S)-5-(6-iodo-2-methylpyrimidin-4-yl)-2-oxa-5-azabicyclo[2.2.1]heptane (115 mg, 0.36 mmol), CuI (63 mg, 0.33 mmol) and $K_3PO_4$ (140 mg, 0.66 mmol) in toluene (10 mL) and THF (2 mL) was added $N_1,N_2$-dimethylethane-1,2-diamine (58 mg, 0.66 mmol). The resulting mixture was degassed with $N_2$ three times. The mixture was warmed at 80° C. for 2 h under $N_2$. EtOAc (20 mL) was added and the resulting mixture was washed with sat. NH$_4$Cl (20 mL) and brine (20 mL), dried over anhydrous $Na_2SO_4$ and concentrated. The residue was purified by prep-HPLC (Gilson 281, YMC-Actus Triart Prep C18-S 250×20 mm 10 μm, Mobile phase: MeCN/$H_2O$ (0.05% TFA): from 15/85 to 95/5, Flow rate: 20 ml/min, Wave length: 254 nm) to give the product as a white solid (142 mg, yield: 87%).

LC-MS [mobile phase: from 70% water (0.1% FA) and 30% ACN (0.1% FA) to 5% water (0.1% FA) and 95% ACN (0.1% FA) in 2.0 min]: Rt=1.13 min; MS Calcd: 492, MS Found: 493[M+H]$^+$.

The compound Cis-(1S,4S)-5-(6-(6-(3-fluoro-1-(tetrahydrofuran-3-yl)piperidin-4-yl)-5-methyl-1H-indazol-1-yl)-2-methylpyrimidin-4-yl)-2-oxa-5-azabicyclo[2.2.1]heptane (from peak 1) (from Peak 1, 140 mg, 0.28 mmol) was purified by chiral prep-HPLC (OZ-H, 0.46 cm I.D.×15 cm L, Mobile phase: CO$_2$:EtOH (0.1% NH$_3$.H$_2$O)=60:40, Flow rate: 0.5 mL/min, Wave length: UV 254 nm, Temperature: 25° C.) to give product as two white solids.

E130 (Single Unknown Enantiomer 1, Rt=7.955 min) (57 mg, yield: 41).

$^1$H NMR (400 MHz, CDCl$_3$): δ 8.89 (s, 1H), 8.06 (s, 1H), 7.53 (s, 1H), 6.68 (br, 0.8H), 5.25 (br, 0.2H), 4.98~4.92 (m, 0.5H), 4.85~4.80 (m, 0.5H), 4.74 (s, 1H), 4.03~3.71 (m, 6H), 3.53~3.42 (m, 3H), 3.19~3.09 (m, 2H), 2.88 (d, J=10.4 Hz, 1H), 2.63 (s, 3H), 2.48 (s, 3H), 2.31~2.22 (m, 2H), 2.14~2.10 (m, 1H), 1.98~1.81 (m, 5H).

$^{19}$F NMR (376 MHz, CDCl$_3$): δ -183.17.

LC-MS [mobile phase: from 90% water (0.1% FA) and 10% ACN (0.1% FA) to 5% water (0.1% FA) and 95% ACN (0.1% FA) in 9 min]: Rt=3.30 min; MS Calcd: 492, MS Found: 493 [M+H]$^+$.

Chiral HPLC [OZ-H 4.6×250 mm, 5 μm (Daicel) (CA-HPLC-023), Phase: Hexane/EtOH (0.2% DEA)=60/40, flow rate: 0.5 mL/min, temperature: 35° C.]: Rt: 7.955 min, ee: 100%

E131 (Single Unknown Enantiomer 1, Rt=9.311 min) (48 mg, yield: 34%).

$^1$H NMR (400 MHz, CDCl$_3$): δ 8.89 (s, 1H), 8.07 (s, 1H), 7.53 (s, 1H), 6.67 (br, 0.8H), 5.29 (br, 0.2H), 4.96~4.90 (m, 0.5H), 4.84~4.77 (m, 0.5H), 4.74 (s, 1H), 4.03~3.74 (m, 6H), 3.56~3.46 (m, 2H), 3.29~3.04 (m, 4H), 2.63 (s, 3H), 2.48 (s, 3H), 2.36~2.29 (m, 1H), 2.25~2.19 (m, 1H), 2.13~2.06 (m, 1H), 1.98~1.86 (m, 5H).

$^{19}$F NMR (376 MHz, CDCl$_3$): δ -183.28.

LC-MS [mobile phase: from 90% water (0.1% FA) and 10% ACN (0.1% FA) to 5% water (0.1% FA) and 95% ACN (0.1% FA) in 9 min]: Rt=3.30 min; MS Calcd: 492.3, MS Found: 493.3 [M+H]$^+$.

Chiral HPLC [OZ-H 4.6×250 mm, 5 μm (Daicel) (CA-HPLC-023), Phase: Hexane/EtOH (0.2% DEA)=60/40, flow rate: 0.5 mL/min, temperature: 35° C.]: Rt: 9.311 min, ee: 99.76%

Examples 132-154

Descriptions D33, D36, D39, D42, D45, D48, D51, D54, D107, D179, D182, D184, D188, D191, D195, D198, D150, D151, D173, D206, D109 and D210 are also Examples, as indicated in the table.

| Example | Description | Name |
|---|---|---|
| 132 | D33 | Cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride |
| 133 | D36 | (Cis-(1R,4R)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride |
| 134 | D39 | (1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane HCl salt |
| 135 | D42 | (1R,4R)-5-(6-(6-(3-fluoropiperidin-4-yl)-5-methyl-1H-indazol-1-yl)-2-methoxypyrimidin-4-yl)-2-oxa-5-azabicyclo[2.2.1]heptane HCl salt |
| 136 | D45 | Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane hydrochloride |
| 137 | D48 | Cis-(1S,4S)-5-(6-(6-(3-fluoropiperidin-4-yl)-5-methyl-1H-indazol-1-yl)-2-methoxypyrimidin-4-yl)-2-oxa-5-azabicyclo[2.2.1]heptane hydrochloride |
| 138 | D51 | Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride |
| 139 | D54 | Cis-(1S,4S)-5-(6-(6-(3-fluoropiperidin-4-yl)-5-methyl-1H-indazol-1-yl)-2-methylpyrimidin-4-yl)-2-oxa-5-azabicyclo[2.2.1]heptane hydrochloride |
| 140 | D107 | (1R,4R)-5-(2-methoxy-6-(5-methyl-6-(piperidin-4-yl)-1H-indazol-1-yl)pyrimidin-4-yl)-2-oxa-5-azabicyclo[2.2.1]heptane hydrochloride |
| 141 | D179 | (1S,4S)-5-(6-(5-chloro-6-(piperidin-4-yl)-1H-indazol-1-yl)-2-methylpyrimidin-4-yl)-2-oxa-5-azabicyclo[2.2.1]heptane |
| 142 | D182 | 3-trans-(1R,4R)-4-(1-(6-(2-oxa-5-azabicyclo[2.2.1]heptan-5-yl)-2-methoxypyrimidin-4-yl)-5-methyl-1H-indazol-6-yl)piperidin-3-ol |
| 143 | D184 | (1R,4R)-5-(6-(5-chloro-6-(piperidin-4-yl)-1H-indazol-1-yl)-2-methoxypyrimidin-4-yl)-2-oxa-5-azabicyclo[2.2.1]heptane |
| 144 | D188 | (1S,4S)-5-(6-(5-chloro-6-(piperidin-4-yl)-1H-indazol-1-yl)-2-methoxypyrimidin-4-yl)-2-oxa-5-azabicyclo[2.2.1]heptane |
| 145 | D191 | (1 R,4R)-5-(6-(5-chloro-6-(piperidin-4-yl)-1H-indazol-1-yl)-2-methylpyrimidin-4-yl)-2-oxa-5-azabicyclo[2.2.1]heptane |
| 146 | D195 | 9-(2-methoxy-6-(5-methyl-6-(piperidin-4-yl)-1H-indazol-1-yl)pyrimidin-4-yl)-3,7-dioxa-9-azabicyclo[3.3.1]nonane |
| 147 | D198 | 8-(2-methoxy-6-(5-methyl-6-(piperidin-4-yl)-1H-indazol-1-yl)pyrimidin-4-yl)-3-oxa-8-azabicyclo[3.2.1]octane |
| 148 | D150 | methyl 3-(6-(6-isopropoxy-5-methyl-1H-indazol-1-yl)-2-methoxypyrimidin-4-yl)-3-azabicyclo[3.1.1]heptane-6-carboxylate |
| 149 | D151 | 2-{2-Methyl-6-[5-methyl-6-(tetrahydro-pyran-4-yl)-indazol-1-yl]-pyrimidin-4-yl}-2-aza-bicyclo[2.2.1]heptane-5-carboxylic acid methyl ester |
| 150 | D172 | 3-{2-Methyl-6-[5-methyl-6-(tetrahydro-pyran-4-yl)-indazol-1-yl]-pyrimidin-4-yl}-3-aza-bicyclo[3.1.1]heptane-6-carboxylic acid methyl ester |
| 151 | D173 | 2-{2-Methyl-6-[5-methyl-6-(tetrahydro-pyran-4-yl)-indazol-1-yl]-pyrimidin-4-yl}-2-aza-bicyclo[2.2.1]heptane-5-carboxylic acid methyl ester |
| 152 | D206 | methyl 2-(6-(5-chloro-6-(((S)-tetrahydrofuran-3-yl)oxy)-1H-indazol-1-yl)-2-methoxypyrimidin-4-yl)-2-azabicyclo[2.2.1]heptane-5-carboxylate (isomer 1) |
| 153 | D209 | methyl 2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylate (isomer 1) |
| 154 | D210 | methyl 2-(6-(5-chloro-6-(((R)-tetrahydrofuran-3-yl)oxy)-1H-indazol-1-yl)-2-methoxypyrimidin-4-yl)-2-azabicyclo[2.2.1]heptane-5-carboxylate (isomer 2) |

Examples 132 and 133

Cis-4-(1-(6-((1R,4R)-2-oxa-5-azabicyclo[2.2.1]heptan-5-yl)-2-methoxypyrimidin-4-yl)-5-methyl-1H-indazol-6-yl)-1-(oxetan-3-yl)piperidin-3-ol

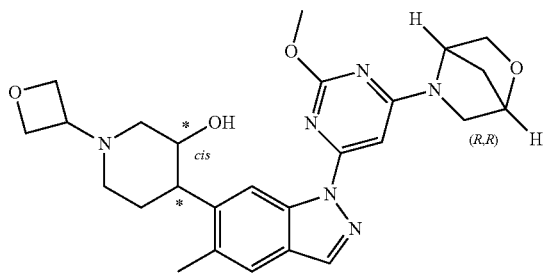 [SMILES: COc1nc(N2CC3CC2CO3)cc(-n2ncc3cc(C)c(C4CCN(C5COC5)CC4O)cc32)n1]

To a stirred mixture of Cis-4-(1-(6-((1R,4R)-2-oxa-5-azabicyclo[2.2.1]heptan-5-yl)-2-methoxypyrimidin-4-yl)-5-methyl-1H-indazol-6-yl)piperidin-3-ol (200 mg, 0.46 mmol), oxetan-3-one (160 mg, 2.23 mmol) in MeOH/DCM (1 mL/4 mL) was added AcOH (10 mg, 0.16 mmol) and NaBH$_3$CN (58 mg, 0.92 mmol). The reaction mixture was stirred at room temperature for 5 hrs, diluted with DCM (50 mL), washed with aqueous NaHCO$_3$ (30 mL), dried over Na$_2$SO$_4$ and concentrated. The residue was purified by silica gel chromatography column (DCM/MeOH=40/1) to give the title compound (80 mg, 35%) as a white solid.

$^1$H NMR (400 MHz, CDCl$_3$): δ 8.91 (s, 1H), 8.07 (s, 1H), 7.53 (s, 1H), 6.54 (br, 1H), 5.23 (br, 1H), 4.74-4.63 (m, 5H), 4.18 (s, 3H), 3.98-3.88 (m, 3H), 3.70-3.53 (m, 3H), 3.06-2.93 (m, 3H), 2.68 (d, J=7.6 Hz, 1H), 2.44 (s, 3H), 2.40-2.35 (m, 1H), 2.28-2.25 (m, 1H), 2.15-2.09 (m, 1H), 2.02-1.94 (m, 2H), 1.78 (d, J=12.4 Hz, 1H).

Chiral Pre-HPLC:
Method: column: Superchiral S-AD; 2 cm I.D.×25 cm L, 5 μm; mobile phase: CO$_2$/IPA/DEA=60/40/0.05; flow rate: 30 mL/min, Wave length: 254 nm, Temperature: 35° C.

Single Unknown Isomer 1 (E132)
The isomer was further purified by flash chromatography column (Petroleum ether/EtOAc=1/1, then DCM/MeOH=30/1) to afford the title compound (18 mg, 24%) as a white solid.

1H NMR (400 MHz, CDCl$_3$): δ 8.92 (s, 1H), 8.07 (s, 1H), 7.53 (s, 1H), 6.54 (br, 1H), 5.26 (br, 1H), 4.74-4.63 (m, 5H), 4.18 (s, 3H), 3.98-3.88 (m, 3H), 3.69-3.44 (m, 3H), 3.06-2.93 (m, 3H), 2.68 (d, J=8.8 Hz, 1H), 2.44 (s, 3H), 2.40-2.33 (m, 1H), 2.27 (d, J=8.8 Hz, 1H), 2.15-2.09 (m, 1H), 2.00-1.92 (m, 2H), 1.78 (d, J=12.4 Hz, 1H).

Chiral HPLC [column: Superchiral S-AD; 0.46 cm I.D.× 15 cm L, 5 μm; mobile phase: CO$_2$/IPA/DEA=60/40/0.05; flow rate: 3 mL/min, Wave length: 254 nm, Temperature: 35° C.]: Rt=5.336 min.

LC-MS [column: C$_{18}$; column size: 4.6×50 mm; mobile phase: B (MeCN), A (0.02% NH$_4$OAc); gradient (B %) in 6 min-05-95-POS; flow rate: 1.5 ml/min]: Rt=3.536 min; MS Calcd.: 492, MS Found: 493 [M+H]$^+$.

Single Unknown Isomer 2 (E133)
The isomer 2 was further purified by flash chromatography column (Petroleum ether/EtOAc=1/1, then DCM/MeOH=30/1) to afford title compound (19 mg, 25%) as a white solid.

1H NMR (400 MHz, CDCl3): δ 8.91 (s, 1H), 8.07 (s, 1H), 7.52 (s, 1H), 6.53 (br, 1H), 5.26 (br, 1H), 4.74-4.63 (m, 5H), 4.18 (s, 3H), 3.97-3.88 (m, 3H), 3.69-3.47 (m, 3H), 3.06-2.93 (m, 3H), 2.73-2.66 (m, 1H), 2.44 (s, 3H), 2.40-2.33 (m, 1H), 2.27 (d, J=11.2 Hz, 1H), 2.12 (t, J=11.2 Hz, 1H), 2.00-1.92 (m, 2H), 1.81-1.73 (m, 1H).

Chiral HPLC [column: Superchiral S-AD; 0.46 cm I.D.× 15 cm L, 5 μm; mobile phase: CO$_2$/IPA/DEA=60/40/0.05; flow rate: 3 mL/min, Wave length: 254 nm, Temperature: 35° C.]: Rt=5.652 min.

LC-MS [column: C$_{18}$; column size: 4.6×50 mm; mobile phase: B (MeCN), A (0.02% NH$_4$OAc); gradient (B %) in 6 min-05-95-POS; flow rate: 1.5 ml/min]: Rt=3.492 min; MS Calcd.: 492, MS Found: 493 [M+H]$^+$.

Examples 134 and 135

Trans-4-(1-(6-((1R,4R)-2-oxa-5-azabicyclo[2.2.1]heptan-5-yl)-2-methoxypyrimidin-4-yl)-5-methyl-1H-indazol-6-yl)-1-(tetrahydrofuran-3-yl)piperidin-3-ol

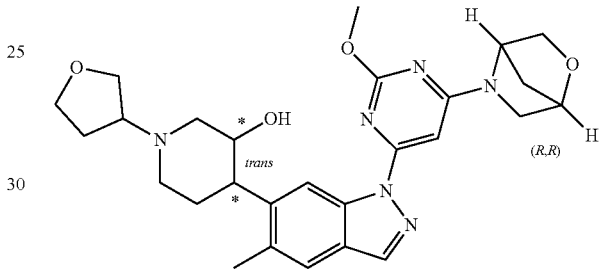

To a solution of 3-trans-(1R,4R)-4-(1-(6-(2-oxa-5-azabicyclo[2.2.1]heptan-5-yl)-2-methoxypyrimidin-4-yl)-5-methyl-1H-indazol-6-yl)piperidin-3-ol (300 mg, 0.69 mmol), dihydrofuran-3(2H)-one (297 mg, 3.45 mmol) and catalyst AcOH (2 drops) in DCM (10 mL) was added NaBH$_3$CN (87 mg, 1.38 mmol). The reaction mixture was stirred at room temperature for 5 hrs, diluted with H$_2$O (30 mL) and extracted with DCM (30 mL×2). The combined organic parts were dried over Na$_2$SO$_4$, filtered and concentrated. The residue was purified by silica gel chromatography column (DCM/MeOH=10:1) to give the title products (E134, 30 mg, 8%; E135, 50 mg, 14%) as a yellow oil.

Single Unknown Isomer 1 (E134)
1HNMR (400 MHz, CD3OD): δ 8.98 (s, 1H), 8.14 (s, 1H), 7.56 (s, 1H), 6.75-6.55 (m, 1H), 4.74 (s, 1H), 4.10 (s, 3H), 3.97-3.70 (m, 6H), 3.57-3.55 (m, 1H), 3.30 (s, 3H), 3.17-3.13 (m, 1H), 2.95-2.92 (m, 1H), 2.80-2.74 (m, 5H), 2.29-1.93 (m, 8H).

LC-MS [Phenomenex Kinetex 5 μm EVO C$_{18}$, 50×4.6 mm; mobile phase: B (MeCN): A (0.1% FA); gradient (B %) in 6 min.]: Rt=3.013 min; MS Calcd.: 506, MS Found: 507 [M+H]$^+$.

Single Unknown Isomer 2 (E135)
$^1$H NMR (400 MHz, CD$_3$OD): δ 8.73 (s, 1H), 8.10 (s, 1H), 7.55 (s, 1H), 6.74-6.51 (m, 1H), 4.72 (s, 1H), 4.08 (s, 3H), 3.99-3.67 (m, 7H), 3.54-3.51 (m, 1H), 3.31 (s, 3H), 3.15-3.01 (m, 2H), 2.93-2.82 (m, 1H), 2.47 (s, 3H), 2.22-1.82 (m, 8H).

LC-MS [Phenomenex Kinetex 5 μm EVO C$_{18}$, 50×4.6 mm; mobile phase: B (MeCN): A (0.1% FA); gradient (B %) in 6 min.]: Rt=3.037 min; MS Calcd.: 506, MS Found: 507 [M+H]$^+$.

Examples 136 and 137

Cis-4-(1-(6-((1R,4R)-2-oxa-5-azabicyclo[2.2.1]heptan-5-yl)-2-methylpyrimidin-4-yl)-5-methyl-1H-indazol-6-yl)-1-((S)-tetrahydrofuran-3-yl)piperidin-3-ol

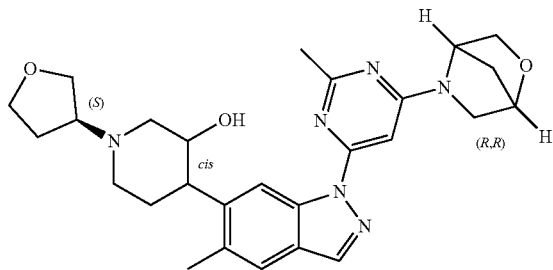

A mixture of Cis-4-(1-(6-((1R,4R)-2-oxa-5-azabicyclo[2.2.1]heptan-5-yl)-2-methylpyrimidin-4-yl)-5-methyl-1H-indazol-6-yl)piperidin-3-ol (1.80 g, 4.29 mmol), (R)-tetrahydrofuran-3-yl methanesulfonate (2.13 g, 6.68 mmol) and $K_2CO_3$ (2.37 g, 17.1 mmol) in MeCN (30 mL) was stirred at 100° C. for 40 hrs in a seal tube, then diluted with $H_2O$ (100 mL), extracted with EtOAc (100 mL×3). The combined organic layers were washed with brine (50 mL), dried over $Na_2SO_4$ and concentrated. The residue was purified by silica gel chromatography column (DCM/MeOH=50/1) to give the mixture (800 mg, 38%) as a light yellow solid.

$^1$H NMR (400 MHz, $CDCl_3$): δ 8.96 (s, 1H), 8.05 (s, 1H), 7.51 (s, 1H), 6.65 (br, 1H), 5.33-5.22 (m, 1H), 4.74 (s, 1H), 4.02-3.73 (m, 7H), 3.56-3.48 (m, 2H), 3.23-3.14 (m, 2H), 3.06-2.98 (m, 2H), 2.66-2.55 (m, 1H), 2.62 (s, 3H), 2.47-2.35 (m, 5H), 2.33-2.28 (m, 1H), 2.15-2.09 (m, 1H), 2.06-1.89 (m, 3H), 1.80-1.74 (m, 1H).

The mixture (300 mg) was separated by chiral-prep-HPLC to give the isomer 1 (E136, 120 mg, 40%) as a white solid and isomer 2 (E137, 105 mg, 35%) as a white solid.

Chiral Pre-HPLC:
Method: column: Chiralpak IB; 2 cm I.D.×25 cm L, 5 μm; mobile phase: $CO_2$/EtOH=40/60; flow rate: 20 mL/min, Wave length: 230 nm, Temperature: 30° C.

Single Unknown Isomer 1 (E136)

$^1$H NMR (400 MHz, $CDCl_3$): δ 8.96 (s, 1H), 8.06 (s, 1H), 7.51 (s, 1H), 6.65 (br, 1H), 5.30 (s, 1H), 4.74 (s, 1H), 4.00-3.91 (m, 5H), 3.84-3.76 (m, 2H), 3.57-3.45 (m, 2H), 3.24-3.16 (m, 2H), 3.06-2.98 (m, 2H), 2.72-2.60 (m, 1H), 2.63 (s, 3H), 2.51-2.31 (m, 6H), 2.12-2.07 (m, 1H), 2.05-1.92 (m, 3H), 1.79-1.64 (m, 1H).

Chiral HPLC [column: Chiralpak IB; 0.46 cm I.D.×25 cm L, 5 μm; mobile phase: Hex/EtOH=40/60; flow rate: 1 mL/min, Wave length: 254 nm, Temperature: 30° C.]: Rt=6.430 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=3.327 min; MS Calcd.: 490, MS Found: 491 [M+H]+.

Single Unknown Isomer 2 (E137)

1H NMR (400 MHz, CDCl3): δ 8.96 (s, 1H), 8.06 (s, 1H), 7.51 (s, 1H), 6.65 (br, 1H), 5.31 (s, 1H), 4.74 (s, 1H), 4.03-3.76 (m, 7H), 3.58-3.46 (m, 2H), 3.22-3.16 (m, 2H), 3.09-3.01 (m, 2H), 2.67-2.58 (m, 1H), 2.63 (s, 3H), 2.54-2.41 (m, 5H), 2.35-2.29 (m, 1H), 2.16-2.09 (m, 1H), 2.03-1.96 (m, 3H), 1.81-1.77 (m, 1H).

Chiral HPLC [column: Chiralpak IB; 0.46 cm I.D.×25 cm L, 5 μm; mobile phase: Hex/EtOH=40/60; flow rate: 1 mL/min, Wave length: 254 nm, Temperature: 30° C.]: Rt=11.173 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=2.437 min; MS Calcd.: 490, MS Found: 491 [M+H]+.

Examples 138 and 139

Cis-4-(1-(6-((1S,4S)-2-oxa-5-azabicyclo[2.2.1]heptan-5-yl)-2-methylpyrimidin-4-yl)-5-methyl-1H-indazol-6-yl)-1-((S)-tetrahydrofuran-3-yl)piperidin-3-ol

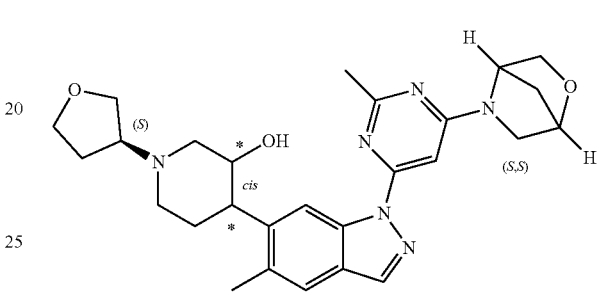

The title compound was prepared by a procedure similar to that described for E136 and E137 starting from a mixture of cis-4-(1-(6-((1S,4S)-2-oxa-5-azabicyclo[2.2.1]heptan-5-yl)-2-methylpyrimidin-4-yl)-5-methyl-1H-indazol-6-yl)piperidin-3-ol, (R)-tetrahydrofuran-3-yl methanesulfonate and $K_2CO_3$ in MeCN at 100° C. for 30 hrs in a sealed tube.

$^1$H NMR (400 MHz, $CDCl_3$): δ 8.96 (s, 1H), 8.06 (s, 1H), 7.51 (s, 1H), 6.65 (br, 1H), 5.29 (s, 1H), 4.74 (s, 1H), 4.01-3.74 (m, 7H), 3.54-3.47 (m, 2H), 3.24-3.15 (m, 2H), 3.06-2.98 (m, 2H), 2.66-2.57 (m, 1H), 2.62 (s, 3H), 2.48-2.34 (m, 5H), 2.33-2.28 (m, 1H), 2.14-2.08 (m, 1H), 2.06-1.90 (m, 3H), 1.80-1.74 (m, 1H).

Chiral Pre-HPLC:
Method: column: Chiralpak IB; 2 cm I.D.×25 cm L, 5 μm; mobile phase: $CO_2$/EtOH=50/50; flow rate: 20 mL/min, Wave length: 230 nm, Temperature: 30° C.

Single Unknown Isomer 1 (E138)

$^1$H NMR (400 MHz, $CDCl_3$): δ 8.96 (s, 1H), 8.06 (s, 1H), 7.51 (s, 1H), 6.66 (br, 1H), 5.29 (s, 1H), 4.74 (s, 1H), 4.01-3.90 (m, 5H), 3.84-3.75 (m, 2H), 3.58-3.47 (m, 2H), 3.24-3.14 (m, 2H), 3.06-2.98 (m, 2H), 2.68-2.59 (m, 1H), 2.62 (s, 3H), 2.50-2.30 (m, 6H), 2.12-2.07 (m, 1H), 2.06-1.90 (m, 3H), 1.78-1.64 (m, 1H).

Chiral HPLC [column: Chiralpak IB; 0.46 cm I.D.×25 cm L, 5 μm; mobile phase: Hex/EtOH=50/50; flow rate: 1 mL/min, Wave length: 230 nm, Temperature: 30° C.]: Rt=6.461 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=3.337 min; MS Calcd.: 490, MS Found: 491 [M+H]+.

Single Unknown Isomer 2 (E139)

$^1$H NMR (400 MHz, $CDCl_3$): δ 8.96 (s, 1H), 8.05 (s, 1H), 7.51 (s, 1H), 6.66 (br, 1H), 5.27 (s, 1H), 4.74 (s, 1H), 4.02-3.74 (m, 7H), 3.58-3.46 (m, 2H), 3.20-3.16 (m, 2H), 3.06-3.00 (m, 2H), 2.68-2.57 (m, 1H), 2.63 (s, 3H), 2.51-2.41 (m, 5H), 2.34-2.29 (m, 1H), 2.16-2.08 (m, 1H), 2.06-1.93 (m, 3H), 1.80-1.67 (m, 1H).

Chiral HPLC [column: Chiralpak IB; 0.46 cm I.D.×25 cm L, 5 μm; mobile phase: Hex/EtOH=50/50; flow rate: 1 mL/min, Wave length: 230 nm, Temperature: 30° C.]: Rt=8.839 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=3.398 min; MS Calcd.: 490, MS Found: 491 [M+H]$^+$.

Example 140 and 141

Cis-4-(1-(6-((1R,4R)-2-oxa-5-azabicyclo[2.2.1]heptan-5-yl)-2-methylpyrimidin-4-yl)-5-methyl-1H-indazol-6-yl)-1-(oxetan-3-yl)piperidin-3-ol

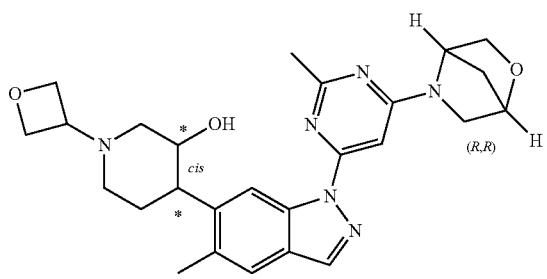

To a stirred mixture of cis-4-(1-(6-((1R,4R)-2-oxa-5-azabicyclo[2.2.1]heptan-5-yl)-2-methylpyrimidin-4-yl)-5-methyl-1H-indazol-6-yl)piperidin-3-ol (300 mg, 0.71 mmol), oxetan-3-one (129 mg, 1.79 mmol) and 4 Å molecular sieves (250 mg) in MeOH/DCM (3 mL/12 mL) at 0° C. was added AcOH (15 mg, 0.25 mmol) and $NaBH_3CN$ (89 mg, 1.42 mmol). The reaction mixture was stirred at room temperature for 4 hrs, then concentrated and purified by silica gel chromatography column (DCM/MeOH=50/1) to give the mixture 100 mg, 30%) as a white solid.

$^1$H NMR (400 MHz, $CDCl_3$): δ 8.98 (s, 1H), 8.06 (s, 1H), 7.52 (s, 1H), 6.65 (br, 1H), 5.32 (s, 1H), 4.77-4.68 (m, 5H), 4.01-3.86 (m, 3H), 3.69-3.62 (m, 1H), 3.55-3.43 (m, 2H), 3.07-2.99 (m, 3H), 2.70-2.60 (m, 4H), 2.52-2.40 (m, 4H), 2.26 (d, J=11.2 Hz, 1H), 2.15-2.09 (m, 1H), 2.01-1.92 (m, 2H), 1.83-1.77 (m, 1H).

The mixture (48 mg, 0.1 mmol) was separated by chiral-prep-HPLC to give the single unknown isomer 1 (18 mg, 37%) as a white solid and the single unknown isomer 2 (14 mg, 29%) as a white solid.

Chiral pre-HPLC: column: Chiralpak IB; 2 cm I.D.×25 cm L, 5 μm; mobile phase: $CO_2$/EtOH=60/40; flow rate: 15 mL/min, Wave length: 230 nm, Temperature: 30° C.

Single Unknown Isomer 1 (E140)

$^1$H NMR (400 MHz, $CDCl_3$): δ 8.91 (s, 1H), 7.99 (s, 1H), 7.45 (s, 1H), 6.60 (br, 1H), 5.31-5.19 (m, 1H), 4.69-4.59 (m, 5H), 3.92 (d, J=11.2 Hz, 1H), 3.83 (s, 2H), 3.61-3.55 (m, 1H), 3.50-3.42 (m, 2H), 3.00-2.92 (m, 3H), 2.61-2.51 (m, 1H), 2.57 (s, 3H), 2.46-2.33 (m, 4H), 2.19 (d, J=11.6 Hz, 1H), 2.05 (t, J=10.8 Hz, 1H), 1.93-1.86 (m, 2H), 1.72 (d, J=12.0 Hz, 1H).

Chiral HPLC [column: Chiralpak IB; 0.46 cm I.D.×25 cm L, 5 μm; mobile phase: Hex/EtOH=60/40; flow rate: 1 mL/min, Wave length: 230 nm, Temperature: 30° C.]: Rt=6.561 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=3.402 min; MS Calcd.: 476, MS Found: 477 [M+H]$^+$.

Single Unknown Isomer 2 (E141)

$^1$H NMR (400 MHz, $CDCl_3$): δ 8.98 (s, 1H), 8.06 (s, 1H), 7.52 (s, 1H), 6.66 (br, 1H), 5.34 (s, 1H), 4.76-4.66 (m, 5H), 3.99 (s, 1H), 3.91 (s, 2H), 3.68-3.62 (m, 1H), 3.57-3.43 (m, 2H), 3.07-2.98 (m, 3H), 2.66-2.61 (m, 1H), 2.63 (s, 3H), 2.52-2.42 (m, 1H), 2.44 (s, 3H), 2.26 (d, J=10.8 Hz, 1H), 2.12 (t, J=11.7 Hz, 1H), 2.01-1.95 (m, 2H), 1.79 (d, J=10.8 Hz, 1H).

Chiral HPLC [column: Chiralpak IB; 0.46 cm I.D.×25 cm L, 5 μm; mobile phase: Hex/EtOH=60/40; flow rate: 1 mL/min, Wave length: 230 nm, Temperature: 30° C.]: Rt=10.158 min.

LC-MS [column: $C_{18}$; column size: 4.6×50 mm; mobile phase: B (MeCN) A (0.02% NH4OAc); gradient (B %) in 6 min-05-95-POS; flow rate: 1.5 ml/min]: Rt=3.461 min; MS Calcd.: 476, MS Found: 477 [M+H]$^+$.

Example 142

((1R,4R)-5-(2-methyl-6-(5-methyl-6-(1-((S)-tetrahydrofuran-3-yl)piperidin-4-yl)-1H-indazol-1-yl)pyrimidin-4-yl)-2-oxa-5-azabicyclo[2.2.1]heptan-1-yl)methanol

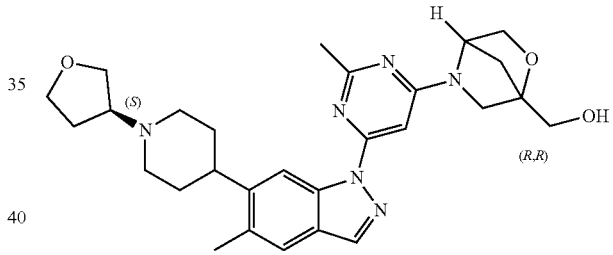

A mixture of ((1R,4R)-5-(2-methyl-6-(5-methyl-6-(piperidin-4-yl)-1H-indazol-1-yl)pyrimidin-4-yl)-2-oxa-5-azabicyclo[2.2.1]heptan-1-yl)methanol (90 mg, 0.21 mmol), (R)-tetrahydrofuran-3-yl methanesulfonate (174 mg, 1.05 mmol) and $K_2CO_3$ (116 mg, 0.84 mmol) in MeCN (2 mL) was stirred at 100° C. for 16 hrs, then concentrated. The residue was purified by silica gel chromatography column (DCM/MeOH=from 30/1 to 20/1) to give the title product (45 mg). The product was re-purified by prep-HPLC (watersgilson-1 X-bridge C18 5 μm 19×150 mm 25-70% B, A: $H_2O$ (0.1% $NH_4HCO_3$), B: MeCN, UV: 254 nm, Flow rate: 15 ml/min, GT: 12 mins) to give the title compound (22 mg, 21%) as a yellow oil.

$^1$H NMR (400 MHz, $CDCl_3$): δ 8.80 (s, 1H), 8.04 (s, 1H), 7.49 (s, 1H), 6.67 (br, 1H), 5.31 (br, 1H), 4.04-3.94 (m, 6H), 3.86-3.80 (m, 1H), 3.74-3.70 (m, 1H), 3.58-3.48 (m, 2H), 3.19 (d, J=10.4 Hz, 1H), 3.06-2.97 (m, 2H), 2.86-2.82 (m, 1H), 2.62 (s, 3H), 2.46 (s, 3H), 2.29-2.20 (m, 2H), 2.15-2.00 (m, 3H), 1.99-1.64 (m, 6H).

LCMS [column: Phenomenex Kinetex 5 μm EVO, $C_{18}$; column size: 4.6×50 mm; mobile phase: B (MeCN) A (0.01% TFA); gradient (B %) in 6 mins]: Rt=2.490 min, MS Calcd.: 504, MS Found: 505 [M+H]$^+$.

Example 143

((1S,4S)-5-(2-methyl-6-(5-methyl-6-(1-((S)-tetrahydrofuran-3-yl)piperidin-4-yl)-1H-indazol-1-yl)pyrimidin-4-yl)-2-oxa-5-azabicyclo[2.2.1]heptan-1-yl)methanol

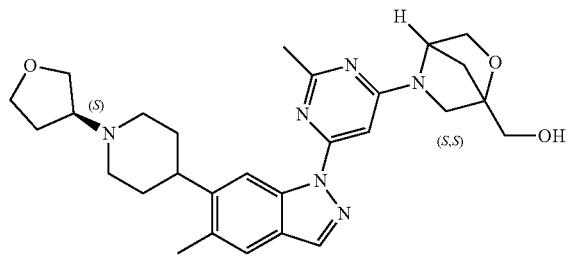

The title compound was prepared by a procedure similar to that described for E142 starting from a mixture of ((1S,4S)-5-(2-methyl-6-(5-methyl-6-(piperidin-4-yl)-1H-indazol-1-yl)pyrimidin-4-yl)-2-oxa-5-azabicyclo[2.2.1]heptan-1-yl)methanol, (R)-tetrahydrofuran-3-yl methanesulfonate and $K_2CO_3$ in MeCN at 100° C. for 20 hrs.

$^1$H NMR (400 MHz, CDCl$_3$): δ 8.80 (s, 1H), 8.04 (s, 1H), 7.49 (s, 1H), 6.67 (br, 1H), 5.31 (br, 1H), 4.04-3.93 (m, 6H), 3.86-3.73 (m, 2H), 3.56-3.42 (m, 2H), 3.29-2.84 (m, 4H), 2.64 (s, 3H), 2.45 (s, 3H), 2.29-1.95 (m, 10H).

LCMS[column: Phenomenex Kinetex 5 μm EVO, C$_{18}$; column size: 4.6×50 mm; mobile phase: B (MeCN): A (0.02% NH$_4$OAc); gradient (B %) in 6 mins]: Rt=3.270 min, MS Calcd.: 504, MS Found: 505 [M+H]$^+$.

Examples 144, 145, 146 and 147

4-(1-(6-((1R,4R)-2-oxa-5-azabicyclo[2.2.1]heptan-5-yl)-2-methylpyrimidin-4-yl)-5-methyl-1H-indazol-6-yl)-3-methyl-1-(oxetan-3-yl)piperidin-3-ol (Isomers 1-4)

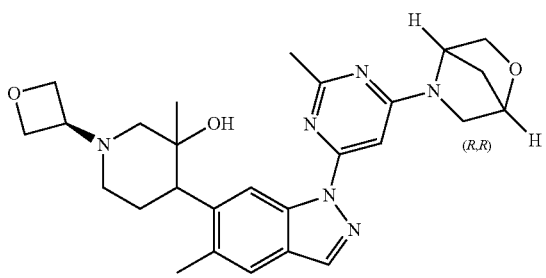

A mixture of 4-(1-(6-((1R,4R)-2-oxa-5-azabicyclo[2.2.1]heptan-5-yl)-2-methylpyrimidin-4-yl)-5-methyl-1H-indazol-6-yl)-3-methylpiperidin-3-ol (320 mg, 0.74 mmol), oxetan-3-one (266 mg, 3.70 mmol), NaBH$_3$CN (233 mg, 3.70 mmol) and AcOH (catalyst) in DCM (10 mL) and MeOH (1 mL) was stirred at room temperature for 3 hrs, then concentrated and purified by silica gel chromatography column (DCM/MeOH=40/1) to give the crude (360 mg). The crude was re-purified by prep-TLC DCM/MeOH=30/1 to give the mixture product (150 mg, 41%) as a yellow solid.

$^1$H NMR (400 MHz, CDCl$_3$): 9.26-8.91 (m, 1H), 8.05 (s, 1H), 7.49 (s, 1H), 6.65 (br, 1H), 5.29 (s, 1H), 4.74-4.67 (m, 5H), 3.90 (s, 2H), 3.66-3.52 (m, 2H), 2.92-2.85 (m, 2H), 2.65-2.62 (m, 4H), 2.55-2.43 (m, 4H), 2.21-1.98 (m, 7H), 1.39 (s, 1H), 0.99 (s, 2H).

The mixture (146 mg) was separated by chiral-prep-HPLC to give isomer A (27 mg, 18%) as a white solid and isomer B (75 mg, 51%) as a yellow solid.

Chiral pre-HPLC: column: Chiralpak ID; 2 cm I.D.×25 cm L, 5 μm; mobile phase: CO$_2$-EtOH—NH$_3$.H$_2$O-60-40-0.2; flow rate: 20 mL/min, Wave length: 230 nm, Temperature: 30° C.

Isomer A

Chiral HPLC [column: Chiralpak ID; 0.46 cm I.D.×25 cm L, 5 μm; mobile phase: Hex-EtOH-DEA-60-40-0.2; flow rate: 1 mL/min, Wave length: 230 nm, Temperature: 30° C.]: Rt=8.064 min and 8.887 min.

LC-MS [column: C$_{18}$; column size: 4.6×50 mm; mobile phase: B (MeCN) A (0.02% NH$_4$OAc); gradient (B %) in 4 min-05-95-POS; flow rate: 1.5 ml/min]: Rt=1.944 min; MS Calcd.: 490, MS Found: 491 [M+H]$^+$.

Isomer B

Chiral HPLC [column: Chiralpak ID; 0.46 cm I.D.×25 cm L, 5 μm; mobile phase: Hex-EtOH-DEA-60-40-0.2; flow rate: 1 mL/min, Wave length: 230 nm, Temperature: 30° C.]: Rt=12.325 min.

LC-MS [column: C$_{18}$; column size: 4.6×50 mm; mobile phase: B (MeCN) A (0.02% NH$_4$OAc);

gradient (B %) in 4 min-05-95-POS; flow rate: 1.5 ml/min]: Rt=2.072 min; MS Calcd.: 490, MS Found: 491 [M+H]$^+$.

The Isomer A (27 mg) was separated by chiral-prep-HPLC to give single unknown isomer 1 (7 mg, 25%) as a white solid and single unknown isomer 2 (2.7 mg, 10%) as a white solid.

Chiral pre-HPLC: column: Chiralpak IG; 2 cm I.D.×25 cm L, 5 μm; mobile phase: CO$_2$-EtOH—NH$_3$.H$_2$O-65-35-0.2; flow rate: 20 mL/min, Wave length: 230 nm, Temperature: 30° C.

Single Unknown Isomer 1 (E144)

$^1$H NMR (400 MHz, CDCl$_3$): δ 8.89 (s, 1H), 8.07 (s, 1H), 7.53 (s, 1H), 6.66 (br, 1H), 5.29 (s, 1H), 4.74-4.63 (m, 5H), 3.93-3.89 (m, 2H), 3.64-3.48 (m, 3H), 3.25-3.20 (m, 1H), 2.90-2.88 (m, 1H), 2.71-2.69 (m, 1H), 2.65 (s, 3H), 2.58 (s, 3H), 2.12-2.09 (m, 3H), 2.06-1.86 (m, 3H), 1.39 (s, 3H).

Chiral HPLC [column: Chiralpak IG; 0.46 cm I.D.×25 cm L, 5 μm; mobile phase: Hex-EtOH-DEA-65-35-0.2; flow rate: 1 mL/min, Wave length: 230 nm, Temperature: 30° C.]: Rt=13.632 min.

LC-MS [column: C$_{18}$; column size: 4.6×50 mm; mobile phase: B (MeCN) A (0.02% NH$_4$OAc); gradient (B %) in 6 min-05-95-POS; flow rate: 1.5 ml/min]: Rt=3.469 min; MS Calcd.: 490, MS Found: 491 [M+H]$^+$.

Single Unknown Isomer 2 (E145)

$^1$H NMR (400 MHz, CDCl$_3$): δ 8.89 (s, 1H), 8.07 (s, 1H), 7.53 (s, 1H), 6.68 (br, 1H), 5.29 (s, 1H), 4.74-4.63 (m, 5H), 3.93-3.89 (m, 2H), 3.62-3.52 (m, 3H), 3.25-3.20 (m, 1H), 2.90-2.88 (m, 1H), 2.71-2.69 (m, 1H), 2.62 (s, 3H), 2.55 (s, 3H), 2.13-2.09 (m, 3H), 2.01-1.87 (m, 3H), 1.39 (s, 3H).

Chiral HPLC [column: Chiralpak IG; 0.46 cm I.D.×25 cm L, 5 μm; mobile phase: Hex-EtOH-DEA-65-35-0.2; flow rate: 1 mL/min, Wave length: 230 nm, Temperature: 30° C.]: Rt=17.359 min.

LC-MS [column: C$_{18}$; column size: 4.6×50 mm; mobile phase: B (MeCN) A (0.02% NH$_4$OAc); gradient (B %) in 6 min-05-95-POS; flow rate: 1.5 ml/min]: Rt=3.526 min; MS Calcd.: 490, MS Found: 491 [M+H]$^+$.

The isomer B (75 mg) was separated by chiral-prep-HPLC to give single unknown isomer 3 (28 mg, 37%) as a white solid and single unknown isomer 4 (31 mg, 41%) as a white solid.

Chiral pre-HPLC: column: Chiralpak IG; 2 cm I.D.×25 cm L, 5 μm; mobile phase: $CO_2$-EtOH—$NH_3H_2O$-40-60-0.2; flow rate: 20 mL/min, Wave length: 230 nm, Temperature: 30

Single Unknown Isomer 3 (E146)

$^1$H NMR (400 MHz, $CDCl_3$): δ 9.27 (s, 1H), 8.05 (s, 1H), 7.48 (s, 1H), 6.66 (br, 1H), 5.29 (s, 1H), 4.75-4.66 (m, 5H), 3.90-3.88 (m, 2H), 3.69-3.66 (m, 1H), 3.55-3.48 (m, 3H), 2.93-2.82 (m, 2H), 2.67-2.64 (m, 4H), 2.43 (s, 3H), 2.21-2.17 (m, 1H), 2.08-1.96 (m, 4H), 1.77-1.73 (m, 1H), 0.99 (s, 3H).

Chiral HPLC [column: Chiralpak IG; 0.46 cm I.D.×25 cm L, 5 μm; mobile phase: Hex-EtOH-DEA-65-35-0.2; flow rate: 1 mL/min, Wave length: 230 nm, Temperature: 30° C.]: Rt=13.111 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=3.873 min; MS Calcd.: 490, MS Found: 491 $[M+H]^+$.

Single Unknown Isomer 4 (E147)

$^1$H NMR (400 MHz, $CDCl_3$): δ 9.26 (s, 1H), 8.05 (s, 1H), 7.48 (s, 1H), 6.66 (br, 1H), 5.29 (s, 1H), 4.75-4.66 (m, 5H), 3.92-3.88 (m, 2H), 3.70-3.64 (m, 1H), 3.53-3.46 (m, 3H), 2.93-2.82 (m, 2H), 2.67-2.65 (m, 4H), 2.42 (s, 3H), 2.22-2.14 (m, 1H), 2.08-1.94 (m, 4H), 1.76-1.73 (m, 1H), 0.99 (s, 3H).

Chiral HPLC [column: Chiralpak IG; 0.46 cm I.D.×25 cm L, 5 μm; mobile phase: Hex-EtOH-DEA-65-35-0.2; flow rate: 1 mL/min, Wave length: 230 nm, Temperature: 30° C.]: Rt=16.941 min.

LC-MS [column: $C_{18}$; column size: 4.6×50 mm; mobile phase: B (MeCN) A (0.02% $NH_4OAc$); gradient (B %) in 6 min-05-95-POS; flow rate: 1.5 ml/min]: Rt=3.730 min; MS Calcd.: 490, MS Found: 491 $[M+H]^+$.

Examples 148 and 149

Cis-(1R,4R)-5-(6-(6-(3-fluoro-1-(tetrahydrofuran-3-yl)piperidin-4-yl)-5-methyl-1H-indazol-1-yl)-2-methylpyrimidin-4-yl)-2-oxa-5-azabicyclo[2.2.1]heptane (from Peak 2) (Single Unknown Isomer 1, Rt=2.232 min; Single Unknown Isomer 2, Rt=3.429 min)

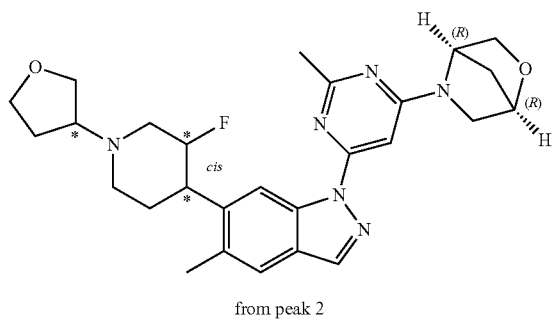

from peak 2

To a mixture of 6-(3-fluoro-1-(tetrahydrofuran-3-yl)piperidin-4-yl)-5-methyl-1H-indazole (100 mg, 0.33 mmol), (1R,4R)-5-(6-iodo-2-methylpyrimidin-4-yl)-2-oxa-5-azabicyclo[2.2.1]heptane (105 mg, 0.33 mmol), CuI (63 mg, 0.33 mmol) and $K_3PO_4$ (140 mg, 0.66 mmol) in toluene (10 mL) was added N,N'-dimethylethylenediamine (58 mg, 0.66 mmol). The reaction mixture was stirred at 90° C. for 2 h, poured into water (50 mL) and extracted with EtOAc (50 mL×2). The organic solution was washed with brine (50 mL), dried over $Na_2SO_4$, filtered and concentrated. The residue was purified by SGC (from PE to EtOAc/PE=10:1) to afford the chiral mixture as a white solid (120 mg, yield: 74%).

The chiral mixture (120 mg) was separated by prep-HPLC (Method: Column: AD-H; Column size: 0.46 cm I.D.×15 cm L; Mobile phase: $CO_2$:EtOH (0.1% $NH_3H_2O$)=60:40; Flow rate: 0.5 mL/min; Wave length: UV 254 nm; Temperature: 25° C.; Sample solution in EtOH) afforded two white solids:

Single Unknown Isomer 1 (peak 1, E148)

White solid (Rt=2.232 min, 18 mg, 11% yield)

$^1$H NMR (400 MHz, $CDCl_3$) δ 8.89 (s, 1H), 8.06 (s, 1H), 7.52 (s, 1H), 6.66 (br, 1H), 5.26 (br, 0.45H), 4.96~4.79 (m, 1H), 4.74 (br, 1H), 4.00~3.99 (m, 1H), 3.99 (s, 3H), 3.94~3.85 (m, 1H), 3.75~3.71 (m, 1H), 3.53~3.47 (m, 3H), 3.17~3.07 (m, 2H), 2.87~2.84 (m, 1H), 2.62 (s, 3H), 2.47 (s, 3H), 2.28~2.24 (m, 2H), 2.11~2.00 (m, 1H), 1.98~1.89 (m, 5H).

$^{19}$F NMR (376 MHz, $CDCl_3$) δ 183.18 (s, 1F),

LC-MS [mobile phase: from 80% water (0.1% FA) and 5% MeCN (0.1% FA) to 20% water (0.1% FA) and 95% MeCN (0.1% FA) in 2.6 min]: Rt=0.946 min; MS Calcd: 492, MS Found: 493.3 $[M+H]^+$.

Chiral HPLC [Column: AD-H; Column size: 0.46 cm I.D.×15 cm L; Mobile phase: Hex:EtOH (0.1% DEA)=60:40; Flow rate: 0.5 mL/min; Wave length: UV 254 nm; Temperature: 25° C.]: Rt=2.232 min, ee 100%;

Single Unknown Isomer 2 (peak 2, E149)

White solid (Rt=3.429 min, 17 mg, 11% yield)

$^1$H NMR (400 MHz, $CDCl_3$) δ 8.89 (s, 1H), 8.06 (s, 1H), 7.52 (s, 1H), 6.67 (br, 1H), 5.26 (br, 0.50H), 4.96~4.81 (m, 1H), 4.74 (br, 1H), 4.00~3.99 (m, 1H), 3.99 (s, 3H), 3.93~3.78 (m, 2H), 3.54~3.53 (m, 2H), 3.33~3.23 (m, 2H), 3.12~3.08 (m, 2H), 2.62 (s, 3H), 2.48 (s, 3H), 2.36~2.34 (m, 1H), 2.25~2.13 (m, 1H), 2.11~2.00 (m, 1H), 1.98~1.89 (m, 5H).

$^{19}$F NMR (376 MHz, $CDCl_3$) δ 183.36 (s, 1F), δ 75.49 (s, 1F), TFA salt

LC-MS [mobile phase: from 80% water (0.1% FA) and 5% MeCN (0.1% FA) to 20% water (0.1% FA) and 95% MeCN (0.1% FA) in 2.6 min]: Rt=0.932 min; MS Calcd: 492, MS Found: 493.3 $[M+H]^+$.

Chiral HPLC [Column: AD-H; Column size: 0.46 cm I.D.×15 cm L; Mobile phase: Hex:EtOH (0.1% DEA)=60:40; Flow rate: 0.5 mL/min; Wave length: UV 254 nm; Temperature: 25° C.]: Rt=3.429 min, ee 100%;

Examples 150 and 151

Cis-(1S,4S)-5-(6-(6-(3-fluoro-1-(tetrahydrofuran-3-yl)piperidin-4-yl)-5-methyl-1H-indazol-1-yl)-2-methylpyrimidin-4-yl)-2-oxa-5-azabicyclo[2.2.1]heptane (from Peak 2) (Single Unknown Isomer 1, Rt=5.203 min; Single Unknown Isomer 2, Rt=5.841 min)

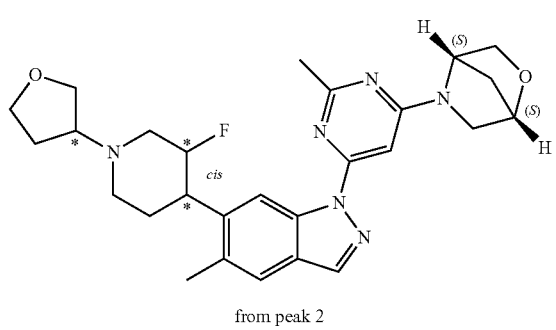

from peak 2

The title compound was prepared by a procedure similar to that described for E148 and E149 starting from a mixture of cis-6-(3-fluoro-1-(tetrahydrofuran-3-yl)piperidin-4-yl)-5-methyl-1H-indazole, (1S,4S)-5-(6-iodo-2-methylpyrimidin-4-yl)-2-oxa-5-azabicyclo-[2.2.1]heptane, CuI and $K_3PO_4$ in toluene and N,N'-dimethylethylenediamine at 90° C. for 2 h.

Prep-HPLC

Method: Column: AD-H; Column size: 0.46 cm I.D.×15 cm L; Mobile phase: $CO_2$:EtOH (0.1% $NH_3.H_2O$)=60:40; Flow rate: 0.5 mL/min; Wave length: UV 254 nm; Temperature: 25° C.; Sample solution in EtOH.

Single Unknown Isomer 1 (peak 1, E150)

White solid (Rt=5.203 min, 18 mg, 11% yield)

$^1$H NMR (400 MHz, CDCl$_3$) δ 8.89 (s, 1H), 8.06 (s, 1H), 7.52 (s, 1H), 6.67 (br, 1H), 5.26 (br, 0.45H), 4.95~4.82 (m, 1H), 4.74 (br, 1H), 4.00~3.99 (m, 1H), 3.98 (s, 3H), 3.94~3.85 (m, 1H), 3.75~3.71 (m, 1H), 3.54~3.46 (m, 3H), 3.19~3.07 (m, 2H), 2.87~2.84 (m, 1H), 2.62 (s, 3H), 2.47 (s, 3H), 2.28~2.24 (m, 2H), 2.11~2.00 (m, 1H), 1.98~1.89 (m, 5H).

$^{19}$F NMR (376 MHz, CDCl$_3$) δ 183.17 (s, 1F),

LC-MS [mobile phase: from 80% water (0.1% FA) and 5% MeCN (0.1% FA) to 20% water (0.1% FA) and 95% MeCN (0.1% FA) in 2.6 min]: Rt=0.940 min; MS Calcd: 492, MS Found: 493.3 [M+H]$^+$.

Chiral HPLC [AD-H; Column size: 0.46 cm I.D.×15 cm L; Injection: 2 μl; Mobile phase: HEP:EtOH (0.1% DEA)=60:40; Flow rate: 0.5 mL/min; Wave length: UV 254 nm; Temperature: 25° C.]: Rt=5.203 min, ee 100%;

Single Unknown Isomer 2 (peak 2, E151)

White solid (Rt=5.841 min, 18 mg, 11% yield)

$^1$H NMR (400 MHz, CDCl3) δ 8.89 (s, 1H), 8.06 (s, 1H), 7.52 (s, 1H), 6.66 (br, 1H), 5.26 (br, 0.50H), 4.94~4.81 (m, 1H), 4.74 (br, 1H), 4.00~3.99 (m, 1H), 3.94 (s, 3H), 3.92~3.78 (m, 2H), 3.52 (br, 2H), 3.29~3.27 (m, 1H), 3.26~3.19 (m, 1H), 3.17~3.15 (m, 2H), 2.62 (s, 3H), 2.48 (s, 3H), 2.36~2.34 (m, 1H), 2.25~2.13 (m, 1H), 2.11~2.00 (m, 1H), 1.98~1.89 (m, 5H).

$^{19}$F NMR (376 MHz, CDCl$_3$) δ 183.28 (s, 1F)

LC-MS [mobile phase: from 80% water (0.1% FA) and 5% MeCN (0.1% FA) to 20% water (0.1% FA) and 95% MeCN (0.1% FA) in 2.6 min]: Rt=0.933 min; MS Calcd: 492, MS Found: 493.3 [M+H]$^+$.

Chiral HPLC [AD-H; Column size: 0.46 cm I.D.×15 cm L; Injection: 2 μl; Mobile phase: HEP:EtOH (0.1% DEA)=60:40; Flow rate: 0.5 mL/min; Wave length: UV 254 nm; Temperature: 25° C.]: Rt=5.841 min, ee 100%;

Examples 152 and 153

(5-(2-methyl-6-(5-methyl-6-(1-(tetrahydrofuran-3-yl)piperidin-4-yl)-1H-indazol-1-yl)pyrimidin-4-yl)-2-oxa-5-azabicyclo[2.2.1]heptan-1-yl)methanol

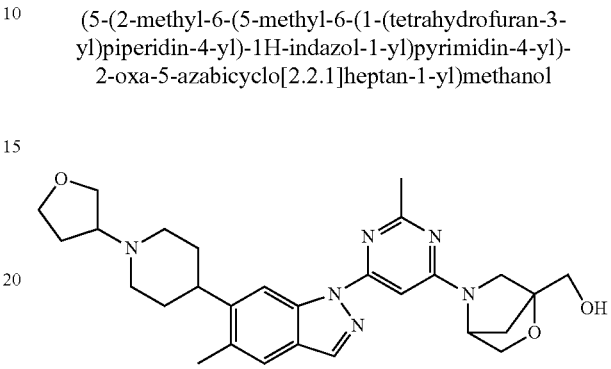

The title compound was prepared by a procedure similar to that described for E148 and E149 starting from a mixture of 5-methyl-6-(1-(tetrahydrofuran-3-yl)piperidin-4-yl)-1H-indazole and (5-(6-iodo-2-methylpyrimidin-4-yl)-2-oxa-5-azabicyclo[2.2.1]heptan-1-yl)methanol in toluene, CuI, $K_3PO_4$ and N,N'-dimethylethylenediamine at 100° C. for 4 h.

LC-MS [mobile phase: from 90% water (0.1% FA) and 10% MeCN (0.1% FA) to 5% water (0.1% FA) and 95% MeCN (0.1% FA) in 2.0 min]: Rt=1.10 min; MS Calcd: 504.28, MS Found: 505.4 [M+H]$^+$.

Chiral Prep-HPLC

Method: Column: AD-H; Column size: 0.46 cm I.D.×15 cm L; Mobile phase: $CO_2$: EtOH (0.1% $NH_3.H_2O$)=60:40; Flow rate: 0.5 ml; Wave length: UV 254 nm; Temperature: 25° C.; Sample solution in EtOH Single Unknown Isomer 1 (Peak 1, E152)

White solid (Rt=2.515 min, 70 mg, yield: 14%)

$^1$H NMR (400 MHz, CDCl$_3$) δ 8.80 (s, 1H), 8.04 (s, 1H), 7.49 (s, 1H), 6.71~6.67 (m, 1H), 6.36~6.27 (m, 1H), 4.05~3.94 (m, 6H), 3.87~3.81 (m, 1H), 3.74~3.70 (m, 1H), 3.58~3.42 (m, 2H), 3.21~3.19 (m, 1H), 3.06~2.97 (m, 2H), 2.87~2.80 (m, 1H), 2.62 (s, 3H), 2.46 (s, 3H), 2.30~2.20 (m, 2H), 2.14~2.08 (m, 1H), 2.08~2.03 (m, 2H), 2.01~1.91 (m, 6H).

LC-MS [mobile phase: from 80% water (0.1% FA) and 20% MeCN (0.1% FA) to 5% water (0.1% FA) and 95% MeCN (0.1% FA) in 2.0 min]: Rt=1.05 min; MS Calcd: 504.28, MS Found: 505.3 [M+H]$^+$.

Chiral HPLC [AD-H; Column size: 0.46 cm I.D.×15 cm L; Injection: 2 μl; Mobile phase: HEP:EtOH (0.1% DEA)=60:40; Flow rate: 0.5 ml; Wave length: 254 nm; Temperature: 25° C.]: Rt=2.515 min, ee 99.2%;

Single Unknown Isomer 2 (Peak 2, E153)

White solid (Rt=2.976 min, 70 mg, yield: 14%).

$^1$H NMR (400 MHz, CDCl$_3$) δ 8.80 (s, 1H), 8.04 (s, 1H), 7.49 (s, 1H), 6.71~6.67 (m, 1H), 6.36~6.27 (m, 1H), 4.05~3.94 (m, 6H), 3.87~3.81 (m, 1H), 3.74~3.70 (m, 1H), 3.60~3.44 (m, 2H), 3.21~3.19 (m, 1H), 3.06~2.97 (m, 2H), 2.85~2.82 (m, 1H), 2.62 (s, 3H), 2.46 (s, 3H), 2.30~2.20 (m, 2H), 2.14~2.08 (m, 1H), 2.07~2.03 (m, 2H), 2.00~1.88 (m, 6H).

LC-MS [mobile phase: from 80% water (0.1% FA) and 20% MeCN (0.1% FA) to 5% water (0.1% FA) and 95% MeCN (0.1% FA) in 2.0 min]: Rt=0.95 min; MS Calcd: 504.28, MS Found: 505.3 [M+H]⁺.

Chiral HPLC [AD-H; Column size: 0.46 cm I.D.×15 cm L; Injection: 2 μl; Mobile phase: HEP:EtOH (0.1% DEA)= 60:40; Flow rate: 0.5 ml; Wave length: 254 nm; Temperature: 25° C.]: Rt=2.976 min, ee 99.6%;

Example 154

3-(4-(1-(6-((1R,4R)-2-oxa-5-azabicyclo[2.2.1]hep-tan-5-yl)-2-methylpyrimidin-4-yl)-5-methyl-1H-indazol-6-yl)-3-fluoropiperidin-1-yl)propanoic Acid (Rt=6.091 min, from Peak 1)

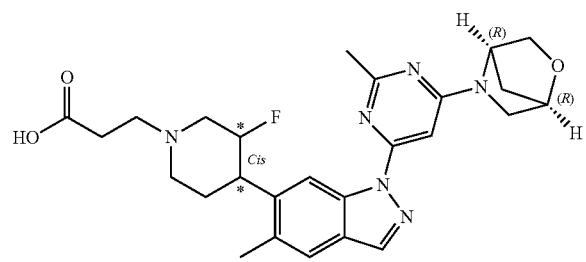

A mixture of methyl 3-(4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidin-1-yl)propanoate (100 mg, 0.20 mmol) and LiOH (14 mg, 0.60 mmol) in MeOH/H₂O (5 mL/1 mL) was stirred at rt overnight. The reaction mixture was concentrated, adjusted to PH=7-8 with 1 N HCl (5 mL) and extracted with DCM (50 mL×3). The combined organic parts were washed with brine (50 mL), dried over Na₂SO₄, filtered and concentrated. The residue was purified by SGC (DCM→DCM:MeOH=10:1) to give the title product as a white solid (50 mg, yield: 52%).

¹H NMR (400 MHz, CDCl₃): δ 8.94 (s, 1H), 8.07 (s, 1H), 7.54 (s, 1H), 6.66 (br, 1H), 5.29 (br, 0.5H), 4.99~4.82 (m, 1H), 4.74 (br, 1H), 3.90~3.89 (m, 2H), 3.57~3.52 (m, 2H), 3.23~3.20 (m, 2H), 2.95~2.88 (m, 2H), 2.65~2.61 (m, 2H), 2.57 (s, 3H), 2.53 (s, 3H), 2.53~2.40 (m, 3H), 2.13~2.09 (m, 1H), 2.04~1.92 (m, 3H).

¹⁹F NMR (376 MHz, CDCl₃): δ 183.82 (s)

LC-MS [mobile phase: from 80% water (0.1% FA) and 20% MeCN (0.1% FA) to 5% water (0.1% FA) and 95% MeCN (0.1% FA) in 2.6 min]: Rt=0.907 min; MS Calcd: 494.5, MS Found: 495.3 [M+H]⁺.

Chiral HPLC [Injection: 5.00 μl; Run time: 10.0 minutes; Mobile phase: CO₂/EtOH/MeCN/DEA 75/21/4/0.03, 1.8 mL/min, IC, 3 μm, 3×100 (Daicel) Wave length: UV 254 nm, Rt=6.091 min, ee: 99.1%

Example 155

3-(4-(1-(6-((1R,4R)-2-oxa-5-azabicyclo[2.2.1]hep-tan-5-yl)-2-methylpyrimidin-4-yl)-5-methyl-1H-indazol-6-yl)-3-fluoropiperidin-1-yl)propanoic Acid (from Peak 2) (Rt=6.956 min)

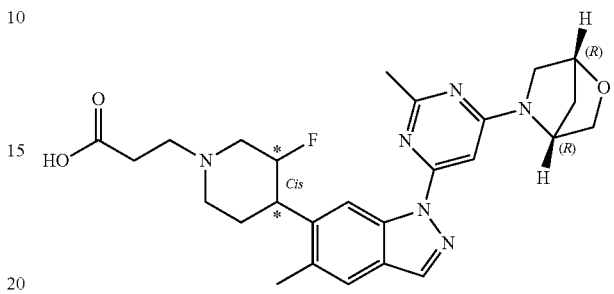

The title compound was prepared by a procedure similar to that described for E154 starting from a solution of methyl 3-(4-(1-(6-((1R,4R)-2-oxa-5-azabicyclo[2.2.1]heptan-5-yl)-2-methylpyrimidin-4-yl)-5-methyl-1H-indazol-6-yl)-3-fluoropiperidin-1-yl) (from Peak 2) in MeOH and a solution of LiOH.H₂O in water at room temperature.

¹H NMR (400 MHz, CDCl₃): δ 8.94 (s, 1H), 8.08 (s, 1H), 7.54 (s, 1H), 6.67 (br, 0.6H), 5.29 (br, 0.4H), 5.02~4.95 (m, 0.5H), 4.90~4.84 (m, 0.5H), 4.75 (br, 1H), 3.93~3.88 (m, 2H), 3.58~3.45 (m, 3H), 3.24~3.17 (m, 2H), 2.97~2.91 (m, 2H), 2.65~2.60 (m, 2H), 2.61 (s, 3H), 2.48 (s, 3H), 2.53~2.39 (m, 3H), 2.13~2.04 (m, 1H), 2.04~1.95 (m, 3H).

¹⁹F NMR (376 MHz, CDCl3): δ 183.97 (s)

LC-MS [mobile phase: from 90% water (0.1% FA) and 10% MeCN (0.1% FA) to 5% water (0.1% FA) and 95% MeCN (0.1% FA) in 9 min]: Rt=3.54 min; MS Calcd: 494.2, MS Found: 495.3 [M+H]⁺.

Chiral HPLC [method: Column: IC Column size: 3×100 mm, 3 μm (Daicel) (UPC). Injection: 5 ul, Mobile phase: CO₂/EtOH/MeCN/DEA: 75/21/4/0.03, Flow rate: 1.8 mL/min, Wave length: UV 254 nm, Temperature: 35° C.]: Rt=6.956 min, ee: 100%

Example 156

3-(4-(1-(6-((1S,4S)-2-oxa-5-azabicyclo[2.2.1]hep-tan-5-yl)-2-methylpyrimidin-4-yl)-5-methyl-1H-indazol-6-yl)-3-fluoropiperidin-1-yl)propanoic Acid (Rt=4.493 min, from Peak 1)

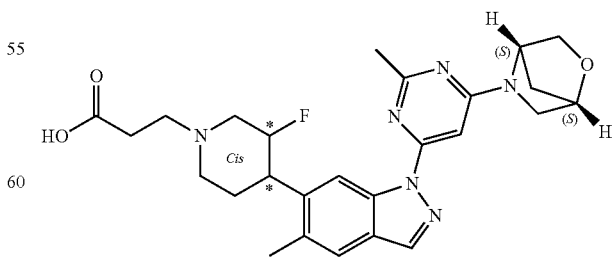

The title compound was prepared by a procedure similar to that described for E154 starting from a mixture of methyl 3-(4-(1-(6-((1S,4S)-2-oxa-5-azabicyclo[2.2.1]heptan-5-yl)-

2-methylpyrimidin-4-yl)-5-methyl-1H-indazol-6-yl)-3-fluoropiperidin-1-yl)propanoate and LiOH in MeOH/H₂O at rt overnight.

¹H NMR (400 MHz, CDCl₃): δ 8.94 (s, 1H), 8.07 (s, 1H), 7.54 (s, 1H), 6.66 (br, 1H), 5.29 (br, 0.5H), 4.98~4.85 (m, 1H), 4.74 (br, 1H), 3.90 (s, 2H), 3.57~3.52 (m, 2H), 3.3~3.20 (m, 2H), 2.91~2.90 (m, 2H), 2.64~2.60 (m, 2H), 2.60 (s, 3H), 2.52 (s, 3H), 2.52~2.39 (m, 3H), 2.10~2.09 (m, 1H), 2.04~1.96 (m, 3H).

¹⁹F NMR (376 MHz, CDCl₃): δ 183.83 (s)

LC-MS [mobile phase: from 80% water (0.1% FA) and 20% MeCN (0.1% FA) to 5% water (0.1% FA) and 95% MeCN (0.1% FA) in 2.6 min]: Rt=0.907 min; MS Calcd: 494.5, MS Found: 495.3 [M+H]⁺.

Chiral HPLC [method: Injection: 6.00 μl; Run time: 10.0 minutes; Mobile phase: CO₂/EtOH/MeCN/DEA 75/21/4/0.03, Flow rate: 1.8 mL/min, IC, 3 μm, 3×100 (Daicel) Wave length: UV 254 nm, Rt=4.493 min, ee: 100%

Example 157

3-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)propanoic Acid (from Peak 2) (Rt=5.067 min)

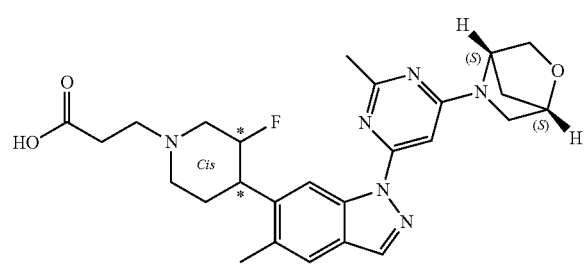

The title compound was prepared by a procedure similar to that described for E154 starting from a solution of methyl 3-(4-(1-(6-((1S,4S)-2-oxa-5-azabicyclo[2.2.1]heptan-5-yl)-2-methylpyrimidin-4-yl)-5-methyl-1H-indazol-6-yl)-3-fluoropiperidin-1-yl)propanoate (from Peak 2) in MeOH and a solution of LiOH.H₂O in water.

¹H NMR (400 MHz, CDCl₃): δ 8.94 (s, 1H), 8.08 (s, 1H), 7.55 (s, 1H), 6.66 (br, 0.6H), 5.30 (br, 0.4H), 5.01-4.94 (m, 0.5H), 4.89-4.82 (m, 0.5H), 4.75 (br, 1H), 3.93-3.88 (m, 2H), 3.58-3.46 (m, 3H), 3.27-3.17 (m, 2H), 2.97-2.87 (m, 2H), 2.65-2.60 (m, 2H), 2.61 (s, 3H), 2.49 (s, 3H), 2.53-2.39 (m, 3H), 2.13-2.04 (m, 1H), 2.04-1.94 (m, 3H).

¹⁹F NMR (376 MHz, CDCl₃): δ 183.83 (s)

LC-MS [mobile phase: from 90% water (0.1% FA) and 10% MeCN (0.1% FA) to 5% water (0.1% FA) and 95% MeCN (0.1% FA) in 9 min]: Rt=3.56 min; MS Calcd: 494.2, MS Found: 495.2 [M+H]⁺.

Chiral HPLC [method: Column: IC Column size: 3×100 mm, 3 μm (Daicel) (UPC). Injection: 6 μl, Mobile phase: CO₂/EtOH/MeCN/DEA: 75/21/4/0.03, Flow rate: 1.8 mL/min, Wave length: UV 254 nm, Temperature: 35° C.]: Rt=5.067 min, ee: 98.72%

Example 158

3-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propanoic Acid (Rt=5.142 min, from Peak 1)

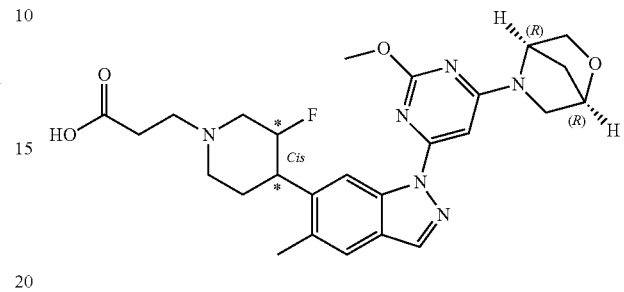

The title compound was prepared by a procedure similar to that described for E154 starting from a mixture of methyl 3-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propanoate and LiOH in MeOH/H₂O at rt overnight.

¹H NMR (400 MHz, CDCl₃): δ 8.88 (s, 1H), 8.08 (s, 1H), 7.55 (s, 1H), 6.66 (br, 1H), 5.26 (br, 0.5H), 4.90~4.77 (m, 1H), 4.73 (br, 1H), 4.15 (s, 3H), 3.92~3.87 (m, 2H), 3.64~3.43 (m, 2H), 3.21~3.17 (m, 2H), 2.89~2.85 (m, 2H), 2.65~2.61 (m, 2H), 2.48 (s, 3H), 2.44~2.34 (m, 3H), 2.06~2.04 (m, 1H), 2.04~1.89 (m, 3H).

¹⁹F NMR (376 MHz, CDCl3): δ 183.97 (s)

LC-MS [mobile phase: from 80% water (0.1% FA) and 20% MeCN (0.1% FA) to 5% water (0.1% FA) and 95% MeCN (0.1% FA) in 2.6 min]: Rt=0.989 min; MS Calcd: 510, MS Found: 511.3 [M+H]⁺.

Chiral HPLC [method: Injection: 3.00 μl; Run time: 10.0 minutes; Mobile phase: CO₂/EtOH/MeCN/DEA 70/26/4/0.03, Flow rate: 1.8 mL/min, IC, 3 μm, 3×100 (Daicel) Wave length: UV 254 nm]: Rt=5.142 min, ee: 100%

Example 159

3-(4-(1-(6-((1R,4R)-2-oxa-5-azabicyclo[2.2.1]heptan-5-yl)-2-methoxypyrimidin-4-yl)-5-methyl-1H-indazol-6-yl)-3-fluoropiperidin-1-yl)propanoic Acid (from Peak 2) (Rt=7.355 min)

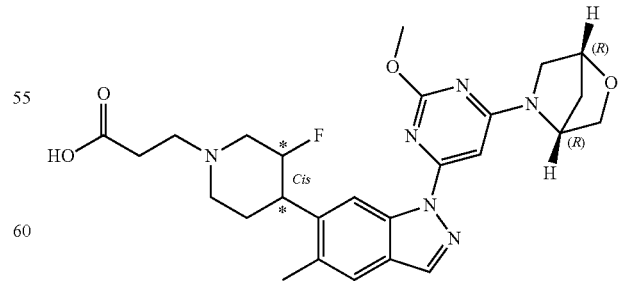

The title compound was prepared by a procedure similar to that described for E154 starting from a solution of methyl 3-(4-(1-(6-((1R,4R)-2-oxa-5-azabicyclo[2.2.1]heptan-5-yl)-2-methoxypyrimidin-4-yl)-5-methyl-1H-indazol-6-yl)-3- fluoropiperidin-1-yl)propanoate (from Peak 2) in MeOH and a solution of LiOH.H₂O in water.

¹H NMR (400 MHz, CDCl₃): δ 8.89 (s, 1H), 8.09 (s, 1H), 7.56 (s, 1H), 6.56 (br, 0.5H), 5.27 (br, 0.5H), 4.93~4.87 (m, 0.5H), 4.82~4.74 (m, 0.5H), 4.74 (br, 1H), 4.13 (s, 3H), 3.93~3.87 (m, 2H), 3.56~3.44 (m, 3H), 3.27~3.18 (m, 2H), 2.94~2.84 (m, 2H), 2.62 (t, J=6.4 Hz, 2H), 2.49 (s, 3H), 2.47~2.36 (m, 3H), 2.12~2.08 (m, 1H), 2.00~1.86 (m, 3H).

¹⁹F NMR (376 MHz, CDCl₃): δ 183.96 (s)

LC-MS [mobile phase: from 90% water (0.1% FA) and 10% MeCN (0.1% FA) to 5% water (0.1% FA) and 95% MeCN (0.1% FA) in 9 min]: Rt=4.04 min; MS Calcd: 510.2, MS Found: 511.2 [M+H]⁺.

Chiral HPLC [method: Column: IC Column size: 3×100 mm, 3 μm (Daicel) (UPC). Injection: 6 μl, Mobile phase: CO₂/EtOH/MeCN/DEA: 70/26/4/0.03, Flow rate: 1.8 mL/min, Wave length: UV 254 nm, Temperature: 35° C.]: Rt=7.355 min, ee: 100%

Example 160

3-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propanoic Acid (Rt=4.028 min, from Peak 1)

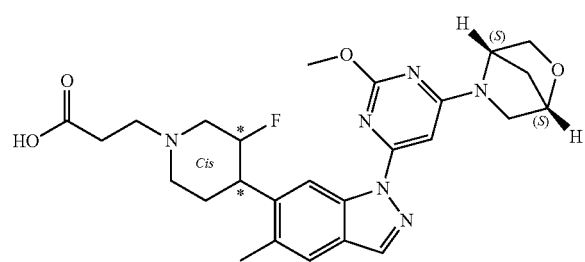

The title compound was prepared by a procedure similar to that described for E154 starting from a mixture of methyl 3-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propanoate and LiOH in MeOH/H₂O (5 mL/1 mL) at rt overnight.

¹H NMR (400 MHz, CDCl₃): δ 8.88 (s, 1H), 8.09 (s, 1H), 7.55 (s, 1H), 6.66 (br, 1H), 5.26 (br, 0.5H), 4.91~4.73 (m, 1H), 4.73 (br, 1H), 4.15 (s, 3H), 3.93~3.87 (m, 2H), 3.56~3.47 (m, 2H), 3.21~3.18 (m, 2H), 2.90~2.88 (m, 2H), 2.63~2.57 (m, 2H), 2.49 (s, 3H), 2.47~2.36 (m, 3H), 2.11~2.00 (m, 1H), 2.00~1.86 (m, 3H).

¹⁹F NMR (376 MHz, CDCl₃): δ183.96 (s)

LC-MS [mobile phase: from 80% water (0.1% FA) and 20% MeCN (0.1% FA) to 5% water (0.1% FA) and 95% MeCN (0.1% FA) in 2.6 min]: Rt=0.988 min; MS Calcd: 510, MS Found: 511.3 [M+H]⁺.

Chiral HPLC [method: Injection: 6.50 μl; Run time: 10.0 minutes; Mobile phase: CO₂/EtOH/MeCN/DEA 70/26/4/0.03, Flow rate: 1.8 mL/min, IC, 3 μm, 3×100 (Daicel) Wave length: UV 254 nm] Rt=4.028 min, ee: 100%

Example 161

3-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propanoic Acid (from Peak 2) (Rt=6.143 min)

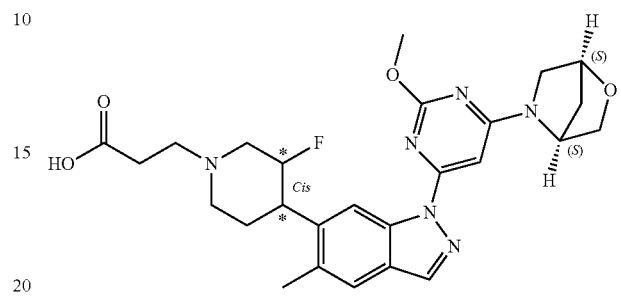

The title compound was prepared by a procedure similar to that described for E154 starting from a solution of methyl 3-(4-(1-(6-((1S,4S)-2-oxa-5-azabicyclo[2.2.1]heptan-5-yl)-2-methoxypyrimidin-4-yl)-5-methyl-1H-indazol-6-yl)-3-fluoropiperidin-1-yl)propanoate (from Peak 2) in MeOH and a solution of LiOH.H₂O in water.

¹H NMR (400 MHz, CDCl₃): δ 8.89 (s, 1H), 8.09 (s, 1H), 7.56 (s, 1H), 6.55 (br, 0.5H), 5.27 (br, 0.5H), 4.93~4.86 (m, 0.5H), 4.81~4.74 (m, 0.5H), 4.74 (br, 1H), 4.13 (s, 3H), 3.93~3.87 (m, 2H), 3.56~3.46 (m, 3H), 3.27~3.18 (m, 2H), 2.94~2.88 (m, 2H), 2.62 (t, J=6.4 Hz, 2H), 2.49 (s, 3H), 2.47~2.37 (m, 3H), 2.12~2.09 (m, 1H), 1.98~1.87 (m, 3H).

¹⁹F NMR (376 MHz, CDCl₃): δ 183.97 (s)

LC-MS [mobile phase: from 90% water (0.1% FA) and 10% MeCN (0.1% FA) to 5% water (0.1% FA) and 95% MeCN (0.1% FA) in 9 min]: Rt=4.07 min; MS Calcd: 510.2, MS Found: 511.3 [M+H]⁺.

Chiral HPLC [method: Column: IC Column size: 3×100 mm, 3 μm (Daicel) (UPC). Injection: 6.5 μl, Mobile phase: CO₂/EtOH/MeCN/DEA: 70/26/4/0.03, Flow rate: 1.8 mL/min, Wave length: UV 254 nm, Temperature: 35° C.]: Rt=6.143 min, ee: 100%.

Example 162

3-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)propanoic Acid

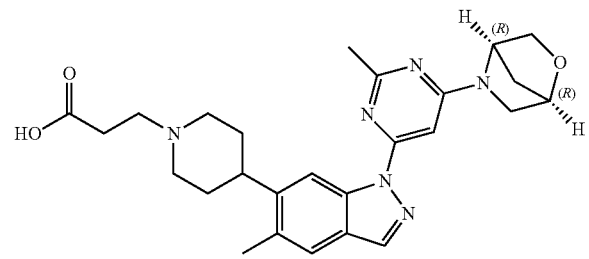

The title compound was prepared by a procedure similar to that described for E154 starting from a solution of methyl 3-(4-(1-(6-((1R,4R)-2-oxa-5-azabicyclo[2.2.1]heptan-5-yl)-

2-methylpyrimidin-4-yl)-5-methyl-1H-indazol-6-yl)piperidin-1-yl)propanoate in MeOH/THF/water and LiOH.H₂O at rt.

¹H NMR (400 MHz, DMSO) δ 8.74 (s, 1H), 8.30 (s, 1H), 7.62 (s, 1H), 6.64-6.59 (m, 0.5H), 5.17 (br, 0.5H), 4.74-4.69 (m, 1H), 3.82-3.80 (m, 1H), 3.69-3.67 (m, 1H), 3.53-3.51 (m, 2H), 3.14-3.11 (d, J=9.6 Hz, 2H), 2.90-2.88 (m, 2H), 2.73-2.67 (m, 3H), 2.52 (s, 3H), 2.48 (s, 3H), 2.32-2.26 (m, 2H), 1.88-1.73 (m, 4H), 1.70-1.64 (m, 2H).

LC-MS [mobile phase: from 90% water (0.1% FA) and 10% MeCN (0.1% FA) to 5% water (0.1% FA) and 95% MeCN (0.1% FA) in 2.6 min]: Rt=1.207 min; MS Calcd: 476.25, MS Found: 477.2 [M+H]⁺.

Example 163

Methyl 3-(4-(1-(6-((1S,4S)-2-oxa-5-azabicyclo[2.2.1]heptan-5-yl)-2-methylpyrimidin-4-yl)-5-methyl-1H-indazol-6-yl)piperidin-1-yl)propanoate

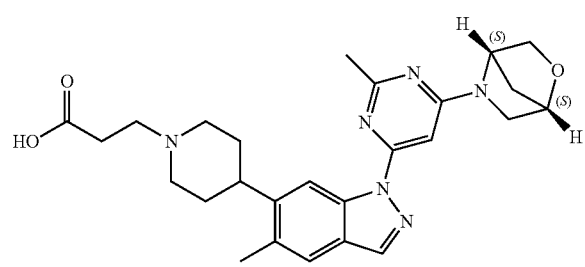

The title compound was prepared by a procedure similar to that described for E154 starting from a solution of (1S,4S)-5-(2-methyl-6-(5-methyl-6-(piperidin-4-yl)-1H-indazol-1-yl)pyrimidin-4-yl)-2-oxa-5-azabicyclo[2.2.1]heptane in MeOH and methyl acrylate at rt then 70° C. for 2 h.

LC-MS [mobile phase: from 90% water (0.1% FA) and 10% MeCN (0.1% FA) to 5% water (0.1% FA) and 95% MeCN (0.1% FA) in 2.0 min]: Rt=1.21 min; MS Calcd.: 490.3, MS Found: 491.2 [M+H]⁺.

Example 164

3-(4-(1-(6-((1R,4R)-2-oxa-5-azabicyclo[2.2.1]heptan-5-yl)-2-methoxypyrimidin-4-yl)-5-methyl-1H-indazol-6-yl)piperidin-1-yl)propanoic Acid

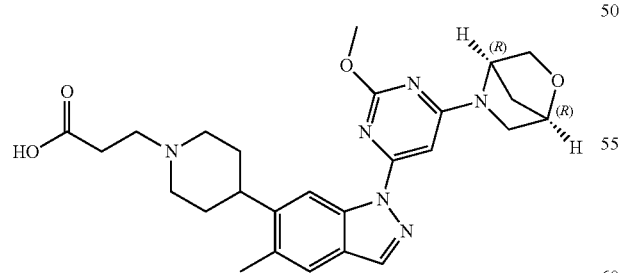

The title compound was prepared by a procedure similar to that described for E154 starting from a solution of methyl 3-(4-(1-(6-((1R,4R)-2-oxa-5-azabicyclo[2.2.1]heptan-5-yl)-2-methoxypyrimidin-4-yl)-5-methyl-1H-indazol-6-yl)piperidin-1-yl)propanoate in MeOH/THF/water and LiOH.H₂O at rt for 16 h.

¹H NMR (400 MHz, DMSO) δ 8.67 (s, 1H), 8.31 (s, 1H), 7.62 (s, 1H), 6.48-6.46 (m, 0.5H), 5.12 (br, 0.6H), 4.72 (br, 1H), 4.01 (s, 3H), 3.81-3.79 (m, 1H), 3.71-3.68 (m, 1H), 3.54-3.51 (m, 2H), 3.09-3.07 (d, J=10.8 Hz, 2H), 2.89-2.84 (m, 2H), 2.73-2.68 (m, 3H), 2.42 (s, 3H), 2.26-2.20 (m, 2H), 1.89-1.82 (m, 4H), 1.68-1.63 (m, 2H).

LC-MS [mobile phase: from 90% water (0.1% FA) and 10% MeCN (0.1% FA) to 5% water (0.1% FA) and 95% MeCN (0.1% FA) in 2.6 min]: Rt=1.254 min; MS Calcd: 492.25, MS Found: 493.2 [M+H]⁺.

Example 165

3-(4-(1-(6-((1S,4S)-2-oxa-5-azabicyclo[2.2.1]heptan-5-yl)-2-methoxypyrimidin-4-yl)-5-methyl-1H-indazol-6-yl)piperidin-1-yl)propanoic Acid

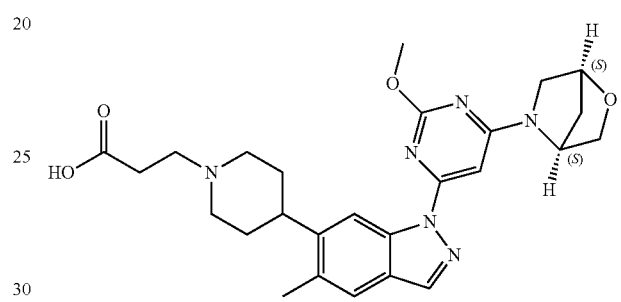

The title compound was prepared by a procedure similar to that described for E154 starting from a solution of methyl 3-(4-(1-(6-((1S,4S)-2-oxa-5-azabicyclo[2.2.1]heptan-5-yl)-2-methoxypyrimidin-4-yl)-5-methyl-1H-indazol-6-yl)piperidin-1-yl)propanoate and LiOH—H₂O in MeOH/THF/H₂O (1/1/1) at rt overnight.

¹H NMR (400 MHz, CDCl₃): δ 8.80 (s, 1H), 8.07 (s, 1H), 7.53 (s, 1H), 6.55 (s, 1H), 5.33 (s, 1H), 4.74 (s, 1H), 4.16 (s, 3H), 3.93~3.88 (m, 2H), 3.54~3.52 (m, 1H), 3.35~3.32 (m, 2H), 3.00~2.95 (m, 1H), 2.87~2.84 (m, 2H), 2.62~2.59 (m, 2H), 2.54~2.46 (m, 5H), 2.06~1.94 (m, 6H), 1.49~1.48 (m, 1H).

LC-MS [mobile phase: from 70% water (0.1% FA) and 30% MeCN (0.1% FA) to 5% water (0.1% FA) and 95% MeCN (0.1% FA) in 2.0 min]: Rt=0.96 min; MS Calcd.: 492.2, MS Found: 493.3[M+H]⁺.

Example 166

(5-(2-methyl-6-(5-methyl-6-(1-(oxetan-3-yl)piperidin-4-yl)-1H-indazol-1-yl)pyrimid-in-4-yl)-2-oxa-5-azabicyclo[2.2.1]heptan-1-yl)methanol

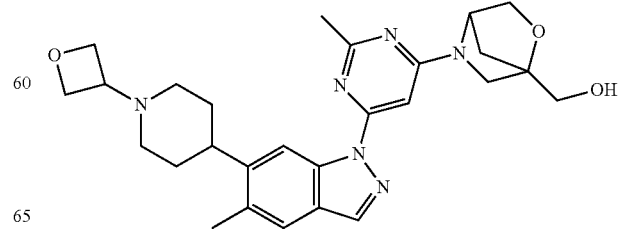

The title compound was prepared by a procedure similar to that described for E148 and E149 starting from a solution of (5-(6-iodo-2-methylpyrimidin-4-yl)-2-oxa-5-azabicyclo[2.2.1]heptan-1-yl)methanol in toluene, 5-methyl-6-(1-(oxetan-3-yl)piperidin-4-yl)-1H-indazole, CuI, K₃PO₄.3H₂O and N,N'-dimethylethylenediamine at 100° C. for 5 h.

¹H NMR (400 MHz, CDCl₃) δ 8.82 (s, 1H), 8.05 (s, 1H), 7.50 (s, 1H), 6.68 (br, 1H), 5.32 (br, 0.6H), 4.72 (d, J=6.4 Hz, 4H), 4.05~3.96 (m, 4H), 3.60~3.48 (m, 2H), 2.99~2.96 (m, 2H), 2.88~2.80 (m, 1H), 2.64 (s, 3H), 2.45 (s, 3H), 2.12~1.92 (m, 10H).

LC-MS [mobile phase: from 70% water (0.1% FA) and 30% MeCN (0.1% FA) to 5% water (0.1% FA) and 95% MeCN (0.1% FA) in 2.6 min]: Rt=0.831 min; MS Calcd: 490.3, MS Found: 491.2 [M+H]⁺.

Example 167

(5-(2-methoxy-6-(5-methyl-6-(1-(oxetan-3-yl)piperidin-4-yl)-1H-indazol-1-yl)pyrim-idin-4-yl)-2-oxa-5-azabicyclo[2.2.1]heptan-1-yl)methanol

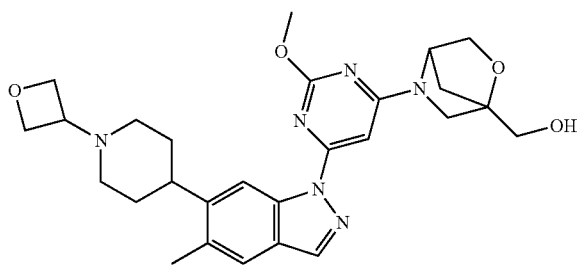 [SMILES: COc1nc(N2CC3(CO)CC2CO3)cc(-n2ncc3cc(C)c(C4CCN(C5COC5)CC4)cc32)n1]

The title compound was prepared by a procedure similar to that described for E148 and E149 starting from a solution of 5-methyl-6-(1-(oxetan-3-yl)piperidin-4-yl)-1H-indazole and (5-(6-iodo-2-methoxypyrimidin-4-yl)-2-oxa-5-azabicyclo[2.2.1]heptan-1-yl)methanol in toluene, CuI, K₃PO₄.3H₂O and N,N'-dimethylethylenediamine at 100° C. for 5 h.

¹H NMR (400 MHz, CDCl₃) δ 8.76 (s, 1H), 8.05 (s, 1H), 7.50 (s, 1H), 6.65 (s, 1H), 5.27 (s, 1H), 4.69~4.68 (d, J=4 Hz, 4H), 4.15 (s, 3H), 3.99 (s, 4H), 3.58~3.53 (m, 2H), 2.94~2.91 (d, J=12 Hz, 2H), 2.86~2.80 (m, 1H), 2.45 (s, 3H), 2.04~2.01 (m, 4H), 1.98~1.85 (m, 6H).

LC-MS [mobile phase: from 50% water (0.1% FA) and 50% MeCN (0.1% FA) to 5% water (0.1% FA) and 95% MeCN (0.1% FA) in 2.0 min]: Rt=0.75 min; MS Calcd: 506.6, MS Found: 507.2 [M+H]⁺.

Examples 168-169

4-(1-(6-(1-(hydroxymethyl)-2-oxa-5-azabicyclo[2.2.1]heptan-5-yl)-2-methylpyrimidin-4-yl)-5-methyl-1H-indazol-6-yl)tetrahydro-2H-pyran-3-ol

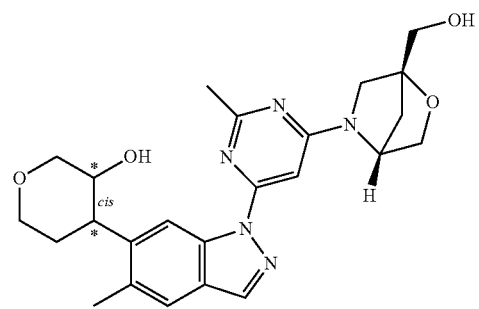 [SMILES: Cc1nc(N2C[C@@]3(CO)C[C@@H]2CO3)cc(-n2ncc3cc(C)c(C4CCOCC4O)cc32)n1]

The title compound was prepared by a procedure similar to that described for E148 and E149 starting from a suspension of 4-(5-methyl-1H-indazol-6-yl)tetrahydro-2H-pyran-3-ol and (5-(6-iodo-2-methylpyrimidin-4-yl)-2-oxa-5-azabicyclo[2.2.1]heptan-1-yl)methanol in toluene, CuI, K₃PO₄.3H₂O and DMEDA at 100° C. and for 4 hrs.

LC-MS [mobile phase: from 70% water (0.1% FA) and 30% MeCN (0.1% FA) to 5% water (0.1% FA) and 95% MeCN (0.1% FA) in 2.6 min]: Rt=1.02 min; MS Calcd.: 451.22, MS Found: 452.4 [M+H]⁺.

Chiral prep-HPLC:
AD-H, Column size: 0.46 cm I.D.×15 cm L, Mobile phase: CO₂:EtOH (0.1% NH₃.H₂O)=70:30, Flow rate: 0.5 mL/min, Wave length: UV 254 nm, Temperature: 25° C.

Single Unknown Isomer 1 (Peak 1, E168)
¹H NMR (400 MHz, CDCl₃): δ 8.77 (s, 1H), 7.96 (s, 1H), 7.48 (s, 1H), 6.44 (br, 1H), 5.12 (br, 1H), 4.23~4.19 (m, 1H), 4.13~4.10 (m, 1H), 4.06~4.03 (m, 1H), 3.99~3.94 (m, 3H), 3.85 (br, 1H), 3.57~3.51 (m, 1H), 3.39~3.34 (m, 2H), 3.13~3.07 (m, 2H), 2.57 (s, 3H), 2.51 (s, 3H), 2.32 (br, 1H), 1.94~1.92 (m, 1H), 1.84~1.75 (m, 3H).

Chiral HPLC [AD-H, Column size: 0.46 cm I.D.×15 cm L, Injection: 2 μl, Mobile phase: HEP:EtOH (0.1% DEA)=70:30, Flow rate: 0.5 mL/min, Wave length: UV 254 nm, Temperature: 25° C.]: Rt=7.590 min, ee: 100%

LC-MS [mobile phase: from 90% water (0.1% FA) and 10% MeCN (0.1% FA) to 5% water (0.1% FA) and 95% MeCN (0.1% FA) in 10.0 min]: Rt=4.76 min; MS Calcd.: 451.22, MS Found: 452.4 [M+H]⁺.

Single Unknown Isomer 2 (Peak 2, E169)
¹H NMR (400 MHz, CDCl₃): δ 8.81 (s, 1H), 8.02 (s, 1H), 7.52 (s, 1H), 6.55 (br, 1H), 5.28 (br, 1H), 4.22~4.19 (m, 1H), 4.12~4.07 (m, 1H), 4.04~4.03 (m, 1H), 3.97~3.91 (m, 4H), 3.58~3.51 (m, 1H), 3.41~3.33 (m, 3H), 3.13~3.06 (m, 1H), 2.59 (s, 3H), 2.51 (s, 3H), 2.19 (br, 1H), 1.86~1.84 (m, 1H), 1.75~1.68 (m, 3H).

Chiral HPLC [AD-H, Column size: 0.46 cm I.D.×15 cm L, Injection: 2 μl, Mobile phase: HEP:EtOH (0.1% DEA)=70:30, Flow rate: 0.5 mL/min, Wave length: UV 254 nm, Temperature: 25° C.]: Rt=17.880 min, ee: 100%

LC-MS [mobile phase: from 90% water (0.1% FA) and 10% MeCN (0.1% FA) to 5% water (0.1% FA) and 95% MeCN (0.1% FA) in 10.0 min]: Rt=4.78 min; MS Calcd.: 451.22, MS Found: 452.4 [M+H]⁺.

Example 170

(1R,4R)-5-(2-methyl-6-(5-methyl-6-(1-(2-(methylsulfonyl)ethyl)piperidin-4-yl)-1H-indazol-1-yl)pyrimidin-4-yl)-2-oxa-5-azabicyclo[2.2.1]heptane

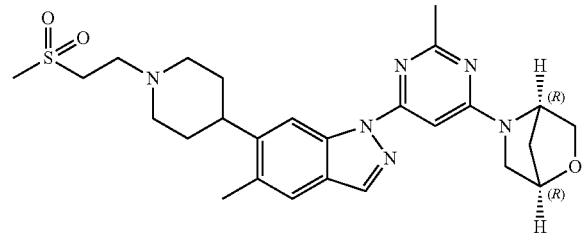

To a solution of tert-butyl (1R,4R)-5-(2-methyl-6-(5-methyl-6-(piperidin-4-yl)-1H-indazol-1-yl)pyrimidin-4-yl)-2-oxa-5-azabicyclo[2.2.1]heptane (100 mg, 0.25 mmol) in EtOH (5 mL) was added (methylsulfonyl)ethene (40 mg, 0.37 mmol). The reaction mixture was stirred at room temperature overnight, concentrated and purified by prep-HPLC to give the title product (73 mg, yield 59%) as a white solid.

Prep-HPLC method: Apparatus model: waters 2767Qda; column: SunFire 19×250 mm 10 μm; Flow rate: 30 mL/min; Wave length: 214 nm/254 nm; trigger: 254 nm; Mobile phase A: H$_2$O (0.1% FA), Mobile phase B: MeCN; Gradient:

| time | B % |
| --- | --- |
| 0 | 5 |
| 1 | 15 |
| 11 | 30 |
| 11.2 | 95 |
| 13 | 95 |
| 13.2 | 5 |
| 15 | 5 |

$^1$H NMR (400 MHz, d$_6$-DMSO): δ 8.68 (s, 1H), 8.27 (s, 1H), 7.67 (s, 1H), 7.21~6.79 (m, 1H), 5.28~5.10 (m, 1H), 4.81 (s, 1H), 3.94~3.90 (m, 2H), 3.85~3.68 (m, 7H), 3.56~3.52 (m, 1H), 3.36~3.30 (m, 3H), 3.13 (s, 3H), 2.70 (s, 3H), 2.53 (s, 3H), 2.22~2.09 (m, 6H).

LC-MS [mobile phase: from 80% water (0.1% FA) and 20% MeCN (0.1% FA) to 5% water (0.1% FA) and 95% MeCN (0.1% FA) in 2.6 min]: Rt=1.128 min; MS Calcd: 510.24, MS Found: 511.3 [M+H]$^+$.

Example 171-172

4-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)tetrahydrofuran-3-ol

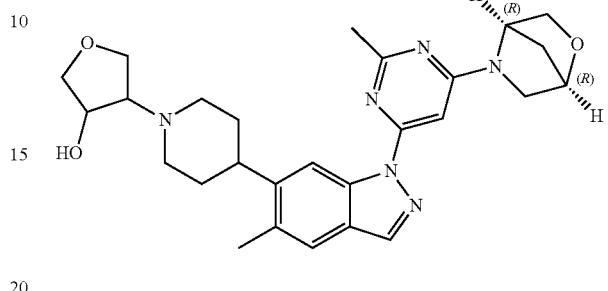

The title compound was prepared by a procedure similar to that described for E148 and E149 starting from a suspension of 4-(4-(5-methyl-1H-indazol-6-yl)piperidin-1-yl)tetrahydrofuran-3-ol, (1R,4R)-5-(6-iodo-2-methylpyrimidin-4-yl)-2-oxa-5-azabicyclo[2.2.1]heptane, CuI and K$_3$PO$_4$ in toluene and N$^1$,N$^2$-dimethylethane-1,2-diamine at 80° C. for 3 h.

$^1$H NMR (400 MHz, CDCl$_3$): δ 8.82 (s, 1H), 8.06 (s, 1H), 7.50 (s, 1H), 6.68 (s, 0.8H), 5.27 (br, 0.2H), 4.74 (s, 1H), 4.27~4.25 (m, 1H), 4.01~3.96 (m, 3H), 3.92~3.88 (m, 2H), 3.83~3.78 (m, 1H), 3.54~3.52 (m, 2H), 3.27~3.23 (m, 1H), 2.93~2.83 (m, 3H), 2.63 (s, 3H), 2.51~2.46 (m, 1H), 2.46 (s, 3H), 2.37~2.30 (m, 1H), 2.00~1.89 (m, 7H).

LC-MS [mobile phase: from 90% water (0.1% FA) and 10% MeCN (0.1% FA) to 5% water (0.1% FA) and 95% MeCN (0.1% FA) in 9 min]: Rt=2.63 min; MS Calcd: 490.3, MS Found: 491.4 [M+H]$^+$.

Chiral HPLC [column: IA Column size: 3×100 mm, 3 μm (Daicel) (UPC). Injection: 10 μl, Mobile phase: CO$_2$/MeOH/DEA: 75/25/0.025, Flow rate: 1.8 mL/min, Wave length: UV 254 nm, Temperature: 35° C.]: Rt=2.67 min, % Area: 1.99%, Rt=2.99 min, % Area: 1.50%, Rt=3.14 min, % Area: 46.89%, Rt=3.56 min, % Area: 49.62%.

Example 171 and 172

4-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)tetrahydrofuran-3-ol (Isomer 1 and Isomer 2)

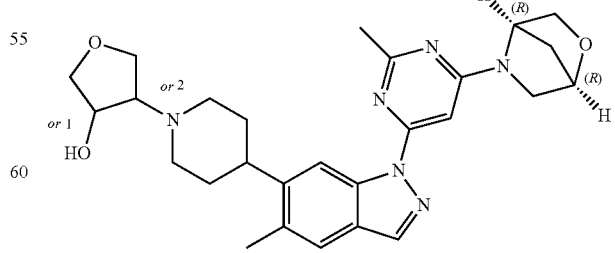

The compound 4-(4-(1-(6-((1R,4R)-2-oxa-5-azabicyclo[2.2.1]heptan-5-yl)-2-methylpyrimidin-4-yl)-5-methyl-1H-indazol-6-yl)piperidin-1-yl)tetrahydrofuran-3-ol (160 mg, 0.33 mmol) was purified by prep-HPLC (AD-H, 0.46 cm I.D.×15 cm L, Mobile phase: Supercritical CO$_2$:EtOH (0.1% NH$_3$H$_2$O)=70:30, Flow rate: 0.5 mL/min, Wave length: UV 254 nm, Temperature: 25° C.) followed by C$_{18}$ column eluting with MeCN/H$_2$O (from 5/95 to 95/5) to give the title product as two white solids.

Single Unknown Isomer 1 (E171)

$^1$H NMR (400 MHz, CDCl$_3$): δ 8.82 (s, 1H), 8.06 (s, 1H), 7.50 (s, 1H), 6.68 (br, 0.84H), 5.27 (br, 0.36H), 4.74 (br, 1H), 4.27~4.25 (m, 1H), 4.04~3.96 (m, 3H), 3.92~3.88 (m, 2H), 3.83~3.78 (m, 1H), 3.54~3.52 (m, 2H), 3.27~3.23 (m, 1H), 2.93~2.83 (m, 3H), 2.63 (s, 3H), 2.51~2.46 (m, 1H), 2.46 (s, 3H), 2.37~2.30 (m, 1H), 2.00~1.86 (m, 7H).

LC-MS [mobile phase: from 80% water (0.1% FA) and 20% MeCN (0.1% FA) to 5% water (0.1% FA) and 95% MeCN (0.1% FA) in 9 min]: Rt=4.06 min; MS Calcd: 490.3, MS Found: 491.4 [M+H]$^+$.

Chiral HPLC [AD-H 4.6×250 mm, 5 μm (Daicel) (CA-HPLC-023), Mobile phase: Hexane/EtOH (0.2% DEA)=60/40, flow rate: 0.5 mL/min, temperature: 35° C.]: Rt=9.622 min, ee: 100%

Single Unknown Isomer 2 (E172)

$^1$H NMR (400 MHz, CDCl$_3$): δ 8.82 (s, 1H), 8.06 (s, 1H), 7.50 (s, 1H), 6.67 (br, 0.8H), 5.27 (br, 0.3H), 4.74 (br, 1H), 4.27~4.25 (m, 1H), 4.01~3.96 (m, 3H), 3.92~3.88 (m, 2H), 3.83~3.78 (m, 1H), 3.54~3.52 (m, 2H), 3.27~3.23 (m, 1H), 2.93~2.83 (m, 3H), 2.63 (s, 3H), 2.51~2.46 (m, 1H), 2.46 (s, 3H), 2.37~2.30 (m, 1H), 2.00~1.89 (m, 7H).

LC-MS [mobile phase: from 80% water (0.1% FA) and 20% MeCN (0.1% FA) to 5% water (0.1% FA) and 95% MeCN (0.1% FA) in 9 min]: Rt=4.00 min; MS Calcd: 490.3, MS Found: 491.4 [M+H]$^+$.

Chiral HPLC [AD-H 4.6×250 mm, 5 μm (Daicel) (CA-HPLC-023), Mobile phase: Hexane/EtOH (0.2% DEA)=60/40, flow rate: 0.5 mL/min, temperature: 35° C.]: Rt=14.858 min, ee: 99.4%

Example 173

((1R,4R)-5-(2-methyl-6-(5-methyl-6-(tetrahydro-2H-pyran-4-yl)-1H-indazol-1-yl)pyrimidin-4-yl)-2-oxa-5-azabicyclo[2.2.1]heptan-1-yl)methanol

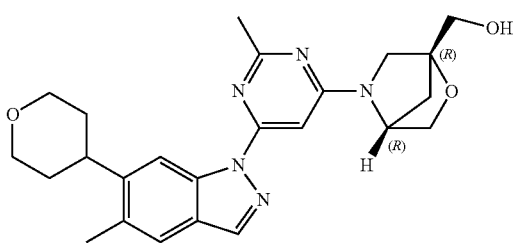

The title compound was prepared by a procedure similar to that described for E148 and E149 starting from a solution of 5-methyl-6-(tetrahydro-2H-pyran-4-yl)-1H-indazole in toluene, ((1R,4R)-5-(6-iodo-2-methylpyrimidin-4-yl)-2-oxa-5-azabicyclo[2.2.1]heptan-1-yl)methanol, CuI, K$_3$PO$_4$.3H$_2$O and N,N'-dimethylethylenediamine at 95° C. for 4 hrs.

$^1$H NMR (400 MHz, CDCl$_3$): δ 8.83 (s, 1H), 8.05 (s, 1H), 7.50 (s, 1H), 6.96 (s, 1H), 5.32 (s, 1H), 4.18~4.15 (m, 2H), 4.08~3.95 (m, 4H), 3.65~3.52 (m, 4H), 3.12~3.06 (m, 1H), 2.62 (s, 3H), 2.47 (s, 3H), 2.05~1.90 (m, 5H), 1.84~1.81 (m, 2H).

LC-MS [mobile phase: from 60% water (0.1% FA) and 40% MeCN (0.1% FA) to 5% water (0.1% FA) and 95% MeCN (0.1% FA) in 2.6 min]: Rt=1.31 min; MS Calcd.: 435.23, MS Found: 436.3 [M+H]$^+$.

Example 174

(1R,4R)-5-(2-methoxy-6-(5-methyl-6-(1-(2-(methylsulfonyl)ethyl)piperidin-4-yl)-1H-indazol-1-yl)pyrimidin-4-yl)-2-oxa-5-azabicyclo[2.2.1]heptane

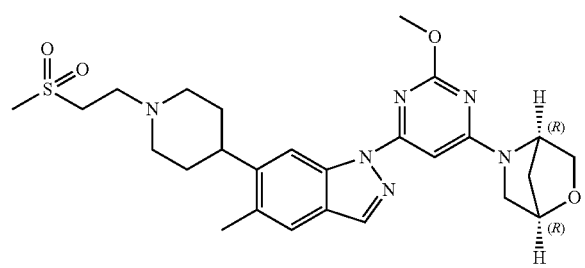

To a solution of tert-butyl (1R,4R)-5-(2-methoxy-6-(5-methyl-6-(piperidin-4-yl)-1H-indazol-1-yl)pyrimidin-4-yl)-2-oxa-5-azabicyclo[2.2.1]heptane (100 mg, 0.24 mmol) in EtOH (10 mL) was added (methylsulfonyl)ethene (51 mg, 0.48 mmol). The reaction mixture was stirred at room temperature overnight, concentrated and purified by prep-HPLC to give the title product (100 mg, yield 80%) as a white solid.

Chiral HPLC [method: Apparatus model: waters 2767; column: Inertsil ODS-3 20×250 mm 10 μm; Flow rate: 20 mL/min; Wave length: 214 nm/254 nm; trigger: 254 nm; Mobile phase A: H$_2$O (0.05% TFA), Mobile phase B: MeCN; Gradient:

| time | B % |
| --- | --- |
| 0 | 25 |
| 15.2 | 40 |
| 15.5 | 95 |
| 17.5 | 95 |
| 17.7 | 10 |
| 20 | 10 |

$^1$H NMR (400 MHz, d$_6$-DMSO): δ 10.01~9.96 (m, 1H), 8.63 (s, 1H), 8.35 (s, 1H), 7.68 (s, 1H), 6.82~6.50 (m, 1H), 5.11~4.83 (m, 1H), 4.73 (s, 1H), 4.01 (s, 3H), 3.83~3.70 (m, 6H), 3.61~3.53 (m, 3H), 3.29~3.21 (m, 3H), 3.16 (s, 3H), 2.51~2.47 (m, 3H), 2.12~2.09 (m, 2H), 1.95~1.87 (m, 4H).

$^{19}$F NMR (376 MHz, d$_6$-DMSO): δ −74.09 (s, 3F)

LC-MS [mobile phase: from 70% water (0.1% FA) and 30% MeCN (0.1% FA) to 5% water (0.1% FA) and 95% MeCN (0.1% FA) in 2.6 min]: Rt=0.861 min; MS Calcd: 526.24, MS Found: 527.2 [M+H]$^+$.

Example 175

(1R,4R)-5-(2-methoxy-6-(5-methyl-6-(3-((S)-tetra-hydrofuran-3-yl)-3-azabicyclo[3.1.0]hexan-6-yl)-1H-indazol-1-yl)pyrimidin-4-yl)-2-oxa-5-azabicyclo[2.2.1]hept-ane

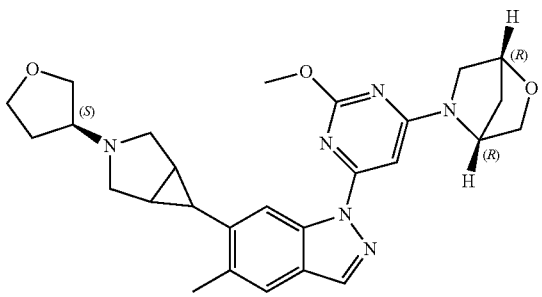

The title compound was prepared by a procedure similar to that described for E148 and E149 starting from a solution of 5-methyl-6-(3-((S)-tetrahydrofuran-3-yl)-3-azabicyclo[3.1.0]hexan-6-yl)-1H-indazole in toluene, (1R,4R)-5-(6-iodo-2-methoxypyrimidin-4-yl)-2-oxa-5-azabicyclo[2.2.1]heptane, CuI, K$_3$PO$_4$·3H$_2$O and N,N'-dimethylethylenediamine at 95° C. for 5 h.

$^1$H NMR (400 MHz, MeOD) δ 8.42 (s, 1H), 8.12 (s, 1H), 7.56 (s, 1H), 6.57 (s, 1H), 5.16 (s, 1H), 4.75 (s, 1H), 4.56 (s, 1H), 4.08 (s, 3H), 4.05~4.01 (m, 1H), 3.90~3.83 (m, 4H), 3.79~3.75 (m, 1H), 3.59~3.51 (m, 4H), 3.19~3.15 (m, 2H), 2.52 (s, 3H), 2.44~2.43 (m, 1H), 2.30~2.25 (m, 1H), 2.05~1.98 (m, 5H).

LC-MS [mobile phase: from 60% water (0.1% FA) and 40% MeCN (0.1% FA) to 5% water (0.1% FA) and 95% MeCN (0.1% FA) in 2.6 min]: Rt=0.82 min; MS Calcd: 488.25, MS Found: 489.2 [M+H]$^+$.

Example 176-177

5-(2-methyl-6-(5-methyl-6-(1-((S)-tetrahydrofuran-3-yl)piperidin-4-yl)-1H-indazol-1-yl)pyrimidin-4-yl)-2-oxa-5-azabicyclo[2.2.1]heptan-7-ol, TFA Salt

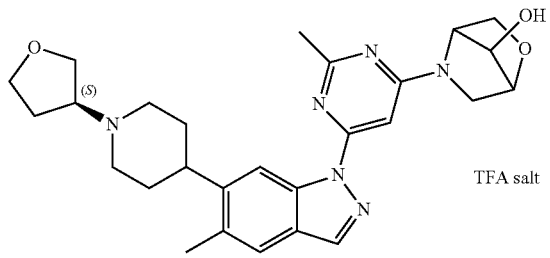

To a suspension of (S)-5-methyl-6-(1-(tetrahydrofuran-3-yl)piperidin-4-yl)-1H-indazole (150 mg, 0.53 mmol), 5-(6-iodo-2-methylpyrimidin-4-yl)-2-oxa-5-azabicyclo[2.2.1]hep-tan-7-ol (175 mg, 0.53 mmol), CuI (100 mg, 0.53 mmol) and K$_3$PO$_4$ (223 mg, 1.05 mmol) in toluene (10 mL) was added DMEDA (93 mg, 1.05 mmol). The resulting mixture was degassed with N$_2$ three times, stirred at 90° C. for 3 h, diluted with EtOAc (50 mL), washed with sat. NH$_4$Cl (50 mL) and brine (50 mL). The organic solution was dried over anhydrous Na$_2$SO$_4$ and concentrated. The residue was purified by prep-HPLC (Waters 2767/Qda, SunFire 19×250 mm 10 μm, Mobile phase: MeCN/H$_2$O (0.1% FA): from 5/95 to 95/5, Flow rate: 30 mL/min, 254 nm) to give the title product as two white solids.

Isomer 1 (E176)

$^1$H NMR (400 MHz, MeOD-d$_4$): δ 8.65 (s, 1H), 8.27 (s, 1H), 7.65 (s, 1H), 7.11 (br, 0.4H), 6.81 (br, 0.4H), 4.40 (s, 2H), 4.24~4.22 (m, 2H), 4.13~3.88 (m, 4H), 3.81~3.55 (m, 5H), 3.35~3.31 (br, 4H), 2.71 (s, 3H), 2.52 (s, 3H), 2.49~2.40 (m, 1H), 2.35~2.28 (m, 1H), 2.17~2.08 (m, 4H).

$^{19}$F NMR (376 MHz, MeOD-d$_4$): δ −77.12.

LC-MS [mobile phase: from 80% water (0.1% FA) and 20% MeCN (0.1% FA) to 5% water (0.1% FA) and 95% MeCN (0.1% FA) in 12 min]: Rt=4.55 min; MS Calcd: 490.3, MS Found: 491.4 [M+H]$^+$.

Isomer 2 (E177)

$^1$H NMR (400 MHz, MeOD-d4): δ 8.74 (s, 1H), 8.22 (s, 1H), 7.65 (s, 1H), 6.93 (br, 1H), 5.28~5.27 (m, 1H), 5.17 (br, 1H), 5.04~5.01 (m, 1H), 4.40~4.03 (m, 7H), 3.93~3.88 (m, 1H), 3.81~3.71 (m, 2H), 3.66~3.63 (m, 1H), 3.31~3.30 (br, 4H), 2.64 (s, 3H), 2.53 (s, 3H), 2.50~2.41 (m, 1H), 2.32~2.21 (m, 3H), 2.14~2.05 (m, 2H), $^{19}$F NMR (376 MHz, MeOD-d$_4$): δ −77.29.

LC-MS [mobile phase: from 80% water (0.1% FA) and 20% MeCN (0.1% FA) to 5% water (0.1% FA) and 95% MeCN (0.1% FA) in 12 min]: Rt=4.64 min; MS Calcd: 490.3, MS Found: 491.4 [M+H]$^+$.

Example 178

((1R,4R)-5-(2-methoxy-6-(5-methyl-6-(tetrahydro-2H-pyran-4-yl)-1H-indazol-1-yl)pyrimidin-4-yl)-2-oxa-5-azabicyclo[2.2.1]heptan-1-yl)methanol

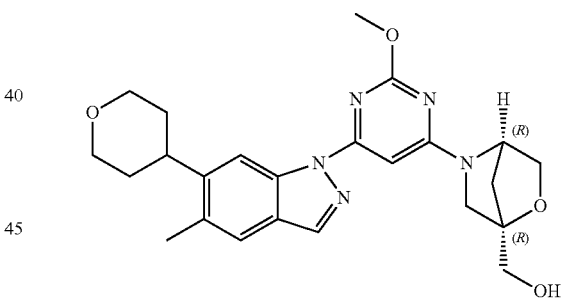

The title compound was prepared by a procedure similar to that described for E148 and E149 starting from a suspension of ((1R,4R)-5-(6-iodo-2-methoxypyrimidin-4-yl)-2-oxa-5-azabicyclo-[2.2.1]heptan-1-yl)methanol and 5-methyl-6-(tetrahydro-2H-pyran-4-yl)-1H-indazole in toluene, CuI, K$_3$PO$_4$ and N$^1$,N$^2$-dimethylethane-1,2-diamine at 100° C. under N$_2$ for 4 h.

Prep-HPLC [method: Apparatus model: waters 2767; column: Inertsil ODS-3 20×250 mm 10 μm; Flow rate: 20 mL/min; Wave length: 214 nm/254 nm; trigger: 254 nm; Mobile phase A: H$_2$O (0.05% TFA), Mobile phase B: MeCN; Gradient:

| time | B % |
| --- | --- |
| 0 | 25 |
| 15.2 | 40 |

-continued

| time | B % |
|---|---|
| 15.5 | 95 |
| 17.5 | 95 |
| 17.7 | 10 |
| 20 | 10 |

$^1$H NMR (400 MHz, CDCl$_3$): δ 8.72 (s, 1H), 8.08 (s, 1H), 7.52 (s, 1H), 6.74~6.59 (m, 1H), 6.36~4.66 (m, 1H), 4.18~4.13 (m, 5H), 4.08~3.98 (m, 4H), 3.65~3.59 (m, 3H), 3.54~3.51 (m, 1H), 3.13~3.08 (m, 1H), 2.48 (s, 3H), 2.01~1.81 (m, 6H). 19F NMR (376 MHz, CDCl$_3$): δ −75.89 (s, 3F)

LC-MS [mobile phase: from 50% water (0.1% FA) and 50% MeCN (0.1% FA) to 5% water (0.1% FA) and 95% MeCN (0.1% FA) in 2.6 min]: Rt=1.177 min; MS Calcd: 451.22, MS Found: 452.2 [M+H]$^+$.

Example 179

(1R,4R)-5-(2-methyl-6-(5-methyl-6-(3-((S)-tetrahydrofuran-3-yl)-3-azabicyclo-[3.1.0]hexan-6-yl)-1H-indazol-1-yl)pyrimidin-4-yl)-2-oxa-5-azabicyclo[2.2.1]heptane

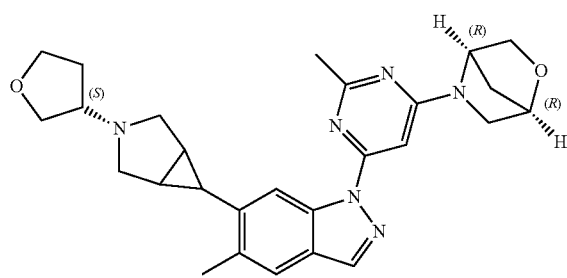

To a solution of (1R,4R)-5-(6-(6-(3-azabicyclo[3.1.0] hexan-6-yl)-5-methyl-1H-indazol-1-yl)-2-methylpyrimidin-4-yl)-2-oxa-5-azabicyclo[2.2.1]heptane (150 mg, 0.37 mmol) in MeCN (20 mL) was added (R)-tetrahydrofuran-3-yl 4-methylbenzenesulfonate (271 mg, 1.12 mmol) and K$_2$CO$_3$ (154 mg, 1.12 mmol) at II under N$_2$. The reaction mixture was stirred at 110° C. for 24 h. The mixture was purified by silica gel chromatography eluted with EtOAc and flash column to give the product as a white solid (35 mg, yield: 19%).

1H NMR (400 MHz, CDCl3) δ 8.52 (s, 1H), 8.03 (s, 1H), 7.46 (s, 1H), 6.66 (s, 1H), 5.25 (m, 0.65H), 4.73 (s, 1H), 3.97-3.93 (m, 1H), 3.92-3.90 (m, 2H), 3.88-3.83 (m, 2H), 3.79-3.77 (m, 1H), 3.65-3.52 (m, 2H), 3.29-3.27 (m, 1H), 3.18-3.16 (m, 1H), 3.07-3.03 (m, 1H), 2.61-2.50 (m, 5H), 2.42 (s, 3H), 2.41-2.40 (m, 1H), 2.06-1.91 (m, 4H), 1.88 (m, 2H).

LC-MS [mobile phase: from 90% water (0.1% FA) and 10% MeCN (0.1% FA) to 5% water (0.1% FA) and 95% MeCN (0.1% FA) in 2.6 min]: Rt=1.12 min; MS Calcd: 472.26, MS Found: 473.5 [M+H]$^+$.

Example 180

(1R,4R)-5-(2-methyl-6-(5-methyl-6-(3-(2-(methylsulfonyl)ethyl)-3-azabicyclo[3.1.0]hexan-6-yl)-1H-indazol-1-yl)pyrimidin-4-yl)-2-oxa-5-azabicyclo[2.2.1]heptane

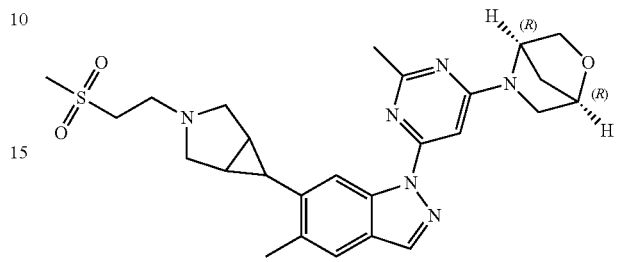

To a solution of (1R,4R)-5-(6-(6-(3-azabicyclo[3.1.0] hexan-6-yl)-5-methyl-1H-indazol-1-yl)-2-methylpyrimidin-4-yl)-2-oxa-5-azabicyclo[2.2.1]heptane (80 mg, 0.20 mmol) in EtOH (10 mL) was added (methylsulfonyl)ethene (42 mg, 0.40 mmol) at rt under N$_2$. The reaction mixture was stirred at rt for 4 h. The mixture was purified by flash column to give the product as a white solid (20 mg, yield: 19%).

$^1$H NMR (400 MHz, CDCl$_3$) δ 8.52 (s, 1H), 8.04 (s, 1H), 7.47 (s, 1H), 6.66 (s, 1H), 5.27 (m, 0.48H), 4.74 (m, 1H), 3.92-3.90 (m, 2H), 3.53-3.32 (m, 2H), 3.30-3.19 (m, 2H), 3.17-3.16 (m, 2H), 3.09-3.07 (m, 2H), 3.06-3.04 (m, 3H), 2.63-2.59 (m, 5H), 2.46 (s, 3H), 2.29-2.27 (m, 1H), 2.00-1.92 (m, 2H), 1.87 (m, 2H).

LC-MS [mobile phase: from 90% water (0.1% FA) and 10% MeCN (0.1% FA) to 5% water (0.1% FA) and 95% MeCN (0.1% FA) in 2.6 min]: Rt=1.13 min; MS Calcd: 508.23, MS Found: 509.4 [M+H]$^+$.

F. Assays and Data

As stated above, the compounds of present invention are LRRK2 kinase inhibitors, and may be useful in the treatment of diseases mediated by LRRK2. The biological activities and/or properties of the compounds of present invention can be determined using any suitable assay, including assays for determining the activity of a candidate compound as a LRRK2 kinase inhibitor, as well as tissue and in vivo models.

1. Assays a. Full Length G2019 Human LRRK2 Inhibition Mass Spectrometry Assay

This assay for Leucine Rich Repeat Kinase 2 (LRRK2) inhibition is based on the direct measurement of the peptide 'LRRKtide' (LRRKtide: RLGRDKYKT*LRQIRQ and "*" refers to the site of phosphorylation.) and phosphorylated 'LRRKtide' using a high throughput RapidFire mass spectrometry assay. Inhibitors are compounds that reduce the conversion of LRRKtide to phospho-LRRKtide.

Human G2019 LRRK2 Plasmid Preparation
Primers used for PCR cloning:
pHTBV-F:SEQ ID No: 1
LRRK2 wt-F1:SEQ ID No: 2
LRRK2 wt-R1: SEQ ID No: 3
LRRK2 wt-F2: SEQ ID No: 4
LRRK2 wt-R2: SEQ ID No: 5
LRRK2 wt-F3:SEQ ID No: 6
pHTBV-R: SEQ ID No: 7 pHTBV1-N-Flag-hu LRRK2 was generated by PCR amplifying the full length LRRK2 sequence with N terminal Flag tag from pcDNA3.1(+)_Human_LRRK2 (NCBI Reference Sequence: NP_940980.3) with the primers described above, and cloned into pHTBV1mcs3 vector between BamHI and KpnI sites.

The G2019 full length Flag-LRRK2 coding sequence is SEQ ID No: 8.

The translated amino acid sequence for human G2019 full length N terminal flag tagged LRRK2 protein is SEQ ID No: 9.

Insect Cell Cultures

Sf9 insect cells (Invitrogen Life Technologies, Carlsbad, Calif.) were maintained at 27° C. in SF 900 II SFM in 500-ml shaker flasks (Erlenmeyer, Corning). The cells were maintained in exponential growth phase and subcultured twice per week. For larger volumes, cells were grown in 2-liter shaker flasks (Erlenmeyer, Corning) while being agitated with 120 rpm at 27° C. incubator shaker.

Generation of the BacMam Virus

To generate the recombinant BacMam virus, DH10Bac competent cells (10361-012, Invitrogen) were transformed by the genotypically normal human LRRK2 BacMam plasmid to generate the recombinant baculovirus DNA. The Sf9 insect cells were co-transfected with the mixture of recombinant baculovirus DNA and cellfectin (10362-100, Invitrogen). After 4 h of incubation at 27° C., the transfection media was replaced with Sf-900 III SFM medium containing 5% HI FBS (Ser. No. 10/100,147, Invitrogen). The cells were further incubated for 4 days. The infected cell culture medium containing the baculovirus (P0 virus stock) was collected and amplified by further infecting the 200 ml Sf9 cells via 200-300 ul P0.

Quantification of BacMam Viral Titre by BacPAKRapid Titer

The viral titre, measured as plaque forming unit (pfu)/ml was determined using BacPAK Papid Titer Kit (631406, Clontech) according to the manufacturer's protocol. The Sf9 cells seeded in 96-well plate with $3\times10^5$ cells per well were incubated with serial dilution of the viral stocks for 1 h at 27° C., 50 µl methyl cellulose overlay was added to each well followed by 43~47 h incubation. The cells were then fixed in 4% paraformaldehyde (PFA). After blocking the cells with diluted normal goat serum, Mouse anti-gp64 antibody was added to the cells. After 30 min incubation, the cells were washed with phosphate buffered saline containing 0.2% Triton-X100 (PBST) and incubated for another 30 min with goat anti-mouse antibody/HRP conjugate. This was followed by blue peroxidase substrate which detects the single infected cells and foci of infected cells by their dark blue color.

Protein Expression & Purification a) Expression of Flag Tagged Full Length G2019 Human LRRK2

HEK293 6E cells were incubated in a 37° C. incubator with a humidified atmosphere of 5% $CO_2$ on an orbital shaker rotating at 110 rpm. On the day of transduction, the cell viability was higher than 98% and the cell density was in the range of $1\times10^6$~$1.5\times10^6$ cells/ml. HEK293 6E cells were centrifuged at 1,000 rpm for 10 min, and then the cells were resuspended in fresh Freestyle 293 expression medium (Invitrogen: 12338) with 0.1% F-68(Invitrogen: 24040-032) but without antibiotics (G418) at density of $1\times10^6$ cells/ml. BacMam virus with Flag-hu LRRK2 (genotypically normal) gene was centrifuged at 40,000 g for 2 hours, then resuspended in fresh Freestyle 293 expression medium. The resuspended virus was added into the cells in at MOI of 10. The cells were incubated in a 37° C. incubator with a humidified atmosphere of 5% $CO_2$ in air on an orbital shaker rotating at 110 rpm. Cultures were harvested at approximately 48 hours post-transduction by centrifugation at 4,000 rpm for 20 min and pellets were frozen for purification.

b) Purification of Flag Tagged Full Length G2019 Human LRRK2

The cell pellet was resuspended in (20 mL/liter cell culture) lysis buffer (50 mM TrisHCl pH7.5 at 4° C., 500 mM NaCl, 0.5 mM EDTA, 0.1% TritonX-100, 10% glycerol, freshly add 2 mM DTT), with protease inhibitors (Roche: 04693132001) and benzonase (Merck Millipore: 70746-3CN) at recommended concentration suggested by suppliers. The suspended cells were lysed by sonication on ice for 30 min (2 secs on/4 sec off, 20% amplitude), and centrifuged at 10,000 rpm for 30 minutes at 4° C. The supernatant was incubated with 1 mL per litre of cell culture of anti-Flag magnetic beads (Sigma-Aldrich: M8823) at 4° C. for 3 hours, then the beads were washed by 5 mL (5 column volume) binding buffer (50 mM Tris pH7.5@ 4 C, 500 mM NaCl, 0.5 mM EDTA, 0.1% TritonX-100, 10% glycerol, freshly add 2 mM DTT) for three times. The Flag tagged LRRK2 proteins were eluted by Elution buffer (50 mM Tris pH7.5@ 4 C, 500 mM NaCl, 0.5 mM EDTA, 0.1% TritonX-100, 10% glycerol, freshly add 2 mM DTT, 250 ug/ml Flag peptide (Sigma-Aldrich:F3290)) at 4° C. for 2 hours. Flag peptide was removed by Zeba Spin Desalting Columns, 7K MWCO (Thermo-Fisher: 89893) and the buffer of eluted LRRK2 proteins was exchanged into Storage Buffer (50 mM Tris pH7.5@4 C, 150 mM NaCl, 0.5 mM EDTA, 0.02% Triton X-100, 2 mM DTT and 50% Glycerol) using Amicon Ultra Centrifugal Filter Units (100 kD) (Merck: UFC910096). Fractions containing LRRK2 proteins were pooled, aliquoted and stored at −80° C. Protein concentration was determined by Bradford protein assay, and protein purity was analyzed by NuPAG Novex 4-12% Bis-Tris Protein Gels (Invitrogen: NP0322BOX).

Assay Protocol

1) A 10 mM test compound was dissolved in 100% DMSO and serially diluted 1 in 4. 100 nL of this dilution series was then added to a 384 well, v bottom polypropylene plate, excluding columns 6 and 18. 100 nL of DMSO was added to columns 6 and 18 as controls wells. Assay dilution gave a top final assay concentration of test compound of 100 µM 2) 50 µl of 1% formic acid in laboratory grade water was added to column 18 using a multidrop combi dispenser to act as a pre stopped assay control.

3) 5 µl of 'enzyme solution' containing 50 nM of purified recombinant Full length Flag-LRRK2 in assay buffer (50 mM Hepes (pH 7.2), 10 mM MgCl2, 150 mM NaCl, 5% glycerol, 0.0025% triton X-100 and 1 mM DTT) was added to all wells using a multidrop combi dispenser, giving a final assay concentration of 25 nM LRRK2 enzyme. This resulted in column 6 (enzyme plus DMSO) giving 0% inhibition and column 18 giving 100% inhibition (pre stopped control). Test plates were then incubated for 30 minutes at room temperature.

4) 5 µl 'substrate solution' containing 50 uM LRRKtide peptide substrate and 4 mM ATP was added to all wells of the plate using a multidrop combi dispenser giving a final assay concentration of 25 uM LRRKtide and 2 mM ATP. Test plates were then incubated for 1 hour at room temperature. (Incubation may vary depending on rate and linearity of reaction with different enzyme batches).

5) 50 µl of 1% formic acid in laboratory grade water was added to all wells (minus column 18) to quench the reaction, and plates were centrifuged at 3000 rpm for 10 minutes. Test plates were then analysed on an Agilent RapidFire High Throughput solid phase extraction system coupled to AB Sciex API 4000 triple quadropole mass spectrometer with the following setting:

RapidFire Settings:

Sip Height=2 mm, Aspirate=500 ms, Load time=3000 ms, Elution time=3000 ms, Requilibration=500 ms.

Flow rates: pump 1=1.5 mL/min, pump 2 1.25 mL/min pump 3=0.8 mL/min Mass Spectrometer Settings:

LRRKtide Detection settings: Q1 mass 644.8 Da, Q3 mass 638.8, declustering potential 76 volts, collision energy 37 volts, CXP 34 volts.

Phospho-LRRKtide Detection settings: Q1 mass 671.4 Da, Q3 mass 638.8, Declustering potential 76 volts, Collision energy 37 volts, CXP 34 volts.

A C4 cartridge was used and running buffers were: A (aqueous) 0.1% formic acid in water B (organic) 0.1% formic acid, 80% acetonitrile, 20% water.

Collision gas: 12, Curtain gas: 25, Ion Source gas (1): 60, Ion Source gas (2): 60, Ion Spray Voltage: 5500, Temperature: 600, Interfaec Heater: ON.

Resolution Q1: low, Resolution Q3: low.

6) Data was analysed using ActivityBase software (IDBS). A percent conversion from LRRKtide to Phospho-LRRKtide was calculated using the following formula:

% conversion=(Phospho-LRRKtide product peak area/(Phospho-LRRKtide product peak area+ LRRKtide substrate peak area))*100 b. Recombinant Cellular LRRK2 AlphaScreen Assay

To determine the activity of compounds against LRRK2 kinase activity in cells, the observed LRRK2 kinase-dependent modulation of LRRK2 Ser 935 phosphorylation (Dzamko et al., 2010, Biochem. J. 430: 405-413) was utilized to develop a quantitative 384 well plate-based immunoassay of LRRK2 Ser935 phosphorylation in the human neuroblastoma cell line SH-SY5Y, engineered to over-express recombinant full length LRRK2 protein.

A BacMam virus expressing full length recombinant LRRK2 was purchased from Invitrogen and amplified by inoculation of SF-9 cells at MOI 0.3 for 4-5 days in Sf-900 III SFM medium supplemented with 3% fetal bovine serum. Infected cell cultures were then centrifuged at 2000 g for 20 minutes, viral supernatant titer determined by anti-gp64 plaque assay and stored at 4° C.

Affinity-purified anti-phospho LRRK2 Ser935 sheep polyclonal antibody (Dzamko et al., 2010, Biochem. J. 430: 405-413) was biotinylated by standard methods (PerkinElmer). Anti-LRRK2 rabbit polyclonal antibody was purchased from Novus Biologicals. AlphaScreen Protein A IgG Kit (including acceptor and donor beads) was purchased from Perkin Elmer.

SH-SY5Y cells were grown in DMEM/F12 medium with 10% dialysed fetal bovine serum and harvested by treatment with 0.5% trypsin-EDTA for 5 minutes at 37° C. followed by centrifugation at 1000 rpm for 4 minutes. The cell pellet was resuspended in Opti-MEM reduced serum media (Invitrogen) at 200,000 cells/ml and mixed with the BacMam LRRK2 virus at MOI=50. 50 µl cell solutions were then dispensed to each well of a 384-well plate and incubated at 37° C., 5% $CO_2$ for 24 hours.

Serial dilutions of test compounds were prepared in Opti-MEM reduced serum media (Invitrogen) and 5.6 ul transferred from compound plate to cell assay plate to achieve a top final assay concentration of 10 uM. DMSO was used in certain wells as controls. Cells were incubated at 37° C., 5% $CO_2$ for 60 minutes. The medium was then removed and cells lysed by addition of 20 ul cell lysis buffer (Cell Signaling Technology) and incubation at 4° C. for 20 minutes. 10 ul of antibody/acceptor bead mix [(1/1000 biotinylated-pS935 LRRK2 antibody, 1/1000 total-LRRK2 antibody, 1/100 Acceptor beads in AlphaScreen detection buffer (25 mM Hepes (pH 7.4), 0.5% Triton X-100, 1 mg/ml Dextran 500 and 0.1% BSA)] was then added to each well and plates incubated for 2 hours at ambient temperature in the dark. 10 µl of donor beads solution (1/33.3 donor beads in AlphaScreen detection buffer) was then added to each well. Following incubation for a further 2 hours at ambient temperature in the dark, plates were read on an EnVision™ plate reader at emission 520-620 nm with excitation 680 nm. Dose response curve data was based on sigmoidal dose-response model.

c. FASSIF Solubility Assay

Compound solubility may be evaluated in the fasted state simulated intestinal media (FaSSIF) at pH 6.5. Certain amount of test compound was admixed with certain volume of FaSSIF to prepare a suspension of about 1 mg/ml. The suspension was incubated at 37° C. in the water bath shaker for 24 hours. At the $4^{th}$ and $24^{th}$ hour, the suspension was centrifugated at 14K rpm for 15 minutes. 100 µl of the supernatant was withdrawn and diluted with the same volume of 50% acetonitrile water solution and analysed with UPLC (Ultra performance Liquid Chromatography). FaSSIF solubility was calculated based on the peak area of the test compound.

The FaSSIF (170 ml) preparation 100 mg of lecithin and 274 mg (anhyd equiv) of NaTaurocholate were dissolved in about 150 ml of pH 6.5 buffer. The solution was made to the volume of 170 ml with the pH 6.5 buffer.

The pH 6.5 buffer solution (1 L) preparation 4.083 g $KH_2PO_4$ and 7.456 g KCl were dissolved in 800 ml of water, with 100 ml 0.1 M NaOH subsequently added. The solution was made to the volume of 1 L with water. The pH value of the buffer solution was measured and adjusted to be 6.50±0.1.

Standard solutions for UPLC calibration and solubility calculation 2 µM, 20 µM and 200 µM DMSO (50% ACN water) solutions.

UPLC Method and Parameter

Instrument: Waters ACQUITY UPLC System

Column: Waters ACQUITY UPLC BEH C18 (1.7 µm, 2.1×50 mm)

Mobile phase: A: 0.1% TFA in water/B: 0.1% TFA in CAN

Gradient: 0 min (A 95%/B 5%), 2 min (A 5%/B 95%), 2.5 min (A 5%/B 95%), 2.6 min (A 95%/B 5%), 3 min (A 95%/B 5%)

Flow rate: 0.8 mL/min; column temperature: 40° C.; injection volume: 1.0 µL; UV detection: 280 nm d. CLND Solubility Assay Kinetic solubility of a compound may be evaluated by the CLND (ChemiLuminescent Nitrogen Detection) solubility assay, based on known protocols (see, e.g., Bhattachar S. N.; Wesley J. A.; Seadeek C., Evaluation of the Chemiluminescent Nitrogen Detector for Solubility Determinations to Support Drug Discovery, J. Pharm. Biomed. Anal. 2006 (41): 152-157; Kestranek A, Chervenek A, Logenberger J, Placko S. Chemiluminescent Nitrogen Detection (CLND) to Measure Kinetic Aqueous Solubility, Curr Protoc Chem Biol., 2013, 5(4):269-80). Typically, 5 µl of 10 mM DMSO stock solution of the test compound was diluted to 100 µl with pH7.4 phosphate buffered saline, equilibrated for 1 hour at room temperature, filtered through Millipore MultiscreenHTS-PCF filter plates (MSSL BPC). The filtrate is quantified by suitably calibrated flow injection Chemi-Luminescent Nitrogen Detection.

2. Assay Data

Compounds of Examples E1-E30, E33-E73, E75-86, E132, E135, E137, E139, E141, E143, E147, E149, E150, E151, E153, E155, E157, E161, E162, E164, E165, E168, E172, E175, E176, E179 and E180 were tested in the recombinant cellular LRRK2 AlphaScreen assay and exhibited a pIC50 of ≥6. Examples E31-32 exhibited a pIC50 of 5.97 and 5.73 respectively. It is noted however that E31 and E32 are two of a number or enantiomers, the other enantiomers exhibiting a pIC50 of ≥6.

Compounds of Examples E1-E3, E5-7, E9, E11, E13, E15, E17-21, E23, E25-29, E56-E59, E67-E69, E71-E73, E75-E78, E81, E84-86, E133, E142, E148, E152, E154, E156, E159, E163, E166, E170, E171 and E173 were tested in the recombinant cellular LRRK2 AlphaScreen assay and exhibited a pIC50 of ≥7. The compound of Example E1 exhibited a pIC50 of 7.7 in the recombinant cellular LRRK2 AlphaScreen assay.

Compounds of Examples E5, E11, E17-E18, E56, E72, E75-76, E78, E81, E158, E160, E167, E174 and E178 were tested in the recombinant cellular LRRK2 AlphaScreen assay and exhibited a pIC50 of ≥8.

Compounds of Examples E1-E2, E5, E7-E11, E25-E26, E32-E34, E39-E45, E47-E48, E50, E53-E54, E56-E58, E60-E63, E80-E83, E132, E137, E139, E147, E151, E157 and E177 were tested in the full length G2019 human LRRK2 Inhibition Mass Spectrometry assay and exhibited a pIC50 of ≥6.0. Compound of Examples E133, E142, E143, E148, E149, E150, E152-E156, E158-E164, E166, E170, E171, and E173-E176. exhibited a pIC50 of ≥7.0. Compound of Examples E167 and E178 exhibited pIC50 of ≥8.0.

```
3. Sequence listing
SEQ ID NO: 1 Primers used for PCR cloning of Human G2019 LRRK2 plasmids
preparation: pHTBV-F
5'-GATCTCGACGGGCGCGGATCCACCATGGATTACAAGGATGACGACGAT-3'

SEQ ID NO: 2 Primers used for PCR cloning of Human G2019 LRRK2 plasmids
preparation: LRRK2 wt-F1
5'-CATGGATTACAAGGATGACGACGATAAGATGGCTAGTGGCAGCTGTCAG-3'

SEQ ID NO: 3 Primers used for PCR cloning of Human G2019 LRRK2 plasmids
preparation: LRRK2 wt-R1
5'-GTTCACGAGATCCACTATTCAGTAAGAGTTCCACCAATTTGGGACTG-3'

SEQ ID NO: 4 Primers used for PCR cloning of Human G2019 LRRK2 plasmids
preparation: LRRK2 wt-F2
5'-GAATAGTGGATCTCGTGAACAAG-3'

SEQ ID NO: 5 Primers used for PCR cloning of Human G2019 LRRK2 plasmids
preparation: LRRK2 wt-R2
5'-GTCAGACAAACTGCTTGGAACCAGC-3'

SEQ ID NO: 6 Primers used for PCR cloning of Human G2019 LRRK2 plasmids
preparation: LRRK2 wt-F3
5'-CTGGTTCCAAGCAGTTTGTCTGACCACAGGCCTGTGATAG-3'

SEQ ID NO: 7 Primers used for PCR cloning of Human G2019 LRRK2 plasmids
preparation: pHTBV-R
5'-GTTCTAGCCAAGCTTGGTACCCTATTACTCAACAGATGTTCGTCTC-3'

SEQ ID NO: 8 G2019 Full length Flag-LRRK2 coding sequence
atggattacaaggatgacgacgataagATGGCTAGTGGCAGCTGTCAGGGGTGCGAAGAGGACGAGGAAAC

TCTGAAGAAGTTGATAGTCAGGCTGAACAATGTCCAGGAAGGAAAACAGATAGAAACGCTGGTC

CAAATCCTGGAGGATCTGCTGGTGTTCACGTACTCCGAGCACGCCTCCAAGTTATTTCAAGGCAA

AAATATCCATGTGCCTCTGTTGATCGTCTTGGACTCCTATATGAGAGTCGCGAGTGTGCAGCAGG

TGGGTTGGTCACTTCTGTGCAAATTAATAGAAGTCTGTCCAGGTACAATGCAAAGCTTAATGGGA

CCCCAGGATGTTGGAAATGATTGGGAAGTCCTTGGTGTTCACCAATTGATTCTTAAAATGCTAAC

AGTTCATAATGCCAGTGTAAACTTGTCAGTGATTGGACTGAAGACCTTAGATCTCCTCCTAACTTC

AGGTAAAATCACCTTGCTGATACTGGATGAAGAAAGTGATATTTTCATGTTAATTTTTGATGCCAT

GCACTCATTTCCAGCCAATGATGAAGTCCAGAAACTTGGATGCAAAGCTTTACATGTGCTGTTTG

AGAGAGTCTCAGAGGAGCAACTGACTGAATTTGTTGAGAACAAAGATTATATGATATTGTTAAGT

GCGTTAACAAATTTTAAAGATGAAGAGGAAATTGTGCTTCATGTGCTGCATTGTTTACATTCCCTA

GCGATTCCTTGCAATAATGTGGAAGTCCTCATGAGTGGCAATGTCAGGTGTTATAATATTGTGGT

GGAAGCTATGAAAGCATTCCCTATGAGTGAAAGAATTCAAGAAGTGAGTTGCTGTTTGCTCCATA

GGCTTACATTAGGTAATTTTTTCAATATCCTGGTATTAAACGAAGTCCATGAGTTTGTGGTGAAAG

CTGTGCAGCAGTACCCAGAGAATGCAGCATTGCAGATCTCAGCGCTCAGCTGTTTGGCCCTCCT
```

-continued

```
CACTGAGACTATTTTCTTAAATCAAGATTTAGAGGAAAAGAATGAGAATCAAGAGAATGATGATGA
GGGGGAAGAAGATAAATTGTTTTGGCTGGAAGCCTGTTACAAAGCATTAACGTGGCATAGAAAGA
ACAAGCACGTGCAGGAGGCCGCATGCTGGGCACTAAATAATCTCCTTATGTACCAAAACAGTTTA
CATGAGAAGATTGGAGATGAAGATGGCCATTTCCCAGCTCATAGGGAAGTGATGCTCTCCATGC
TGATGCATTCTTCATCAAAGGAAGTTTTCCAGGCATCTGCGAATGCATTGTCAACTCTCTTAGAAC
AAAATGTTAATTTCAGAAAAATACTGTTATCAAAAGGAATACACCTGAATGTTTTGGAGTTAATGCA
GAAGCATATACATTCTCCTGAAGTGGCTGAAAGTGGCTGTAAAATGCTAAATCATCTTTTTGAAGG
AAGCAACACTTCCCTGGATATAATGGCAGCAGTGGTCCCCAAAATACTAACAGTTATGAAACGTC
ATGAGACATCATTACCAGTGCAGCTGGAGGCGCTTCGAGCTATTTTACATTTTATAGTGCCTGGC
ATGCCAGAAGAATCCAGGGAGGATACAGAATTTCATCATAAGCTAAATATGGTTAAAAAACAGTG
TTTCAAGAATGATATTCACAAACTGGTCCTAGCAGCTTTGAACAGGTTCATTGGAAATCCTGGGAT
TCAGAAATGTGGATTAAAAGTAATTTCTTCTATTGTACATTTTCCTGATGCATTAGAGATGTTATCC
CTGGAAGGTGCTATGGATTCAGTGCTTCACACACTGCAGATGTATCCAGATGACCAAGAAATTCA
GTGTCTGGGTTTAAGTCTTATAGGATACTTGATTACAAAGAAGAATGTGTTCATAGGAACTGGACA
TCTGCTGGCAAAAATTCTGGTTTCCAGCTTATACCGATTTAAGGATGTTGCTGAAATACAGACTAA
AGGATTTCAGACAATCTTAGCAATCCTCAAATTGTCAGCATCTTTTTCTAAGCTGCTGGTGCATCA
TTCATTTGACTTAGTAATATTCCATCAAATGTCTTCCAATATCATGGAACAAAAGGATCAACAGTTT
CTAAACCTCTGTTGCAAGTGTTTTGCAAAAGTAGCTATGGATGATTACTTAAAAAATGTGATGCTA
GAGAGAGCGTGTGATCAGAATAACAGCATCATGGTTGAATGCTTGCTTCTATTGGGAGCAGATG
CCAATCAAGCAAAGGAGGGATCTTCTTTAATTTGTCAGGTATGTGAGAAAGAGAGCAGTCCCAAA
TTGGTGGAACTCTTACTGAATAGTGGATCTCGTGAACAAGATGTACGAAAAGCGTTGACGATAAG
CATTGGGAAAGGTGACAGCCAGATCATCAGCTTGCTCTTAAGGAGGCTGGCCCTGGATGTGGCC
AACAATAGCATTTGCCTTGGAGGATTTTGTATAGGAAAAGTTGAACCTTCTTGGCTTGGTCCTTTA
TTTCCAGATAAGACTTCTAATTTAAGGAAACAAACAAATATAGCATCTACACTAGCAAGAATGGTG
ATCAGATATCAGATGAAAAGTGCTGTGGAAGAAGGAACAGCCTCAGGCAGCGATGGAAATTTTTC
TGAAGATGTGCTGTCTAAATTTGATGAATGGACCTTTATTCCTGACTCTTCTATGGACAGTGTGTT
TGCTCAAAGTGATGACCTGGATAGTGAAGGAAGTGAAGGCTCATTTCTTGTGAAAAAGAAATCTA
ATTCAATTAGTGTAGGAGAATTTTACCGAGATGCCGTATTACAGCGTTGCTCACCAAATTTGCAAA
GACATTCCAATTCCTTGGGGCCCATTTTTGATCATGAAGATTTACTGAAGCGAAAAAGAAAAATAT
TATCTTCAGATGATTCACTCAGGTCATCAAAACTTCAATCCCATATGAGGCATTCAGACAGCATTT
CTTCTCTGGCTTCTGAGAGAGAATATATTACATCACTAGACCTTTCAGCAAATGAACTAAGAGATA
TTGATGCCCTAAGCCAGAAATGCTGTATAAGTGTTCATTTGGAGCATCTTGAAAAGCTGGAGCTT
CACCAGAATGCACTCACGAGCTTTCCACAACAGCTATGTGAAACTCTGAAGAGTTTGACACATTT
GGACTTGCACAGTAATAAATTTACATCATTTCCTTCTTATTTGTTGAAAATGAGTTGTATTGCTAAT
CTTGATGTCTCTCGAAATGACATTGGACCCTCAGTGGTTTTAGATCCTACAGTGAAATGTCCAACT
CTGAAACAGTTTAACCTGTCATATAACCAGCTGTCTTTTGTACCTGAGAACCTCACTGATGTGGTA
GAGAAACTGGAGCAGCTCATTTTAGAAGGAAATAAAATATCAGGGATATGCTCCCCCTTGAGACT
GAAGGAACTGAAGATTTTAAACCTTAGTAAGAACCACATTTCATCCCTATCAGAGAACTTTCTTGA
GGCTTGTCCTAAAGTGGAGAGTTTCAGTGCCAGAATGAATTTTCTTGCTGCTATGCCTTTCTTGC
CTCCTTCTATGACAATCCTAAAATTATCTCAGAACAAATTTTCCTGTATTCCAGAAGCAATTTTAAA
```

-continued

```
TCTTCCACACTTGCGGTCTTTAGATATGAGCAGCAATGATATTCAGTACCTACCAGGTCCCGCAC
ACTGGAAATCTTTGAACTTAAGGGAACTCTTATTTAGCCATAATCAGATCAGCATCTTGGACTTGA
GTGAAAAAGCATATTTATGGTCTAGAGTAGAGAAACTGCATCTTTCTCACAATAAACTGAAAGAGA
TTCCTCCTGAGATTGGCTGTCTTGAAAATCTGACATCTCTGGATGTCAGTTACAACTTGGAACTAA
GATCCTTTCCCAATGAAATGGGGAAATTAAGCAAAATATGGGATCTTCCTTTGGATGAACTGCAT
CTTAACTTTGATTTTAAACATATAGGATGTAAAGCCAAAGACATCATAAGGTTTCTTCAACAGCGA
TTAAAAAAGGCTGTGCCTTATAACCGAATGAAACTTATGATTGTGGGAAATACTGGGAGTGGTAA
AACCACCTTATTGCAGCAATTAATGAAAACCAAGAAATCAGATCTTGGAATGCAAAGTGCCACAG
TTGGCATAGATGTGAAAGACTGGCCTATCCAAATAAGAGACAAAAGAAAGAGAGATCTCGTCCTA
AATGTGTGGGATTTTGCAGGTCGTGAGGAATTCTATAGTACTCATCCCCATTTTATGACGCAGCG
AGCATTGTACCTTGCTGTCTATGACCTCAGCAAGGGACAGGCTGAAGTTGATGCCATGAAGCCTT
GGCTCTTCAATATAAAGGCTCGCGCTTCTTCTTCCCCTGTGATTCTCGTTGGCACACATTTGGAT
GTTTCTGATGAGAAGCAACGCAAAGCCTGCATGAGTAAAATCACCAAGGAACTCCTGAATAAGCG
AGGGTTCCCTGCCATACGAGATTACCACTTTGTGAATGCCACCGAGGAATCTGATGCTTTGGCAA
AACTTCGGAAAACCATCATAAACGAGAGCCTTAATTTCAAGATCCGAGATCAGCTTGTTGTTGGA
CAGCTGATTCCAGACTGCTATGTAGAACTTGAAAAAATCATTTTATCGGAGCGTAAAAATGTGCCA
ATTGAATTTCCCGTAATTGACCGGAAACGATTATTACAACTAGTGAGAGAAAATCAGCTGCAGTTA
GATGAAAATGAGCTTCCTCACGCAGTTCACTTTCTAAATGAATCAGGAGTCCTTCTTCATTTTCAA
GACCCAGCACTGCAGTTAAGTGACTTGTACTTTGTGGAACCCAAGTGGCTTTGTAAAATCATGGC
ACAGATTTTGACAGTGAAAGTGGAAGGTTGTCCAAAACACCCTAAGGGAATTATTTCGCGTAGAG
ATGTGGAAAAATTTCTTTCAAAGAAAAGGAAATTTCCAAAGAACTACATGTCACAGTATTTTAAGC
TCCTAGAAAAATTCCAGATTGCTTTGCCAATAGGAGAAGAATATTTGCTGGTTCCAAGCAGTTTGT
CTGACCACAGGCCTGTGATAGAGCTTCCCCATTGTGAGAACTCTGAAATTATCATCCGACTATAT
GAAATGCCTTATTTTCCAATGGGATTTTGGTCAAGATTAATCAATCGATTACTTGAGATTTCACCTT
ACATGCTTTCAGGGAGAGAACGAGCACTTCGCCCAAACAGAATGTATTGGCGACAAGGCATTTA
CTTAAATTGGTCTCCTGAAGCTTATTGTCTGGTAGGATCTGAAGTCTTAGACAATCATCCAGAGA
GTTTCTTAAAAATTACAGTTCCTTCTTGTAGAAAAGGCTGTATTCTTTTGGGCCAAGTTGTGGACC
ACATTGATTCTCTCATGGAAGAATGGTTTCCTGGGTTGCTGGAGATTGATATTTGTGGTGAAGGA
GAAACTCTGTTGAAGAAATGGGCATTATATAGTTTTAATGATGGTGAAGAACATCAAAAAATCTTA
CTTGATGACTTGATGAAGAAAGCAGAGGAAGGAGATCTCTTAGTAAATCCAGATCAACCAAGGCT
CACCATTCCAATATCTCAGATTGCCCCTGACTTGATTTTGGCTGACCTGCCTAGAAATATTATGTT
GAATAATGATGAGTTGGAATTTGAACAAGCTCCAGAGTTTCTCCTAGGTGATGGCAGTTTTGGAT
CAGTTTACCGAGCAGCCTATGAAGGAGAAGAAGTGGCTGTGAAGATTTTTAATAAACATACATCA
CTCAGGCTGTTAAGACAAGAGCTTGTGGTGCTTTGCCACCTCCACCACCCCAGTTTGATATCTTT
GCTGGCAGCTGGGATTCGTCCCCGGATGTTGGTGATGGAGTTAGCCTCCAAGGGTTCCTTGGAT
CGCCTGCTTCAGCAGGACAAAGCCAGCCTCACTAGAACCCTACAGCACAGGATTGCACTCCACG
TAGCTGATGGTTTGAGATACCTCCACTCAGCCATGATTATATACCGAGACCTGAAACCCACAAT
GTGCTGCTTTTCACACTGTATCCCAATGCTGCCATCATTGCAAAGATTGCTGACTACGGCATTGC
TCAGTACTGCTGTAGAATGGGGATAAAAACATCAGAGGGCACACCAGGGTTTCGTGCACCTGAA
GTTGCCAGAGGAAATGTCATTTATAACCAACAGGCTGATGTTTATTCATTTGGTTTACTACTCTAT
GACATTTTGACAACTGGAGGTAGAATAGTAGAGGGTTTGAAGTTTCCAAATGAGTTTGATGAATTA
```

-continued

```
GAAATACAAGGAAAATTACCTGATCCAGTTAAAGAATATGGTTGTGCCCCATGGCCTATGGTTGA

GAAATTAATTAAACAGTGTTTGAAAGAAAATCCTCAAGAAAGGCCTACTTCTGCCCAGGTCTTTGA

CATTTTGAATTCAGCTGAATTAGTCTGTCTGACGAGACGCATTTTATTACCTAAAAACGTAATTGTT

GAATGCATGGTTGCTACACATCACAACAGCAGGAATGCAAGCATTTGGCTGGGCTGTGGGCACA

CCGACAGAGGACAGCTCTCATTICTTGACTTAAATACTGAAGGATACACTTCTGAGGAAGTTGCT

GATAGTAGAATATTGTGCTTAGCCTTGGTGCATCTTCCTGTTGAAAAGGAAAGCTGGATTGTGTC

TGGGACACAGTCTGGTACTCTCCTGGTCATCAATACCGAAGATGGGAAAAAGAGACATACCCTA

GAAAAGATGACTGATTCTGTCACTTGTTTGTATTGCAATTCCTTTTCCAAGCAAAGCAAACAAAAA

AATTTTCTTTTGGTTGGAACCGCTGATGGCAAGTTAGCAATTTTTGAAGATAAGACTGTTAAGCTT

AAAGGAGCTGCTCCTTTGAAGATACTAAATATAGGAAATGTCAGTACTCCATTGATGTGTTTGAGT

GAATCCACAAATTCAACGGAAAGAAATGTAATGTGGGGAGGATGTGGCACAAAGATTTTCTCCTT

TTCTAATGATTTCACCATTCAGAAACTCATTGAGACAAGAACAAGCCAACTGTTTTCTTATGCAGC

TTTCAGTGATTCCAACATCATAACAGTGGTGGTAGACACTGCTCTCTATATTGCTAAGCAAAATAG

CCCTGTTGTGGAAGTGTGGGATAAGAAAACTGAAAAACTCTGTGGACTAATAGACTGCGTGCACT

TTTTAAGGGAGGTAATGGTAAAAGAAAACAAGGAATCAAAACACAAAATGTCTTATTCTGGGAGA

GTGAAAACCCTCTGCCTTCAGAAGAACACTGCTCTTTGGATAGGAACTGGAGGAGGCCATATTTT

ACTCCTGGATCTTTCAACTCGTCGACTTATACGTGTAATTTACAACTTTTGTAATTCGGTCAGAGT

CATGATGACAGCACAGCTAGGAAGCCTTAAAAATGTCATGCTGGTATTGGGCTACAACCGGAAAA

ATACTGAAGGTACACAAAAGCAGAAAGAGATACAATCTTGCTTGACCGTTTGGGACATCAATCTT

CCACATGAAGTGCAAAATTTAGAAAAACACATTGAAGTGAGAAAAGAATTAGCTGAAAAAATGAG

ACGAACATCTGTTGAGTAA
```

SEQ ID NO: 9 Translated protein sequence for human G2019 Full length LRRK2 flag tagged protein

MDYKDDDDKMASGSCQGCEEDEETLKKLIVRLNNVQEGKQIETLVQ1LEDLLVFTYSEHASKLFQGKN

IHVPLLIVLDSYMRVASVQQVGWSLLCKLIEVCPGTMQSLMGPQDVGNDWEVLGVHQLILKMLTVHN

ASVNLSVIGLKTLDLLLTSGKITLLILDEESDIFMLIFDAMHSFPANDEVQKLGCKALHVLFERVSEEQLT

EFVENKDYMILLSALTNFKDEEEIVLHVLHCLHSLAIPCNNVEVLMSGNVRCYNIVVEAMKAFPMSERI

QEVSCCLLHRLTLGNFFNILVLNEVHEFVVKAVQQYPENAALQISALSCLALLTETIFLNQDLEEKNEN

QENDDEGEEDKLFWLEACYKALTWHRKNKHVQEAACWALNNLLMYQNSLHEKIGDEDGHFPAHRE

VMLSMLMHSSSKEVFQASANALSTLLEQNVNFRKILLSKGIHLNVLELMQKHIHSPEVAESGCKMLNH

LFEGSNTSLDIMAAVVPKILTVMKRHETSLPVQLEALRAILHFIVPGMPEESREDTEFHHKLNMVKKQC

FKNDIHKLVLAALNRFIGNPGIQKCGLKVISSIVHFPDALEMLSLEGAMDSVLHTLQMYPDDQEIQCLG

LSLIGYLITKKNVFIGTGHLLAKILVSSLYRFKDVAEIQTKGFQTILAILKLSASFSKLLVHHSFDLVIFHQM

SSNIMEQKDQQFLNLCCKCFAKVAMDDYLKNVMLERACDQNNSIMVECLLLLGADANQAKEGSSLIC

QVCEKESSPKLVELLLNSGSREQDVRKALTISIGKGDSQIISLLLRRLALDVANNSICLGGFCIGKVEPS

WLGPLFPDKTSNLRKQTNIASTLARMVIRYQMKSAVEEGTASGSDGNFSEDVLSKFDEWTFIPDSSM

DSVFAQSDDLDSEGSEGSFLVKKKSNSISVGEFYRDAVLQRCSPNLQRHSNSLGPIFDHEDLLKRKR

KILSSDDSLRSSKLQSHMRHSDSISSLASEREYITSLDLSANELRDIDALSQKCCISVHLEHLEKLELHQ

NALTSFPQQLCETLKSLTHLDLHSNKFTSFPSYLLKMSCIANLDVSRNDIGPSVVLDPTVKCPTLKQFN

LSYNQLSFVPENLTDVVEKLEQLILEGNKISGICSPLRLKELKILNLSKNHISSLSENFLEACPKVESFSA

RMNFLAAMPFLPPSMTILKLSQNKFSCIPEAILNLPHLRSLDMSSNDIQYLPGPAHWKSLNLRELLFSH

-continued

NQISILDLSEKAYLWSRVEKLHLSHNKLKEIPPEIGCLENLTSLDVSYNLELRSFPNEMGKLSKIWDLPL

DELHLNFDFKHIGCKAKDIIRFLQQRLKKAVPYNRMKLMIVGNTGSGKTTLLQQLMKTKKSDLGMQSA

TVGIDVKDWPIQIRDKRKRDLVLNVWDFAGREEFYSTHPHFMTQRALYLAVYDLSKGQAEVDAMKP

WLFNIKARASSSPVILVGTHLDVSDEKQRKACMSKITKELLNKRGFPAIRDYHFVNATEESDALAKLRK

TIINESLNFKIRDQLVVGQLlPDCYVELEKIILSERKNVPIEFPVIDRKRLLQLVRENQLQLDENELPHAVH

FLNESGVLLHFQDPALQLSDLYFVEPKWLCKIMAQILTVKVEGCPKHPKGIISRRDVEKFLSKKRKFPK

NYMSQYFKLLEKFQIALPIGEEYLLVPSSLSDHRPVIELPHCENSEIIIRLYEMPYFPMGFWSRLINRLLE

ISPYMLSGRERALRPNRMYWRQGIYLNWSPEAYCLVGSEVLDNHPESFLKITVPSCRKGCILLGQVV

DHIDSLMEEWFPGLLEIDICGEGETLLKKWALYSFNDGEEHQKILLDDLMKKAEEGDLLVNPDQPRLTI

PISQIAPDLILADLPRNIMLNNDELEFEQAPEFLLGDGSFGSVYRAAYEGEEVAVKIFNKHTSLRLLRQE

LVVLCHLHHPSLISLLAAGIRPRMLVMELASKGSLDRLLQQDKASLTRTLQHRIALHVADGLRYLHSAM

IIYRDLKPHNVLLFTLYPNAAIIAKIADYGIAQYCCRMGIKTSEGTPGFRAPEVARGNVIYNQQADVYSF

GLLLYDILTTGGRIVEGLKFPNEFDELEIQGKLPDPVKEYGCAPWPMVEKLIKQCLKENPQERPTSAQ

VFDILNSAELVCLTRRILLPKNVIVECMVATHHNSRNASIWLGCGHTDRGQLSFLDLNTEGYTSEEVAD

SRILCLALVHLPVEKESWIVSGTQSGTLLVINTEDGKKRHTLEKMTDSVICLYCNSFSKOSKQKNFLLV

GTADGKLAIFEDKTVKLKGAAPLKILNIGNVSTPLMCLSESTNSTERNVMWGGCGTKIFSFSNDFTIQK

LIETRTSQLFSYAAFSDSNIITVVVDTALYIAKQNSPVVEVWDKKTEKLCGLIDCVHFLREVMVKENKES

KHKMSYSGRVKTLCLQKNTALWIGTGGGHILLLDLSTRRLIRVIYNFCNSVRVMMTAQLGSLKNVMLV

LGYNRKNTEGTQKQEIQSCLTVWDINLPHEVQNLEKHIEVRKELAEKMRRTSVE

SEQ ID NO: 10: 'LRRKtide' peptide
H-RLGRDKYKTLRQIRQ-OH

What is claimed is:

1. A compound of Formula (I):

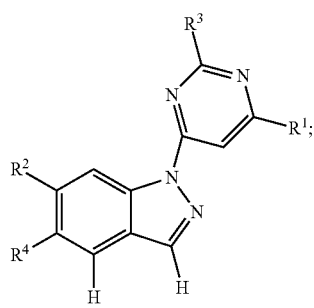

Formula (I)

wherein:

$R^1$ is an N-linked 6-9 membered bridged heterocyclyl ring optionally substituted with one, two or three substituents independently selected from the group consisting of $C_{3-6}$cycloalkyl, $C_{4-6}$ heterocyclyl, halo, hydroxyl, $C_{1-3}$ alkyl, $C_{1-3}$ alkoxyl and —$CO_2R^5$;

wherein:

each $C_{3-6}$cycloalkyl, $C_{4-6}$heterocyclyl, $C_{1-3}$alkyl and $C_{1-3}$ alkoxyl as defined for $R^1$ optionally is substituted with one, two or three substituents independently selected from the group consisting of halo, hydroxyl, unsubstituted $C_{1-3}$alkyl and unsubstituted $C_{1-3}$ alkoxyl, $R^5$ is selected from the group consisting of H, methyl, NH2, and NHCH3;

provided that:

the $C_{3-6}$cycloalkyl or $C_{4-6}$heterocyclyl substituent is only permitted on a substitutable nitrogen atom of the N-linked 6-9 membered bridged heterocyclyl ring;

$R^2$ is selected from the group consisting of:

a) 4-7 membered heterocyclyl ring, optionally substituted with one, two or three substituents independently selected from the group of substituents consisting of —$C_{1-3}$alkyl, -halo, -hydroxyl, —$SO_2CH_3$, —$COCH_3$, and —$COCH_2OH$;

wherein:
   the —$C_{1-3}$ alkyl group is optionally substituted with one, two or three substituents independently selected from the group consisting of: halo, hydroxyl, $CO_2H$, —$CH_2CH_2$—, $C_{1-3}$alkoxy and cyano;
   wherein:
      when the 4-7 membered heterocyclyl ring contains a substitutable nitrogen atom, the group of substituents defined for the 4-7 membered heterocyclyl ring also includes a 4-6 membered heterocyclyl ring attached to said substitutable nitrogen atom;
   wherein,
      the 4-6 membered heterocyclyl ring optionally is substituted with one or two substituents independently selected from the group consisting of cyano, halo, hydroxyl, $C_{1-3}$alkyl, $C_{1-3}$alkoxyl, $CH_2OH$ and $C_{3-6}$cycloalkyl; and
      wherein:
         said $C_{3-6}$ cycloalkyl, optionally is substituted with one or two substituents independently selected from the group consisting of halo, hydroxyl, cyano, $CH_2OH$, unsubstituted $C_{1-3}$alkyl and unsubstituted $C_{1-3}$ alkoxyl;
b) O-linked 4-6 membered heterocyclyl ring, optionally substituted with one or two substituents independently selected from the group consisting of: cyano, hydroxyl, $C_{1-3}$alkyl, $C_{1-3}$alkoxyl, $CH_2OH$ and $CO_2H$;
c) $C_{3-6}$ cycloalkyl optionally substituted with one or two substituents independently selected from the group consisting of cyano, halo, hydroxyl, $C_{1-3}$alkyl, $C_{1-3}$alkoxyl, $CO_2H$ and a 4-6 membered heterocyclyl ring;
d) O-linked $C_{3-6}$ cycloalkyl;
   wherein:
      the cycloalkyl group is optionally substituted with one or two substituents independently selected from the group consisting of cyano, hydroxyl, $C_{1-3}$alkyl, $C_{1-3}$alkoxyl, $CH_2OH$ and $CO_2H$;
e) $C_{1-6}$alkoxy optionally substituted by one or two substituents independently selected from the group consisting of halo, hydroxyl, $C_{1-3}$alkyl, $C_{1-3}$alkoxyl, $CO_2H$ and a 4-6 membered heterocyclyl ring; and
f) C-linked 6-9 membered fused cyclyl ring, optionally having one or two heteroatom ring members independently selected from O and N, optionally substituted with one, two or three substituents independently selected from the group of substituents consisting of —$C_{1-3}$alkyl, -cyano, -halo, -hydroxyl, —$SO_2CH_3$, —$COCH_3$, and —$COCH_2OH$,
   wherein:
      which alkyl group is optionally substituted with one, two or three substituents independently selected from the group consisting of: -halo, -hydroxyl, —$CO_2H$, —$CH_2CH_2$— and —$C_{1-3}$ alkoxy;
      when the C-linked 6-9 membered fused cyclyl ring contains a substitutable nitrogen atom, the group of substituents for the C-linked 6-9 membered fused cyclyl ring also includes a 4-6 membered heterocyclyl ring attached to said substitutable nitrogen atom;
   wherein:
      the 4-6 membered heterocyclyl ring optionally is substituted with one or two substituents independently selected from the group consisting of cyano, halo, hydroxyl, $C_{1-3}$alkyl, $C_{1-3}$alkoxyl, $CH_2OH$ and $C_{3-6}$ cycloalkyl;
   wherein:
      the $C_{3-6}$cycloalkyl optionally is substituted with one or two substituents independently selected from the group consisting of halo, hydroxyl, cyano, $CH_2OH$, unsubstituted $C_{1-3}$alkyl and unsubstituted $C_{1-3}$ alkoxyl;
$R^3$ is selected from the group consisting of halo CN, $C_{1-3}$ alkyl, $C_{1-3}$ alkoxy, $C_{1-3}$haloalkyl, $C_{1-3}$haloalkoxy and $C_{3-6}$cycloalkyl;
$R^4$ is selected from the group consisting of H, halo, CN, $C_{1-3}$alkyl, $C_{1-3}$alkoxy, $C_{1-3}$haloalkyl, $C_{1-3}$haloalkoxy and $C_{3-6}$cycloalkyl; or
a pharmaceutically acceptable salt thereof.

2. The compound of Formula (I) or a pharmaceutically acceptable salt thereof according to claim 1, wherein:
   $R^1$ is an N-linked 7-9 membered bridged heterocyclyl ring optionally substituted with one substituent selected from the group consisting of oxetanyl, halo, hydroxyl, $C_{1-3}$alkyl, $C_{1-3}$alkoxy and $CO_2R^5$,
   wherein:
      $R^5$ is selected from the group consisting of H, methyl, $NH_2$ and $NHCH_3$;
      provided that:
         the oxetanyl substituent is only permitted on a substitutable nitrogen atom.

3. The compound of Formula (I) or a pharmaceutically acceptable salt according to claim 2, wherein $R^1$ is an unsubstituted N-linked 7-9 membered bridged heterocyclyl ring.

4. The compound of Formula (I) or a pharmaceutically acceptable salt thereof according to claim 1, wherein:
   $R^2$ is O-linked $C_{3-6}$cycloalkyl; wherein the cycloalkyl group is optionally substituted with one or two substituents independently selected from the group consisting of cyano, hydroxyl, $C_{1-3}$alkyl, $C_{1-3}$alkoxy, $CH_2OH$ and $CO_2H$.

5. The compound of Formula (I) or a pharmaceutically acceptable salt thereof according to claim 1, wherein:
   $R^2$ is cyclopropyloxy wherein the cyclopropyl group is optionally substituted with one or two substituents independently selected from the roup consisting of hydroxyl and $C_{1-3}$alkyl.

6. The compound of Formula (I) or a pharmaceutically acceptable salt thereof according to claim 1, wherein $R^3$ is selected from the group consisting of $C_{1-3}$ alkyl and $C_{1-3}$ alkoxyl.

7. The compound of Formula (I) or a pharmaceutically acceptable salt thereof according to claim 1, wherein $R^4$ is selected from the group consisting of H, halo and $C_{1-3}$alkyl.

8. A compound which is

[Chemical structure] or a pharmaceutically acceptable salt thereof.

9. A pharmaceutical composition comprising a compound of Formula (I) or a pharmaceutically acceptable salt thereof according to claim 1 and a pharmaceutically acceptable excipient.

10. A method for treating a neurodegenerative disease, which comprises administering to a subject in need thereof a therapeutically effective amount of a compound of Formula (I) or a pharmaceutically acceptable salt according to claim 1.

11. The method for treating a neurodegenerative disease according to claim 10, wherein the neurodegenerative disease is Parkinson's disease.

12. The method for treating a neurodegenerative disease according to claim 11, wherein the subject is a human.

13. The method for treating a neurodegenerative disease according to claim 12, wherein the subject is a human expressing the G2019S mutation in the LRRK2 kinase.

14. A pharmaceutical composition comprising a compound of Formula (I) or a pharmaceutically acceptable salt thereof according to claim 8 and a pharmaceutically acceptable excipient.

15. A method for treating a neurodegenerative disease, which comprises administering to a subject in need thereof a therapeutically effective amount of a compound of Formula (I) or a pharmaceutically acceptable salt according to claim 8.

16. The method for treating a neurodegenerative disease according to claim 15, wherein the neurodegenerative disease is Parkinson's disease.

17. The method for treating a neurodegenerative disease according to claim 16, wherein the subject is a human.

18. The method for treating a neurodegenerative disease according to claim 17, wherein the subject is a human expressing the G2019S mutation in the LRRK2 kinase.

* * * * *

```
                              SEQUENCE LISTING

<160> NUMBER OF SEQ ID NOS: 10

<210> SEQ ID NO 1
<211> LENGTH: 48
<212> TYPE: DNA
<213> ORGANISM: Artificial
<220> FEATURE:
<223> OTHER INFORMATION: Primers used for PCR cloning of Human G2019
      LRRK2 plasmids preparation: pHTBV-F

<400> SEQUENCE: 1
gatctcgacg ggcgcggatc caccatggat tacaaggatg acgacgat                   48

<210> SEQ ID NO 2
<211> LENGTH: 49
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-F1

<400> SEQUENCE: 2
catggattac aaggatgacg acgataagat ggctagtggc agctgtcag                  49

<210> SEQ ID NO 3
<211> LENGTH: 47
<212> TYPE: DNA
<213> ORGANISM: Artificial
<220> FEATURE:
<223> OTHER INFORMATION: Primers used for PCR cloning of Human G2019
```

LRRK2 plasmids preparation: LRRK2 wt-R1

<400> SEQUENCE: 3
gttcacgaga tccactattc agtaagagtt ccaccaattt gggactg      47

<210> SEQ ID NO 4
<211> LENGTH: 23
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-F2

<400> SEQUENCE: 4
gaatagtgga tctcgtgaac aag      23

<210> SEQ ID NO 5
<211> LENGTH: 25
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-R2

<400> SEQUENCE: 5
gtcagacaaa ctgcttggaa ccagc      25

<210> SEQ ID NO 6
<211> LENGTH: 40
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-F3

<400> SEQUENCE: 6
ctggttccaa gcagtttgtc tgaccacagg cctgtgatag      40

<210> SEQ ID NO 7
<211> LENGTH: 46
<212> TYPE: DNA
<213> ORGANISM: Artificial
<220> FEATURE:
<223> OTHER INFORMATION: Primers used for PCR cloning of Human G2019
      LRRK2 plasmids preparation: pHTBV-R

<400> SEQUENCE: 7
gttctagcca agcttggtac cctattactc aacagatgtt cgtctc      46

<210> SEQ ID NO 8
<211> LENGTH: 7611
<212> TYPE: DNA
<213> ORGANISM: Artificial
<220> FEATURE:
<223> OTHER INFORMATION: G2019  Full length Flag-LRRK2 coding sequence

<400> SEQUENCE: 8
atggattaca aggatgacga cgataagatg gctagtggca gctgtcaggg gtgcgaagag      60
gacgaggaaa ctctgaagaa gttgatagtc aggctgaaca atgtccagga aggaaaacag     120
atagaaacgc tggtccaaat cctggaggat ctgctggtgt tcacgtactc cgagcacgcc     180
tccaagttat ttcaaggcaa aaatatccat gtgcctctgt tgatcgtctt ggactcctat     240
atgagagtcg cgagtgtgca gcaggtgggt tggtcacttc tgtgcaaatt aatagaagtc     300
tgtccaggta caatgcaaag cttaatggga ccccaggatg ttggaaatga ttgggaagtc     360

```
cttggtgttc accaattgat tcttaaaatg ctaacagttc ataatgccag tgtaaacttg    420
tcagtgattg gactgaagac cttagatctc ctcctaactt caggtaaaat caccttgctg    480
atactggatg aagaaagtga tattttcatg ttaattttg atgccatgca ctcatttcca    540
gccaatgatg aagtccagaa acttggatgc aaagctttac atgtgctgtt tgagagagtc    600
tcagaggagc aactgactga atttgttgag aacaaagatt atatgatatt gttaagtgcg    660
ttaacaaatt ttaaagatga agaggaaatt gtgcttcatg tgctgcattg tttacattcc    720
ctagcgattc cttgcaataa tgtggaagtc ctcatgagtg gcaatgtcag gtgttataat    780
attgtggtgg aagctatgaa agcattccct atgagtgaaa gaattcaaga agtgagttgc    840
tgtttgctcc ataggcttac attaggtaat tttttcaata tcctggtatt aaacgaagtc    900
catgagtttg tggtgaaagc tgtgcagcag tacccagaga atgcagcatt gcagatctca    960
gcgctcagct gtttggccct cctcactgag actattttct taaatcaaga tttagaggaa   1020
aagaatgaga atcaagagaa tgatgatgag ggggaagaag ataaattgtt ttggctggaa   1080
gcctgttaca aagcattaac gtggcataga aagaacaagc acgtgcagga ggccgcatgc   1140
tgggcactaa ataatctcct tatgtaccaa aacagtttac atgagaagat tggagatgaa   1200
gatggccatt tcccagctca tagggaagtg atgctctcca tgctgatgca ttcttcatca   1260
aaggaagttt tccaggcatc tgcgaatgca ttgtcaactc tcttagaaca aaatgttaat   1320
ttcagaaaaa tactgttatc aaaaggaata cacctgaatg ttttggagtt aatgcagaag   1380
catatacatt ctcctgaagt ggctgaaagt ggctgtaaaa tgctaaatca tcttttttgaa   1440 ggaagcaaca cttccctgga tataatggca gcagtggtcc ccaaaatact aacagttatg   1500
aaacgtcatg agacatcatt accagtgcag ctggaggcgc ttcgagctat tttacatttt   1560
atagtgcctg gcatgccaga agaatccagg gaggatacag aatttcatca taagctaaat   1620
atggttaaaa aacagtgttt caagaatgat attcacaaac tggtcctagc agctttgaac   1680
aggttcattg gaaatcctgg gattcagaaa tgtggattaa aagtaatttc ttctattgta   1740
cattttcctg atgcattaga gatgttatcc ctgaaggtg ctatggattc agtgcttcac   1800
acactgcaga tgtatccaga tgaccaagaa attcagtgtc tgggtttaag tcttatagga   1860
tacttgatta caaagaagaa tgtgttcata ggaactggac atctgctggc aaaaattctg   1920
gtttccagct ataccgatt taaggatgtt gctgaaatac agactaaagg atttcagaca   1980
atcttagcaa tcctcaaatt gtcagcatct tttctaagc tgctggtgca tcattcattt   2040
gacttagtaa tattccatca aatgtcttcc aatatcatgg aacaaaagga tcaacagttt   2100
ctaaacctct gttgcaagtg ttttgcaaaa gtagctatgg atgattactt aaaaaatgtg   2160
atgctagaga gagcgtgtga tcagaataac agcatcatgg ttgaatgctt gcttctattg   2220
ggagcagatg ccaatcaagc aaaggaggga tcttctttaa tttgtcaggt atgtgagaaa   2280
gagagcagtc ccaaattggt ggaactctta ctgaatagtg gatctcgtga acaagatgta   2340
cgaaaagcgt tgacgataag cattgggaaa ggtgacagcc agatcatcag cttgctctta   2400
aggaggctgg ccctggatgt ggccaacaat agcatttgcc ttggaggatt tgtatagga   2460 aaagttgaac cttcttggct tggtcccttta tttccagata agacttctaa tttaaggaaa   2520
caaacaaata tagcatctac actagcaaga atggtgatca gatatcagat gaaaagtgct   2580
gtggaagaag aacagcctc aggcagcgat ggaaatttt ctgaagatgt gctgtctaaa   2640
tttgatgaat ggacctttat tcctgactct tctatggaca gtgtgtttgc tcaaagtgat   2700
```

```
gacctggata gtgaaggaag tgaaggctca tttcttgtga aaaagaaatc taattcaatt    2760
agtgtaggag aattttaccg agatgccgta ttacagcgtt gctcaccaaa tttgcaaaga    2820
cattccaatt ccttggggcc cattttttgat catgaagatt tactgaagcg aaaaagaaaa   2880
atattatctt cagatgattc actcaggtca tcaaaacttc aatcccatat gaggcattca    2940
gacagcattt cttctctggc ttctgagaga gaatatatta catcactaga cctttcagca    3000
aatgaactaa gagatattga tgccctaagc cagaaatgct gtataagtgt tcatttggag    3060
catcttgaaa agctggagct tcaccagaat gcactcacga gctttccaca acagctatgt    3120
gaaactctga agagtttgac acatttggac ttgcacagta taaaatttac atcatttcct    3180
tcttatttgt tgaaaatgag ttgtattgct aatcttgatg tctctcgaaa tgacattgga    3240
ccctcagtgg ttttagatcc tacagtgaaa tgtccaactc tgaaacagtt taacctgtca    3300
tataaccagc tgtcttttgt acctgagaac ctcactgatg tggtagagaa actggagcag    3360 ctcatttttag aaggaaataa aatatcaggg atatgctccc ccttgagact gaaggaactg    3420
aagattttaa accttagtaa gaaccacatt tcatccctat cagagaactt tcttgaggct    3480
tgtcctaaag tggagagttt cagtgccaga atgaattttc ttgctgctat gcctttcttg    3540
cctccttcta tgacaatcct aaaattatct cagaacaaat tttcctgtat tccagaagca    3600
attttaaatc ttccacactt gcggtcttta gatatgagca gcaatgatat tcagtaccta    3660
ccaggtcccg cacactggaa atctttgaac ttaagggaac tcttatttag ccataatcag    3720
atcagcatct tggacttgag tgaaaaagca tatttatggt ctagagtaga gaaactgcat    3780 cttttctcaca ataaactgaa agagattcct cctgagattg gctgtcttga aaatctgaca    3840
tctctggatg tcagttacaa cttggaacta agatcctttc ccaatgaaat ggggaaatta    3900
agcaaaatat gggatcttcc tttggatgaa ctgcatctta actttgattt taaacatata    3960
ggatgtaaag ccaaagacat cataaggttt cttcaacagc gattaaaaaa ggctgtgcct    4020
tataaccgaa tgaaacttat gattgtggga aatactggga gtggtaaaac caccttattg    4080
cagcaattaa tgaaaaccaa gaaatcagat cttggaatgc aaagtgccac agttggcata    4140
gatgtgaaag actggcctat ccaaataaga gacaaaagaa agagagatct cgtcctaaat    4200
gtgtgggatt ttgcaggtcg tgaggaattc tatagtactc atccccatttt tatgacgcag    4260 cgagcattgt accttgctgt ctatgacctc agcaagggac aggctgaagt tgatgccatg    4320
aagccttggc tcttcaatat aaaggctcgc gcttcttctt cccctgtgat tctcgttggc    4380
acacatttgg atgtttctga tgagaagcaa cgcaaagcct gcatgagtaa aatcaccaag    4440
gaactcctga ataagcgagg gttccctgcc atacgagatt accactttgt gaatgccacc    4500
gaggaatctg atgctttggc aaaacttcgg aaaaccatca taaacgagag ccttaatttc    4560
aagatccgag atcagcttgt tgttggacag ctgattccag actgctatgt agaacttgaa    4620
aaaatcattt tatcggagcg taaaaatgtg ccaattgaat ttcccgtaat tgaccggaaa    4680
cgattattac aactagtgag agaaaatcag ctgcagttag atgaaaatga gcttcctcac    4740
gcagttcact ttctaaatga atcaggagtc cttcttcatt ttcaagaccc agcactgcag    4800
ttaagtgact tgtactttgt ggaacccaag tggctttgta aaatcatggc acagattttg    4860
acagtgaaag tggaaggttg tccaaaacac cctaagggaa ttatttcgcg tagagatgtg    4920
gaaaaatttc tttcaaagaa aaggaaattt ccaaagaact acatgtcaca gtattttaag    4980
ctcctagaaa aattccagat tgctttgcca ataggagaag aatatttgct ggttccaagc    5040
agtttgtctg accacaggcc tgtgatagag cttccccatt gtgagaactc tgaaattatc    5100
```

```
atccgactat atgaaatgcc ttattttcca atgggatttt ggtcaagatt aatcaatcga    5160
ttacttgaga tttcacctta catgctttca gggagagaac gagcacttcg cccaaacaga    5220
atgtattggc gacaaggcat ttacttaaat tggtctcctg aagcttattg tctggtagga    5280
tctgaagtct tagacaatca tccagagagt ttcttaaaaa ttacagttcc ttcttgtaga    5340
aaaggctgta ttcttttggg ccaagttgtg gaccacattg attctctcat ggaagaatgg    5400
tttcctgggt tgctggagat tgatatttgt ggtgaaggag aaactctgtt gaagaaatgg    5460
gcattatata gttttaatga tggtgaagaa catcaaaaaa tcttacttga tgacttgatg    5520
aagaaagcag aggaaggaga tctcttagta aatccagatc aaccaaggct caccattcca    5580
atatctcaga ttgcccctga cttgattttg gctgacctgc ctagaaatat tatgttgaat    5640
aatgatgagt tggaatttga acaagctcca gagtttctcc taggtgatgg cagttttgga    5700
tcagtttacc gagcagccta tgaaggagaa gaagtggctg tgaagatttt taataaacat    5760
acatcactca ggctgttaag acaagagctt gtggtgcttt gccacctcca ccacccagt    5820 ttgatatctt tgctggcagc tgggattcgt ccccggatgt tggtgatgga gttagcctcc    5880
aagggttcct tggatcgcct gcttcagcag gacaaagcca gcctcactag aaccctacag    5940
cacaggattg cactccacgt agctgatggt ttgagatacc tccactcagc catgattata    6000
taccgagacc tgaaacccca caatgtgctg cttttcacac tgtatcccaa tgctgccatc    6060
attgcaaaga ttgctgacta cggcattgct cagtactgct gtagaatggg gataaaaaca    6120
tcagagggca caccagggtt tcgtgcacct gaagttgcca gaggaaatgt catttataac    6180
caacaggctg atgtttattc atttggttta ctactctatg acattttgac aactggaggt    6240
agaatagtag agggtttgaa gtttccaaat gagtttgatg aattagaaat acaaggaaaa    6300
ttacctgatc cagttaaaga atatggttgt gccccatggc ctatggttga gaaattaatt    6360
aaacagtgtt tgaaagaaaa tcctcaagaa aggcctactt ctgcccaggt ctttgacatt    6420
ttgaattcag ctgaattagt ctgtctgacg agacgcattt tattacctaa aaacgtaatt    6480
gttgaatgca tggttgctac acatcacaac agcaggaatg caagcatttg ctgggctgt    6540 gggcacaccg acagaggaca gctctcattt cttgacttaa atactgaagg atacacttct    6600
gaggaagttg ctgatagtag aatattgtgc ttagccttgg tgcatcttcc tgttgaaaag    6660
gaaagctgga ttgtgtctgg gacacagtct ggtactctcc tggtcatcaa taccgaagat    6720
gggaaaaaga gacatacccct agaaaagatg actgattctg tcacttgttt gtattgcaat    6780 tcctttttcca agcaaagcaa acaaaaaaat tttcttttgg ttggaaccgc tgatggcaag    6840
ttagcaattt ttgaagataa gactgttaag cttaaaggag ctgctccttt gaagatacta    6900
aatataggaa atgtcagtac tccattgatg tgtttgagtg aatccacaaa ttcaacggaa    6960
agaaatgtaa tgtggggagg atgtggcaca aagatttct ccttttctaa tgatttcacc    7020
attcagaaac tcattgagac aagaacaagc caactgtttt cttatgcagc tttcagtgat    7080
tccaacatca taacagtggt ggtagacact gctctctata ttgctaagca aaatagccct    7140
gttgtggaag tgtgggataa gaaaactgaa aaactctgtg gactaataga ctgcgtgcac    7200 ttttttaaggg aggtaatggt aaaagaaaac aaggaatcaa aacacaaaat gtcttattct    7260
gggagagtga aaaccctctg ccttcagaag aacactgctc tttggatagg aactggagga    7320
ggccatattt tactcctgga tctttcaact cgtcgactta cgtgtaat ttacaacttt    7380 tgtaattcgg tcagagtcat gatgacagca cagctaggaa gccttaaaaa tgtcatgctg    7440
```

-continued

```
gtattgggct acaaccggaa aaatactgaa ggtacacaaa agcagaaaga gatacaatct      7500
tgcttgaccg tttgggacat caatcttcca catgaagtgc aaaatttaga aaaacacatt      7560
gaagtgagaa aagaattagc tgaaaaaatg agacgaacat ctgttgagta a               7611
```

<210> SEQ ID NO 9
<211> LENGTH: 2536
<212> TYPE: PRT
<213> ORGANISM: Artificial
<220> FEATURE:
<223> OTHER INFORMATION: Translated protein sequence for human G2019
      Full length LRRK2 flag tagged protein

<400> SEQUENCE: 9

```
Met Asp Tyr Lys Asp Asp Asp Lys Met Ala Ser Gly Ser Cys Gln
1               5                   10                  15

Gly Cys Glu Glu Asp Glu Glu Thr Leu Lys Lys Leu Ile Val Arg Leu
            20                  25                  30

Asn Asn Val Gln Glu Gly Lys Gln Ile Glu Thr Leu Val Gln Ile Leu
        35                  40                  45

Glu Asp Leu Leu Val Phe Thr Tyr Ser Glu His Ala Ser Lys Leu Phe
    50                  55                  60

Gln Gly Lys Asn Ile His Val Pro Leu Leu Ile Val Leu Asp Ser Tyr
65                  70                  75                  80

Met Arg Val Ala Ser Val Gln Gln Val Gly Trp Ser Leu Leu Cys Lys
                85                  90                  95

Leu Ile Glu Val Cys Pro Gly Thr Met Gln Ser Leu Met Gly Pro Gln
            100                 105                 110

Asp Val Gly Asn Asp Trp Glu Val Leu Gly Val His Gln Leu Ile Leu
        115                 120                 125

Lys Met Leu Thr Val His Asn Ala Ser Val Asn Leu Ser Val Ile Gly
    130                 135                 140

Leu Lys Thr Leu Asp Leu Leu Leu Thr Ser Gly Lys Ile Thr Leu Leu
145                 150                 155                 160

Ile Leu Asp Glu Glu Ser Asp Ile Phe Met Leu Ile Phe Asp Ala Met
                165                 170                 175

His Ser Phe Pro Ala Asn Asp Glu Val Gln Lys Leu Gly Cys Lys Ala
            180                 185                 190

Leu His Val Leu Phe Glu Arg Val Ser Glu Glu Gln Leu Thr Glu Phe
        195                 200                 205

Val Glu Asn Lys Asp Tyr Met Ile Leu Leu Ser Ala Leu Thr Asn Phe
    210                 215                 220

Lys Asp Glu Glu Glu Ile Val Leu His Val Leu His Cys Leu His Ser
225                 230                 235                 240

Leu Ala Ile Pro Cys Asn Asn Val Glu Val Leu Met Ser Gly Asn Val
                245                 250                 255

Arg Cys Tyr Asn Ile Val Val Glu Ala Met Lys Ala Phe Pro Met Ser
            260                 265                 270

Glu Arg Ile Gln Glu Val Ser Cys Cys Leu Leu His Arg Leu Thr Leu
        275                 280                 285

Gly Asn Phe Phe Asn Ile Leu Val Leu Asn Glu Val His Glu Phe Val
    290                 295                 300

Val Lys Ala Val Gln Gln Tyr Pro Glu Asn Ala Ala Leu Gln Ile Ser
305                 310                 315                 320

Ala Leu Ser Cys Leu Ala Leu Leu Thr Glu Thr Ile Phe Leu Asn Gln
                325                 330                 335
```

```
Asp Leu Glu Glu Lys Asn Glu Asn Gln Glu Asn Asp Asp Glu Gly Glu
            340                 345                 350

Glu Asp Lys Leu Phe Trp Leu Glu Ala Cys Tyr Lys Ala Leu Thr Trp
            355                 360                 365

His Arg Lys Asn Lys His Val Gln Glu Ala Ala Cys Trp Ala Leu Asn
            370                 375                 380

Asn Leu Leu Met Tyr Gln Asn Ser Leu His Glu Lys Ile Gly Asp Glu
385                 390                 395                 400

Asp Gly His Phe Pro Ala His Arg Glu Val Met Leu Ser Met Leu Met
                405                 410                 415

His Ser Ser Ser Lys Glu Val Phe Gln Ala Ser Ala Asn Ala Leu Ser
            420                 425                 430

Thr Leu Leu Glu Gln Asn Val Asn Phe Arg Lys Ile Leu Leu Ser Lys
            435                 440                 445

Gly Ile His Leu Asn Val Leu Glu Leu Met Gln Lys His Ile His Ser
            450                 455                 460

Pro Glu Val Ala Glu Ser Gly Cys Lys Met Leu Asn His Leu Phe Glu
465                 470                 475                 480

Gly Ser Asn Thr Ser Leu Asp Ile Met Ala Ala Val Val Pro Lys Ile
                485                 490                 495

Leu Thr Val Met Lys Arg His Glu Thr Ser Leu Pro Val Gln Leu Glu
            500                 505                 510

Ala Leu Arg Ala Ile Leu His Phe Ile Val Pro Gly Met Pro Glu Glu
            515                 520                 525

Ser Arg Glu Asp Thr Glu Phe His His Lys Leu Asn Met Val Lys Lys
            530                 535                 540

Gln Cys Phe Lys Asn Asp Ile His Lys Leu Val Leu Ala Ala Leu Asn
545                 550                 555                 560

Arg Phe Ile Gly Asn Pro Gly Ile Gln Lys Cys Gly Leu Lys Val Ile
                565                 570                 575

Ser Ser Ile Val His Phe Pro Asp Ala Leu Glu Met Leu Ser Leu Glu
            580                 585                 590

Gly Ala Met Asp Ser Val Leu His Thr Leu Gln Met Tyr Pro Asp Asp
            595                 600                 605

Gln Glu Ile Gln Cys Leu Gly Leu Ser Leu Ile Gly Tyr Leu Ile Thr
            610                 615                 620

Lys Lys Asn Val Phe Ile Gly Thr Gly His Leu Leu Ala Lys Ile Leu
625                 630                 635                 640

Val Ser Ser Leu Tyr Arg Phe Lys Asp Val Ala Glu Ile Gln Thr Lys
                645                 650                 655

Gly Phe Gln Thr Ile Leu Ala Ile Leu Lys Leu Ser Ala Ser Phe Ser
            660                 665                 670

Lys Leu Leu Val His His Ser Phe Asp Leu Val Ile Phe His Gln Met
            675                 680                 685

Ser Ser Asn Ile Met Glu Gln Lys Asp Gln Gln Phe Leu Asn Leu Cys
            690                 695                 700

Cys Lys Cys Phe Ala Lys Val Ala Met Asp Asp Tyr Leu Lys Asn Val
705                 710                 715                 720

Met Leu Glu Arg Ala Cys Asp Gln Asn Asn Ser Ile Met Val Glu Cys
                725                 730                 735

Leu Leu Leu Leu Gly Ala Asp Ala Asn Gln Ala Lys Glu Gly Ser Ser
            740                 745                 750
```

```
Leu Ile Cys Gln Val Cys Glu Lys Glu Ser Ser Pro Lys Leu Val Glu
            755                 760                 765

Leu Leu Leu Asn Ser Gly Ser Arg Glu Gln Asp Val Arg Lys Ala Leu
        770                 775                 780

Thr Ile Ser Ile Gly Lys Gly Asp Ser Gln Ile Ile Ser Leu Leu Leu
785                 790                 795                 800

Arg Arg Leu Ala Leu Asp Val Ala Asn Asn Ser Ile Cys Leu Gly Gly
                805                 810                 815

Phe Cys Ile Gly Lys Val Glu Pro Ser Trp Leu Gly Pro Leu Phe Pro
                820                 825                 830

Asp Lys Thr Ser Asn Leu Arg Lys Gln Thr Asn Ile Ala Ser Thr Leu
            835                 840                 845

Ala Arg Met Val Ile Arg Tyr Gln Met Lys Ser Ala Val Glu Glu Gly
    850                 855                 860

Thr Ala Ser Gly Ser Asp Gly Asn Phe Ser Glu Asp Val Leu Ser Lys
865                 870                 875                 880

Phe Asp Glu Trp Thr Phe Ile Pro Asp Ser Ser Met Asp Ser Val Phe
                    885                 890                 895

Ala Gln Ser Asp Asp Leu Asp Ser Glu Gly Ser Glu Gly Ser Phe Leu
                900                 905                 910

Val Lys Lys Lys Ser Asn Ser Ile Ser Val Gly Glu Phe Tyr Arg Asp
            915                 920                 925

Ala Val Leu Gln Arg Cys Ser Pro Asn Leu Gln Arg His Ser Asn Ser
    930                 935                 940

Leu Gly Pro Ile Phe Asp His Glu Asp Leu Leu Lys Arg Lys Arg Lys
945                 950                 955                 960

Ile Leu Ser Ser Asp Asp Ser Leu Arg Ser Ser Lys Leu Gln Ser His
                965                 970                 975

Met Arg His Ser Asp Ser Ile Ser Ser Leu Ala Ser Glu Arg Glu Tyr
            980                 985                 990

Ile Thr Ser Leu Asp Leu Ser Ala  Asn Glu Leu Arg Asp  Ile Asp Ala
                995                 1000                1005

Leu Ser  Gln Lys Cys Cys Ile  Ser Val His Leu Glu  His Leu Glu
    1010                1015                1020

Lys Leu  Glu Leu His Gln Asn  Ala Leu Thr Ser Phe  Pro Gln Gln
    1025                1030                1035

Leu Cys  Glu Thr Leu Lys Ser  Leu Thr His Leu Asp  Leu His Ser
    1040                1045                1050

Asn Lys  Phe Thr Ser Phe Pro  Ser Tyr Leu Leu Lys  Met Ser Cys
    1055                1060                1065

Ile Ala  Asn Leu Asp Val Ser  Arg Asn Asp Ile Gly  Pro Ser Val
    1070                1075                1080

Val Leu  Asp Pro Thr Val Lys  Cys Pro Thr Leu Lys  Gln Phe Asn
    1085                1090                1095

Leu Ser  Tyr Asn Gln Leu Ser  Phe Val Pro Glu Asn  Leu Thr Asp
    1100                1105                1110

Val Val  Glu Lys Leu Glu Gln  Leu Ile Leu Glu Gly  Asn Lys Ile
    1115                1120                1125

Ser Gly  Ile Cys Ser Pro Leu  Arg Leu Lys Glu Leu  Lys Ile Leu
    1130                1135                1140

Asn Leu  Ser Lys Asn His Ile  Ser Ser Leu Ser Glu  Asn Phe Leu
    1145                1150                1155

Glu Ala  Cys Pro Lys Val Glu  Ser Phe Ser Ala Arg  Met Asn Phe
```

-continued

```
             1160                1165                1170

Leu Ala  Ala Met Pro Phe Leu  Pro Pro Ser Met Thr  Ile Leu Lys
    1175             1180                 1185

Leu Ser  Gln Asn Lys Phe Ser  Cys Ile Pro Glu Ala  Ile Leu Asn
    1190             1195                 1200

Leu Pro  His Leu Arg Ser Leu  Asp Met Ser Ser Asn  Asp Ile Gln
    1205             1210                 1215

Tyr Leu  Pro Gly Pro Ala His  Trp Lys Ser Leu Asn  Leu Arg Glu
    1220             1225                 1230

Leu Leu  Phe Ser His Asn Gln  Ile Ser Ile Leu Asp  Leu Ser Glu
    1235             1240                 1245

Lys Ala  Tyr Leu Trp Ser Arg  Val Glu Lys Leu His  Leu Ser His
    1250             1255                 1260

Asn Lys  Leu Lys Glu Ile Pro  Pro Glu Ile Gly Cys  Leu Glu Asn
    1265             1270                 1275

Leu Thr  Ser Leu Asp Val Ser  Tyr Asn Leu Glu Leu  Arg Ser Phe
    1280             1285                 1290

Pro Asn  Glu Met Gly Lys Leu  Ser Lys Ile Trp Asp  Leu Pro Leu
    1295             1300                 1305

Asp Glu  Leu His Leu Asn Phe  Asp Phe Lys His Ile  Gly Cys Lys
    1310             1315                 1320

Ala Lys  Asp Ile Ile Arg Phe  Leu Gln Gln Arg Leu  Lys Lys Ala
    1325             1330                 1335

Val Pro  Tyr Asn Arg Met Lys  Leu Met Ile Val Gly  Asn Thr Gly
    1340             1345                 1350

Ser Gly  Lys Thr Thr Leu Leu  Gln Gln Leu Met Lys  Thr Lys Lys
    1355             1360                 1365

Ser Asp  Leu Gly Met Gln Ser  Ala Thr Val Gly Ile  Asp Val Lys
    1370             1375                 1380

Asp Trp  Pro Ile Gln Ile Arg  Asp Lys Arg Lys Arg  Asp Leu Val
    1385             1390                 1395

Leu Asn  Val Trp Asp Phe Ala  Gly Arg Glu Glu Phe  Tyr Ser Thr
    1400             1405                 1410

His Pro  His Phe Met Thr Gln  Arg Ala Leu Tyr Leu  Ala Val Tyr
    1415             1420                 1425

Asp Leu  Ser Lys Gly Gln Ala  Glu Val Asp Ala Met  Lys Pro Trp
    1430             1435                 1440

Leu Phe  Asn Ile Lys Ala Arg  Ala Ser Ser Pro Val  Ile Leu
    1445             1450                 1455

Val Gly  Thr His Leu Asp Val  Ser Asp Glu Lys Gln  Arg Lys Ala
    1460             1465                 1470

Cys Met  Ser Lys Ile Thr Lys  Glu Leu Leu Asn Lys  Arg Gly Phe
    1475             1480                 1485

Pro Ala  Ile Arg Asp Tyr His  Phe Val Asn Ala Thr  Glu Glu Ser
    1490             1495                 1500

Asp Ala  Leu Ala Lys Leu Arg  Lys Thr Ile Ile Asn  Glu Ser Leu
    1505             1510                 1515

Asn Phe  Lys Ile Arg Asp Gln  Leu Val Val Gly Gln  Leu Ile Pro
    1520             1525                 1530

Asp Cys  Tyr Val Glu Leu Glu  Lys Ile Ile Leu Ser  Glu Arg Lys
    1535             1540                 1545

Asn Val  Pro Ile Glu Phe Pro  Val Ile Asp Arg Lys  Arg Leu Leu
    1550             1555                 1560
```

```
Gln Leu Val Arg Glu Asn Gln Leu Gln Leu Asp Glu Asn Glu Leu
    1565                1570                1575

Pro His Ala Val His Phe Leu Asn Glu Ser Gly Val Leu Leu His
    1580                1585                1590

Phe Gln Asp Pro Ala Leu Gln Leu Ser Asp Leu Tyr Phe Val Glu
    1595                1600                1605

Pro Lys Trp Leu Cys Lys Ile Met Ala Gln Ile Leu Thr Val Lys
    1610                1615                1620

Val Glu Gly Cys Pro Lys His Pro Lys Gly Ile Ile Ser Arg Arg
    1625                1630                1635

Asp Val Glu Lys Phe Leu Ser Lys Lys Arg Lys Phe Pro Lys Asn
    1640                1645                1650

Tyr Met Ser Gln Tyr Phe Lys Leu Leu Glu Lys Phe Gln Ile Ala
    1655                1660                1665

Leu Pro Ile Gly Glu Glu Tyr Leu Leu Val Pro Ser Ser Leu Ser
    1670                1675                1680

Asp His Arg Pro Val Ile Glu Leu Pro His Cys Glu Asn Ser Glu
    1685                1690                1695

Ile Ile Ile Arg Leu Tyr Glu Met Pro Tyr Phe Pro Met Gly Phe
    1700                1705                1710

Trp Ser Arg Leu Ile Asn Arg Leu Leu Glu Ile Ser Pro Tyr Met
    1715                1720                1725

Leu Ser Gly Arg Glu Arg Ala Leu Arg Pro Asn Arg Met Tyr Trp
    1730                1735                1740

Arg Gln Gly Ile Tyr Leu Asn Trp Ser Pro Glu Ala Tyr Cys Leu
    1745                1750                1755

Val Gly Ser Glu Val Leu Asp Asn His Pro Glu Ser Phe Leu Lys
    1760                1765                1770

Ile Thr Val Pro Ser Cys Arg Lys Gly Cys Ile Leu Leu Gly Gln
    1775                1780                1785

Val Val Asp His Ile Asp Ser Leu Met Glu Glu Trp Phe Pro Gly
    1790                1795                1800

Leu Leu Glu Ile Asp Ile Cys Gly Glu Gly Glu Thr Leu Leu Lys
    1805                1810                1815

Lys Trp Ala Leu Tyr Ser Phe Asn Asp Gly Glu Glu His Gln Lys
    1820                1825                1830

Ile Leu Leu Asp Asp Leu Met Lys Lys Ala Glu Glu Gly Asp Leu
    1835                1840                1845

Leu Val Asn Pro Asp Gln Pro Arg Leu Thr Ile Pro Ile Ser Gln
    1850                1855                1860

Ile Ala Pro Asp Leu Ile Leu Ala Asp Leu Pro Arg Asn Ile Met
    1865                1870                1875

Leu Asn Asn Asp Glu Leu Glu Phe Glu Gln Ala Pro Glu Phe Leu
    1880                1885                1890

Leu Gly Asp Gly Ser Phe Gly Ser Val Tyr Arg Ala Ala Tyr Glu
    1895                1900                1905

Gly Glu Glu Val Ala Val Lys Ile Phe Asn Lys His Thr Ser Leu
    1910                1915                1920

Arg Leu Leu Arg Gln Glu Leu Val Val Leu Cys His Leu His His
    1925                1930                1935

Pro Ser Leu Ile Ser Leu Leu Ala Ala Gly Ile Arg Pro Arg Met
    1940                1945                1950
```

```
Leu Val Met Glu Leu Ala Ser Lys Gly Ser Leu Asp Arg Leu Leu
1955                1960                1965

Gln Gln Asp Lys Ala Ser Leu Thr Arg Thr Leu Gln His Arg Ile
1970                1975                1980

Ala Leu His Val Ala Asp Gly Leu Arg Tyr Leu His Ser Ala Met
1985                1990                1995

Ile Ile Tyr Arg Asp Leu Lys Pro His Asn Val Leu Leu Phe Thr
2000                2005                2010

Leu Tyr Pro Asn Ala Ala Ile Ile Ala Lys Ile Ala Asp Tyr Gly
2015                2020                2025

Ile Ala Gln Tyr Cys Cys Arg Met Gly Ile Lys Thr Ser Glu Gly
2030                2035                2040

Thr Pro Gly Phe Arg Ala Pro Glu Val Ala Arg Gly Asn Val Ile
2045                2050                2055

Tyr Asn Gln Gln Ala Asp Val Tyr Ser Phe Gly Leu Leu Leu Tyr
2060                2065                2070

Asp Ile Leu Thr Thr Gly Gly Arg Ile Val Glu Gly Leu Lys Phe
2075                2080                2085

Pro Asn Glu Phe Asp Glu Leu Glu Ile Gln Gly Lys Leu Pro Asp
2090                2095                2100

Pro Val Lys Glu Tyr Gly Cys Ala Pro Trp Pro Met Val Glu Lys
2105                2110                2115

Leu Ile Lys Gln Cys Leu Lys Glu Asn Pro Gln Glu Arg Pro Thr
2120                2125                2130

Ser Ala Gln Val Phe Asp Ile Leu Asn Ser Ala Glu Leu Val Cys
2135                2140                2145

Leu Thr Arg Arg Ile Leu Leu Pro Lys Asn Val Ile Val Glu Cys
2150                2155                2160

Met Val Ala Thr His His Asn Ser Arg Asn Ala Ser Ile Trp Leu
2165                2170                2175

Gly Cys Gly His Thr Asp Arg Gly Gln Leu Ser Phe Leu Asp Leu
2180                2185                2190

Asn Thr Glu Gly Tyr Thr Ser Glu Glu Val Ala Asp Ser Arg Ile
2195                2200                2205

Leu Cys Leu Ala Leu Val His Leu Pro Val Glu Lys Glu Ser Trp
2210                2215                2220

Ile Val Ser Gly Thr Gln Ser Gly Thr Leu Leu Val Ile Asn Thr
2225                2230                2235

Glu Asp Gly Lys Lys Arg His Thr Leu Glu Lys Met Thr Asp Ser
2240                2245                2250

Val Thr Cys Leu Tyr Cys Asn Ser Phe Ser Lys Gln Ser Lys Gln
2255                2260                2265

Lys Asn Phe Leu Leu Val Gly Thr Ala Asp Gly Lys Leu Ala Ile
2270                2275                2280

Phe Glu Asp Lys Thr Val Lys Leu Lys Gly Ala Ala Pro Leu Lys
2285                2290                2295

Ile Leu Asn Ile Gly Asn Val Ser Thr Pro Leu Met Cys Leu Ser
2300                2305                2310

Glu Ser Thr Asn Ser Thr Glu Arg Asn Val Met Trp Gly Gly Cys
2315                2320                2325

Gly Thr Lys Ile Phe Ser Phe Ser Asn Asp Phe Thr Ile Gln Lys
2330                2335                2340

Leu Ile Glu Thr Arg Thr Ser Gln Leu Phe Ser Tyr Ala Ala Phe
```

```
                          2345                2350                2355
Ser Asp Ser Asn Ile Ile Thr Val Val Asp Thr Ala Leu Tyr
    2360                2365                2370

Ile Ala Lys Gln Asn Ser Pro Val Val Glu Val Trp Asp Lys Lys
    2375                2380                2385

Thr Glu Lys Leu Cys Gly Leu Ile Asp Cys Val His Phe Leu Arg
    2390                2395                2400

Glu Val Met Val Lys Glu Asn Lys Glu Ser Lys His Lys Met Ser
    2405                2410                2415

Tyr Ser Gly Arg Val Lys Thr Leu Cys Leu Gln Lys Asn Thr Ala
    2420                2425                2430

Leu Trp Ile Gly Thr Gly Gly His Ile Leu Leu Leu Asp Leu
    2435                2440                2445

Ser Thr Arg Arg Leu Ile Arg Val Ile Tyr Asn Phe Cys Asn Ser
    2450                2455                2460

Val Arg Val Met Met Thr Ala Gln Leu Gly Ser Leu Lys Asn Val
    2465                2470                2475

Met Leu Val Leu Gly Tyr Asn Arg Lys Asn Thr Glu Gly Thr Gln
    2480                2485                2490

Lys Gln Lys Glu Ile Gln Ser Cys Leu Thr Val Trp Asp Ile Asn
    2495                2500                2505

Leu Pro His Glu Val Gln Asn Leu Glu Lys His Ile Glu Val Arg
    2510                2515                2520

Lys Glu Leu Ala Glu Lys Met Arg Arg Thr Ser Val Glu
    2525                2530                2535

<210> SEQ ID NO 10
<211> LENGTH: 15
<212> TYPE: PRT
<213> ORGANISM: Artificial
<220> FEATURE:
<223> OTHER INFORMATION: 'LRRKtide' peptide

<400> SEQUENCE: 10

Arg Leu Gly Arg Asp Lys Tyr Lys Thr Leu Arg Gln Ile Arg Gln
1               5                   10                  15
```